(12) United States Patent
Dahmann et al.

(10) Patent No.: US 8,772,305 B2
(45) Date of Patent: Jul. 8, 2014

(54) SUBSTITUTED PYRIDINYL-PYRIMIDINES AND THEIR USE AS MEDICAMENTS

(75) Inventors: Georg Dahmann, Warthausen-Birkenhard (DE); Dennis Fiegen, Biberach an der Riss (DE); Martin Fleck, Warthausen (DE); Matthias Hoffmann, Mittelbiberach (DE); Jasna Klicic, Biberach an der Riss (DE); Stephen Peter East, Wallingford (GB); Spencer Charles R. Napier, Abingdon (GB); John Scott, Abingdon (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/357,734

(22) Filed: Jan. 25, 2012

(65) Prior Publication Data

US 2013/0023502 A1    Jan. 24, 2013

(30) Foreign Application Priority Data

Jan. 28, 2011 (EP) .................................. 11152528

(51) Int. Cl.
*A01N 43/54* (2006.01)
*A61K 31/505* (2006.01)

(52) U.S. Cl.
USPC .......................................... 514/275; 544/331

(58) Field of Classification Search
USPC .......................................... 514/275; 544/331
See application file for complete search history.

(56) References Cited

U.S. PATENT DOCUMENTS

| 4,792,547 | A  |   | 12/1988 | Itoh et al. |         |
|-----------|----|---|---------|-------------|---------|
| 5,635,527 | A  | * | 6/1997  | Ono et al.  | 514/414 |
| 6,225,331 | B1 | * | 5/2001  | Cupps et al.| 514/367 |

FOREIGN PATENT DOCUMENTS

| WO |    2006041773 A2    | 4/2006 |
| WO |    2008024634 A1    | 2/2008 |
| WO | WO 2008079933 A2 *  | 7/2008 |
| WO |    2012101013 A1    | 8/2012 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
U.E.W. Lange et al., 16 Bioorganic & Medicinal Chemistry Letters, 2648-2653 (2006).*
R. Singh et al., 42 Annual Reports in Medicinal Chemistry, 379-391, 380 (2007).*
M.E. Weinblatt et al., 363 The New England Journal of Medicine 1303-1312 (2010).*
N. Yamamoto et al., 306 The Journal of Pharmacology and Experimental Therapeutics, 1174-1181 (2003).*
E.S. Masuda et al., 21 Pulmonary Pharmacology & Therapeutics, 461-467 (2008).*
I. Collins, Current Signal Transduction Therapy, 1, 13-23, 13 (2006).*
M. Gonzalez et al., 22 Expert Opinion Therapeutic Patents, 1289-1302 (2012).*
S. Malhotra et al., 11 Expert Opinion Therapeutic Patents, 275-291 (2006).*
M. Rlccaboni et al., 15 Drug Discovery Today, 517-530 (2010).*
International Search Report for PCT/EP2012/050672 mailed Mar. 28, 2012.
Ruzza, P. et al., "Therapeutic prospect of Syk inhibitors". Expert Opinion on Therapeutic Patents, Informa Healthcare, GB, vol. 19, No. 10, Oct. 1, 2009, pp. 1361-1376.
Bingham, A.H. et al., "A novel series of potent and selection IKK2 inhibitors". Bioorganic and Medicinal Chemistry Letters, Pergamon, Elsevier Science, GB, vol. 14, No. 2, Jan. 19, 2004, pp. 409-412.
Rodriguez, F. et al., "New Bis(2-aminoimidazoline) and Bisguanidine DNA Minor Groove Binders with Potent in Vivo Antitrypanosomal and Antiplasmodial Activity". Journal of Medicianl Chemistry, American Chemical Society, Wash. D. C., vol. 51, Jan. 1, 2008, pp. 909-923.

* cited by examiner

*Primary Examiner* — Deepak Rao
*Assistant Examiner* — Alexander R Pagano
(74) *Attorney, Agent, or Firm* — Michael P. Morris; Anthony Bottino; Usha R. Patel

(57) ABSTRACT

The invention relates to new substituted pyridinyl-pyrimidines of formula 1

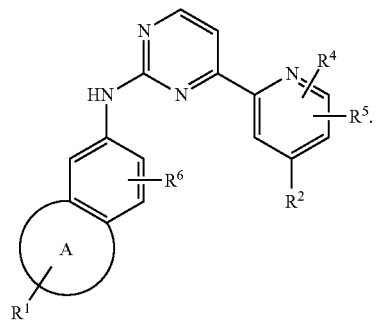

wherein
ring A is a five-membered saturated or unsaturated carbocyclic ring which optionally comprises one, two or three heteroatoms each independently from each other selected from the group N, S and O,
wherein $R^1$, $R^2$, $R^4$, $R^3$, $R^5$ and $R^6$ are defined as in claim 1 and wherein ring A is further optionally substituted by one or two further substituents and the pharmaceutically acceptable salts, diastereomers, enantiomers, racemates, hydrates and solvates of the aforementioned compounds.

22 Claims, No Drawings

SUBSTITUTED PYRIDINYL-PYRIMIDINES AND THEIR USE AS MEDICAMENTS

The invention relates to new substituted pyridinyl-pyrimidines of formula 1

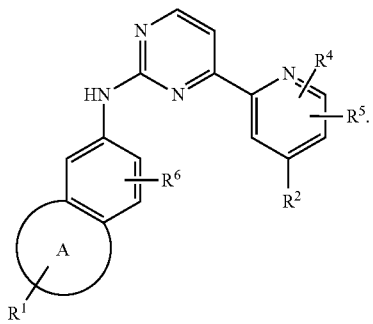

1 wherein
ring A is a five-membered saturated or unsaturated carbocyclic ring which optionally comprises one, two or three heteroatoms each independently from each other selected from the group N, S and O,
wherein $R^1$, $R^2$, $R^4$, $R^3$, $R^5$ and $R^6$ are defined as in claim 1 and wherein ring A is further optionally substituted by one or two further substituents and the pharmaceutically acceptable salts, diastereomers, enantiomers, racemates, hydrates and solvates of the aforementioned compounds.

1. BACKGROUND TO THE INVENTION

1.1 SYK-Inhibitors

The present invention describes new substituted pyridinyl-pyrimidines that inhibit the protein kinase Syk (spleen tyrosine kinase), the preparation and formulation thereof and their use for preparing a medicament.

Syk is an intracellular tyrosine kinase that has an important mediator function in the signal transduction of different receptors in B-cells, mast cells, monocytes, macrophages, neutrophils, T-cells, dendritic cells and epithelial cells. The receptors in which Syk performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Wong et al.; Expert Opin. Investig. Drugs (2004) 13(7), 743-762; Ulanova et al.; Expert Opin. Ther. Target (2005) 9(5); 901-921; Wang et al.; J. Immunol. (2006) 177, 6859-6870; Leib and Gut-Landmann et al.; Nature Immunology (2007) 8, 630-638; Slack et al., European J. Immunol. (2007) 37, 1600-1612). The best description is of the molecular processes during the signal transduction of the FcεRI. In mast cells the binding of IgE to FcεRI causes the cross-linking of IgE-receptors and the recruiting and activation of Lyn (a tyrosine kinase from the Src family). Active Lyn phoshorylates so-called ITAM motifs, which are present in many of the receptors listed above, and thereby generates binding sites for the SH2-domain of Syk. As a result of the binding to the ITAM motif Syk is activated and then phosphorylates various substrates which are needed for the release of allergic and inflammatory mediators such as e.g. histamine and β-hexosamidase (βHA), as well as for the synthesis of lipid mediators, such as e.g. prostaglandins and leukotrienes.

In view of its central function in different signal transduction pathways Syk has been discussed as a therapeutic target for different diseases such as e.g. Allergic rhinitis, asthma, autoimmune diseases, rheumatoid arthritis, osteopenia, osteoporosis, COPD and various leukaemias and lymphomas (Wong et al.; Expert Opin. Investig. Drugs (2004) 13(7), 743-762; Ulanova et al.; Expert Opin. Ther. Target (2005) 9(5); 901-921; Sigh and Masuda. Annual Reports in Medicinal Chemistry (2007) Vol 42; 379-391; Bajpai et al.; Expert Opin. Investig. Drugs (2008) Vol 15 (5); 641-659; Masuda and Schmitz; PPT (2008) Vol 21; 461-467).

Allergic rhinitis and asthma are diseases associated with allergic reactions and inflammatory processes and involving different cell types such as e.g. Mast cells, eosinophils, T-cells and dendritic cells. After exposure to allergens has occurred, the high affinity immunoglobulin receptors for IgE (FcεRI) and IgG (FcγR1) are activated and induce the release of pro-inflammatory mediators and bronchoconstrictors. An inhibitor of the Syk kinase activity should thus be able to inhibit these steps.

Rheumatoid arthritis (RA) is an autoimmune disease in which the bones and ligaments structures surrounding the joints are progressively destroyed. In the pathophysiology of RA, B-cells play a significant role, as has been demonstrated for example by the therapeutic use of rituximab, a B cell-depleting antibody. In addition to the function of Syk in the signal transduction of the BCR (which after being stimulated also induces the release of pro-inflammatory mediators), Syk also plays an important part in the maturation and proliferation of B cells (Cheng et al. Nature (1995) 378, 303-306, Cornell et al., PNAS (2000) 97(4), 1713-1718). An inhibitor of the Syk kinase activity may thus offer a therapeutic option for the treatment of autoimmune diseases such as RA and diseases with an increased proliferation of B cells, such as e.g. B-cell lymphomas.

Chronic obstructive pulmonary disease (COPD) is characterised by a successive deterioration in lung function and chronic inflammation of the airways, which is initiated and produced by noxious substances of all kinds and contributes to the maintenance of the course of the disease. At a cellular level, in COPD there is in particular a multiplication of T-lymphocytes, neutrophils, granulocytes and macrophages. In particular, there is an increase in the number of CD8-positive lymphocytes, that is directly connected with the impairment of lung function. Another characteristic of COPD are acute deteriorations in lung function (exacerbations), characterised by viral (e.g. Rhinovirus), or bacterial (e.g. *Streptococcus pneumoniae*, *Haemophilus influenzae* and *Moraxella catarrhalis*) infections.

In view of the pro-inflammatory function of Syk in macrophages, T-cells and neutrophils as described above (see: Wong et al.; Expert Opin. Investig. Drugs (2004) 13(7), 743-762; and references cited therein) an inhibitor of the Syk kinase activity could be a new therapeutic approach to the treatment of the inflammatory processes that underlie COPD. It has also been shown that Syk in epithelial cells of the respiratory tract is involved in the ICAM1R-mediated uptake and subsequent replication of the Rhinovirus and that a si-RNA against Syk blocks these steps (Wang et al.; J. Immunol. (2006) 177, 6859-6870; Lau et al.; J. Immunol. (2008) 180, 870-880). Thus, an inhibitor of the Syk kinase activity could also be used therapeutically in exacerbations caused by Rhinoviruses.

Various studies suggest that Syk is involved in the malignant transformation of lymphocytes (summarised in Sigh and Masuda. Annual Reports in Medicinal Chemistry (2007) Vol 42; 379-391). A TEL-Syk fusion protein with a constitutive Syk activity transformed B cells of a patient with myelodysplastic syndrome, a constitutively active ITK-Syk fusion protein was isolated from patients with T-cell lymphomas. Moreover, constitutively active Syk was found in B-cell lymphoma cells of patients. On the basis of these data it seems that Syk is a proto-oncogene in haematopoietic cells and represents a potential target for the treatment of certain leukaemias and lymphomas.

1.2 Prior Art

WO98/11095 discloses substituted 2-pyrimidineamines and their use as selective protein kinase inhibitors, in particular inhibitors of the kinases ZAP-70 and protein kinase C, for the treatment of immune diseases and hyperproliferative disorders. However, none of the compounds disclosed in WO98/11095 carries a 2-pyridinyl residue in the 4-position.

WO03/030909 discloses 2- and 4-aminopyrimidines N-substituted by a bicyclic ring for use as kinase inhibitors in the treatment of cancer and viral infections. However none of the compounds disclosed in WO03/030909 carries a 2-pyridinyl-residue in the 4-position.

WO98/18782 discloses 2-pyrimidineamine derivatives and their use as selective protein tyrosine kinase inhibitors, particularly inhibitors of the kinases ZAP-70 and SYK, for the treatment of immune or allergic diseases and diseases involving platelet activation. However, none of the compounds disclosed in WO98/18782 is a 2-pyrimidineamine substituted by a 2-pyridinyl-residue in the 4-position and substituted by a 9-membered annellated bicyclic heterocycle according to formula 1.

U.S. Pat. No. 4,876,252 discloses 4,5,6-substituted-N-(substituted phenyl)-2-pyrimidineamines with antiasthmatic activity. However, none of the pyrimidineamines of U.S. Pat. No. 4,876,252 is a 2-pyrimidineamine substituted by a 2-pyridinyl in the 4-position and substituted by a 9-membered annellated bicyclic heterocycles according to formula 1.

WO2006/021458 and WO2002/093164 both disclose pyridinyl-pyrimidines for the treatment of a large variety of diseases such as for instance prion diseases and inflammatory diseases. However, none of the pyridinyl-pyrimidines mentioned in WO2006/021458 or WO2002/093164 carries a 9-membered annellated bicyclic heterocycle according to formula 1.

Surprisingly it has now been found that specifically substituted pyridinyl-pyrimidines of formula 1 are particularly effective SYK-inhibitors and are therefore particularly suitable for the treatment of respiratory complaints, allergic diseases, osteoporosis, gastrointestinal diseases, autoimmune diseases, inflammatory diseases and diseases of the peripheral or central nervous system, particularly for the treatment of asthma, allergic rhinitis, rheumatoid arthritis, allergic dermatitis and COPD.

2. DESCRIPTION OF THE INVENTION

The instant invention concerns compounds of formula 1

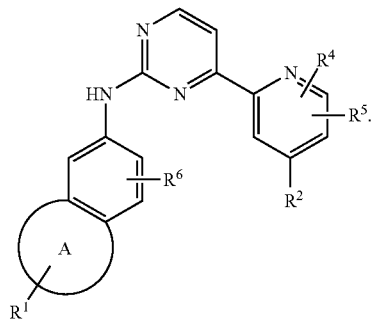

wherein
ring A is a five-membered saturated or unsaturated carbocyclic ring which optionally comprises one, two or three heteroatoms each independently from each other selected from the group N, S and O, wherein ring A may optionally be further substituted by one or two residues which are both independently from each other selected from the group consisting of H, halogen, $C_{1-3}$-alkyl, -oxo, —$NH_2$, —CO—($C_{1-3}$-alkyl), —CO—NH($C_{1-3}$-alkyl), —CO—N($C^{1-3}$-alkyl)$_2$, —$SO_2$-phenyl and —$SO_2$—($C_{1-3}$-alkyl), and wherein
$R^1$ is selected from the group consisting of
H, -halogen, SH, -oxo, —$NH_2$, —CO—Y, —CO—N($CH_3$)—Y, —CO—N($CH_3$)—($C_{1-3}$-alkylene)-Y, —CS—Y, —CS—N($CH_3$)—Y, —CS—N($CH_3$)—($C_{1-3}$-alkylene)-Y, —$C_{1-6}$-alkyl, —$C_{1-3}$-haloalkyl, —CO—NH—Y, —CO—NH—$C_{1-4}$-alkylene-Y, —CO—NH—$C_{1-4}$-alkylene-(Y)$_2$, —CO—N($CH_3$)—($C_{2-3}$-alkylene)-O—($C_{1-3}$-alkyl), —$NH_2$, —$C_{1-6}$-alkylene-L, —$SO_2$-phenyl, —$SO_2$—($C_{1-3}$-alkyl), —CO—N($C_{1-4}$-alkyl)$_2$, —CO—N($C_{2-4}$-alkylene-O—$C_{1-3}$-alkyl)$_2$, a five- or six-membered heteroaromatic group comprising 1, 2 or 3 heteroatoms each independently selected from the group N, S and O, with Y being a group selected from the group consisting of —$NH_2$, —NH($CH_3$), —N($CH_3$)$_2$, —$C_{1-6}$-alkylene-N($CH_3$)$_2$, —O—$C_{1-3}$-alkyl, —OH and —N(ethyl)$_2$, or with Y being a group selected from the group consisting of a four-, five-, six- or seven-membered monocyclic fully saturated or partially unsaturated heterocycle comprising 1, 2 or 3 heteroatoms each independently selected from the group N, S and O, with the proviso hat this heterocycle comprises at least one N-atom and that this heterocycle is directly attached to the molecule via this N-atom, a five- or six-membered monocyclic heteroaromatic group comprising 1, 2 or 3 heteroatoms each independently selected from the group of N, S and O, and a $C_{3-6}$-cycloalkyl, or with Y being a 9- to 11-membered bicyclic annellated fully saturated or partially unsaturated heterocycle comprising 1, 2, 3 or 4 heteroatoms each independently from each other selected from the group N, S and O, or with Y being an 8- to 11-membered bicyclic fully saturated spiro-heterocycle comprising 1, 2 or 3 heteroatoms each independently selected from the group N, S and O, with the proviso hat this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional $C_{1-3}$-alkylene-unit, whereby each Y may optionally be substituted by one or more groups Z each independently from each other selected from the group consisting of halogen, -oxo, OH, $C_{1-5}$-alkyl, —$C_{1-5}$-alkanol, —O—$C_{1-3}$-alkyl, a five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO-L, —$C_{1-3}$-alkylene-CO-L, —$C_{1-3}$-alkylen-O—$C_{1-3}$-alkyl, —N($CH_3$)$_2$ and —N(ethyl)$_2$, whereby each group Z may optionally be further substituted by one, two or three groups T each independently selected from the group consisting of -oxo, OH, halogen, —$C_{1-3}$-alkyl, —O—$C_{1-3}$-alkyl, —N(methyl)$_2$, —N(ethyl)$_2$, 5- to 6-membered fully saturated, partially unsaturated or aromatic heterocycle comprising 1 or 2 heteroatoms each independently selected from the group N, O and S, a $C_{3-6}$-cycloalkyl and —CN, wherein each group T may also optionally be substituted by a group selected from the group consisting of $C_{1-3}$-alkyl, halogen, OH, oxo and —O—$C_{1-3}$-alkyl, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, halogen, OH and -oxo, wherein $R^2$ denotes a group selected from the group consisting of hydrogen, —OH, halogen, —CO—NH—$NH_2$ and —CO—$NH_2$, or $R^2$ denotes a group selected from the group consisting of linear or branched $C_{1-6}$-alkyl, —$C_{1-6}$-haloalkyl, —$R^3$, —O—$R^3$, —O—$C_{1-3}$-alkylene-$R^3$, —$C_{1-3}$-alkylene-O—$C_{1-3}$-alkyl, linear or branched —O—$C_{2-8}$-alkanol, linear or branched —O—$C_{1-3}$-haloalkyl, —$C_{3-6}$-cycloalkyl, —O—$C_{2-4}$-alkylene-O—$C_{1-3}$-alkyl, —CO—$R^3$, —$C_{1-4}$-alkylene-$R^3$, —O—$C_{2-6}$-alkenyl, —O—$C_{2-3}$-alkylene-N($CH_3$)—$C_{1-3}$-alkyl, —CO—N($C_{1-3}$-alkyl)$_2$ and —CO—NH($C_{1-3}$-alkyl), which may optionally be substituted by one, two or three substituents each independently selected from the group consisting of —CN, —$NH_2$, —$C_{1-2}$-alkylene-CN, —OH, —$C_{1-2}$-alkylene-OH, halogen, -oxo, —$C_{1-3}$-alkyl, —O—$R^3$, —$C_{1-3}$-alkylene-O—$R^3$, —CO—$C_{1-6}$-alkyl, —CO—$NH_2$, —CO—N($CH_3$)$_2$, —$C_{1-3}$-alkylene-$NH_2$, phenyl, —$C_{1-2}$-alkylene-OH and —CO—$C_{1-2}$-alkyl, wherein each $R^3$ denotes independently from each other a group selected from a linear or branched $C_{1-10}$-alkyl, linear or branched $C_{1-4}$-haloalkyl, fully saturated or partially unsaturated —$C_{3-8}$-cycloalkyl, —$C_{1-3}$-alkylene-$C_{3-6}$-cycloalkyl, a four-, five- or six-membered monocyclic either fully saturated or partially unsaturated heterocycle comprising 1, 2 or 3 heteroatoms each independently selected from N, S or O, a five- to six-membered heteroaromatic group comprising 1, 2 or 3 heteroatoms each independently selected from the group N, S and O, linear or branched —$C_{2-5}$-alkenyl, phenyl, a nine- or ten-membered fully saturated, aromatic or partially unsaturated, bicyclic heterocycle comprising 1, 2 or 3 heteroatoms each independently selected from the group N, S and O, wherein $R^4$ denotes a group selected from H, F, Cl, Br, OH, —O—$C_{1-3}$-alkyl (OCH$_3$), —$C_{1-4}$-alkyl, —$C_{1-3}$-alkylene-OH and —CN, wherein $R^5$ denotes a group selected from H, F, Cl, Br, OH, —O—$C_{1-3}$-alkyl, —$C_{1-4}$-alkyl, —$C_{1-3}$-alkylene-OH and —CN, wherein $R^6$ denotes a group selected from H, halogen, $C_{1-3}$-alkyl, —$NH_2$, —$C_{1-3}$-haloalkyl and —$C_{1-4}$-alkoxy, and the pharmaceutically acceptable salts of the aforementioned compounds.

Another preferred embodiment of the instant inventions refers to the aforementioned compounds of formula 1, wherein ring A is selected from the group consisting of

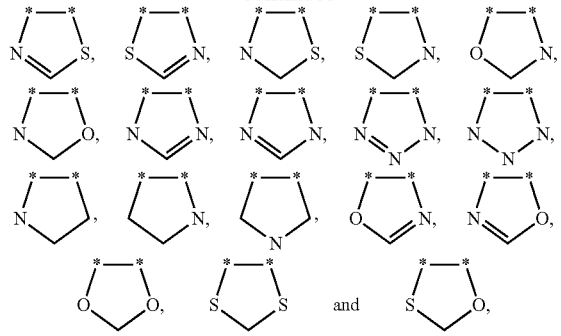

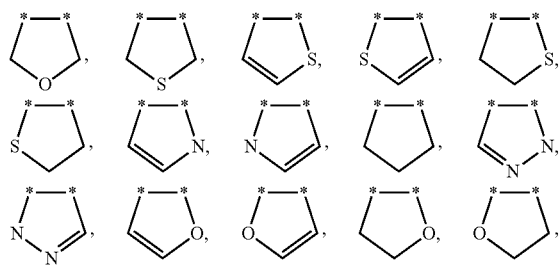

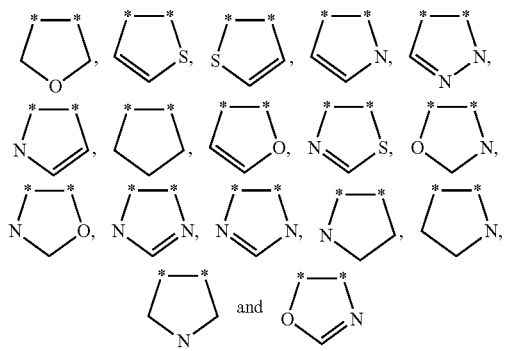

and the pharmaceutically acceptable salts of these compounds.

Another preferred embodiment of the instant invention is drawn to the aforementioned compounds of formula 1, wherein ring A is selected from the group consisting of and the pharmaceutically acceptable salts of these compounds.

Further the instant invention preferably concerns the aforementioned compounds of formula 1, wherein $R^2$ denotes a group selected from the group consisting of hydrogen, —OH, F, Cl, —CO—NH—$NH_2$ and —CO—$NH_2$, or wherein $R^2$ denotes a group selected from the group consisting of linear or branched $C_{1-6}$-alkyl, —$C_{1-6}$-fluoroalkyl, —$C_{1-6}$-chloroalkyl, —$R^3$, —O—$R^3$, —O—$C_{1-3}$-alkylene-$R^3$, —$C_{1-3}$-alkylene-O—$C_{1-3}$-alkyl, linear or branched —O—$C_{2-8}$-alkanol, linear or branched —O—$C_{1-3}$-haloalkyl, cyclopropyl, cyclobutyl, cyclopentyl, cyclohexyl, —O—$C_{2-4}$-alkylene-O—$C_{1-3}$-alkyl, —CO—$R^3$, —$C_{1-4}$-alkylene-$R^3$, —O—$C_{2-6}$-alkenyl, —O—$C_{2-3}$-alkylene-N($CH_3$)—$C_{1-3}$-alkyl, —CO—N($CH_3$)$_2$ and —CO—NH—$C_{1-3}$-alkyl, which may optionally be substituted by one, two or three substituents each independently selected from the group consisting of —CN, —$NH_2$, —$C_{1-2}$-alkylene-CN, —OH, —$C_{1-2}$-alkylene-OH, F, Cl, -oxo, —$C_{1-3}$-alkyl, —O—$R^3$, —$C_{1-3}$-alkylene-O—$R^3$, —CO—$C_{1-6}$-alkyl, —CO—$NH_2$, —CO—N($CH_3$)$_2$, —$C_{1-3}$-alkylene-$NH_2$, phenyl, —$C_{1-2}$-alkylene-OH and —CO—$C_{1-2}$-alkyl, wherein each $R^3$ denotes independently from each other a group selected from a linear or branched $C_{1-6}$-alkyl, linear or branched $C_{1-4}$-fluoroalkyl, linear or branched $C_{1-4}$-chloroalkyl, linear or branched $C_{2-5}$-alkenyl, fully saturated or partially unsaturated $C_{3-8}$-cycloalkyl, —$C_{1-3}$-alkylene-$C_{3-6}$-cycloalkyl, a four-, five- or six-membered monocyclic either fully saturated or partially unsaturated heterocycle comprising 1, 2 or 3 heteroatoms each independently selected from the group N, S and O, a five- to six-membered heteroaromatic group comprising 1, 2 or 3 heteroatoms each independently selected from the group N, S and O, phenyl and a nine- or ten-membered fully saturated, aromatic or partially unsaturated, bicyclic heterocycle comprising 1, 2 or 3 heteroatoms each independently selected from the group N, S and O, and the pharmaceutically acceptable salts of these compounds.

In another preferred embodiment the invention concerns the aforementioned compounds of formula 1, wherein
$R^1$ is selected from the group consisting of H, F, Cl, SH, -oxo, —$NH_2$, —CO—Y, —CO—N($CH_3$)—Y, —CO—N($CH_3$)—($C_{1-3}$-alkylene)-Y, —CS—Y, —CS—N($CH_3$)—Y, —CS—N($CH_3$)—($C_{1-3}$-alkylene)-Y, methyl, ethyl, propyl, isopropyl, butyl, tert-butyl, —$C_{1-3}$-fluoroalkyl, —$C_{1-3}$-chloroalkyl, —CO—NH—Y, —CO—NH—$C_{1-4}$-alkylene-Y, —CO—NH—$C_{1-4}$-alkylene-(Y)$_2$, —CO—N($CH_3$)—($C_{2-3}$-alkylene)-O—($C_{1-3}$-alkyl), —$NH_2$, —$C_{1-6}$-alkylene-L, —$SO_2$-phenyl, —$SO_2$—($C_{1-3}$-alkyl), —CO—N($C_{1-4}$-alkyl)$_2$, —CO—N($C_{2-4}$-alkylene-O—$C_{1-3}$-alkyl)$_2$, a five- or six-membered heteroaromatic group comprising 1, 2 or 3 heteroatoms each independently selected from the group N, S and O,
with Y being a group selected from the group consisting of —$NH_2$, —NH($CH_3$), —N($CH_3$)$_2$, —$C_{1-6}$-alkylene-N($CH_3$)$_2$, —O—$C_{1-3}$-alkyl, OH and —N(ethyl)$_2$,
or with Y being a group selected from the group consisting of a four-, five-, six- or seven-membered monocyclic fully saturated or partially unsaturated heterocycle comprising 1, 2 or 3 heteroatoms each independently selected from the group N, S and O with the proviso hat this heterocycle comprises at least one N-atom and that this heterocycle is directly attached to the molecule via this N-atom, a five- or six-membered monocyclic heteroaromatic group comprising 1, 2 or 3 heteroatoms each independently selected from the group of N, S and O, and a $C_{3-6}$-cycloalkyl,
or with Y being a 9- to 11-membered bicyclic annellated fully saturated or partially unsaturated heterocycle comprising 1, 2, 3 or 4 heteroatoms each independently from each other selected from the group N, S and O,
or with Y being an 8- to 11-membered bicyclic fully saturated spiro-heterocycle comprising 1, 2 or 3 heteroatoms each independently selected from the group N, S and O with the proviso that this spiro-heterocycle comprises at least one N-atom and that this heterocycle is directly attached to the molecule via this N-atom,
or with Y being a six- or seven-membered fully saturated heterocycle comprising 1, 2 or 3 heteroatoms each independently selected from the group N, S and O, which is bridged by an additional $C_{1-3}$-alkylene-unit,
whereby each Y may optionally be substituted by one or more groups Z each independently from each other selected from the group consisting of F, Cl, -oxo, OH, $C_{1-5}$-alkyl, —$C_{1-5}$-alkanol, —O—$C_{1-3}$-alkyl, a five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO-L, —$C_{1-3}$-alkylene-CO-L, —$C_{1-3}$-alkylene-O—$C_{1-3}$-alkyl, —N($CH_3$)$_2$ and —N(ethyl)$_2$,
whereby each group Z may optionally be further substituted by one, two or three groups T each independently selected from the group consisting of -oxo, OH, F, Cl, methyl, ethyl, propyl, —O-methyl, —O-ethyl, —O-propyl, —O-isopropyl, —N(methyl)$_2$, —N(ethyl)$_2$, 5- to 6-membered fully saturated, partially unsaturated or aromatic heterocycle comprising 1 or 2 heteroatoms each independently selected from the group N, O and S, a cyclopropyl, cyclobutyl, cyclopentyl, cyclohexyl and —CN,
wherein each group T may also optionally be substituted by a group selected from the group consisting of methyl, ethyl, propyl, isopropyl, F, Cl, OH, oxo and —O-methyl, —O-ethyl, —O-propyl and —O-isopropyl,
whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, F, Cl, OH and -oxo,
and the pharmaceutically acceptable salts of the these compounds.

Another preferred embodiment of the invention concerns the aforementioned compounds of formula 1,
wherein
$R^6$ denotes a group selected from H, Br, Cl, F, methyl,
and the pharmaceutically acceptable salts of these compounds.

A further preferred embodiment of the instant invention concerns the aforementioned compounds of formula 1,
wherein $R^4$ denotes a group selected from H, F, Cl, OH, —$OCH_3$, —$CH_2$—OH, —CN and
wherein $R^5$ denotes a group selected from H, F, Cl, OH, —$OCH_3$, —$C_{1-4}$-alkyl, —$CH_2$—OH and —CN,
and the pharmaceutically acceptable salts of the these compounds.

In a further preferred embodiment the invention concerns the aforementioned compounds of formula 1,
wherein $R^1$ is not hydrogen and wherein $R^1$ is attached to a C-atom of ring A,
and the pharmaceutically acceptable salts of the these compounds.

Additionally the invention preferably concerns the aforementioned compounds of formula 1,
wherein ring A is selected from the group consisting of

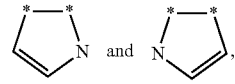

and the pharmaceutically acceptable salts of these compounds.

Another preferred embodiment of the instant invention concerns the aforementioned compounds of formula 1, wherein
$R^1$ is selected from the group consisting of
—CO—Y, —CO—N($CH_3$)—Y, —CO—N($CH_3$)—($C_{1-3}$-alkylene)-Y, —CO—NH—Y,
with Y being a group selected from the group consisting of —$NH_2$, —NH($CH_3$), —N($CH_3$)$_2$, —$C_{1-4}$-alkylene-N($CH_3$)$_2$, —O-methyl, —O-ethyl, —OH and —N(ethyl)$_2$,
or with Y being selected from the group consisting of a five- or six-membered monocyclic fully saturated or partially unsaturated heterocycle comprising 1, 2 or 3 heteroatoms each independently selected from the group N, S and O with the proviso hat this heterocycle comprises at least one N-atom and that this heterocycle is directly attached to the molecule via this N-atom, a five- or six-membered monocyclic heteroaromatic group comprising 1, 2 or 3 heteroatoms each independently selected from the group of N, S and O; a $C_{3-6}$-cycloalkyl and a 9- to 10-membered bicyclic fully saturated spiro-heterocycle comprising 1, 2 or 3 heteroatoms each independently selected from the group N, S and O, with the proviso that this heterocycle is directly attached to the molecule via this N-atom,
whereby each Y may optionally be substituted by one or more groups Z as defined above,
whereby each group Z may optionally be further substituted by one, two or three groups T as defined above,
wherein each group T may also optionally be substituted by a group as defined above,
and the pharmaceutically acceptable salts of these compounds.

In another preferred embodiment the instant invention concerns the aforementioned compounds of formula 1,
wherein
Y is selected from the group consisting of —$NH_2$, —NH($CH_3$), —N($CH_3$)$_2$, —$C_{1-4}$-alkylene-N($CH_3$)$_2$, —O-methyl, —O-ethyl and —N(ethyl)$_2$,
or wherein
Y is selected from the group consisting of
piperazine-1-yl, piperidine-1-yl, morpholine-4-yl, pyrrolidine-1-yl, azetidine-1-yl, [1,4]oxazepane-4-yl, [1,4]diazepane-1-yl), pyridine-1-yl, 4-Oxa-1,9-diaza-spiro[5.5]undecan-9-yl and cyclohexyl,
whereby each Y may optionally be substituted by one or more groups Z as defined above,
whereby each group Z may optionally be further substituted by one, two or three groups T as defined above,
wherein each group T may also optionally be substituted by a group as defined above,
and the pharmaceutically acceptable salts of these compounds.

The instant invention further concerns the aforementioned compounds of formula 1, wherein $R^1$ is CO—Y,
wherein
Y is selected from the group consisting of —NH($CH_3$), —N($CH_3$)$_2$,

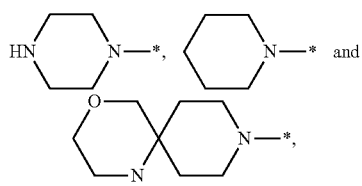

whereby each Y may optionally be substituted by one or more groups Z, each Z independently from one another selected from the group consisting of methyl, oxo, CO-L, pyrrolidinyl, tetrahydrofuranyl, tetrahydrothiophenyl, piperidinyl, piperazinyl, pyranyl and morpholinyl,
whereby each group Z may optionally be further substituted by one, two or three groups T, each T independently from one another selected from the group consisting of methyl, oxo, F and Cl,
whereby each L is selected from the group consisting of pyrrolidinyl, tetrahydrofuranyl, tetrahydrothiophenyl, piperidinyl, piperazinyl, pyranyl and morpholinyl,
and the pharmaceutically acceptable salts of these compounds.

The instant invention further preferably regards the aforementioned compounds of formula 1,
wherein
$R^2$ is selected from the group consisting of H, —$R^3$, —O—$R^3$, —O—$C_{1-3}$-alkylene-$R^3$ and —$C_{1-3}$-alkylene-O—$C_{1-3}$-alkyl,
which may optionally be substituted by one, two or three substituents as defined above,
wherein $R^3$ is selected from the group consisting of linear or branched $C_{1-6}$-alkyl, linear or branched $C_{1-4}$-haloalkyl,
and the pharmaceutically acceptable salts of these compounds.

In another preferred embodiment the instant invention concerns the aforementioned compounds of formula 1,
wherein
$R^2$ is H or
wherein
$R^2$ is selected from the group consisting of —$R^3$, —O—$R^3$, —O—$C_{1-3}$-alkylene-$R^3$ and —$C_{1-3}$-alkylene-O—$C_{1-3}$-alkyl,
which may optionally be substituted by one or more substituents selected from the group consisting of —OH, -oxo, -methyl, —CN, F, Cl, —O—$CH_3$,
wherein $R^3$ is selected from the group consisting of linear or branched $C_{1-6}$-alkyl, linear or branched $C_{1-4}$-haloalkyl,
and the pharmaceutically acceptable salts of these compounds.

In a further particularly preferred embodiment the instant invention concerns the aforementioned compounds of formula 1,
wherein $R^6$ is selected from the group consisting of H, Cl and methyl,
and the pharmaceutically acceptable salts of these compounds.

In a particularly preferred embodiment the instant invention concerns the following compounds of formula 1 selected from the group consisting of

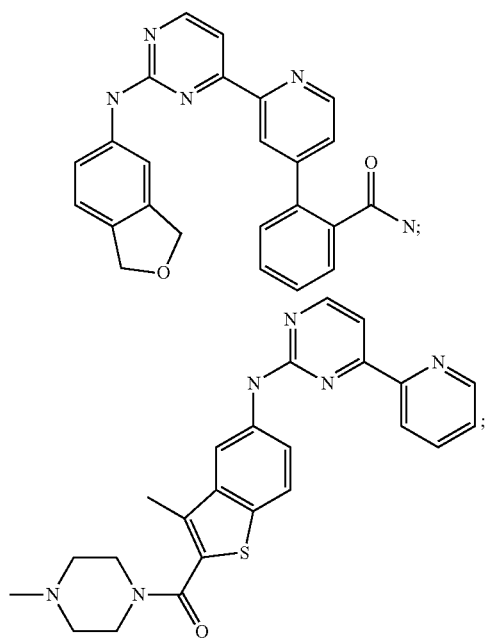

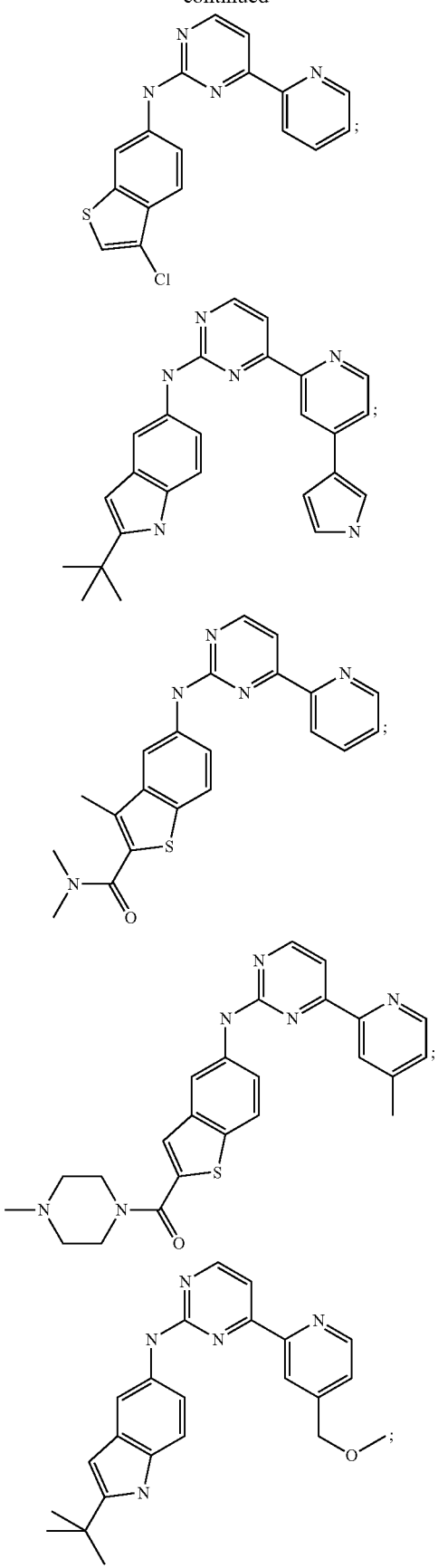
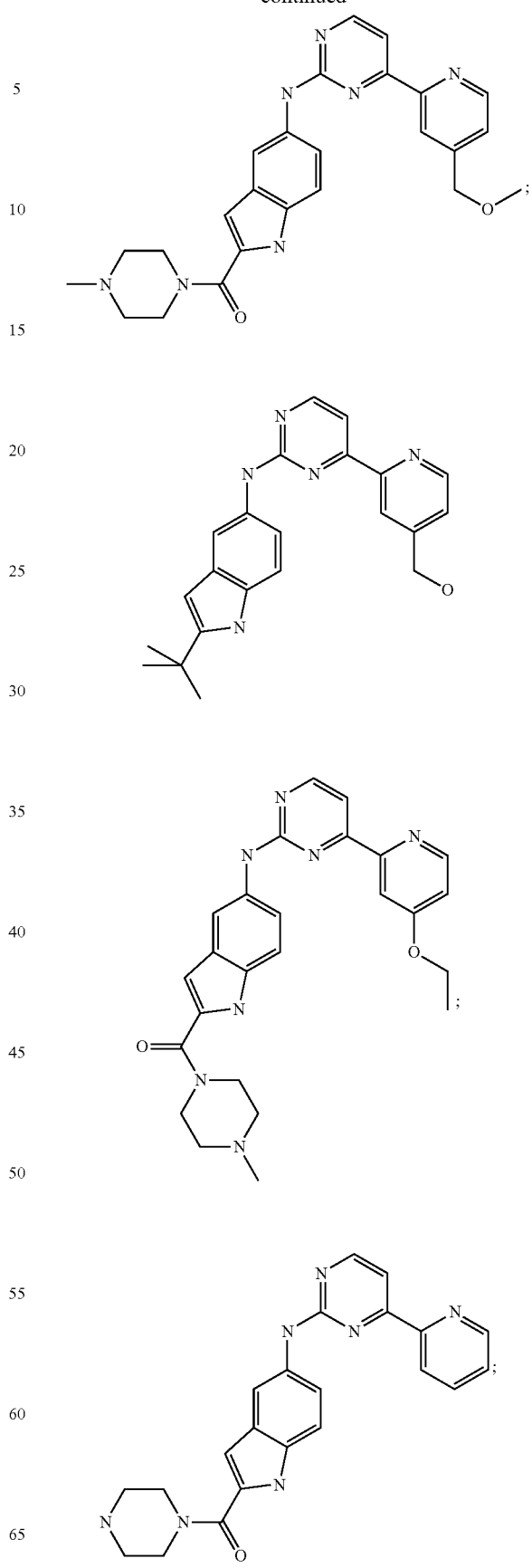

-continued
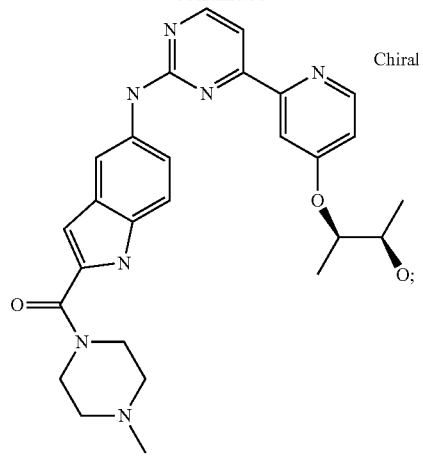
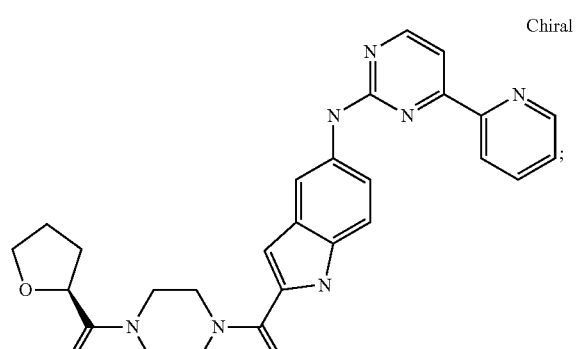
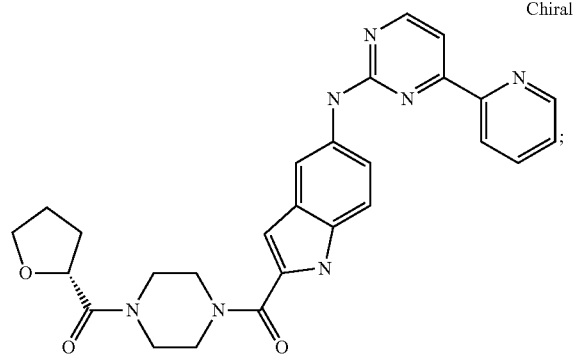
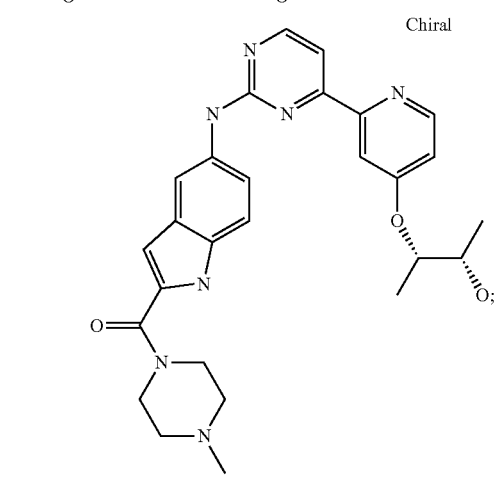
-continued
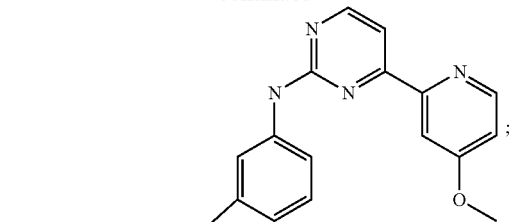
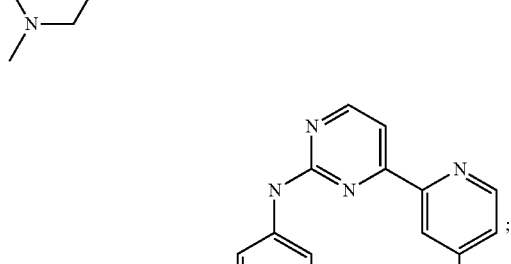
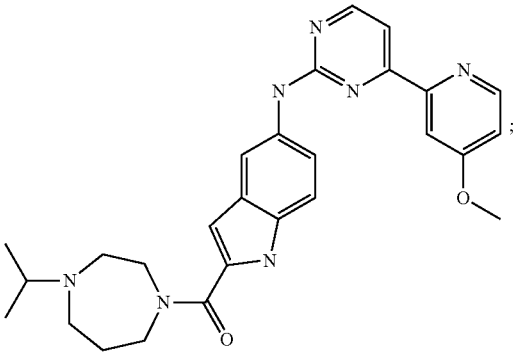

15
-continued
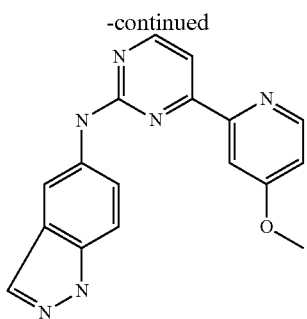
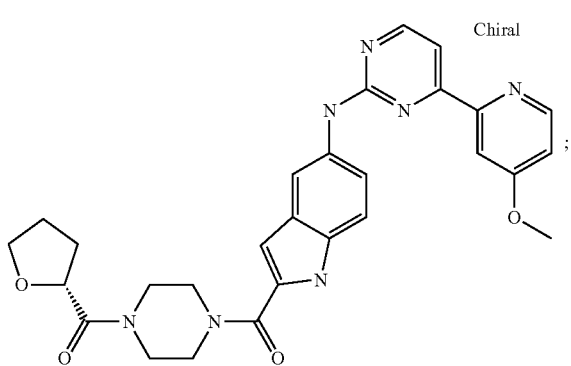
Chiral
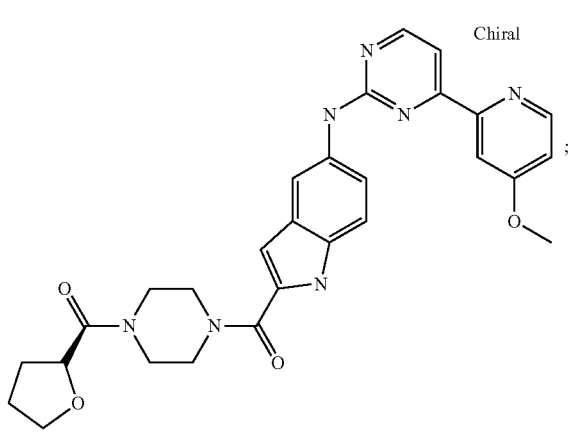
Chiral
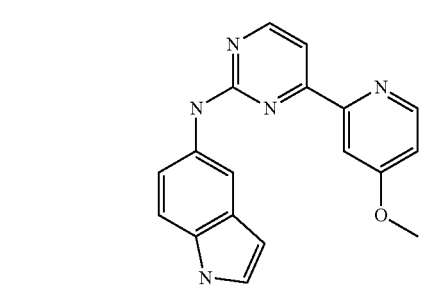
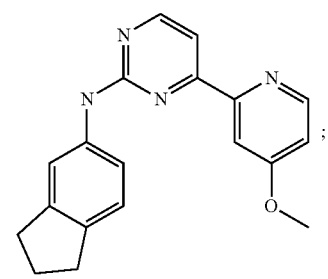
16
-continued
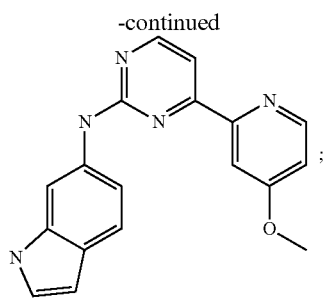;
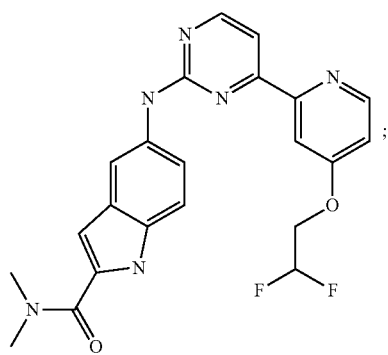;
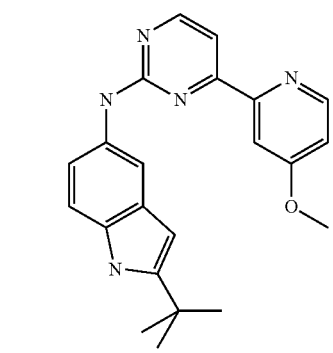
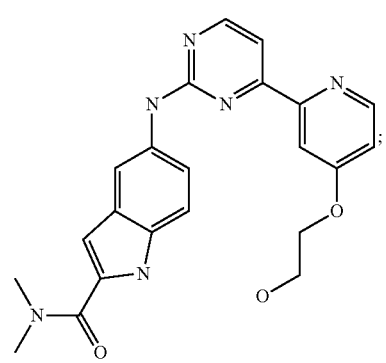;
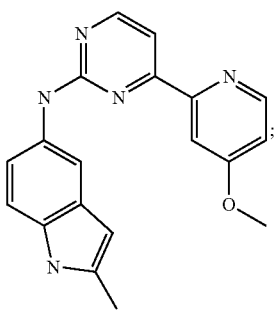;

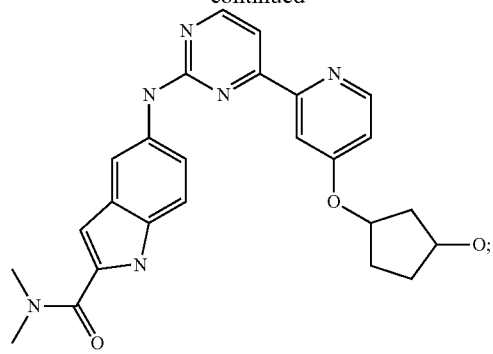
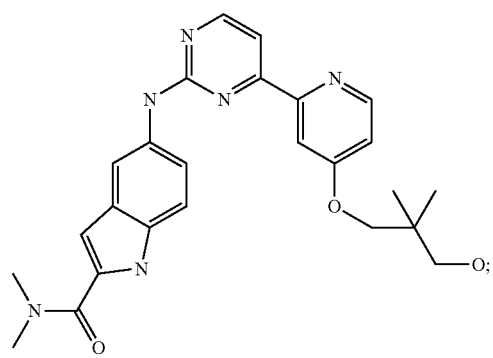
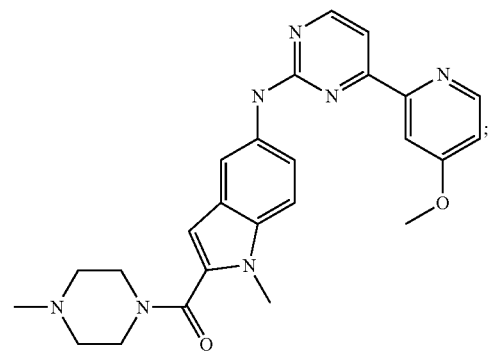
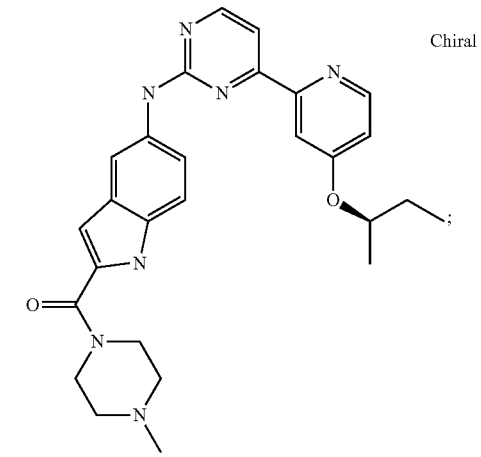
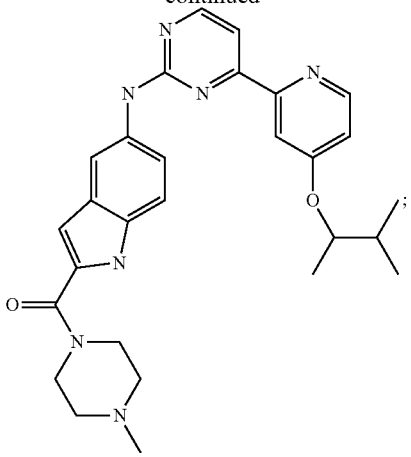
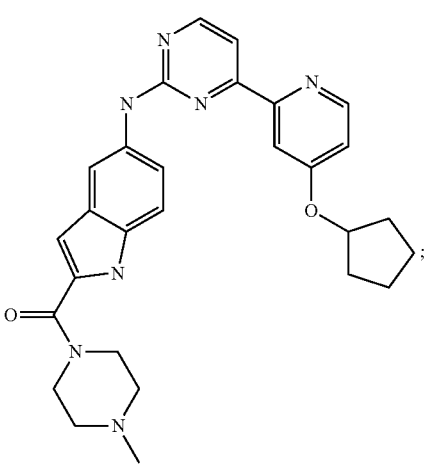
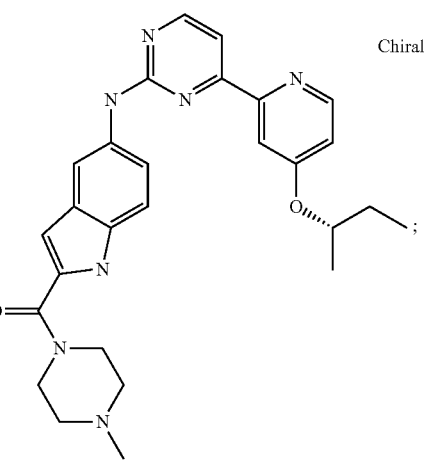

-continued
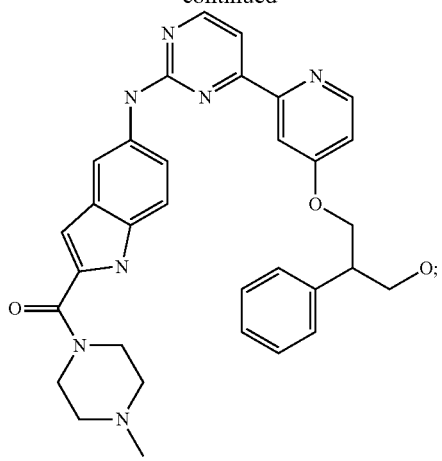
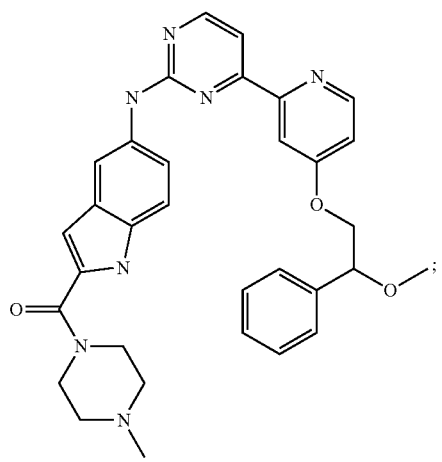
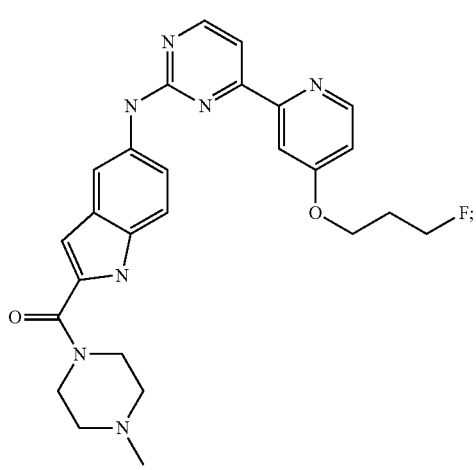
-continued
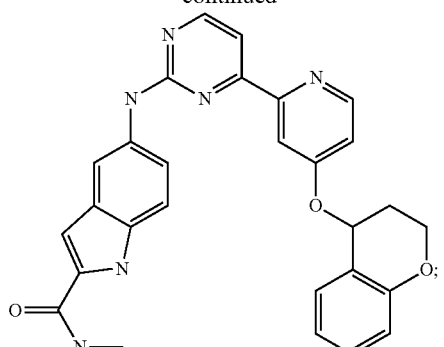
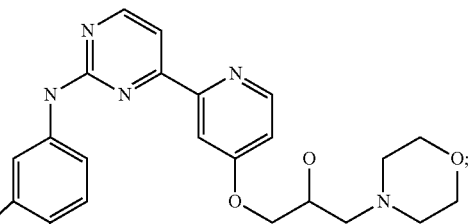
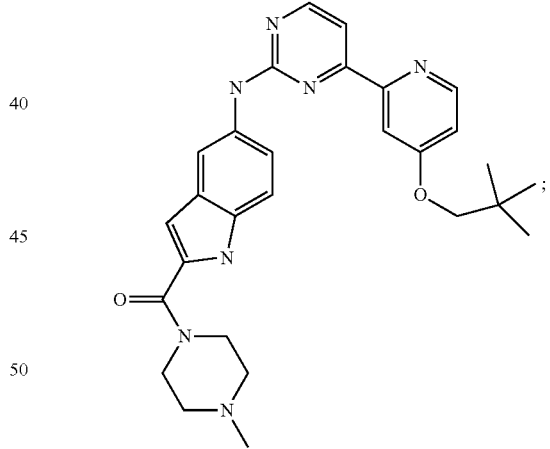
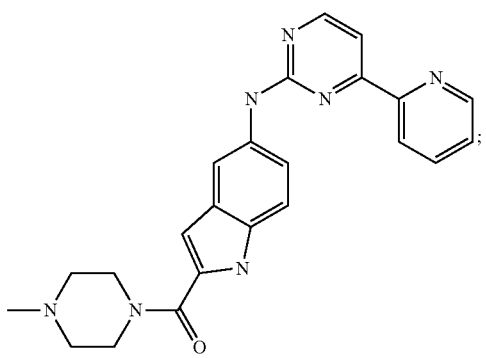

-continued
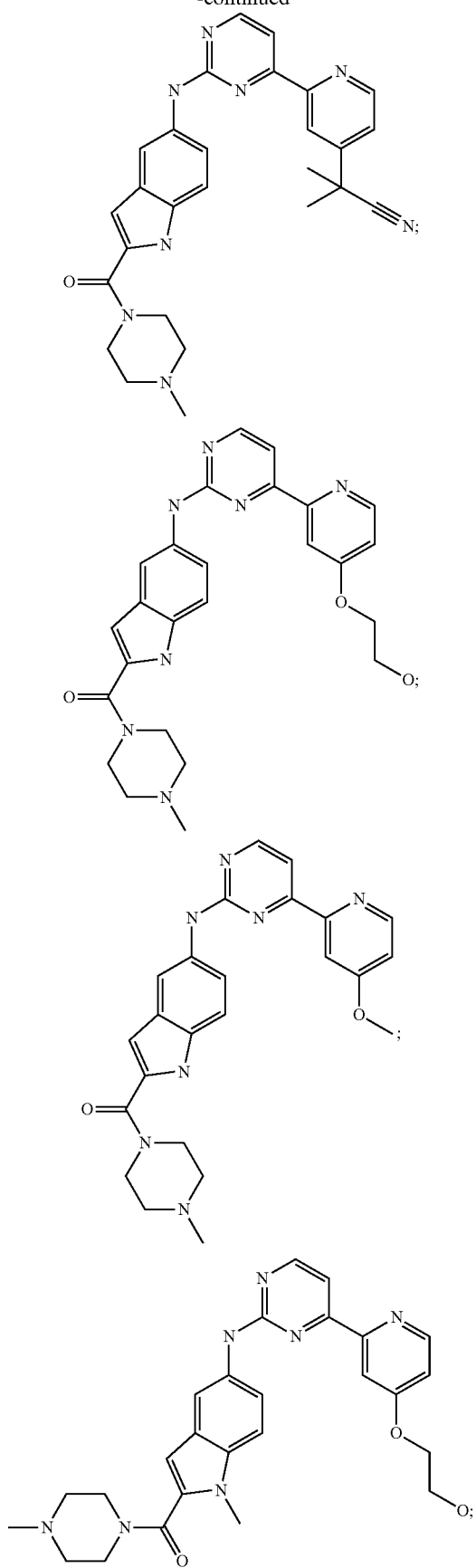
-continued
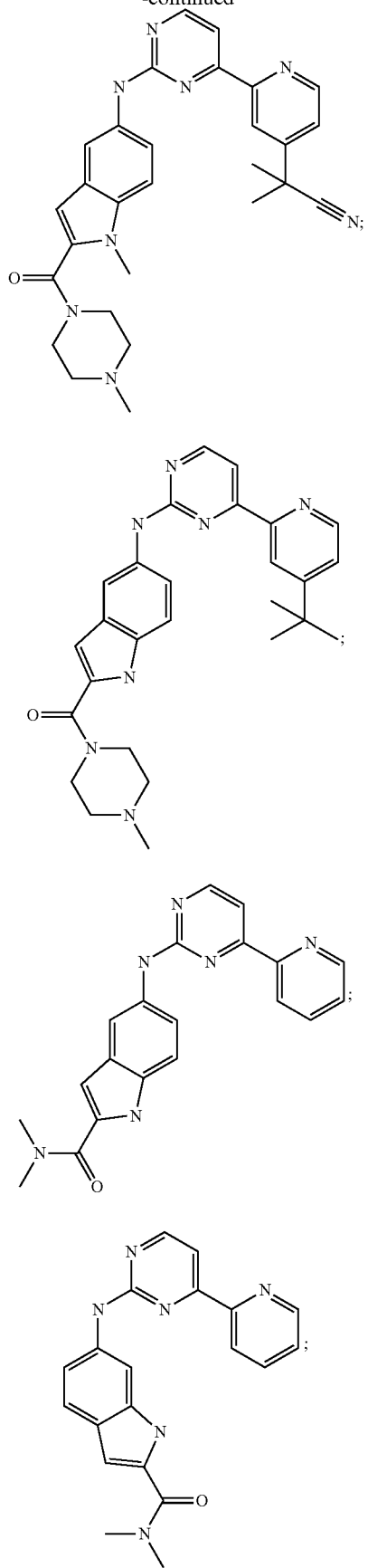

23
-continued
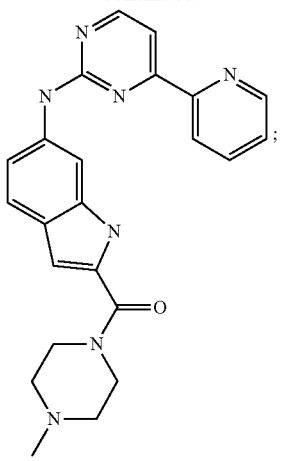
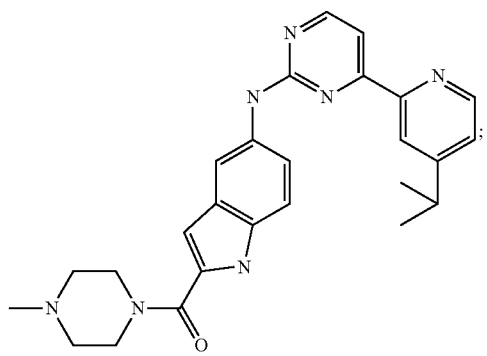
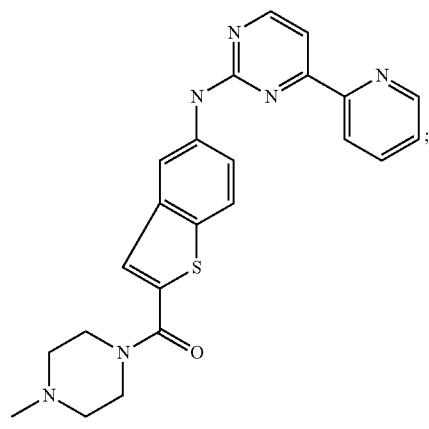
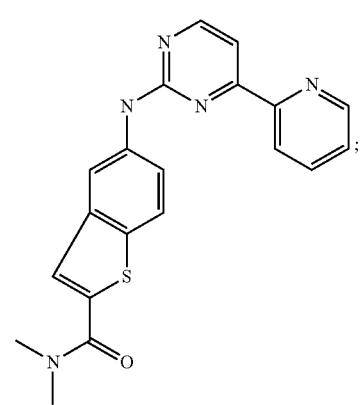
24
-continued
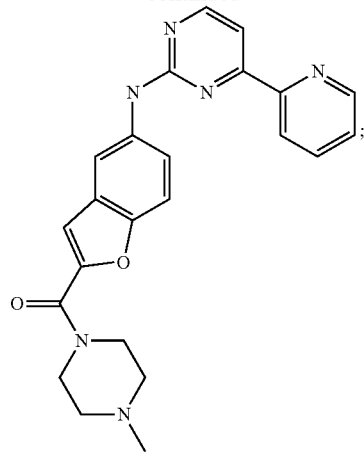
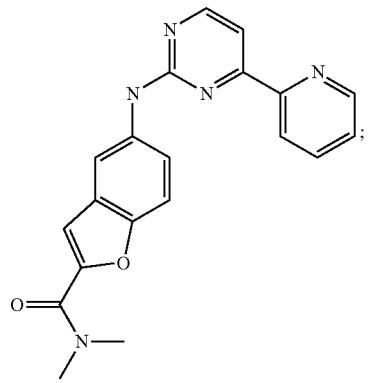
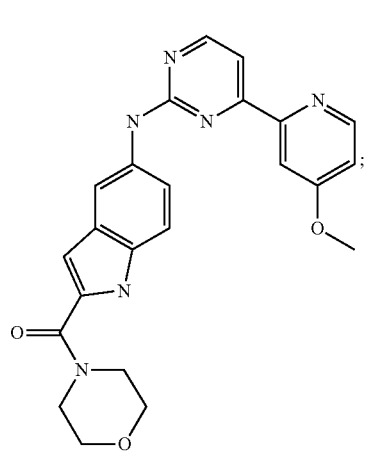

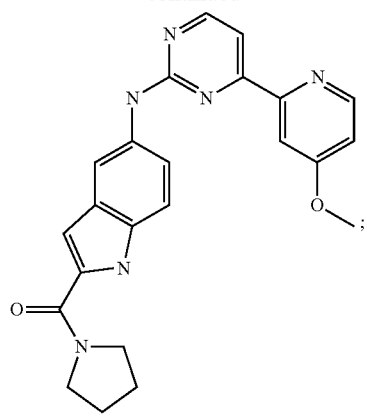
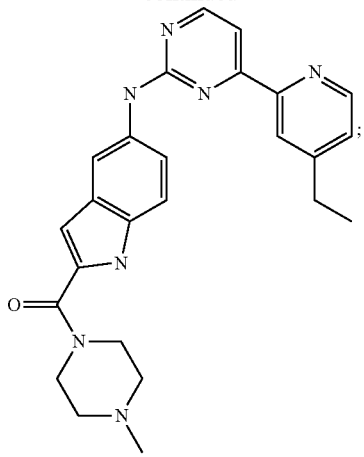
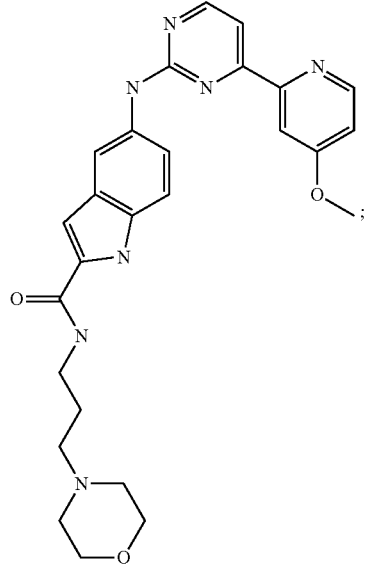
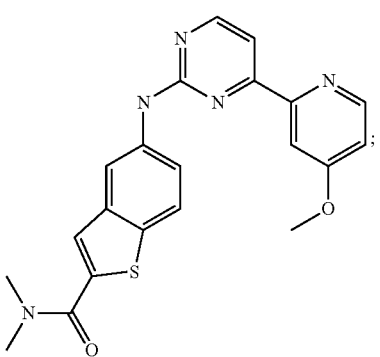
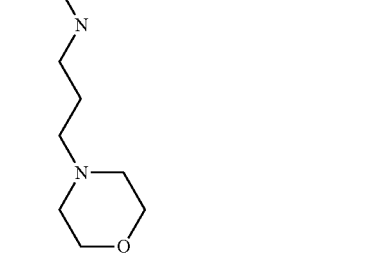
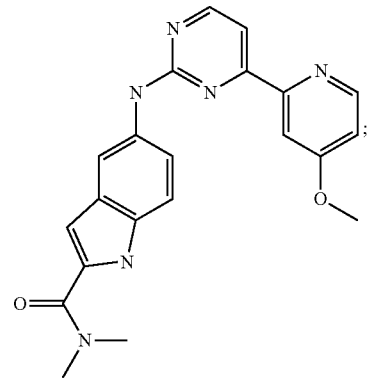
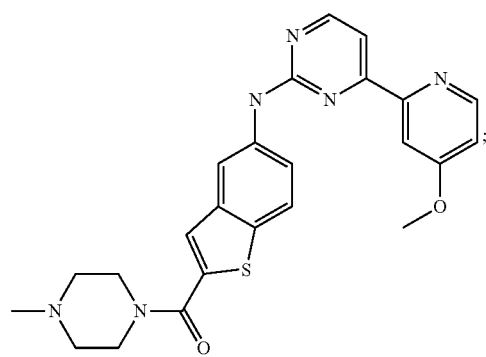
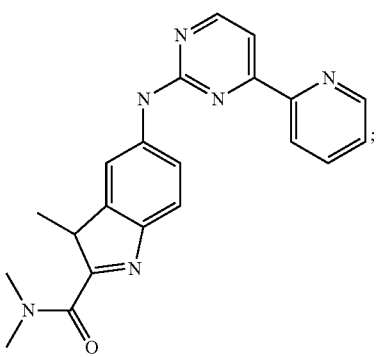

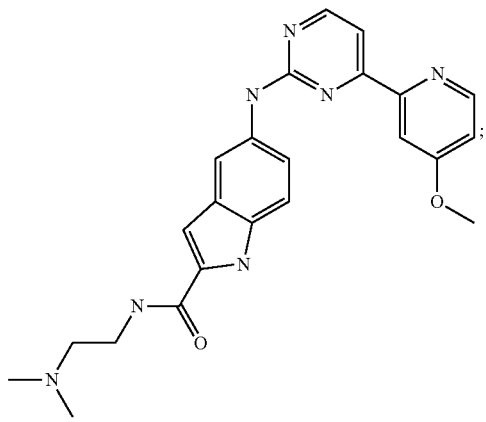
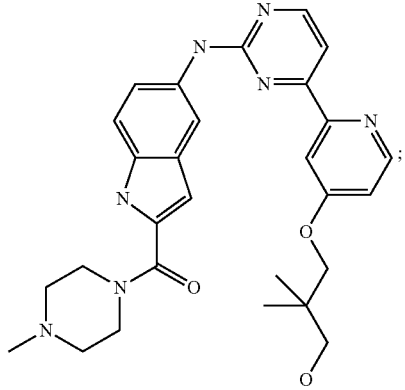
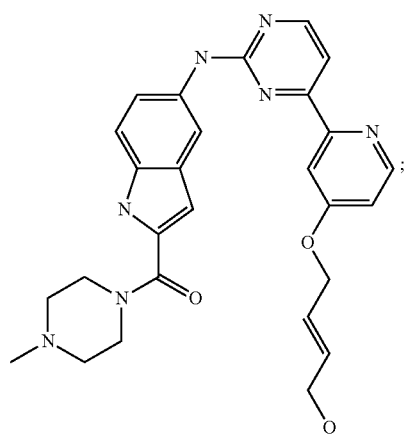
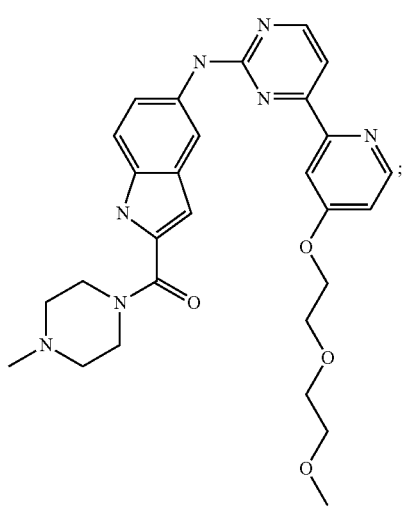
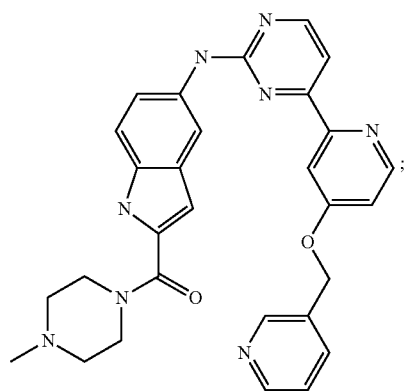
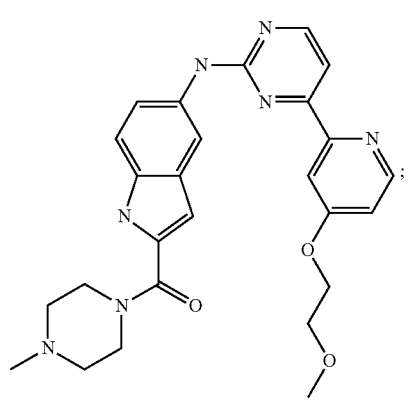
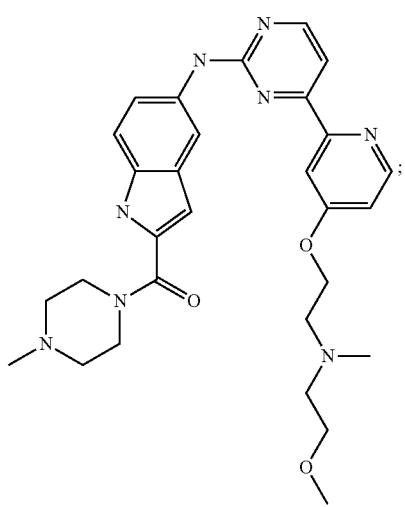

-continued
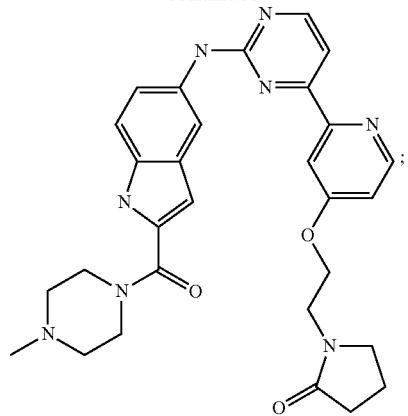
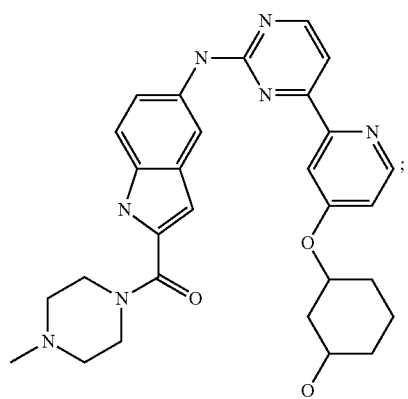
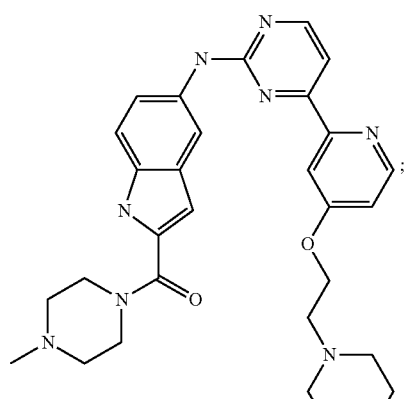
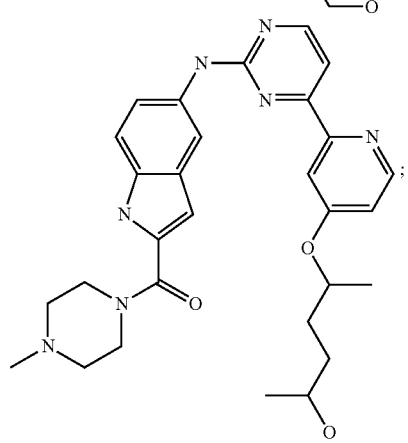
-continued
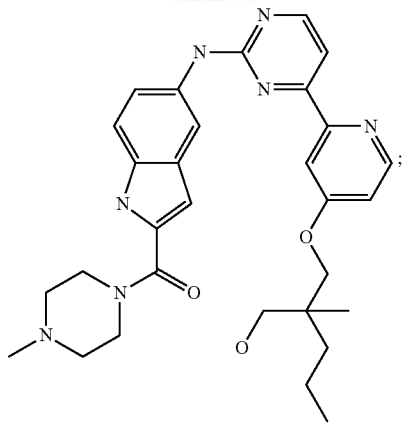
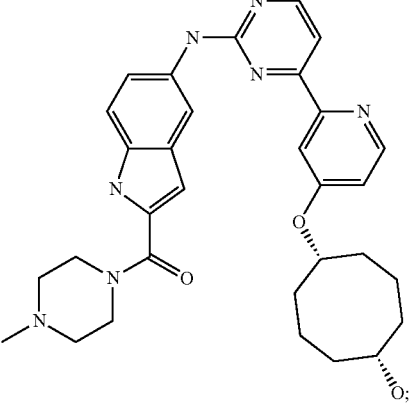
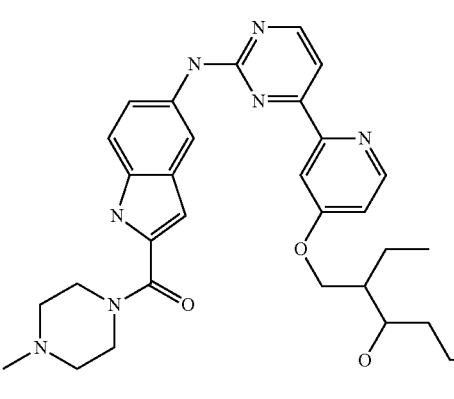
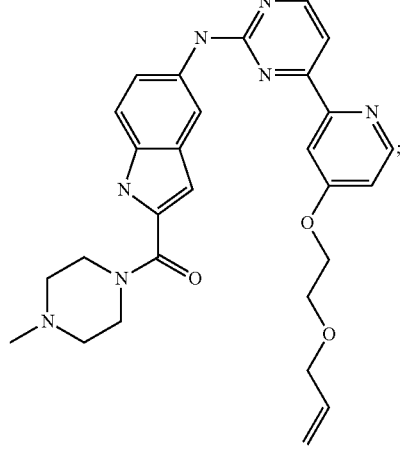

31
-continued
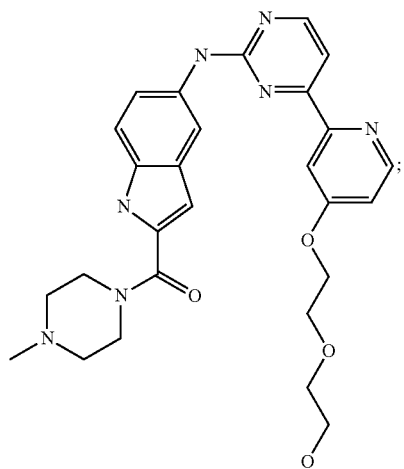
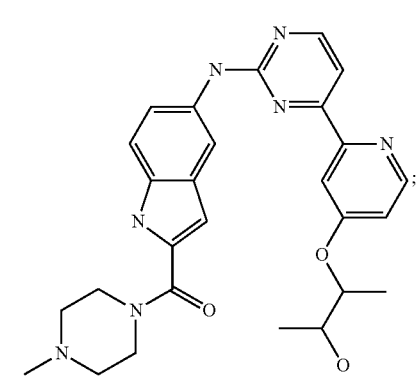
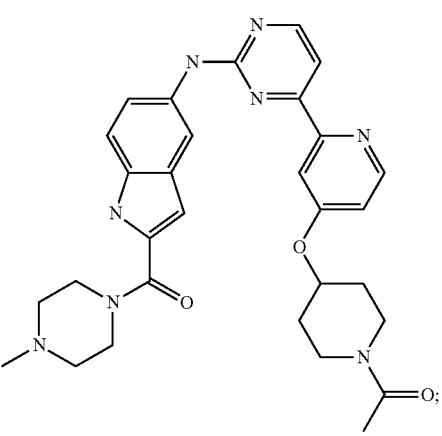
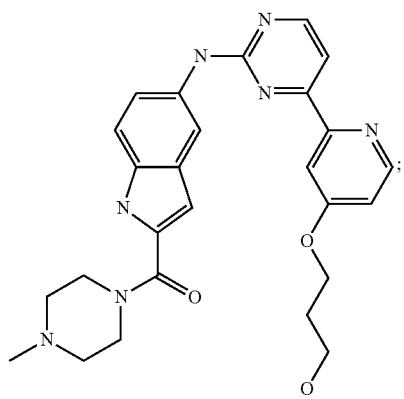
32
-continued
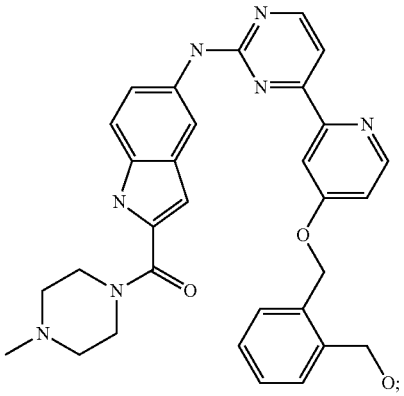
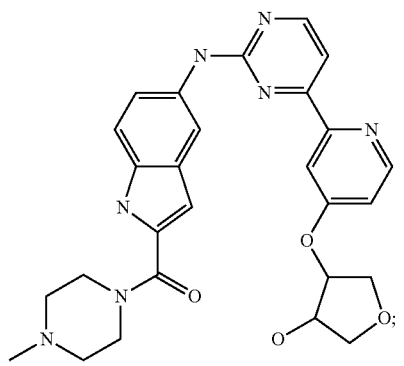
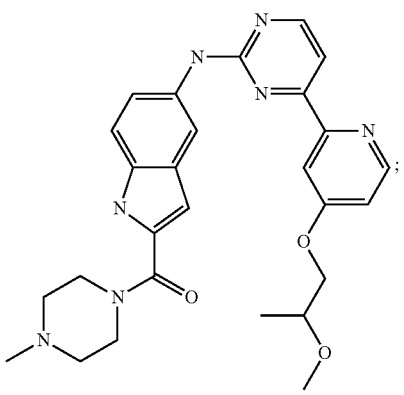
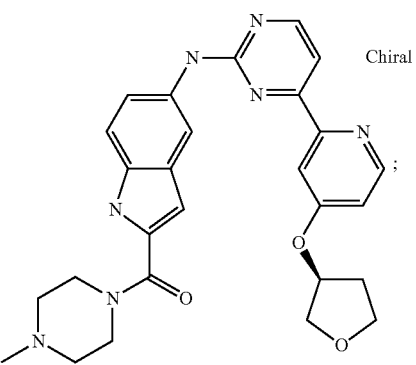

33
-continued
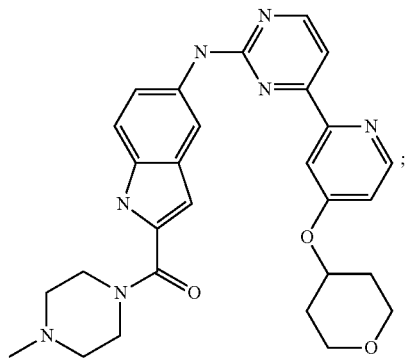
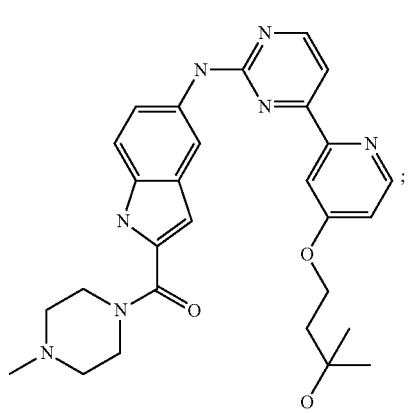
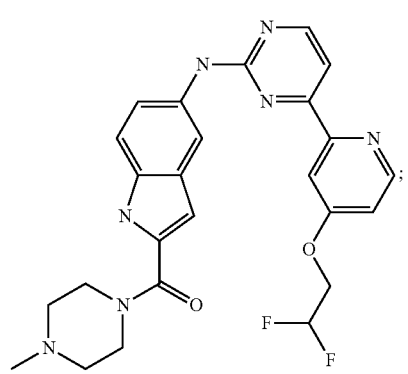
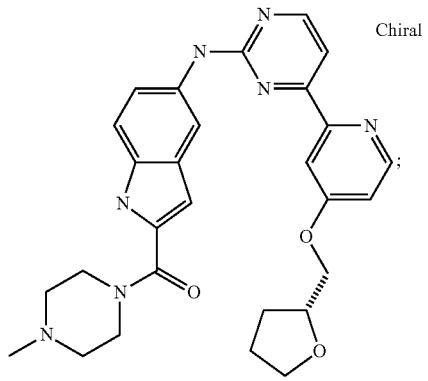
34
-continued
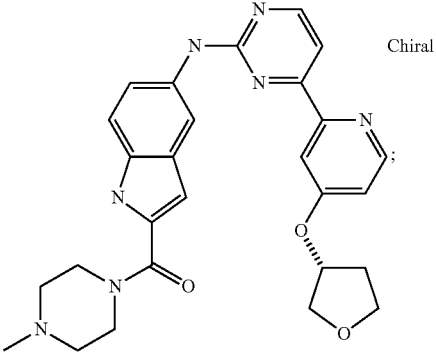
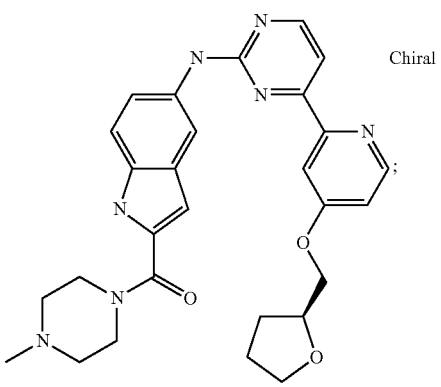
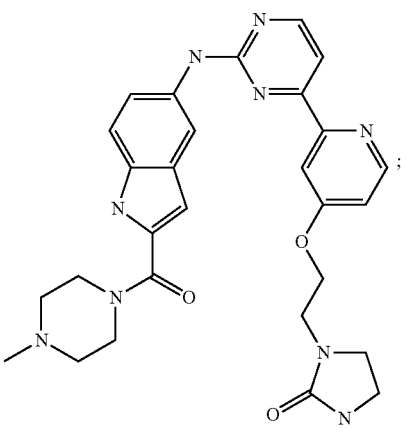
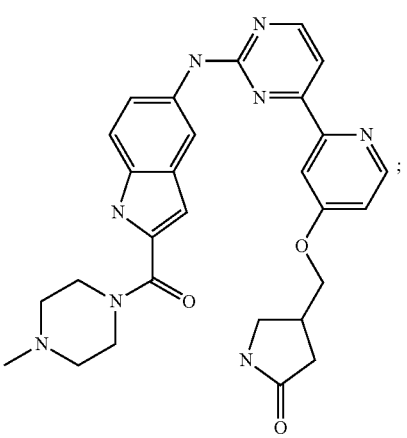

35
-continued
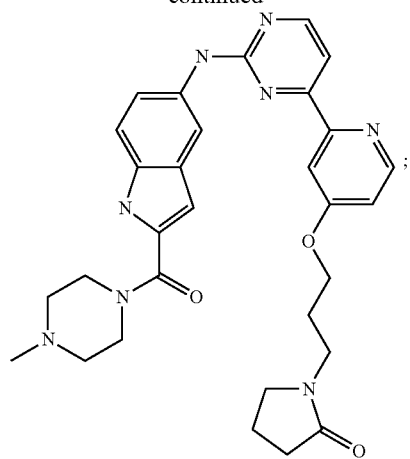
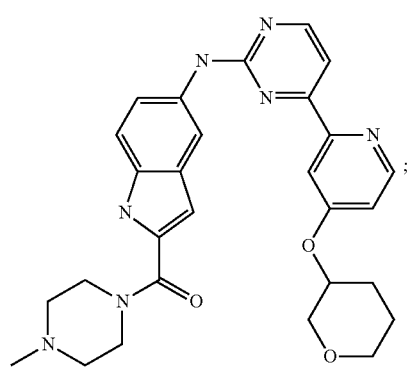
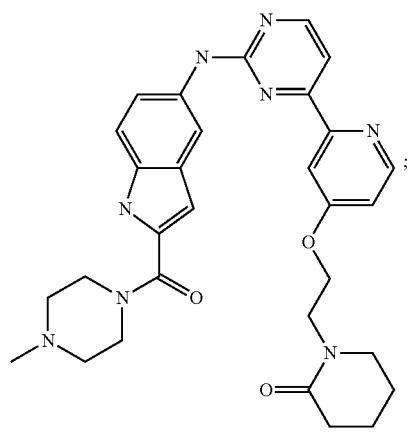
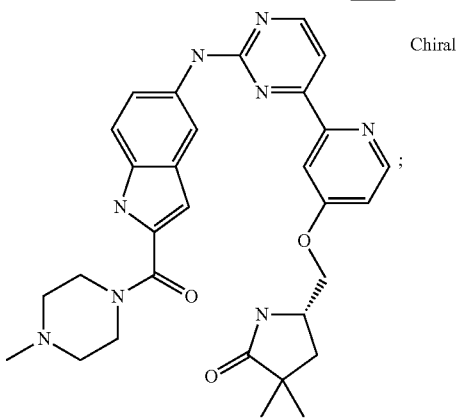
36
-continued
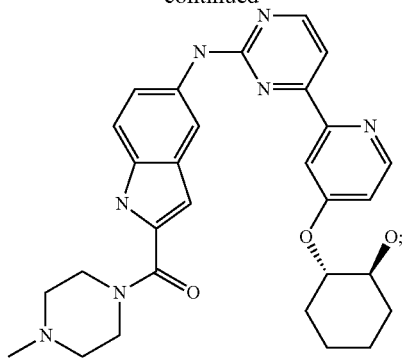
Chiral
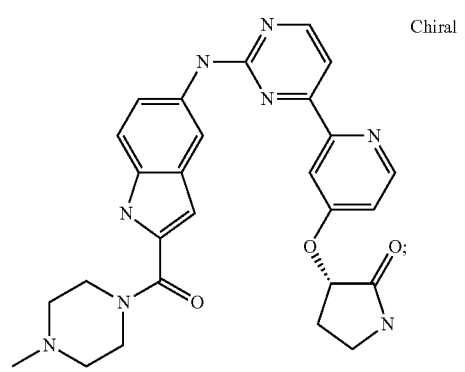
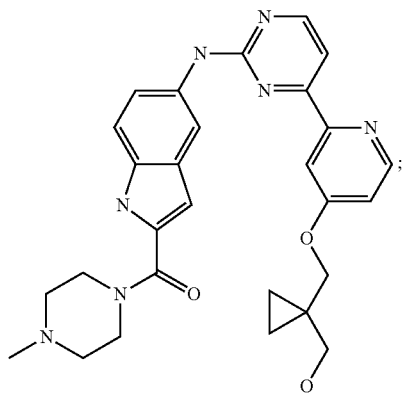
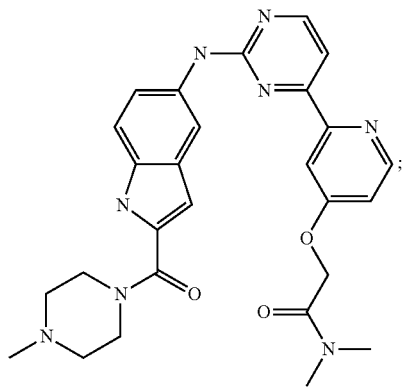

37
-continued
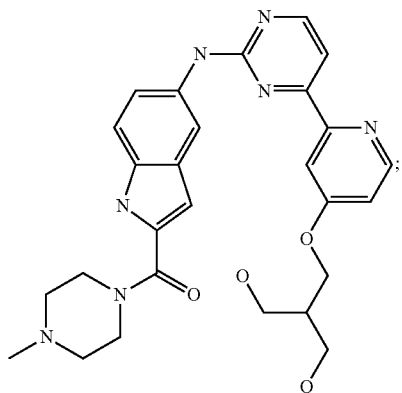
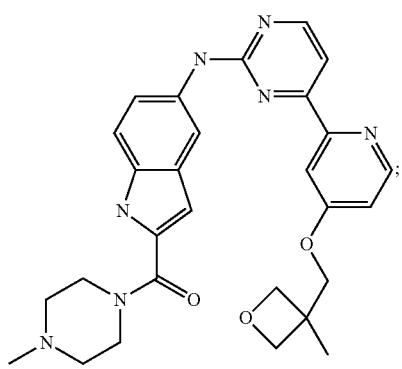
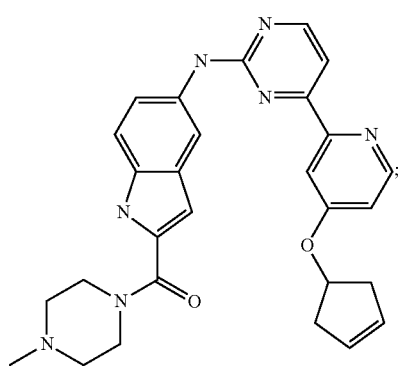
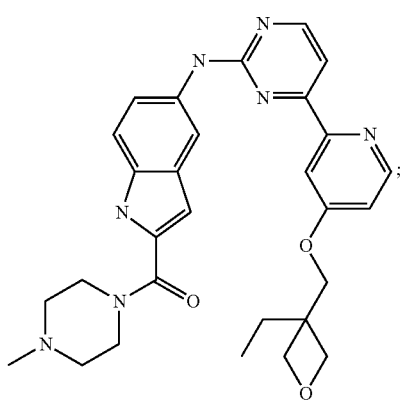
38
-continued
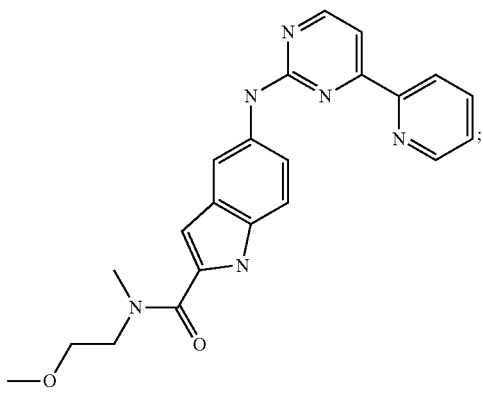
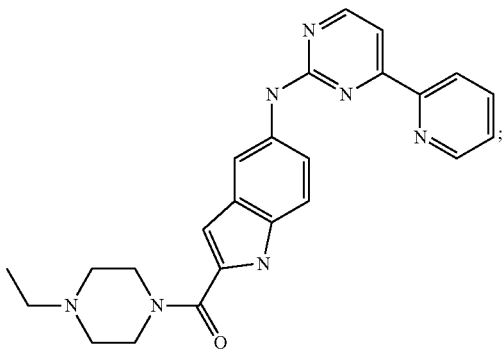
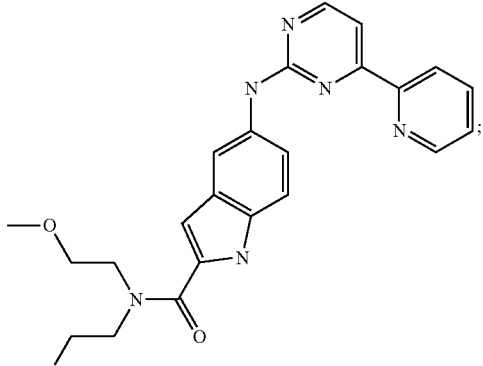
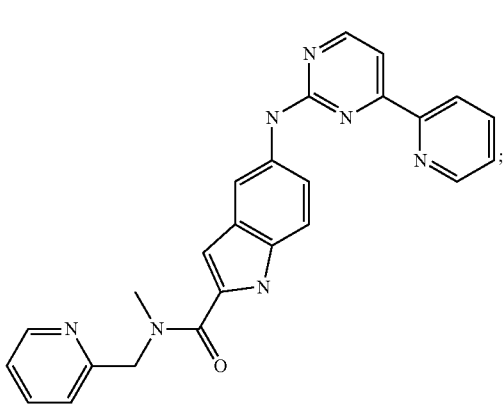

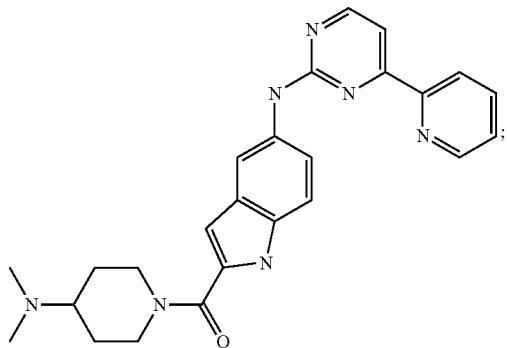
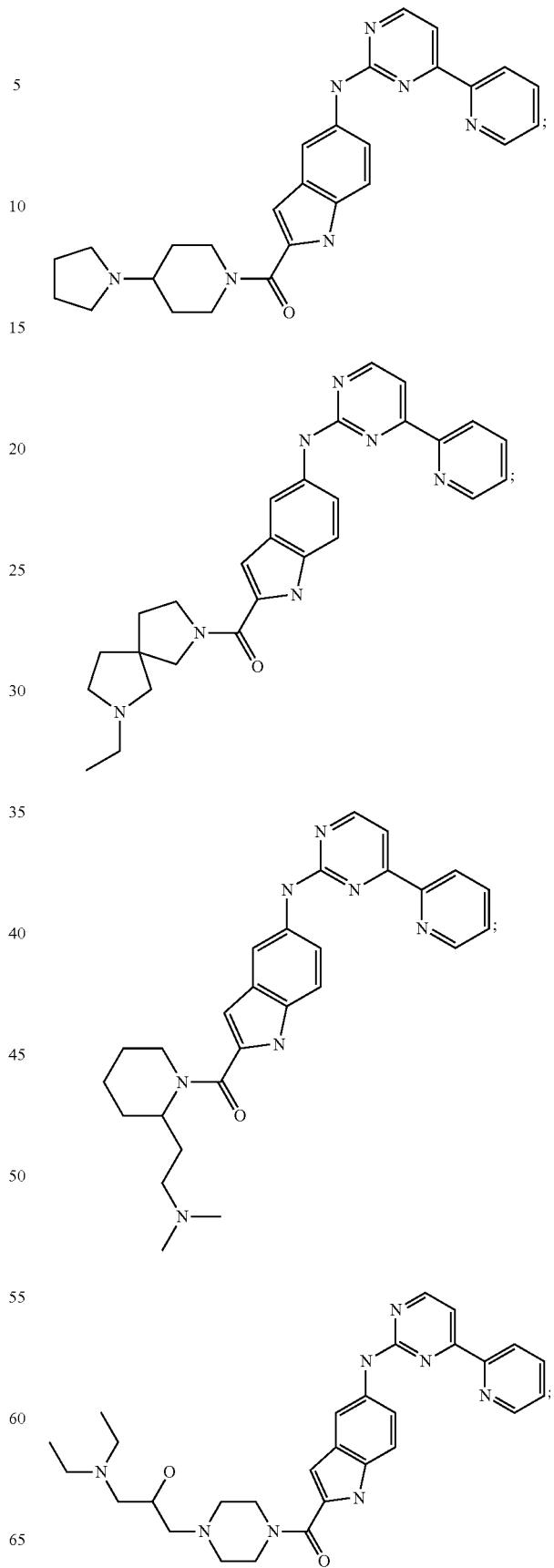

41
-continued
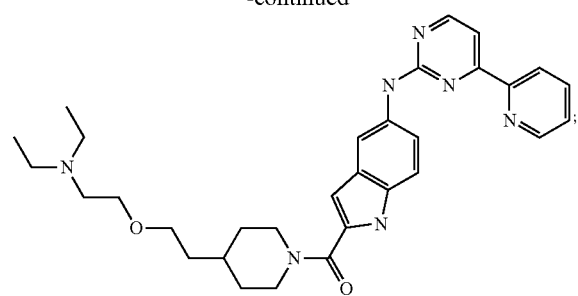
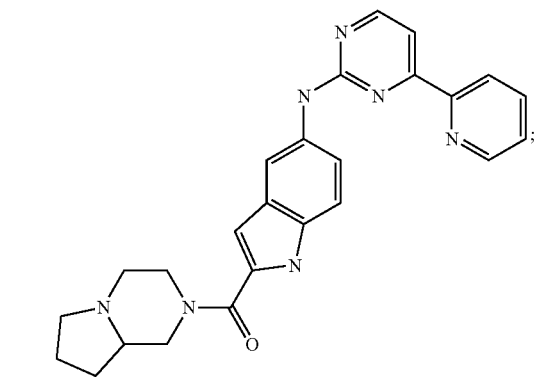
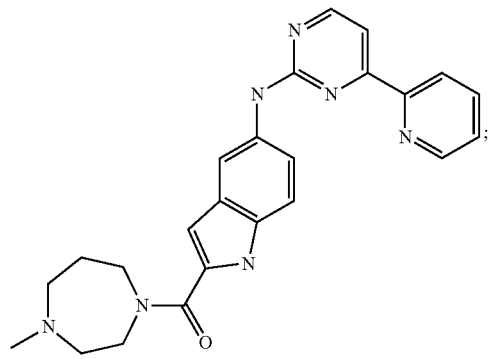
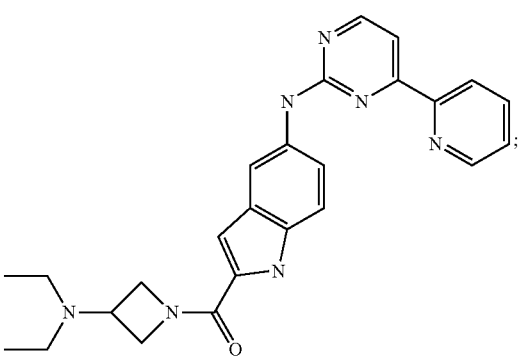
42
-continued
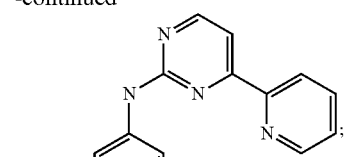
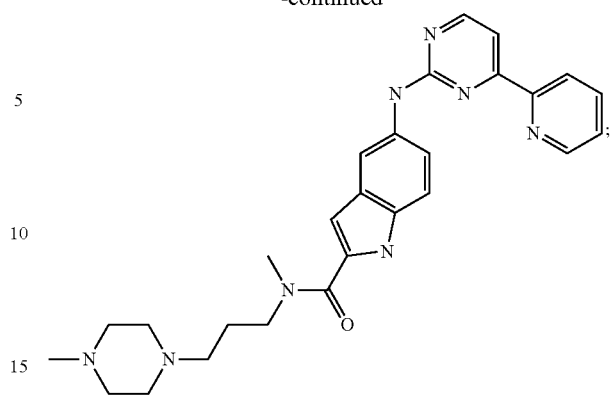

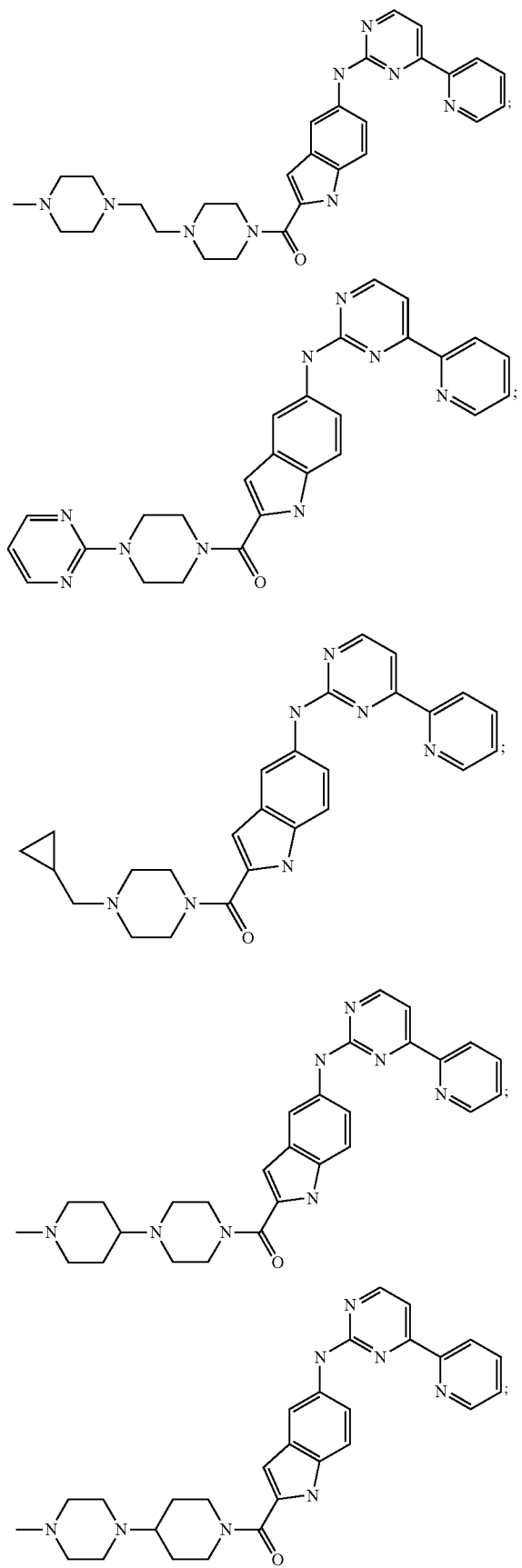
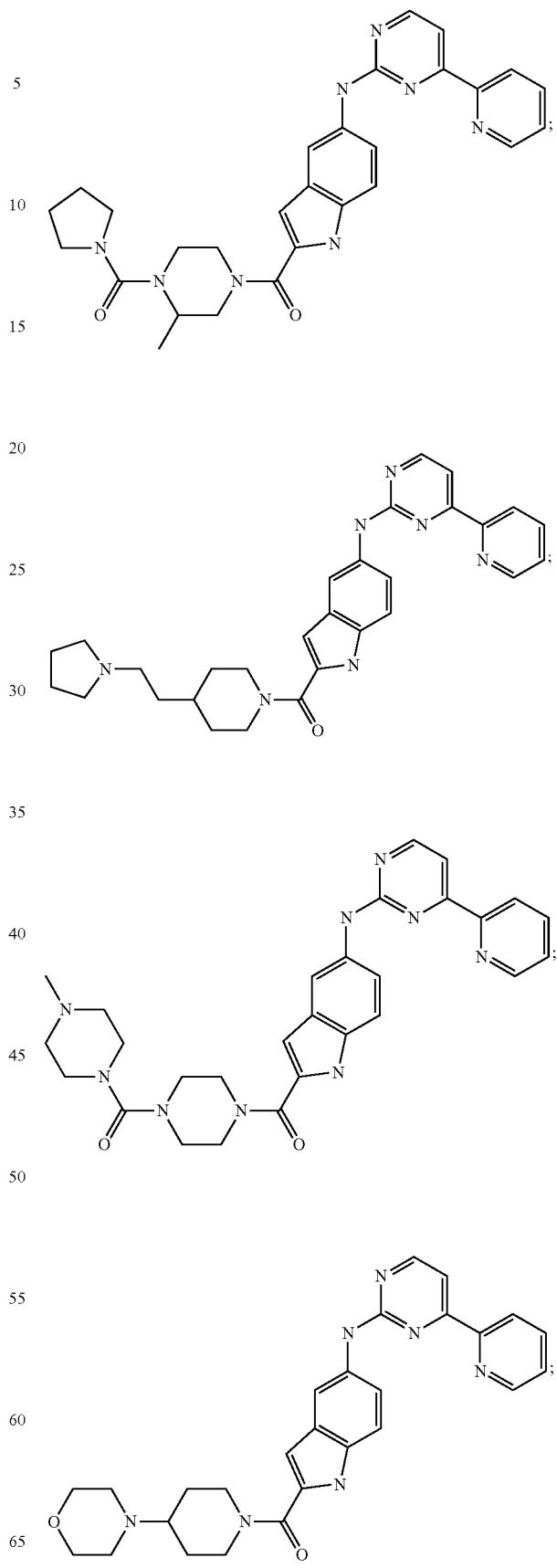

45
-continued
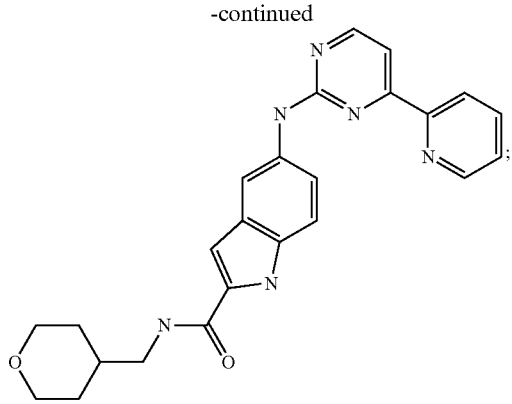
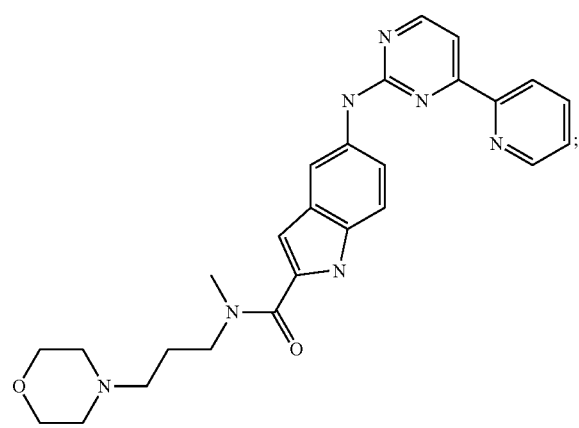
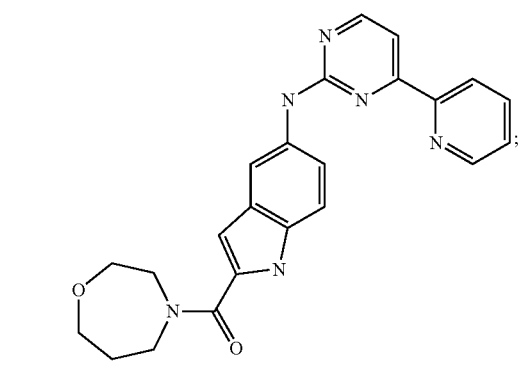
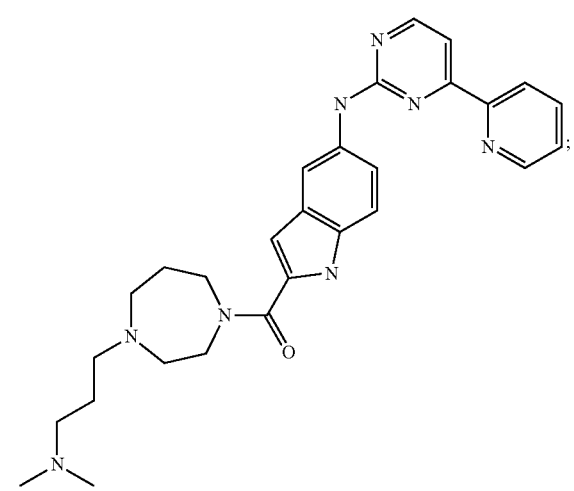
46
-continued
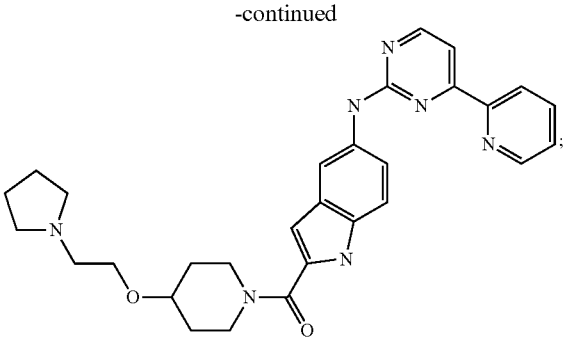
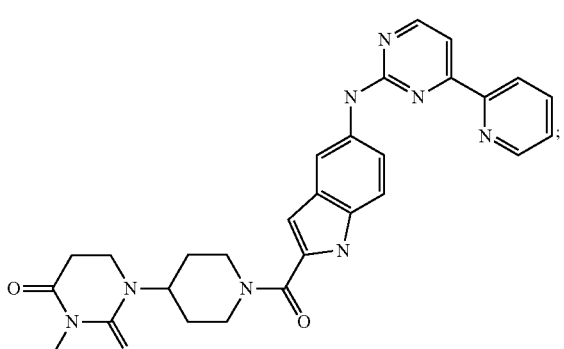
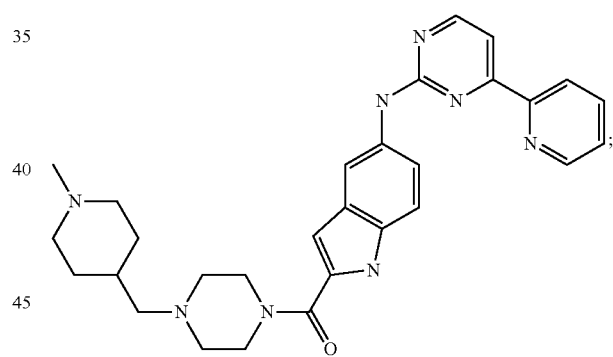

47
-continued
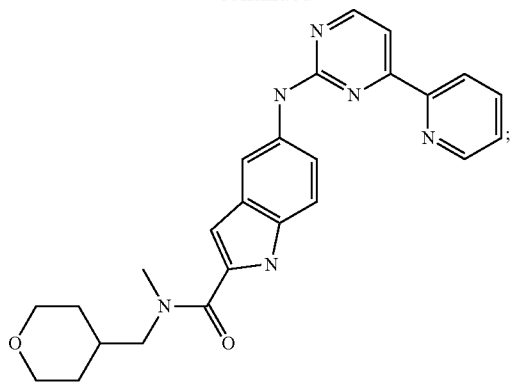
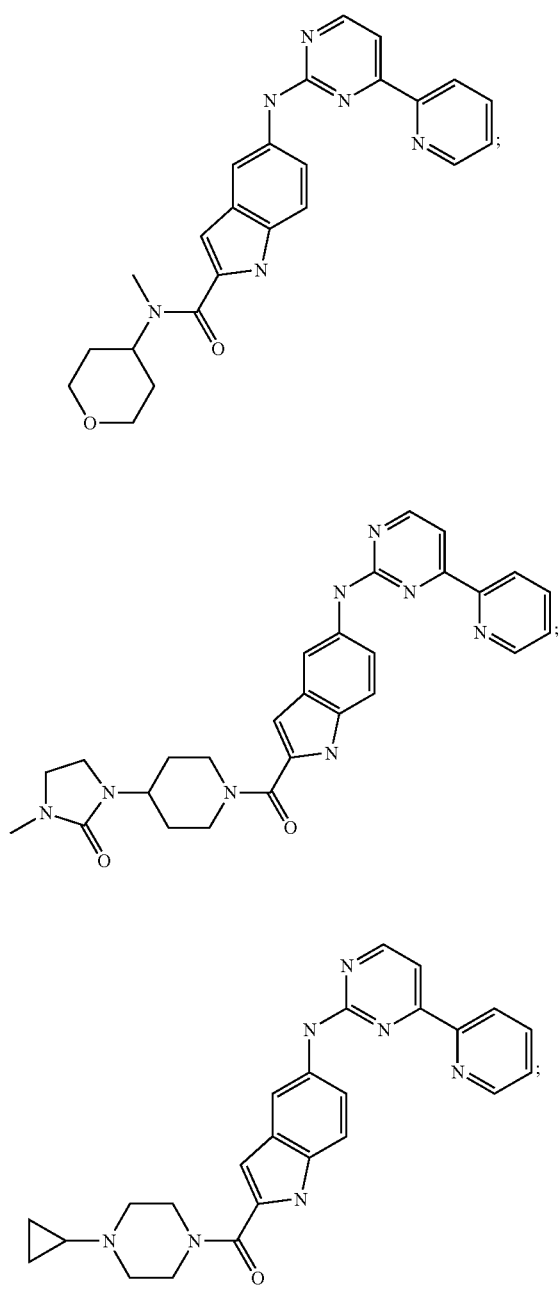
48
-continued
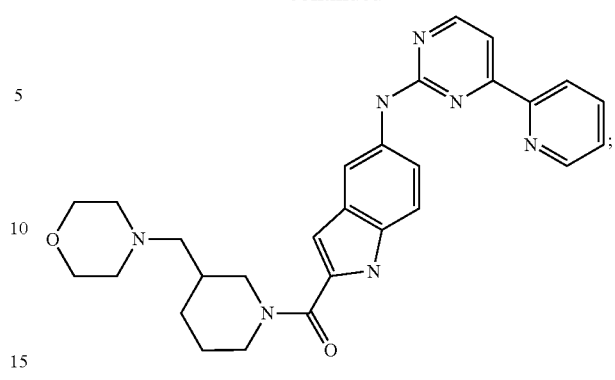
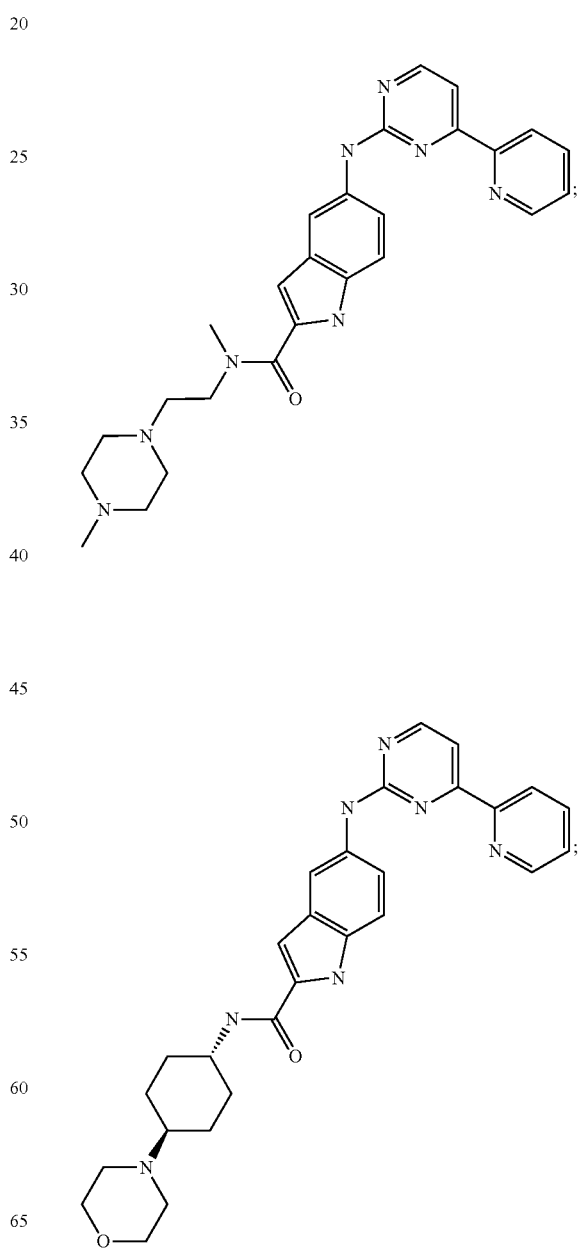

49
-continued
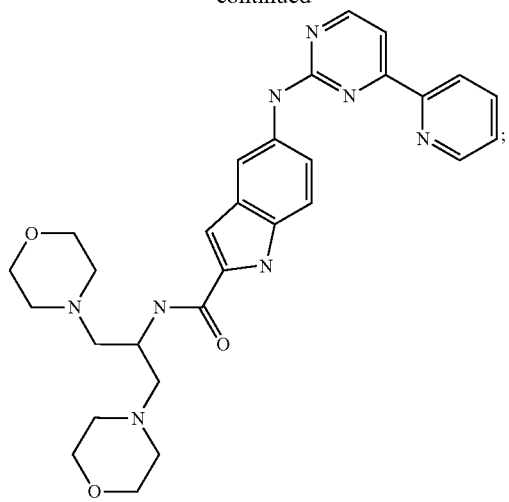
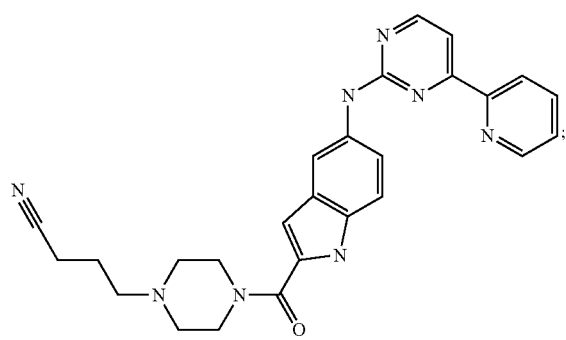
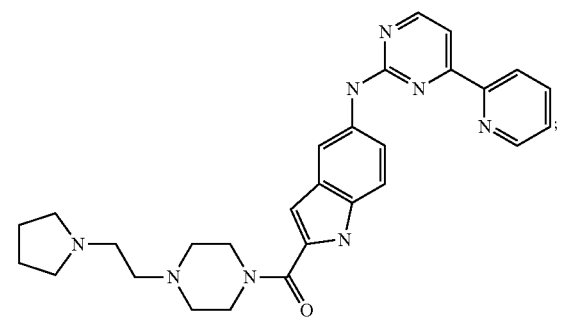
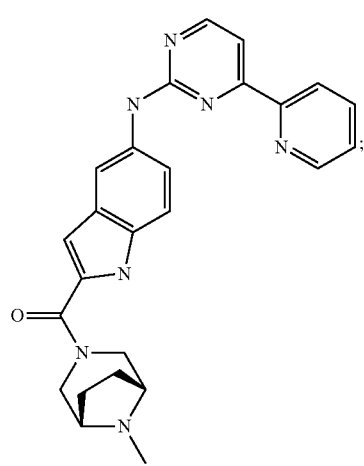
50
-continued
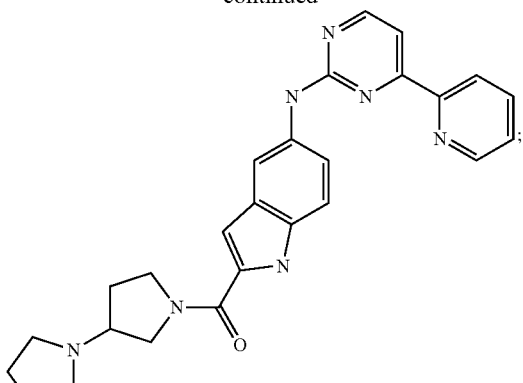
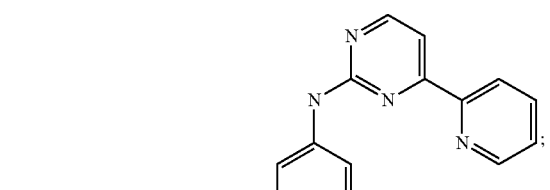
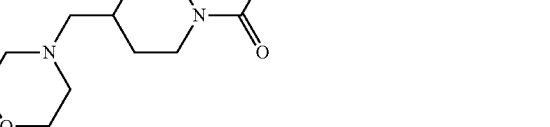
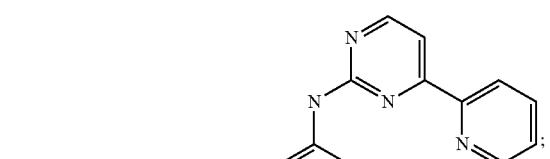
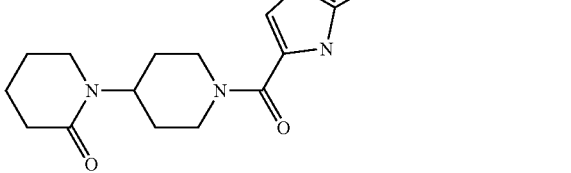
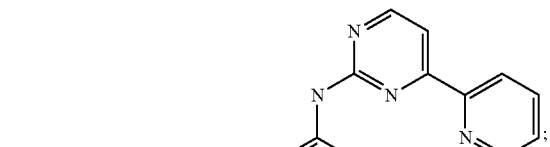
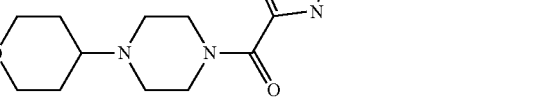

51
-continued
52
-continued
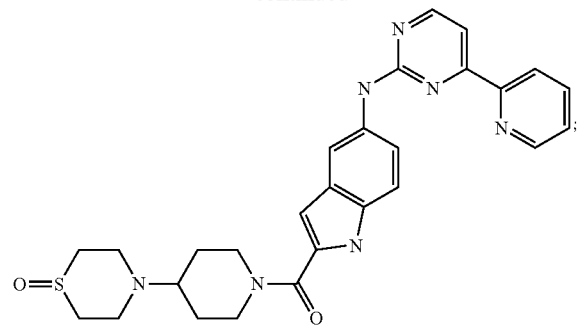
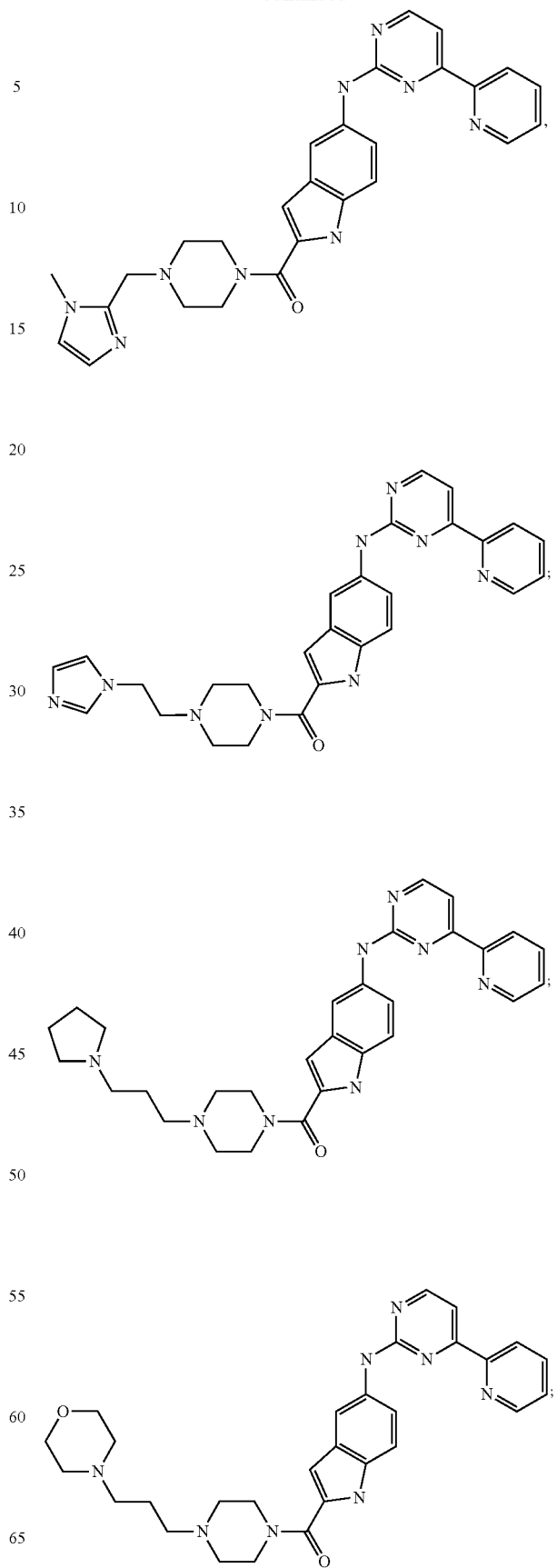

53
-continued
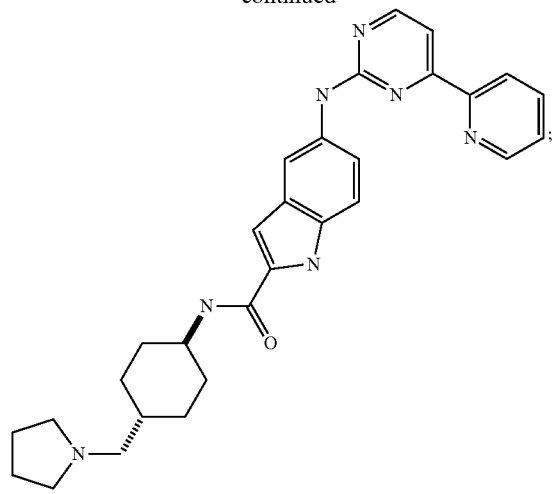
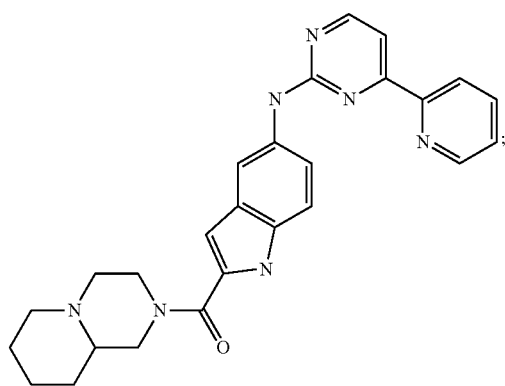
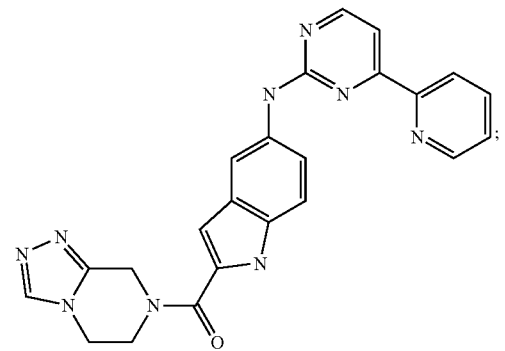
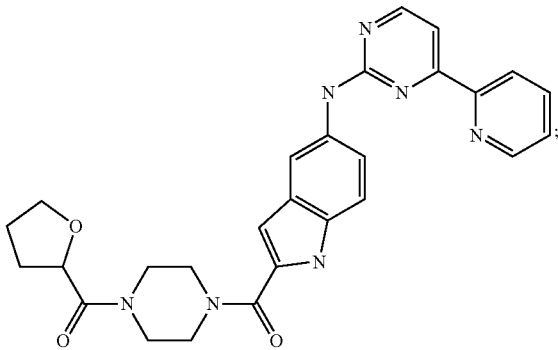
54
-continued
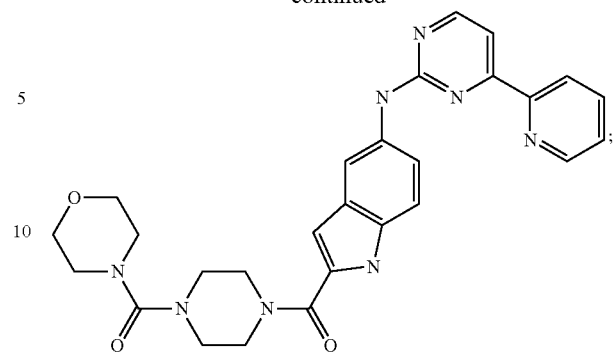
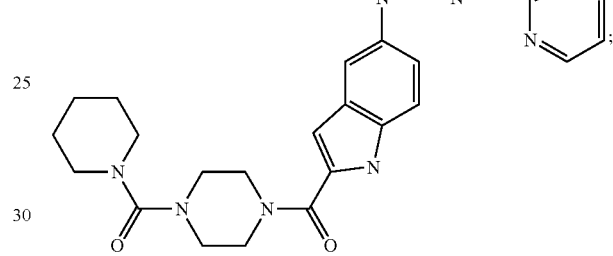
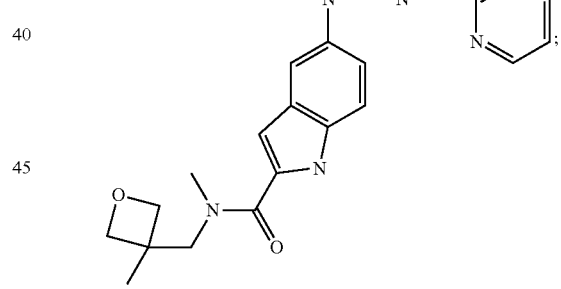
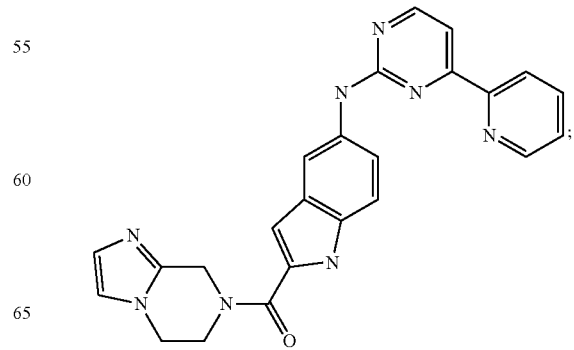

55
-continued
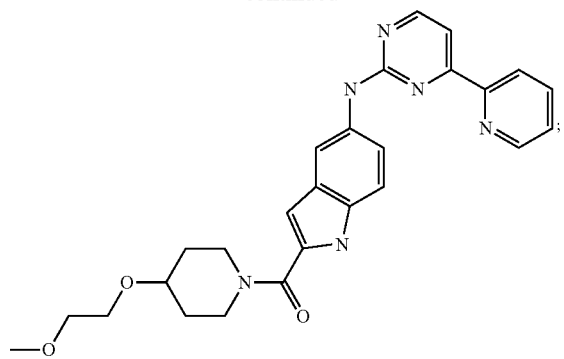
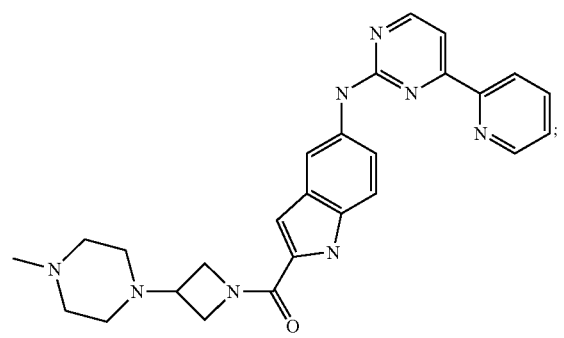
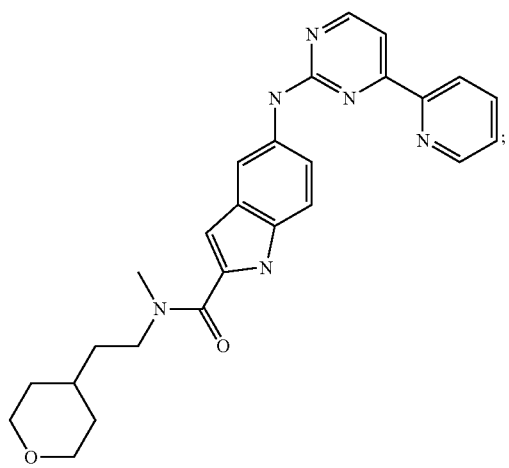
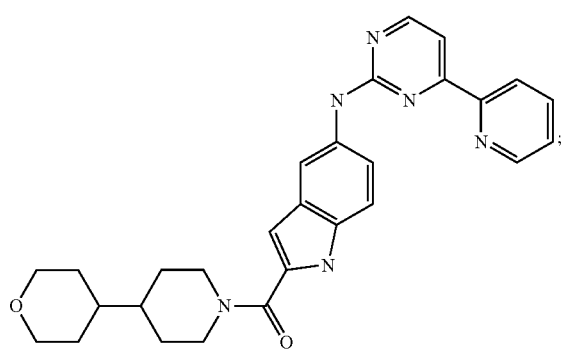
56
-continued
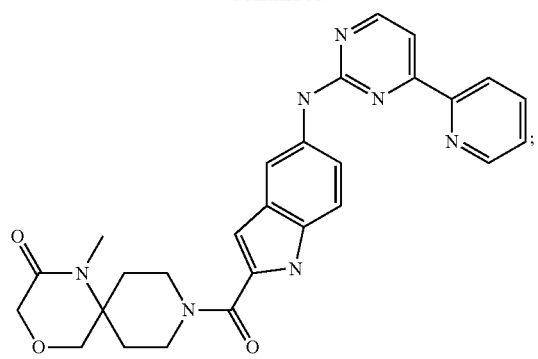
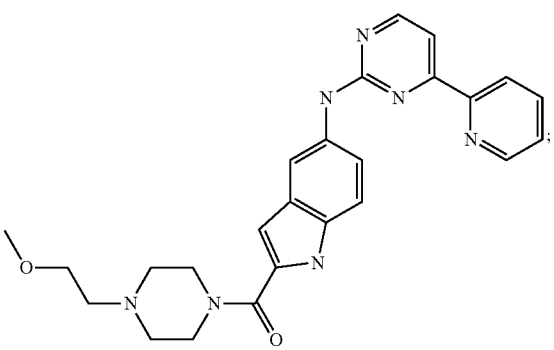
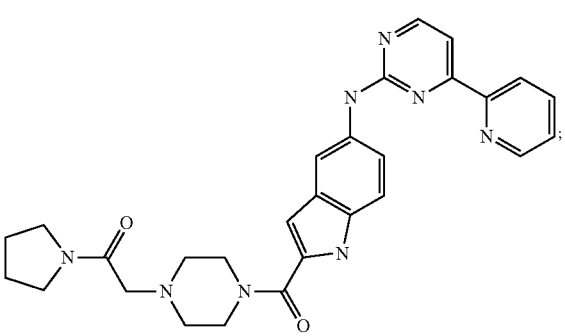

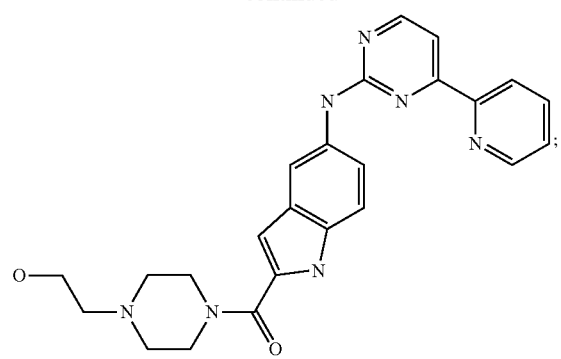
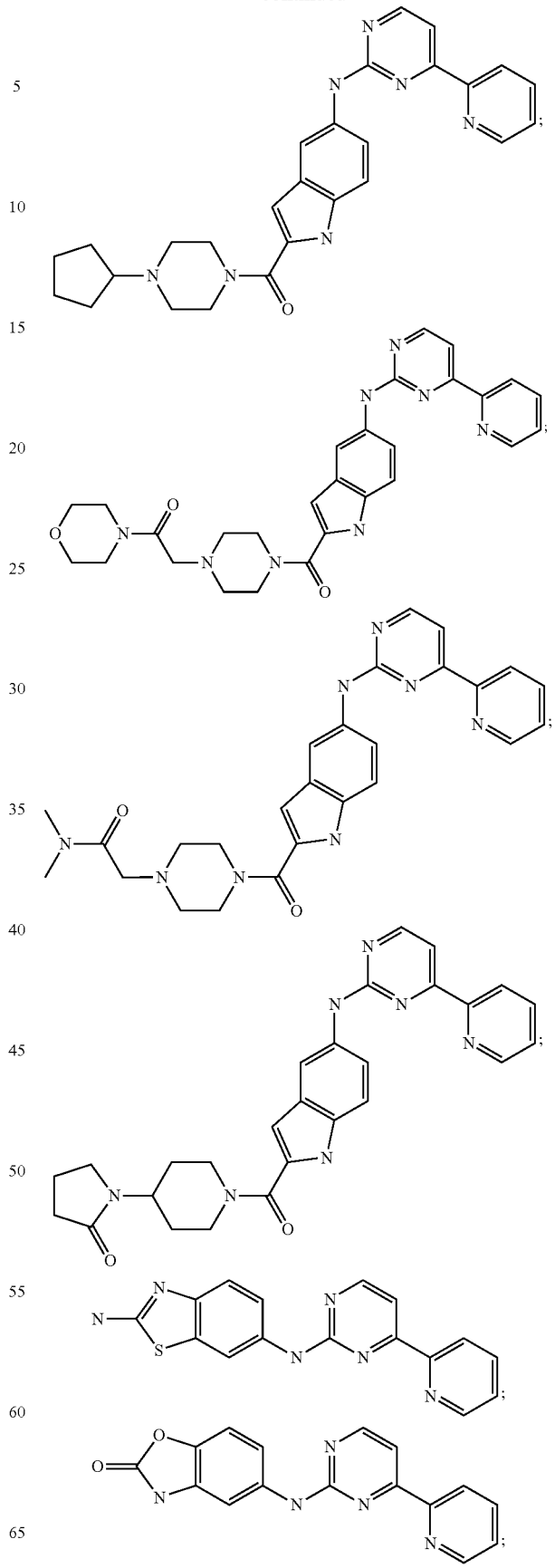

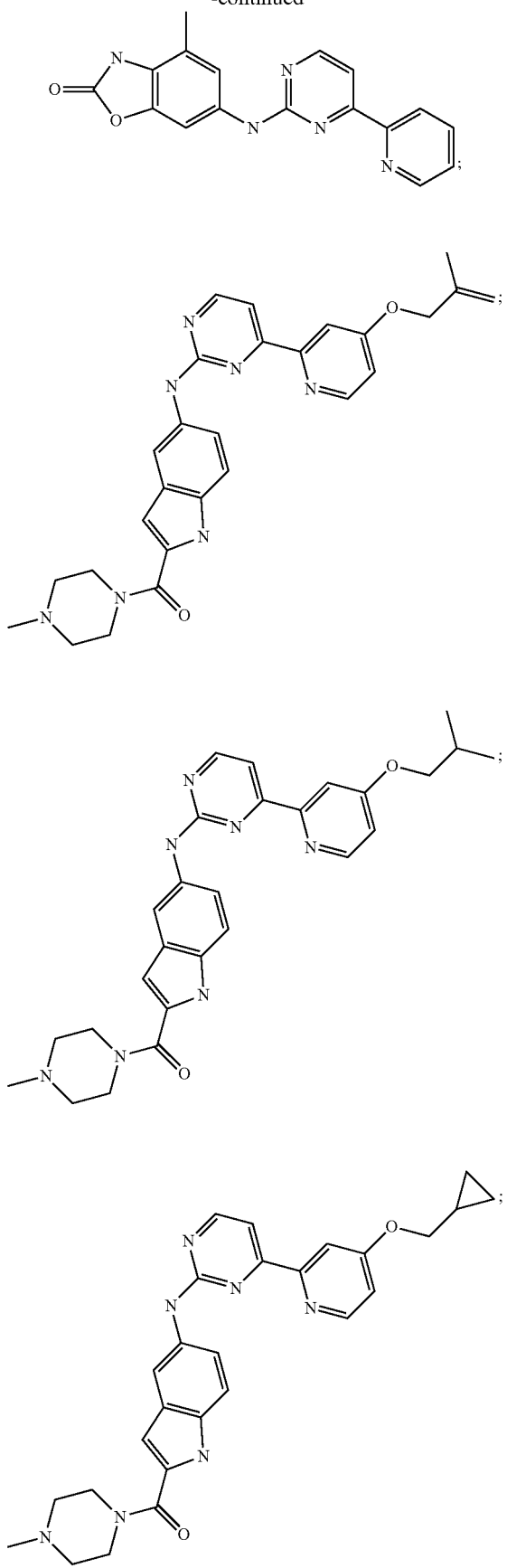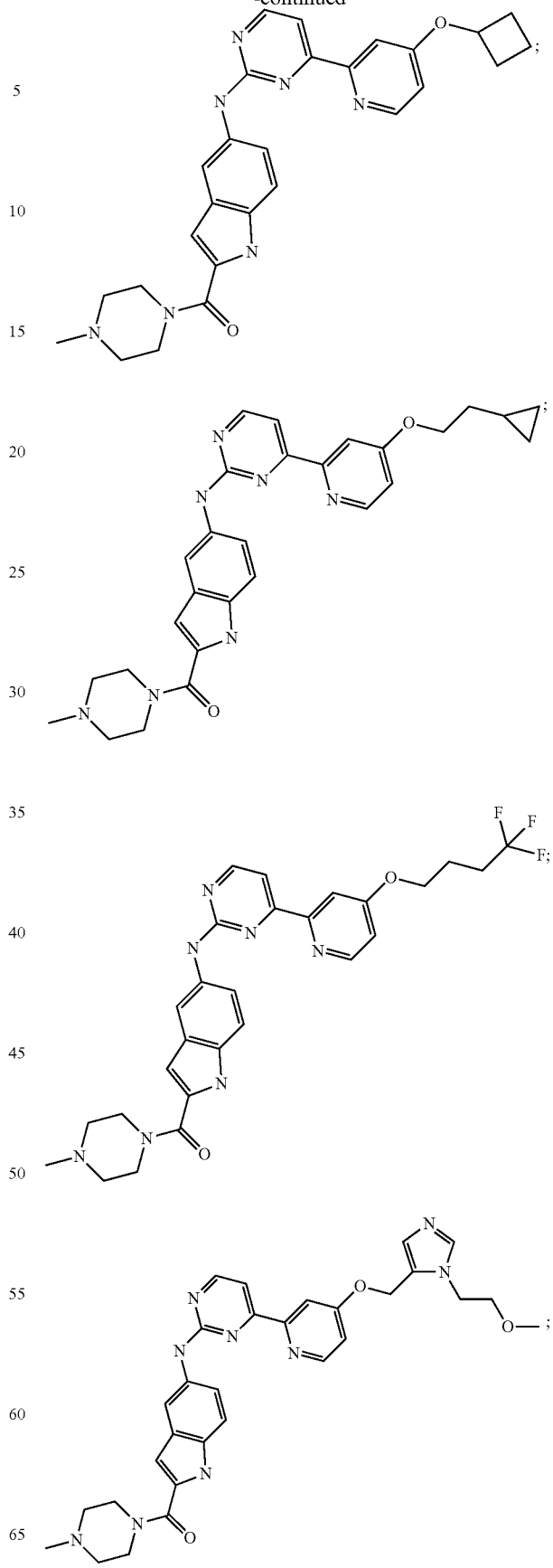

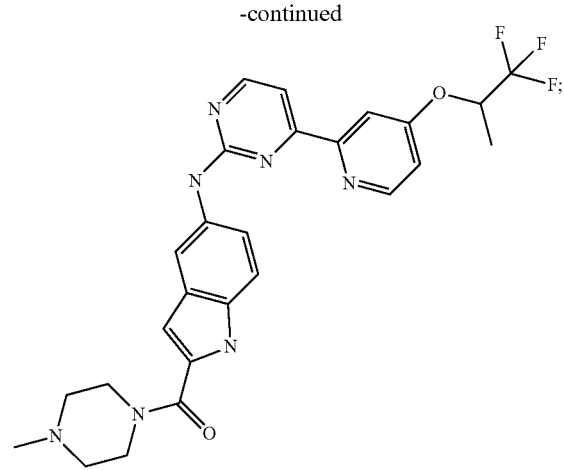
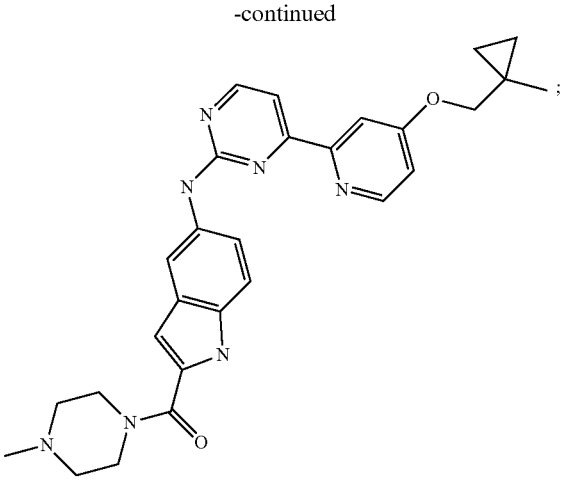

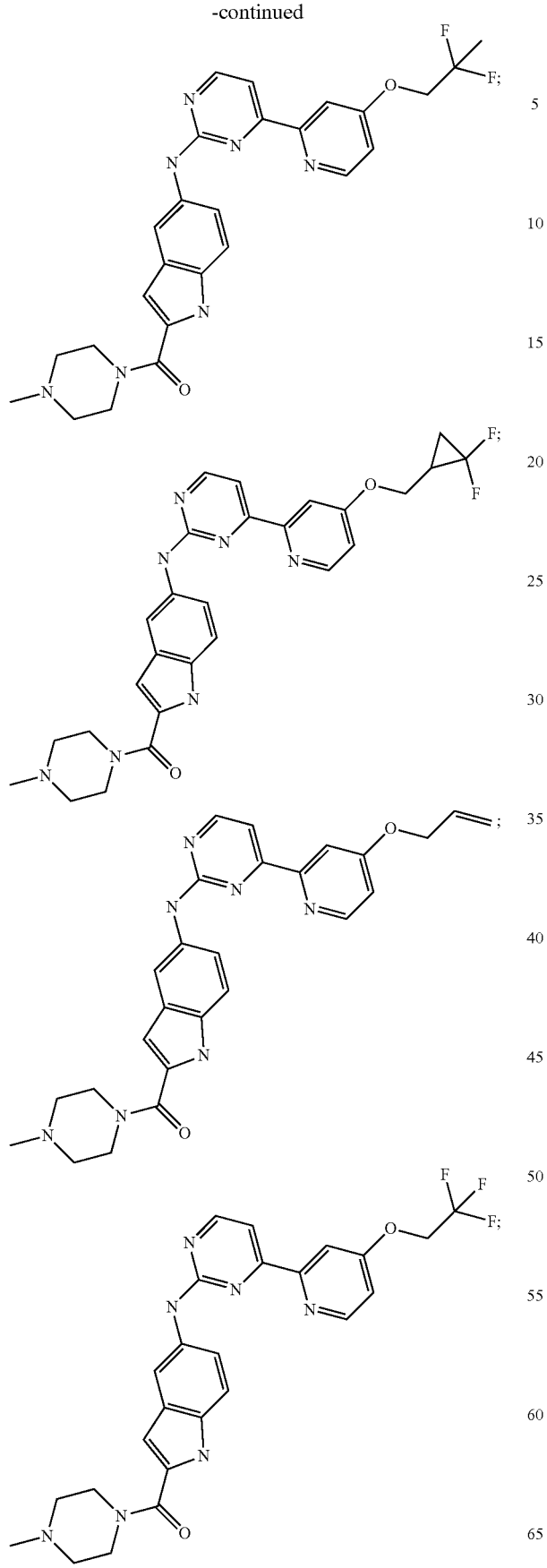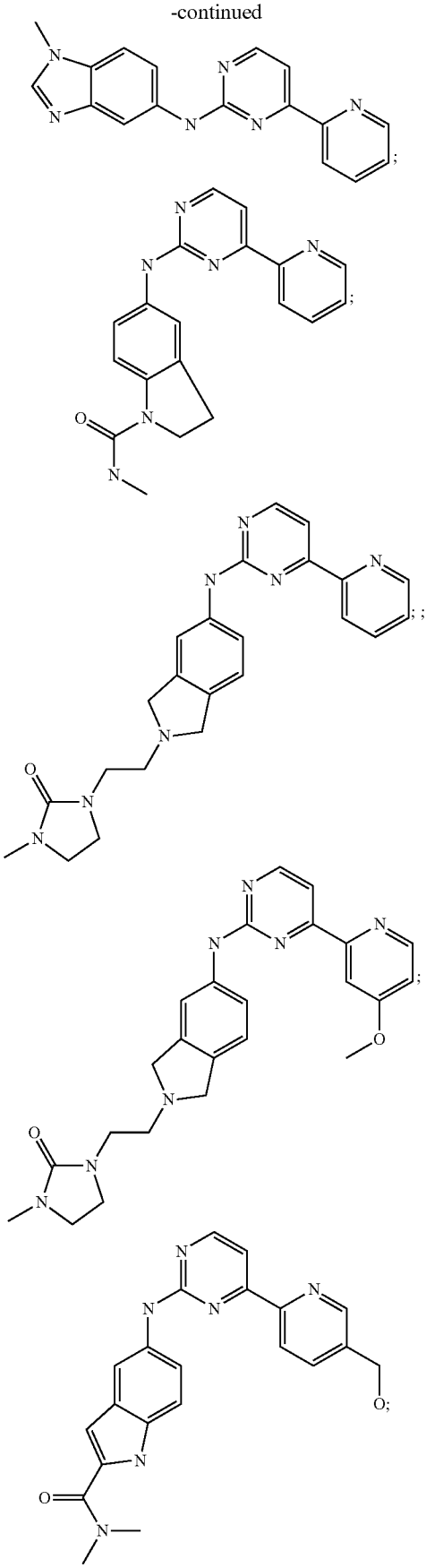

65
-continued
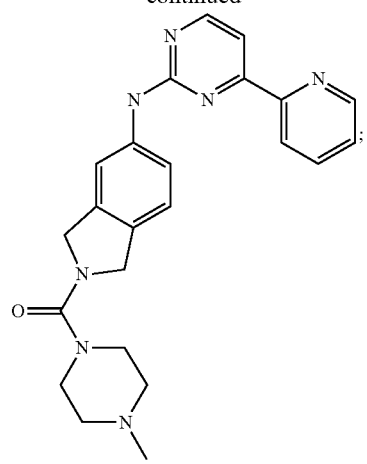
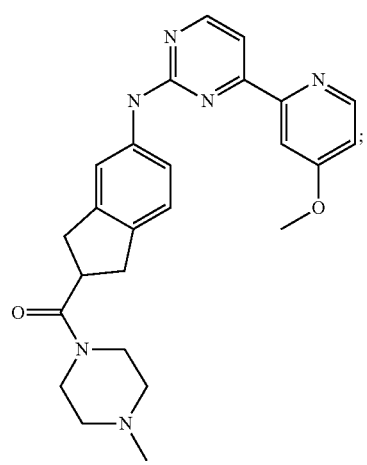
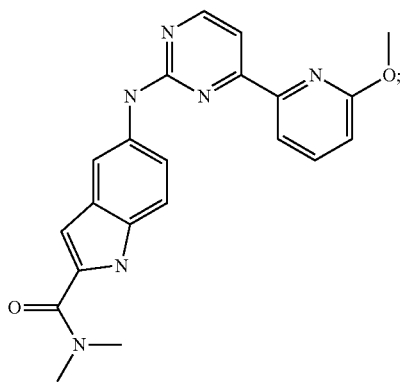
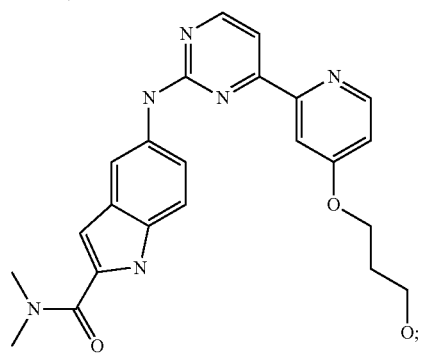
66
-continued
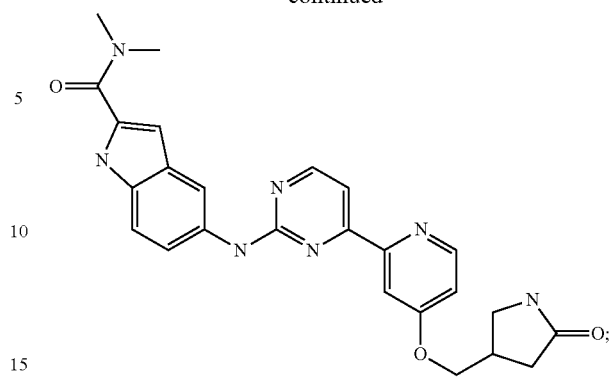
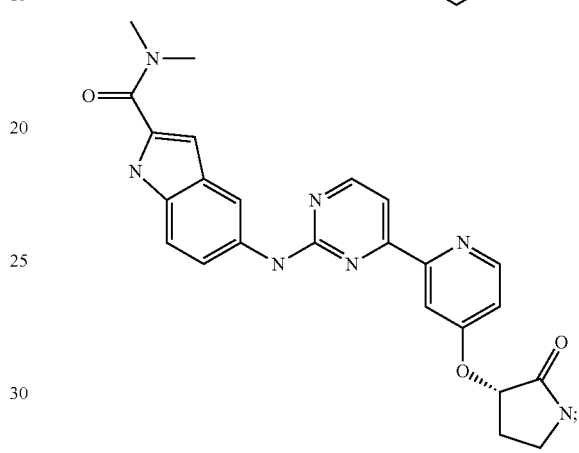
Chiral
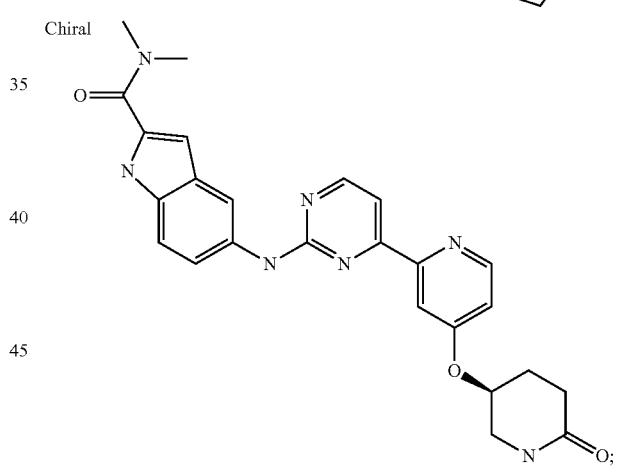
Chiral
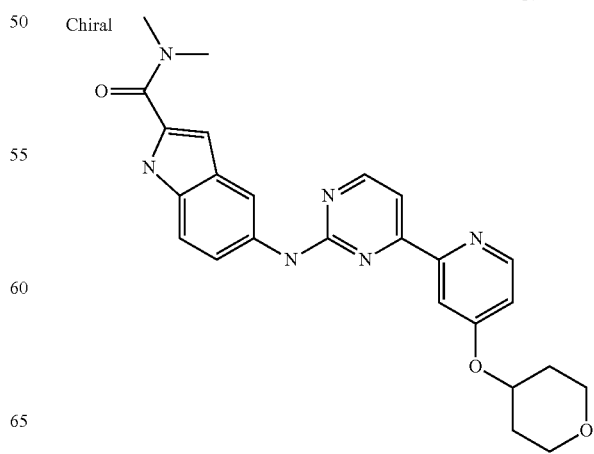

67
-continued
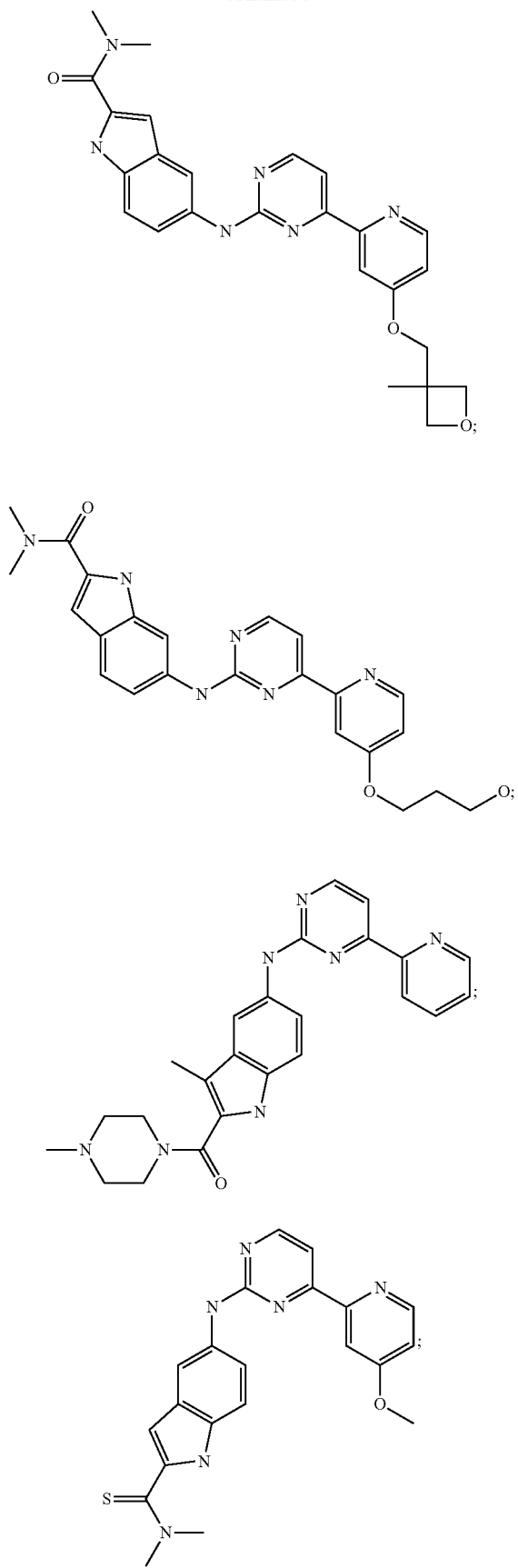
68
-continued
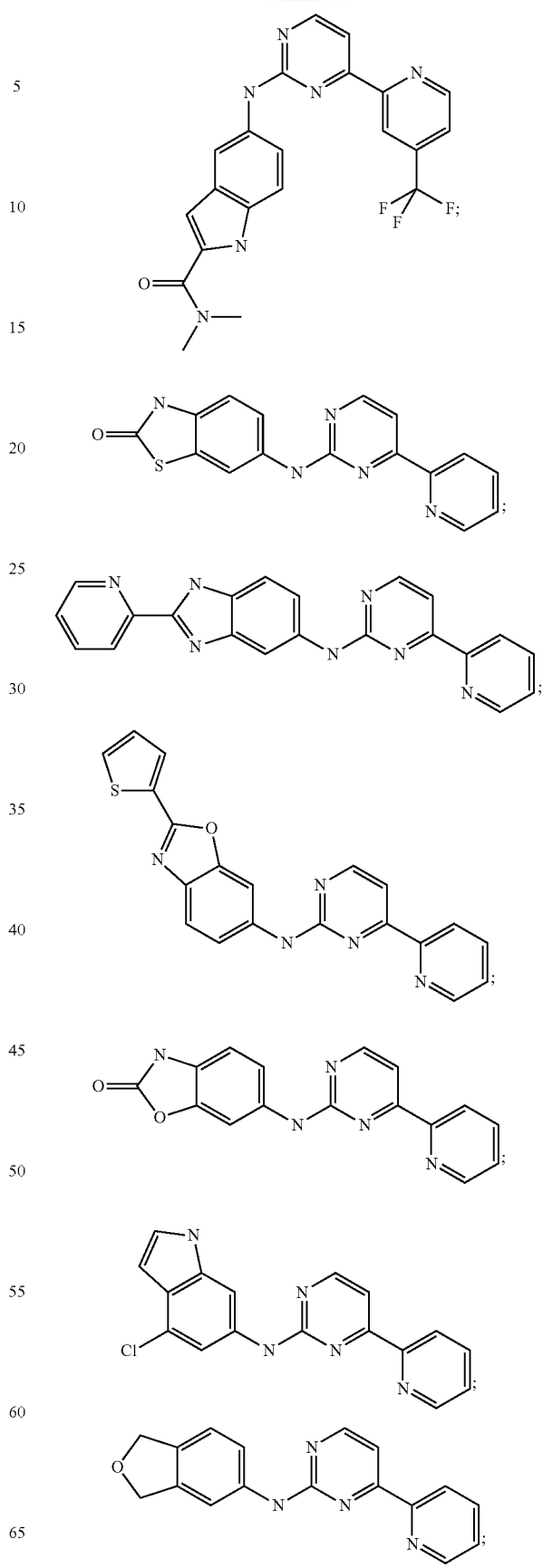

69
-continued
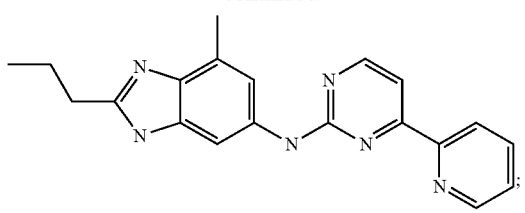
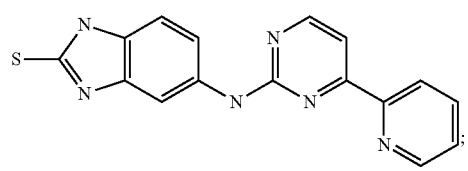
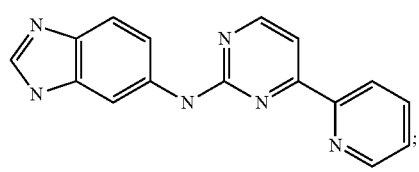
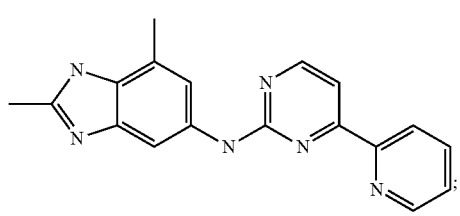
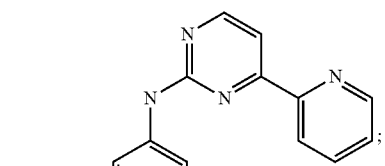
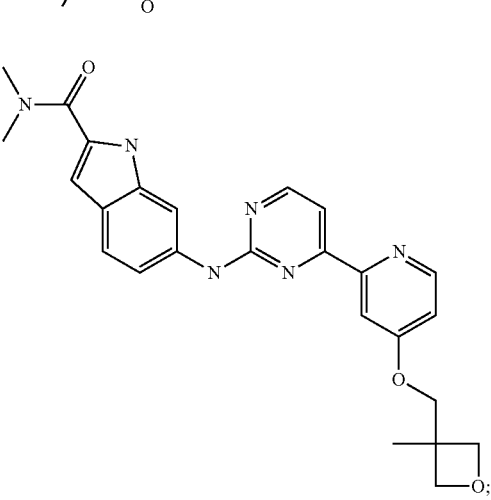
70
-continued
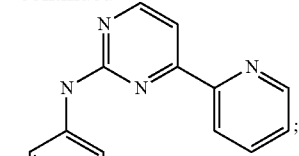
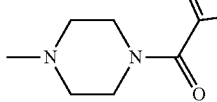
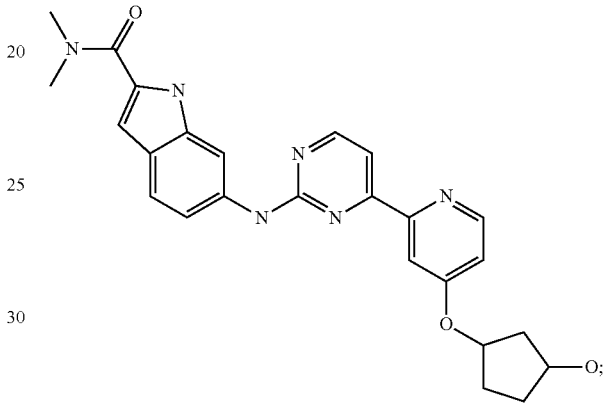
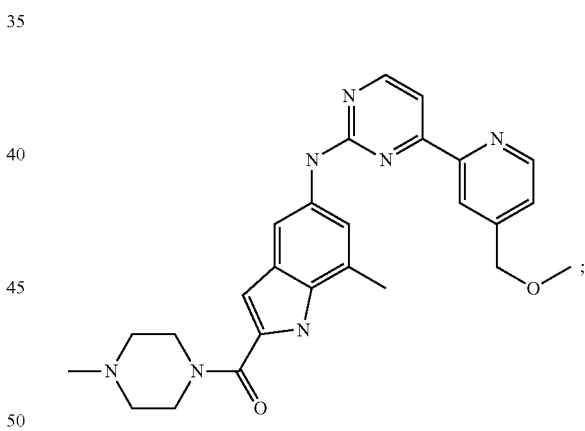
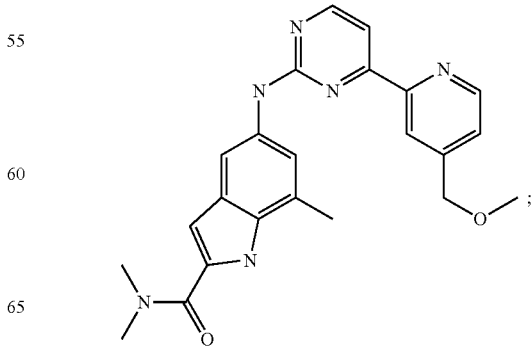

-continued
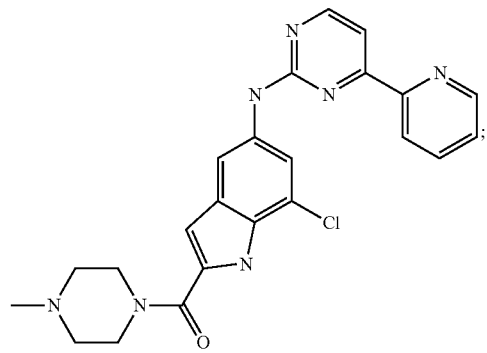
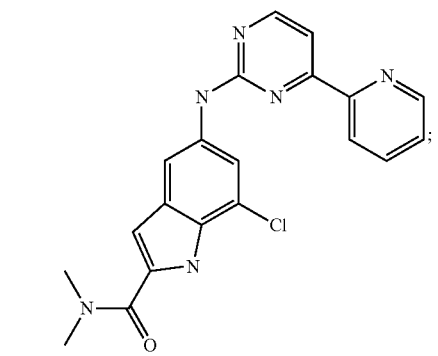
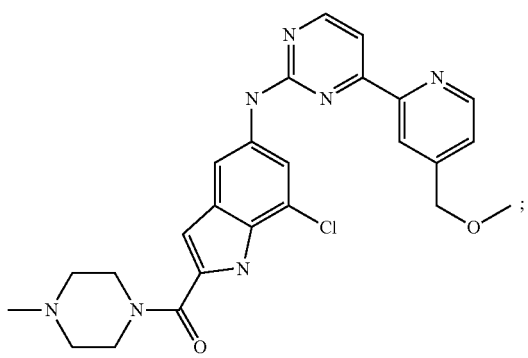
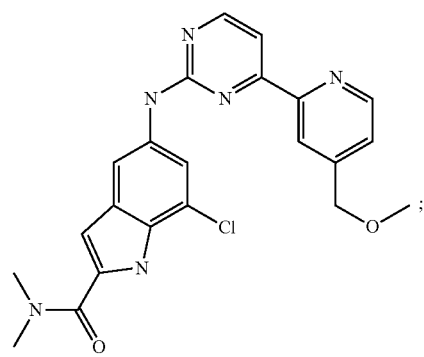
-continued
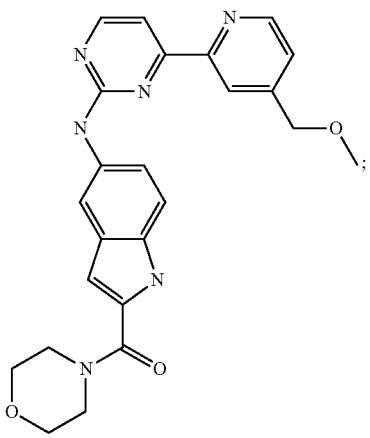
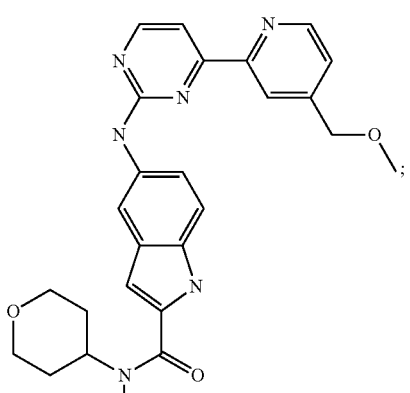
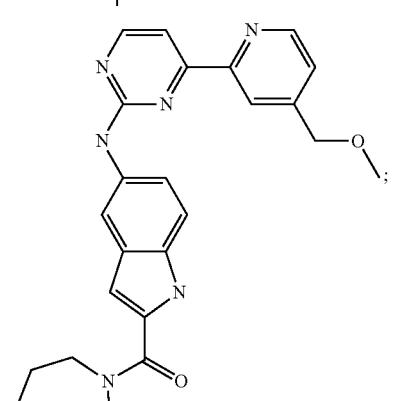
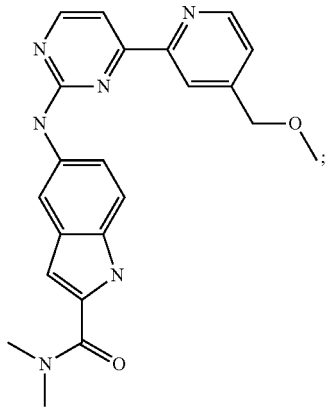

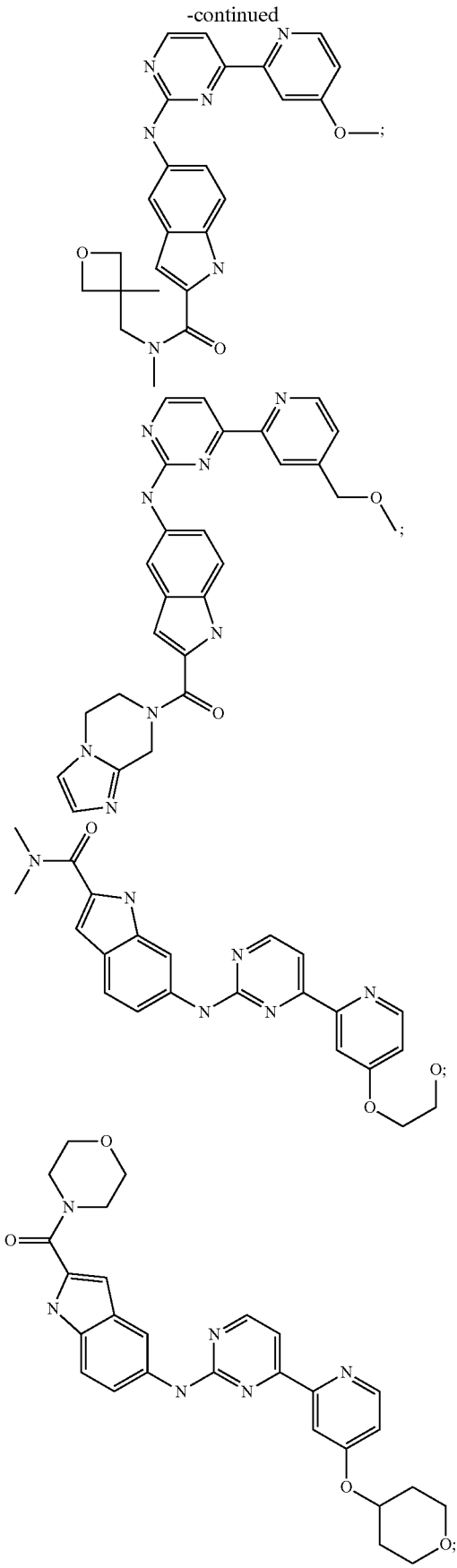
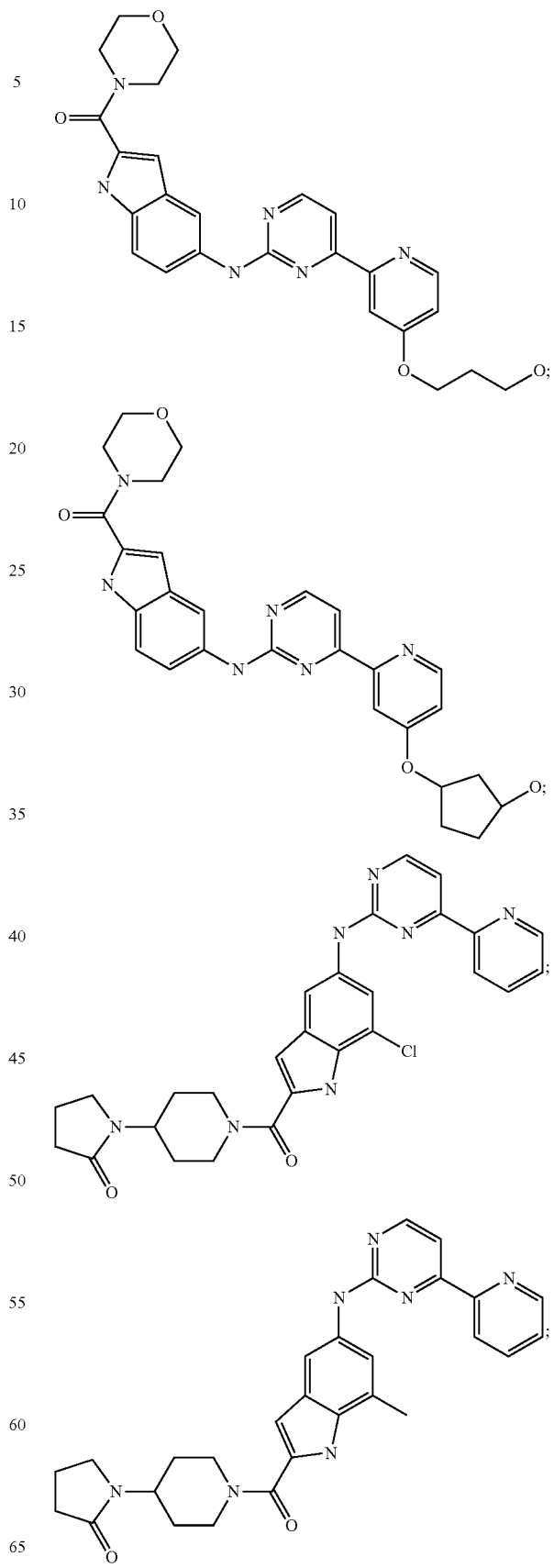

75
-continued
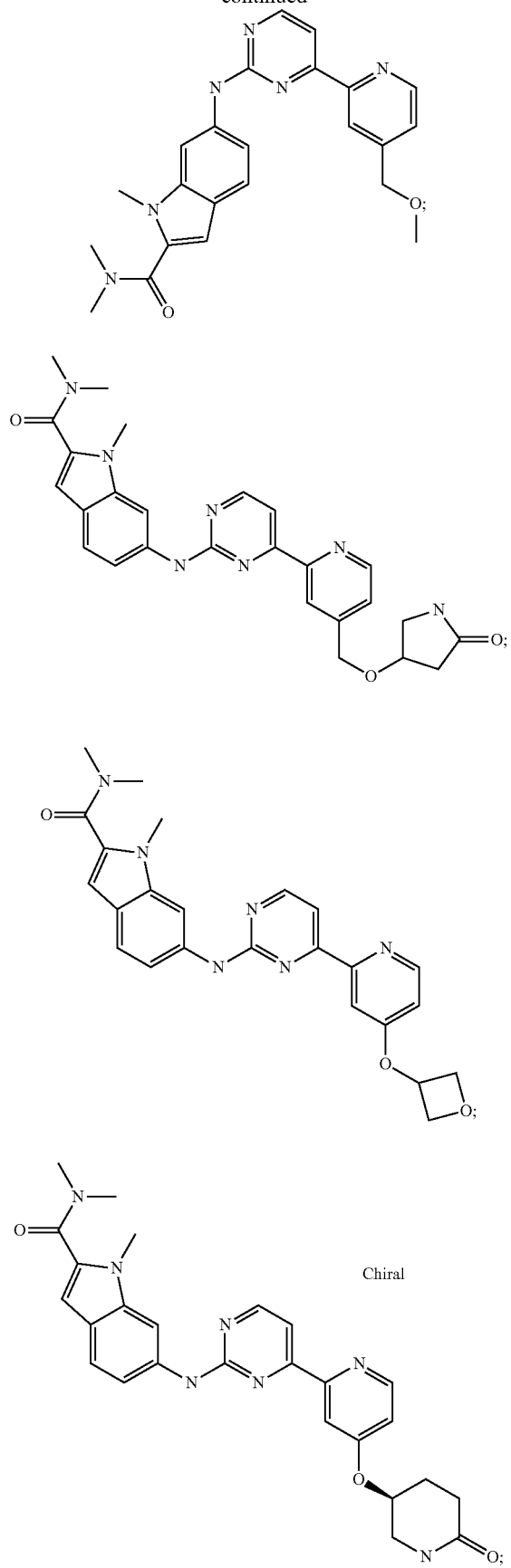
76
-continued
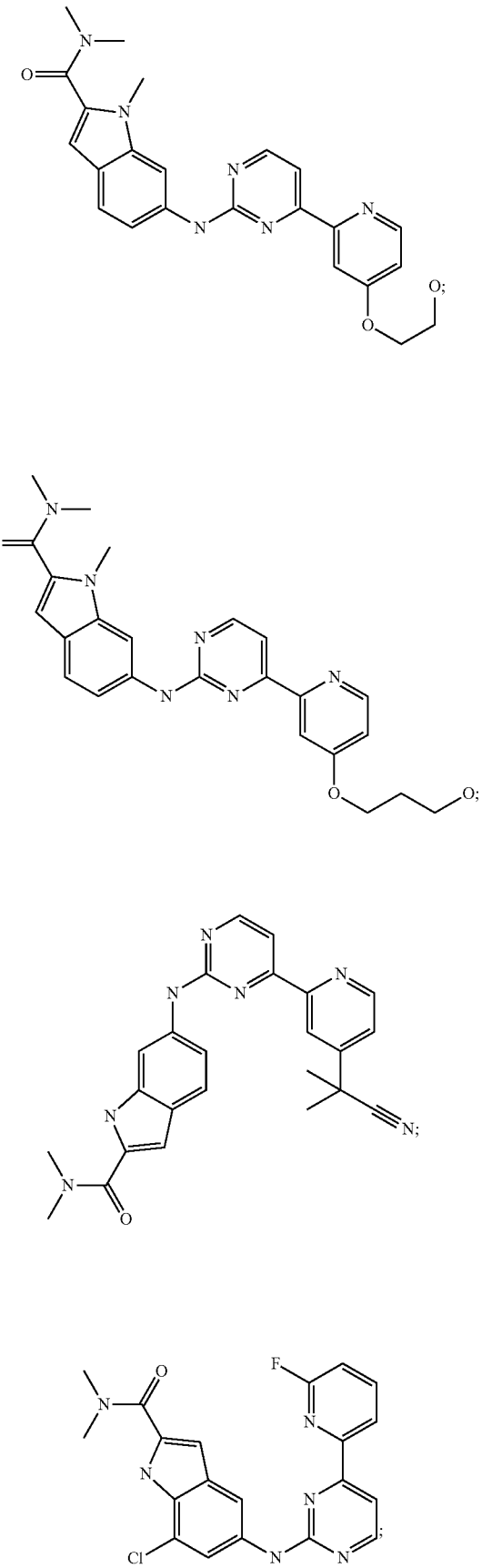

77
-continued
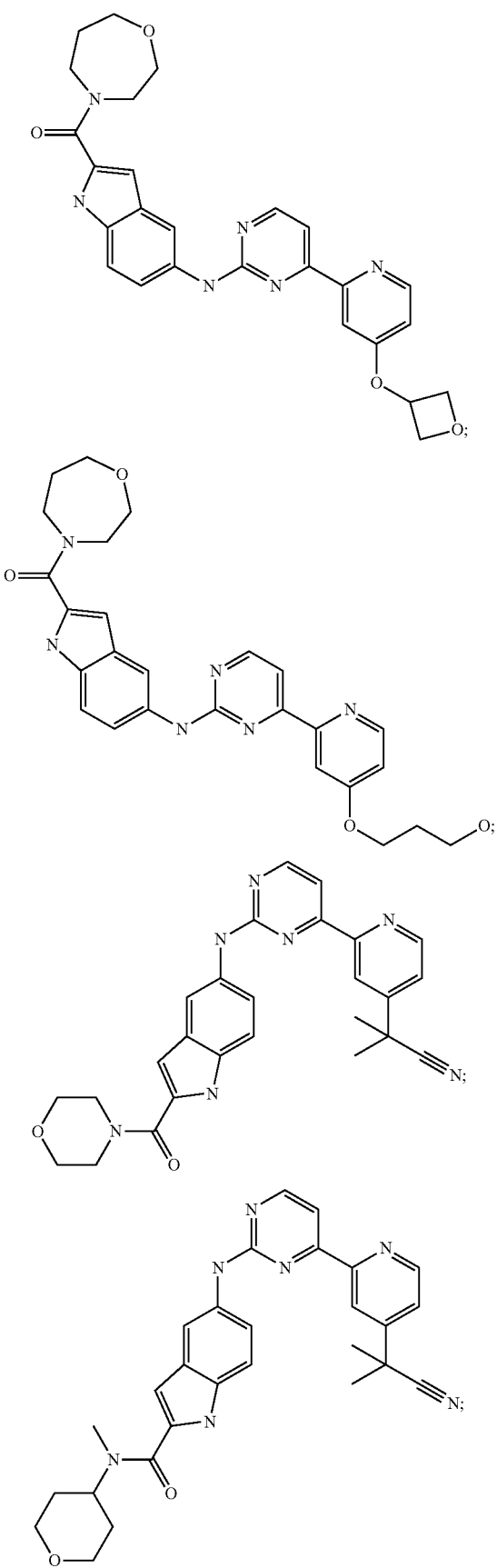
78
-continued
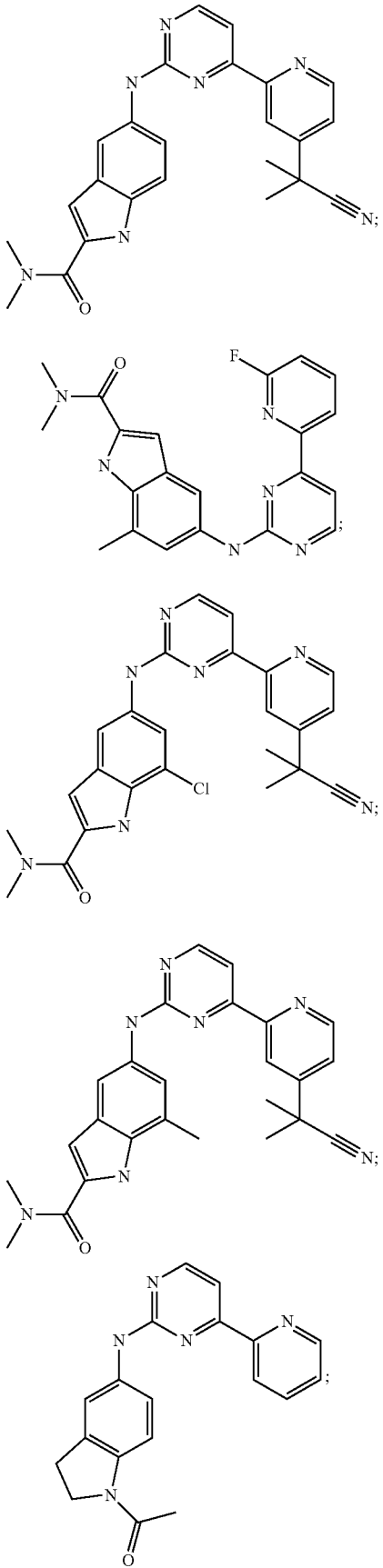

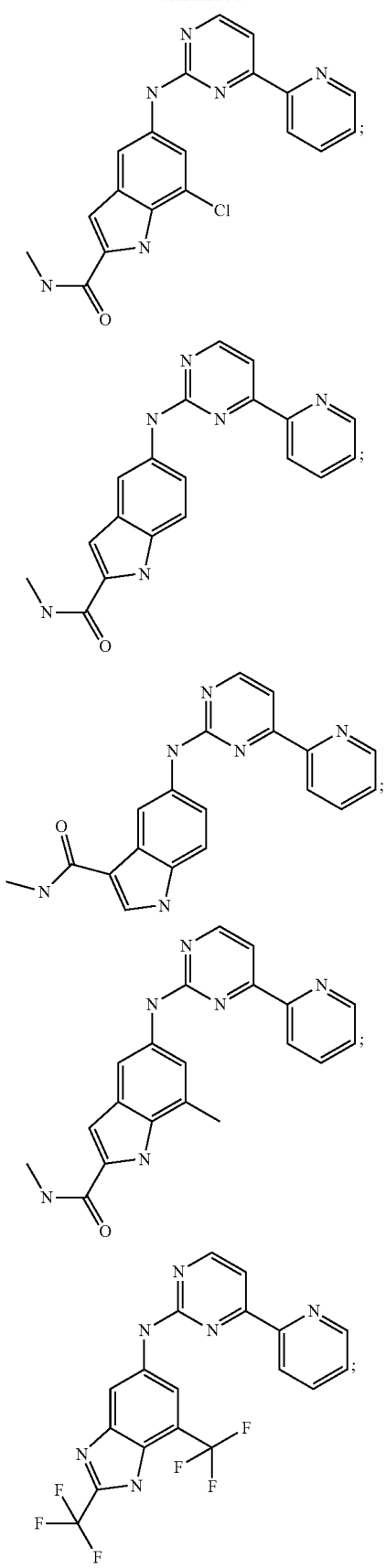
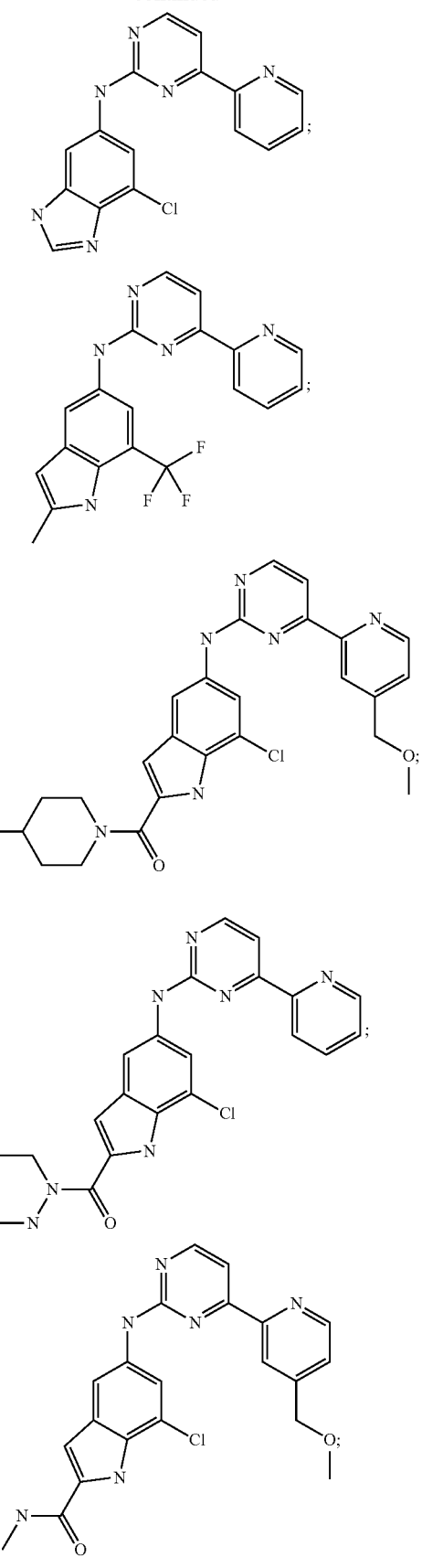

-continued

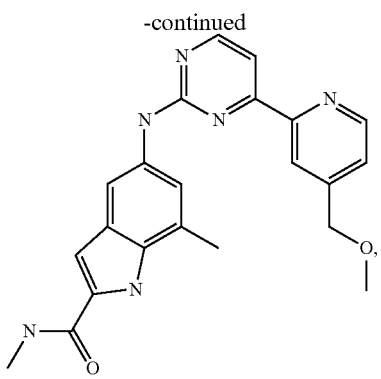

and the pharmaceutically acceptable salts of these compounds.

The instant invention further concerns the use of the aforementioned compounds of formula 1 for preparing a medicament for the treatment of diseases which can be treated by inhibition of the SYK enzyme.

In a preferred embodiment the instant invention concerns the use of the aforementioned compounds of formula 1 for preparing a medicament for the treatment of diseases selected from the group consisting of allergic rhinitis, asthma, COPD, adult respiratory distress syndrome, bronchitis, B-cell lymphoma, dermatitis and contact dermatitis, allergic dermatitis, allergic rhinoconjunctivitis, rheumatoid arthritis, anti-phospholipid syndrome, Berger's disease, Evans's syndrome, ulcerative colitis, allergic antibody-based glomerulonephritis, granulocytopenia, Goodpasture's syndrome, hepatitis, Henoch-Schönlein purpura, hypersensitivity vasculitis, immunohaemolytic anaemia, autoimmune haemolytic anemia, idiopathic thrombocytopenic purpura, Kawasaki syndrome, allergic conjunctivitis, lupus erythematodes, capsule cell lymphoma, neutropenia, non-familial lateral sclerosis, Crohn's disease, multiple sclerosis, myasthenia gravis, osteoporosis, osteolytic diseases, osteopenia, psoriasis, Sjögren's syndrome, sclerodermy, T-cell lymphoma, urticaria/angiooedema, Wegener's granulomatosis and coeliac disease.

In a further preferred embodiment the invention concerns the use of the aforementioned compounds of formula 1 for preparing a medicament for the treatment of diseases selected from the group consisting of asthma, COPD, allergic rhinitis, adult respiratory distress syndrome, bronchitis, allergic dermatitis, contact dermatitis, idiopathic thrombocytopenic purpura, rheumatoid arthritis and allergic rhinoconjunctivitis.

The instant invention further preferably concerns the use of the aforementioned compounds of formula 1 for preparing a medicament for the treatment of diseases selected from the group consisting of asthma, COPD, allergic rhinitis, allergic dermatitis and rheumatoid arthritis.

In another preferred embodiment the invention concerns also pharmaceutical formulations, characterised in that they contain one or more of the aforementioned compounds of formula 1.

In a further preferred embodiment the invention concerns pharmaceutical formulations, characterised in that they contain one or more of the aforementioned compounds of formula 1 in combination with an active substance selected from the group consisting of anticholinergics, betamimetics, corticosteroids, PDE4-inhibitors, EGFR-inhibitors, LTD4-antagonists, CCR3-inhibitors, iNOS-inhibitors, CRTH2-antagonists and HMG-CoA reductase inhibitors.

In another preferred embodiment the instant invention regards compounds selected from the group of the following formulas consisting of formula 6

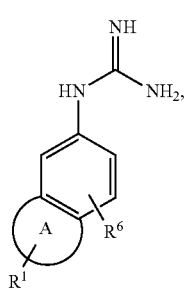

6 formula 10

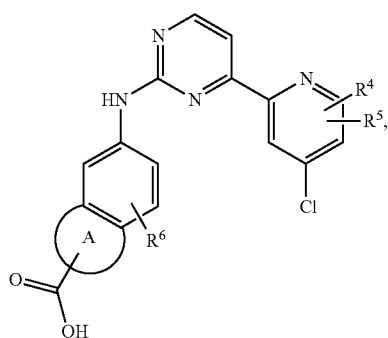

10' formula 12

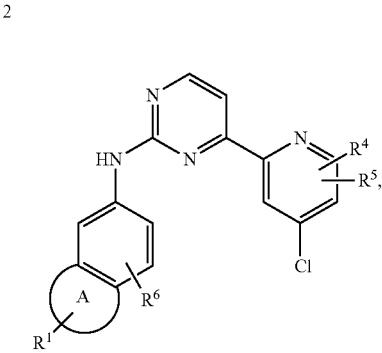

10 formula 15

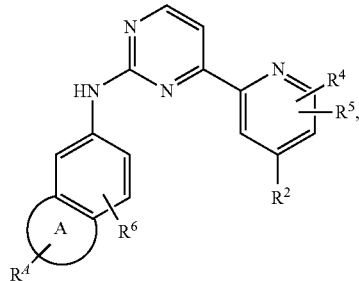

15 formula 15'

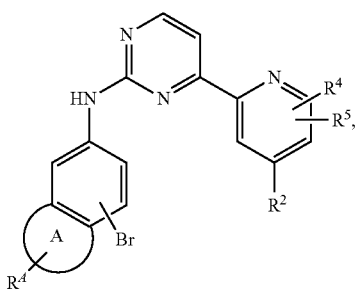

formula 16

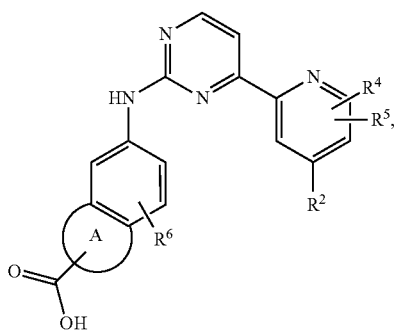

formula 16'

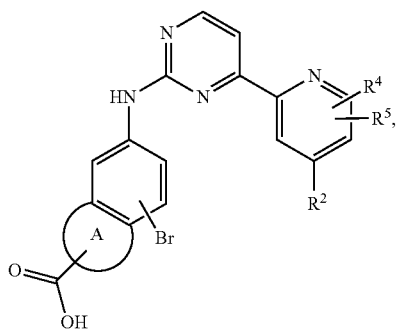

formula 17

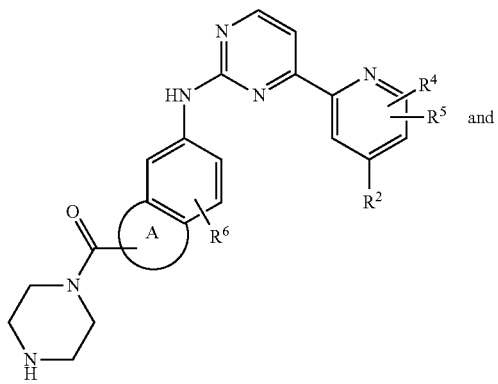

and formula 19

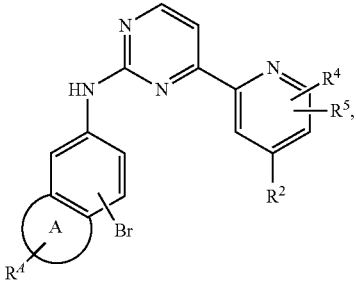

wherein $R^1$, $R^2$, $R^4$, $R^5$, $R^6$ and A are defined as previously mentioned,
wherein $R^4$ is —CO—O—CH$_3$ or —CO—O—CH$_2$—CH$_3$, and the pharmaceutically acceptable salts of these compounds.

3. TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Moreover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

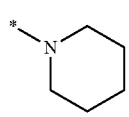

I

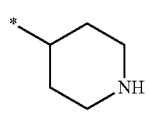

II

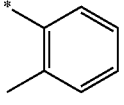

III

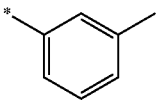

IV

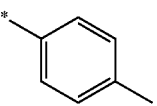

V

If there is no asterisk (*) in the structural formula of the substituent, each hydrogen atom may be removed at the substituent and the valency thus freed may serve as a binding site to the rest of a molecule. Thus, for example, VI

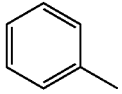

VI may represent 2-tolyl, 3-tolyl, 4-tolyl and benzyl.

Alternatively to the * within the scope of this application $X_1$ is also understood as being the linking point of the group $R^1$ to the structure of formula 1 and $X_2$ as being the linking point of the group $R^2$ to the structure of formula 1.

For an annellated ring B such as

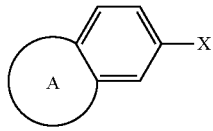

(B)

the linking atoms are also depicted with an asterix (*). This means if ring A is defined for example as

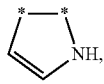

then this would mean an annellated ring B

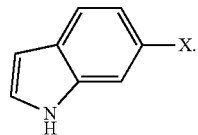

(B)

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

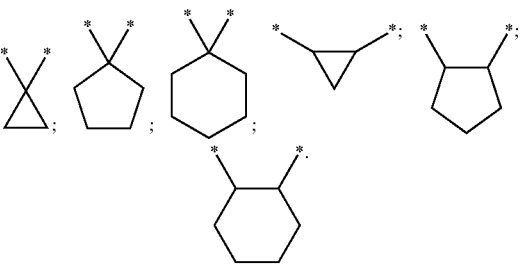

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"—branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which—in case it is not differently defined—may contain one, two, three or four heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

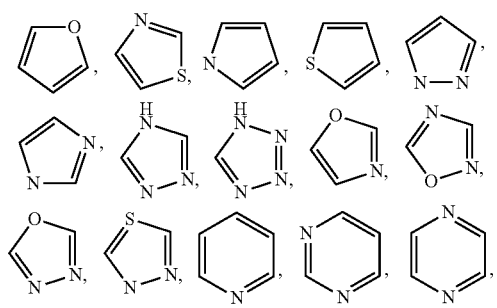

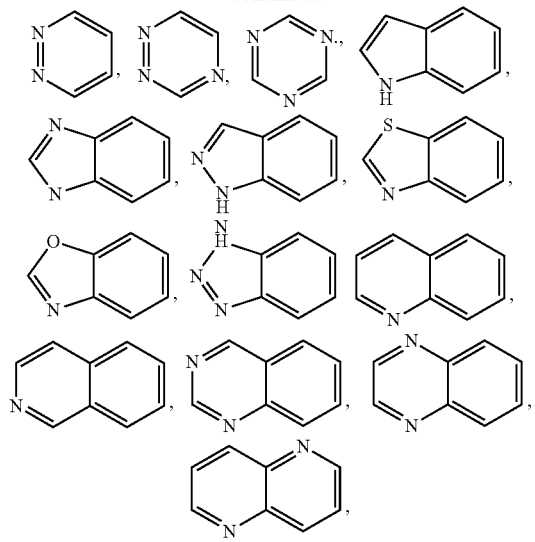

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

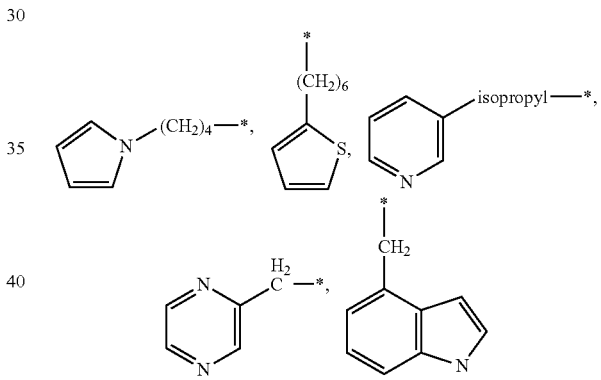

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-haloalkyl" are meant branched and unbranched alkyl groups with 1 to 4 carbon atoms, which are substituted by one or more halogen atoms. Haloalkyl groups with 1 to 4 carbon atoms are preferred. Examples include: $CF_3$, $CHF_2$, $CH_2F$, $CH_2CF_3$.

By the terms "$C_{3-7}$-cycloalkyl" or by "3- to 7-membered carbocyclic rings" (including those which are part of other groups) are meant—unless otherwise defined—cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the terms "$C_{3-10}$-cycloalkyl" or "3- to 10-membered carbocyclic ring" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

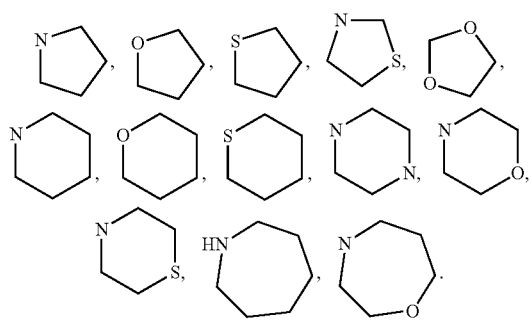

Although included by the term "heterocyclic rings" or "heterocyclic group", the term "partially saturated heterocyclic group" refers to five-, six- or seven-membered partially saturated rings which contain one or two double bonds, but which have only so many double bonds that an aromatic system may not be formed. Examples include:

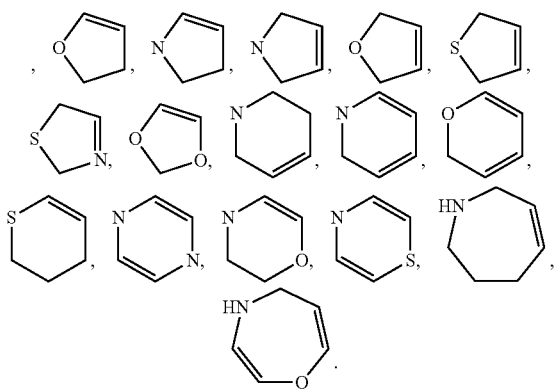

Although included by the term "heterocyclic rings" or "heterocycles", the term "heterocyclic aromatic rings", "unsaturated heterocyclic group" or "heteroaryl" refers to five- or six-membered heterocyclic aromatic groups or to 9-10-membered, bicyclic heteroaryl rings which may contain one, two, three or four heteroatoms, selected from among oxygen, sulphur and nitrogen, and contain so many conjugated double bonds that an aromatic system is formed. Examples of five- or six-membered heterocyclic aromatic groups include:

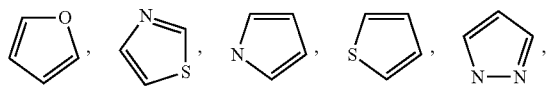

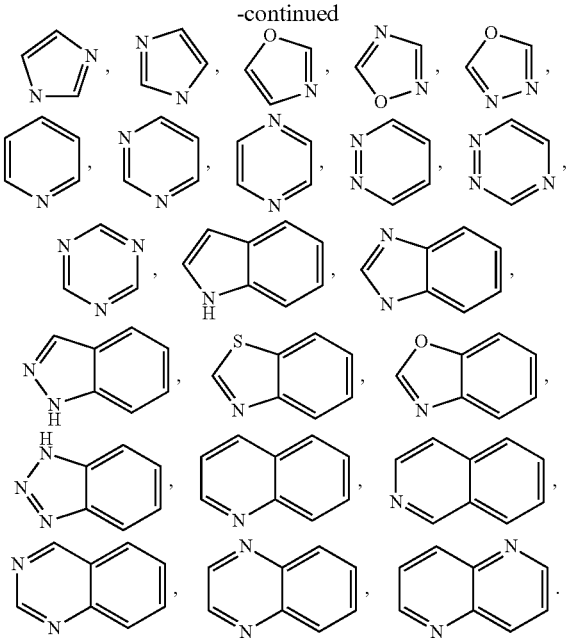

Unless otherwise mentioned, a heterocyclic ring (or heterocycle) may be provided with a keto group. Examples include:

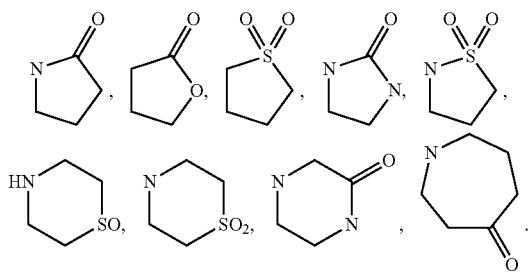

Although covered by the term "cycloalkyl" or "carbocyclic ring", the term "bicyclic cycloalkyls" generally denotes eight-, nine- or ten-membered bicyclic carbon rings. Examples include

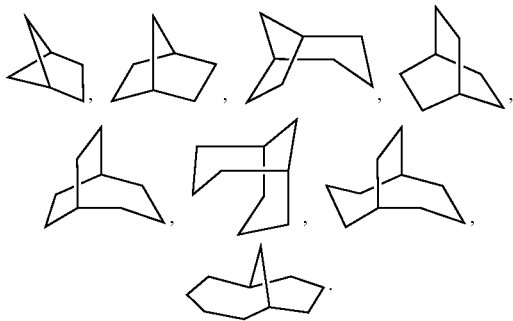

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen. The ring may be linked to the molecule through a carbon atom of the ring or through a nitrogen atom of the ring, if there is one, if not expressively stated otherwise. Examples include:

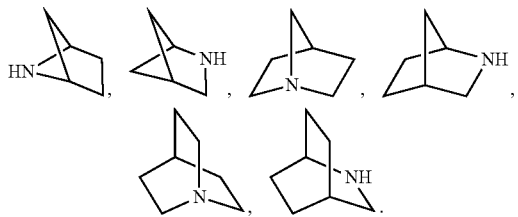

Although already included by the term "aryl", the term "bicyclic aryl" denotes a 9-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 9-10 membered, bicyclic heteroaryl ring which may contain one, two, three or four heteroatoms, selected from among oxygen, sulphur and nitrogen, and contains sufficient conjugated double bonds to form an aromatic system. Examples for a "bicyclic heteroaryl" include

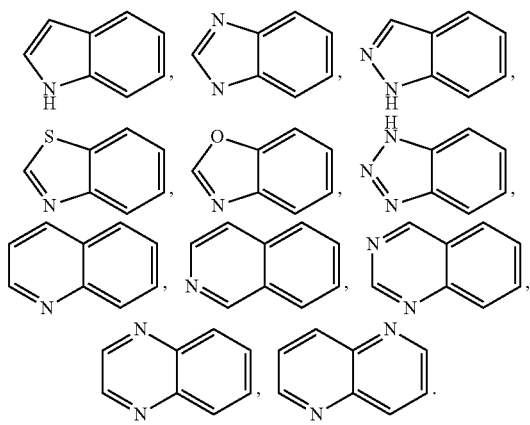

Although included by the term "bicyclic cycloalkyls" or "bicyclic aryl", the term "fused cycloalkyl" or "fused aryl" or "annellated cycloalkyl" or "annellated aryl" denotes bicyclic rings wherein the bridge separating the rings denotes a direct single bond. The following are examples of a fused or annellated, bicyclic cycloalkyl:

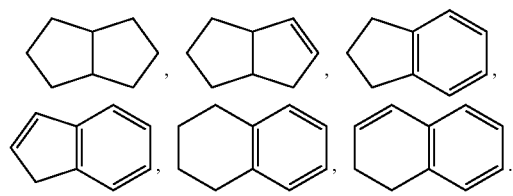

Although included by the term "bicyclic heterocycles" or "bicyclic heteroaryls", the term "fused bicyclic heterocycles", "fused bicyclic heteroaryls", "annellated heteroaryls" or "annellated heterocycles" denote bicyclic 9-10 membered heterorings which contain one, two, three or four heteroatoms, selected from among oxygen, sulphur and nitrogen and wherein the bridge separating the rings denotes a direct single bond. The "fused" or "annellated" bicyclic heteroaryls moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

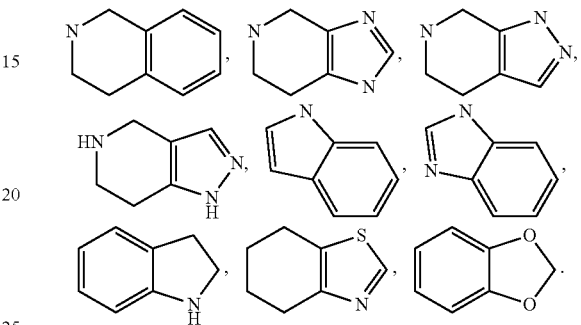

By the term "spiro group" or "Spiro heterocycle" (spiro) are meant 8-10 membered, spirocyclic rings which may optionally contain one, two or three heteroatoms, selected from among oxygen, sulphur and nitrogen, while the spiro-ring comprises at least one nitrogen atom and may be linked to the molecule through this nitrogen atom. Unless otherwise mentioned, a spirocyclic ring may be provided with an oxo, methyl or ethyl group as substituent. Examples of this include:

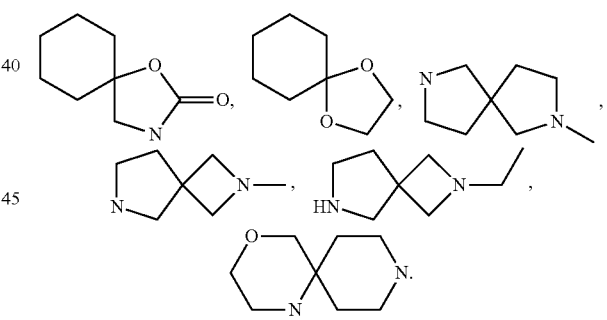

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, mainly carboxyl groups, and/or basic groups such as e.g. amino functions. Compounds of general formula 1 may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formula 1 may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formula 1 when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compound of formula 1 wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formula 1 may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds according to the invention may optionally be present as racemates, but may also be obtained as pure enantiomers.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formula 1 in the form of the pharmacologically acceptable salts thereof. These pharmacologically acceptable salts of the compounds of formula 1 may also be present in the form of their respective hydrates (e.g. Monohydrates, dihydrates, etc.) as well as in the form of their respective solvates.

By a hydrate of the compound according to the formula 1 is meant, for the purposes of the invention, a crystalline salt of the compound according to formula 1, containing water of crystallisation.

By a solvate of the compound according to formula 1 meant, for the purposes of the invention, a crystalline salt of the compound according to formula 1, which contains solvent molecules (e.g. Ethanol, methanol etc) in the crystal lattice.

The skilled man will be familiar with the standard methods of obtaining hydrates and solvates (e.g. recrystallisation from the corresponding solvent or from water).

4. METHODS OF PREPARATION

The Examples 1 according to the invention were prepared according to Scheme 1-8.

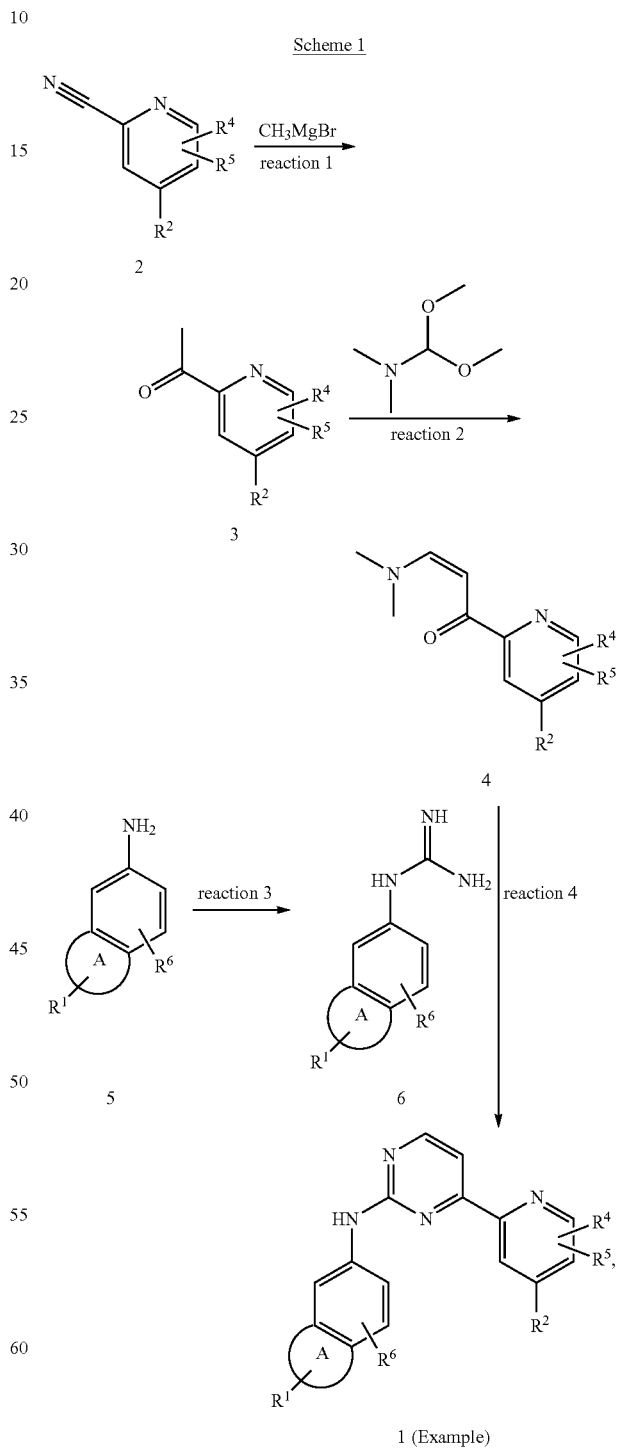

wherein $R^1$, $R^2$, $R^4$, $R^5$ $R^6$ and A are herein defined as aforementioned.

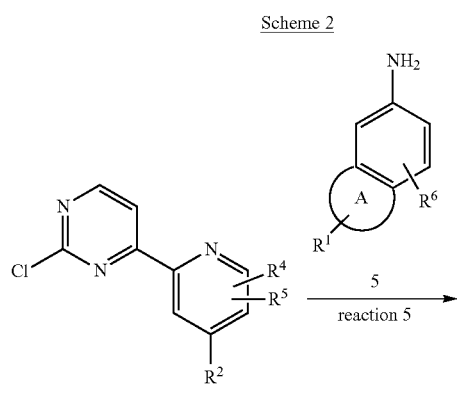
wherein $R^1$, $R^2$, $R^4$, $R^5$, $R^6$ and A are herein defined as aforementioned.
wherein $R^1$, $R^2$, $R^4$, $R^5$, $R^6$ and A are herein defined as aforementioned
wherein $R^7$ is selected from the group consisting of —Y, —N(CH$_3$)—Y and —N(CH$^3$)—(C$_{1-3}$-alkylene)-Y, and
wherein Y is defined as previously and in the subsequent claims described.

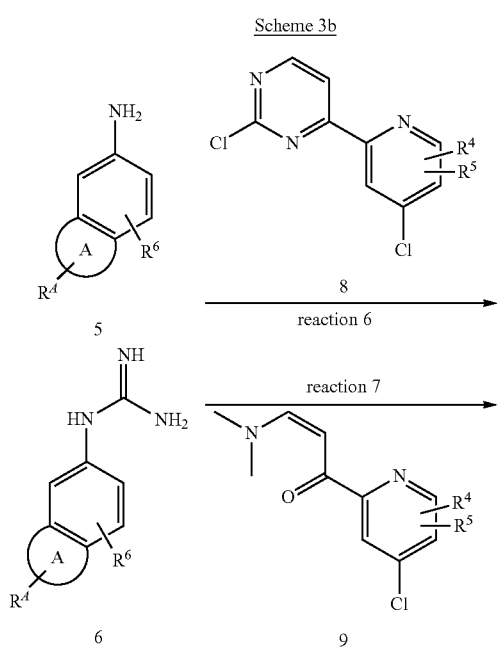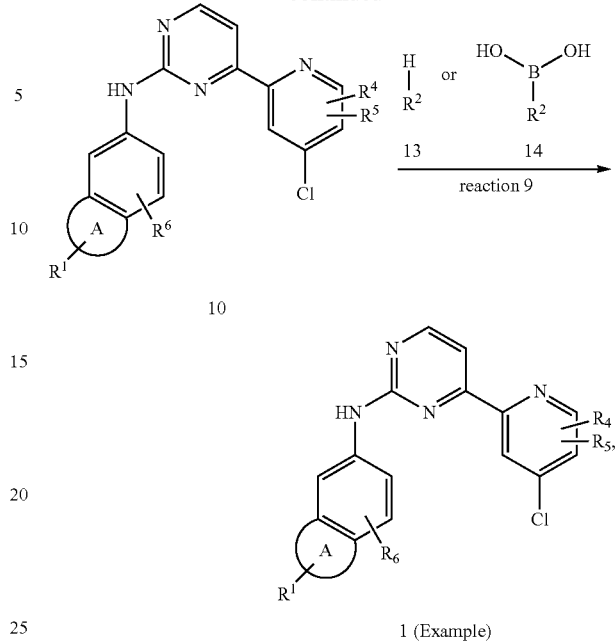
wherein $R^1$, $R^2$, $R^4$, $R^5$, $R^6$ and A are defined as previously disclosed.
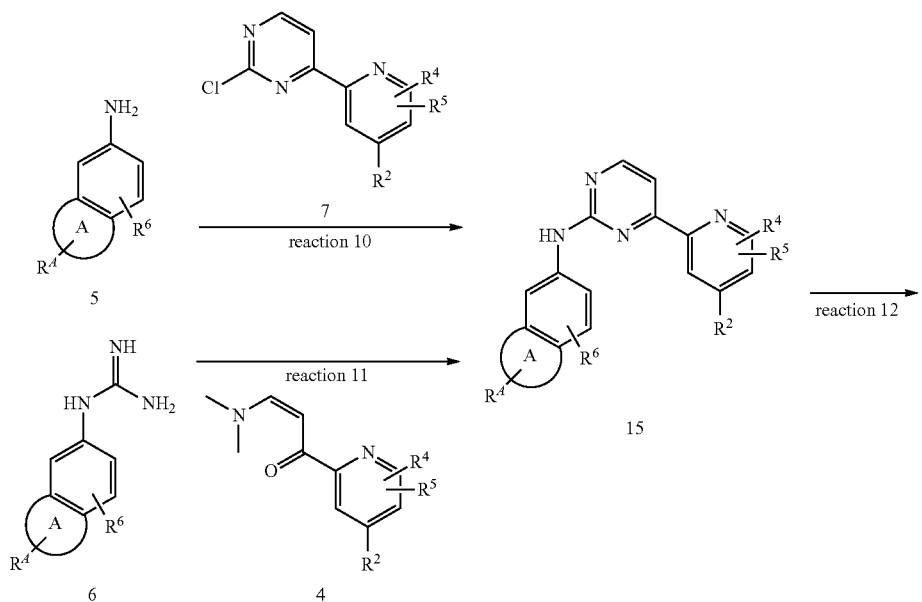

-continued
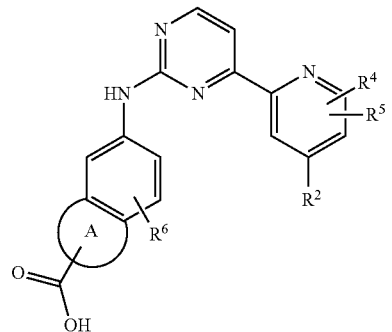
16
R⁷—H  reaction 13
11
1 (Example)
R⁴ = COOMe; COOEt
wherein R¹, R², R⁴, R⁵, R⁶ and A are defined as herein previously disclosed,
wherein R⁴ denotes —CO—O(CH₃) or —CO—O—(CH₂)—(CH₃) and
wherein R⁷ denotes —Y, —N(CH₃)—Y and —N(CH³)—(C₁₋₃-alkylene)-Y,
wherein Y is defined as previously and in the subsequent claims described.
Scheme 5
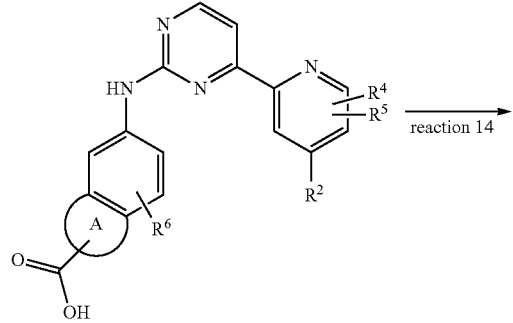
16
reaction 14
-continued
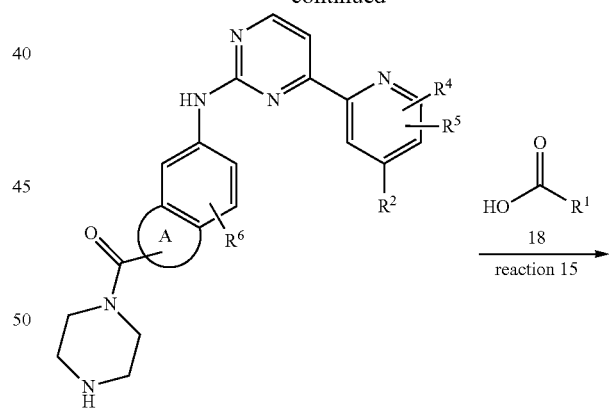
17
1 (Example)

wherein $R^1$, $R^2$, $R^4$, $R^5$, $R^6$ and A are defined as herein previously disclosed.
Scheme 6
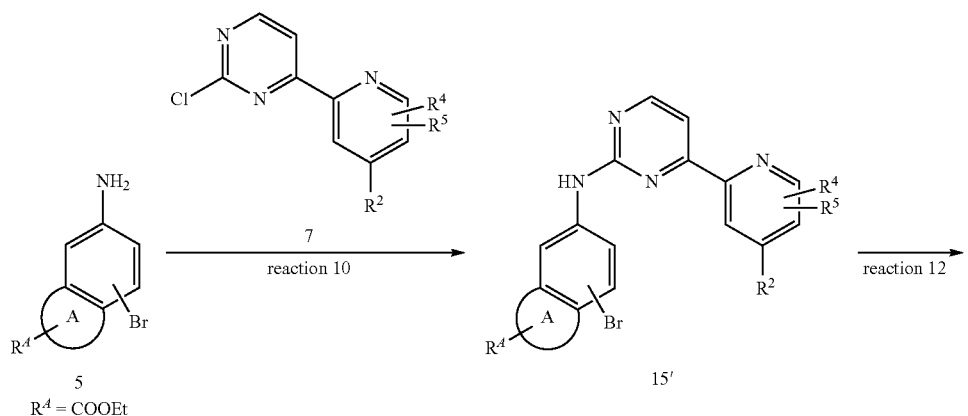
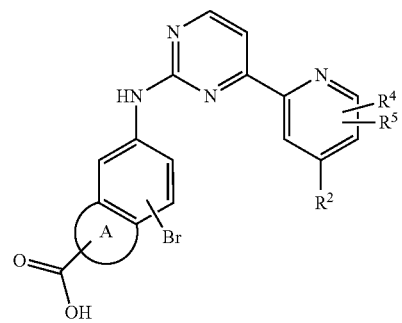
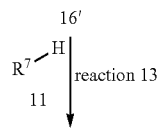
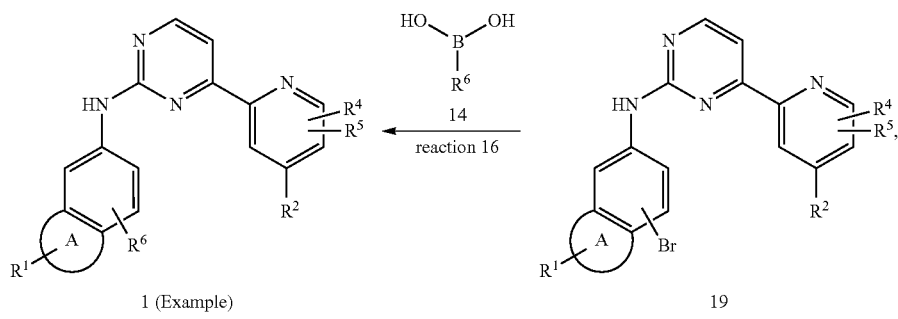
wherein $R^1$, $R^2$, $R^4$, $R^5$, $R^6$ and A are defined as herein previously disclosed
and wherein $R^7$ denotes a group selected from —Y, —N(CH$_3$)—Y and —N(CH$_3$)—(C$_{1-3}$-alkylene)-Y and
wherein Y is defined as previously and in the subsequent claims described.
Scheme 7
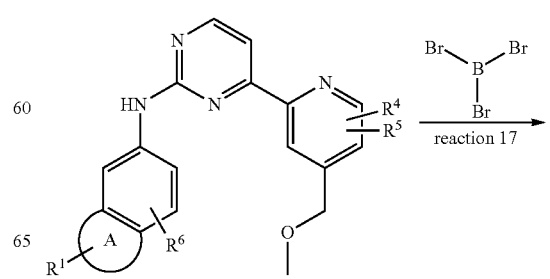

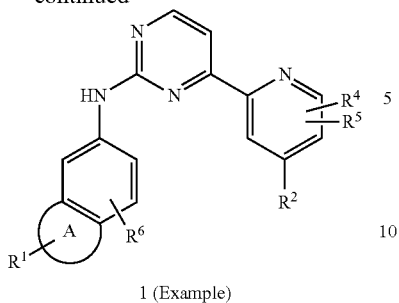

1 (Example)

wherein $R^1$, $R^2$, $R^4$, $R^5$, $R^6$ and A are defined as herein previously disclosed.

Scheme 8

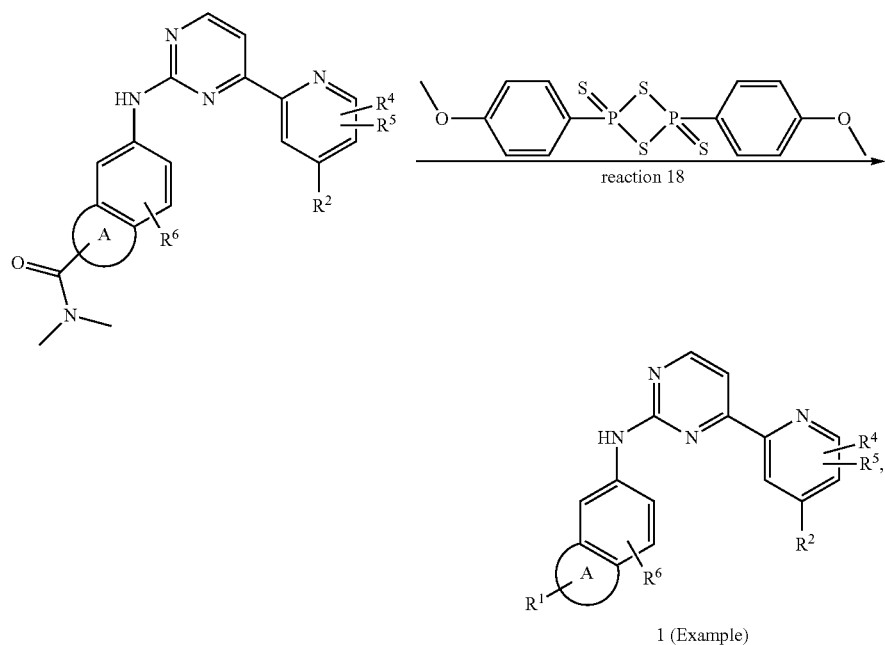

1 (Example)

wherein $R^1$, $R^2$, $R^4$, $R^5$, $R^6$ and A are defined as herein previously disclosed.

Optionally the groups $R^1$ or $R^2$ (Scheme 1-5) may subsequently be changed.

4.1 Intermediate Products

4.1.1 Synthesis of Compounds with Formula 3: Reaction 1 from Scheme 1

Synthesis of 1-(4-methoxymethyl-pyridin-2-yl)-ethanone (3.1) for Example 7, 8, 247, 248, 251-256, 258, 265, 289, 291, 292

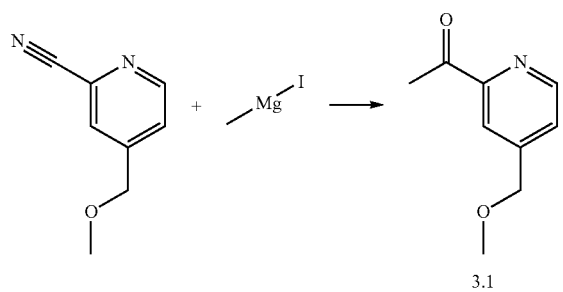

The synthesis of the starting material 4-methoxymethyl-pyridine-2-carbonitrile is described in the literature: Journal of the Chemical Society; 1963; page 3440-3444.

8.7 ml 3N methylmagnesiumiodide in tetrahydrofuran were added dropwise to a mixture of 3.4 g 4-methoxymethyl-pyridine-2-carbonitrile in 80 ml diethylether at 0° C. The mixture was warmed up to room temperature. After 2 h the reaction was cooled with an ice bath to 0° C. and diluted with 25 ml 1N hydrochloric acid. The reaction mixture was extracted with diethylether. The organic layer was dried with magnesium sulfate and concentrated under reduced pressure to obtain the title compound.

Yield: 3.2 g of 3.1 (84% of theory); Analysis: $[M+H]^+=166$

The Synthesis of the Following Compounds is Described in the Literature:

2-Acetyl-4-methoxypyridine (3.2) for Examples 16, 58-61, 64, 65, 67, 257: Pfizer Inc.; U.S. Pat. No. 6,300,363; 2001

1-(4-tert-Butyl-pyridin-2-yl)-ethanone (3.3) for Example 49: Journal of the American Chemical Society, 1997, vol. 119, page 5606-5617

1-(4-Isopropyl-pyridin-2-yl)-ethanone (3.4) for Example 53: Shiono Koryo Kaisha, Ltd.: Lion Corporation Patent: U.S. Pat. No. 5,214,027 A1, 1993

1-(4-Ethyl-pyridin-2-yl)-ethanone (3.5) for Example 63: Journal of American Chemical Society, 1997, vol. 119, page 5606-5617)

All of the Following Ketones are Commercially Available:
1-(6-Fluoro-pyridin-2-yl)-ethanone (3.6) for Examples 272, 278
1-(6-Methoxy-pyridin-2-yl)-ethanone (3.7) for Example 222
1-(4-Chloro-pyridin-2-yl)-ethanone (3.8) for Examples 1, 4, 15, 26, 28, 30, 31, 32, 33, 35, 37-42, 46-48, 68-109, 197-214, 218, 221, 229, 244, 246, 259-262, 266-271, 273-277, 280

4.1.2 Synthesis of Compounds with Formula 4: Reaction 2 from Scheme 1

Synthesis of 3-dimethylamino-1-(4-methoxymethyl-pyridin-2-yl)-propenone (4.1) for Example 7, 8, 247, 248, 251-256, 258, 265, 289, 291, 292

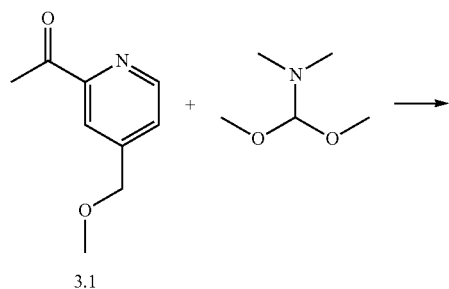

3.1

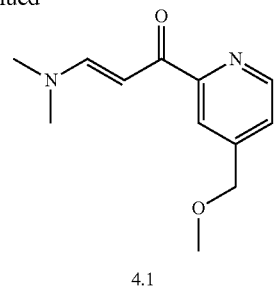

4.1

A mixture of 0.65 g 3.1 (1-(4-methoxymethyl-pyridin-2-yl)-ethanone) and 10 ml dimethoxymethyl-dimethyl-amine was heated at 110° C. for 21 h. The solvent was evaporated and the residue was purified by silica gel chromatography (SiO$_2$; ethyl acetate—0-10% methanol 9/1).

Yield: 0.304 g 4.1 (92% content, 35% of theory)

The Following Compounds were Produced by a Process Analogous to 4.1 Using the Corresponding Aryl Ketones:
3-Dimethylamino-1-(4-methoxy-pyridin-2-yl)-propenone (4.2) for Examples 16, 58-61, 64, 65, 67, 257
1-(4-tert-Butyl-pyridin-2-yl)-3-dimethylamino-propenone (4.3) for Example 49
3-Dimethylamino-1-(4-isopropyl-pyridin-2-yl)-propenone (4.4) for Example 53
3-Dimethylamino-1-(4-ethyl-pyridin-2-yl)-propenone (4.5) for Example 63
3-Dimethylamino-1-(6-fluoro-pyridin-2-yl)-propenone (4.6) for Examples 272, 278
3-Dimethylamino-1-(6-methoxy-pyridin-2-yl)-propenone (4.7) for Example 222

Synthesis of 3-dimethylamino-1-(5-hydroxymethyl-pyridin-2-yl)-propenone (4.8) for Example 219

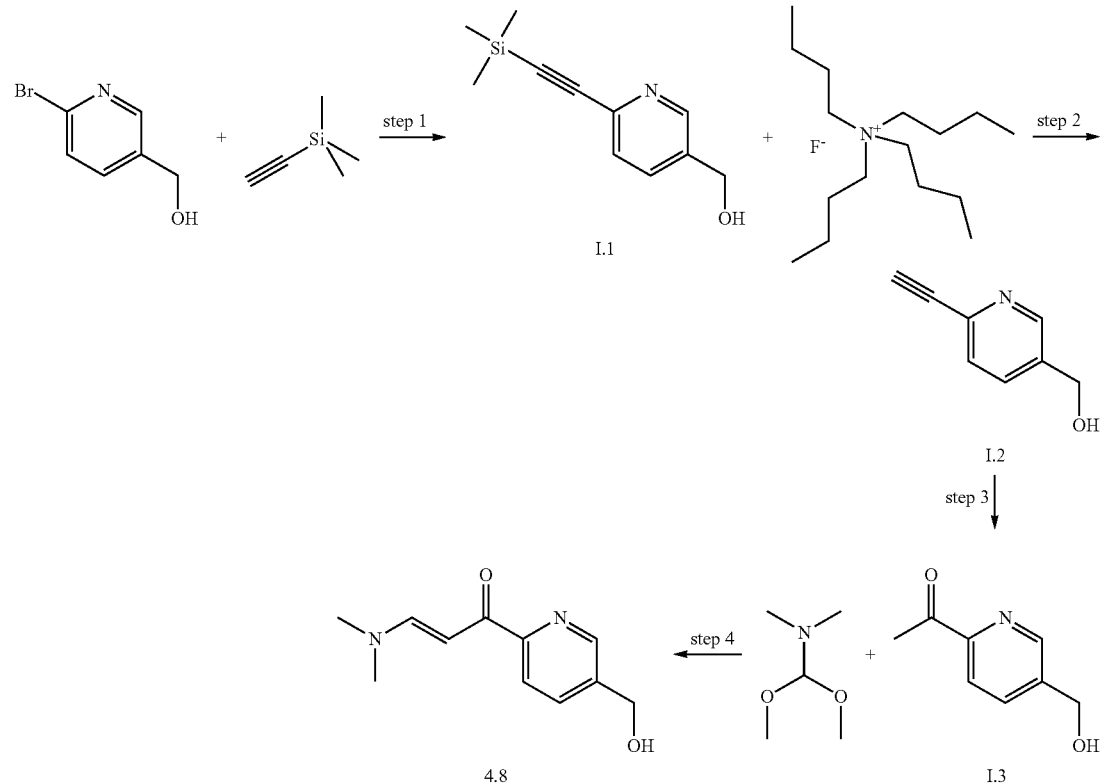

Step 1

3.07 ml Trimethylsilylacetylene in 8 ml tetrahydrofuran were added dropwise to a mixture of 3.4 g (6-bromo-pyridin-3-yl)-methanol, 0.254 g bis-(triphenylphospine)-palladium-II-chloride, 70 mg copper (I) iodide and 10 ml triethylamine in 40 ml tetrahydrofuran (slightly exothermic). The resulting mixture was stirred at ambient temperature for 1 h. The reaction mixture was concentrated under reduced pressure and diluted with 100 ml water. The aqueous mixture was extracted with ethyl acetate (3×). The combined organic layers were washed with an aqueous ammonia solution and water, dried with magnesium sulfate and evaporated to obtain the intermediate I.1.

Yield: 4.0 g of I.1 (90% content; 97% of theory) Analysis: $[M+H]^+=206$; HPLC-MS (method F): $R_t=1.3$ min Step 2

A mixture of 12.3 g intermediate I.1 (6-trimethylsilanyl-ethynyl-pyridin-3-yl)-methanol, 16.57 g tetrabutylammonium fluoride hydrate (TBAF) and 250 ml dichloromethane was stirred at ambient temperature for 20 min. The reaction mixture was extracted with 150 ml water (3×). The organic layer was dried with magnesium sulfate and concentrated under reduced pressure. The residue was purified by silica gel chromatography ($SiO_2$; petroleum ether/ethyl acetate: 1/1) to give 1.3 g of the intermediate I.2.

The aqueous layer was washed with dichloromethane (3×). The combined organic layers were dried with magnesium sulfate and evaporated under reduced pressure to give 2.2 g of the intermediate I.2.

Yield: 3.5 g I.2 (49% of theory) Analysis: $[M+H]^+=134$; HPLC-MS (method F): $R_t=0.56$ min Step 3

A mixture of 3.3 g I.2 (6-ethynyl-pyridin-3-yl)-methanol), 0.735 g mercury sulfate and 25 ml 25% aqueous sulfuric acid in 70 ml acetone was stirred at reflux for 3 h, then at ambient temperature overnight. Additional 0.5 g mercury sulfate was added and stirred for 10 min at reflux. The mixture was evaporated under reduced pressure, diluted with water and the pH was adjusted to ~7 with sodium carbonate. The aqueous layer was extracted with ethyl acetate (4×) and dried with magnesium sulfate. The solvent was evaporated under reduced pressure. The resulting residue was purified by silica gel chromatography ($SiO_2$; petroleum ether/ethyl acetate 1:1).

Yield: 2.1 g I.3 (56% of theory) Analysis: $[M+H]^+=152$; HPLC-MS (method F): $R_t=0.61$ min Step 4

Compound 4.8 was prepared by a process analogous to procedure 4.1 using intermediate I.3.

The Synthesis of the Following Compounds is Described in the Literature:

3-Dimethylamino-1-pyridin-2-yl-propenone (4.9) for Examples 11, 43, 50-52, 54, 55, 66, 110-193, 215, 217, 220, 283: European Journal of Inorganic Chemistry; 26; 2007; page 4197-4206

3-Dimethylamino-1-(4-trifluoromethyl-pyridin-2-yl)-propenone (4.10) for Example 232: Patent; Ishihara Sangyo Kaisha; WO2008-99902; 2008

3-Dimethylamino-1-(4-methyl-pyridin-2-yl)-propenone (4.11) for Example 6: Journal of the American Chemical Society; vol. 119; 1997; page 5606-5617

4.1.3 Synthesis of Compounds with Formula 5 from Scheme 1, 2, 3a, 3b and 4

All of the Following Anilines are Commercially Available:

1,3-Dihydro-isobenzofuran-5-ylamine (5.1) for Examples 1, 238

2-tert-Butyl-1H-indol-5-ylamine (5.2) for Examples 4, 7, 27

1-Methyl-1H-benzoimidazol-5-ylamine (5.3) for Example 215

6-Amino-1H-indole-2-carboxylic acid methyl ester (5.4) for Examples 51, 52, 229, 244, 246, 259, 271

5-Amino-benzo[b]thiophene-2-carboxylic acid methyl ester (5.5) for Examples 54, 55, 62

5-Amino-3-methyl-benzo[b]thiophene-2-carboxylic acid ethyl ester (5.6) for Example 2

6-Amino-3-chloro-benzo[b]thiophene-2-carboxylic acid methyl ester (5.7) for Example 3

1H-Indazol-5-ylamine (5.8) for Example 20

Indan-5-ylamine (5.9) for Example 24

1H-Indol-5-ylamine (5.10) for Example 23

1H-Indol-6-ylamine (5.11) for Example 25

5-Amino-benzofuran-2-carboxylic acid ethyl ester (5.12) for Examples 56, 57

2-Methyl-1H-indol-5-ylamine (5.13) for Example 29

1-(5-Amino-2,3-dihydro-1H-indol-3-yl)-ethanone (5.14) for Example 281

5-Amino-3H-benzooxazol-2-one (5.15) for Example 195

Benzothiazole-2,6-diamine (5.16) for Example 194

6-Amino-3H-benzothiazol-2-one (5.17) for Example 233

2-Pyridin-2-yl-1H-benzoimidazol-5-ylamine (5.18) for Example 234

2-Thiophen-2-yl-benzooxazol-6-ylamine (5.19) for Example 235

6-Amino-3H-benzooxazol-2-one (5.20) for Example 236

4-Chloro-1H-indol-6-ylamine hydrochloride (5.21) for Example 237

6-Amino-1H-benzoimidazole-2-thiol (5.22) for Example 240

Benzothiazol-6-ylamine (5.23) for Example 241

The Synthesis of the Following Compounds is Described in the Literature:

5-Amino-2,3-dihydro-indole-1-carboxylic acid methylamide (5.24) for Example 216: Boehringer Ingelheim International GmbH Patent: WO2009/16119 A1, 2009

5-Amino-1-methyl-1H-indole-2-carboxylic acid methyl ester/5-Amino-1-methyl-1H-indole-2-carboxylic acid ethyl ester (5.25) for Example 32, 47: Pharmagene Laboratories Limited Patent: WO2005/80367 A1; 2005/Boehringer Ingelheim (Canada) Ltd. Patent: US2003/236251 A1; 2003)

5-Amino-1H-indole-2-carboxylic acid ethyl ester (5.26) for Examples 6, 8, 10-12, 16, 26, 28, 30, 31, 33-44, 49, 50, 53, 58-61, 63, 65, 67-193, 197-214, 253-258, 260-262, 273-277, 283: Bayer Healthcare AG; WO2008/56768; A2; 2004)

5-Amino-1H-indole-2-carboxylic acid dimethylamide (5.27) for Example 219, 222, 232: Vertex Pharmaceuticals Incorporated Patent: WO2006/10008; A1; 2006)

6-Amino-1-methyl-1H-indole-2-carboxylic acid methyl ester (5.28) for Examples 66, 265, 266-270: Banyu Pharmaceutical Co. Patent: WO2007/29847 A1; 2007

Synthesis of 5-amino-7-chloro-1H-indole-2-carboxylic acid ethyl ester (5.29) for Example 249-252, 263, 272, 282, 289-291

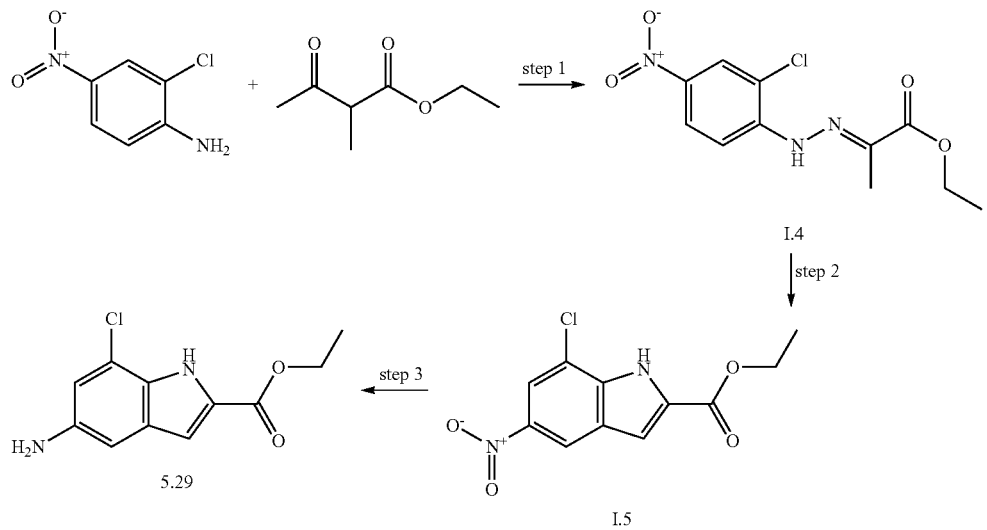

Step 1

A solution of 138 g sodium nitrite in 500 ml water was added dropwise at 0° C. to a solution of 345 g 2-chloro-4-nitro-phenylamine in 2.5 L 4N aqueous hydrochloride acid. The resulting mixture was stirred for 30 min. The reaction mixture was added to a stirred mixture of 317 g 2-methyl-3-oxo-butyric acid ethyl ester, 582 g potassium hydroxide and 582 g sodium acetate in 2.5 L ethanol and 3.3 L water. The resulting reaction mixture was stirred for 1 h at 0° C. The precipitate was filtered, washed with water and ethanol to give I.4.

Yield: 241 g I.4 (42% of theory)

Step 2

A mixture of 245 g I.4 (2-[(2-chloro-4-nitro-phenyl)-hydrazono]-propionic acid ethyl ester) in 1.5 kg polyphosphoric acid was stirred for 1 h at 70° C. The mixture was quenched with ice-water and the precipitate was filtered. The solid was washed with ethyl acetate and ethanol to give the intermediate I.5.

Yield: 36 g I.5 (16% of theory)

Step 3

In a pressure vessel a mixture of 5 g I.5 (7-chloro-5-nitro-1H-indole-2-carboxylic acid ethyl ester) with 0.5 g Pt/C 10% and 200 ml tetrahydrofuran/methanol 3:1 was stirred for 20 h under a pressure of 50 psi hydrogen. The catalyst was filtered and the solvent was evaporated under reduced pressure. The residue was purified by silica gel chromatography (SiO$_2$; cyclohexane/ethyl acetate 75:25→50:50) to obtain the compound 5.29.

Yield: 1.3 g 5.29 (29% of theory)

Synthesis of 5-amino-7-chloro-1H-indole-2-carboxylic acid dimethylamide (5.30) for Example 279

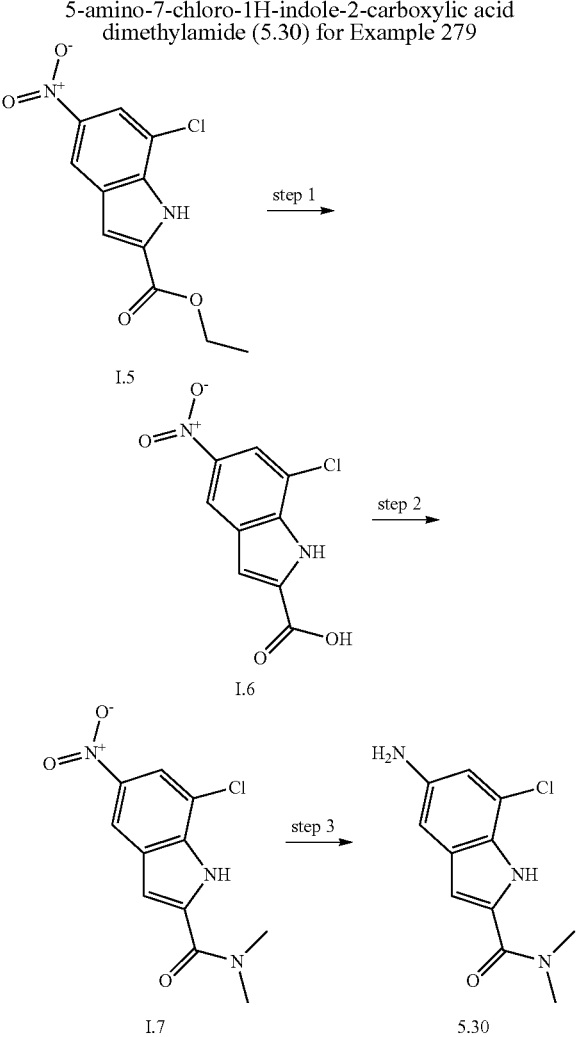

Step 1

A mixture of 5 g I.5 (7-chloro-5-nitro-1H-indole-2-carboxylic acid ethyl ester) in 100 ml ethanol and 47 ml 1N aqueous sodium hydroxide was stirred for 2 h at 60° C. The solvent was evaporated and the residue was acidified with aqueous hydrochloric acid to pH 5-6. The resulting precipitate was filtered, washed with water and dried.

Yield: 4.6 g I.6 (quantitative); Analysis: $[M+H]^+=241$ (Cl isotope pattern); HPLC-MS (method A): $R_t=1.93$ min Step 2

7.5 g [(Benzotriazol-1-yloxy)-dimethylamino-methylene]-dimethyl-ammonium tetrafluoro-borate (TBTU) was added to a solution of 4.6 g I.6 (7-chloro-5-nitro-1H-indole-2-carboxylic acid), 6.7 ml N,N-diisopropylethylamine in 50 ml N,N-dimethylformamide. The resulting mixture was stirred for 2 min at ambient temperature. 19 ml 2N dimethylamine in tetrahydrofuran were added and the resulting reaction mixture was stirred at ambient temperature overnight. The reaction mixture was filtered through a pad of aluminium oxide, the pad was washed with N,N-dimethylformamide/methanol 9:1 and the solvent was evaporated under reduced pressure. The crude product was triturated with water, the solid was filtered, washed with water and dried.

Yield: 4.96 g I.7 (97% of theory); Analysis: $[M+H]^+=241$; HPLC-MS (method A): $R_t=2.05$ min Step 3

A mixture of 2.6 g I.7 (7-chloro-5-nitro-1H-indole-2-carboxylic acid dimethylamide), 0.3 g Pt/C 10%, 10 ml methanol and 90 ml tetrahydrofuran was stirred ambient temperature under a pressure of 50 psi hydrogen. The catalyst was filtered and the solvent was evaporated. The resulting crude material was used for the next step without purification.

Yield: 2.2 g 5.30 (95% of theory); Analysis: $[M+H]^+=238$; HPLC-MS (method B): $R_t=1.86$ min Synthesis of 5-amino-1H-indole-2-carboxylic acid methylamide (5.31) for Example 284

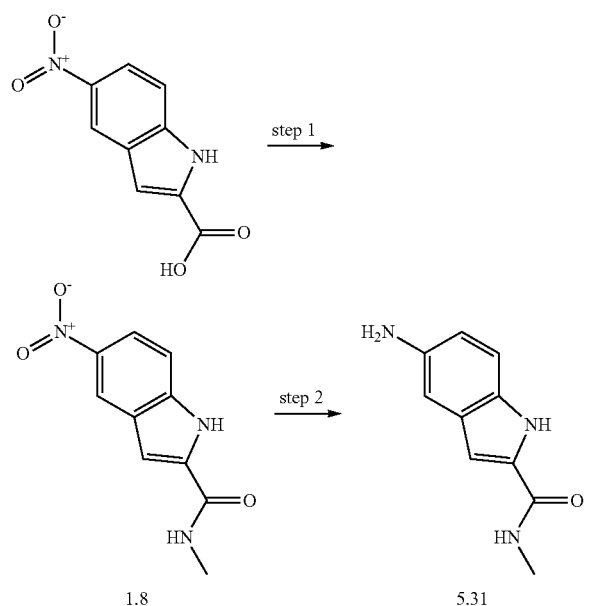

Step 1

A mixture of 0.62 g 5-nitro-1H-indole-2-carboxylic acid, 0.96 g [(benzotriazol-1-yloxy)-dimethylamino-methylene]-dimethyl-ammonium tetrafluoroborate (TBTU), 0.516 N,N-diisopropylethylamine in 3 ml N,N-dimethylformamide was stirred at ambient temperature for a few minutes before 3 ml of 2N methylamine in tetrahydrofuran were added and the reaction mixture was stirred 2 h at ambient temperature. The reaction solvent was evaporated. The resulting residue was diluted with water, the aqueous layer was treated with 1N aqueous sodium hydroxide to reach a basic pH. The yellow precipitate was filtered and washed with water.

Yield: 0.5 g I.8 (76% of theory)

Step 2

A suspension of 0.5 g I.8 (5-nitro-1H-indole-2-carboxylic acid methylamide), 0.1 g Pd/C 10% in 30 ml methanol and 35 ml tetrahydrofuran was stirred under a pressure of 3 bar hydrogen at ambient temperature. The catalyst was filtered and the solvent was removed under reduced pressure. The residue was triturated with diethylether/dichloromethane. The solvent was distilled off to obtain compound 5.31 as a yellow solid.

Yield: 0.397 g 5.31 (92% of theory)

Synthesis of 2,7-bis-trifluoromethyl-1H-benzoimidazol-5-ylamine (5.32) for Example 286

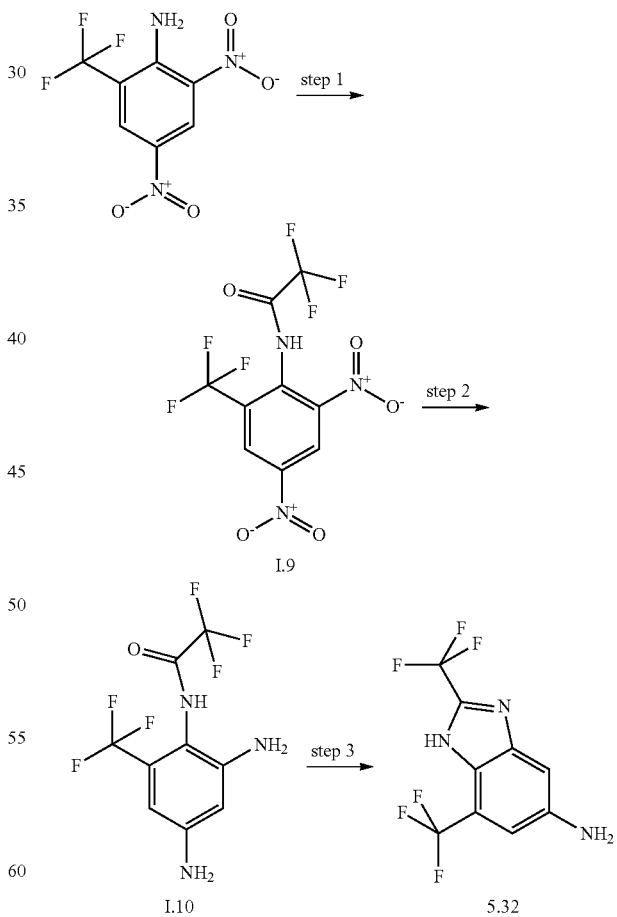

Step 1

The synthesis of the starting material 2,4-dinitro-6-trifluoromethyl-phenylamine is described in the literature: Du Pont de Nemours and Co. Patent: U.S. Pat. No. 2,194,925, 1937

0.632 ml Trifluoroacetic anhydride was added slowly dropwise to a suspension of 0.76 g 2.4-dinitro-6-trifluoromethyl-phenylamine and 0.631 ml triethylamine in 8 ml dichloromethane. The resulting solution (exothermic) was stirred at ambient temperature overnight. The reaction mixture was cooled down, additional 5.9 ml trifluoroacetic anhydride were added in portions over 5 days followed by warming up to 45° C. The reaction mixture contains still 2.4-dinitro-6-trifluoromethyl-phenylamine. 3 ml Triethylamine were added (reacts violently) and the mixture was stirred another 2 h at 45° C. The reaction mixture was cooled down to ambient temperature and treated with water. The aqueous reaction mixture was extracted with dichloromethane. The organic layer was washed with water (2×) and dried with sodium sulfate. The solvent was evaporated and the crude I.9 was used for the next step without purification.

Yield: 1.17 g I.9 crude

Step 2

1.17 g I.9 (N-(2,4-Dinitro-6-trifluoromethyl-phenyl)-2,2,2-trifluoro-acetamide) was mixed with 0.3 g Raney-nickel and 50 ml tetrahydrofuran. The mixture was stirred at ambient temperature under a pressure of 3 bar hydrogen. The catalyst was filtered. The solvent was evaporated to give 1.10 which was used in the next step without purification.

Yield: 1.09 g I.10 (crude)

Step 3

A mixture of 1.1 g I.10 (N-(2,4-diamino-6-trifluoromethyl-phenyl)-2,2,2-trifluoro-acetamide) and 10 ml glacial acetic acid was stirred at 55° C. for 4 h and then at ambient temperature overnight. The solvent was evaporated and the resulting residue was purified by silica gel chromatography (SiO$_2$; dichloromethane/0-4% ethanol) to obtain compound 5.32.

Yield: 0.46 g 5.32 (45% of theory); Analysis [M+H]$^+$=270

Synthesis of 2-methyl-7-trifluoromethyl-1H-benzoimidazol-5-ylamine (5.33) for Example 288

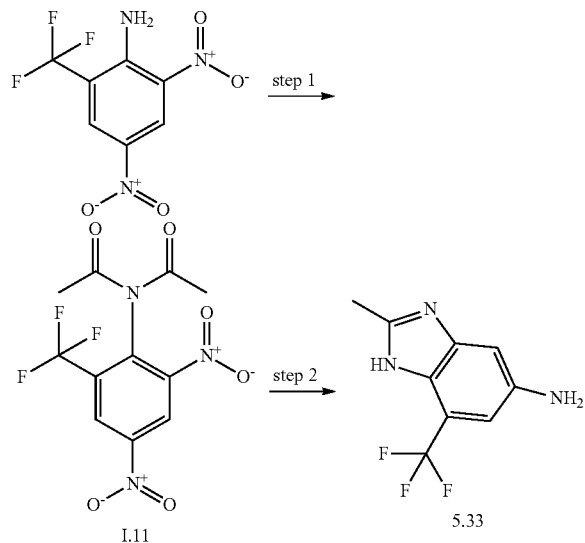

Step 1

A mixture of 1.45 g 2,4-dinitro-6-trifluoromethyl-phenylamine in 20 ml acetic anhydride was refluxed for 3 h. The reaction mixture was concentrated. The residue was purified by preparative HPLC to give the intermediate I.11.

Yield: 1.45 g I.11 (75% of theory); Analysis: HPLC-MS (method F): R$_t$=1.7 min

Step 2

A mixture of 0.63 g I.11 (N-acetyl-N-(2,4-dinitro-6-trifluoromethyl-phenyl)-acetamide) and 0.2 g Pd/C 10% in 20 ml glacial acetic acid was stirred for 5 h at 80° C. under a pressure of hydrogen of 50 psi. The catalyst was filtered and the solvent was evaporated. To the residue, 30 ml glacial acetic acid were added and the mixture was stirred for 2 h at reflux. The solvent was removed. The residue was treated with 50 ml 4 N aqueous hydrochloric acid and stirred for 1 h at reflux. The reaction mixture was cooled down to ambient temperature and the pH was adjusted to ~7 with potassium carbonate. The resulting precipitate was filtered, washed with 30 ml water and dried.

Yield: 0.34 g 5.33 (84% of theory); Analysis [M+H]$^+$=216;

Synthesis of 7-chloro-3H-benzoimidazol-5-ylamine (5.34) for Example 287

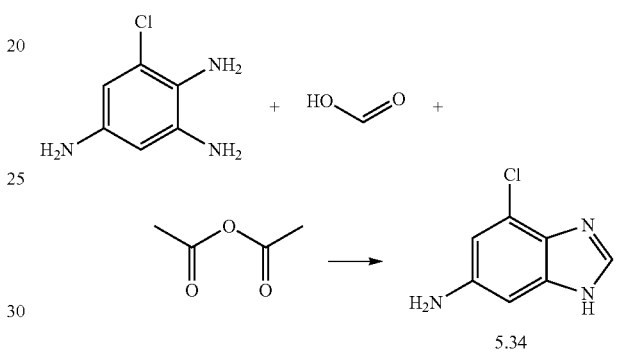

The synthesis of the starting material 6-chloro-benzene-1,2,4-triamine is described in the literature: Journal of the Chemical Society, Perkin Transactions 1: Organic and Bio-Organic Chemistry (1972-1999); 1987; page 2317-2320

65 ml Acetic anhydride were added to a mixture of 10 g 6-chloro-benzene-1,2,4-triamine in 65 ml formic acid and the mixture was stirred for 5 h at 100° C. The solvent was removed before 100 ml of 10N hydrochloric acid in ethanol were added to the residue, and the mixture was stirred at ambient temperature overnight. The solvent was evaporated, the residue was suspended in ethyl acetate, and the solid was filtered. The filtrate was purified by silica gel chromatography (SiO$_2$; ethyl acetate/(methanol/ammonia 9/1) 95:5→75:25). The combined product fractions were concentrated to obtain compound 5.34.

Yield: 0.8 g 5.34 (8% of theory); Analysis [M+H]$^+$=168; HPLC-MS (method C): R$_t$=1.39 min Synthesis of 5-amino-1H-indole-3-carboxylic acid methylamide (5.35) for Example 284

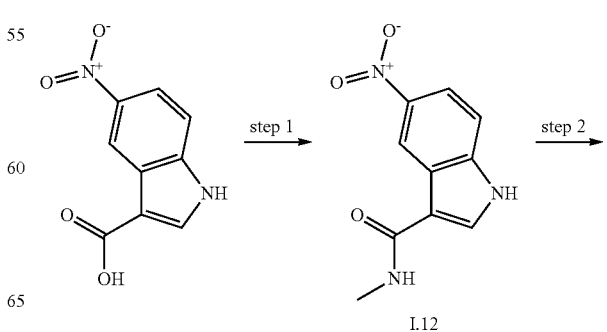

-continued

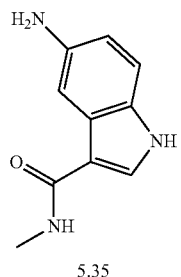

5.35

Step 1

3 ml 2N Methylamine in tetrahydrofuran were added to a mixture of 0.62 g 5-nitro-1H-indole-3-carboxylic acid, 0.96 g [(benzotriazol-1-yloxy)-dimethylamino-methylene]-dimethyl-ammonium tetrafluoroborate (TBTU) and 0.516 ml N,N-diisopropylethylamine in 3 ml N,N-dimethylformamide. The reaction mixture was stirred for 2 h at ambient temperature and then the solvent was evaporated. The residue was diluted with water and the aqueous layer was treated with 1N aqueous sodium hydroxide to obtain a basic pH. The yellow precipitate was filtered, washed with water and dried.

Yield: 0.5 g I.12 (76% of theory)

Step 2

A suspension of 0.5 g I.12 (5-nitro-1H-indole-3-carboxylic acid methylamide), 0.1 g Pd/C 10% in 35 ml tetrahydrofuran and 30 ml methanol was stirred at ambient temperature under a pressure of hydrogen of 50 psi. The catalyst was filtered and the solvent was evaporated. The residue was triturated with diethylether/dichloromethane and the solvent was evaporated to obtain the compound 5.35.

Yield: 0.397 g 5.35 (92% of theory)

Synthesis of
5-amino-7-methyl-1H-indole-2-carboxylic acid ethyl ester (5.36) for Examples 243, 245, 247, 264, 278, 285, 292

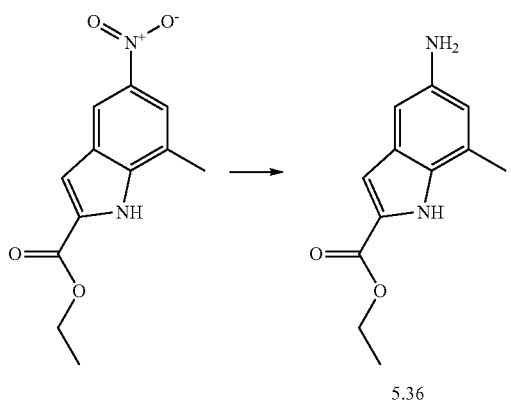 [SMILES: CCOC(=O)c1cc2cc([N+](=O)[O-])cc(C)c2[nH]1 ; CCOC(=O)c1cc2cc(N)cc(C)c2[nH]1]

5.36

The synthesis of the starting material 7-methyl-5-nitro-1H-indole-2-carboxylic acid ethyl ester is described in the literature: Journal of the Indian Chemical Society; 1964; vol. 41; page 357-361.

A mixture of 5 g 7-methyl-5-nitro-1H-indole-2-carboxylic acid ethyl ester and 0.5 g Pd/C 10% in 200 ml tetrahydrofuran/methanol (3:1) was stirred for 5 h under a pressure of 3 bar of hydrogen. The catalyst was filtered and the mixture was evaporated under reduced pressure. The residue was purified by silica gel chromatography (SiO$_2$; cyclohexane/ethyl acetate 75:25→50:50).

Yield: 1.3 g 5.36 (30% of theory)

Synthesis of
5-amino-7-methyl-1H-indole-2-carboxylic acid dimethylamide (5.37) for Example 280

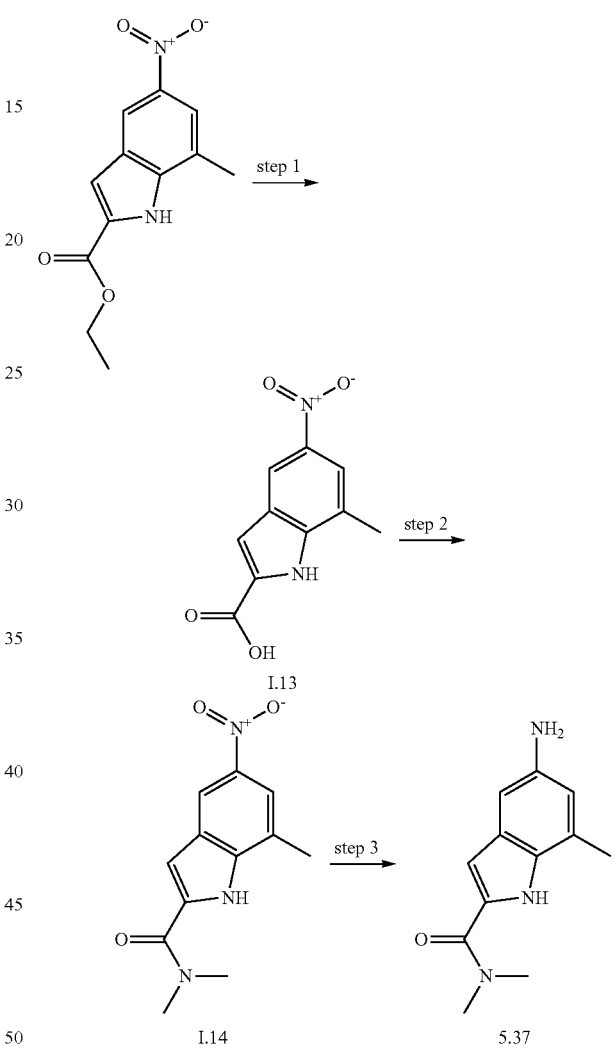

Step 1

A mixture of 5 g 7-methyl-5-nitro-1H-indole-2-carboxylic acid ethylester in 100 ml ethanol and 40 ml 1N sodium hydroxide was stirred for 2 h at 65° C. The mixture was evaporated and the residue was treated with 40 ml 1N hydrochloric acid. The resulting precipitate was filtered and dried.

Yield: 4.2 g I.13 (95% of theory)

Step 2

20 ml 2N Dimethylamine in tetrahydrofuran was added to a mixture of 4.2 g I.13 (7-methyl-5-nitro-1H-indole-2-carboxylic acid), 6.26 g [(benzotriazol-1-yloxy)-dimethylamino-methylene]-dimethyl-ammonium tetrafluoroborate (TBTU) in 3.44 ml N,N-diisopropylethylamine and 100 ml N,N-dimethylformamide. After stirring for 2 h at ambient temperature, the solvent was removed. The residue was diluted with 60 ml 1N sodium hydroxide. The precipitate was filtered to obtain the intermediate I.14.

Yield: 3.8 g I.14 (81% of theory)

Step 3

3.8 g I.14 (7-Methyl-5-amino-1H-indole-2-carboxylic acid dimethylamide) was mixed with 0.5 g Pd/C 10%, 40 ml methanol and 70 ml tetrahydrofuran. The mixture was stirred at ambient temperature under a pressure of 3 bar of hydrogen. The catalyst was filtered and the solvent was evaporated to give the compound 5.37.

Yield: 3.2 g 5.37 (96% of theory)

Synthesis of (5-amino-3-methyl-1H-indol-2-yl)-(4-methyl-piperazin-1-yl)-methanone hydrochloride (5.38) for Example 230

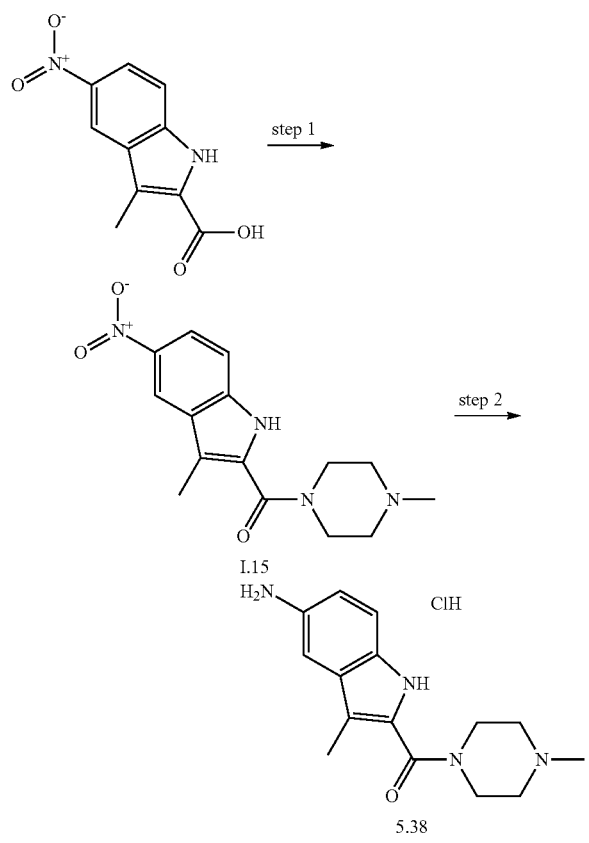

Step 1

To a stirred solution of 78 mg 3-methyl-5-nitro-1H-indole-2-carboxylic acid and 520 mg O-(7-azobenzotriazol-1-yl)-1,1,3,3-tetramethyluronium hexafluorophosphate (HATU) in 6 ml N,N-dimethylformamide were added 259 µl N-methylpiperazine. The reaction mixture was stirred at ambient temperature overnight. The solvent was evaporated and the resulting brown oil was dissolved in 30 ml ethyl acetate. The organic layer was washed with water (1×). The aqueous phase was washed with ethyl acetate (2×). The combined organic phases were washed with brine (1×), dried with sodium sulfate, filtered and evaporated. The solid was suspended in hot methanol. After cooling to ambient temperature, the solid was filtered to obtain I.15 as a yellow solid.

Yield: 262 mg I.15 (76% of theory) Analysis [M+H]$^+$=303; HPLC-MS (method H): R$_t$=1.18 min Step 2

A mixture of 0.245 g I.15 ((3-methyl-5-nitro-1H-indol-2-yl)-(4-methyl-piperazin-1-yl)-methanone), 25 mg Pd/C 10% in 25 ml ethanol and 20 ml ethyl acetate was stirred at ambient temperature under a hydrogen atmosphere. The reaction mixture was treated with 1N aqueous hydrochloric acid and stirring was continued under a hydrogen pressure of 50 psi for 16 h. The reaction mixture was filtered through a pad of Celite. The Celite pad was washed with ethanol and the solvent was evaporated to give a brown solid.

Yield: 245 mg 5.38 (98% of theory); Analysis [M+H]$^+$=273; HPLC-MS (method H): R$_t$=2.21 min Synthesis of 6-amino-4-methyl-3H-benzooxazol-2-one (5.39) for Example 196

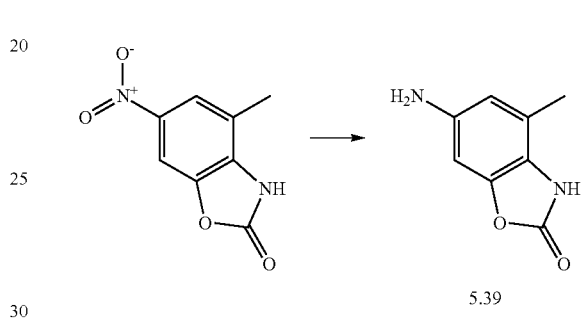

The synthesis of the starting material 4-methyl-6-nitro-3H-benzooxazol-2-one is described in literature: Journal of the Chemical Society; 1930; 2346-2353.

A mixture of 1.8 g 4-methyl-6-nitro-3H-benzooxazol-2-one and 0.2 g Pd/C 10% in 10 ml methanol was stirred for 3 h at ambient temperature under a pressure of 3 bar of hydrogen. The catalyst was filtered and the residue was triturated with diethylether. The solid was filtered and dried.

Yield: 1 g 5.39 (69% of theory); Analysis [M+H]$^+$=165

Synthesis of 5-amino-7-methoxy-1H-indole-2-carboxylic acid (5.40) for Examples 122, 144

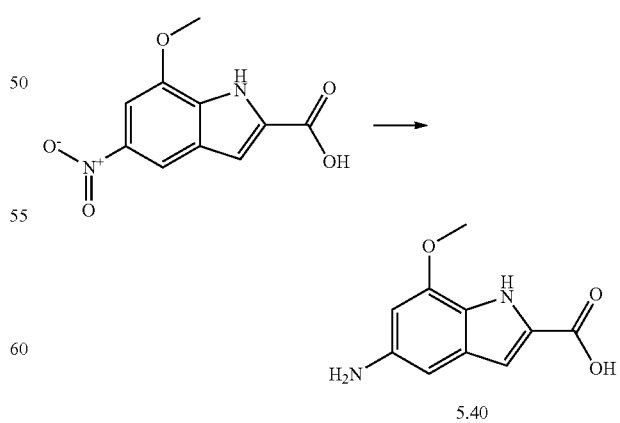

A mixture of 472 mg 7-methoxy-5-nitro-1H-indole-2-carboxylic acid and 0.1 g Pd/C 10% in 10 ml methanol and 20 ml tetrahydrofuran was stirred for 2 h at ambient temperature under a pressure of 3 bar of hydrogen. The catalyst was filtered and the filtrate was evaporated to obtain brown solid.

Yield: 1 g 5.40 (92% of theory); Analysis [M+H]⁺=330; HPLC-MS (method N): $R_t$=1.48 min Synthesis of
5-amino-7-methoxy-1H-indole-2-carboxylic acid hydrochloride (5.40) for Examples 239, 242

Step 4

A mixture of 9.6 g polyphosphoric acid and 963 mg I.18 (2-[(4-acetylamino-2-bromo-phenyl)-hydrazono]-propionic acid ethyl ester) was stirred in a pressure vessel for 1 h at 90° C. The reaction mixture was diluted with water. The resulting mixture was degassed in an ultrasound bath, filtered and the precipitate and was dried to obtain the intermediate I.19.

Yield: 997 mg I.19 (90% content; 98% of theory); Analysis [M+H]⁺=325

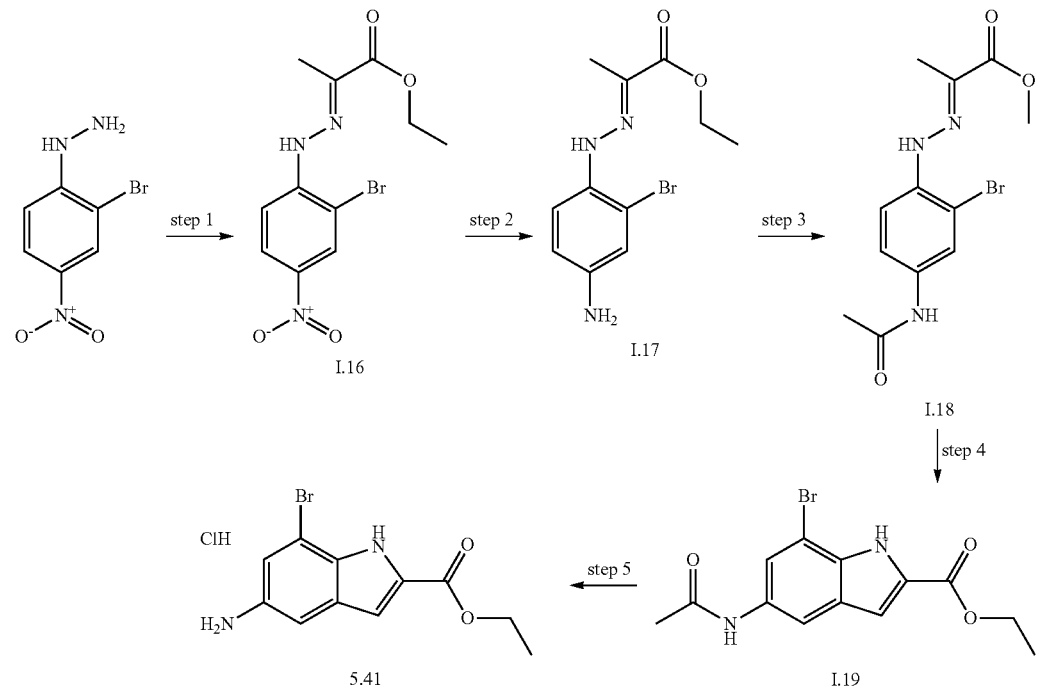

Step 1

A mixture of 4.79 g (2-bromo-4-nitro-phenyl)-hydrazine, 2.34 ml etyhl pyruvate in 25 ml dioxane were stirred for 30 minutes at ambient temperature. The reaction mixture was evaporated and the residue was triturated with diethylether. The solid was filtered and dried.

Yield: 4.8 g I.16 (71% of theory); Analysis [M+H]⁺=330; HPLC-MS (method N): $R_t$=1.48 min Step 2

A mixture of 2 g I.16 (2-[(2-bromo-4-nitro-phenyl)-hydrazono]-propionic acid ethyl ester) and 0.2 g Raney-nickel in 60 ml ethyl acetate was stirred for 6 h at ambient temperature and 6 h at 40° C. under a pressure of 3 bar of hydrogen. The catalyst was filtered and the filtrate was evaporated. The residue was used in the next step without purification.

Yield: 1.97 g I.17 (80% contain; 87% of theory)

Step 3

A mixture of 1.97 g I.17 (2-[(4-amino-2-bromo-phenyl)-hydrazono]-propionic acid ethyl ester) and 620 µl acetic anhydride in 30 ml N,N-dimethylformamide was stirred at ambient temperature overnight. The reaction mixture was evaporated, the residue dissolved in dichloromethane and purified by silica gel chromatography (SiO₂; cyclohexane/ethyl acetate 8/2→1/1). The combined product fractions were concentrated to give an orange product.

Yield: 1.21 g I.18 (54% of theory); Analysis [M+H]⁺=342

Step 5

A mixture of 982 mg I.19 (5-acetylamino-7-bromo-1H-indole-2-carboxylic acid ethyl ester), 10 ml ethanol and 1.8 ml concentrated hydrochloric acid was stirred for 4.5 h at reflux. The reaction mixture was evaporated. The residue was used in the next step without purification.

Yield: 916 mg 5.41 (95% of theory); Analysis [M+H]⁺= 283

4.1.4 Synthesis of Compounds with Formula 6:
Reaction 3 from Scheme 1

Synthesis of
N-(1,3-Dihydro-isobenzofuran-5-yl)-guanidine tosylate (6.1) for Example 1

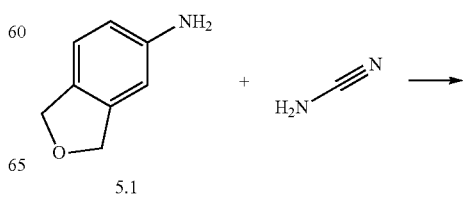

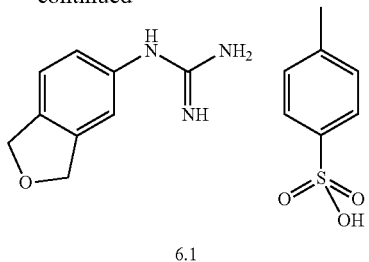

6.1

To a stirred mixture of 2.7 g 5.1 (1,3-dihydro-isobenzofuran-5-ylamine) in 40 ml dioxane was added 3.8 g p-toluenesulfonic acid and 1 g cyanamide. The reaction mixture was stirred at reflux for 2 h then at ambient temperature for 3 days. The precipitate was filtered, washed with dioxane and dried to give the compound 6.1.

Yield: 6.3 g 6.1 (90% of theory) Analysis: [M+H]⁺=178
The Following Guanidines are Prepared by Using an Procedure Analogous to 6.1 with the Corresponding Anilines:

N-(2-tert-Butyl-1H-indol-5-yl)-guanidine as toluene-4-sulfonic acid salt (6.2) for Example 7

N-(1-Methyl-1H-benzoimidazol-5-yl)-guanidine (6.3) for Example 215

6-Guanidino-1H-indole-2-carboxylic acid methyl ester tosylate (6.4) for Examples 51, 52, 229, 244, 246, 259, 271

5-Guanidino-benzo[b]thiophene-2-carboxylic acid methyl ester (6.5) for Examples 54, 55, 62, 64

5-Guanidino-1-methyl-1H-indole-2-carboxylic acid methyl ester/5-Guanidino-1-methyl-1H-indole-2-carboxylic acid ethyl ester (6.6) for Examples 32, 47, 48

5-Guanidino-1H-indole-2-carboxylic acid ethyl ester (6.7) for Examples 6, 8, 10-12, 16, 26, 28, 30, 31, 33-44, 49, 50, 53, 58-61, 63, 65, 67-193, 197-214, 253-258, 260-262, 273-277, 283

5-Guanidino-1H-indole-2-carboxylic acid dimethylamide (6.8) for Examples 219, 222, 232

6-Guanidino-1-methyl-1H-indole-2-carboxylic acid methyl ester (6.9) for Examples 66, 265, 266-270

5-Guanidino-7-methyl-1H-indole-2-carboxylic acid ethyl ester (6.10) for Examples 247, 278, 292

5-Guanidino-7-methyl-1H-indole-2-carboxylic acid dimethylamide tosylate (6.11) for Example 280

7-Chloro-5-guanidino-1H-indole-2-carboxylic acid ethyl ester (6.12) for Examples 251, 252, 272, 289-291

Synthesis of N-{2-[2-(3-methyl-2-oxo-imidazolidin-1-yl)-ethyl]-2,3-dihydro-1H-isoindol-5-yl}-guanidine hydrochloride (6.13) for Examples 217, 218

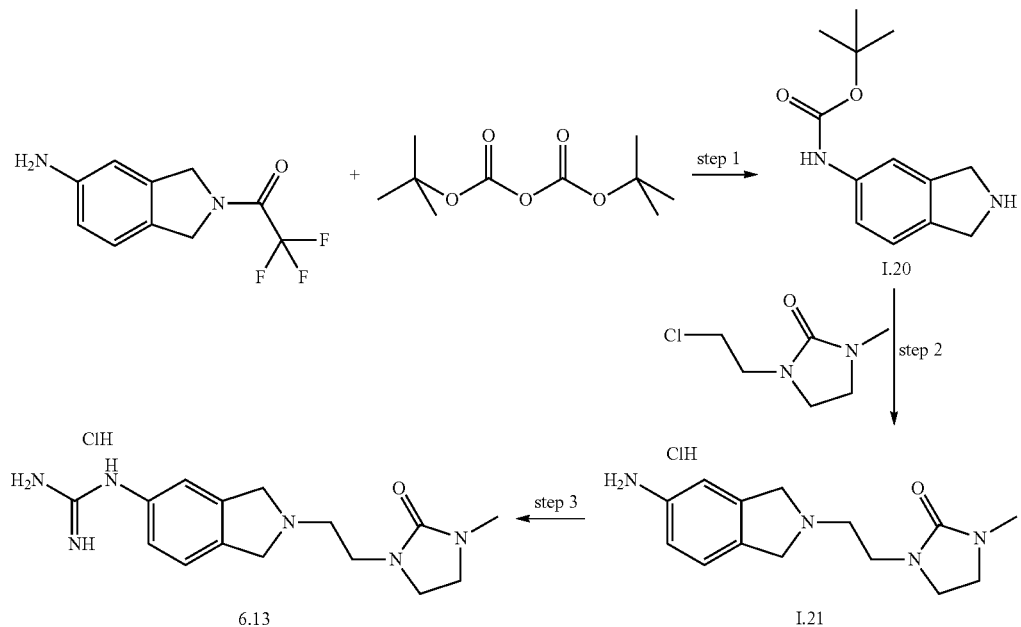

Step 1
The synthesis of the starting material 1-(5-amino-1,3-dihydro-isoindol-2-yl)-2,2,2-trifluoro-ethanone is described in the literature: Takeda Chemical Industries Patent: WO2004/46107 A1; 2004

0.57 g Di-tert-butylcarbonate were added to a mixture of 0.5 g 1-(5-amino-1,3-dihydro-isoindol-2-yl)-2,2,2-trifluoro-ethanone in 10 ml acetonitrile and the mixture was stirred overnight at ambient temperature. The solvent was evaporated and 15 ml 15% aqueous ammonia solution was added. The precipitate was filtered and washed with 5 ml water (2×). 30 ml dioxane/aqueous sodium hydroxide (4N) 1:1 were added, and the reaction mixture was stirred for 40 min at ambient temperature. The solvent was evaporated and the aqueous layer was extracted with 20 ml dichloromethane. The organic layer was evaporated.

Yield: 0.5 g I.20 (98% of theory)

Step 2

1.041 g 1-(2-chloro-ethyl)-3-methyl-imidazolidin-2-one were added to a solution of 0.5 g I.20 ((2,3-dihydro-1H-isoindol-5-yl)-carbamic acid tert-butyl ester) and 377 µl N,N-diisopropylethylamine in 8 ml dioxane. The reaction mixture was irradiated in a microwave for 90 min at 100° C. The solvent was evaporated and the residue was purified by preparative HPLC. The combined product fractions were concentrated. The residue was treated with 8 ml 4 N hydrochloric acid in dioxane. The mixture was stirred for 2 h at ambient temperature. The solvent was evaporated to give a yellow solid.

Yield: 400 mg I.21 (72% of theory)

Step 3

0.4 g I.21 (1-[2-(5-amino-1,3-dihydro-isoindol-2-yl)-ethyl]-3-methyl-imidazolidin-2-one hydrochloride) was added to a mixture of 0.37 g cyanamide in 3 ml dioxane and 1 ml 4 N hydrochloric acid in dioxane. The mixture was irradiated at 140° C. in a microwave for 30 min. The solvent was evaporated and the residue was used in the next step without purification.

Yield: 0.457 g 6.13 (100% of theory)

Synthesis of N-[2-(4-methyl-piperazine-1-carbonyl)-indan-5-yl]-guanidine hydrochloride (6.14) for Example 221 cooled to 0° C. and treated with saturated potassium hydroxide to pH 13. The aqueous layer was extracted with 30 ml dichloromethane (2×). The organic layer was filtered and evaporated. The residue contains two isomers, which were used without further purification in the next step.

Yield: 1.5 g I.23 (isomeric mixture)

Step 3

1.5 g I.23 (Isomers) was treated with 10 ml dioxane, 15 ml 4N aqueous hydrochloric acid and 0.68 g zinc. The mixture was stirred for 2 h at ambient temperature. The reaction mixture was treated with 4N aqueous sodium hydroxide to obtain a basic pH. The aqueous layer was extracted with dichloromethane. The organic layer was evaporated under reduced pressure. The residue was purified by preparative HPLC to obtain the desired isomer I.24.

Yield: 0.4 g I.24 (42% of theory)

Step 4

Compound 6.14 was prepared analogous to procedure 6.12 step 3 using intermediate I.24.

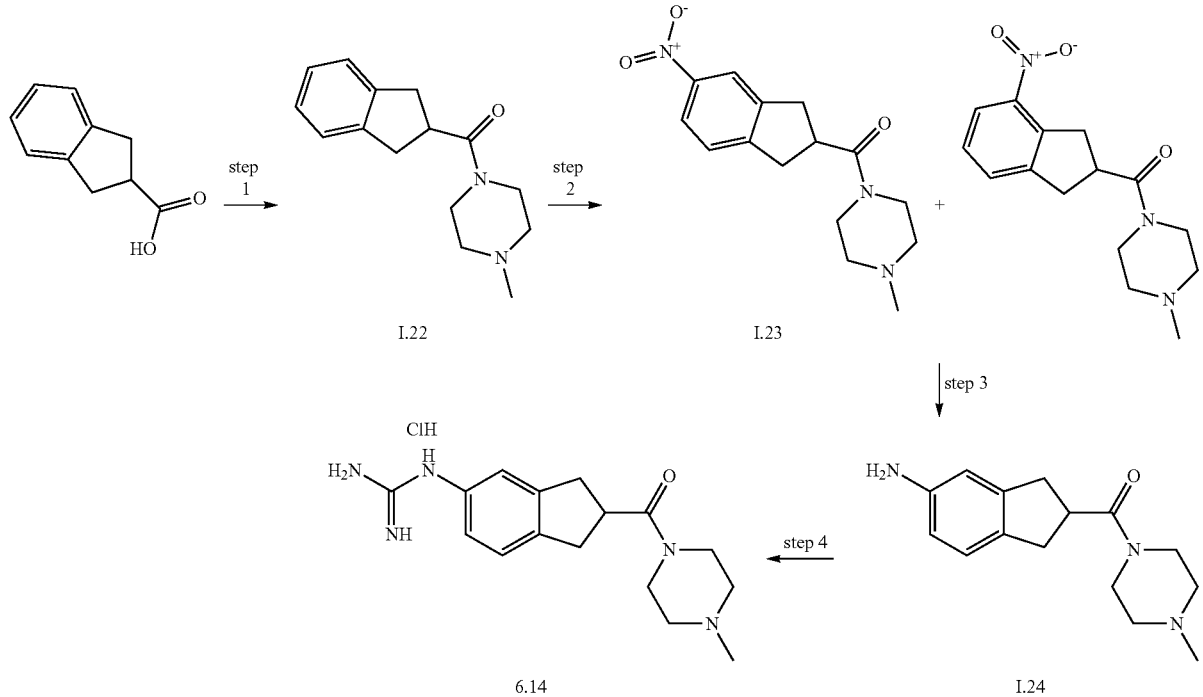

Step 1

1 g N-Methylpiperazine were added to a mixture of 1.62 g 2-indancarboxylic acid, 3.21 g [(benzotriazol-1-yloxy)-dimethylamino-methylene]-dimethyl-ammonium tetrafluoroborate (TBTU) and 1.72 ml N,N-diisopropylethylaminie (DIPEA) in 20 ml N,N-dimethylformamide. The mixture was stirred at ambient temperature overnight. The reaction mixture was filtered through a pad of aluminum oxide. The solvent was evaporated to obtain I.22.

Yield: 2.3 g I.22 (94% of theory)

Step 2

1.8 g I.22 (Indan-2-yl-(4-methyl-piperazin-1-yl)-methanone) was slowly added at 0° C. to 6 ml 65% aqueous nitric acid. After the addition the mixture was stirred for 20 min at 0° C. The reaction mixture was warmed to ambient temperature and stirred overnight. The reaction mixture was then

Synthesis of N-[2-(4-methyl-piperazine-1-carbonyl)-2,3-dihydro-1H-isoindol-5-yl]-guanidine hydrochloride (6.15) for Example 220

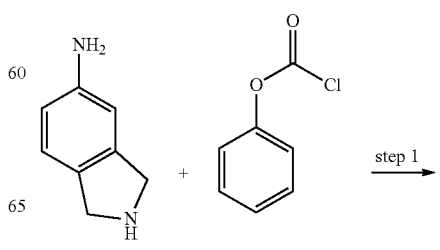

-continued

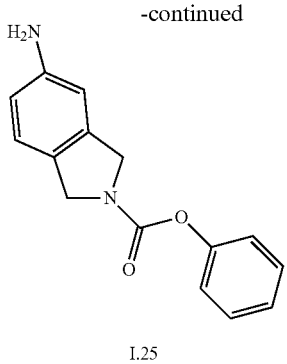

I.25

↓ step 2

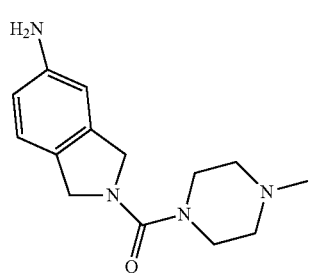

I.26

↓ step 3

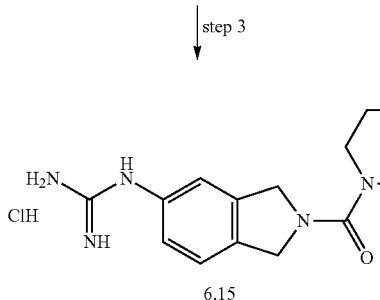

6.15

Step 1

0.945 g Phenylchloroformate were added slowly to a solution of 0.9 g 2,3-dihydro-1H-isoindol-5-ylamine and 0.231 ml N,N-diisopropylethylamine (DIPEA) in 20 ml dioxane. The reaction mixture was stirred for 6 h at ambient temperature. The solvent was evaporated and the residue was purified by preparative HPLC.

Yield: 1.2 g I.25 (70% of theory) Analysis: HPLC-MS (method B) $R_t$=2.38

Step 2

1.2 g I.25 (5-Amino-1,3-dihydro-isoindole-2-carboxylic acid phenyl ester), 1.89 g N-methylpiperazine and 6 ml 1-methyl-2-pyrrolidone were mixed. The mixture was irradiated in a microwave oven for 1 h at 250° C. and then purified by preparative HPLC.

Yield: 0.676 g I.26 (55% of theory)

Step 3

Compound 6.15 was prepared analogous to procedure 6.12 step 3 using intermediate I.26.

4.1.5 Synthesis of Compound with Formula 7 from Scheme 2, 4 and Scheme 6

2-Chloro-4-pyridin-2-yl-pyrimidine (7.1) for Examples 2, 3, 56, 57, 66, 122, 194-196, 216, 230, 233-238, 240, 241, 243, 245, 249, 250, 263, 264, 281, 282, 284, 286-288, 290

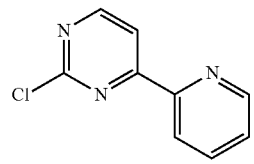 [SMILES: Clc1nccc(-c2ccccn2)n1]

The synthesis of 2-chloro-4-pyridin-2-yl-pyrimidine (7.1) is described in the literature: Patent; SmithKline Beecham corporation; WO2003/101442; 2003; A1

4.1.6 Synthesis of Compound with Formula 8 from Scheme 3a and 3b

Synthesis of 2-chloro-4-(4-chloro-pyridin-2-yl)-pyrimidine (8.1) for Examples 4, 10, 12, 20, 23-25, 27, 29, 44, 279

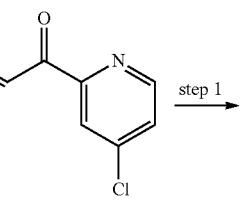

4.8

↓ step 1

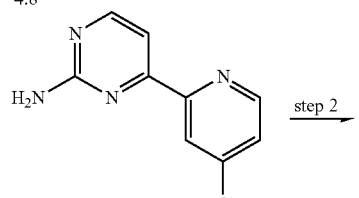

I.27

↓ step 2

I.28

↓ step 3

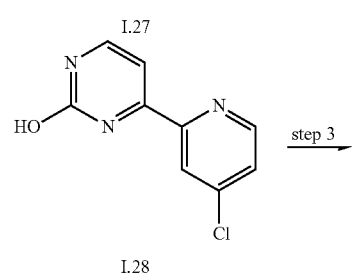

8.1

Step 1

A mixture of 16.8 g 4.8 (1-(4-chloro-pyridin-2-yl)-3-dimethylamino-propenone), 27.03 g guanidine carbonate, 33.69 g sodium methanolate and 240 ml ethanol was stirred at reflux overnight. The reaction was diluted with water and the solvent was evaporated under reduced pressure. The yellow precipitate was filtered, washed with water and dried.

Yield: 12.6 g I.27 (76% of theory); Analysis: [M+H]$^+$=207 (Cl isotope pattern); HPLC-MS (method): R$_t$=1.63 min Step 2

20 g Sodium nitrite were added in portions at 10° C. to 260 ml concentrated sulfuric acid. After the addition the mixture was stirred for 30 min at ambient temperature. The mixture was warmed up to 70° C., then cooled to 10° C. The cold mixture was slowly added dropwise to a solution of 21.1 g I.27 (4-(4-chloro-pyridin-2-yl)-pyrimidin-2-ylamine) in 150 ml glacial acetic acid while maintaining the temperature between 10° C. and 20° C. during the addition. After stirring at ambient temperature for 2 h, 200 ml water were added (highly exothermic!). The mixture was stirred for 1 h at 70° C. The mixture was treated (under cooling) with 10N sodium hydroxide solution (highly exothermic!) and then the solid was filtered and dried to give 1.28.

Yield: 22.4 g I.28 (quantitative) Analysis: [M+H]$^+$=208 (Cl isotope pattern)

Step 3

A mixture of 10 g I.28 (4-(4-chloro-pyridin-2-yl)-pyrimidin-2-ol) in 100 ml phosphorus oxychloride was stirred for 3 h at reflux. The solvent was evaporated and the crude 8.1 was used in the next step without purification.

Yield: 7.3 g 8.1 (67% of theory) Analysis: [M+H]$^+$=226

4.1.7 Synthesis of Compound with Formula 9 from Scheme 3a and 3b

Synthesis of 1-(4-chloro-pyridin-2-yl)-3-dimethylamino-propenon (9.1) for Examples 1, 4, 15, 26, 28, 30-33, 35, 37-42, 46-48, 68-109, 197-214, 218, 221, 229, 244, 246, 259-262, 266-271, 273-277, 280

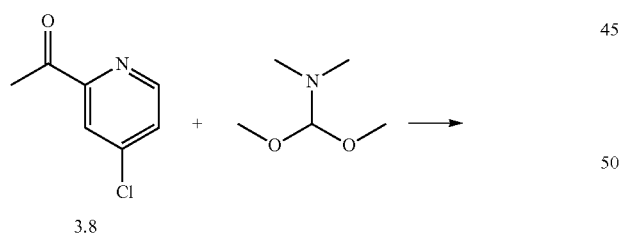

3.8

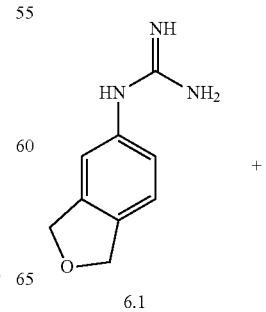

9.1

Compound 9.1 was prepared analogous to procedure 4.1 using ketone 3.8. The brown solid was used for the next steps without purification.

Yield: 49 g 9.1 (crude; 100% of theory)

4.1.8 Synthesis of Compounds with Formula 10 and 10': Reaction 6 and 7 from Scheme 3a and 3b Synthesis of the Compound with the Formula 10.1: Reaction 6

Synthesis of (2-tert-butyl-1H-indol-5-yl)-[4-(4-chloro-pyridin-2-yl)-pyrimidin-2-yl]-amine (10.1) for Examples 4, 28

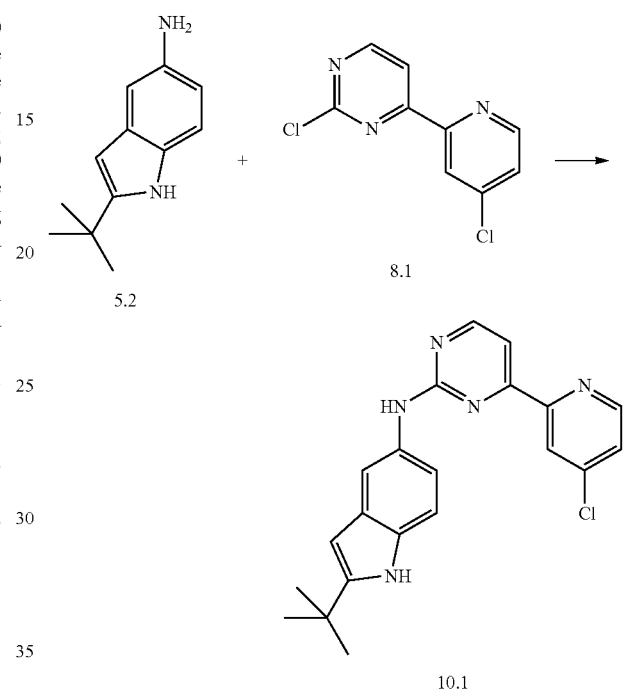

A mixture of 226 mg 8.1 (2-chloro-4-(4-chloro-pyridin-2-yl)-pyrimidine), 181 mg 5.2 (2-tert-butyl-1H-indol-5-ylamine) and 138 µl N,N-diisopropylethylamine in 4 ml 1-methyl-2-pyrrolidone was stirred for 2 h at 150° C. The mixture was purified by preparative HPLC. The combined fractions were evaporated. The residue was dissolved in acetonitrile/water and lyophilized to obtain a red solid 10.1.

Yield: 265 mg 10.1 (88% of theory)

Synthesis of the Compounds with the Formula 10.2-10.10: Reaction 7

Synthesis of [4-(4-chloro-pyridin-2-yl)-pyrimidin-2-yl]-(1,3-dihydro-isobenzofuran-5-yl)-amine (10.2) for Example 1

-continued

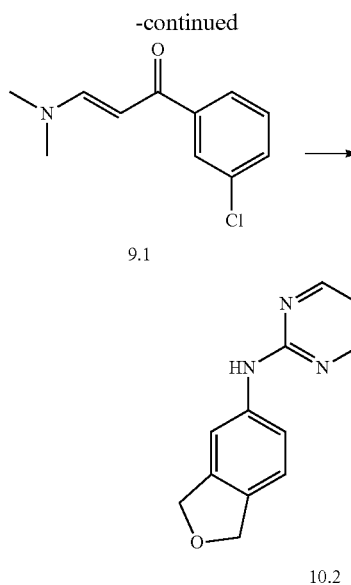

9.1

10.2

A mixture of 0.527 g 9.1 (1-(3-chloro-phenyl)-3-dimethylamino-propenone), 1.223 g (6.1) (N-(1,3-dihydro-isobenzofuran-5-yl)-guanidine) and 324 mg sodium methylate in 10 ml methanol was irradiated in a microwave oven for 20 min at 160° C. The precipitate was filtered, washed with methanol and dried to give 10.2.

Yield: 405 mg 10.2 (50% of theory) Analysis: [M+H]$^+$=325; HPLC-MS (method I): R$_f$=2.45 min The following compounds were produced by a process analogously to 10.2 with the corresponding starting material:

1-(2-{5-[4-(4-Chloro-pyridin-2-yl)-pyrimidin-2-ylamino]-1,3-dihydro-isoindol-2-yl}-ethyl)-3-methyl-imidazolidin-2-one (10.3) for Example 218

{5-[4-(4-Chloro-pyridin-2-yl)-pyrimidin-2-ylamino]-indan-2-yl}-(4-methyl-piperazin-1-yl)-methanone (10.4) for Example 221

5-[4-(4-Chloro-pyridin-2-yl)-pyrimidin-2-ylamino]-7-methyl-1H-indole-2-carboxylic acid dimethylamide (10.5) for Example 280

6-[4-(4-Chloro-pyridin-2-yl)-pyrimidin-2-ylamino]-1H-indole-2-carboxylic acid (10.6) for Examples 229, 244, 246, 259, 271

6-[4-(4-Chloro-pyridin-2-yl)-pyrimidin-2-ylamino]-1-methyl-1H-indole-2-carboxylic acid (10.7) for Examples 266-270

5-[4-(4-Chloro-pyridin-2-yl)-pyrimidin-2-ylamino]-1-methyl-1H-indole-2-carboxylic acid (10.8) for Example 32, 47, 48

7-Chloro-5-[4-(4-chloro-pyridin-2-yl)-pyrimidin-2-ylamino]-1H-indole-2-carboxylic acid dimethylamide (10.9) for Example 279

5-[4-(4-Chloro-pyridin-2-yl)-pyrimidin-2-ylamino]-1H-indole-2-carboxylic acid (10.10) for Examples 10, 12, 15, 26, 28, 30, 31, 33-42, 44-46, 68-109, 197-214, 223-228, 260-262, 273-277

4.1.9 Synthesis of Compound with Formula 11 from Scheme 3a, 4 and Scheme 6

Synthesis of (2-methyl-piperazin-1-yl)-pyrrolidin-1-yl-methanone (11.1) for Example 135

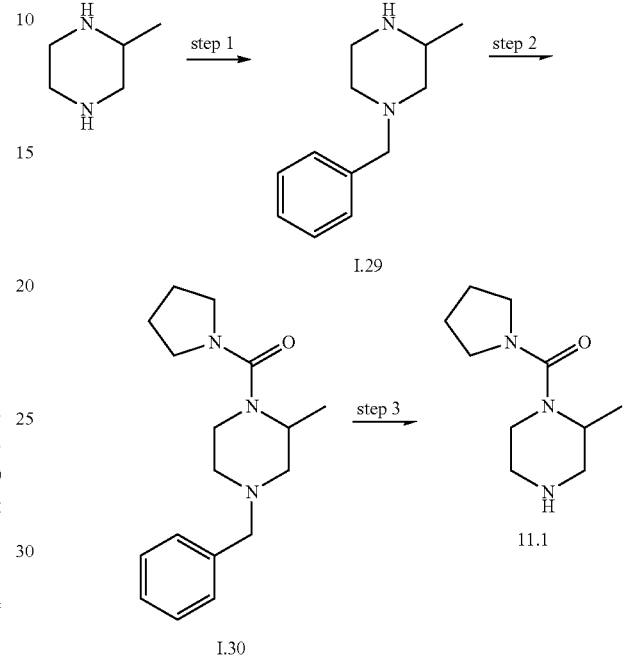

Step 1

A mixture of 17.55 g 2-methylpiperazine, 20.2 ml benzoylchloride and 44.2 g sodium hydrogencarbonate in 150 ml ethanol was stirred for 12 h at reflux. The suspension was filtered and the resulting yellow solution was evaporated. The residue was treated with 150 ml 1N hydrochloric acid and extracted with dichloromethane. The aqueous layer was treated with 20% aqueous sodium hydroxide to obtain pH 13 and extracted with dichloromethane (3×). The organic layer was dried with sodium sulfate and concentrated to give the intermediate I.29.

Yield: 19.48 g I.29 (58% of theory) Analysis: [M+H]$^+$=131

Step 2

25 ml N,N-Diisopropylethylamine and 0.1 g 4-dimethylaminopyridine were added to a solution of 10 g of I.29 (1-benzyl-3-methyl-piperazine) in 200 ml tetrahydrofuran and the mixture was stirred for 5 min at ambient temperature. 6.38 g 1-Pyrrolidincarbonyl chloride in tetrahydrofuran were added dropwise to the reaction mixture and the mixture was stirred under an atmosphere of nitrogen at ambient temperature overnight. The solvent was evaporated, water was added and the mixture was extracted with ethyl acetate (2×). The combined organic phases were dried with sodium sulfate and concentrated to give a yellow oil.

Yield: 15.17 g I.30 (quantitative) Analysis: [M+H]$^+$=288

Step 3

A mixture of 18.79 g I.30 ((4-benzyl-2-methyl-piperazin-1-yl)-pyrrolidin-1-yl-methanone) and 1.5 g Pd/C 10% in 150 ml methanol was stirred at ambient temperature under a pressure of 3 bar hydrogen. The catalyst was filtered and the solvent was evaporated under reduced pressure to obtain the compound 11.1.

Yield: 12.63 g 11.1 (98% of theory) Analysis: [M+H]$^+$= 198

Synthesis of
1-methyl-3-piperidin-4-yl-imidazolin-2-one
hydrochloride (11.2) for Example 149

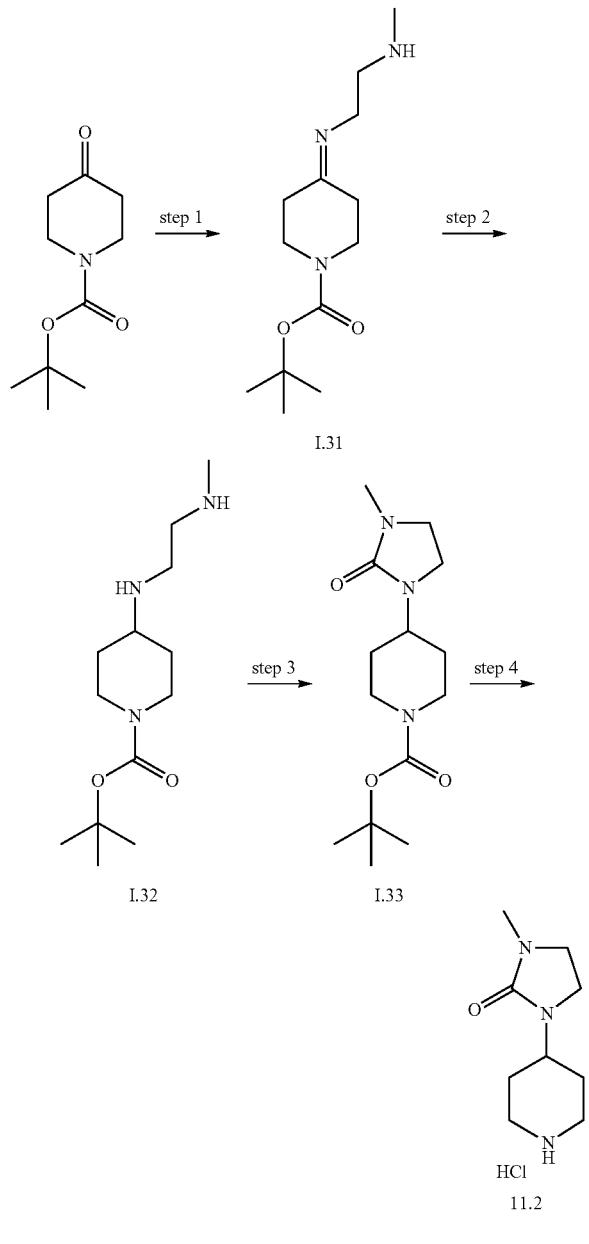

Step 1

A mixture of 133.73 g Boc-4-piperidone and 49.73 g N-methylendiamine in 670 ml toluene was refluxed overnight. The solvent was evaporated and the crude 1.31 was used for the next step without purification.

Yield: 171.3 g I.31 (crude)

Step 2

A solution of 171.36 g I.31 (1-boc-4-(2-methylamino-ethylimino)-piperidin) in 340 ml toluene was added dropwise to a suspension of 18.14 g sodium borohydride in 340 ml ethanol and the mixture was stirred at ambient temperature for 3 days. The ethanol was removed and the residue was diluted with 340 ml water. The aqueous solution was extracted with ethyl acetate (3×). The organic layer was washed with water, dried with sodium sulfate and concentrated. The residue was dissolved in ethanol, treated at 0° C. with hydrochloric acid and the crude I.32 was filtered as a dihydrochloride salt. The solid was dissolved in water and treated under ice cooling with sodium hydroxide to obtain a basic pH. The aqueous layer was extracted with ethyl acetate (3×). The combined organic layers were dried with sodium sulfate and evaporated to give I.32.

Yield: 46.6 I.32 (27% of theory)

Step 3

A mixture of 46.52 g I.32 (1-boc-4-(2-methylamino-ethylamino)-piperidine) and 40.2 g triethylamine in 450 ml chloroform was cooled down to −10° C. A solution of 18 g triphosgene in 90 ml chloroform was added dropwise to the reaction mixture. The resulting mixture was warmed to ambient temperature and diluted with water. The phases were separated and the organic layer was washed with water (2×). The organic layer was dried with sodium sulfate and concentrated. The residue was triturated with ethyl acetate/hexanes, the precipitate was filtered and dried to obtain the intermediate I.33.

Yield: 38.7 g I.33 (76% of theory)

Step 4

A solution of 15.56 g I.33 (1-boc-4-(2-methyl-2-oxo-imidazolin-1-yl)-piperidin) in 28 ml ethanol was added dropwise to 55 ml concentrated hydrochloric acid in 110 ml water. The mixture was evaporated and the crude 11.2 was used in the next step without purification.

Yield: 11.2 (quantitative)

Synthesis of
2-morpholin-4-yl-1-morpholin-4-ylmethyl-ethylamine
(11.3) for Example 154

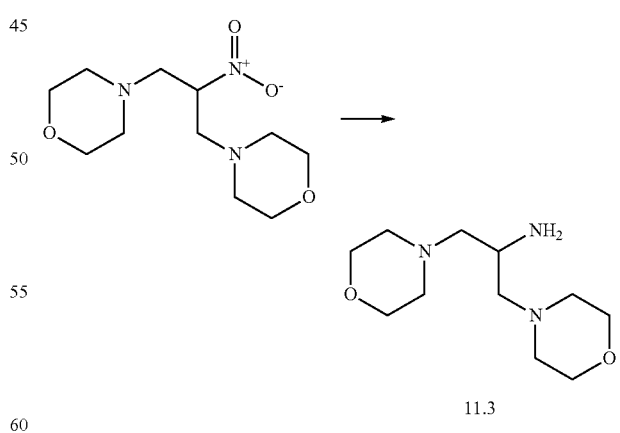

A mixture of 5 g 1,3-dimorpholin-2-nitropropane, 2 g Raney-nickel in 80 ml methanol and 20 ml ammonia in methanol were stirred under a pressure of 50 psi hydrogen at 30° C. for 5.5 h. The catalyst was filtered and the solvent was evaporated under reduced pressure to give compound 11.3.

Yield: 4.15 g 11.3 (95% of theory) Analysis: [M+H]$^+$=230

Synthesis of 4-piperidin-4-yl-thiomorpholine 1-oxide dihydrochloride (11.4) for Example 162

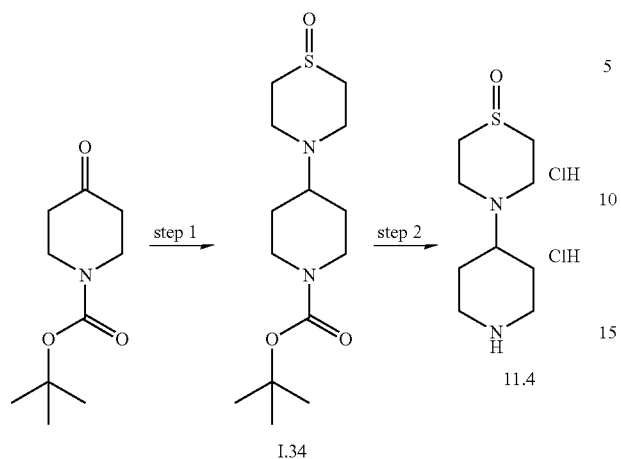

Step 1

A mixture of 8.8 g 1-boc-4-piperidone and 5.4 g thiomorpholin-1-oxide in 2.5 ml glacial acetic acid was diluted with 100 ml dichloromethane and stirred for 1 h at ambient temperature. The reaction mixture was cooled with an ice bath and 14.9 g sodium triacetoxyborohydride were added in portions over a period of 1 h. The reaction mixture was stirred at ambient temperature overnight. The mixture was cautiously treated with 150 ml aqueous saturated sodium bicarbonate solution (foams strongly!) and stirred for 1 h. The phases were separated and the aqueous layer was extracted with dichloromethane (2×). The combined organic phases were washed with brine, dried with magnesium sulfate and evaporated to give the intermediate I.34.

Yield: 11.3 g I.34 (85% of theory)

Step 2

To a mixture of 11.4 g I.34 (4-(1-oxo-4*-thiomorpholin-4-yl)-1-boc-piperidine) in 30 ml dioxane were added 60 ml 4N hydrochloric acid in dioxane. A thick suspension was formed, 40 ml methanol were added and the reaction mixture was stirred for 3 h at ambient temperature. The precipitate was filtered (hygroscopic), washed with diisopropylether and dried to give the compound 11.4.

Yield: 6.2 g 11.4 (60% of theory)

Synthesis of 4-methyl-1-piperidin-4-yl-[1,4]diazepan-5-one dihydrochloride (11.5) for Example 163

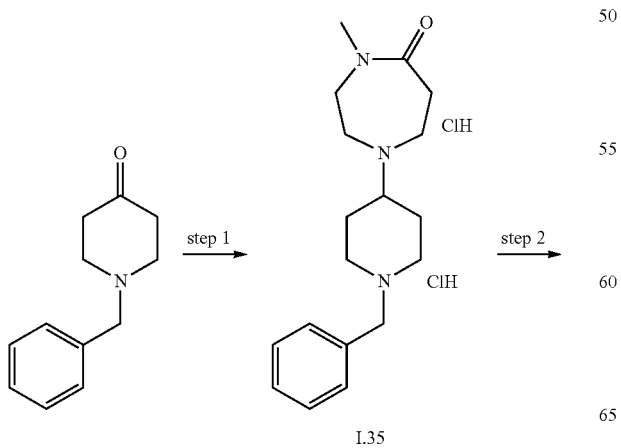

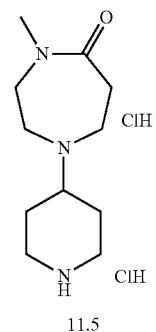

Step 1

A mixture of 6.04 g 1-benzyl-4-piperidone and 4.3 g 4-methyl-1,4-diazepan-5-one in 150 ml dichloromethane was treated with glacial acetic acid to obtain a pH 5 (~3.7 ml). The mixture was stirred for 1 h at ambient temperature, then cooled with an ice bath and treated with 9.54 g sodium triacetoxy borohydride (in portions). The reaction mixture was stirred at ambient temperature overnight. 400 ml 30% aqueous potassium carbonate solution were added dropwise to the reaction mixture over a period of 45 min until pH 8 was reached. The aqueous layer was extracted with 200 ml dichloromethane (3×). The combined organic layers were dried with magnesium sulfate and evaporated. The residue was dissolved in 100 ml methanol and acidified with 1.25N hydrochloric acid in methanol. The resulting precipitate was filtered, washed with 30 ml methanol and 50 ml diisopropyl ether and dried.

Yield: 7 g I.35 (56% of theory) Analysis: [M+H]$^+$=302

Step 2

1 g of Pd/C 10% were added to a solution of 7 g I.35 (1-(1-benzyl-piperidin-4-yl)-4-methyl-[1,4]diazepan-5-one) in 150 ml methanol and 50 ml water. The reaction mixture was stirred for 1.5 h at 50° C. under a pressure of hydrogen. The catalyst was filtered and the solvent was removed. The residue was diluted with 10 ml ethanol and the solvent was removed. The residue was triturated with 100 ml diisopropylether. The precipitate was filtered, washed with 30 ml diisopropylether and dried to give the compound 11.5.

Yield: 5.3 g 11.5 (100% of theory) Analysis: [M+H]$^+$=212

Synthesis of 4-pyrrolidin-1-yl-methyl-cyclohexylamine dihydrochloride (11.6) for Example 170

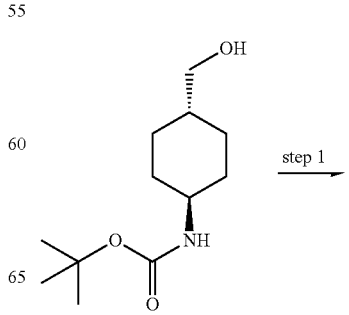

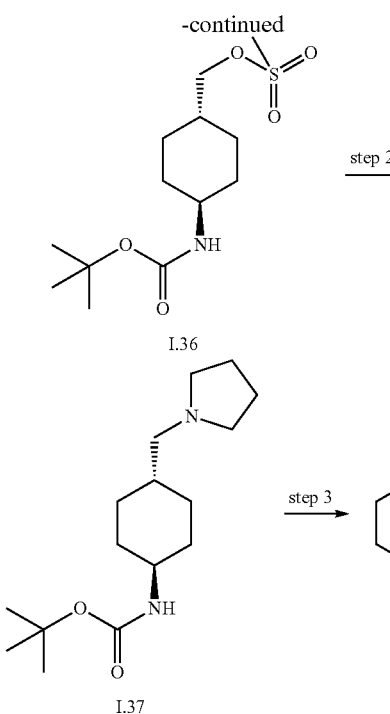

Step 1

A solution of 5.73 g methylsulfonyl chloride in 10 ml dichloromethane was slowly added dropwise under ice cooling to a solution of 10.1 g trans-(4-hydroxymethyl-cyclohexyl)-carbamic acid tert-butyl ester and 7.63 ml triethylamine in 140 ml dichloromethane. The reaction mixture was stirred at ambient temperature for 3 h. Additional 1.5 ml triethylamine and 0.7 ml methylsulfonyl chloride were added and the mixture was stirred at ambient temperature overnight. The reaction mixture was extracted with ice-water (1×), citric acid (1×) and water (1×). The organic layer was dried and evaporated under reduced pressure. The resulting crude material was triturated with petroleum ether, the precipitate was filtered, washed with diethylether and dried to give the intermediate I.36.

Yield: 9.14 g I.36 (68% of theory) Analysis: [M−H]⁻=306

Step 2

A mixture of 1.5 g I.36 (methanesulfonic acid 4-tert-butoxycarbonylamino-cyclohexylmethyl ester) and 1.046 g pyrrolidine was stirred under an atmosphere of nitrogen at 100° C. for 1.5 h. A clear melt was formed. The mixture was concentrated under reduced pressure. The residue was diluted with dioxane and concentrated. The crude material was triturated with 3 ml 2N aqueous sodium hydroxide solution and cooled using an ice bath. The precipitate was filtered, washed with 2.5 ml ice water and dried to give the intermediate I.37.

Yield: 571 mg I.37 (41% of theory) Analysis: $[M+H]^+$=283

Step 3

550 mg I.37 ((4-pyrrolidin-1-ylmethyl-cyclohexyl)-carbamic acid tert-butyl ester) in 6N aqueous hydrochloric acid were stirred overnight. The solvent was removed. Toluene (15 ml) was added and the mixture was evaporated. The addition of toluene and evaporation was repeated twice. The crude material was triturated with acetone, the precipitate was filtered and dried (hygroscopic).

Yield: 473 mg 11.6 (95% of theory) $[M+H]^+$=183

Synthesis of
1-methyl-4-oxa-1,9-diaza-spiro[5,5]undecan-2-one hydrochloride (11.7) for Examples 19, 182

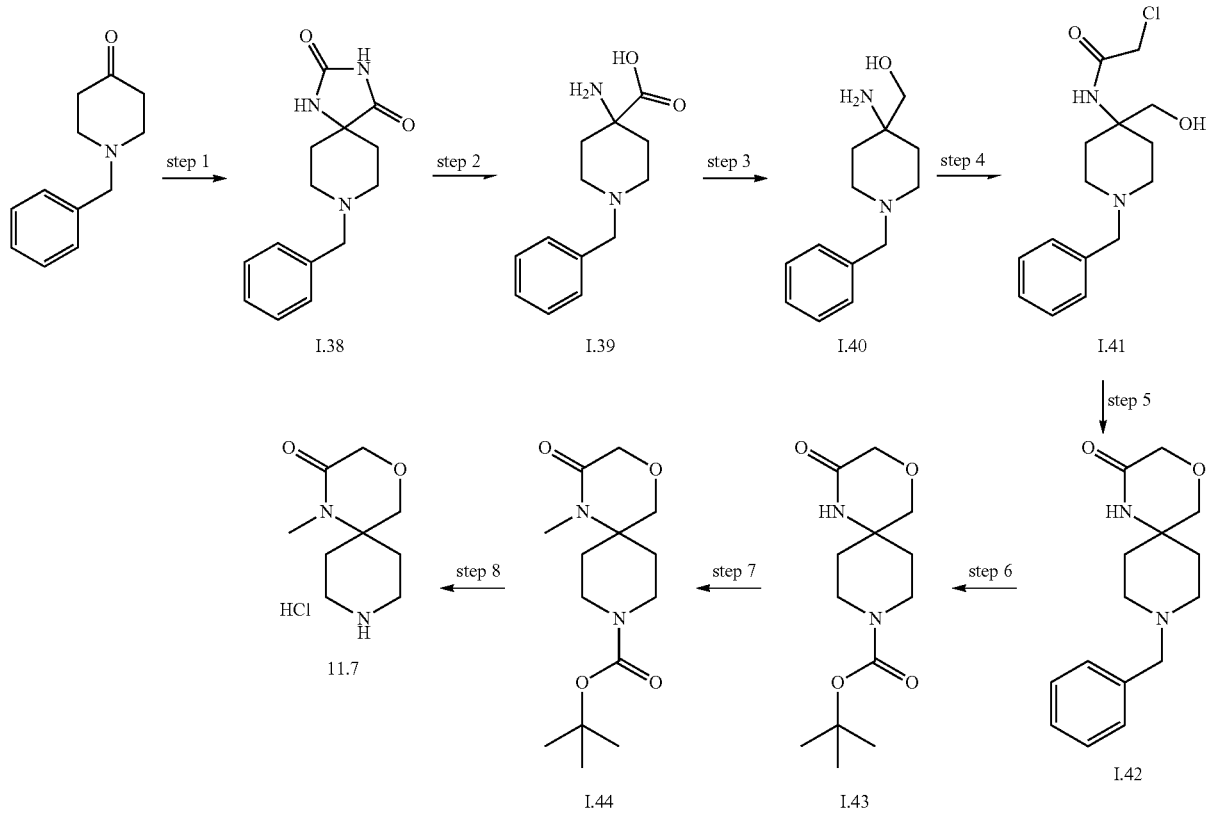

Step 1

A solution of 294.14 g 1-benzylpiperidin-4-one in 2.1 L methanol was added to a solution of 448 g ammonium carbonate in 2.1 L hot water. The yellow turbid reaction mixture was cooled with an ice bath. A solution of 77 g sodium cyanide in 200 ml water was added dropwise over 10 min (exothermic!). After the addition the ice bath was removed and the reaction mixture was stirred at ambient temperature for 3 days. The resulting precipitate was filtered, washed with water (3×) and dried in a vacuum oven at 50° C. to obtain the intermediate I.38.

Yield: quantitative

Step 2

In a 20 L reactor 2.4 kg sodium hydroxide were dissolved in 10 L water. The solution was mixed with 614 g I.38 (8-benzyl-1,3,8-triaza-spiro[4.5]decane-2,4-dione) and the resulting reaction suspension was heated to 80° C. When 80° C. was reached, the reaction mixture was heated in steps of 10° C. When the temperature reached 105° C. the mixture started to foam strongly. Stirring was continued at 108° C. overnight. The reaction mixture was cooled to 10° C. and 5 L concentrated hydrochloric acid were added dropwise to obtain a pH 7-8. During the addition the temperature was kept at 23° C. The precipitate was filtered and dried in vacuo at 40° C. over 3 days, then at 80° C. overnight.

Yield: 469.7 g I.39 (85% of theory)

Step 3

750 ml 2.4N Lithium aluminium hydride in tetrahydrofuran was cautiously added to a suspension of 202 g I.39 (4-amino-1-benzyl-piperidine-4-carboxylic acid) in 2 L tetrahydrofuran at 19° C. Upon addition of the first few milliliters of lithium aluminium hydride, the temperature rose. The temperature was kept between 28-29° C. with a cooling bath. When the addition was completed, the reaction mixture was stirred for 2 h at ambient temperature. The mixture was cooled down to 8° C. A solution of 70 ml water in 140 ml tetrahydrofuran was added dropwise (gas evolution). To the thick suspension 70 ml 4N aqueous sodium hydroxide and 140 ml water were sequentially added, the mixture was warmed to 56° C. and stirred overnight. The reaction mixture was then cooled to ambient temperature and sodium sulfate was added. The salts were filtered and washed with dichloromethane (2×). The filtrate was evaporated to obtain the intermediate I.40.

Yield: 76.78 g I.40 (67% contain; 27% of theory)

Step 4

70.83 g I.41 ((4-Amino-1-benzyl-piperidin-4-yl)-methanol) were dissolved in 235 ml dichloromethane and 770 ml water were added under stirring. The vigorously stirred reaction mixture was cooled with an ice bath, and 51 ml chloroacetyl chloride were added in 5 equal portions in 10 min intervals. The reaction mixture was stirred for 35 min, the precipitate was filtered, washed with water (3×) and diethylether (2×). The white solid was dried overnight.

Yield: 65.77 g I.41 (97% contains; 52% of theory)

Step 5

Under an atmosphere of argon, 103 mg I.41 N-(1-benzyl-4-hydroxymethyl-piperidin-4-yl)-2-chloro-acetamide were dissolved in 2 ml tert-amyl alcohol. 46.9 mg Potassium tert-butoxide were added and the solution was stirred for 30 min at ambient temperature. The solvent was evaporated and 20 ml dichloromethane were added. The organic layer was washed with brine (3×), dried with sodium sulfate and concentrated to obtain a colourless oil which crystallized upon standing.

Yield: 0.09 g I.42 (75% contains; 75% of theory)

Step 6

Under an nitrogen atmosphere, 116.8 g I.42 (9-benzyl-4-oxa-1,9-diaza-spiro[5.5]undecan-2-one) were dissolved in 1.2 L tetrahydrofuran. Some undissolved material was filtered and washed with 100 ml tetrahydrofuran. To the combined filtrates were added 64.2 g di-tert-butyl dicarbonate and 14.2 g Pd/C 10%. The mixture was stirred under a hydrogen atmosphere for 45 min. Additional 43.8 g di-tert-butyl dicarbonate were added and the mixture was stirred under hydrogen atmosphere overnight. The reaction mixture was flushed with nitrogen. Additional 7.93 g Pd/C 10% were added and the mixture was stirred under hydrogen atmosphere overnight. The reaction mixture was flushed with nitrogen and filtered through a pad of Extrelute™. The pad was washed with dichloromethane and the solvent was evaporated under reduced pressure. The residue (white solid) was suspended in 250 ml hot ethyl acetate and cooled to ambient temperature. The precipitate was filtered, washed with isopropanol (×3) and dried.

Yield: 101.09 g I.43 (83% of theory)

Step 7

To a solution of 6.7 g I.43 (2-oxo-4-oxa-1,9-diaza-spiro [5.5]undecane-9-carboxylic acid tert-butyl ester) in 70 ml hot tert-amyl alcohol 4.17 g potassium tert-butoxide and 2.31 ml iodomethane were added. The reaction mixture was stirred at ambient temperature overnight. Additional 1.45 ml iodomethane were added and the mixture was stirred for 1.5 h at ambient temperature. The reaction mixture was concentrated in vacuo, the residue was stirred in hot ethyl acetate and the precipitate was filtered. The solid was triturated with dichloromethane and filtered. The residue was suspended in hot ethyl acetate. The suspension was filtered and the filtrate was evaporated to give a colourless oil, which was dissolved in hot ethyl acetate and left to crystallize. The precipitate was filtered and washed with ethyl acetate to give a white solid which was purified by silica gel chromatography (SiO$_2$; dichloromethane/methanol 9/1). The combined product fractions were concentrated to give the intermediate I.44.

Yield: 5.68 g I.44 (81% of theory)

Step 8

To a solution of 5.68 g I.44 (1-methyl-2-oxo-4-oxa-1,9-diaza-spiro[5.5]undecane-9-carboxylic acid tert-butyl ester) in 15 ml dioxane were added 14.98 ml 4N hydrochloric acid in dioxane. A white precipitate formed slowly and the mixture was stirred at ambient temperature overnight. Additional 7.5 ml 4N hydrochloride acid in dioxane was added and the mixture was stirred overnight. Isopropanol was added to the mixture. The precipitate was filtered, washed with isopropanol and dried in vacuo to afford a white solid 11.7.

Yield: 4.38 11.7 (100% of theory)

The synthesis of the following compounds is described in the literature:

1-(2-Methylamino-ethyl)-pyrrolidin-2-one (11.8) for Example 165: Patent Boehringer Ingelheim Pharma KG: Publ.: US2003/171359 A1 (2003/09/11), Appl: US2002-271763 (2002/10/13)

4-(Tetrahydro-pyran-4-yl)-piperidine (11.9) for Example 181: Pfizer INC. Pfizer Limited Patent: EP992493 A1; 2000

The Following Amines are Commercially Available:

1-Methyl-piperazine (11.10) for Examples 2, 6, 10, 12, 15, 32-49, 52-54, 56, 62, 63, 68-109, 122, 245, 247, 249, 251

Dimethyl-amine (11.11) for Examples 5, 26, 30, 50, 51, 55, 57, 64-66, 229, 242, 243, 248, 250, 252, 256, 265, 272, 278

Piperazine-1-carboxylic acid tert-butyl ester (11.12) for Examples 11, 13, 14, 21, 22

N,N-Dimethyl-propane-1,3diamine (11.13) for Example 16

2-Morpholin-4-yl-ethylamine (11.14) for Example 17

1-Isopropyl-[1,4]diazepane (11.15) for Examples 18, 184
Azetidine (11.16) for Example 59
Pyrrolidine (11.17) for Example 60
3-Morpholin-4-yl-propylamine (11.18) for Example 61
N,N-Dimethyl-ethane-1,2-diamine (11.19) for Example 67
Methyl-(tertrahydropyran-4-yl)-amine (11.20) for Examples 148, 254
Hexahydro-pyridazine dihydrochloride (11.21) for Example 290
(2-Methoxy-ethyl)-methyl-amine (11.22) for Example 110
1-Ethyl-piperazine (11.23) for Example 111
Bis-(2-methoxy-ethyl)-amine (11.24) for Example 112
Methyl-pyridin-2-yl-methyl-amine (11.25) for Example 113
Dimethyl-piperidin-4-yl-amine (11.26) for Example 114
1-Isopropyl-piperazine (11.27) for Example 115
2-Ethyl-2,6-diaza-spiro[3,4]octane (11.28) for Example 116
2-Methyl-2,7-diaza-spiro[4,4]nonane (11.29) for Example 117
4-Pyrrolidin-1-yl-piperidine (11.30) for Example 118
2-Ethyl-2,7-diaza-spiro[4,4]nonane (11.31) for Example 119
Dimethyl-(2-piperidin-2-yl-ethyl)-amine (11.32) for Example 120
1-Diethylamino-3-piperazin-1-yl-propan-2-ol (11.33) for Example 121
Octahydro-pyrrolo[1,2-a]pyrazine (11.34) for Example 123
1-Methyl-1[1,4]diazepane (11.35) for Example 124
Azetidin-3-yl-diethylamine (11.36) for Example 125
Methyl-[3-(4-methyl-piperazin-1-yl)-propyl]-amine (11.37) for Example 126
3-Pyrrolidin-1-ylmethyl-piperidine (11.38) for Example 127
1-(1-Ethyl-piperidin-4-yl)-piperazine (11.39) for Example 128
Methyl-(1-methylpiperidin-4-ylmethyl)-amine (11.40) for Example 129
1-Methyl-4-(2-piperazin-1-yl-ethyl)-piperazine (11.41) for Example 130
2-piperazin-1-yl-pyrimidine (11.42) for Example 131
1-Cyclopropylmethyl-piperazine (11.43) for Example 132
1-(1-Methyl-piperidin-4-yl)-piperazine (11.44) for Example 133
1-Methyl-4-piperidin-4-yl-piperazine (11.45) for Example 134
4-(2-Pyrrolidin-1-yl-ethyl)-piperidine (11.46) for Example 136
(4-Methyl-piperazin-1-yl)-piperazin-1-yl-methanone (11.47) for Example 137
4-Piperidin-4-yl-morpholine (11.48) for Example 138
C-(Tetrahydro-pyran-4-yl)-methylamine (11.49) for Example 139
Methyl-3(morpholin-4-yl-propyl)-amine (11.50) for Example 140
[1,4]Oxazepane (11.51) for Examples 141, 255, 273, 274
4-(2-Pyrrolidin-1-yl-ethoxy)-piperidine (11.52) for Example 143
1-(1-Methyl-piperidin-4-ylmethyl)-piperazine (11.53) for Example 145
(3-Methoxy-propyl)-methylamine (11.54) for Example 146
Methyl-(tetrahydro-pyran-4-ylmethyl)-amine (11.55) for Example 147
Pyrrole (11.56) for Example 4
1-Cyclopropyl-piperazine (11.57) for Example 150
4-Piperidin-4-ylmethyl-morpholine (11.58) for Example 151
Methyl-[2-(4-methyl-piperazin-1-yl)-ethyl]-amine (11.59) for Example 152
4-piperazine-1-yl-butyronitrile (11.60) for Example 155
1-(2-Pyrrolidin-1-yl-ethyl)-piperazine (11.61) for Example 156
8-Methyl-3,8-diaza-bicyclo[3.2.1]octane dihydrochloride (11.62) for Example 157
[1,3']Bipyrrolidinyl (11.63) for Example 158
4-Piperidin-4-ylmethyl-morpholine (11.64) for Example 159
[1,4]-Bipipendinyl-2-one (11.65) for Example 160
1-(Tetrahydro-pyran-4-yl)-piperazine (11.66) for Example 161
Methyl-3(methyl-3H-imidazol-4-ylmethyl)-amine (11.67) for Example 164
1-(1-Methyl-1H-imidazol-2-ylmethyl)-piperazine (11.68) for Example 166
1-(2-Imidazol-1-yl-ethyl)-piperazine (11.69) for Example 167
1-(3-Pyrrolidin-1-yl-propyl)-piperazine (11.70) for Example 168
4-(3-piperazine-1-yl-propyl)-morpholine (11.71) for Example 169
Octahydro-pyrido[1,2-a]pyrazine (11.72) for Example 171
5,6,7,8-Tetrahydro-[1,2,4]triazolo[4,3-a]pyrazine (11.73) for Example 172
Piperazin-1-yl-(tetrahydrofuran-2-yl)-methanone (11.74) for Example 173
Morpholin-4-yl-piperazin-1-yl-methanone (11.75) for Example 174
Piperazin-1-yl-piperidin-1-yl-methanone (11.76) for Example 175
Methyl-(3-methyl-oxetan-3-ylmethyl)-amine (11.77) for Examples 176, 257
5,6,7,8-Tetrahydro-imidazo[1,2-a]pyrazine (11.78) for Examples 177, 258
4-(2-Methoxy-ethoxy)-piperidine (11.79) for Example 178
1-Azetidin-3-yl-4-methyl-piperazine (11.80) for Example 179
Methyl-[2-(tetrahydro-pyran-4-yl)-ethyl]-amine (11.81) for Example 180
1-(2-Methoxy-ethyl)-piperazine (11.82) for Example 183
2-piperazin-1-yl-1-pyrrolidin-1-yl-ethanone (11.83) for Example 185
2-piperazin-1-yl-ethanol (11.84) for Example 186
1-Pyridin-2-yl-piperazine (11.85) for Example 187
[1,4]Bipipendinyl (11.86) for Example 188
Morpholine (11.87) for Examples 189, 253
1-Cyclopentyl-piperazine (11.88) for Example 190
1-Morpholin-4-yl-2-piperazin-1-yl-ethanone (11.89) for Example 191
Dimethyl-(2-piperazin-1-yl-ethyl)-amine (11.90) for Example 192
1-Piperidin-4-yl-pyrrolidin-2-one (11.91) for Examples 193, 263, 264, 289
Methylamine (11.92) for Examples 144, 282, 283, 285, 291, 292
4-Morpholine-4-yl-cyclohexylamine (11.93) for Example 153
(3-[1,4]diazepane-1-yl-propyl)-dimethyl-amine (11.94) for Example 142

4.1.10 Synthesis of Compound with Formula 10: Reaction 8 from Scheme 3a

Synthesis of {5-[4-(4-chloro-pyridin-2-yl)-pyrimidin-2-ylamino]-1H-indol-2-yl}-(4-methyl-piperazin-1-yl)-methanone (10.11) for Examples 10, 12, 15, 33-42, 44-46, 68-109, 197-214

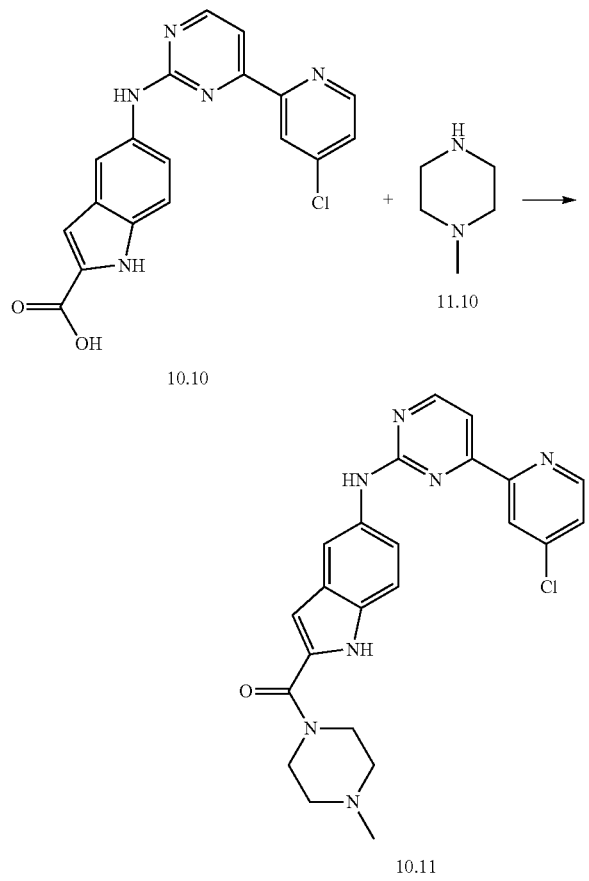

A mixture of 3.9 g 10.10 (5-[4-(4-chloro-pyridin-2-yl)-pyrimidin-2-ylamino]-1H-indole-2-carboxylic acid), 1.1 g 11.10 (N-methylpiperazine), 3.42 g [(benzotriazol-1-yloxy)-dimethylamino-methylene]-dimethyl-ammonium tetrafluoroborate (TBTU) and 1.89 ml N,N-diisopropylethylamine in 100 ml N,N-dimethylformamide was stirred at ambient temperature for 2 h. The reaction mixture was filtered through a pad of basic aluminum oxide. The filtrate was evaporated. The resulting crude material was triturated with diethylether and the solid was filtered. The precipitate was dissolved in dichloromethane/methanol and filtered through a pad of silica gel. The filtrate was evaporated and the residue was triturated with diethylether. The solid was filtered to yield the compound 10.11 as a yellow solid.

Yield: 3.6 g 10.11 (75% of theory) Analysis: [M+H]$^+$=448

The following compounds were produced by a process analogously to 10.11 with the corresponding starting material:

6-[4-(4-Chloro-pyridin-2-yl)-pyrimidin-2-ylamino]-1H-indole-2-carboxylic acid dimethylamide (10.12) for Examples 229, 244, 246, 259, 271

5-[4-(4-Chloro-pyridin-2-yl)-pyrimidin-2-ylamino]-1H-indole-2-carboxylic acid dimethylamide (10.13) for Examples 26, 28, 30, 31, 223-228, 277

6-[4-(4-Chloro-pyridin-2-yl)-pyrimidin-2-ylamino]-1-methyl-1H-indole-2-carboxylic acid dimethylamide (10.14) for Examples 266-270

{5-[4-(4-Chloro-pyridin-2-yl)-pyrimidin-2-ylamino]-1-methyl-1H-indol-2-yl}-(4-methyl-piperazin-1-yl)-methanone (10.15) for Examples 32, 47, 48

{5-[4-(4-Chloro-pyridin-2-yl)-pyrimidin-2-ylamino]-1H-indol-2-yl}-morpholin-4-yl-methanone (10.16) for Examples 260-262, 275

5-[4-(4-Chloro-pyridin-2-yl)-pyrimidin-2-ylamino]-1H-indole-2-carboxylic acid methyl-(tetrahydro-pyran-4-yl)-amide (10.17) for Example 276

{5-[4-(4-Chloro-pyridin-2-yl)-pyrimidin-2-ylamino]-1H-indol-2-yl}-[1,4]oxazepan-4-yl-methanone (10.18) for Examples 273, 274

4.1.11 Synthesis of Compounds with Formula 13 and 14 from Scheme 3a, 3b and 6

The Following Alcohols/Nitriles are Commercially Available:

2,2-Difluoroethanol (13.1) for Examples 26, 92
2-Phenyl-propane-1,3-diol (13.2) for Example 37
Ethane-1,2-diol (13.3) for Examples 28, 45, 47, 259, 269
3-Methoxy-2-phenyl-propanol (13.4) for Example 38
Cyclopentane-1,3-diol (13.5) for Examples 30, 246, 262
3-Fluoro-propanol (13.6) for Example 39
2,2-Dimethyl-propane-1,3-diol (13.7) for Examples 31, 71
Chroman-4-ol (13.8) for Example 40
(R)-2-Hydroxybutane (13.09) for Example 33
3-Morpholin-4-yl-propane-1,2-diol (13.10) for Example 41
3-Methyl-2-butanol (13.11) for Example 34
2,2-Dimethyl-propanol (13.12) for Example 42
Cyclopentanol (13.13) for Example 35
(S)-(+)-2-butanol (13.14) for Example 36
Propane-1,3-diol (13.15) for Examples 85, 223, 229, 261, 270, 274
4-Hydroxymethyl-pyrrolidin-2-one (13.16) for Examples 224, 266
(S)-3-Hydroxy-pyrrolidin-2-one (13.17) for Example 225
(S)-5-Hydroxy-piperidin-2-one (13.18) for Examples 226, 268
(3-Methyl-oxetan-3-yl)-methanol (13.19) for Examples 107, 228, 244
Oxetan-3-ol (13.20) for Examples 210, 267, 273
Tetrahydro-pyran-4-ol (13.21) for Examples 90, 227, 260
But-2-ene-1,4-diol (13.22) for Example 68
Pyridin-2-yl-methanol (13.23) for Example 69
3-Methoxy-propanol (13.24) for Example 70
2-(2-Methoxy-ethoxy)-ethanol (13.25) for Example 72
2-(2-Hydroxy-ethyl)-methyl-amino-ethanol (13.26) for Example 73
1-(2-Hydroxy-ethyl)-pyrrolidin-2-one (13.27) for Example 74
Cyclohexane-1,3-diol (13.28) for Example 75
2-Morpholin-4-yl-ethanol (13.29) for Example 76
Hexane-2,5-diol (13.30) for Example 77
2-Methyl-2-propyl-propane-1,3-diol (13.31) for Example 78
2-(2-Hydroxy-ethoxy)-ethanol (13.32) for Example 82
2-Ethyl-hexan-1,3-diol (13.33) for Example 80
2-Vinyloxy-ethanol (13.34) for Example 81
Butane-2,3-diol (13.35) for Example 83
1-(4-Hydroxy-piperidin-1-yl)-ethanone (13.36) for Example 84
(2-Hydroxymethyl-phenyl)-methanol (13.37) for Example 86
Tetrahydro-furan-3,5-diol (13.38) for Example 87

2-Methyl-propane-1,3-diol (13.39) for Example 88
(R)-(−)-3-Hydroxytetrahydrofuran (13.40) for Example 89
3-Methyl-butane-1,3-diol (13.41) for Example 91
(S)-(+)-3-Hydroxytetrahydrofuran (13.42) for Example 94
(R)-Tetrahydrofuran-2-methanol (13.43) for Example 95
1-(2-Hydroxy-ethyl)-imidazolidin-2-one (13.44) for Example 96
4-Hydroxymethyl-pyrrolidin-2-one (13.45) for Examples 97, 266
1-(3-Hydroxy-propyl)-pyrrolidin-2-one (13.46) for Example 98
Tetrahydropyran-3-ol (13.47) for Example 99
1-(2-Hydroxy-ethyl)-piperidin-2-one (13.48) for Example 100
(1S)-Trans-1,2-cyclohexanediol (13.49) for Example 102
(S)-3-Hydroxy-pyrrolidin-2-one (13.50) for Example 103
(1-Hydroxymethyl-cyclopropyl)-methanol (13.51) for Example 104
2-Hydroxy-N,N-dimethylacetamide (13.52) for Example 105
2-Hydroxymethyl-propane-1,3-diol (13.53) for Example 106
Cyclopent-3-enol (13.54) for Example 108
2-Methyl-propanol (13.56) for Example 198
Cyclopropyl-methanol (13.57) for Example 199
Cyclobutanol (13.58) for Example 200
Cyclopropyl-ethanol (13.59) for Example 201
4,4,4-Trifluoro-butanol (13.60) for Example 202
[3-(2-Methoxy-ethyl)-3H-imidazol-4-yl]-methanol (13.61) for Example 203
1,1,1-Trifluoro-propan-2-ol (13.62) for Example 204
(1-Hydroxymethyl-cyclopropyl)-acetonitrile (13.63) for Example 205
(1-Methyl-1H-imidazol-4-yl)-methanol (13.64) for Example 206
(1-Methyl-cyclopropyl)-methanol (13.65) for Example 207
Propanol (13.66) for Example 208
(1-Methyl-1H-imidazol-2-yl)-methanol (13.67) for Example 209
2,2-Difluoro-propanol (13.68) for Example 211
(2,2-Difluoro-cyclopropyl)-methanol (13.69) for Example 212
2-Propenol (13.70) for Example 213
2,2,2-Trifluoro-ethanol (13.71) for Example 214
(S)-1-(Tetrahydrofuran-2-yl)-methanol (13.72) for Example 93
Isobutylnitrile (13.73) for Examples 44, 48, 271, 275, 276, 277, 279, 280
Cis-1,5-cyclooctandiol (13.74) for Example 79
2,2-Diethyl-propane-1,3-diol (13.75) for Example 109
(R,R)-2,3-butandiol (13.76) for Example 12
(S,S)-2,3-butandiol (13.77) for Example 15

Synthesis of (S)-5-hydroxymethyl-3,3-dimethyl-pyrrolidin-2-one (13.78) for Example 101

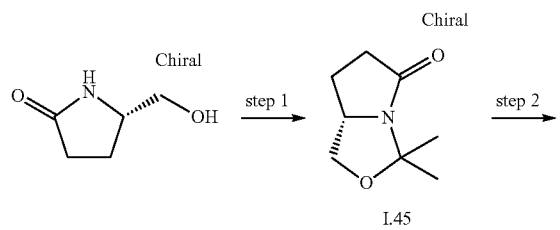

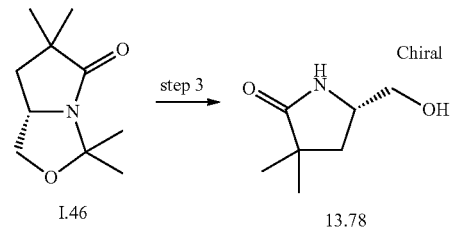

Step 1

70 ml 2,2-dimethoxypropane were added at ambient temperature to a mixture of 23.12 g 5-(S)-hydroxymethyl-pyrrolidone and 0.18 g p-toluenesulfonic acid in 500 ml toluene. The mixture was stirred for 2 h at reflux. Volatile components were distilled off at 65° C.-92° C. The residue was treated with 70 ml 2,2-dimethoxypropan and the mixture was heated at reflux for 2 h. The reaction mixture was cooled down and concentrated to give the crude 1.45.

Yield: 29.82 g I.45 (96% of theory)

Step 2

A solution of 29.8 g I.45 (3,3-dimethyl-tetrahydro-pyrrolo[1,2-c]oxazol-5-one) in 700 ml tetrahydrofuran was cooled down to −78° C. 115.2 ml Lithium diisopropylamide was slowly added dropwise to the reaction mixture and stirring was continued for 30 min at −78° C. After this time, 14.5 ml iodomethane were slowly added. The reaction mixture was warmed up to ambient temperature and cooled down again to −78° C. Additional 115.2 ml lithium diisopropylamide were added dropwise and stirred at −78° C. for 1 h. Additionally 14.5 ml iodomethane were slowly added to the reaction mixture. Stirring was continued at ambient temperature overnight. The solvent was evaporated, the residue was diluted with water and the aqueous layer was extracted with dichloromethane. In this process a precipitate formed which was dissolved with methanol. The organic layer was washed with brine, dried with sodium sulfate and the solvent was evaporated. The resulting black oil (a mixture of I.46 (3,3,6,6-tetramethyl-tetrahydro-pyrrolo[1,2-c]oxazol-5-one) and 3,3,6-trimethyl-tetrahydro-pyrrolo[1,2-c]oxazol-5-one) was dissolved in 500 ml tetrahydrofuran and the solution was cooled down to −78° C. 115.2 ml Lithium diisopropylamide were slowly added. Stirring was continued for 60 h at −78° C., 14.5 ml iodomethane were slowly added to the mixture and the mixture was stirred overnight at ambient temperature. The solvent was removed under reduced pressure. Water was added to the residue and the mixture was extracted with dichloromethane. The organic layer was washed with brine, dried with sodium sulfate and concentrated.

Yield: 27.15 g I.46 (77% of theory)

Step 3

A mixture of 27.15 g I.46 (3,3,6,6-tetramethyl-tetrahydro-pyrrolo[1,2-c]oxazol-5-one) and 0.282 g p-toluenesulfonic acid in 500 ml methanol was stirred at reflux overnight. The mixture was concentrated. Additional 500 ml methanol and 2.8 g p-toluenesulfonic acid were added and the mixture was stirred 4 h at reflux. The mixture was diluted with water and treated with sodium carbonate to obtain a basic pH. The organic layer was separated, dried with magnesium sulfate and concentrated to give 1 g (60% content; 3% of theory)

The aqueous layer was concentrated under reduced pressure, the residue was triturated with dichloromethane, the precipitate was filtered and the filtrate was concentrated to give 13.78 as yellow oil which crystallized slowly.

Yield: 12 g 13.78 (57% of theory)

The compounds (2-aminocarbonylphenyl)boronic acid (14.1) for Example 1 and ethylboronic acid (14.2) for Example 239 and 242 which were used in Scheme 3 are commercially available.

4.1.12 Synthesis of Compounds with Formula 15, 15', 16 and 16': Reaction 10; 11 and 12 from Schemes 4 and 6

In some cases, the esters 15 were isolated and characterised. Subsequent saponification with aqueous sodium hydroxide or aqueous lithium hydroxide solution and acidification yielded the acids 16.

In other cases the esters 15 were saponified in a one-pot-procedure to yield the acids 16.

Synthesis of 3-methyl-5-(4-pyridin-2-yl-pyrimidin-2-ylamino)-benzo[b]thiophene-2-carboxylic acid (16.1) for Examples 2, 5

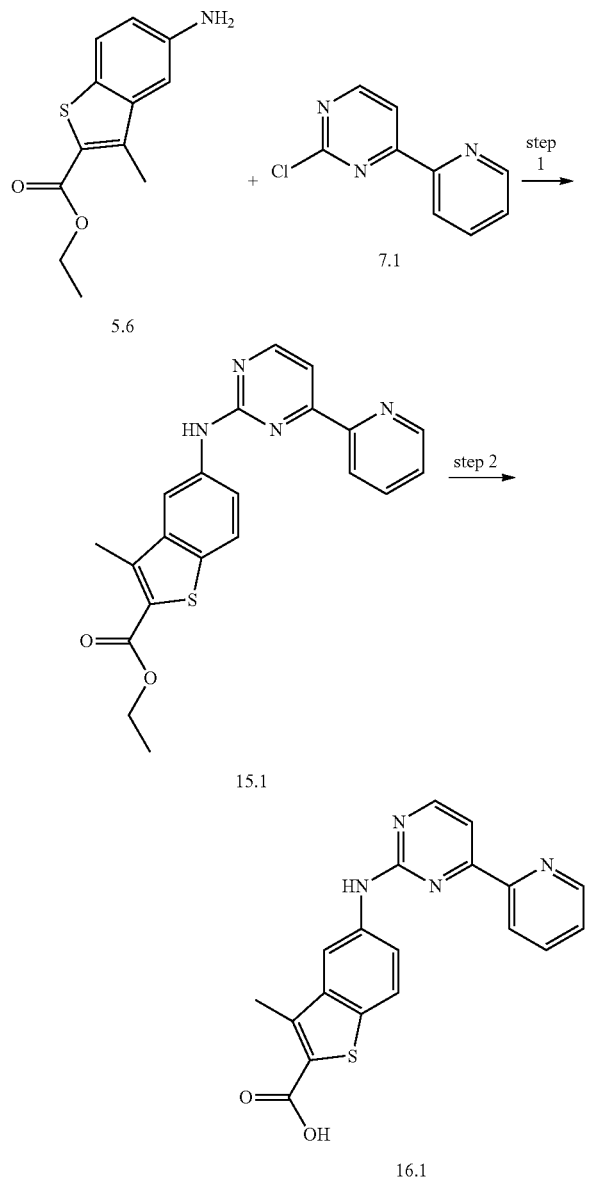 [SMILES: CCOC(=O)c1sc2ccc(N)cc2c1C ; Clc1nccc(-c2ccccn2)n1 ; CCOC(=O)c1sc2ccc(Nc3nccc(-c4ccccn4)n3)cc2c1C ; Cc1c(C(=O)O)sc2ccc(Nc3nccc(-c4ccccn4)n3)cc12]

Step 1

A mixture of 100 mg 7.1 (2-chloro-4-pyridin-2-yl-pyrimidine), 184 mg 5.6 (5-amino-3-methyl-benzo[b]thiophene-2-carboxylic acid ethyl ester) and 90 µl N,N-diisopropylethylamine in 2 ml 1-methyl-2-pyrrolidone were irradiated in a microwave oven at 150° C. for 3 h and allowed to stand at ambient temperature overnight. 90 µl N,N-diisopropylethylamine were added and the mixture was irradiated at 150° C. for 24 h. The reaction mixture was cooled to ambient temperature and diluted with 30 ml ethyl acetate. The resulting solution was washed with water (1×), saturated sodium bicarbonate (1×), 10% aqueous citric acid (1×) and brine (1×). The organic phase was dried with sodium sulfate and evaporated to give 310 mg brown oil. The oil was purified by silica gel chromatography (SiO$_2$, dichloromethane—dichloromethane/methanol 99/1 to give compound 15.1.

Yield: 102 mg 15.1 (50% of theory) Analysis: [M+H]$^+$= 391, HPLC (method H) R$_t$=2.76 min

Step 2

To a stirred suspension of 138 mg 15.1 (3-methyl-5-(4-pyridin-2-yl-pyrimidin-2-ylamino)-benzo[b]thiophene-2-carboxylic acid ethyl ester) in 6 ml ethanol were added 68 mg lithium hydroxide dissolved in 1.5 ml water and stirring was continued at 70° C. for 16 h. The reaction mixture was cooled to ambient temperature and the solvent was evaporated. The yellow solid was suspended in water and the mixture was acidified with 2N aqueous hydrochloric acid to pH 6.5. The precipitate was filtered, washed with water and dried to give 16.1 as a pale yellow solid.

Yield: 119 mg 16.1 (93% of theory) Analysis: [M+H]$^+$= 363; HPLC-MS (method H) R$_t$=1.93 min Synthesis of 6-[4-(4-methoxymethyl-pyridin-2-yl)-pyrimidin-2-ylamino]-1-methyl-1H-indole-2-carboxylic acid (16.2) for Example 265

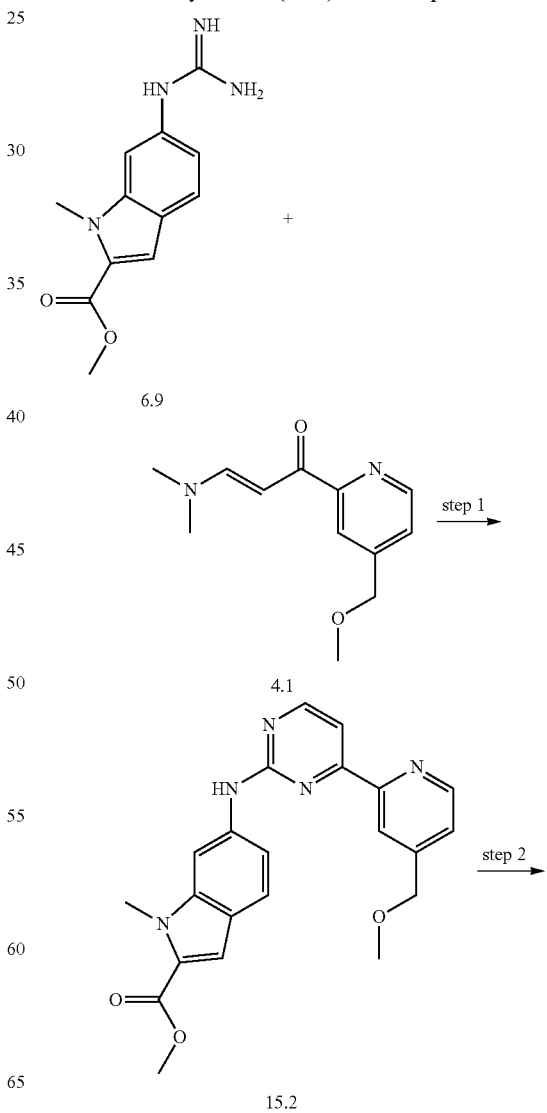

-continued

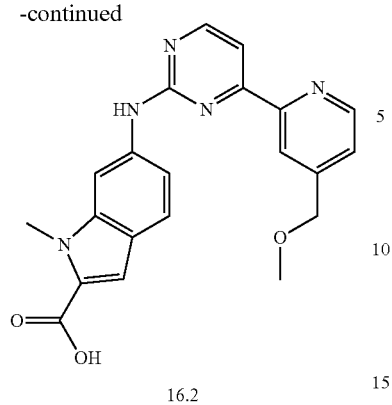

16.2

Step 1

251 mg 6.9 (6-Guanidino-1-methyl-1H-indole-2-carboxylic acid methyl ester), 0.11 g 4.1 (3-dimethylamino-1-(4-methoxymethyl-pyridin-2-yl)-propenone) and 108 mg sodium methoxide in 3 ml methanol were irradiated for 20 min at 150° C. in a microwave oven. The resulting precipitate was filtered, washed with methanol and dried to obtain 15.5 as a yellow solid.

Yield: 110 mg 15.2 (55% of theory)

Step 2

A mixture of 75 mg 15.5 (6-[4-(4-methoxymethyl-pyridin-2-yl)-pyrimidin-2-ylamino]-1-methyl-1H-indole-2-carboxylic acid methyl ester), 10 ml methanol, 5 ml tetrahydrofuran and 1 ml 1N aqueous sodium hydroxide was stirred for 3 h at 65° C. The solvent was evaporated and the crude 16.2 was used in the next step without purification.

Yield: 72.3 mg 16.2 (crude)

Synthesis of 7-bromo-5-(4-pyridin-2-yl-pyrimidin-2-ylamino)-1H-indole-2-carboxylic acid (16.3) for Examples 239, 242

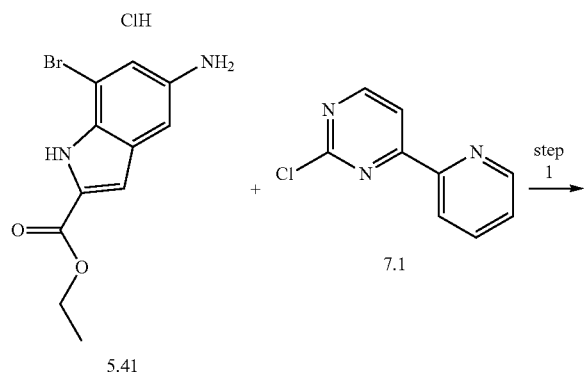

-continued

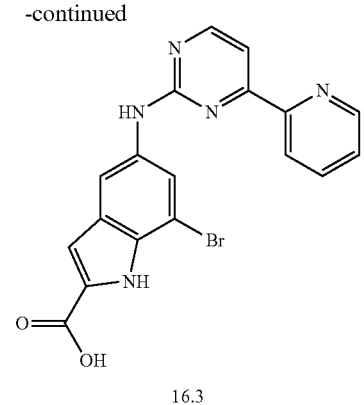

16.3

Step 1

A mixture of 880 mg 5.41 (5-amino-7-bromo-1H-indole-2-carboxylic acid ethyl ester hydrochloride), 475 mg 7.1 (2-chloro-4-pyridin-2-yl-pyrimidine) and 420 mg p-toluenesulfonic acid momohydrate in 4 ml dioxane was stirred for 2 h at reflux. The reaction mixture was evaporated, the residue was adsorbed on silica gel and purified by silica gel chromatography (SiO$_2$; dichloromethane/methanol 100/0→80/20) to obtain the compound 15.3.

Yield: 1.33 g 15.3 (90% content; 99% of theory); Analysis: [M+H]$^+$: 438

Step 2

A mixture of 1.33 g 15.3 (7-bromo-5-(4-pyridin-2-yl-pyrimidin-2-ylamino)-1H-indole-2-carboxylic acid ethyl ester) and 3.5 ml 4N aqueous sodium hydroxide solution in 20 ml tetrahydrofuran/methanol 1/1 was stirred for 1 h at 40° C. The reaction mixture was evaporated, the residue was diluted with water and acidified with 11.7 ml 1N aqueous hydrochloric acid. The resulting precipitate was filtered and dried at 50° C. overnight.

Yield: 560 mg 16.3 (45% of theory); Analysis: [M+H]$^+$: 410

Synthesis of 7-methyl-5-(4-pyridin-2-yl-pyrimidin-2-ylamino)-1H-indole-2-carboxylic acid (16.4) for Examples 243, 245, 264, 285

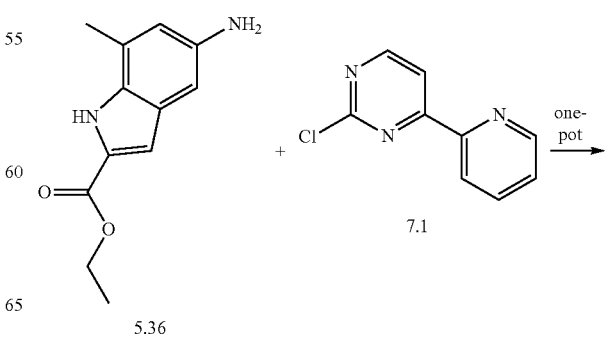

-continued

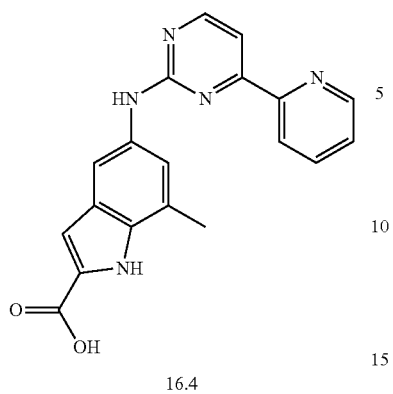

16.4

A mixture of 262 mg 7.1 (2-chloro-4-pyridin-2-yl-pyrimidine) and 192 mg 5.36 (5-amino-7-methyl-1H-indole-2-carboxylic acid ethyl ester) in 4 ml 1-methyl-2-pyrrolidone was stirred for 2 h at 160° C. The reaction mixture was purified by preparative HPLC and the combined product fractions were concentrated. The residue was suspended in 50 ml methanol and 5 ml 1N aqueous sodium hydroxide. 5 ml tetrahydrofuran were added to obtain a solution. The solution was stirred at 60° C. for 2 h. The solvent was evaporated, the residue was treated with 5 ml 1N aqueous hydrochloric acid, the solvent was removed and the crude 16.4 was used for the next reaction without purification.

Yield: 550 mg 16.4 (159% of theory, contains salts)

The following compounds were produced by a process analogously to 16.4 with the corresponding starting material:

7-Chloro-5-(4-pyridin-2-yl-pyrimidin-2-ylamino)-1H-indole-2-carboxylic acid (16.5) for Examples 249, 250, 263, 282, 290

5-(4-Pyridin-2-yl-pyrimidin-2-ylamino)-benzofuran-2-carboxylic acid (16.6) for Examples 56, 57

Synthesis of 6-(4-pyridin-2-yl-pyrimidin-2-ylamino)-1H-indole-2-carboxylic acid (16.7) for Examples 51, 52

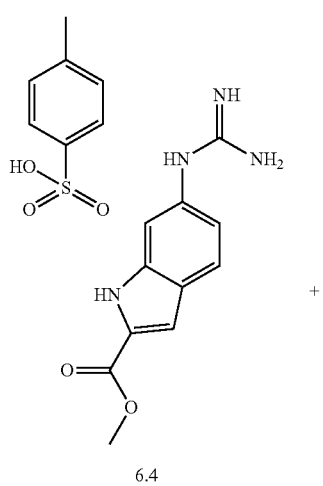

6.4

-continued

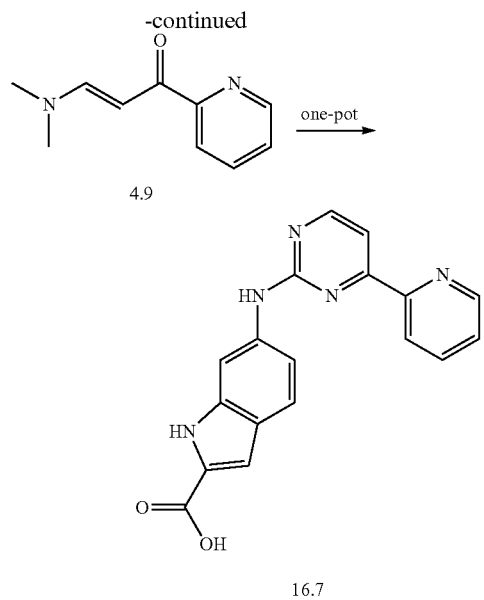

16.7

881 mg 6.4 (6-Guanidino-1H-indole-2-carboxylic acid methyl ester), 2.427 g 4.9 (3-dimethylamino-1-pyridin-2-yl-propenone) and 378 mg sodium methoxide in 10 ml methanol were irradiated for 45 min at 160° C. in a microwave oven. The reaction suspension was filtered, the solid was dissolved in 40 ml methanol/tetrahydrofuran 1:1 and treated with 10 ml 1N aqueous sodium hydroxide. The reaction mixture was stirred at 60° C. for 2 h. The organic solvent was evaporated and the aqueous residue was acidified with 1N hydrochloric acid. A precipitate formed which was filtered and dried to give the compound 16.7 as a red/brown solid.

Yield: 1.1 g 16.7 (66% of theory) Analysis: $[M+H]^+=332$

The following compounds were produced by a process analogously to 16.7 with the corresponding starting materials:

7-Chloro-5-[4-(4-methoxymethyl-pyridin-2-yl)-pyrimidin-2-ylamino]-1H-indole-2-carboxylic acid (16.8) for Examples 251, 252, 289, 291

5-(4-Pyridin-2-yl-pyrimidin-2-ylamino)-1H-indole-2-carboxylic acid (16.9) for Examples 11, 43, 50, 110-121; 123-143; 145-193, 283

5-[4-(4-Ethyl-pyridin-2-yl)-pyrimidin-2-ylamino]-1H-indole-2-carboxylic acid (16.10) for Example 63

1-Methyl-6-(4-pyridin-2-yl-pyrimidin-2-ylamino)-1H-indole-2-carboxylic acid (16.11) for Example 66

5-[4-(6-Fluoro-pyridin-2-yl)-pyrimidin-2-ylamino]-7-methyl-1H-indole-2-carboxylic acid (16.12) for Example 278

5-[4-(4-Methoxymethyl-pyridin-2-yl)-pyrimidin-2-ylamino]-1H-indole-2-carboxylic acid (16.13) for Examples 8, 253-256, 258

5-[4-(4-Methoxymethyl-pyridin-2-yl)-pyrimidin-2-ylamino]-7-methyl-1H-indole-2-carboxylic acid (16.14) for Examples 247, 248, 292

7-Chloro-5-[4-(6-fluoro-pyridin-2-yl)-pyrimidin-2-ylamino]-1H-indole-2-carboxylic acid (16.15) for Example 272

5-[4-(4-tert-Butyl-pyridin-2-yl)-pyrimidin-2-ylamino]-1H-indole-2-carboxylic acid (16.16) for Example 49

5-[4-(4-Isopropyl-pyridin-2-yl)-pyrimidin-2-ylamino]-1H-indole-2-carboxylic acid (16.17) for Example 53

5-[4-(4-Methoxy-pyridin-2-yl)-pyrimidin-2-ylamino]-1H-indole-2-carboxylic acid (16.18) for Examples 16-19, 21, 22, 58-61, 65, 67, 231, 257

5-(4-Pyridin-2-yl-pyrimidin-2-ylamino)-benzo[b]thiophene-2-carboxylic acid (16.19) for Examples 54, 55

5-[4-(4-Methoxy-pyridin-2-yl)-pyrimidin-2-ylamino]-benzo[b]thiophene-2-carboxylic acid (15.20) for Examples 62, 64

5-[4-(4-Methyl-pyridin-2-yl)-pyrimidin-2-ylamino]-1H-indole-2-carboxylic acid (16.21) for Example 6

Synthesis of 7-methoxy-5-(4-pyridin-2-yl-pyrimidin-2-ylamino)-1H-indole-2-carboxylic acid (16.22) for Examples 122; 144

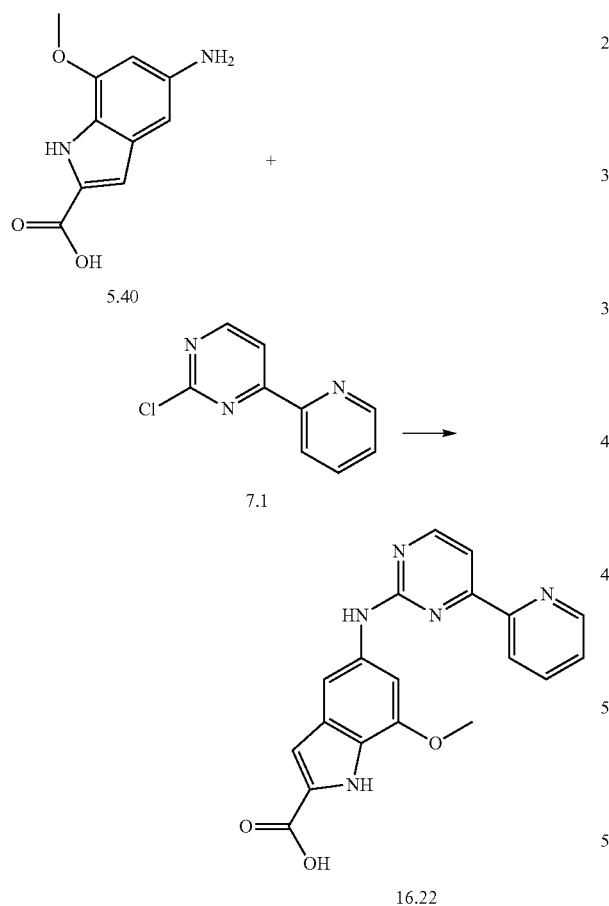

A mixture of 96 mg 7.1 (2-chloro-4-pyridin-2-yl-pyrimidine) and 103 mg 5.40 (5-amino-7-methoxy-1H-indole-2-carboxylic acid) in 1 ml N-methylpyrrolidine was stirred for 1 h at 140° C. The residue was purified by preparative HPLC. The combined product fractions were evaporated and the residue was dissolved in acetonitrile/water and lyophilized to obtain the compound 16.22 as a yellow solid.

Yield: 160 mg 16.22 (89% of theory); HPLC-MS (method A) $R_t$=1.53 min 4.1.13 Synthesis of Compounds with the Formula 17: Reaction 14 from Scheme 5

Synthesis of piperazin-1-yl-[5-(4-pyridin-2-yl-pyrimidin-2-ylamino)-1H-indol-2-yl]-methanone (17.1) for Examples 13, 14

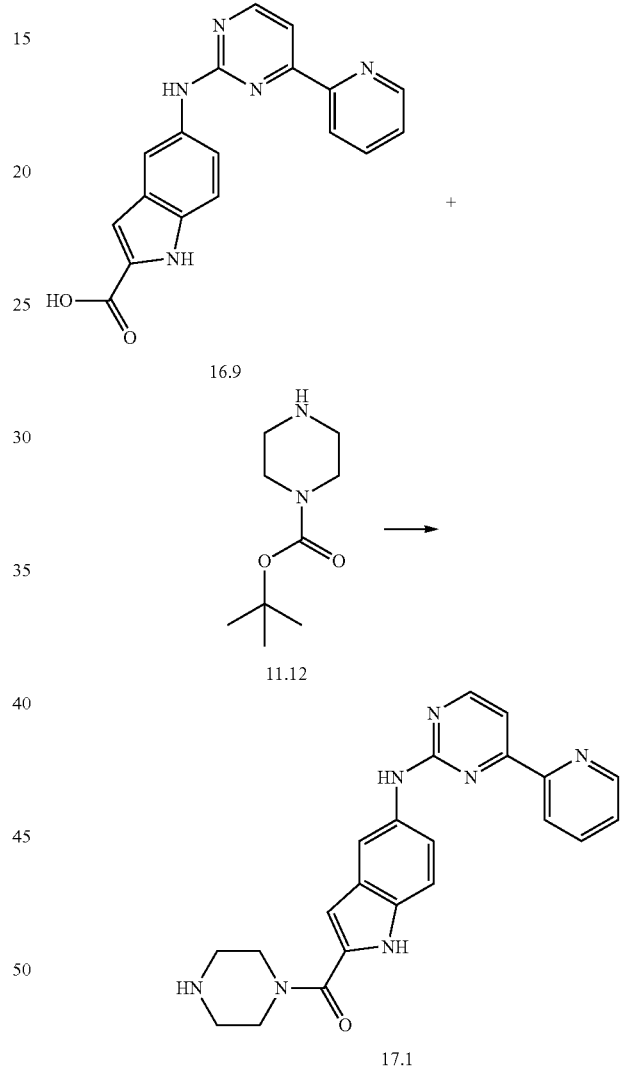

A mixture of 330 mg 16.9 (5-(4-pyridin-2-yl-pyrimidin-2-ylamino)-1H-indole-2-carboxylic acid), 186 mg 11.12 (boc-piperazine), 321 mg [(benzotriazol-1-yloxy)-dimethylamino-methylene]-dimethyl-ammonium tetrafluoroborate (TBTU) and 344 ml N,N-diisopropylethylamine in 5 ml N,N-dimethylformamide was stirred at ambient temperature for 2 h. The reaction mixture was filtered through a pad of aluminum oxide and the solvent was evaporated. The residue was treated with 20 ml dichloromethane/trifluoroacetic 1/1 acid and stirred at ambient temperature overnight. The solvents were distilled and the residue was purified by preparative HPLC. The combined product fractions were concentrated. The crude material was dissolved in acetonitrile/water and lyophilized to give an orange solid 17.1.

Yield: 343 mg 17.1 (86% of theory) Analysis $[M+H]^+$= 400; HPLC (method D): $R_t$=1.59 min The following compound {5-[4-(4-Methoxy-pyridin-2-yl)-pyrimidin-2-ylamino]-1H-indol-2-yl}-piperazin-1-yl-methanone (17.2) for Examples 21, 22 was prepared analogous to 17.1 with the corresponding intermediate 16.18.

4.1.14 Synthesis of Compounds with the Formula 18 from Scheme 5

All of the Following Acids are Commercially Available:
(S)-(−)-Tetrahydrofuran-2-carboxylic acid (18.1) for Examples 13, 22
(R)-(+)-Tetrahydrofuran-2-carboxylic acid (18.2) for Examples 14, 21

4.1.15 Synthesis of Compounds with the Formula 19: Reaction 13 from Scheme 6

Synthesis of 7-bromo-5-(4-pyridin-2-yl-pyrimidin-2-ylamino)-1H-indole-2-carboxylic acid methylamide (19.1) for Example 239

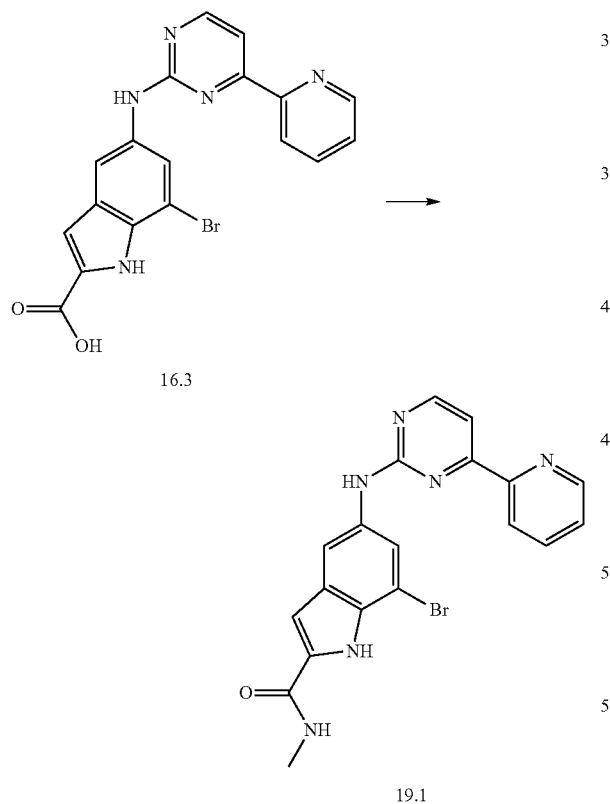

A mixture of 100 mg 16.3 (7-bromo-5-(4-pyridin-2-yl-pyrimidin-2-ylamino)-1H-indole-2-carboxylic acid), 78 mg [(benzotriazol-1-yloxy)-dimethylamino-methylene]-dimethyl-ammonium tetrafluoroborate (TBTU), 42 µl N,N-diisopropylethylamine in 3 ml N,N-dimethylformamide was stirred at ambient temperature for 20 minutes. 122 µl 2N Methylamine in tetrahydrofuran were added and the reaction mixture was stirred at ambient temperature for 1 h. The reaction mixture was evaporated. The residue was dissolved in methanol/water and aqueous ammonia solution and purified by preparative HPLC. The combined product fractions were concentrated and lyophilized.

Yield: 36 mg 19.1 (35% of theory) Analysis $[M-H]^-$=421; HPLC (method O): $R_t$=1.35 min The following compound 7-bromo-5-(4-pyridin-2-yl-pyrimidin-2-ylamino)-1H-indole-2-carboxylic acid dimethylamide (19.2) for Example 242 was prepared analogously to 19.1 with the corresponding intermediate 16.3.

4.2 Synthesis of the Examples of Formula 1

4.2.1 Reaction 4 from Scheme 1

Example 215

(1-methyl-1H-benzoimidazol-5-yl)-(4-pyridin-2-yl-pyrimidin-2-yl)-amine

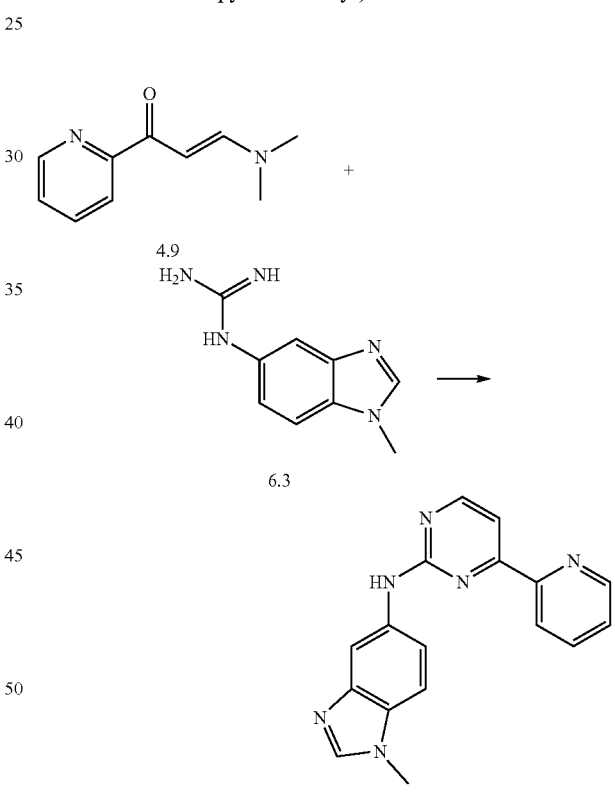

Example 215

A mixture of 88 mg 4.9 (3-dimethylamino-1-pyridin-2-yl-propenone), 189 mg 6.3 (N-(1-methyl-1H-benzoimidazol-5-yl)-guanidine) and 100 mg sodium methylate in 4 ml methanol was irradiated for 30 min at 150° C. in a microwave oven. The resulting mixture was purified by preparative HPLC. The combined product fractions were evaporated. The residue was dissolved in acetonitrile/water 1/1 and lyophilized to obtain the product example 215 a yellow solid.

Yield: 72 mg Example 215 (24% of theory); Analysis $[M+H]^+$=303; HPLC-MS (method D) $R_t$=1.64 min

Example 7

(2-tert-butyl-1H-indol-5-yl)-[4-(4-methoxymethyl-pyridin-2-yl)-pyrimidin-2-yl]-amine

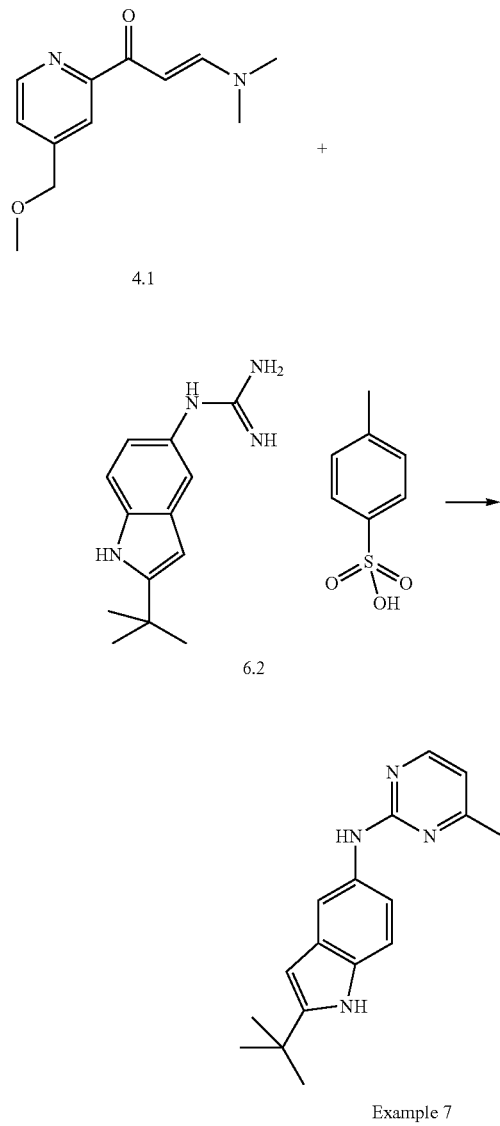

Example 7

A mixture of 100 mg 4.1 (3-dimethylamino-1-(4-methoxymethyl-pyridin-2-yl)-propenone), 183 mg 6.2 (N-(2-tert-butyl-1H-indol-5-yl)-guanidine 4-toluenesulfonic acid salt) and 63 mg potassium carbonate in 3 ml isopropanol and the mixture was irradiated for 1.5 h at 150° C. in a microwave oven. 20 ml Brine were added and the reaction mixture was extracted with 20 ml ethyl acetate (3×). The combined organic phases were dried with sodium sulfate and the solvent was evaporated. The crude material was recrystallized from methanol to give example 7.

Yield: 97 mg Example 7 (55% of theory); Analysis: HPLC-MS (method E) $R_t$=4.71 min

4.2.2 Reaction 5 from Scheme 2

Example 287

(7-chloro-1H-benzoimidazol-5-yl)-(4-pyridin-2-yl-pyrimidin-2-yl)-amine

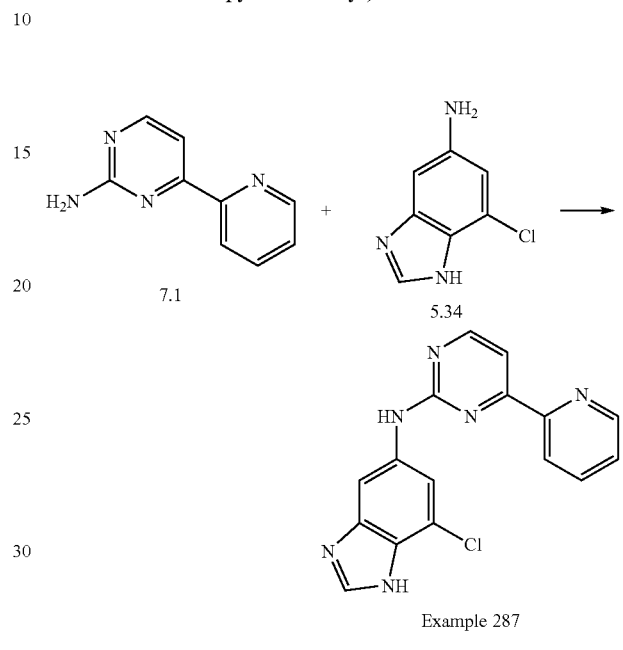

Example 287

A mixture of 38 mg 7.1 (4-pyridin-2-yl-pyrimidin-2-ylamine) and 42 mg 5.34 (7-chloro-1H-benzoimidazol-5-ylamine) in 1 ml 1-methyl-2-pyrrolidone was stirred at 150° C. for 1 h. The reaction mixture was purified by preparative HPLC. The combined product fractions were concentrated. The residue was dissolved in acetonitrile/water 1/1 and lyophilized to obtain a yellow solid.

Yield: 22 mg Example 287 (34% of theory); Analysis [M+H]$^+$=323; HPLC-MS (method A) $R_t$=1.56 min

Example 230

(4-methyl-piperazin-1-yl)-[3-methyl-5-(4-pyridin-2-yl-pyrimidin-2-ylamino)-1H-indol-2-yl]-methanone hydrochloride

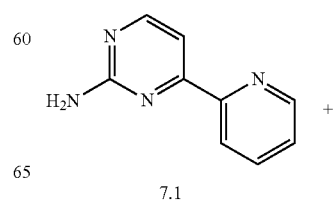

7.1

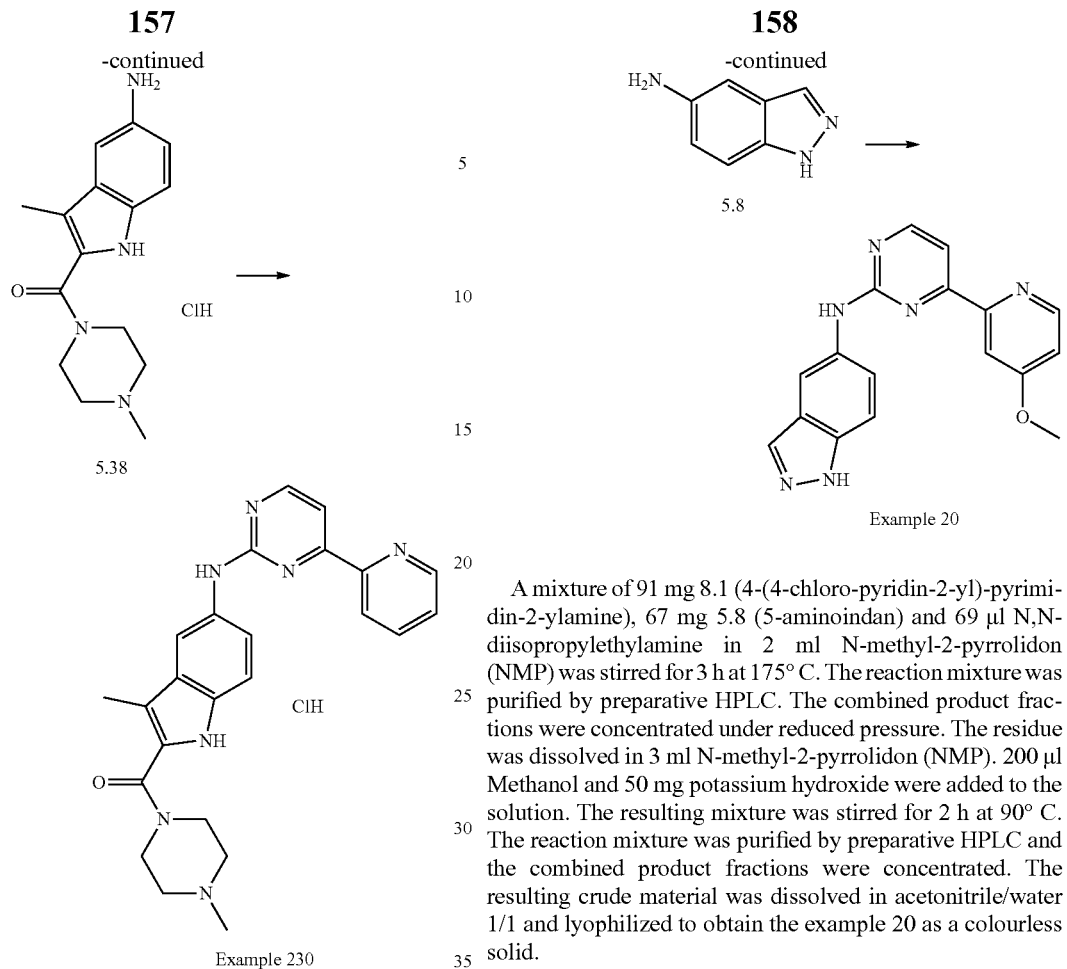

21 mg 7.1 (4-pyridin-2-yl-pyrimidin-2-ylamine), 36 mg 5.38 ((5-amino-3-methyl-1H-indol-2-yl)-(4-methyl-piperazin-1-yl)-methanone hydrochloride) and 11 µl concentrated hydrochloric acid in 1 ml n-butanole were irradiated at 160° C. for 1 h in a microwave oven. The solvent was evaporated, the residue was dissolved in dichloromethane/methanol and pre-absorbed on silica gel. The material was purified by silica gel chromatography (SiO$_2$; dichloromethane/methanol 99/1-97/3) to give a solid.

Yield: 11 mg Example 230 (22% of theory); Analysis [M+H]$^+$=428; HPLC-MS (method H) R$_t$=2.72 min Example 20

(1H-indazol-5-yl)-[4-(4-methoxy-pyridin-2-yl)-pyrimidin-2-yl]-amine

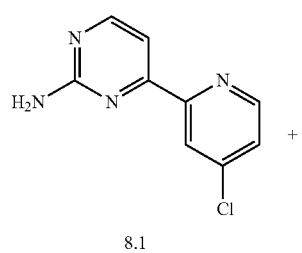

A mixture of 91 mg 8.1 (4-(4-chloro-pyridin-2-yl)-pyrimidin-2-ylamine), 67 mg 5.8 (5-aminoindan) and 69 µl N,N-diisopropylethylamine in 2 ml N-methyl-2-pyrrolidon (NMP) was stirred for 3 h at 175° C. The reaction mixture was purified by preparative HPLC. The combined product fractions were concentrated under reduced pressure. The residue was dissolved in 3 ml N-methyl-2-pyrrolidon (NMP). 200 µl Methanol and 50 mg potassium hydroxide were added to the solution. The resulting mixture was stirred for 2 h at 90° C. The reaction mixture was purified by preparative HPLC and the combined product fractions were concentrated. The resulting crude material was dissolved in acetonitrile/water 1/1 and lyophilized to obtain the example 20 as a colourless solid.

Yield: 30 mg Example 20 (24% of theory); Analysis [M+H]$^+$=319; HPLC-MS (method D) R$_t$=1.67 min 4.2.3 Reaction 9 of Scheme 3a and 3b Example 1

2-{2-[2-(1,3-dihydro-isobenzofuran-5-ylamino)-pyrimidin-4-yl]-pyridin-4-yl}-benzamide

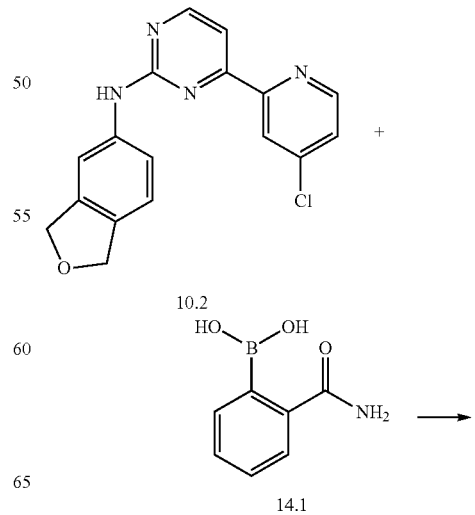

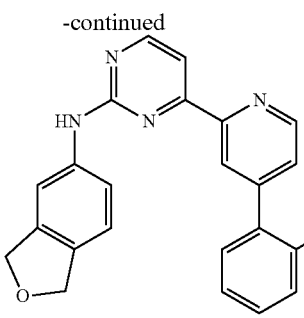

Example 1

A mixture of 97 mg 10.2 ([4-(4-chloro-pyridin-2-yl)-pyrimidin-2-yl]-(1,3-dihydro-isobenzofuran-5-yl)-amine), 49 mg 14.1 ((2-aminocarbonylphenyl) boronic acid), 11 mg 1,1'bis(diphenylphospino)ferrocene dichloropalladium(II), 41 mg potassium carbonate, 3 ml 1,2-dimethoxyethane and 1 ml water was irradiated in a microwave oven at 120° C. for 20 min. The reaction mixture was submitted to preparative HPLC. The combined product fractions were lyophilized to obtain a yellow solid.

Yield: 10 mg Example 1 (8% of theory); Analysis [M+H]$^+$=410; HPLC-MS (method B) $R_t$=1.90 min Example 4

(2-tert-butyl-1H-indol-5-yl)-{4-[4-(1H-pyrrol-3-yl)-pyridin-2-yl]-pyrimidin-2-yl}-amine

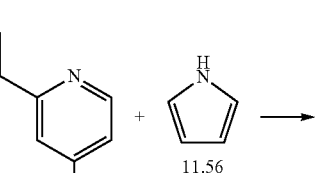

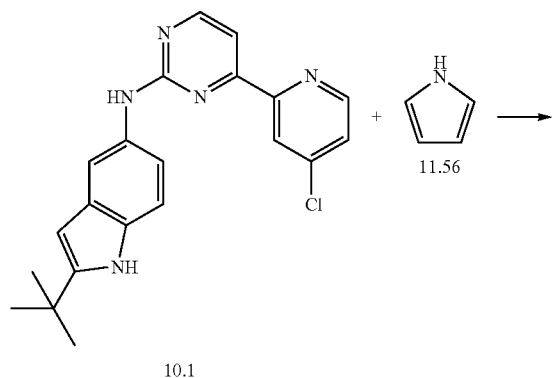

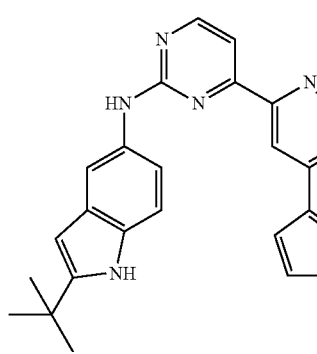

Example 4

A suspension of 100 mg 10.1 ((2-tert-butyl-1H-indol-5-yl)-[4-(4-chloro-pyridin-2-yl)-pyrimidin-2-yl]-amine), 19 µl 11.56 (pyrrole), 172 mg cesium carbonate, 1 mg palladium (II) acetate and 5 mg 4,5-bis(diphenylphosphino)-9,9-dimethylxanthene in 2 ml N,N-dimethylformamide was irradiated in a microwave at 150° C. for 20 min. The solids were filtered and washed with N,N-dimethylformamide. The filtrate was diluted with ethyl acetate/heptane 2/1 and extracted with brine. The organic phase was dried with sodium sulfate and concentrated. The residue was purified by silica gel chromatography (SiO$_2$; dichloromethane/methanol 100/0-95/5). The product fractions were evaporated. The resulting crude material was purified by preparative HPLC Yield: 5.5 mg Example 4 (5% of theory); Analysis [M+H]$^+$=409; HPLC-MS (method E) $R_t$=3.98 min Example 92

(5-{4-[4-(2,2-difluoro-ethoxy)-pyridin-2-yl]-pyrimidin-2-ylamino}-1H-indol-2-yl)-(4-methyl-piperazin-1-yl)-methanone

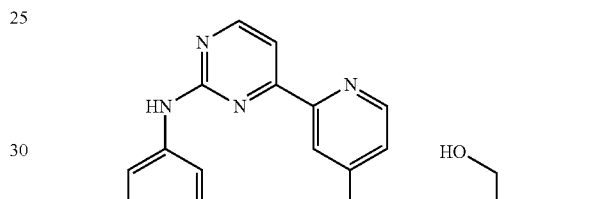

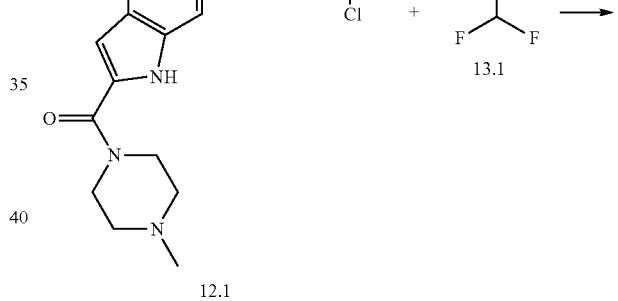

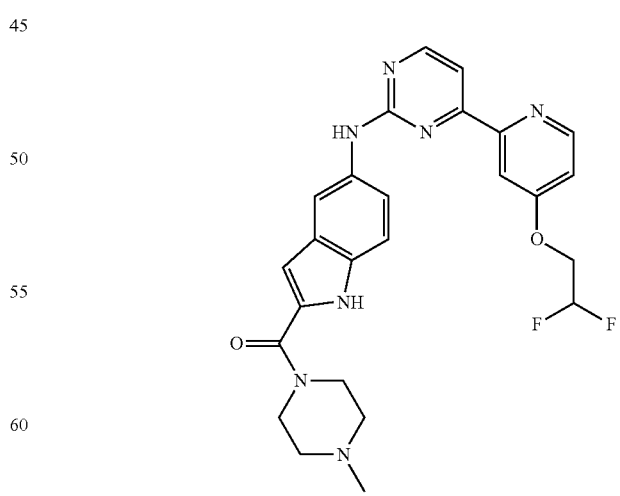

Example 92

A mixture of 448 mg 10.11 ({5-[4-(4-chloro-pyridin-2-yl)-pyrimidin-2-ylamino]-1H-indol-2-yl}-(4-methyl-piperazin- 1-yl)-methanone), 633 µl 13.1 (2,2-difluoroethanol) and 561 mg potassium hydroxide in 4 ml N-methyl-2-pyrrolidone (NMP) was stirred at 80° C. for 2 h. The reaction mixture was purified by preparative HPLC. The combined product fractions were evaporated to obtain a yellow solid as example 92.

The reaction was repeated on the same scale and the products from both runs were combined.

Yield: 180 mg Example 92 (73% of theory); Analysis [M+H]$^+$=494; HPLC-MS (method K) $R_t$=0.97 min

Example 44

2-methyl-2-(2-{2-[2-(4-methyl-piperazine-1-carbonyl)-1H-indol-5-ylamino]-pyrimidin-4-yl}-pyridin-4-yl)-propionitrile

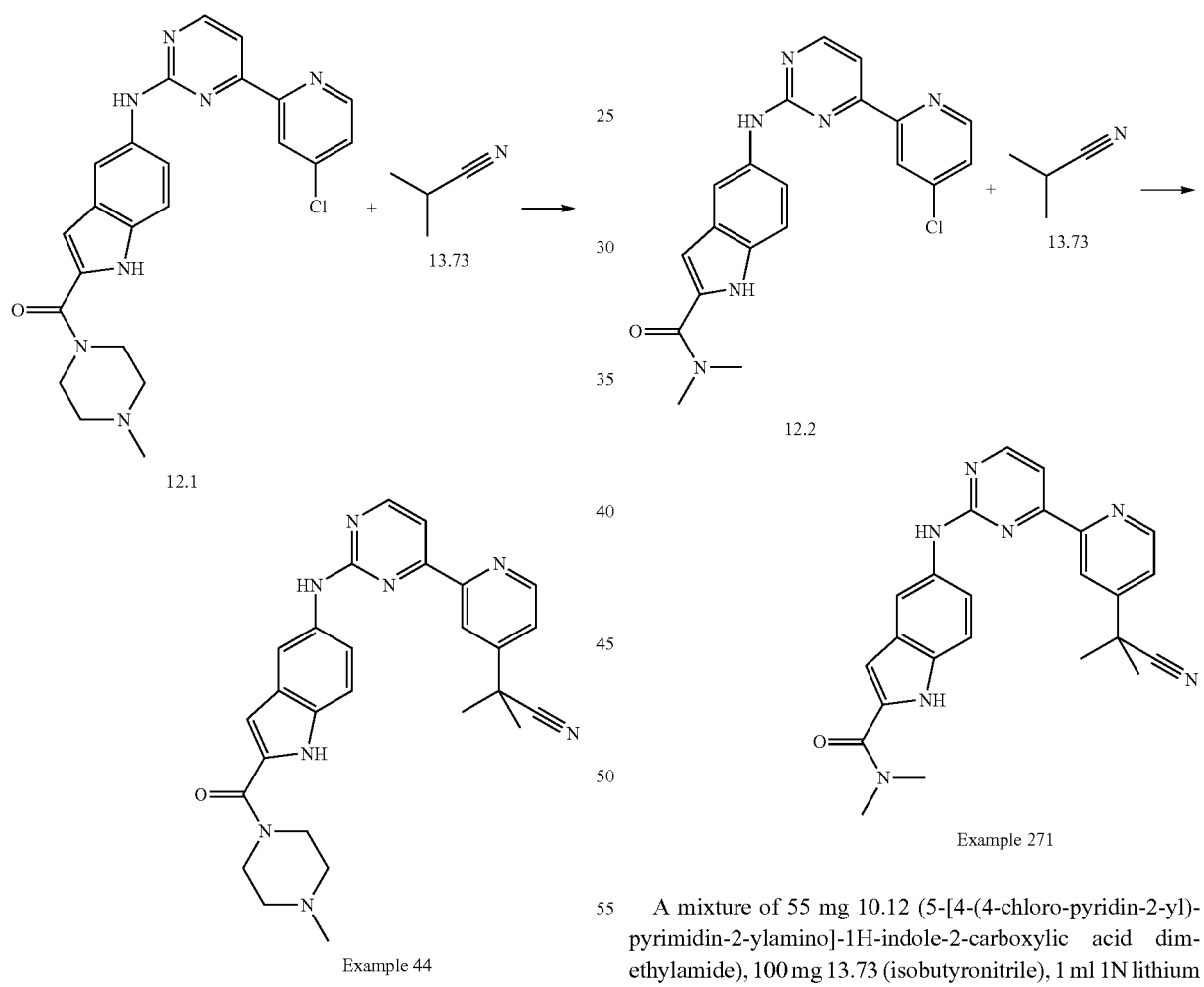

Example 44

96 mg Sodium hydride (60% content) was added to a solution of 55 mg 13.73 (isobutyronitrile) in 2 ml N,N-dimethylformamide and the mixture was stirred at ambient temperature for 10 min. 45 mg 10.11 ({5-[4-(4-Chloro-pyridin-2-yl)-pyrimidin-2-ylamino]-1H-indol-2-yl}-(4-methyl-piperazin-1-yl)-methanone) was added and the mixture was stirred 10 min at ambient temperature. The mixture was irradiated in a microwave oven at 140° C. for 10 min. The reaction mixture was degassed in an ultrasound bath, flushed with nitrogen and irradiated in a microwave oven at 100° C. for 20 min. The reaction mixture was purified by preparative HPLC. The combined product fractions were evaporated and the resulting residue was dissolved in acetonitrile/water 1/1 and lyophilized.

Yield: 15 mg Example 44 (31% of theory); Analysis [M+H]$^+$=481; HPLC-MS (method G) $R_t$=1.64 min

Example 271

5-{4-[4-(cyano-dimethyl-methyl)-pyridin-2-yl]-pyrimidin-2-ylamino}-1H-indole-2-carboxylic acid dimethylamide

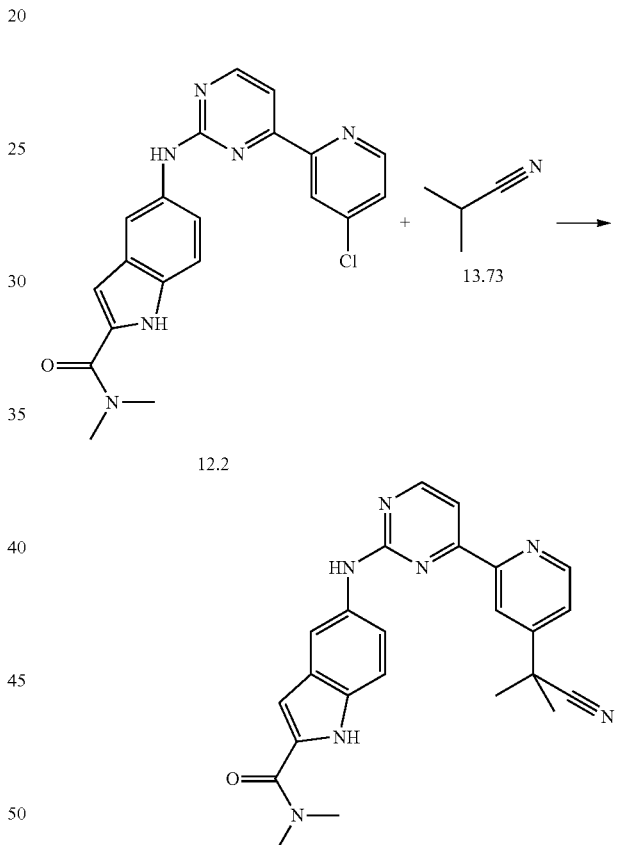

Example 271

A mixture of 55 mg 10.12 (5-[4-(4-chloro-pyridin-2-yl)-pyrimidin-2-ylamino]-1H-indole-2-carboxylic acid dimethylamide), 100 mg 13.73 (isobutyronitrile), 1 ml 1N lithium bis(trimethylsilyl)amide in tetrahydrofuran and 1 ml tetrahydrofuran was irradiated in a microwave oven at 100° C. for 10 min. The reaction mixture was treated with water and the tetrahydrofuran was evaporated. The resulting precipitate was filtered, washed with water and dried to obtain the example 271 as a yellow solid.

Yield: 33 mg Example 271 (55% of theory); Analysis [M+H]$^+$=426; HPLC-MS (method A) $R_t$=1.97 min

4.2.4 Reaction 13 of Scheme 4

Example 8

{5-[4-(4-methoxymethyl-pyridin-2-yl)-pyrimidin-2-ylamino]-1H-indol-2-yl}-(4-methyl-piperazin-1-yl)-methanone

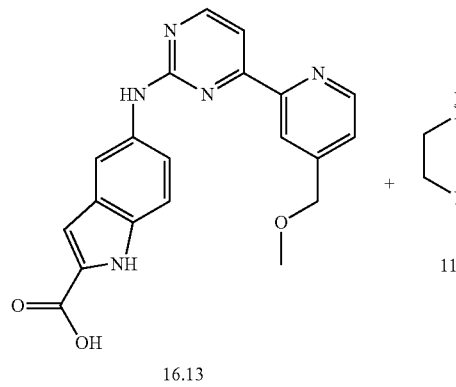

16.13

11.10

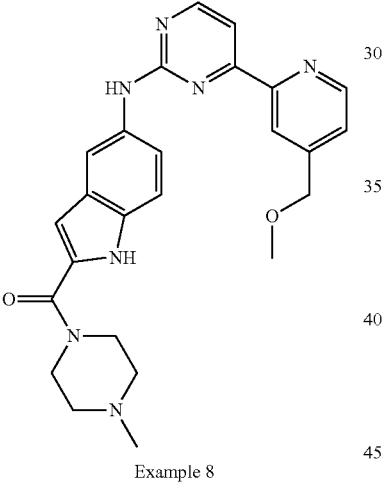

Example 8

A mixture of 340 mg 16.13 (5-[4-(4-methoxymethyl-pyridin-2-yl)-pyrimidin-2-ylamino]-1H-indole-2-carboxylic acid), 321 mg [(benzotriazol-1-yloxy)-dimethylamino-methylene]-dimethyl-ammonium tetrafluoroborate (TBTU) and 344 µl N,N-diisopropylethylamine in 7 ml N,N-dimethylformamide was stirred at ambient temperature for 10 minutes. 100 mg 11.10 (N-Methylpiperazine) were added and the reaction mixture was stirred at ambient temperature for 2 h. The mixture was diluted with 10 ml water and 1.5 ml 1 N aqueous sodium hydroxide solution. The yellow solid was filtered and dried to obtain the example 8.

Yield: 350 mg Example 8 (84% of theory); Analysis [M+H]$^+$=458; HPLC-MS (method A) R$_t$=1.35 min Instead of [(benzotriazol-1-yloxy)-dimethylamino-methylene]-dimethyl-ammonium tetrafluoroborate (TBTU), O-(7-azobenzotriazol-1-yl)-1,1,3,3-tetramethyluronium hexafluoro-phosphate (HATU) was used in some cases.

4.2.5 Reaction 15 of Scheme 5

Example 13

[5-(4-pyridin-2-yl-pyrimidin-2-ylamino)-1H-indol-2-yl]-[4-(tetrahydro-furan-2-carbonyl)-piperazin-1-yl]-methanone

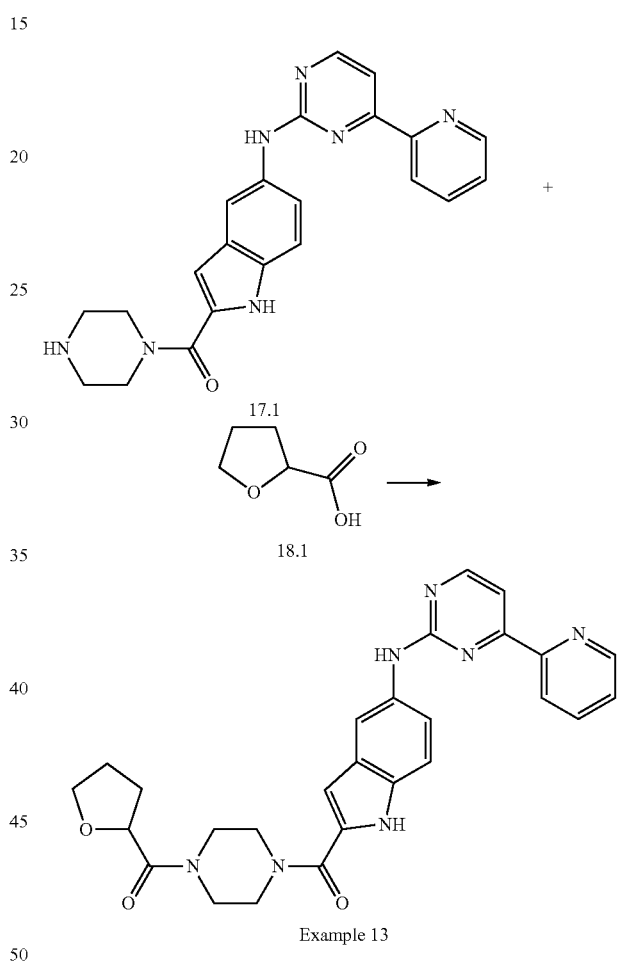

Example 13

A mixture of 50 mg 17.1 (piperazin-1-yl-[5-(4-pyridin-2-yl-pyrimidin-2-ylamino)-1H-indol-2-yl]-methanone), 12 mg 18.1 ((S)-(−)-tertahydrofuran-2-carboxylic acid), 32 mg [(benzotriazol-1-yloxy)-dimethylamino-methylene]-dimethyl-ammonium tetrafluoroborate (TBTU) and 52 µl N,N-diisopropylethylamine in 2 ml N,N-dimethylformamide was stirred for 2 h at ambient temperature. The reaction mixture was purified by preparative HPLC. The combined product fractions were concentrated. The resulting residue was dissolved in acetonitrile/water 1/1 and lyophilized to obtain example 13 as a yellow solid.

Yield: 31 mg Example 13 (50% of theory); Analysis [M+H]$^+$=498; HPLC-MS (method C) R$_t$=2.33 min

4.2.6 Reaction 16 of Scheme 6

Example 239

7-ethyl-5-(4-pyridin-2-yl-pyrimidin-2-ylamino)-1H-indole-2-carboxylic acid methylamide

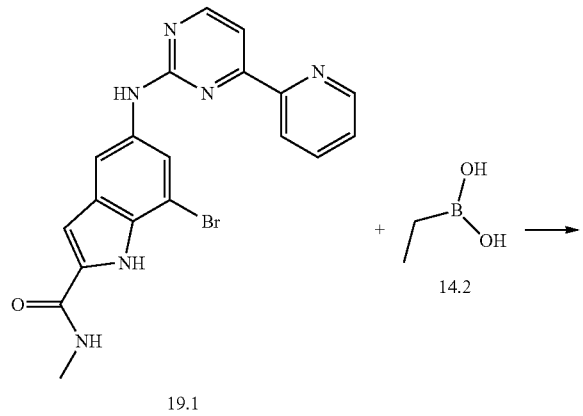

19.1

14.2

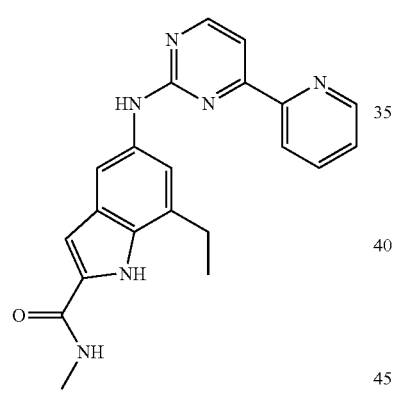

Example 239

A mixture of 35 mg 19.1 (7-bromo-5-(4-pyridin-2-yl-pyrimidin-2-ylamino)-1H-indole-2-carboxylic acid methylamide), 14 mg 14.2 (ethylboronicboronic acid), 6 mg 1,1'bis(diphenylphospino)ferrocene dichloropalladium(II), 20 mg potassium carbonate, 1.2 ml dioxane/water 2/1 were stirred in a tube at 100° C. for 3.5 h. Additional 3 mg 14.2 (ethylboronicboronic acid), 6 mg 1,1'bis(diphenylphospino)ferrocene dichloropalladium(II) and 9 mg potassium carbonate were added to the reaction mixture and stirred at 100° C. overnight. The reaction mixture was treated with water, the aqueous phase was washed with dichloromethane (2×) and the combined organic layers were evaporated. The residue was purified by silica gel chromatography (SiO$_2$, dichloromethane/methanol 100/0→98/2).

Yield: 10 mg Example 239 (32% of theory); Analysis [M+H]$^+$=373; HPLC-MS (method O) R$_f$=1.12 min

4.2.7 Reaction 17 of Scheme 7

Example 9

{2-[2-(2-tert-butyl-1H-indol-5-ylamino)-pyrimidin-4-yl]-pyridin-4-yl}-methanol

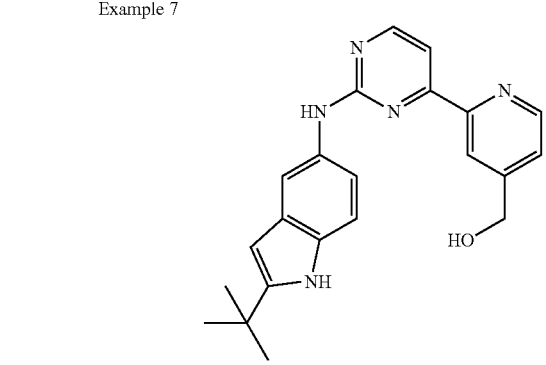

Example 7

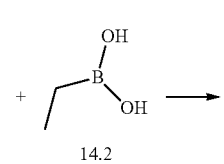

Example 9

A mixture of 72 mg example 7 ((2-tert-butyl-1H-indol-5-yl)-[4-(4-methoxymethyl-pyridin-2-yl)-pyrimidin-2-yl]-amine) in 1 ml dichloromethane was cooled to −78° C. under an atmosphere of nitrogen. 279 µl Boron tribromide were added and the reaction mixture was warmed to ambient temperature and stirred for 3 h. The reaction mixture was quenched with 0.5 ml water and 25 ml aqueous sodium bicarbonate solution. The aqueous layer was extracted with 15 ml dichloromethane (3×). The combined organic layers were washed with brine and evaporated. The residue was purified by silica gel chromatography (SiO$_2$; dichloromethane/ethyl acetate 100/0→0/100). The combined product fractions were evaporated under reduced pressure to obtain example 8.

Yield: 36 mg Example 8 (51% of theory); Analysis [M+H]$^+$=374; HPLC-MS (method E) R$_f$=3.83 min

4.2.8 Reaction 18 of Scheme 8

Example 231

5-[4-(4-methoxy-pyridin-2-yl)-pyrimidin-2-ylamino]-1H-indole-2-carbothioic acid dimethylamide

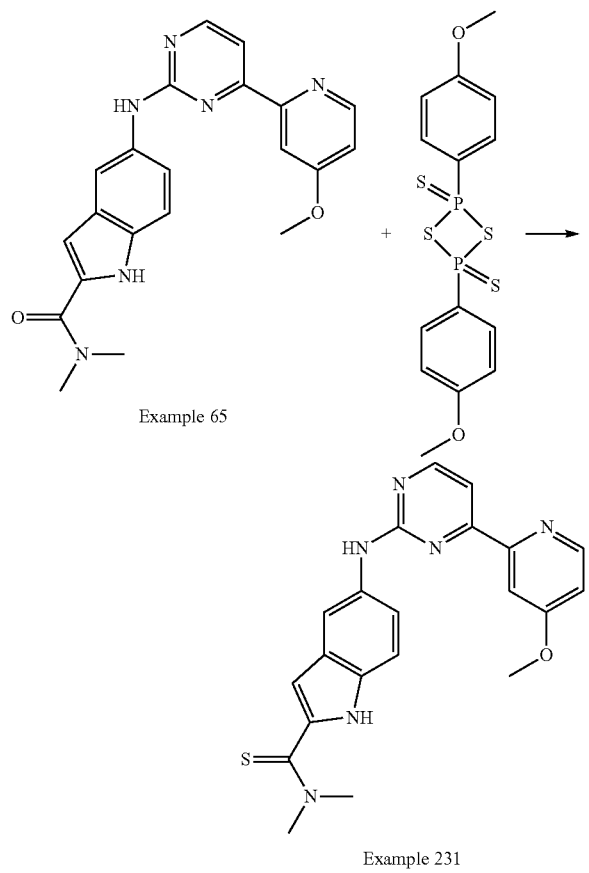

A suspension of 116 mg of example 65 (5-[4-(4-methoxy-pyridin-2-yl)-pyrimidin-2-ylamino]-1H-indole-2-carboxylic acid dimethylamide) and 121 mg of Lawesson's reagent in 1 ml tetrahydrofuran was heated for 18 h. After this time, 60 mg of Lawesson's reagent were added and the mixture was stirred for 24 h under heating. The reaction mixture was cooled down and diluted with dichloromethane and aqueous sodium bicarbonate solution were added and the mixture was stirred for 5 min. The organic layer was separated and dried with sodium sulfate, filtered and concentrated to give brown oil. The oil was purified by silica gel chromatography (SiO$_2$; dichloromethane; 0-6% methanol). The combined product fractions were concentrated to give a crystalline yellow solid.

Yield: 44 mg Example 231 (36% of theory); Analysis [M+H]$^+$=405; HPLC-MS (method E) R$_t$=3.47 min

4.3 Chromatographic Methods (HPLC-MS Methods)

The example compounds prepared according to the foregoing synthesis scheme were characterised by the following chromatographic methods, which—if they were carried out are specified individually in Table 1.

Method A:
Waters ZQ2000 MS; Alliance 2695 HPLC pump, PD2996 210-500 nm detector, Waters 2700 AS.
Eluent A: Water (+0.1% TFA)
Eluent B: Methanol

| Time [min] | % A | % B | Flow rate [mL/min] |
|---|---|---|---|
| 0.00 | 80 | 20 | 2 |
| 1.70 | 0 | 100 | 2 |
| 2.50 | 0 | 100 | 2 |
| 2.60 | 80 | 20 | 2 |

The stationary phase used was a Waters Sunfire C18, 4.6×50 mm, 3.5 μm, column temperature: 60° C.

Method B:
Waters ZQ2000 MS; Agilent HP100, binäre Pumpe, DAD 210-500 nm detector, Waters 2700AS.
Eluent A: Water (+0.032% NH$_4$OH)
Eluent B: Methanol

| Time [min] | % A | % B | Flow rate [mL/min] |
|---|---|---|---|
| 0.00 | 95 | 5 | 1.5 |
| 2.00 | 0 | 100 | 1.5 |

The stationary phase used was a Waters XBridge C18, 4.6×50 mm, 3.5 μm, column temperature: 40° C.

Method C:
Waters ZQ2000 MS; Alliance 2790 pump, PDA2996 210-500 nm detector, Waters 2700AS.
Eluent A: Water (+0.01% TFA)
Eluent B: Acetonitrile (+0.008% TFA)

| Time [min] | % A | % B | Flow rate [mL/min] |
|---|---|---|---|
| 0.00 | 95 | 5 | 1.5 |
| 2.00 | 0 | 100 | 1.5 |
| 3.00 | 0 | 100 | 1.5 |
| 3.40 | 95 | 5 | 1.5 |

The stationary phase used was a Waters Atlantis C18, 4.6×50 mm, 3.5 μm, column temperature: 40° C.

Method D:
Waters ZQ2000 MS; Alliance 2695 pump, PDA2996 210-500 nm detector, Waters 2700AS.
Eluent A: Water (+0.1% TFA)
Eluent B: Methanol

| Time [min] | % A | % B | Flow rate [mL/min] |
|---|---|---|---|
| 0.00 | 95 | 5 | 1.5 |
| 1.30 | 0 | 100 | 1.5 |
| 3.00 | 0 | 100 | 1.5 |
| 3.40 | 95 | 5 | 1.5 |

The stationary phase used was a Waters Sunfire C18, 4.6×50 mm, 3.5 μm, column temperature: 40° C.

Method E:
Waters ZQ, Agilent G1312A HPLC pump, Waters 2996 PDA detector, Waters 2420 ancillary detector.
Eluent A: Water (+0.01% formic acid)
Eluent B: Acetonitrile (+0.1% formic acid)

| Time [min] | % A | % B | Flow rate [mL/min] |
|---|---|---|---|
| 0.00 | 95 | 5 | 0.6 |
| 5.00 | 0 | 100 | 0.6 |
| 5.40 | 0 | 100 | 0.6 |
| 5.42 | 95 | 5 | 0.6 |
| 7.00 | 95 | 5 | 0.6 |

The stationary phase used was a Waters Atlantis dC18, 2.1×1000 mm, 3 μm, column temperature: 40° C.
Method F:
Agilent HP1100; Agilent 1100 MS, binäre Pumpe, 254 nm, 230 nm; Pos-Neg; ESI, 100-1000, 80V
Eluent A: Water (+0.1% formic acid)
Eluent B: Acetonitrile (+0.1% formic acid)

| Time [min] | % A | % B | Flow rate [mL/min] |
|---|---|---|---|
| 0.10 | 95 | 5 | 1.6 |
| 1.75 | 5 | 95 | 1.6 |
| 1.90 | 5 | 95 | 1.6 |
| 1.95 | 95 | 5 | 1.6 |
| 2.00 | 95 | 5 | 1.6 |

The stationary phase used was a StableBond C18, 3.0×30 mm, 1.8 μm, column temperature: rt.
Method G:
Waters ZQ2000 MS; Alliance 2790 pump, PDA2996 210-500 nm detector, Waters 2700AS.
Eluent A: Water (+0.01% TFA)
Eluent B: Acetonitrile (+0.08% TFA)

| Time [min] | % A | % B | Flow rate [mL/min] |
|---|---|---|---|
| 0.00 | 95 | 5 | 1.5 |
| 2.00 | 0 | 100 | 1.5 |
| 3.00 | 0 | 100 | 1.5 |
| 3.40 | 95 | 5 | 1.5 |

The stationary phase used was a Waters Sunfire C18, 4.6×50 mm, 3.5 μm, column temperature: 40° C.
Method H:
Shimadzu LCMS2010EV, Shimadzu LC-20AB pump, SPD-M20A PDA detector, PL2100 ancillary
Eluent A: Water (+0.1% formic acid)
Eluent B: Acetonitrile (+0.1% formic acid)

| Time [min] | % A | % B | Flow rate [mL/min] |
|---|---|---|---|
| 0.00 | 95 | 5 | 1.0 |
| 2.50 | 0 | 100 | 1.0 |
| 2.70 | 0 | 100 | 1.0 |
| 2.71 | 95 | 5 | 1.0 |
| 3.50 | 95 | 5 | 1.0 |

The stationary phase used was a Waters Atlantis dC18, 2.1×50 mm, 3 μm, column temperature: 40° C.
Method I:
Waters ZQ2000 MS; Alliance 2795 pump, PDA2996 210-500 nm detector, Waters 2700AS.
Eluent A: Water (+0.01% TFA)
Eluent B: Acetonitrile

| Time [min] | % A | % B | Flow rate [mL/min] |
|---|---|---|---|
| 0.00 | 95 | 5 | 1.5 |
| 2.00 | 0 | 100 | 1.5 |
| 3.00 | 0 | 100 | 1.5 |
| 3.40 | 95 | 5 | 1.5 |

The stationary phase used was a Waters Sunfire C18, 4.6×50 mm, 3.5 μm, column temperature: 40° C.
Method J:
Waters ZQ2000 MS; Alliance 2695 pump, HP1100 210-500 nm, Gilson 215 AS.
Eluent A: Water (+0.1% TFA)
Eluent B: Acetonitrile (+0.1% TFA)

| Time [min] | % A | % B | Flow rate [mL/min] |
|---|---|---|---|
| 0.00 | 95 | 5 | 1.5 |
| 2 | 0 | 100 | 1.5 |
| 2.50 | 0 | 100 | 1.5 |
| 2.60 | 95 | 5 | 1.5 |

The stationary phase used was a Waters Sunfire C18, 4.6×50 mm, 3.5 μm, column temperature: 40° C.
Method K:
Waters ZQ2000 MS; Alliance 2695 pump, HP1100 210-500 nm, Gilson 215 AS.
Eluent A: Water (+0.1% TFA)
Eluent B: Methanol

| Time [min] | % A | % B | Flow rate [mL/min] |
|---|---|---|---|
| 0.00 | 95 | 5 | 1.5 |
| 2.00 | 0 | 100 | 1.5 |
| 2.50 | 0 | 100 | 1.5 |
| 2.60 | 95 | 5 | 1.5 |
| 2.90 | 95 | 5 | 1.5 |

The stationary phase used was a Waters Sunfire C18, 4.6×50 mm, 3.5 μm, column temperature: 40° C.
Method L:
Waters SQD MS; Acquity HPLC pump, HP1100 210-500 nm.
Eluent A: Water (+0.1% TFA)
Eluent B: Acetonitrile (+0.1% TFA)

| Time [min] | % A | % B | Flow rate [mL/min] |
|---|---|---|---|
| 0.00 | 95 | 5 | 1.5 |
| 2.00 | 0 | 100 | 1.5 |
| 2.50 | 0 | 100 | 1.5 |
| 2.60 | 95 | 5 | 1.5 |

The stationary phase used was a Waters Sunfire C18, 2.1×50 mm, 2.5 μm, column temperature: 60° C.
Method M:
Waters ZQ2000 MS; Agilent HP100 pump; Gilson 215 AS; DAD 210-500 nm.
Eluent A: Water (+0.1% TFA)
Eluent B: Methanol

| Time [min] | % A | % B | Flow rate [mL/min] |
|---|---|---|---|
| 0.00 | 95 | 5 | 1.5 |
| 1.30 | 0 | 100 | 1.5 |
| 2.50 | 0 | 100 | 1.5 |
| 2.60 | 95 | 5 | 1.5 |

The stationary phase used was a Waters Sunfire C18, 4.6×50 mm, 3.5 µm, column temperature: 40° C.
Method N:
Waters ZQ MS; Waters 2690/2695; Waters AS; DAD 210-400 nm.
Eluent A: Water (+0.1% TFA)
Eluent B: Methanol

| Time [min] | % A | % B | Flow rate [mL/min] |
|---|---|---|---|
| 0.00 | 95 | 5 | 4.0 |
| 0.20 | 0 | 100 | 4.0 |
| 1.60 | 0 | 100 | 4.0 |
| 2.10 | 95 | 5 | 4.0 |

The stationary phase used was a Waters Xbridge C18, 4.6×20 mm, 3.5 µm, column temperature: 40° C.
Method O:
Waters ZQ MS; Alliance 2695 AS; DAD 2996 (210-400 nm).
Eluent A: Water (+0.1% TFA)
Eluent B: Methanol (+0.1% TFA)

| Time [min] | % A | % B | Flow rate [mL/min] |
|---|---|---|---|
| 0.00 | 95 | 5 | 4.0 |
| 0.20 | 95 | 5 | 4.0 |
| 1.50 | 0 | 100 | 4.0 |
| 1.90 | 0 | 100 | 4.0 |
| 2.00 | 95 | 5 | 4.0 |

The stationary phase used was a Waters Xbridge C18, 4.6×30 mm, 3.5 µm, column temperature: 60° C.

5. EXAMPLES

The following Examples were prepared analogously to the methods of synthesis described above. These compounds are suitable as SYK inhibitors and have $IC_{50}$-values measured in the in vitro assay of less than or equal to 1 µM. The $IC_{50}$-values are shown in the following Table 1 and were experimentally determined as follows:

In Vitro Syk Kinase Test

Recombinant human Syk (amino acids 342-635) was expressed as a fusion protein with an N-terminal GST tag, affinity-purified and deep-frozen at a concentration of approx. 50-100 µM in test buffer (25 mM HEPES pH7.5; 25 mM $MgCl_2$; 5 mM $MnCl_2$; 50 mM KCl; 0.2% BSA; 0.01% CHAPS; 100 µM $Na_3VO_4$; 0.5 mM DTT) and 10% glycerol at −80° C. until use.

The catalytic activity of the GST-Syk kinase fusion protein was determined using the Kinase Glo® Luminescence Kinase test (Promega; V6712). In this homogeneous test the amount of ATP remaining after the kinase reaction is quantified by a luciferin-luciferase reaction using luminescence. The luminescence signal obtained correlates with the amount of ATP still present and thus correlates inversely with the activity of the protein kinase.

Method

The test compounds were dissolved in 100% DMSO at a concentration of 10 mM and diluted in DMSO to a concentration of 1 mM. All further dilutions of the substances were carried out with 7.5% DMSO in test buffer until a concentration was reached which was 7.5 times above the final test concentration (final concentration of the compounds: 30 µM to 1 nM). 2 µl aliquots of these dilutions were transferred into a 384-well Optiplate (Perkin Elmer, #6007290). GST-Syk was diluted to 6.0 nM in the test buffer and 10 µl of this dilution were used in the kinase test (final concentration of Syk=4 nM in a total volume of 15 µl). After 15 minutes incubation at room temperature 3 µl of a mixture of 750 nM ATP and 100 µg/ml poly (L-Glutamic acid L-Tyrosine 4:1), Fluka #81357) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 µl Kinase-Glo® solution (Promega, Cat. #V6712) (heated to room temperature) were added to each well and incubation was continued for a further 15 minutes. The plates were read in a Microplate Scintillation and Luminescence Counter (Canberra Packard GmbH).

Data Evaluation and Calculation:

The output file of the "Counter" is a text file that contains the well number and measured counts in two columns. For data evaluation and calculation, the measurement of the negative control was set as 100% inhibition and the measurement of the positive control was set as 0% inhibition. Based on this values the % inherent value for the measurement of each substance concentration was calculated using an "MS-Excel—VB macro". Normally, the % inhibition values calculated are between 100% and 0% inhibition values but may also occur outside these limits in individual cases. The $IC_{50}$ values were calculated from the % inhibition values using "GraphPadPrism" software (Version 5) (GraphPad Software Inc.).

The following Examples of formula 1

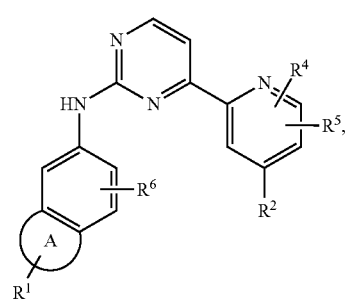

1 having the following properties were prepared according to the methods of synthesis described above:

TABLE 1

| Example No. | Structure | SYK Enzyme IC50 [μM] | Method of preparation | Analytical data |
|---|---|---|---|---|
| 1 | 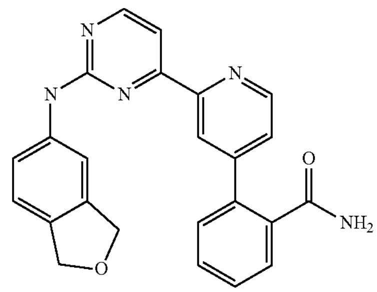 [SMILES: NC(=O)c1ccccc1-c1ccnc(-c2ccnc(Nc3ccc4c(c3)COC4)n2)c1] | 0.0150 | see description 4.2.3 | HPLC-MS: method B Rt = 1.9 min |
| 2 | 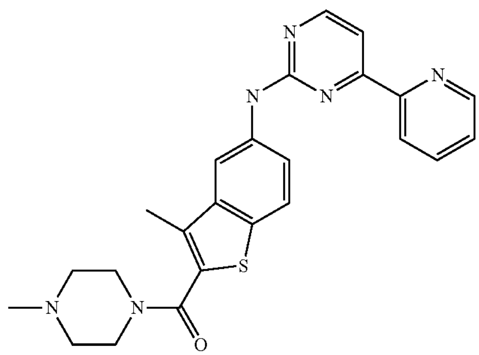 [SMILES: Cc1c(C(=O)N2CCN(C)CC2)sc2ccc(Nc3nccc(-c4ccccn4)n3)cc12] | 0.0253 | analogous to Example 8 | HPLC-MS: method H Rt = 1.93 min |
| 3 | 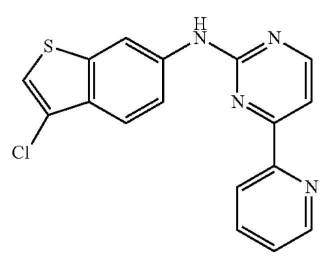 [SMILES: Clc1csc2cc(Nc3nccc(-c4ccccn4)n3)ccc12] | 0.2474 | analogous to Example 287 | HPLC-MS: method E Rt = 5.28 min |
| 4 | 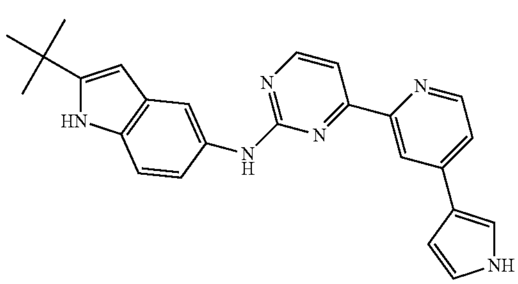 [SMILES: CC(C)(C)c1cc2cc(Nc3nccc(-c4cc(-c5cc[nH]c5)ccn4)n3)ccc2[nH]1] | 0.0137 | see description 4.2.3 | HPLC-MS: method E Rt = 3.98 min |
| 5 | 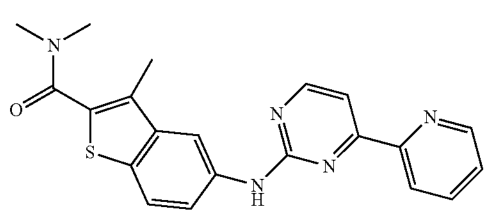 [SMILES: Cc1c(C(=O)N(C)C)sc2ccc(Nc3nccc(-c4ccccn4)n3)cc12] | 0.0200 | analogous to Example 8 | HPLC-MS: method E Rt = 4.09 min |

TABLE 1-continued

| Example No. | Structure | SYK Enzyme IC50 [μM] | Method of preparation | Analytical data |
|---|---|---|---|---|
| 6 | 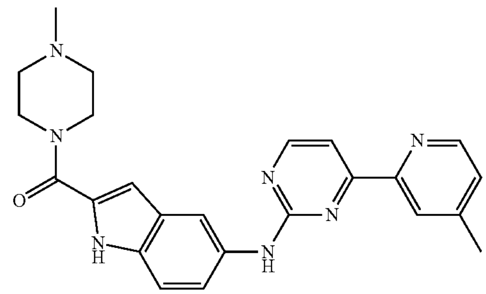 [SMILES: Cc1ccnc(-c2ccnc(Nc3ccc4[nH]c(C(=O)N5CCN(C)CC5)cc4c3)n2)c1] | 0.0152 | analogous to Example 8 | HPLC-MS: method E Rt = 2.57 min |
| 7 | 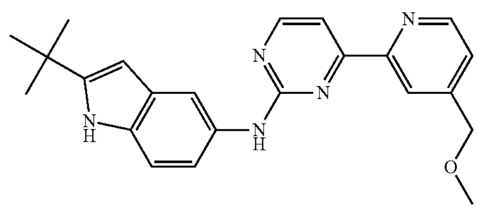 [SMILES: COCc1ccnc(-c2ccnc(Nc3ccc4[nH]c(C(C)(C)C)cc4c3)n2)c1] | 0.0211 | see description 4.2.1 | HPLC-MS: method E Rt = 4.71 min |
| 8 | 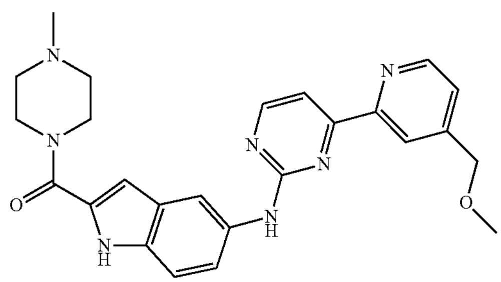 [SMILES: COCc1ccnc(-c2ccnc(Nc3ccc4[nH]c(C(=O)N5CCN(C)CC5)cc4c3)n2)c1] | 0.0066 | see description 4.2.4 | HPLC-MS: method A Rt = 1.35 min |
| 9 | 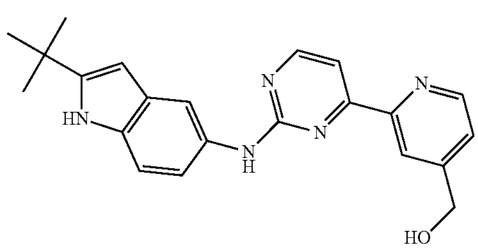 [SMILES: CC(C)(C)c1cc2cc(Nc3nccc(-c4cc(CO)ccn4)n3)ccc2[nH]1] | 0.0640 | see description 4.2.7 | HPLC-MS: method Rt = 3.83 min |
| 10 | 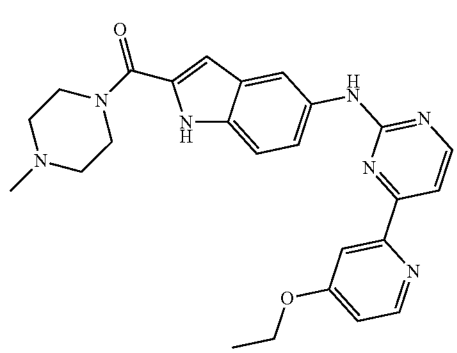 [SMILES: CCOc1ccnc(-c2ccnc(Nc3ccc4[nH]c(C(=O)N5CCN(C)CC5)cc4c3)n2)c1] | 0.0228 | analogous to Example 92 | HPLC-MS: method B Rt = 2.49 min |

TABLE 1-continued

| Example No. | Structure | SYK Enzyme IC50 [μM] | Method of preparation | Analytical data |
|---|---|---|---|---|
| 11 | 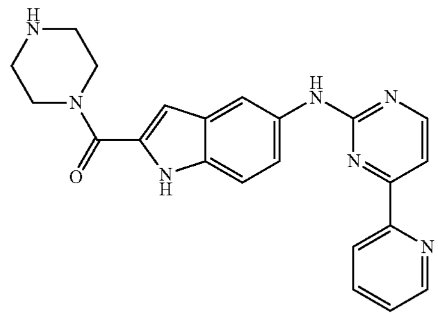 [SMILES: O=C(c1cc2cc(Nc3nccc(-c4ccccn4)n3)ccc2[nH]1)N1CCNCC1] | 0.0607 | analogous to Example 8 | HPLC-MS: method A Rt = 1.59 min |
| 12 | Chiral | 0.0151 | analogous to Example 92 | HPLC-MS: method B Rt = 2.42 min |
| 13 | Chiral | 0.0290 | see description 4.2.5 | HPLC-MS: method B Rt = 2.33 min |
| 14 | Chiral | 0.0321 | analogous to Example 13 | HPLC-MS: method B Rt = 2.36 min |

TABLE 1-continued
| Example No. | Structure | SYK Enzyme IC50 [μM] | Method of preparation | Analytical data |
|---|---|---|---|---|
| 15 | 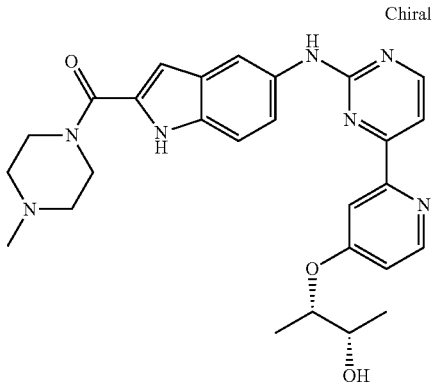 [SMILES: C[C@H](O)[C@H](C)Oc1ccnc(-c2ccnc(Nc3ccc4[nH]c(C(=O)N5CCN(C)CC5)cc4c3)n2)c1] Chiral | 0.0409 | analogous to Example 92 | HPLC-MS: method B Rt = 2.42 min |
| 16 | 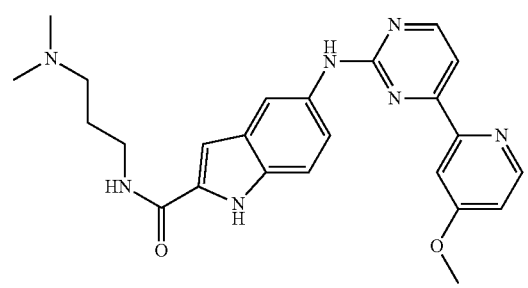 [SMILES: COc1ccnc(-c2ccnc(Nc3ccc4[nH]c(C(=O)NCCCN(C)C)cc4c3)n2)c1] | 0.0086 | analogous to Example 8 | HPLC-MS: method C Rt = 1.46 min |
| 17 | 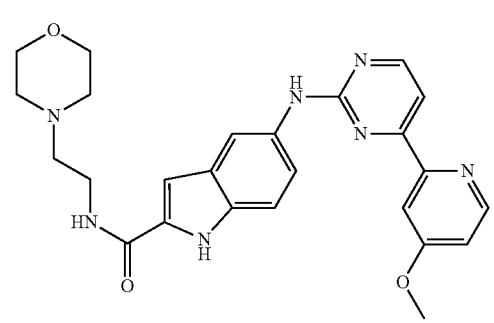 [SMILES: COc1ccnc(-c2ccnc(Nc3ccc4[nH]c(C(=O)NCCN5CCOCC5)cc4c3)n2)c1] | 0.0100 | analogous to Example 8 | HPLC-MS: method C Rt = 1.46 min |
| 18 | 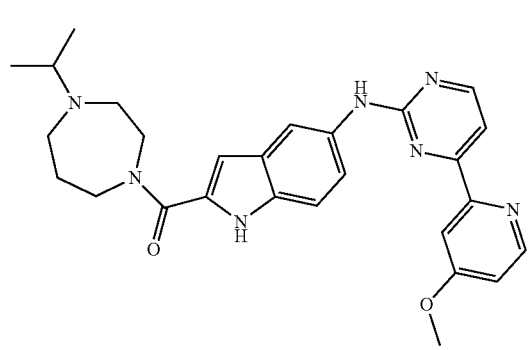 [SMILES: COc1ccnc(-c2ccnc(Nc3ccc4[nH]c(C(=O)N5CCCN(C(C)C)CC5)cc4c3)n2)c1] | 0.0241 | analogous to Example 8 | HPLC-MS: method C Rt = 1.45 min |

TABLE 1-continued

| Example No. | Structure | SYK Enzyme IC50 [μM] | Method of preparation | Analytical data |
|---|---|---|---|---|
| 19 | 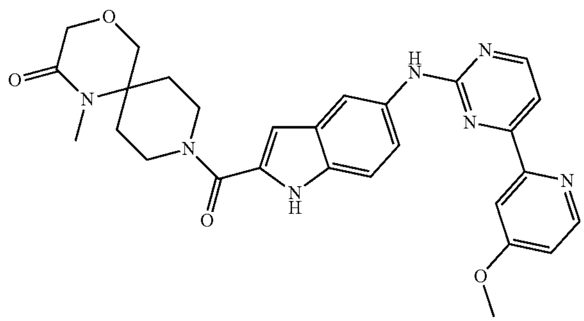 [SMILES: COc1ccnc(-c2ccnc(Nc3ccc4[nH]c(C(=O)N5CCC6(CC5)COCC(=O)N6C)cc4c3)n2)c1] | 0.0012 | analogous to Example 8 | HPLC-MS: method C Rt = 1.61 |
| 20 | 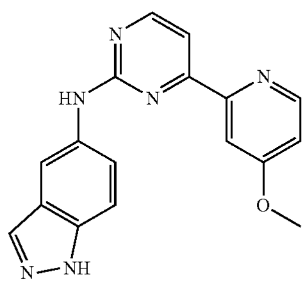 [SMILES: COc1ccnc(-c2ccnc(Nc3ccc4[nH]ncc4c3)n2)c1] | 0.0305 | see description 4.2.2 | HPLC-MS: method A Rt = 1.67 min |
| 21 | Chiral | 0.0382 | analogous to Example 13 | HPLC-MS: method C Rt = 1.62 min |
| 22 | Chiral | 0.0058 | analogous to Example 8 | HPLC-MS: method C Rt = 1.63 min |

TABLE 1-continued

| Example No. | Structure | SYK Enzyme IC50 [μM] | Method of preparation | Analytical data |
|---|---|---|---|---|
| 23 | 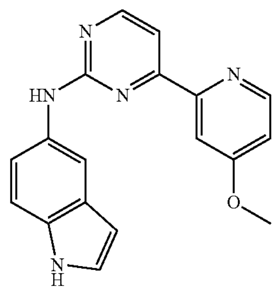 [SMILES: COc1ccnc(-c2ccnc(Nc3ccc4[nH]ccc4c3)n2)c1] | 0.0206 | analogous to Example 20 | HPLC-MS: method D Rt = 1.70 min |
| 24 | 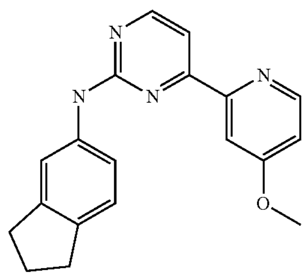 [SMILES: COc1ccnc(-c2ccnc(Nc3ccc4c(c3)CCC4)n2)c1] | 0.1114 | analogous to Example 20 | HPLC-MS: method D Rt = 2.01 min |
| 25 | 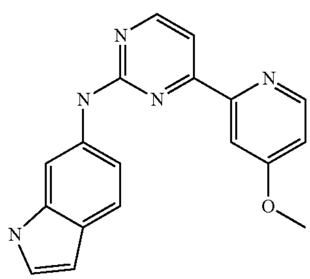 [SMILES: COc1ccnc(-c2ccnc(Nc3ccc4cc[nH]c4c3)n2)c1] | 0.0185 | analogous to Example 20 | HPLC-MS: method D Rt = 1.75 min |
| 26 | 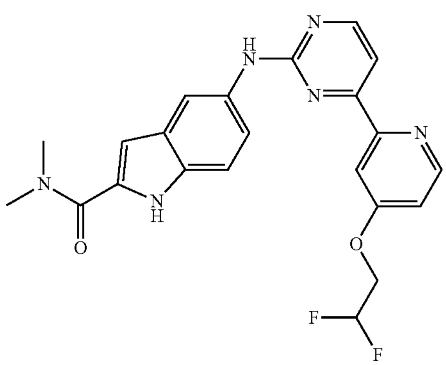 [SMILES: CN(C)C(=O)c1cc2cc(Nc3nccc(-c4cc(OCC(F)F)ccn4)n3)ccc2[nH]1] | 0.0025 | analogous to Example 92 | HPLC-MS: method D Rt = 1.92 min |
| 27 | 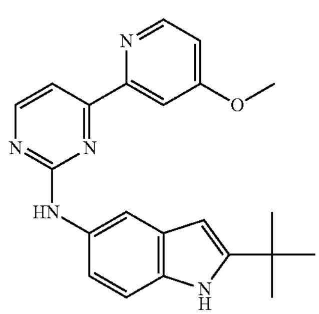 [SMILES: COc1ccnc(-c2ccnc(Nc3ccc4[nH]c(C(C)(C)C)cc4c3)n2)c1] | 0.0080 | analogous to Example 20 | HPLC-MS: method D Rt = 1.95 min |

TABLE 1-continued

| Example No. | Structure | SYK Enzyme IC50 [μM] | Method of preparation | Analytical data |
|---|---|---|---|---|
| 28 | 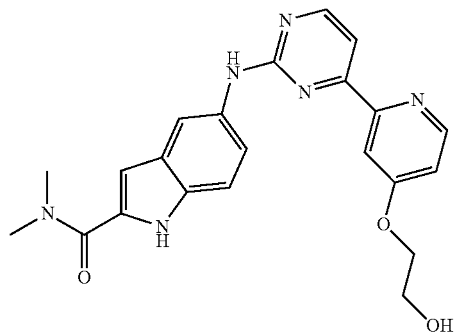 [SMILES: CN(C)C(=O)c1cc2cc(Nc3nccc(-c4cc(OCCO)ccn4)n3)ccc2[nH]1] | 0.0499 | analogous to Example 92 | HPLC-MS: method D Rt = 1.65 min |
| 29 | 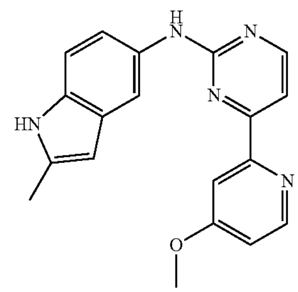 [SMILES: COc1ccnc(-c2ccnc(Nc3ccc4[nH]c(C)cc4c3)n2)c1] | 0.0099 | analogous to Example 20 | HPLC-MS: method D Rt = 1.79 min |
| 30 | 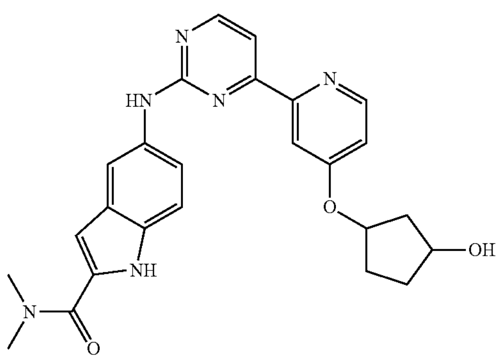 [SMILES: CN(C)C(=O)c1cc2cc(Nc3nccc(-c4cc(OC5CCC(O)C5)ccn4)n3)ccc2[nH]1] | 0.0012 | analogous to Example 92 | HPLC-MS: Method D Rt = 1.74 min |
| 31 | 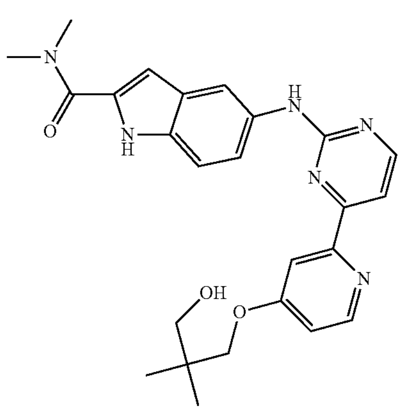 [SMILES: CN(C)C(=O)c1cc2cc(Nc3nccc(-c4cc(OCC(C)(C)CO)ccn4)n3)ccc2[nH]1] | 0.0051 | analogous to Example 92 | HPLC-MS: method D Rt = 1.80 min |

TABLE 1-continued

| Example No. | Structure | SYK Enzyme IC50 [μM] | Method of preparation | Analytical data |
|---|---|---|---|---|
| 32 | 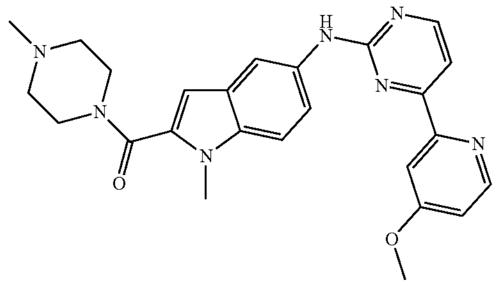 | 0.0194 | analogous to Example 92 | HPLC-MS: method B Rt = 2.44 min |
| 33 | Chiral | 0.0024 | analogous to Example 92 | HPLC-MS: method C Rt = 1.59 min |
| 34 | 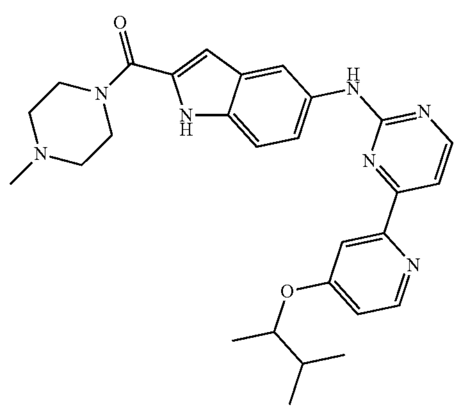 [SMILES: CC(C)C(C)Oc1ccnc(-c2ccnc(Nc3ccc4[nH]c(C(=O)N5CCN(C)CC5)cc4c3)n2)c1] | 0.0052 | analogous to Example 92 | HPLC-MS: method C Rt = 1.66 min |
| 35 | 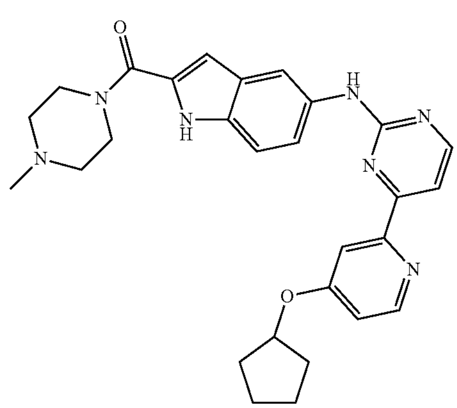 [SMILES: CN1CCN(C(=O)c2cc3cc(Nc4nccc(-c5cc(OC6CCCC6)ccn5)n4)ccc3[nH]2)CC1] | 0.0079 | analogous to Example 92 | HPLC-MS: method C Rt = 1.63 min |

TABLE 1-continued

| Example No. | Structure | SYK Enzyme IC50 [μM] | Method of preparation | Analytical data |
|---|---|---|---|---|
| 36 | Chiral | 0.0016 | analogous to Example 92 | HPLC-MS: method C Rt = 1.59 min |
| 37 | 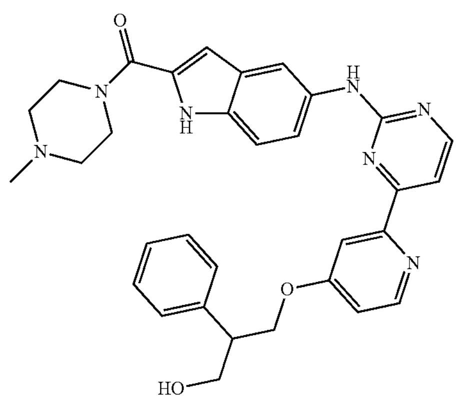 [SMILES: CN1CCN(C(=O)c2cc3cc(Nc4nccc(-c5cc(OCC(CO)c6ccccc6)ccn5)n4)ccc3[nH]2)CC1] | 0.1107 | analogous to Example 92 | HPLC-MS: method B Rt = 2.53 min |
| 38 | 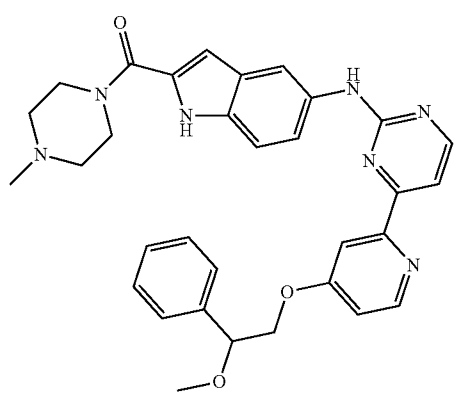 [SMILES: COC(COc1ccnc(-c2ccnc(Nc3ccc4[nH]c(C(=O)N5CCN(C)CC5)cc4c3)n2)c1)c1ccccc1] | 0.2161 | analogous to Example 92 | HPLC-MS: method B Rt = 2.63 min |

TABLE 1-continued

| Example No. | Structure | SYK Enzyme IC50 [μM] | Method of preparation | Analytical data |
|---|---|---|---|---|
| 39 | 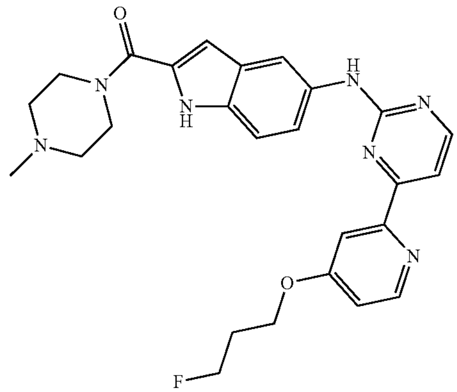 [SMILES: CN1CCN(C(=O)c2cc3cc(Nc4nccc(-c5cc(OCCCF)ccn5)n4)ccc3[nH]2)CC1] | 0.0283 | analogous to Example 92 | HPLC-MS: method B Rt = 2.48 min |
| 40 | 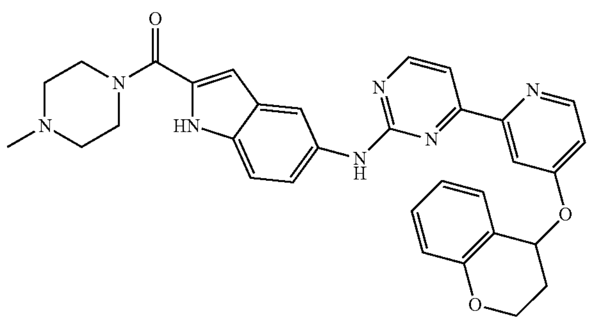 [SMILES: CN1CCN(C(=O)c2cc3cc(Nc4nccc(-c5cc(OC6CCOc7ccccc76)ccn5)n4)ccc3[nH]2)CC1] | 0.0301 | analogous to Example 92 | HPLC-MS: method B Rt = 2.64 min |
| 41 | 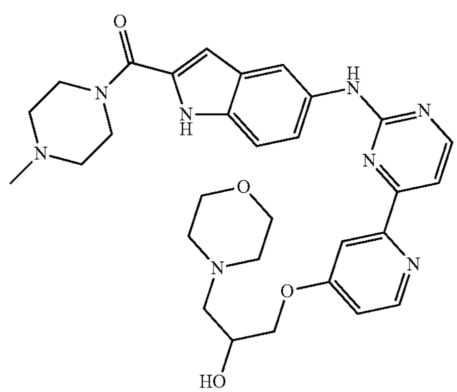 [SMILES: CN1CCN(C(=O)c2cc3cc(Nc4nccc(-c5cc(OCC(O)CN6CCOCC6)ccn5)n4)ccc3[nH]2)CC1] | 0.5950 | analogous to Example 92 | HPLC-MS: method B Rt = 2.31 min |
| 42 | 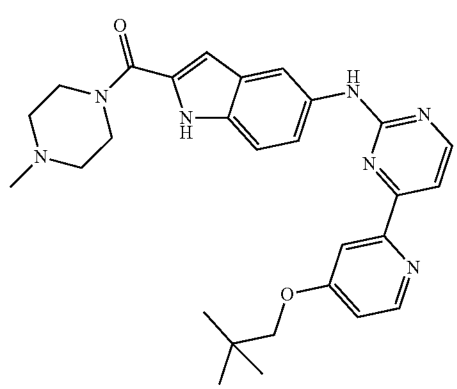 [SMILES: CN1CCN(C(=O)c2cc3cc(Nc4nccc(-c5cc(OCC(C)(C)C)ccn5)n4)ccc3[nH]2)CC1] | 0.0118 | analogous to Example 92 | HPLC-MS: method B Rt = 2.72 min |

TABLE 1-continued
| Example No. | Structure | SYK Enzyme IC50 [μM] | Method of preparation | Analytical data |
|---|---|---|---|---|
| 43 | 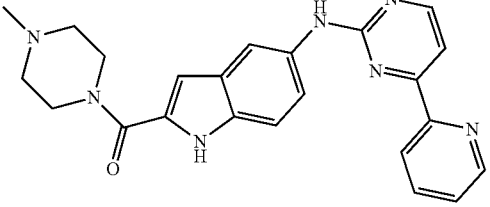 | 0.0116 | analogous to Example 92 | HPLC-MS: method D Rt = 1.6 min |
| 44 | 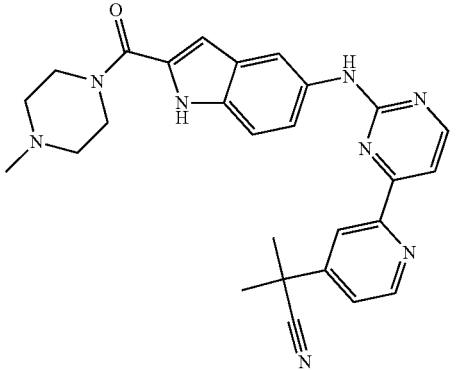 [SMILES: CN1CCN(C(=O)c2cc3cc(Nc4nccc(-c5cc(C(C)(C)C#N)ccn5)n4)ccc3[nH]2)CC1] | 0.0025 | see description 4.2.3 | HPLC-MS: method G Rt = 1.64 min |
| 45 | 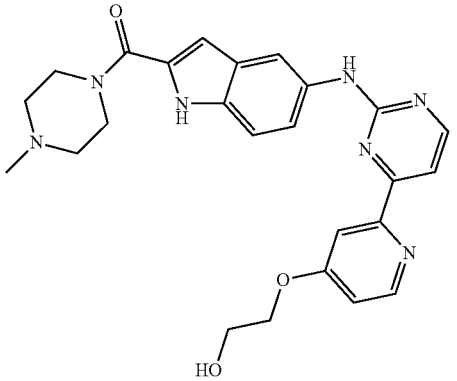 [SMILES: CN1CCN(C(=O)c2cc3cc(Nc4nccc(-c5cc(OCCO)ccn5)n4)ccc3[nH]2)CC1] | 0.0151 | analogous to Example 92 | HPLC-MS: method G Rt = 1.34 min |
| 46 | 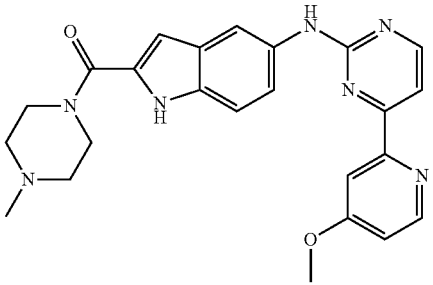 [SMILES: COc1ccnc(-c2ccnc(Nc3ccc4[nH]c(C(=O)N5CCN(C)CC5)cc4c3)n2)c1] | 0.0088 | analogous to Example 92 | HPLC-MS: method B Rt = 2.41 min |

TABLE 1-continued
| Example No. | Structure | SYK Enzyme IC50 [μM] | Method of preparation | Analytical data |
|---|---|---|---|---|
| 47 | 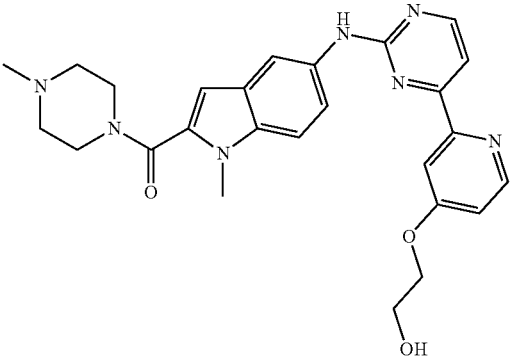 [SMILES: CN1CCN(C(=O)c2cc3cc(Nc4nccc(-c5cc(OCCO)ccn5)n4)ccc3n2C)CC1] | 0.0420 | analogous to Example 92 | HPLC-MS: method D Rt = 1.5 min |
| 48 | 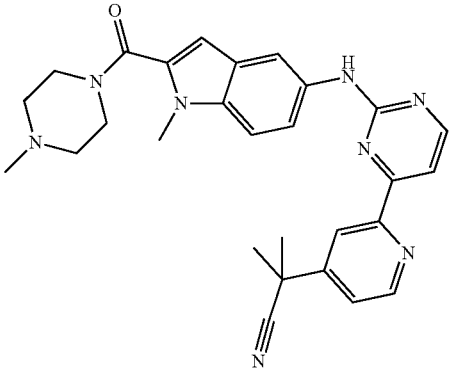 [SMILES: CN1CCN(C(=O)c2cc3cc(Nc4nccc(-c5cc(C(C)(C)C#N)ccn5)n4)ccc3n2C)CC1] | 0.0032 | analogous to Example 44 | HPLC-MS: method B Rt = 2.49 min |
| 49 | 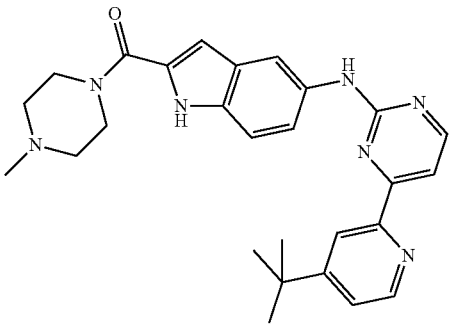 [SMILES: CN1CCN(C(=O)c2cc3cc(Nc4nccc(-c5cc(C(C)(C)C)ccn5)n4)ccc3[nH]2)CC1] | 0.0094 | analogous to Example 8 | HPLC-MS: method D Rt = 1.85 min |
| 50 | 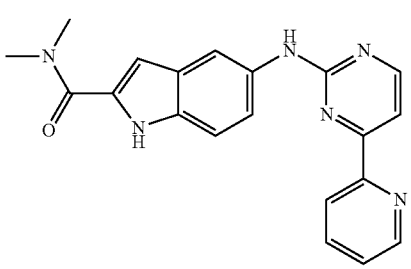 [SMILES: CN(C)C(=O)c1cc2cc(Nc3nccc(-c4ccccn4)n3)ccc2[nH]1] | 0.0237 | analogous to Example 8 | HPLC-MS: method C Rt = 1.82 min |

TABLE 1-continued

| Example No. | Structure | SYK Enzyme IC50 [μM] | Method of preparation | Analytical data |
|---|---|---|---|---|
| 51 | 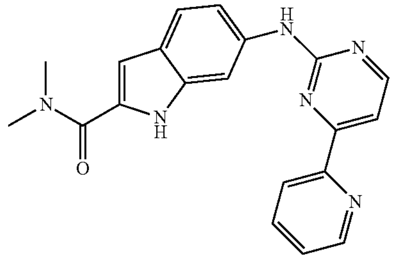 [SMILES: CN(C)C(=O)c1cc2ccc(Nc3nccc(-c4ccccn4)n3)cc2[nH]1] | 0.0130 | analogous to Example 8 | HPLC-MS: method D Rt = 2.06 min |
| 52 | 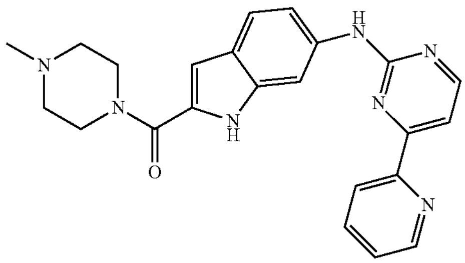 [SMILES: CN1CCN(C(=O)c2cc3ccc(Nc4nccc(-c5ccccn5)n4)cc3[nH]2)CC1] | 0.0466 | analogous to Example 8 | HPLC-MS: method D Rt = 1.66 min |
| 53 | 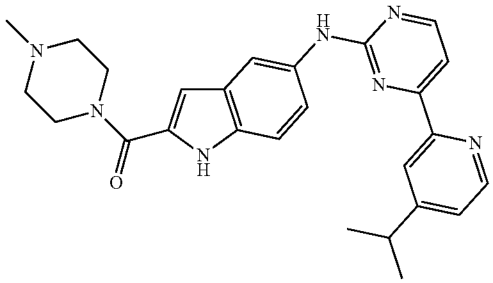 [SMILES: CC(C)c1ccnc(-c2ccnc(Nc3ccc4[nH]c(C(=O)N5CCN(C)CC5)cc4c3)n2)c1] | 0.0024 | analogous to Example 8 | HPLC-MS: method D Rt = 1.75 min |
| 54 | 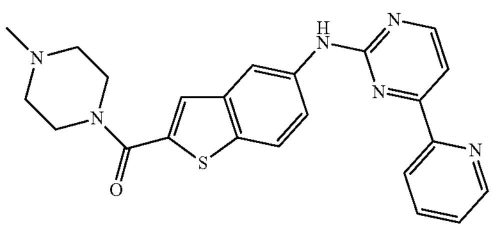 [SMILES: CN1CCN(C(=O)c2cc3cc(Nc4nccc(-c5ccccn5)n4)ccc3s2)CC1] | 0.0180 | analogous to Example 8 | HPLC-MS: method D Rt = 1.78 min |
| 55 | 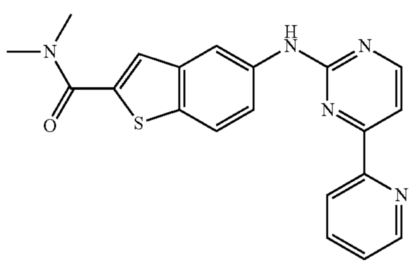 [SMILES: CN(C)C(=O)c1cc2cc(Nc3nccc(-c4ccccn4)n3)ccc2s1] | 0.0155 | analogous to Example 8 | HPLC-MS: method D Rt = 2.02 min |
| 56 | 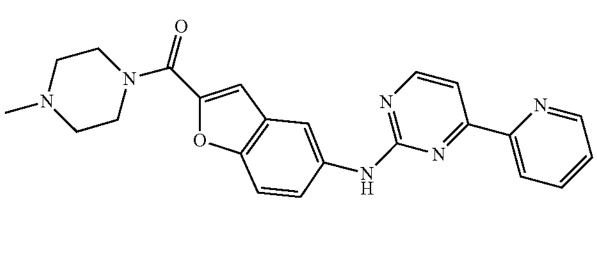 [SMILES: CN1CCN(C(=O)c2cc3cc(Nc4nccc(-c5ccccn5)n4)ccc3o2)CC1] | 1.7305 | analogous to Example 8 | HPLC-MS: method B Rt = 2.47 min |

TABLE 1-continued

| Example No. | Structure | SYK Enzyme IC50 [μM] | Method of preparation | Analytical data |
|---|---|---|---|---|
| 57 | 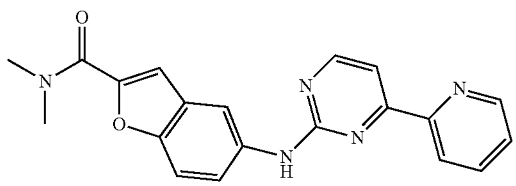 [SMILES: CN(C)C(=O)c1cc2cc(Nc3nccc(-c4ccccn4)n3)ccc2o1] | 0.2407 | analogous to Example 8 | HPLC-MS: method B Rt = 2.46 min |
| 58 | 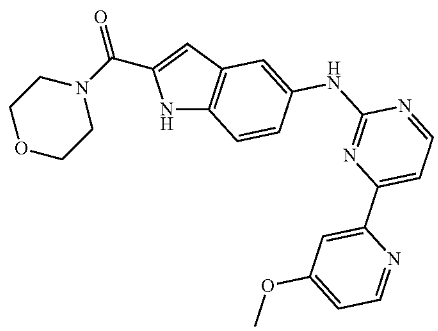 [SMILES: COc1ccnc(-c2ccnc(Nc3ccc4[nH]c(C(=O)N5CCOCC5)cc4c3)n2)c1] | 0.0512 | analogous to Example 8 | HPLC-MS: method B Rt = 2.44 min |
| 59 | 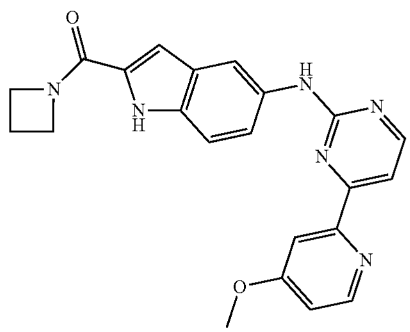 [SMILES: COc1ccnc(-c2ccnc(Nc3ccc4[nH]c(C(=O)N5CCC5)cc4c3)n2)c1] | 0.0250 | analogous to Example 8 | HPLC-MS: method C Rt = 1.66 min |
| 60 | 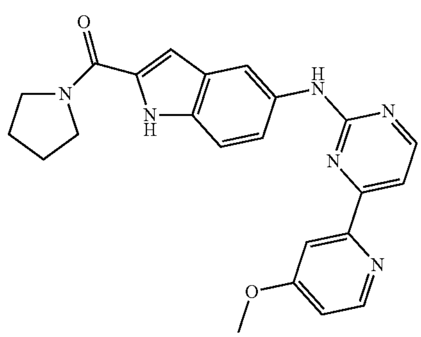 [SMILES: COc1ccnc(-c2ccnc(Nc3ccc4[nH]c(C(=O)N5CCCC5)cc4c3)n2)c1] | 0.0814 | analogous to Example 8 | HPLC-MS: method C Rt = 1.73 min |
| 61 | 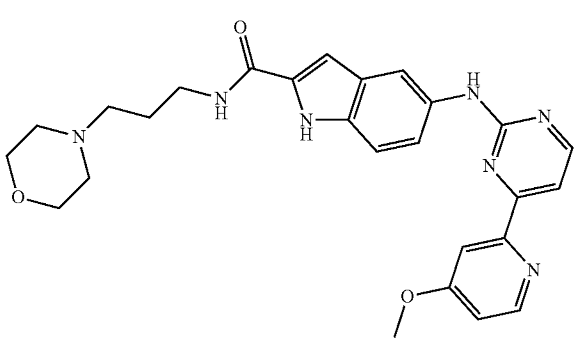 [SMILES: COc1ccnc(-c2ccnc(Nc3ccc4[nH]c(C(=O)NCCCN5CCOCC5)cc4c3)n2)c1] | 0.0410 | analogous to Example 8 | HPLC-MS: method B Rt = 2.44 min |

TABLE 1-continued

| Example No. | Structure | SYK Enzyme IC50 [μM] | Method of preparation | Analytical data |
|---|---|---|---|---|
| 62 | 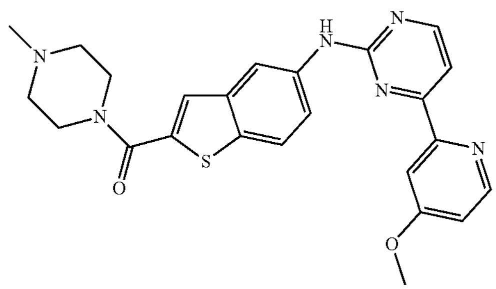 [SMILES: COc1ccnc(-c2ccnc(Nc3ccc4sc(C(=O)N5CCN(C)CC5)cc4c3)n2)c1] | 0.0213 | analogous to Example 8 | HPLC-MS: method D Rt = 1.60 min |
| 63 | 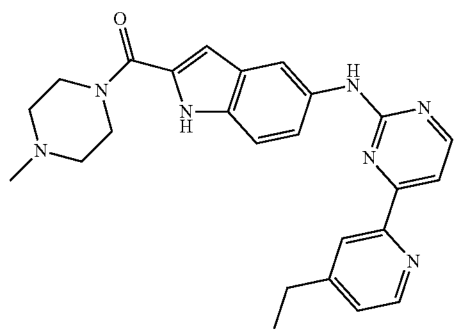 [SMILES: CCc1ccnc(-c2ccnc(Nc3ccc4[nH]c(C(=O)N5CCN(C)CC5)cc4c3)n2)c1] | 0.0449 | analogous to Example 8 | HPLC-MS: method B Rt = 2.57 min |
| 64 | 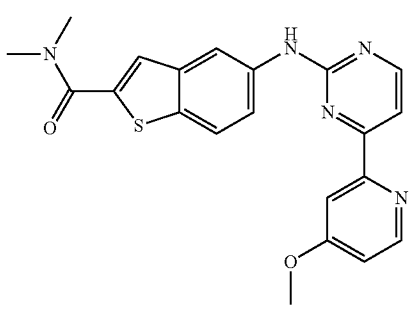 [SMILES: COc1ccnc(-c2ccnc(Nc3ccc4sc(C(=O)N(C)C)cc4c3)n2)c1] | 0.0154 | analogous to Example 8 | HPLC-MS: method B Rt = 2.57 min |
| 65 | 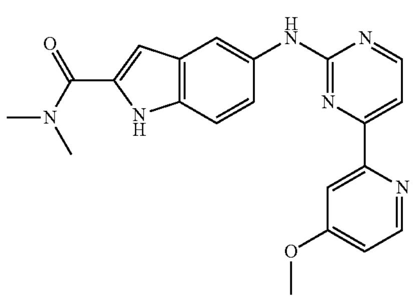 [SMILES: COc1ccnc(-c2ccnc(Nc3ccc4[nH]c(C(=O)N(C)C)cc4c3)n2)c1] | 0.0519 | analogous to Example 8 | HPLC-MS: method D Rt = 1.73 min |
| 66 | 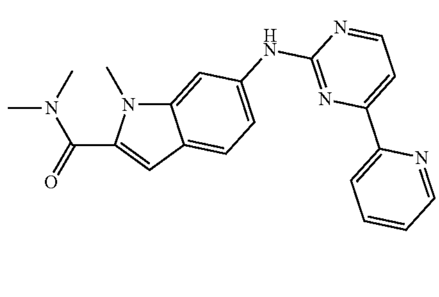 [SMILES: CN(C)C(=O)c1cc2ccc(Nc3nccc(-c4ccccn4)n3)cc2n1C] | 0.0058 | analogous to Example 8 | HPLC-mS: Method D Rt = 2.05 min |

TABLE 1-continued

| Example No. | Structure | SYK Enzyme IC50 [μM] | Method of preparation | Analytical data |
|---|---|---|---|---|
| 67 | 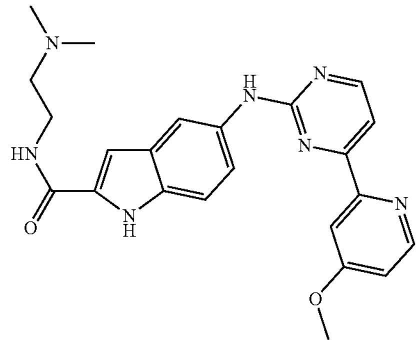 [SMILES: COc1ccnc(-c2ccnc(Nc3ccc4[nH]c(C(=O)NCCN(C)C)cc4c3)n2)c1] | 0.0362 | analogous to Example 8 | HPLC-MS: method C Rt = 1.44 min |
| 68 | 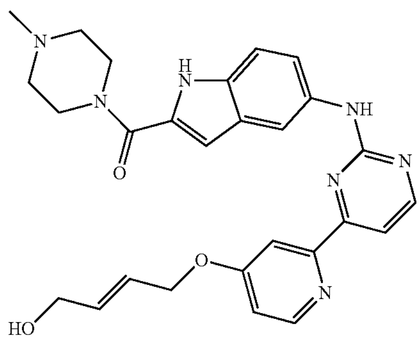 [SMILES: CN1CCN(C(=O)c2cc3cc(Nc4nccc(-c5cc(OC/C=C/CO)ccn5)n4)ccc3[nH]2)CC1] | 0.0303 | analogous to Example 92 | HPLC-MS: method K Rt = 0.85 min |
| 69 | 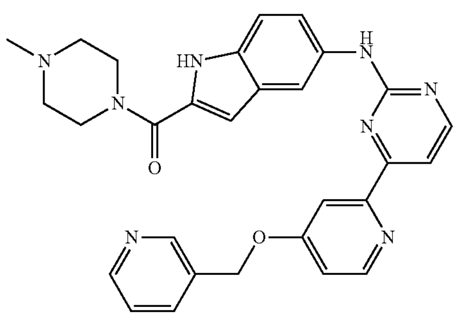 [SMILES: CN1CCN(C(=O)c2cc3cc(Nc4nccc(-c5cc(OCc6cccnc6)ccn5)n4)ccc3[nH]2)CC1] | 0.1579 | analogous to Example 92 | HPLC-MS: method K Rt = 0.91 min |
| 70 | 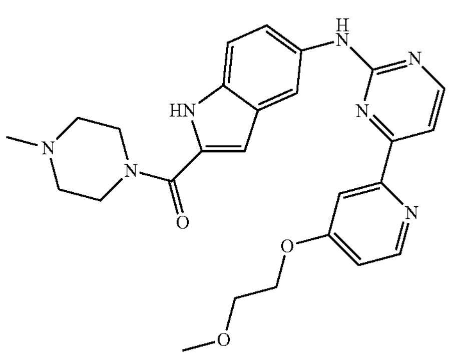 [SMILES: COCCOc1ccnc(-c2ccnc(Nc3ccc4[nH]c(C(=O)N5CCN(C)CC5)cc4c3)n2)c1] | 0.0561 | analogous to Example 92 | HPLC-MS: method K Rt = 0.92 min |

TABLE 1-continued

| Example No. | Structure | SYK Enzyme IC50 [μM] | Method of preparation | Analytical data |
|---|---|---|---|---|
| 71 | 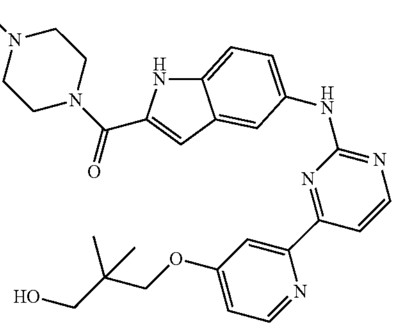 | 0.0009 | analogous to Example 92 | HPLC-MS: method K Rt = 0.98 min |
| 72 | 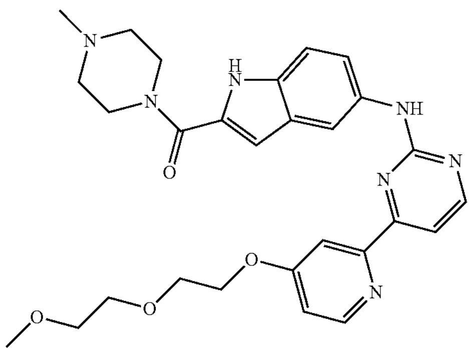 [SMILES: COCCOCCOc1ccnc(-c2ccnc(Nc3ccc4[nH]c(C(=O)N5CCN(C)CC5)cc4c3)n2)c1] | 0.3980 | analogous to Example 92 | HPLC-MS: method K Rt = 0.92 min |
| 73 | 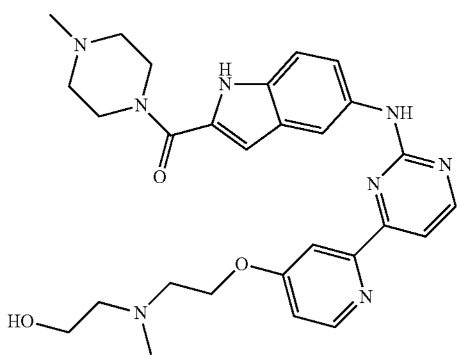 [SMILES: CN(CCO)CCOc1ccnc(-c2ccnc(Nc3ccc4[nH]c(C(=O)N5CCN(C)CC5)cc4c3)n2)c1] | 0.6015 | analogous to Example 92 | HPLC-MS: method K Rt = 0.82 min |
| 74 | 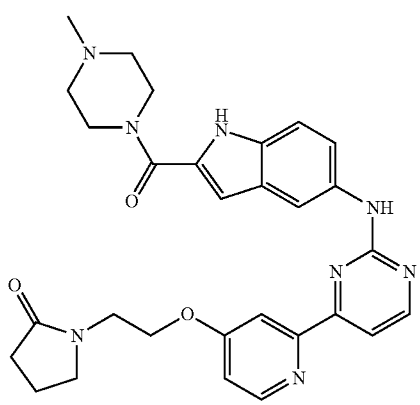 [SMILES: CN1CCN(C(=O)c2cc3cc(Nc4nccc(-c5cc(OCCN6CCCC6=O)ccn5)n4)ccc3[nH]2)CC1] | 0.2277 | analogous to Example 92 | HPLC-MS: method K Rt = 0.85 min |

TABLE 1-continued

| Example No. | Structure | SYK Enzyme IC50 [μM] | Method of preparation | Analytical data |
|---|---|---|---|---|
| 75 | 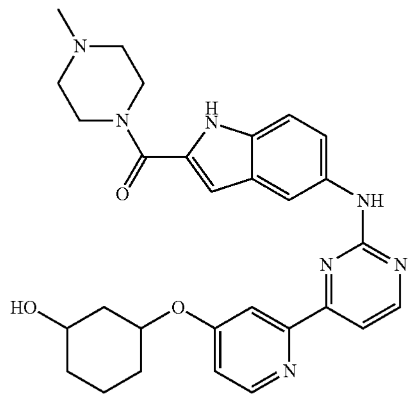 [SMILES: CN1CCN(C(=O)c2cc3cc(Nc4nccc(-c5cc(OC6CCCC(O)C6)ccn5)n4)ccc3[nH]2)CC1] | 0.0111 | analogous to Example 92 | HPLC-MS: method K Rt = 0.91 min |
| 76 | 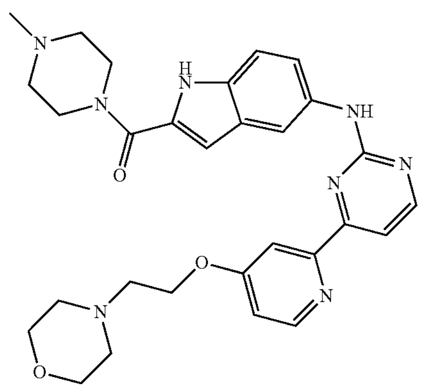 [SMILES: CN1CCN(C(=O)c2cc3cc(Nc4nccc(-c5cc(OCCN6CCOCC6)ccn5)n4)ccc3[nH]2)CC1] | 0.4491 | analogous to Example 92 | HPLC-MS: method K Rt = 0.87 min |
| 77 | 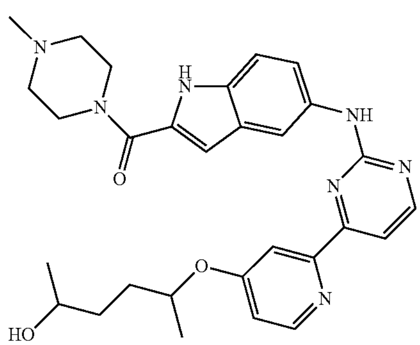 [SMILES: CC(O)CCC(C)Oc1ccnc(-c2ccnc(Nc3ccc4[nH]c(C(=O)N5CCN(C)CC5)cc4c3)n2)c1] | 0.0205 | analogous to Example 92 | HPLC-MS: method K Rt = 0.97 min |
| 78 | 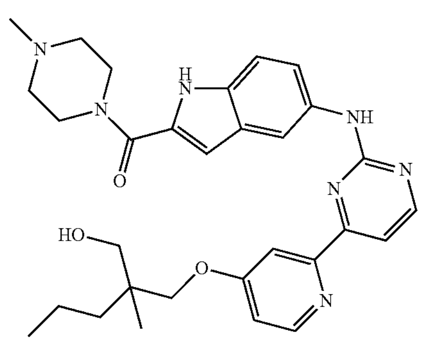 [SMILES: CCCC(C)(CO)COc1ccnc(-c2ccnc(Nc3ccc4[nH]c(C(=O)N5CCN(C)CC5)cc4c3)n2)c1] | 0.0243 | analogous to Example 92 | HPLC-MS: method K Rt = 1.13 min |

TABLE 1-continued

| Example No. | Structure | SYK Enzyme IC50 [μM] | Method of preparation | Analytical data |
|---|---|---|---|---|
| 79 | 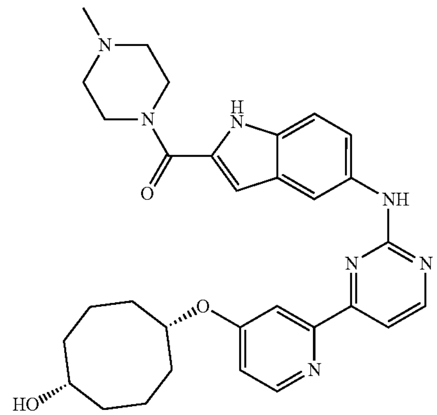 [SMILES: CN1CCN(C(=O)c2cc3cc(Nc4nccc(-c5cc(O[C@H]6CCC[C@@H](O)CCC6)ccn5)n4)ccc3[nH]2)CC1] | 0.0303 | analogous to Example 92 | HPLC-MS: method K Rt = 1.00 min |
| 80 | 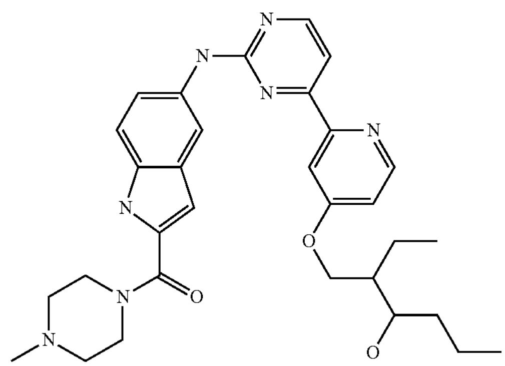 [SMILES: CCCC(O)C(CC)COc1ccnc(-c2ccnc(Nc3ccc4[nH]c(C(=O)N5CCN(C)CC5)cc4c3)n2)c1] | 0.0587 | analogous to Example 92 | HPLC-MS: method K Rt = 1.19 min |
| 81 | 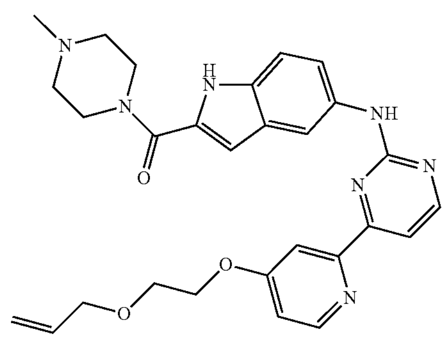 [SMILES: C=CCOCCOc1ccnc(-c2ccnc(Nc3ccc4[nH]c(C(=O)N5CCN(C)CC5)cc4c3)n2)c1] | 0.3690 | analogous to Example 92 | HPLC-MS: method K Rt = 1.03 min |
| 82 | 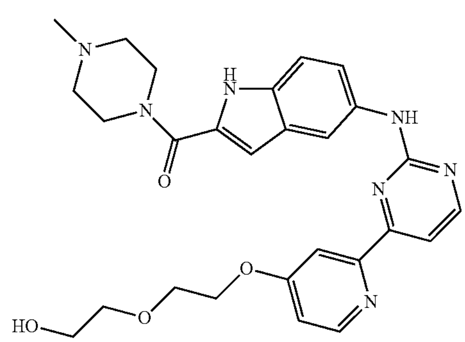 [SMILES: CN1CCN(C(=O)c2cc3cc(Nc4nccc(-c5cc(OCCOCCO)ccn5)n4)ccc3[nH]2)CC1] | 0.1153 | analogous to Example 92 | HPLC-MS: method K Rt = 0.79 min |

TABLE 1-continued

| Example No. | Structure | SYK Enzyme IC50 [μM] | Method of preparation | Analytical data |
| --- | --- | --- | --- | --- |
| 83 | 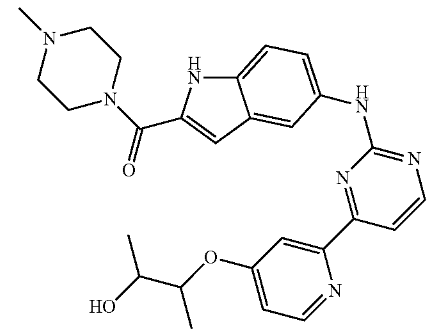 [SMILES: CC(O)C(C)Oc1ccnc(-c2ccnc(Nc3ccc4[nH]c(C(=O)N5CCN(C)CC5)cc4c3)n2)c1] | 0.0077 | analogous to Example 92 | HPLC-MS: method K Rt = 0.87 min |
| 84 | 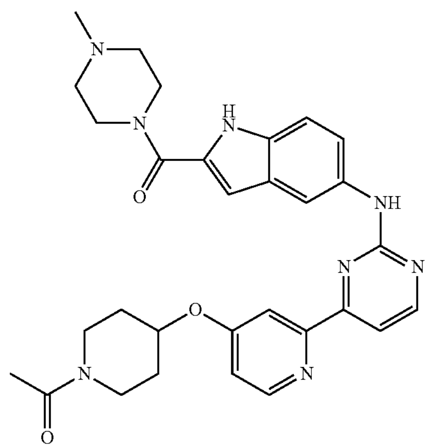 [SMILES: CC(=O)N1CCC(Oc2ccnc(-c3ccnc(Nc4ccc5[nH]c(C(=O)N6CCN(C)CC6)cc5c4)n3)c2)CC1] | 0.0473 | analogous to Example 92 | HPLC-MS: method K Rt = 0.87 min |
| 85 | 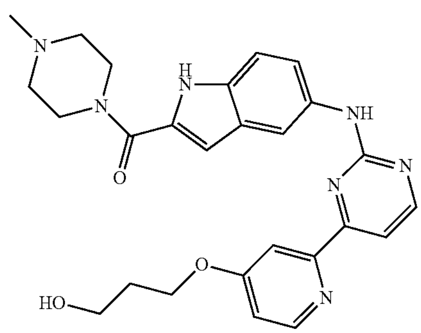 [SMILES: CN1CCN(C(=O)c2cc3cc(Nc4nccc(-c5cc(OCCCO)ccn5)n4)ccc3[nH]2)CC1] | 0.0084 | analogous to Example 92 | HPLC-MS: method K Rt = 0.82 min |
| 86 | 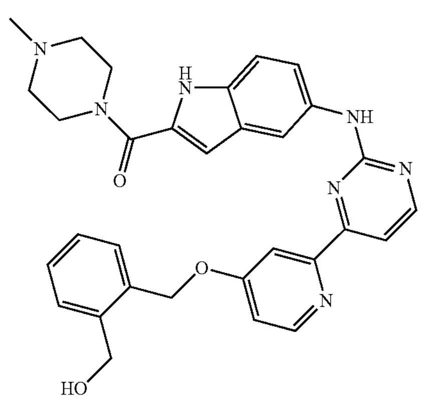 [SMILES: CN1CCN(C(=O)c2cc3cc(Nc4nccc(-c5cc(OCc6ccccc6CO)ccn5)n4)ccc3[nH]2)CC1] | 0.1084 | analogous to Example 92 | HPLC-MS: method K Rt = 0.98 min |

TABLE 1-continued

| Example No. | Structure | SYK Enzyme IC50 [μM] | Method of preparation | Analytical data |
|---|---|---|---|---|
| 87 | 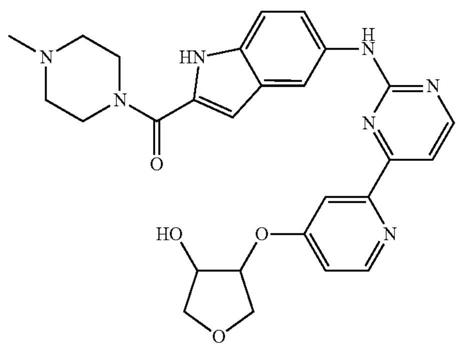 [SMILES: CN1CCN(C(=O)c2cc3cc(Nc4nccc(-c5cc(OC6COCC6O)ccn5)n4)ccc3[nH]2)CC1] | 0.0134 | analogous to Example 92 | HPLC-MS: method K Rt = 0.75 min |
| 88 | 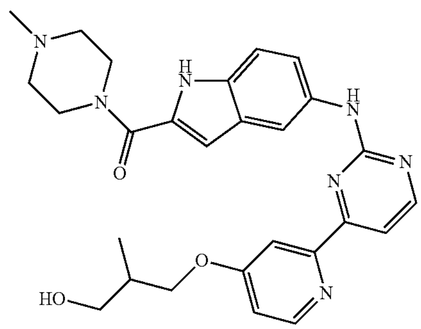 [SMILES: CC(CO)COc1ccnc(-c2ccnc(Nc3ccc4[nH]c(C(=O)N5CCN(C)CC5)cc4c3)n2)c1] | 0.0079 | analogous to Example 92 | HPLC-MS: method K Rt = 0.89 min |
| 89 | Chiral | 0.0208 | analogous to Example 92 | HPLC-MS: method K Rt = 0.91 min |
| 90 | 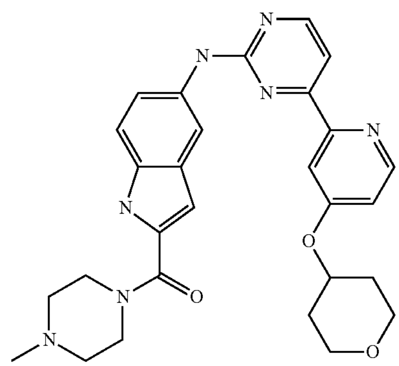 [SMILES: CN1CCN(C(=O)c2cc3cc(Nc4nccc(-c5cc(OC6CCOCC6)ccn5)n4)ccc3[nH]2)CC1] | 0.0083 | analogous to Example 92 | HPLC-MS: method K Rt = 0.96 min |

TABLE 1-continued

| Example No. | Structure | SYK Enzyme IC50 [μM] | Method of preparation | Analytical data |
|---|---|---|---|---|
| 91 | 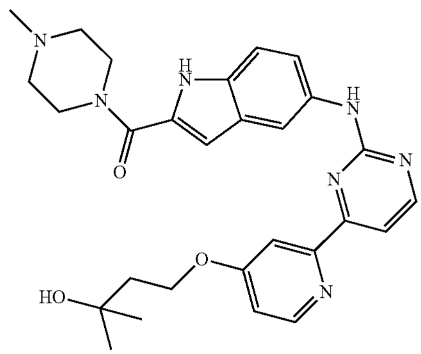 [SMILES: CN1CCN(C(=O)c2cc3cc(Nc4nccc(-c5cc(OCCC(C)(C)O)ccn5)n4)ccc3[nH]2)CC1] | 0.0149 | analogous to Example 92 | HPLC-MS: method K Rt = 0.93 min |
| 92 | 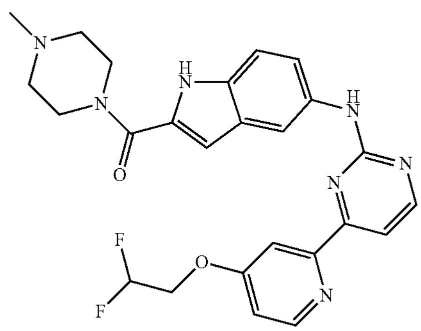 [SMILES: CN1CCN(C(=O)c2cc3cc(Nc4nccc(-c5cc(OCC(F)F)ccn5)n4)ccc3[nH]2)CC1] | 0.0038 | see description 4.2.3 | HPLC-MS: method K Rt = 0.97 min |
| 93 | Chiral | 0.0302 | analogous to Example 92 | HPLC-MS: method K Rt = 0.96 min |
| 94 | Chiral | 0.0254 | analogous to Example 92 | HPLC-MS: method K Rt = 0.91 min |

TABLE 1-continued

| Example No. | Structure | SYK Enzyme IC50 [μM] | Method of preparation | Analytical data |
|---|---|---|---|---|
| 95 | Chiral | 0.0288 | analogous to Example 92 | HPLC-MS: method K Rt = 0.97 min |
| 96 | 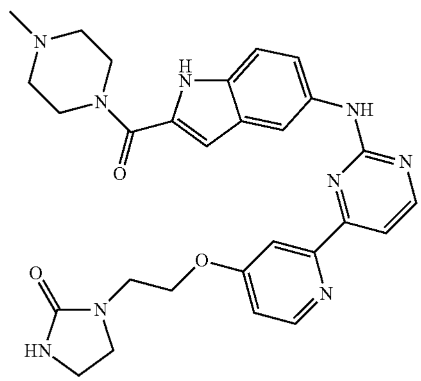 [SMILES: CN1CCN(C(=O)c2cc3cc(Nc4nccc(-c5cc(OCCN6CCNC6=O)ccn5)n4)ccc3[nH]2)CC1] | 0.0598 | analogous to Example 92 | HPLC-MS: method K Rt = 0.97 min |
| 97 | 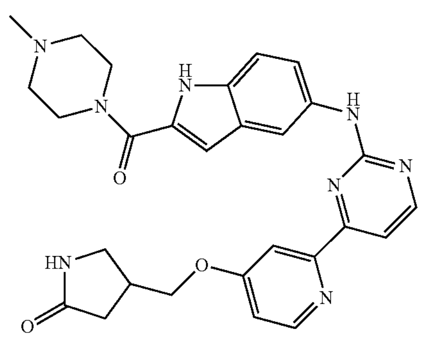 [SMILES: CN1CCN(C(=O)c2cc3cc(Nc4nccc(-c5cc(OCC6CNC(=O)C6)ccn5)n4)ccc3[nH]2)CC1] | 0.0172 | analogous to Example 92 | HPLC-MS: method K Rt = 0.78 min |
| 98 | 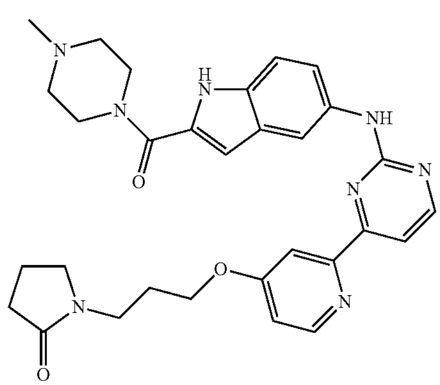 [SMILES: CN1CCN(C(=O)c2cc3cc(Nc4nccc(-c5cc(OCCCN6CCCC6=O)ccn5)n4)ccc3[nH]2)CC1] | 0.0602 | analogous to Example 92 | HPLC-MS: method K Rt = 0.87 min |

TABLE 1-continued
| Example No. | Structure | SYK Enzyme IC50 [μM] | Method of preparation | Analytical data |
|---|---|---|---|---|
| 99 | 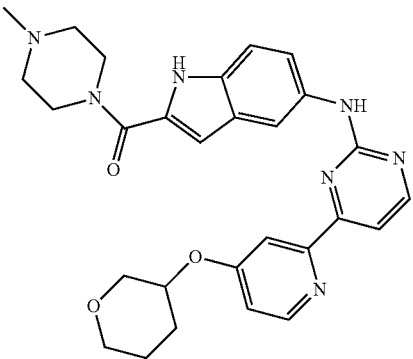 [SMILES: CN1CCN(C(=O)c2cc3cc(Nc4nccc(-c5cc(OC6CCCOC6)ccn5)n4)ccc3[nH]2)CC1] | 0.0350 | analogous to Example 92 | HPLC-MS: method K Rt = 0.97 min |
| 100 | 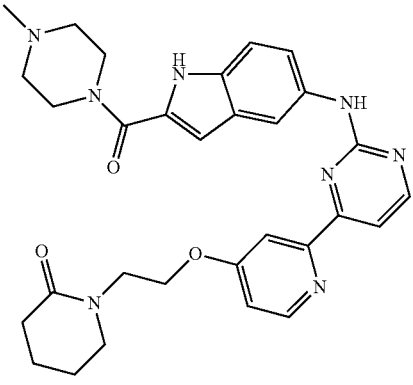 [SMILES: CN1CCN(C(=O)c2cc3cc(Nc4nccc(-c5cc(OCCN6CCCCC6=O)ccn5)n4)ccc3[nH]2)CC1] | 0.2213 | analogous to Example 92 | HPLC-MS: method K Rt = 0.89 min |
| 101 | Chiral 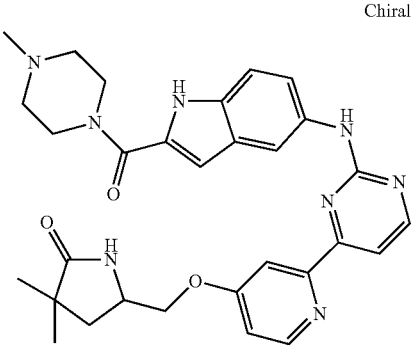 [SMILES: CN1CCN(C(=O)c2cc3cc(Nc4nccc(-c5cc(OCC6CC(C)(C)C(=O)N6)ccn5)n4)ccc3[nH]2)CC1] | 0.0511 | analogous to Example 92 | HPLC-MS: method K Rt = 0.89 min |
| 102 | 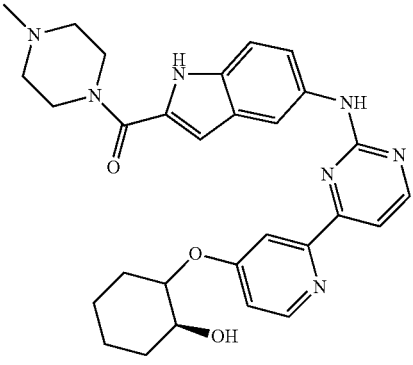 [SMILES: CN1CCN(C(=O)c2cc3cc(Nc4nccc(-c5cc(OC6CCCC[C@@H]6O)ccn5)n4)ccc3[nH]2)CC1] | 0.0128 | analogous to Example 92 | HPLC-MS: method K Rt = 0.96 min |

TABLE 1-continued
| Example No. | Structure | SYK Enzyme IC50 [μM] | Method of preparation | Analytical data |
|---|---|---|---|---|
| 103 | 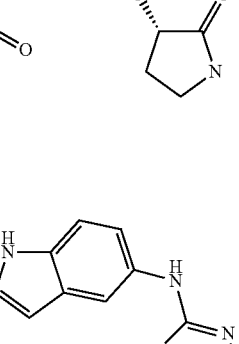 Chiral | 0.0500 | analogous to Example 92 | HPLC-MS: method K Rt = 0.75 min |
| 104 | 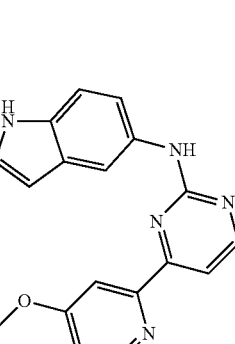 | 0.0067 | analogous to Example 92 | HPLC-MS: method K Rt = 1.01 min |
| 105 | 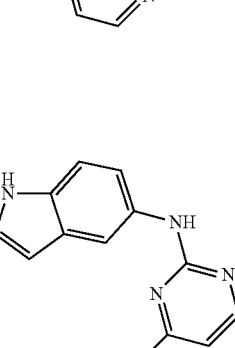 | 0.1512 | analogous to Example 92 | HPLC-MS: method K Rt = 0.77 min |
| 106 | 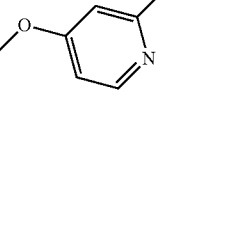 | 0.0244 | analogous to Example 92 | HPLC-MS: method K Rt = 0.74 min |

TABLE 1-continued
| Example No. | Structure | SYK Enzyme IC50 [μM] | Method of preparation | Analytical data |
|---|---|---|---|---|
| 107 | 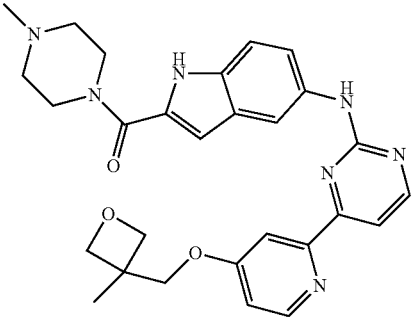 [SMILES: CN1CCN(C(=O)c2cc3cc(Nc4nccc(-c5cc(OCC6(C)COC6)ccn5)n4)ccc3[nH]2)CC1] | 0.0182 | analogous to Example 92 | HPLC-MS: method K Rt = 0.95 min |
| 108 | 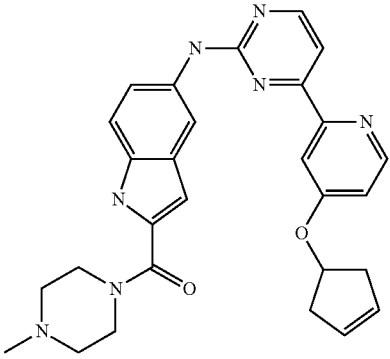 [SMILES: CN1CCN(C(=O)c2cc3cc(Nc4nccc(-c5cc(OC6CC=CC6)ccn5)n4)ccc3[nH]2)CC1] | 0.0158 | analogous to Example 92 | HPLC-MS: method K Rt = 1.12 min |
| 109 | 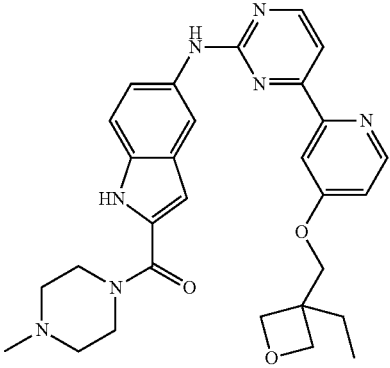 [SMILES: CCC1(COc2ccnc(-c3ccnc(Nc4ccc5[nH]c(C(=O)N6CCN(C)CC6)cc5c4)n3)c2)COC1] | 0.0031 | analogous to Example 92 | HPLC-MS: method K Rt = 1.11 min |
| 110 | 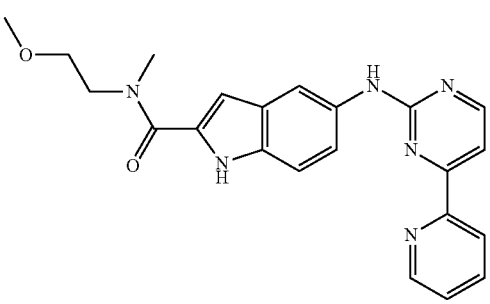 [SMILES: COCCN(C)C(=O)c1cc2cc(Nc3nccc(-c4ccccn4)n3)ccc2[nH]1] | 0.0614 | analogous to Example 8 | HPLC-MS: method B Rt = 2.41 min |

TABLE 1-continued

| Example No. | Structure | SYK Enzyme IC50 [μM] | Method of preparation | Analytical data |
|---|---|---|---|---|
| 111 | 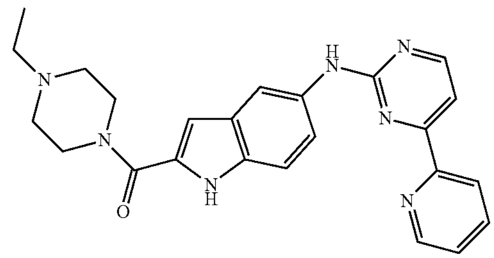 [SMILES: CCN1CCN(C(=O)c2cc3cc(Nc4nccc(-c5ccccn5)n4)ccc3[nH]2)CC1] | 0.0434 | analogous to Example 8 | HPLC-MS: method B Rt = 2.45 min |
| 112 | 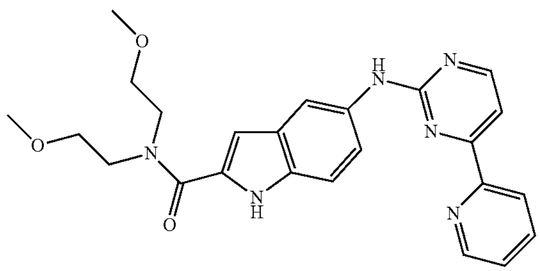 [SMILES: COCCN(CCOC)C(=O)c1cc2cc(Nc3nccc(-c4ccccn4)n3)ccc2[nH]1] | 0.0474 | analogous to Example 8 | HPLC-MS: method B Rt = 2.45 min |
| 113 | 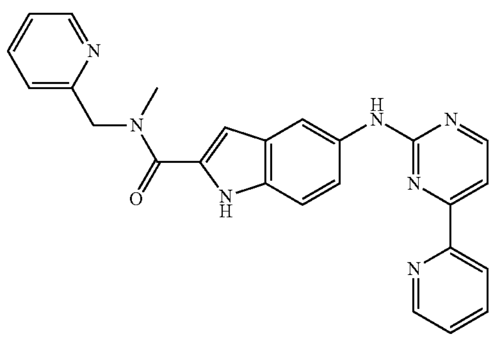 [SMILES: CN(Cc1ccccn1)C(=O)c1cc2cc(Nc3nccc(-c4ccccn4)n3)ccc2[nH]1] | 0.0156 | analogous to Example 8 | HPLC-MS: method B Rt = 2.42 min |
| 114 | 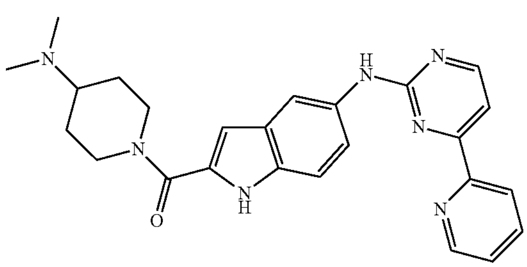 [SMILES: CN(C)C1CCN(C(=O)c2cc3cc(Nc4nccc(-c5ccccn5)n4)ccc3[nH]2)CC1] | 0.0321 | analogous to Example 8 | HPLC-MS: method B Rt = 2.44 min |
| 115 | 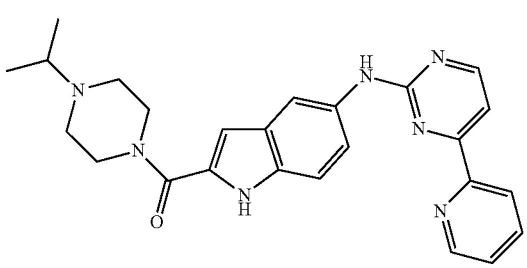 [SMILES: CC(C)N1CCN(C(=O)c2cc3cc(Nc4nccc(-c5ccccn5)n4)ccc3[nH]2)CC1] | 0.0410 | analogous to Example 8 | HPLC-MS: method B Rt = 2.51 min |

TABLE 1-continued

| Example No. | Structure | SYK Enzyme IC50 [μM] | Method of preparation | Analytical data |
|---|---|---|---|---|
| 116 | 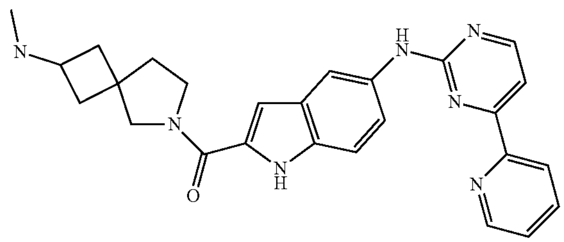 [SMILES: CNC1CC2(CCN(C(=O)c3cc4cc(Nc5nccc(-c6ccccn6)n5)ccc4[nH]3)C2)C1] | 0.0242 | analogous to Example 8 | HPLC-MS: method B Rt = 2.48 min |
| 117 | 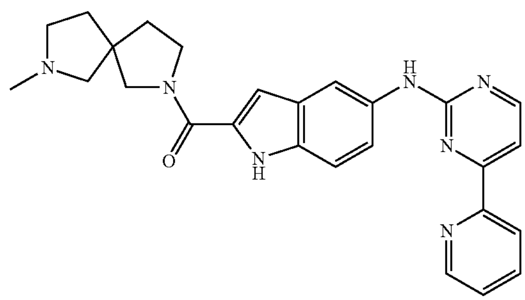 [SMILES: CN1CCC2(CCN(C(=O)c3cc4cc(Nc5nccc(-c6ccccn6)n5)ccc4[nH]3)C2)C1] | 0.0106 | analogous to Example 8 | HPLC-MS: method B Rt = 2.47 min |
| 118 | 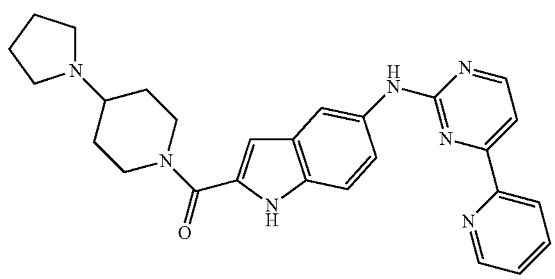 [SMILES: O=C(c1cc2cc(Nc3nccc(-c4ccccn4)n3)ccc2[nH]1)N1CCC(N2CCCC2)CC1] | 0.0303 | analogous to Example 8 | HPLC-MS: method B Rt = 2.56 min |
| 119 | 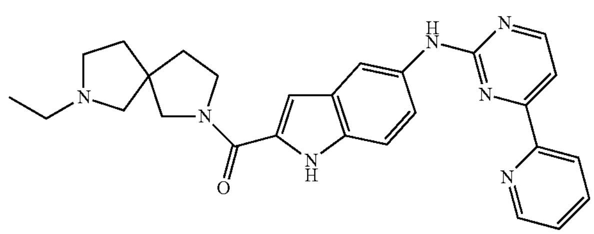 [SMILES: CCN1CCC2(CCN(C(=O)c3cc4cc(Nc5nccc(-c6ccccn6)n5)ccc4[nH]3)C2)C1] | 0.0188 | analogous to Example 8 | HPLC-MS: method B Rt = 2.56 min |
| 120 | 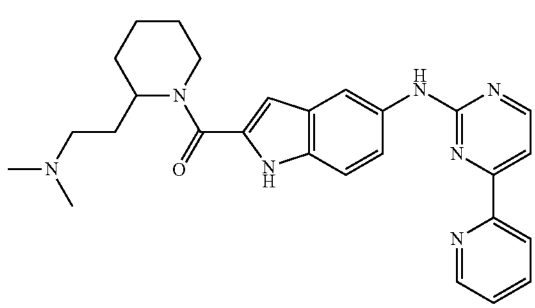 [SMILES: CN(C)CCC1CCCCN1C(=O)c1cc2cc(Nc3nccc(-c4ccccn4)n3)ccc2[nH]1] | 0.0774 | analogous to Example 8 | HPLC-MS: method B Rt = 2.60 min |

US 8,772,305 B2

TABLE 1-continued

| Example No. | Structure | SYK Enzyme IC50 [µM] | Method of preparation | Analytical data |
|---|---|---|---|---|
| 121 | 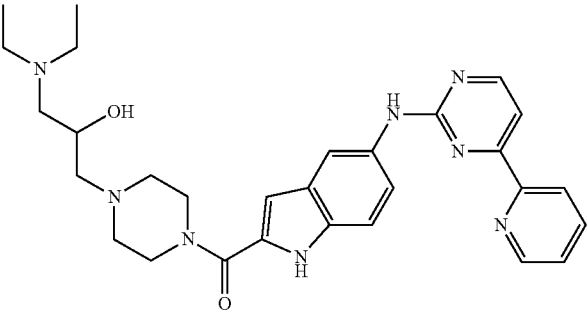 [SMILES: CCN(CC)CC(O)CN1CCN(C(=O)c2cc3cc(Nc4nccc(-c5ccccn5)n4)ccc3[nH]2)CC1] | 0.0250 | analogous to Example 8 | HPLC-MS: method B Rt = 2.65 min |
| 122 | 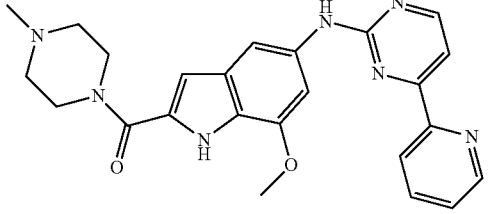 | 0.0047 | analogous to Example 8 | HPLC-MS: method A Rt = 1.34 min |
| 123 | 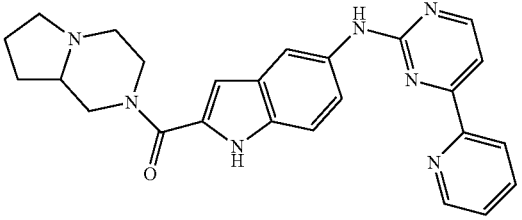 [SMILES: O=C(c1cc2cc(Nc3nccc(-c4ccccn4)n3)ccc2[nH]1)N1CCN2CCCC2C1] | 0.0187 | analogous to Example 8 | HPLC-MS: method L Rt = 0.44 min |
| 124 | 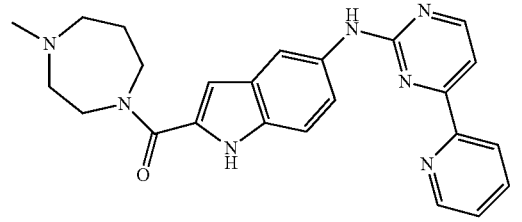 [SMILES: CN1CCCN(C(=O)c2cc3cc(Nc4nccc(-c5ccccn5)n4)ccc3[nH]2)CC1] | 0.0361 | analogous to Example 8 | HPLC-MS: method B Rt = 2.40 min |
| 125 | 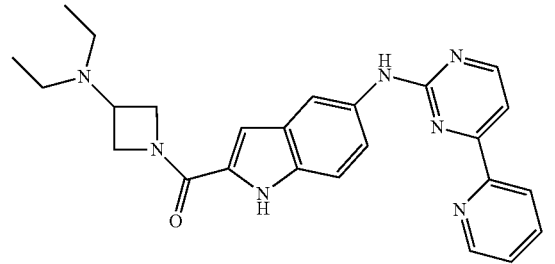 [SMILES: CCN(CC)C1CN(C(=O)c2cc3cc(Nc4nccc(-c5ccccn5)n4)ccc3[nH]2)C1] | 0.0058 | analogous to Example 8 | HPLC-MS: method B Rt = 2.51 min |
| 126 | 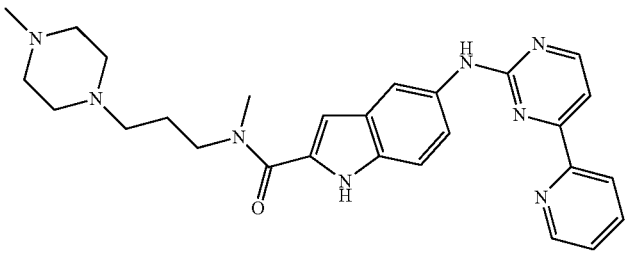 [SMILES: CN1CCN(CCCN(C)C(=O)c2cc3cc(Nc4nccc(-c5ccccn5)n4)ccc3[nH]2)CC1] | 0.0472 | analogous to Example 8 | HPLC-MS: method B Rt = 2.40 min |

TABLE 1-continued
| Example No. | Structure | SYK Enzyme IC50 [μM] | Method of preparation | Analytical data |
|---|---|---|---|---|
| 127 | 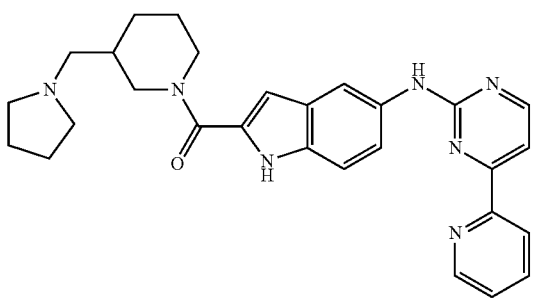 [SMILES: O=C(c1cc2cc(Nc3nccc(-c4ccccn4)n3)ccc2[nH]1)N1CCCC(CN2CCCC2)C1] | 0.0484 | analogous to Example 8 | HPLC-MS: method B Rt = 2.68 min |
| 128 | 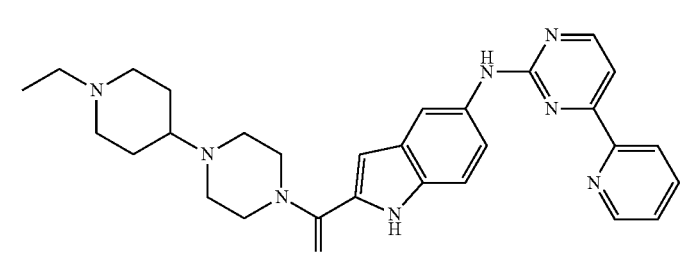 | 0.0286 | analogous to Example 8 | HPLC-MS: method B Rt = 2.55 min |
| 129 | 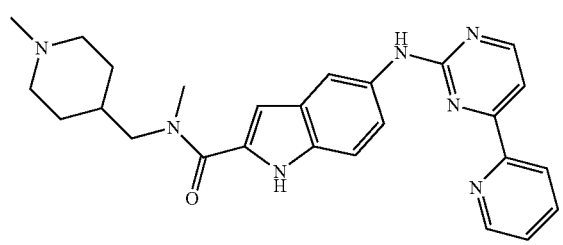 [SMILES: CN1CCC(CN(C)C(=O)c2cc3cc(Nc4nccc(-c5ccccn5)n4)ccc3[nH]2)CC1] | 0.0289 | analogous to Example 8 | HPLC-MS: method B Rt = 2.54 min |
| 130 | 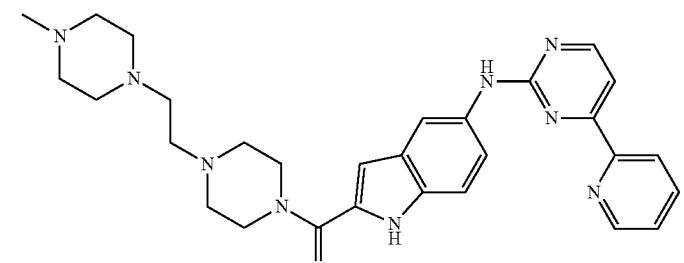 | 0.0455 | analogous to Example 8 | HPLC-MS: method B Rt = 2.36 min |
| 131 | 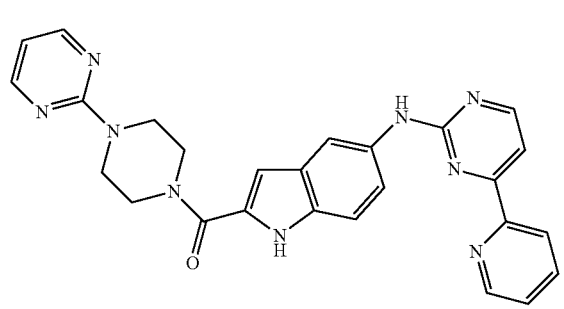 [SMILES: O=C(c1cc2cc(Nc3nccc(-c4ccccn4)n3)ccc2[nH]1)N1CCN(c2ncccn2)CC1] | 0.1781 | analogous to Example 8 | HPLC-MS: method B Rt = 2.82 min |

TABLE 1-continued

| Example No. | Structure | SYK Enzyme IC50 [μM] | Method of preparation | Analytical data |
|---|---|---|---|---|
| 132 | 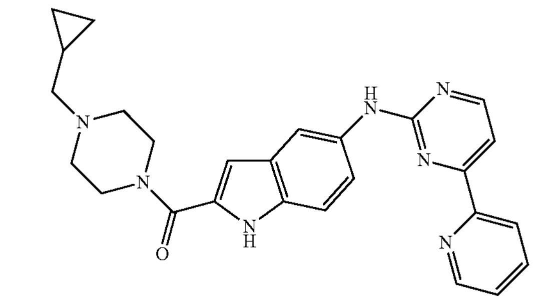 [SMILES: O=C(c1cc2cc(Nc3nccc(-c4ccccn4)n3)ccc2[nH]1)N1CCN(CC2CC2)CC1] | 0.0190 | analogous to Example 8 | HPLC-MS: method B Rt = 2.55 min |
| 133 | 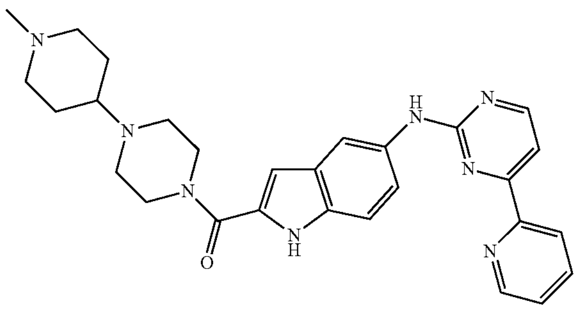 [SMILES: CN1CCC(N2CCN(C(=O)c3cc4cc(Nc5nccc(-c6ccccn6)n5)ccc4[nH]3)CC2)CC1] | 0.0315 | analogous to Example 8 | HPLC-MS: method B Rt = 2.41 min |
| 134 | 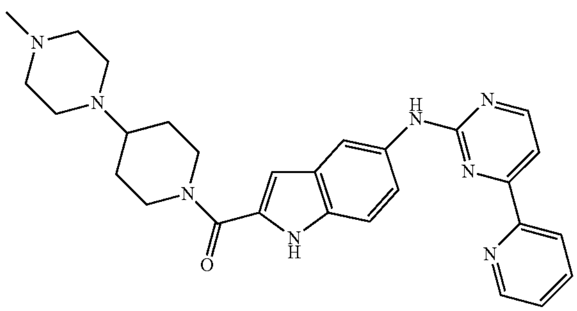 [SMILES: CN1CCN(C2CCN(C(=O)c3cc4cc(Nc5nccc(-c6ccccn6)n5)ccc4[nH]3)CC2)CC1] | 0.0171 | analogous to Example 8 | HPLC-MS: method B Rt = 2.38 min |
| 135 | 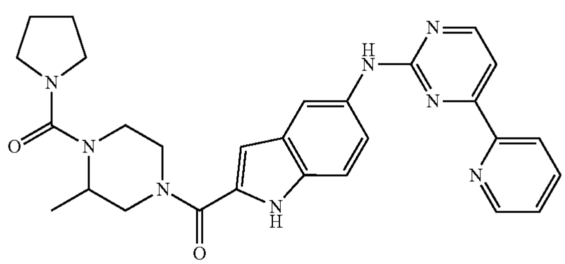 [SMILES: CC1CN(C(=O)c2cc3cc(Nc4nccc(-c5ccccn5)n4)ccc3[nH]2)CCN1C(=O)N1CCCC1] | 0.0222 | analogous to Example 8 | HPLC-MS: method B Rt = 2.46 min |
| 136 | 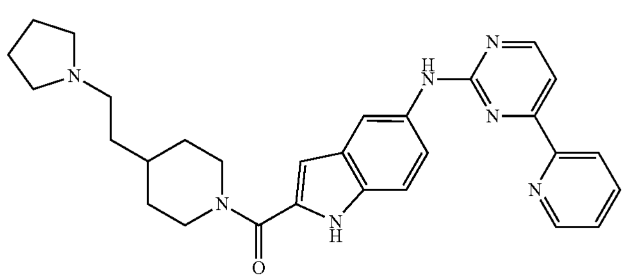 [SMILES: O=C(c1cc2cc(Nc3nccc(-c4ccccn4)n3)ccc2[nH]1)N1CCC(CCN2CCCC2)CC1] | 0.0607 | analogous to Example 8 | HPLC-MS: method B Rt = 2.76 min |

TABLE 1-continued

| Example No. | Structure | SYK Enzyme IC50 [μM] | Method of preparation | Analytical data |
|---|---|---|---|---|
| 137 | 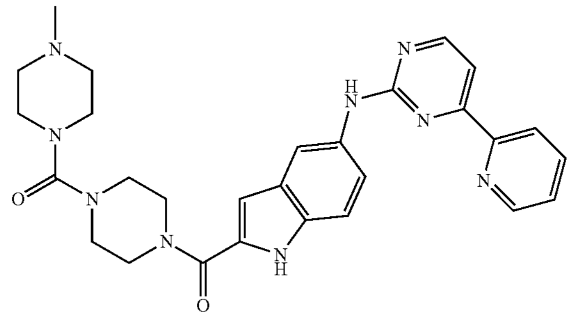 | 0.0325 | analogous to Example 8 | HPLC-MS: method B Rt = 2.33 min |
| 138 | 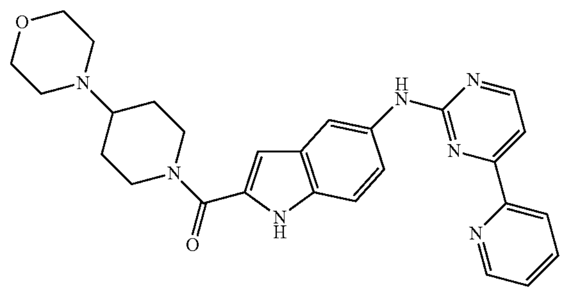 [SMILES: O=C(c1cc2cc(Nc3nccc(-c4ccccn4)n3)ccc2[nH]1)N1CCC(N2CCOCC2)CC1] | 0.0242 | analogous to Example 8 | HPLC-MS: method B Rt = 2.37 min |
| 139 | 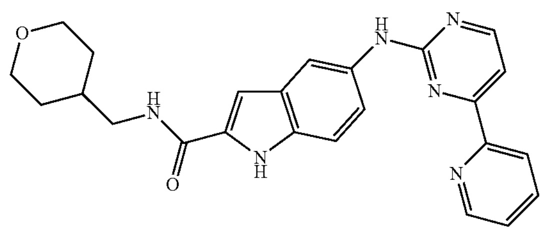 [SMILES: O=C(NCC1CCOCC1)c1cc2cc(Nc3nccc(-c4ccccn4)n3)ccc2[nH]1] | 0.0123 | analogous to Example 8 | HPLC-MS: method B Rt = 2.37 min |
| 140 | 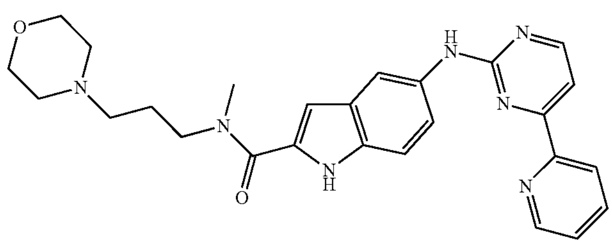 [SMILES: CN(CCCN1CCOCC1)C(=O)c1cc2cc(Nc3nccc(-c4ccccn4)n3)ccc2[nH]1] | 0.0228 | analogous to Example 8 | HPLC-MS: method B Rt = 2.40 min |
| 141 | 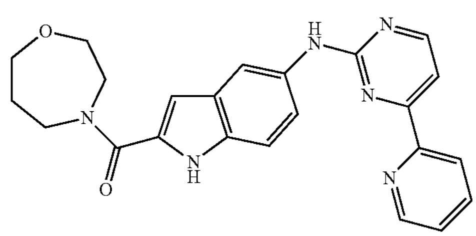 [SMILES: O=C(c1cc2cc(Nc3nccc(-c4ccccn4)n3)ccc2[nH]1)N1CCCOCC1] | 0.0172 | analogous to Example 8 | HPLC-MS: method B Rt = 2.36 min |
| 142 | 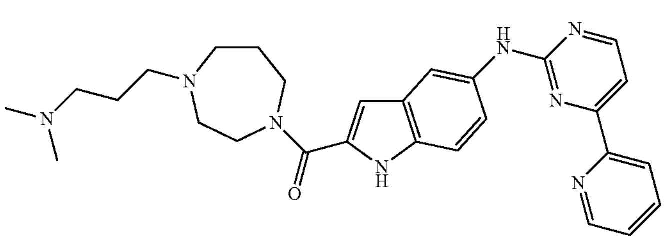 [SMILES: CN(C)CCCN1CCCN(C(=O)c2cc3cc(Nc4nccc(-c5ccccn5)n4)ccc3[nH]2)CC1] | 0.0425 | analogous to Example 8 | HPLC-MS: method B Rt = 2.82 min |

TABLE 1-continued

| Example No. | Structure | SYK Enzyme IC50 [µM] | Method of preparation | Analytical data |
|---|---|---|---|---|
| 143 | 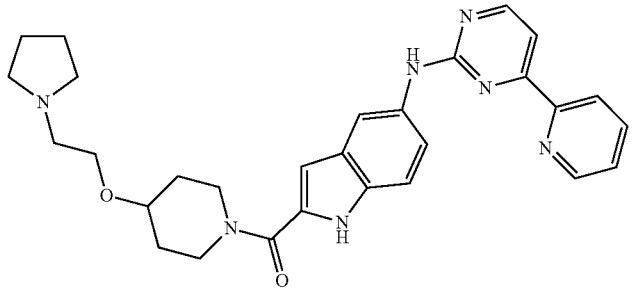 [SMILES: O=C(c1cc2cc(Nc3nccc(-c4ccccn4)n3)ccc2[nH]1)N1CCC(OCCN2CCCC2)CC1] | 0.0256 | analogous to Example 8 | HPLC-MS: method B Rt = 2.81 min |
| 144 | 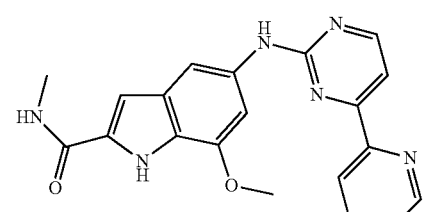 | 0.0041 | analogous to Example 8 | HPLC-MS: method A Rt = 1.70 min |
| 145 | 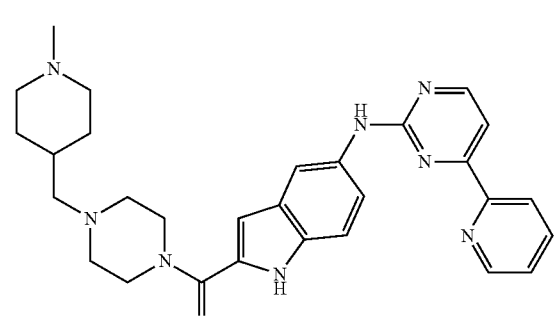 | 0.0168 | analogous to Example 8 | HPLC-MS: method B Rt = 2.60 min |
| 146 | 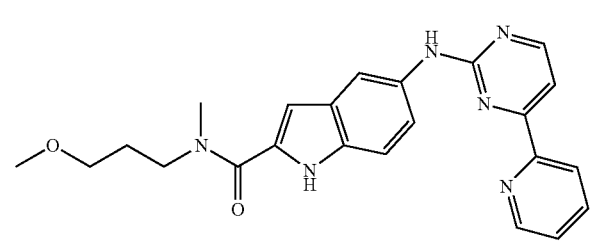 [SMILES: COCCCN(C)C(=O)c1cc2cc(Nc3nccc(-c4ccccn4)n3)ccc2[nH]1] | 0.0288 | analogous to Example 8 | HPLC-MS: method B Rt = 2.44 min |
| 147 | 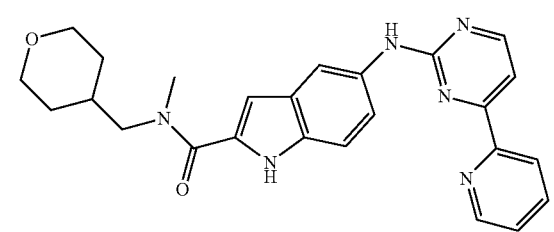 [SMILES: CN(CC1CCOCC1)C(=O)c1cc2cc(Nc3nccc(-c4ccccn4)n3)ccc2[nH]1] | 0.0138 | analogous to Example 8 | HPLC-MS: method B Rt = 2.44 min |
| 148 | 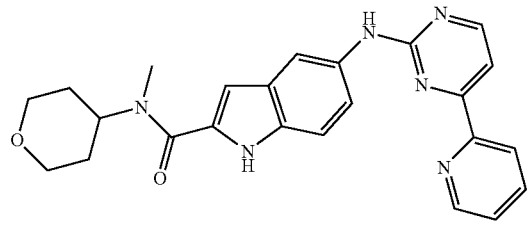 [SMILES: CN(C(=O)c1cc2cc(Nc3nccc(-c4ccccn4)n3)ccc2[nH]1)C1CCOCC1] | 0.0855 | analogous to Example 8 | HPLC-MS: method B Rt = 2.82 min |

TABLE 1-continued

| Example No. | Structure | SYK Enzyme IC50 [μM] | Method of preparation | Analytical data |
|---|---|---|---|---|
| 149 | 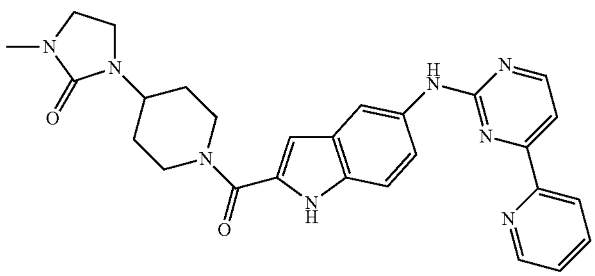 [SMILES: CN1CCN(C2CCN(C(=O)c3cc4cc(Nc5nccc(-c6ccccn6)n5)ccc4[nH]3)CC2)C1=O] | 0.0182 | analogous to Example 8 | HPLC-MS: method B Rt = 2.35 min |
| 150 | 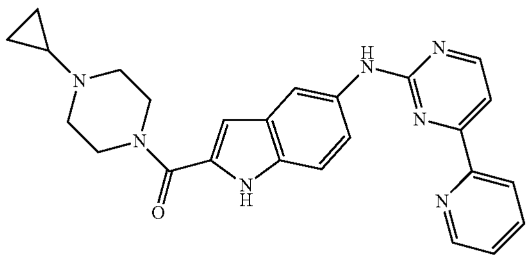 [SMILES: O=C(c1cc2cc(Nc3nccc(-c4ccccn4)n3)ccc2[nH]1)N1CCN(C2CC2)CC1] | 0.0433 | analogous to Example 8 | HPLC-MS: method B Rt = 2.53 min |
| 151 | 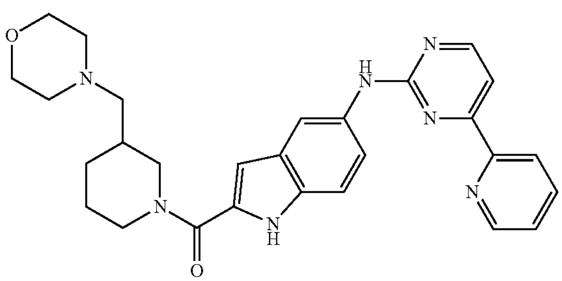 [SMILES: O=C(c1cc2cc(Nc3nccc(-c4ccccn4)n3)ccc2[nH]1)N1CCCC(CN2CCOCC2)C1] | 0.0410 | analogous to Example 8 | HPLC-MS: method B Rt = 2.82 min |
| 152 | 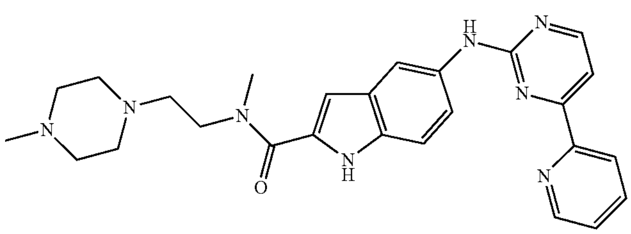 [SMILES: CN1CCN(CCN(C)C(=O)c2cc3cc(Nc4nccc(-c5ccccn5)n4)ccc3[nH]2)CC1] | 0.0773 | analogous to Example 8 | HPLC-MS: method B Rt = 2.81 min |
| 153 | 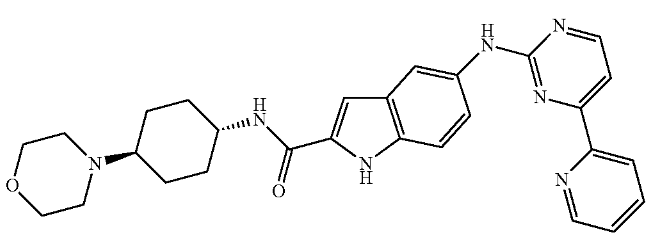 [SMILES: O=C(N[C@H]1CC[C@H](N2CCOCC2)CC1)c1cc2cc(Nc3nccc(-c4ccccn4)n3)ccc2[nH]1] | 0.0327 | analogous to Example 8 | HPLC-MS: method B Rt = 2.42 min |

TABLE 1-continued

| Example No. | Structure | SYK Enzyme IC50 [μM] | Method of preparation | Analytical data |
|---|---|---|---|---|
| 154 | 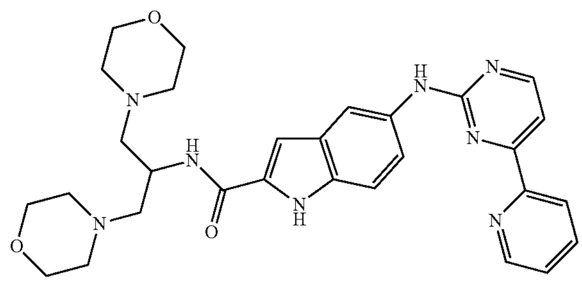 [SMILES: O=C(NC(CN1CCOCC1)CN1CCOCC1)c1cc2cc(Nc3nccc(-c4ccccn4)n3)ccc2[nH]1] | 0.0402 | analogous to Example 8 | HPLC-MS: method B Rt = 2.36 min |
| 155 | 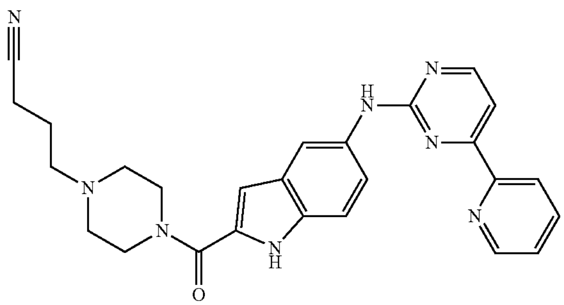 [SMILES: N#CCCCN1CCN(C(=O)c2cc3cc(Nc4nccc(-c5ccccn5)n4)ccc3[nH]2)CC1] | 0.0301 | analogous to Example 8 | HPLC-MS: method B Rt = 2.35 min |
| 156 | 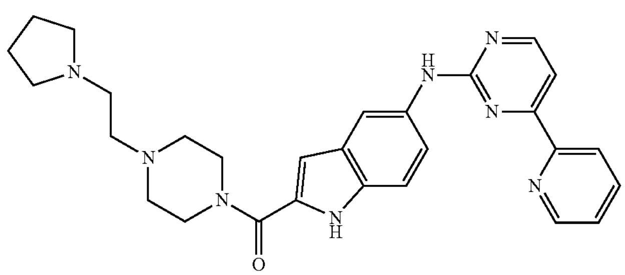 [SMILES: O=C(c1cc2cc(Nc3nccc(-c4ccccn4)n3)ccc2[nH]1)N1CCN(CCN2CCCC2)CC1] | 0.0290 | analogous to Example 8 | HPLC-MS: method B Rt = 2.56 min |
| 157 | 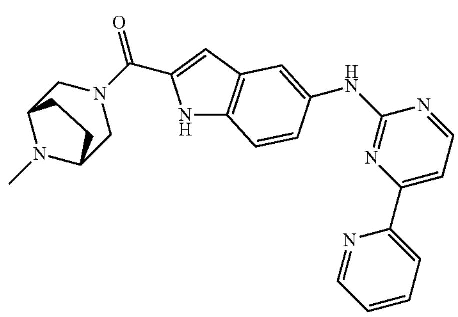 [SMILES: CN1[C@@H]2CC[C@H]1CN(C(=O)c1cc3cc(Nc4nccc(-c5ccccn5)n4)ccc3[nH]1)C2] | 0.0128 | analogous to Example 8 | HPLC-MS: method B Rt = 2.48 min |
| 158 | 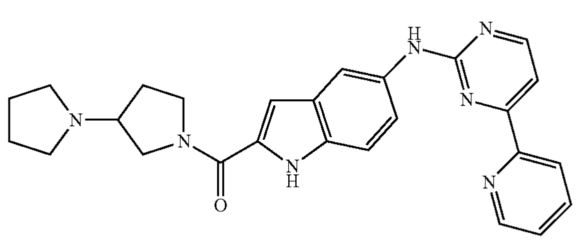 [SMILES: O=C(c1cc2cc(Nc3nccc(-c4ccccn4)n3)ccc2[nH]1)N1CCC(N2CCCC2)C1] | 0.0047 | analogous to Example 8 | HPLC-MS: method B Rt = 2.52 min |

TABLE 1-continued

| Example No. | Structure | SYK Enzyme IC50 [μM] | Method of preparation | Analytical data |
|---|---|---|---|---|
| 159 | 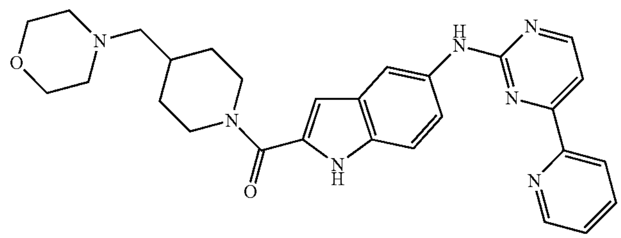 [SMILES: O=C(c1cc2cc(Nc3nccc(-c4ccccn4)n3)ccc2[nH]1)N1CCC(CN2CCOCC2)CC1] | 0.0289 | analogous to Example 8 | HPLC-MS: method B Rt = 2.49 min |
| 160 | 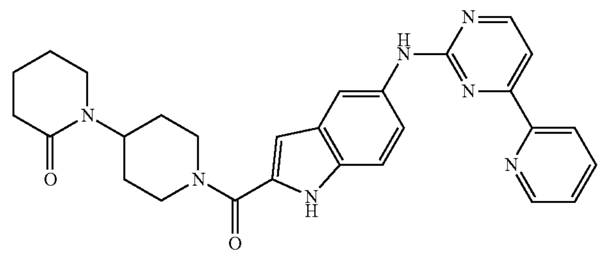 [SMILES: O=C(c1cc2cc(Nc3nccc(-c4ccccn4)n3)ccc2[nH]1)N1CCC(N2CCCCC2=O)CC1] | 0.0450 | analogous to Example 8 | HPLC-MS: method B Rt = 2.38 min |
| 161 | 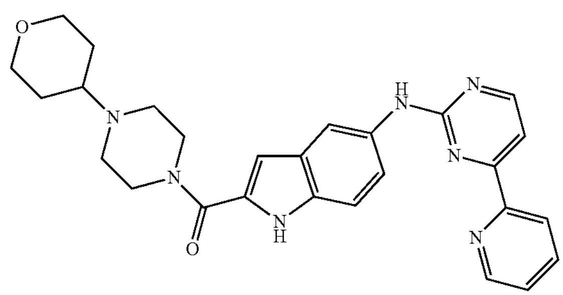 [SMILES: O=C(c1cc2cc(Nc3nccc(-c4ccccn4)n3)ccc2[nH]1)N1CCN(C2CCOCC2)CC1] | 0.0335 | analogous to Example 8 | HPLC-MS: method B Rt = 2.38 min |
| 162 | 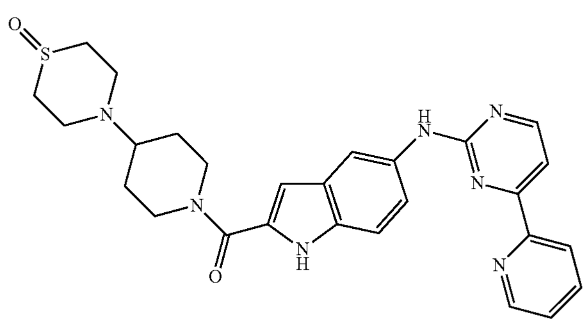 [SMILES: O=C(c1cc2cc(Nc3nccc(-c4ccccn4)n3)ccc2[nH]1)N1CCC(N2CCS(=O)CC2)CC1] | 0.0264 | analogous to Example 8 | HPLC-MS: method B Rt = 2.24 min |
| 163 | 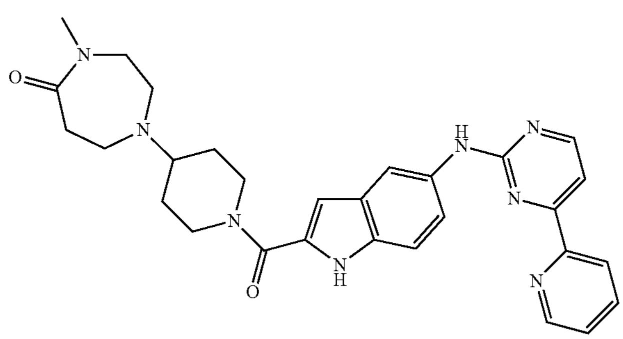 [SMILES: CN1CCN(C2CCN(C(=O)c3cc4cc(Nc5nccc(-c6ccccn6)n5)ccc4[nH]3)CC2)CCC1=O] | 0.0470 | analogous to Example 8 | HPLC-MS: method B Rt = 2.30 min |

TABLE 1-continued

| Example No. | Structure | SYK Enzyme IC50 [μM] | Method of preparation | Analytical data |
|---|---|---|---|---|
| 164 | 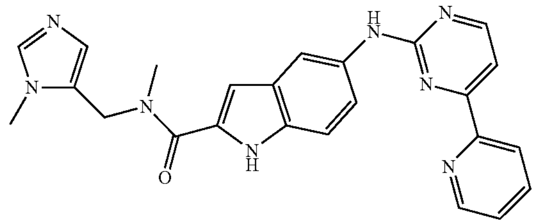 [SMILES: CN(Cc1cncn1C)C(=O)c1cc2cc(Nc3nccc(-c4ccccn4)n3)ccc2[nH]1] | 0.0183 | analogous to Example 8 | HPLC-MS: method B Rt = 2.31 min |
| 165 | 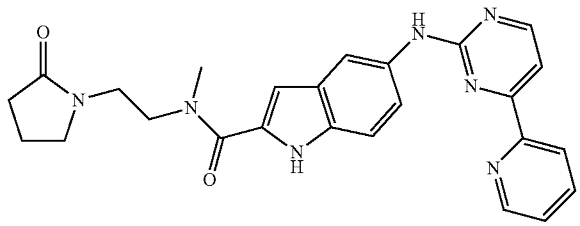 [SMILES: CN(CCN1CCCC1=O)C(=O)c1cc2cc(Nc3nccc(-c4ccccn4)n3)ccc2[nH]1] | 0.0312 | analogous to Example 8 | HPLC-MS: method B Rt = 2.82 min |
| 166 | 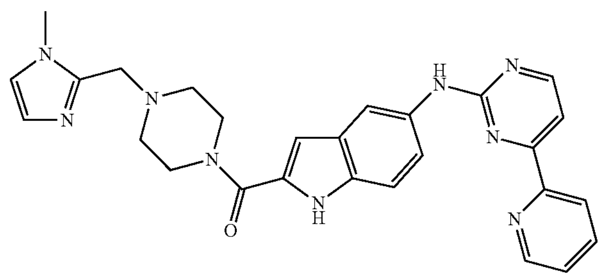 [SMILES: Cn1ccnc1CN1CCN(C(=O)c2cc3cc(Nc4nccc(-c5ccccn5)n4)ccc3[nH]2)CC1] | 0.0329 | analogous to Example 8 | HPLC-MS: method B Rt = 2.37 min |
| 167 | 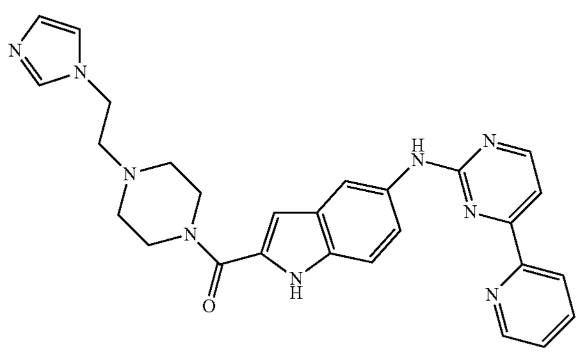 [SMILES: O=C(c1cc2cc(Nc3nccc(-c4ccccn4)n3)ccc2[nH]1)N1CCN(CCn2ccnc2)CC1] | 0.0363 | analogous to Example 8 | HPLC-MS: method B Rt = 2.36 min |
| 168 | 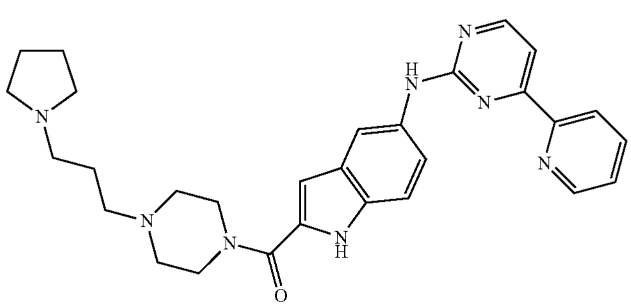 [SMILES: O=C(c1cc2cc(Nc3nccc(-c4ccccn4)n3)ccc2[nH]1)N1CCN(CCCN2CCCC2)CC1] | 0.0209 | analogous to Example 8 | HPLC-MS: method B Rt = 2.65 min |

TABLE 1-continued
| Example No. | Structure | SYK Enzyme IC50 [µM] | Method of preparation | Analytical data |
|---|---|---|---|---|
| 169 | 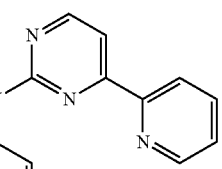 | 0.0355 | analogous to Example 8 | HPLC-MS: method B Rt = 2.39 min |
| 170 | 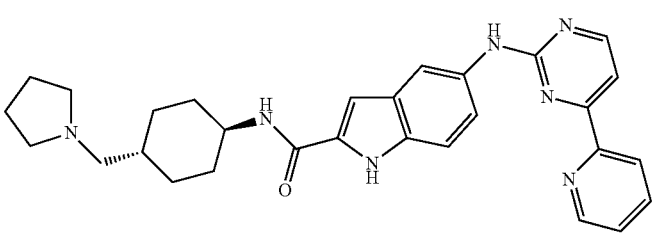 [SMILES: O=C(N[C@H]1CC[C@H](CN2CCCC2)CC1)c1cc2cc(Nc3nccc(-c4ccccn4)n3)ccc2[nH]1] | 0.1936 | analogous to Example 8 | HPLC-MS: method B Rt = 2.81 min |
| 171 | 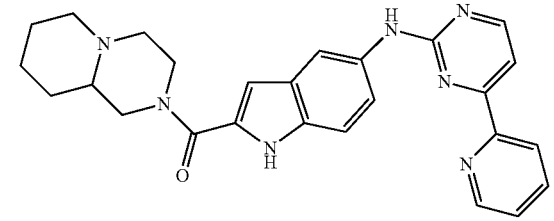 [SMILES: O=C(c1cc2cc(Nc3nccc(-c4ccccn4)n3)ccc2[nH]1)N1CCN2CCCCC2C1] | 0.0474 | analogous to Example 8 | HPLC-MS: method B Rt = 2.54 min |
| 172 | 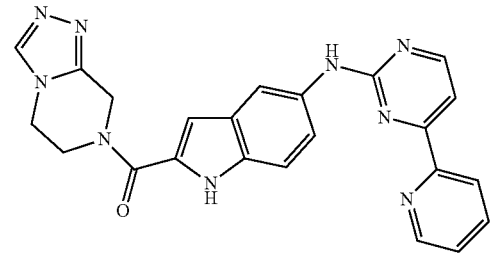 [SMILES: O=C(c1cc2cc(Nc3nccc(-c4ccccn4)n3)ccc2[nH]1)N1CCn2cnnc2C1] | 0.0849 | analogous to Example 8 | HPLC-MS: method B Rt = 2.17 min |
| 173 | 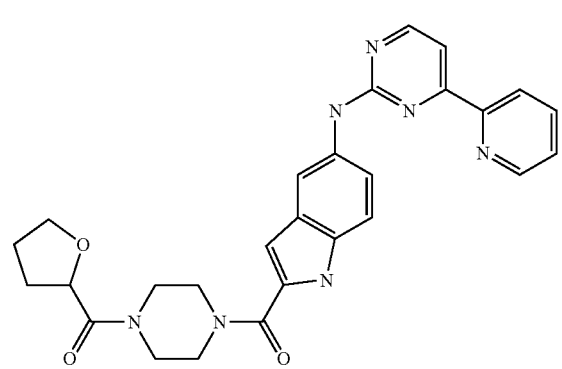 [SMILES: O=C(c1cc2cc(Nc3nccc(-c4ccccn4)n3)ccc2[nH]1)N1CCN(C(=O)C2CCCO2)CC1] | 0.0295 | analogous to Example 8 | HPLC-MS: method B Rt = 2.32 min |

TABLE 1-continued

| Example No. | Structure | SYK Enzyme IC50 [μM] | Method of preparation | Analytical data |
|---|---|---|---|---|
| 174 | 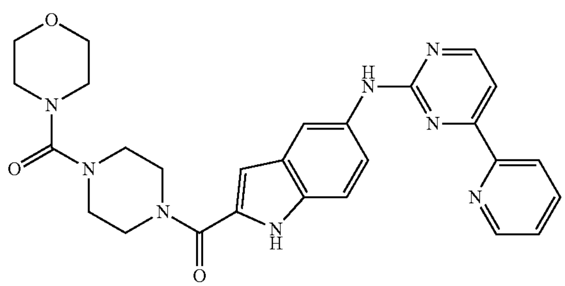 [SMILES: O=C(c1cc2cc(Nc3nccc(-c4ccccn4)n3)ccc2[nH]1)N1CCN(C(=O)N2CCOCC2)CC1] | 0.0283 | analogous to Example 8 | HPLC-MS: method B Rt = 2.31 min |
| 175 | 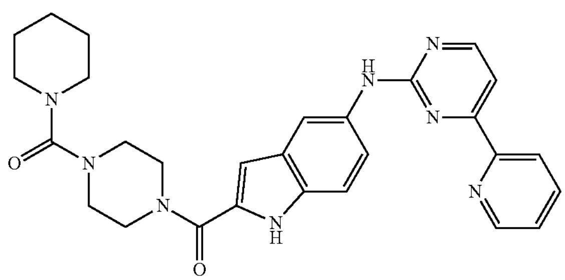 [SMILES: O=C(c1cc2cc(Nc3nccc(-c4ccccn4)n3)ccc2[nH]1)N1CCN(C(=O)N2CCCCC2)CC1] | 0.0579 | analogous to Example 8 | HPLC-MS: method B Rt = 2.52 min |
| 176 | 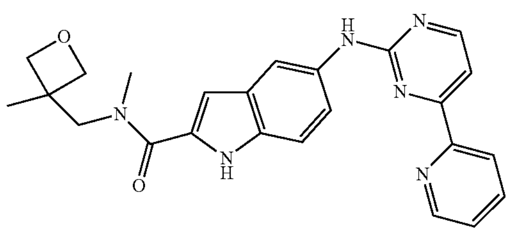 [SMILES: CN(CC1(C)COC1)C(=O)c1cc2cc(Nc3nccc(-c4ccccn4)n3)ccc2[nH]1] | 0.0373 | analogous to Example 8 | HPLC-MS: method B Rt = 2.38 min |
| 177 | 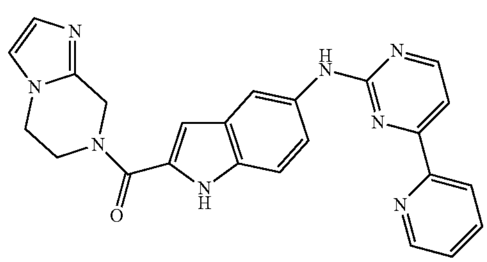 [SMILES: O=C(c1cc2cc(Nc3nccc(-c4ccccn4)n3)ccc2[nH]1)N1CCn2ccnc2C1] | 0.0282 | analogous to Example 8 | HPLC-MS: method B Rt = 2.32 min |
| 178 | 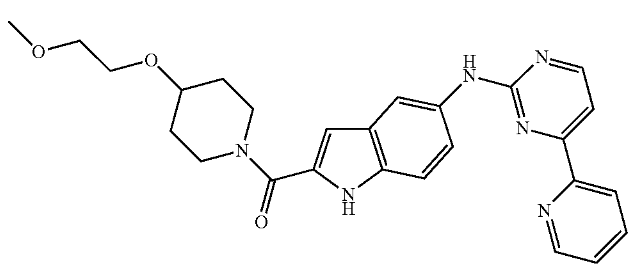 [SMILES: COCCOC1CCN(C(=O)c2cc3cc(Nc4nccc(-c5ccccn5)n4)ccc3[nH]2)CC1] | 0.0429 | analogous to Example 8 | HPLC-MS: method B Rt = 2.44 min |

TABLE 1-continued
| Example No. | Structure | SYK Enzyme IC50 [μM] | Method of preparation | Analytical data |
|---|---|---|---|---|
| 179 | 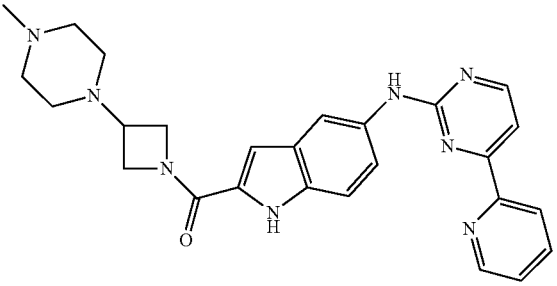 [SMILES: CN1CCN(C2CN(C(=O)c3cc4cc(Nc5nccc(-c6ccccn6)n5)ccc4[nH]3)C2)CC1] | 0.0123 | analogous to Example 8 | HPLC-MS: method L Rt = 0.45 min |
| 180 | 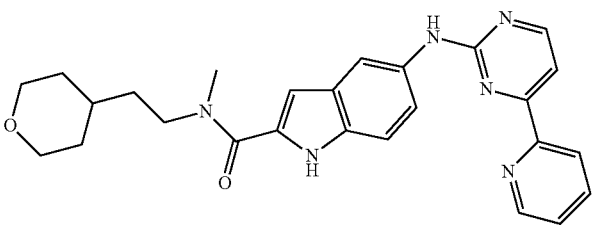 [SMILES: CN(CCC1CCOCC1)C(=O)c1cc2cc(Nc3nccc(-c4ccccn4)n3)ccc2[nH]1] | 0.0339 | analogous to Example 8 | HPLC-MS: method B Rt = 2.81 min |
| 181 | 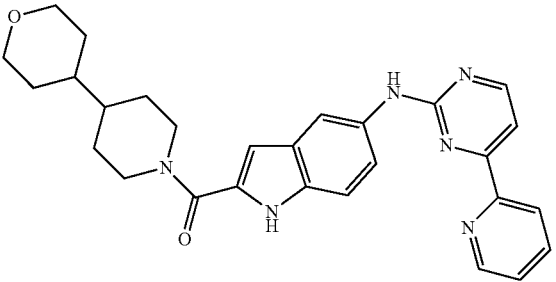 [SMILES: O=C(c1cc2cc(Nc3nccc(-c4ccccn4)n3)ccc2[nH]1)N1CCC(C2CCOCC2)CC1] | 0.0523 | analogous to Example 8 | HPLC-MS: method B Rt = 2.56 min |
| 182 | 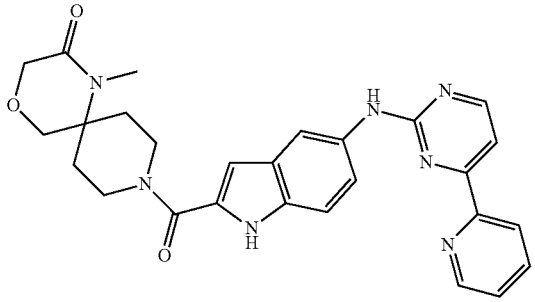 [SMILES: CN1C(=O)COCC12CCN(C(=O)c1cc3cc(Nc4nccc(-c5ccccn5)n4)ccc3[nH]1)CC2] | 0.0197 | analogous to Example 8 | HPLC-MS: method B Rt = 2.29 min |
| 183 | 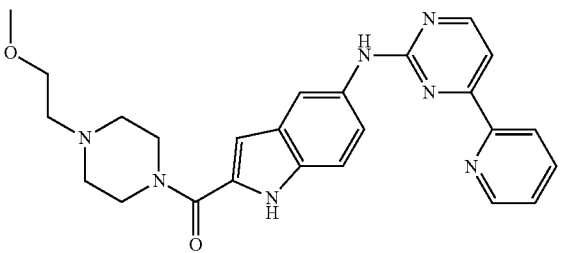 [SMILES: COCCN1CCN(C(=O)c2cc3cc(Nc4nccc(-c5ccccn5)n4)ccc3[nH]2)CC1] | 0.0468 | analogous to Example 8 | HPLC-MS: method B Rt = 2.40 min |

TABLE 1-continued

| Example No. | Structure | SYK Enzyme IC50 [μM] | Method of preparation | Analytical data |
|---|---|---|---|---|
| 184 | 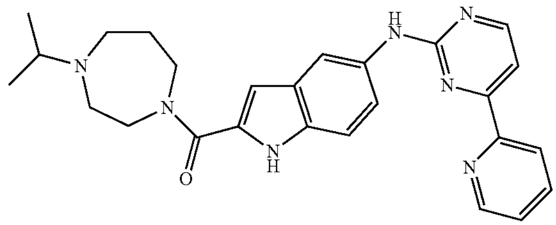 [SMILES: CC(C)N1CCCN(C(=O)c2cc3cc(Nc4nccc(-c5ccccn5)n4)ccc3[nH]2)CC1] | 0.0239 | analogous to Example 8 | HPLC-MS: method B Rt = 2.57 min |
| 185 | 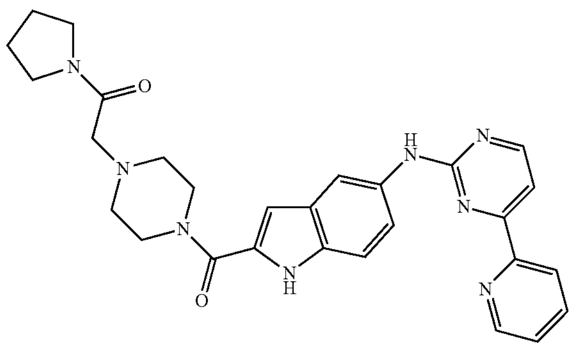 [SMILES: O=C(CN1CCN(C(=O)c2cc3cc(Nc4nccc(-c5ccccn5)n4)ccc3[nH]2)CC1)N1CCCC1] | 0.0281 | analogous to Example 8 | HPLC-MS: method B Rt = 2.37 min |
| 186 | 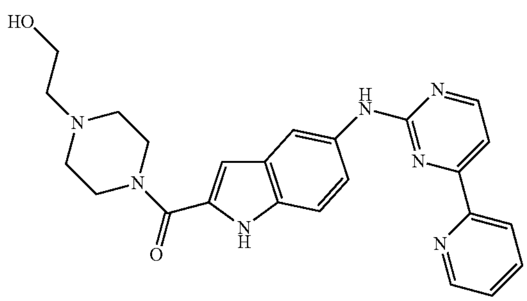 [SMILES: O=C(c1cc2cc(Nc3nccc(-c4ccccn4)n3)ccc2[nH]1)N1CCN(CCO)CC1] | 0.0281 | analogous to Example 8 | HPLC-MS: method B Rt = 2.27 min |
| 187 | 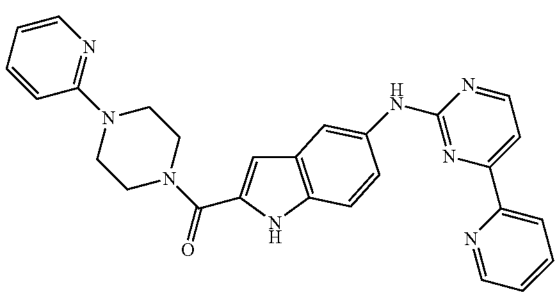 [SMILES: O=C(c1cc2cc(Nc3nccc(-c4ccccn4)n3)ccc2[nH]1)N1CCN(c2ccccn2)CC1] | 0.0634 | analogous to Example 8 | HPLC-MS: method B Rt = 2.83 min |
| 188 | 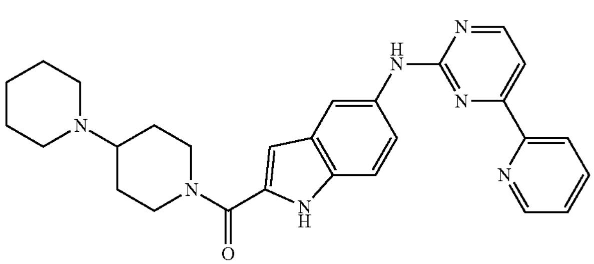 [SMILES: O=C(c1cc2cc(Nc3nccc(-c4ccccn4)n3)ccc2[nH]1)N1CCC(N2CCCCC2)CC1] | 0.0172 | analogous to Example 8 | HPLC-MS: method B Rt = 2.63 min |

TABLE 1-continued
| Example No. | Structure | SYK Enzyme IC50 [μM] | Method of preparation | Analytical data |
|---|---|---|---|---|
| 189 | 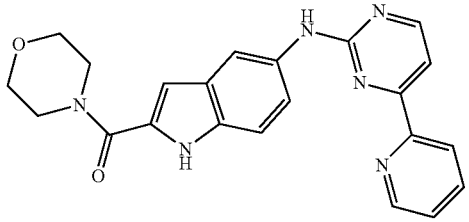 [SMILES: O=C(c1cc2cc(Nc3nccc(-c4ccccn4)n3)ccc2[nH]1)N1CCOCC1] | 0.0257 | analogous to Example 8 | HPLC-MS: method B Rt = 2.34 min |
| 190 | 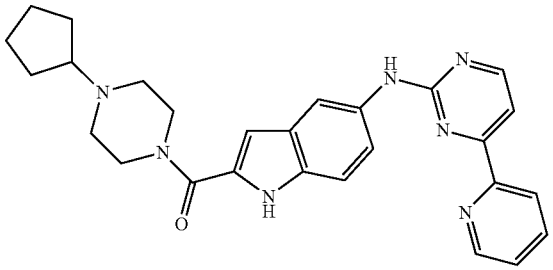 [SMILES: O=C(c1cc2cc(Nc3nccc(-c4ccccn4)n3)ccc2[nH]1)N1CCN(C2CCCC2)CC1] | 0.0207 | analogous to Example 8 | HPLC-MS: method B Rt = 2.83 min |
| 191 | 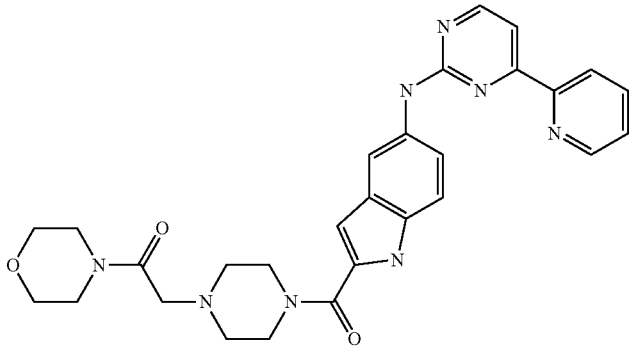 [SMILES: O=C(CN1CCN(C(=O)c2cc3cc(Nc4nccc(-c5ccccn5)n4)ccc3[nH]2)CC1)N1CCOCC1] | 0.0137 | analogous to Example 8 | HPLC-MS: method B Rt = 2.31 min |
| 192 | 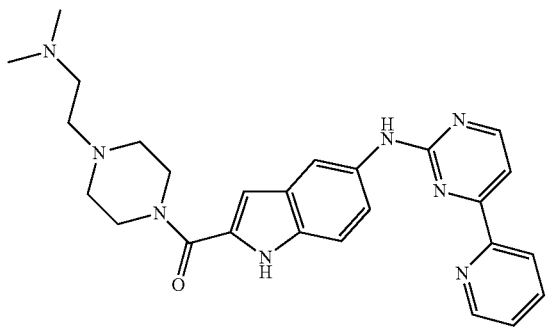 [SMILES: CN(C)CCN1CCN(C(=O)c2cc3cc(Nc4nccc(-c5ccccn5)n4)ccc3[nH]2)CC1] | 0.0374 | analogous to Example 8 | HPLC-MS: method B Rt = 2.44 min |
| 193 | 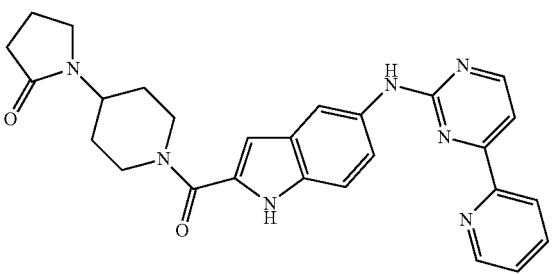 [SMILES: O=C(c1cc2cc(Nc3nccc(-c4ccccn4)n3)ccc2[nH]1)N1CCC(N2CCCC2=O)CC1] | 0.0109 | analogous to Example 8 | HPLC-MS: method B Rt = 2.34 min |

TABLE 1-continued

| Example No. | Structure | SYK Enzyme IC50 [µM] | Method of preparation | Analytical data |
|---|---|---|---|---|
| 194 | 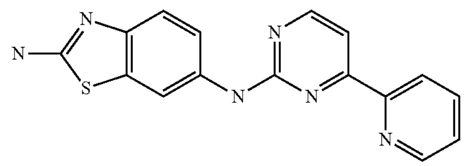 [SMILES: Nc1nc2ccc(Nc3nccc(-c4ccccn4)n3)cc2s1] | 0.0923 | analogous to Example 287 | HPLC-MS: method J Rt = 1.31 min |
| 195 | 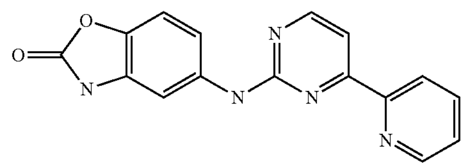 [SMILES: O=c1[nH]c2cc(Nc3nccc(-c4ccccn4)n3)ccc2o1] | 0.0367 | analogous to Example 287 | HPLC-MS: method J Rt = 1.49 min |
| 196 | 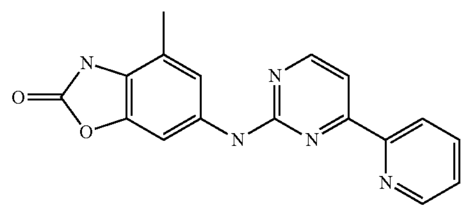 | 0.0170 | analogous to Example 287 | HPLC-MS: method J Rt = 1.53 min |
| 197 | 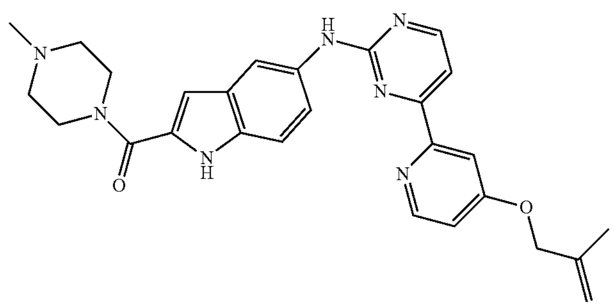 [SMILES: C=C(C)COc1ccnc(-c2ccnc(Nc3ccc4[nH]c(C(=O)N5CCN(C)CC5)cc4c3)n2)c1] | 0.0303 | analogous to Example 92 | HPLC-MS: method J Rt = 1.40 min |
| 198 | 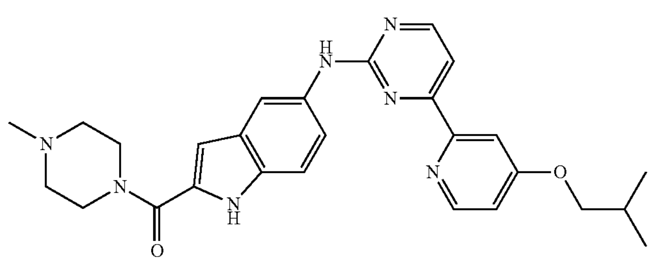 [SMILES: CC(C)COc1ccnc(-c2ccnc(Nc3ccc4[nH]c(C(=O)N5CCN(C)CC5)cc4c3)n2)c1] | 0.0100 | analogous to Example 92 | HPLC-MS: method J Rt = 1.43 min |
| 199 | 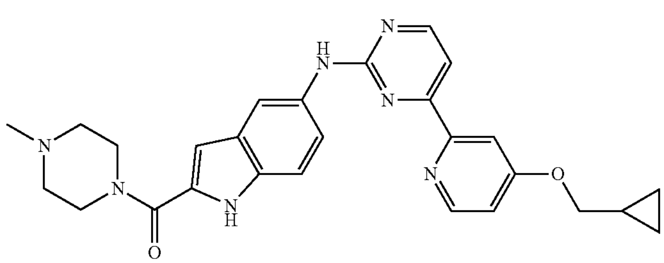 [SMILES: CN1CCN(C(=O)c2cc3cc(Nc4nccc(-c5cc(OCC6CC6)ccn5)n4)ccc3[nH]2)CC1] | 0.0146 | analogous to Example 92 | HPLC-MS: method J Rt = 1.38 min |

TABLE 1-continued
| Example No. | Structure | SYK Enzyme IC50 [μM] | Method of preparation | Analytical data |
|---|---|---|---|---|
| 200 | 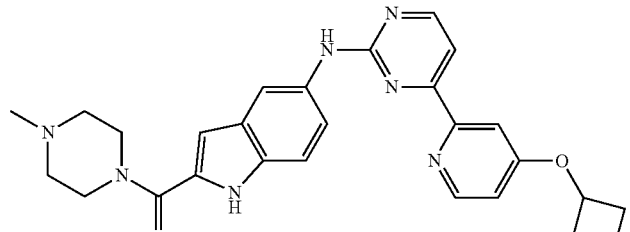 | 0.0252 | analogous to Example 92 | HPLC-MS: method J Rt = 1.38 min |
| 201 | 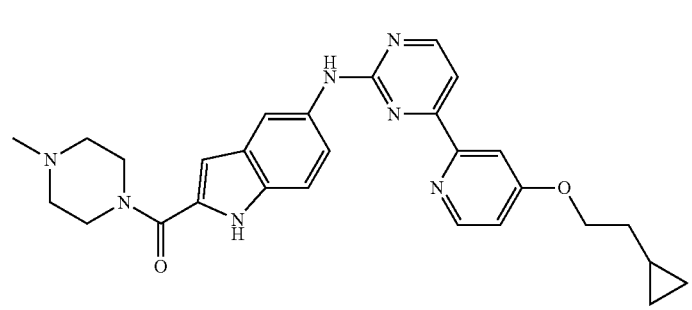 [SMILES: CN1CCN(C(=O)c2cc3cc(Nc4nccc(-c5cc(OCCC6CC6)ccn5)n4)ccc3[nH]2)CC1] | 0.0256 | analogous to Example 92 | HPLC-MS: method J Rt = 1.44 min |
| 202 | 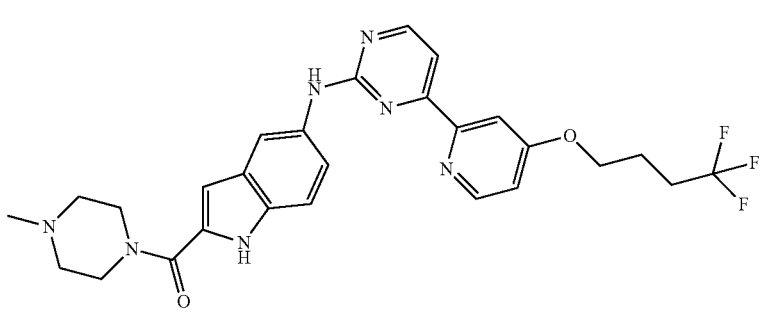 [SMILES: CN1CCN(C(=O)c2cc3cc(Nc4nccc(-c5cc(OCCCC(F)(F)F)ccn5)n4)ccc3[nH]2)CC1] | 0.0506 | analogous to Example 92 | HPLC-MS: method J Rt = 1.46 min |
| 203 | 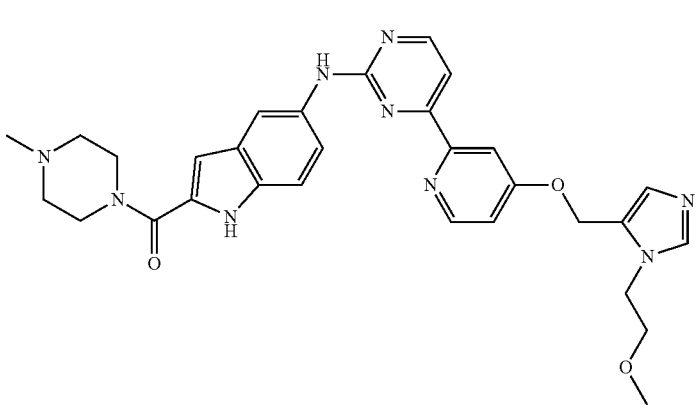 [SMILES: COCCn1cncc1COc1ccnc(-c2ccnc(Nc3ccc4[nH]c(C(=O)N5CCN(C)CC5)cc4c3)n2)c1] | 0.1002 | analogous to Example 92 | HPLC-MS: method J Rt = 1.18 min |
| 204 | 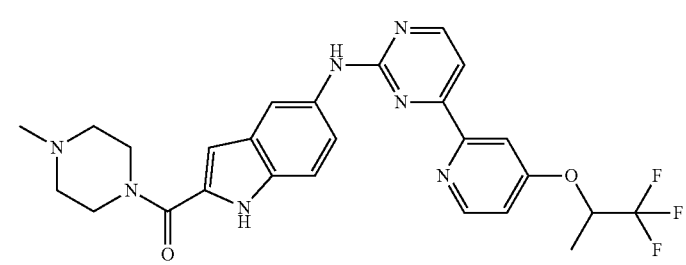 | 0.0033 | analogous to Example 92 | HPLC-MS: method J Rt = 1.47 min |

| Example No. | Structure | SYK Enzyme IC50 [μM] | Method of preparation | Analytical data |
|---|---|---|---|---|
| 205 | 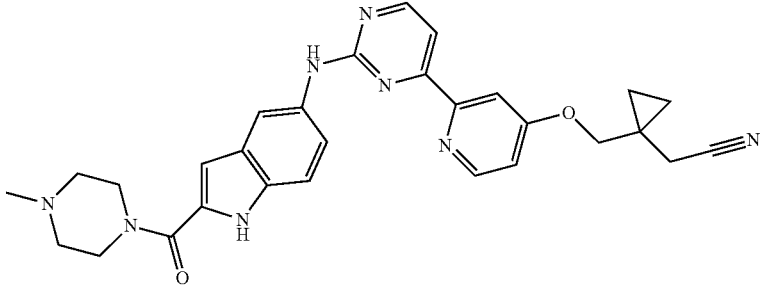 [SMILES: CN1CCN(C(=O)c2cc3cc(Nc4nccc(-c5cc(OCC6(CC#N)CC6)ccn5)n4)ccc3[nH]2)CC1] | 0.0101 | analogous to Example 92 | HPLC-MS: method J Rt = 1.35 min |
| 206 | 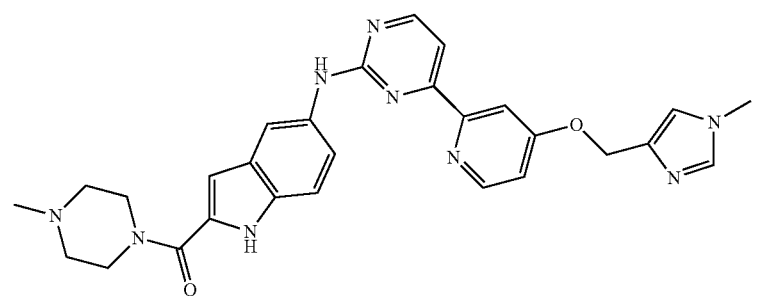 | 0.2938 | analogous to Example 92 | HPLC-MS: method J Rt = 1.13 min |
| 207 | 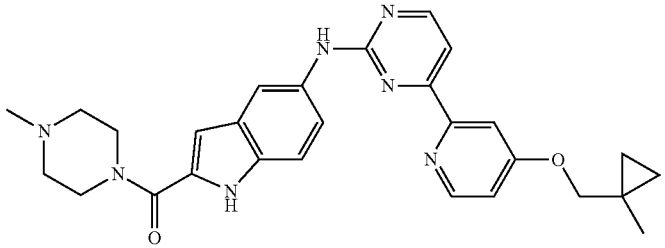 [SMILES: CN1CCN(C(=O)c2cc3cc(Nc4nccc(-c5cc(OCC6(C)CC6)ccn5)n4)ccc3[nH]2)CC1] | 0.0043 | analogous to Example 92 | HPLC-MS: method J Rt = 1.45 min |
| 208 | 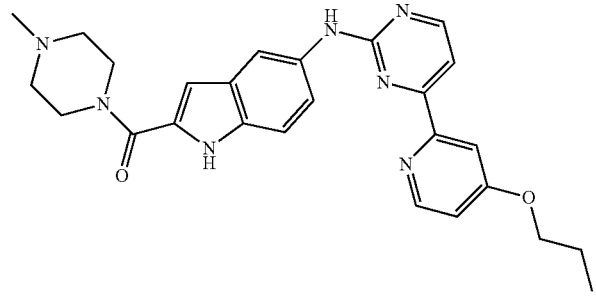 [SMILES: CCCOc1ccnc(-c2ccnc(Nc3ccc4[nH]c(C(=O)N5CCN(C)CC5)cc4c3)n2)c1] | 0.0229 | analogous to Example 92 | HPLC-MS: method J Rt = 1.37 min |
| 209 | 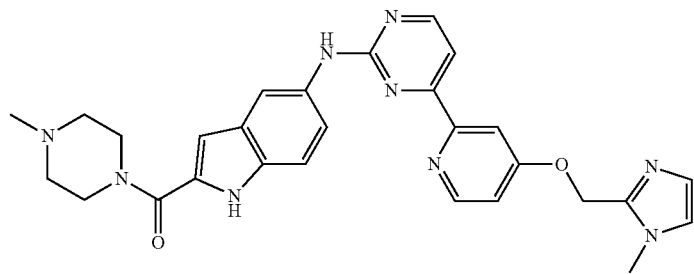 [SMILES: CN1CCN(C(=O)c2cc3cc(Nc4nccc(-c5cc(OCc6nccn6C)ccn5)n4)ccc3[nH]2)CC1] | 0.0573 | analogous to Example 92 | HPLC-MS: method J Rt = 1.14 min |

TABLE 1-continued
| Example No. | Structure | SYK Enzyme IC50 [μM] | Method of preparation | Analytical data |
|---|---|---|---|---|
| 210 | 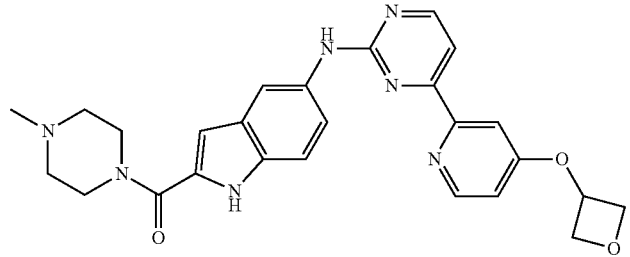 [SMILES: CN1CCN(C(=O)c2cc3cc(Nc4nccc(-c5cc(OC6COC6)ccn5)n4)ccc3[nH]2)CC1] | 0.0365 | analogous to Example 92 | HPLC-MS: method J Rt = 1.26 min |
| 211 | 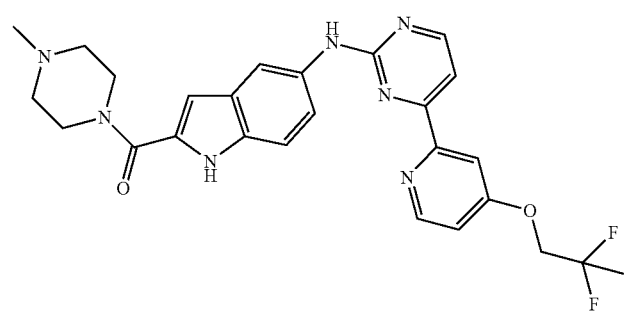 [SMILES: CN1CCN(C(=O)c2cc3cc(Nc4nccc(-c5cc(OCC(C)(F)F)ccn5)n4)ccc3[nH]2)CC1] | 0.0038 | analogous to Example 92 | HPLC-MS: method J Rt = 1.39 min |
| 212 | 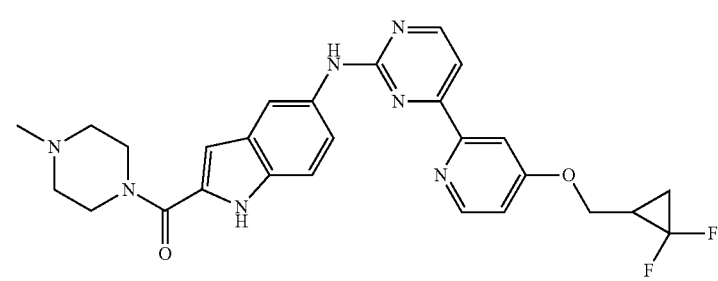 [SMILES: CN1CCN(C(=O)c2cc3cc(Nc4nccc(-c5cc(OCC6CC6(F)F)ccn5)n4)ccc3[nH]2)CC1] | 0.0015 | analogous to Example 92 | HPLC-MS: method J Rt = 1.40 min |
| 213 | 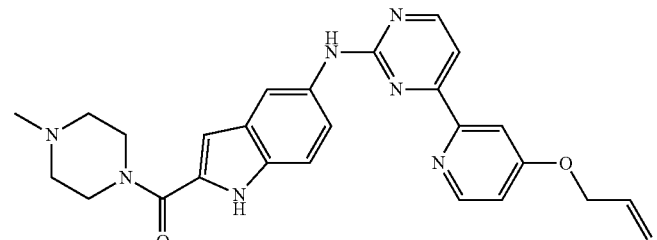 | 0.0132 | analogous to Example 92 | HPLC-MS: method J Rt = 1.34 min |
| 214 | 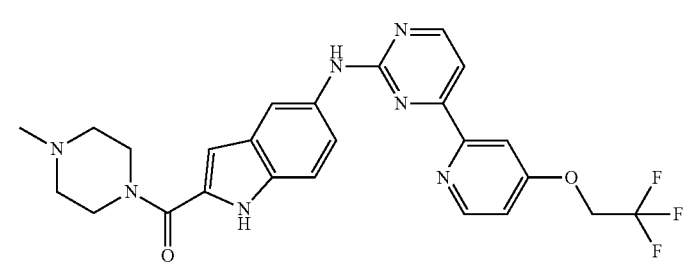 [SMILES: CN1CCN(C(=O)c2cc3cc(Nc4nccc(-c5cc(OCC(F)(F)F)ccn5)n4)ccc3[nH]2)CC1] | 0.0098 | analogous to Example 92 | HPLC-MS: method J Rt = 1.42 min |

TABLE 1-continued

| Example No. | Structure | SYK Enzyme IC50 [μM] | Method of preparation | Analytical data |
|---|---|---|---|---|
| 215 | 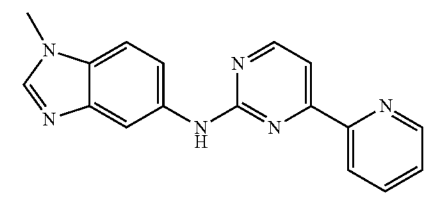 [SMILES: Cn1cnc2cc(Nc3nccc(-c4ccccn4)n3)ccc21] | 0.1373 | see description 4.2.1 | HPLC-MS: method D Rt = 1.64 min |
| 216 | 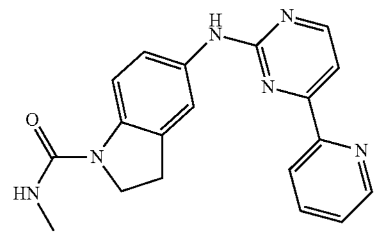 | 0.1115 | analogous to Example 287 | HPLC-MS: method B Rt = 2.32 min |
| 217 | 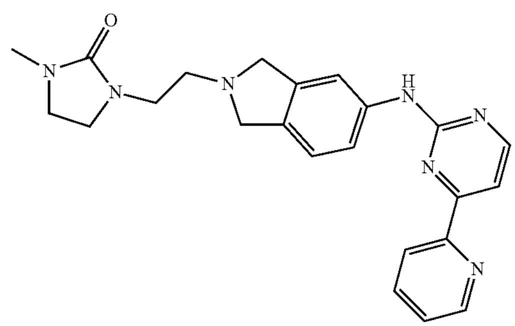 | 0.3842 | analogous to Example 215 | HPLC-MS: method B Rt = 2.46 min |
| 218 | 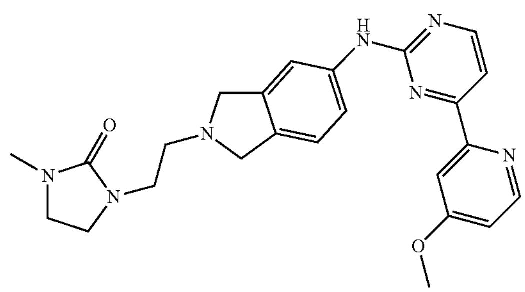 [SMILES: COc1ccnc(-c2ccnc(Nc3ccc4c(c3)CN(CCN3CCN(C)C3=O)C4)n2)c1] | 0.9416 | analogous to Example 92 | HPLC-MS: method B Rt = 1.89 min |
| 219 | 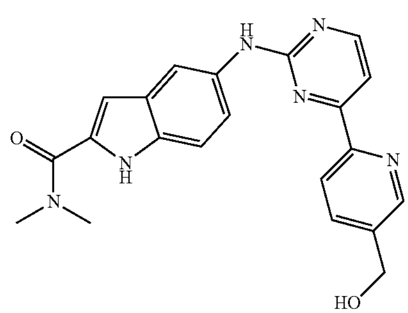 | 0.1431 | analogous to Example 215 | HPLC-MS: method C Rt = 1.74 min |

TABLE 1-continued
| Example No. | Structure | SYK Enzyme IC50 [μM] | Method of preparation | Analytical data |
|---|---|---|---|---|
| 220 | 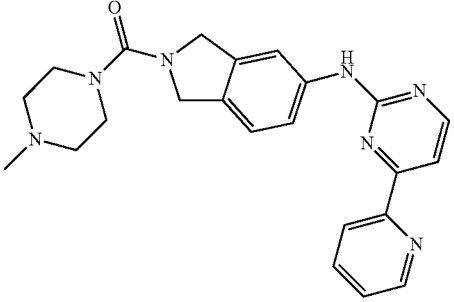 | 0.1145 | analogous to Example 215 | HPLC-MS: method A Rt = 1.94 min |
| 221 | 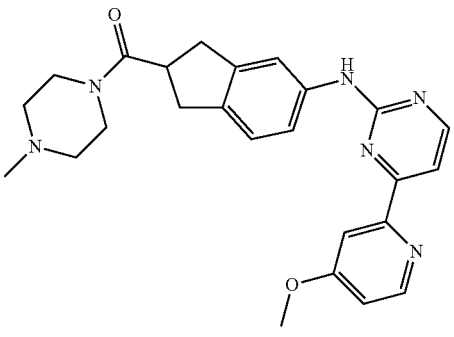 [SMILES: COc1ccnc(-c2ccnc(Nc3ccc4c(c3)CC(C(=O)N3CCN(C)CC3)C4)n2)c1] | 0.0950 | analogous to Example 92 | HPLC-MS: method B Rt = 2.48 min |
| 222 | 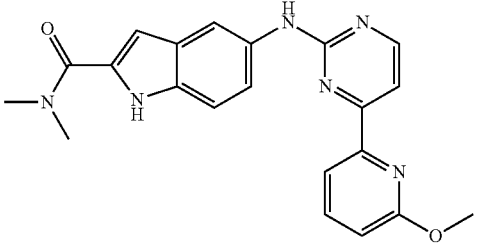 | 0.5148 | analogous to Example 215 | HPLC-MS: method D Rt = 1.74 min |
| 223 | 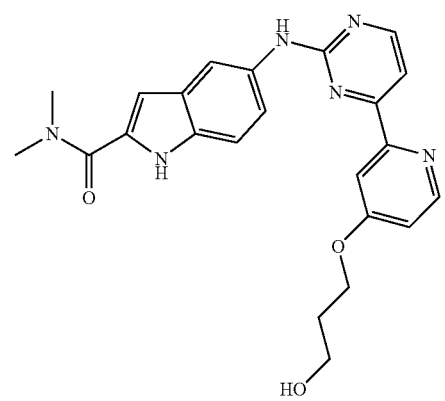 [SMILES: CN(C)C(=O)c1cc2cc(Nc3nccc(-c4cc(OCCCO)ccn4)n3)ccc2[nH]1] | 0.0618 | analogous to Example 92 | HPLC-MS: method D Rt = 1.67 min |

TABLE 1-continued

| Example No. | Structure | SYK Enzyme IC50 [μM] | Method of preparation | Analytical data |
|---|---|---|---|---|
| 224 | 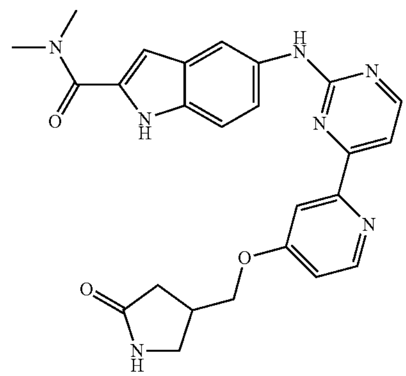 [SMILES: CN(C)C(=O)c1cc2cc(Nc3nccc(-c4cc(OCC5CNC(=O)C5)ccn4)n3)ccc2[nH]1] | 0.0331 | analogous to Example 92 | HPLC-MS: method B Rt = 2.27 min |
| 225 | Chiral | 0.1394 | analogous to Example 92 | HPLC-MS: method D Rt = 1.69 min |
| 226 | Chiral | 0.0037 | analogous to Example 92 | HPLC-MS: method D Rt = 1.64 min |
| 227 | 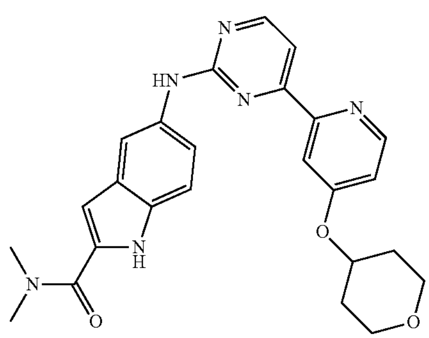 [SMILES: CN(C)C(=O)c1cc2cc(Nc3nccc(-c4cc(OC5CCOCC5)ccn4)n3)ccc2[nH]1] | 0.0404 | analogous to Example 92 | HPLC-MS: method M Rt = 1.89 min |

TABLE 1-continued
| Example No. | Structure | SYK Enzyme IC50 [μM] | Method of preparation | Analytical data |
|---|---|---|---|---|
| 228 | 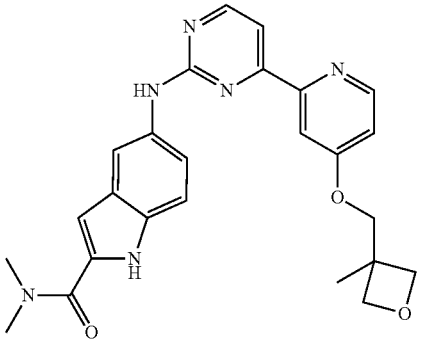 [SMILES: CN(C)C(=O)c1cc2cc(Nc3nccc(-c4cc(OCC5(C)COC5)ccn4)n3)ccc2[nH]1] | 0.0402 | analogous to Example 92 | HPLC-MS: method M Rt = 1.85 min |
| 229 | 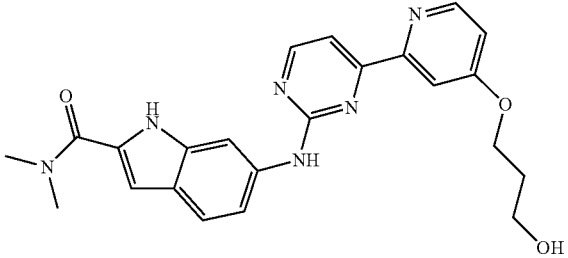 [SMILES: CN(C)C(=O)c1cc2ccc(Nc3nccc(-c4cc(OCCCO)ccn4)n3)cc2[nH]1] | 0.0410 | analogous to Example 92 | HPLC-MS: method M Rt = 1.90 min |
| 230 | 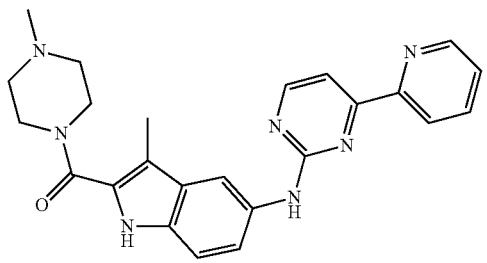 [SMILES: Cc1c(C(=O)N2CCN(C)CC2)[nH]c2ccc(Nc3nccc(-c4ccccn4)n3)cc12] | 0.0817 | see description 4.2.2 | HPLC-MS: method H Rt = 2.72 min |
| 231 | 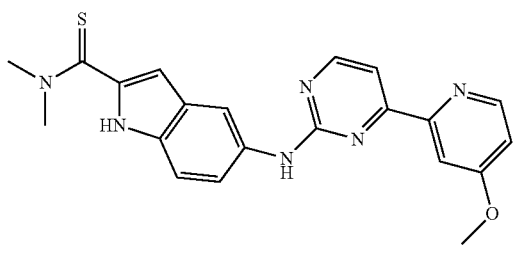 [SMILES: COc1ccnc(-c2ccnc(Nc3ccc4[nH]c(C(=S)N(C)C)cc4c3)n2)c1] | 0.2954 | see description 4.2.8 | HPLC-MS: method E Rt = 3.47 min |
| 232 | 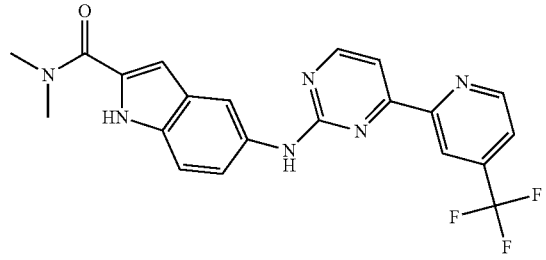 [SMILES: CN(C)C(=O)c1cc2cc(Nc3nccc(-c4cc(C(F)(F)F)ccn4)n3)ccc2[nH]1] | 0.1733 | analogous to Example 7 | HPLC-MS: method E Rt = 4.33 min |

TABLE 1-continued

| Example No. | Structure | SYK Enzyme IC50 [μM] | Method of preparation | Analytical data |
|---|---|---|---|---|
| 233 | 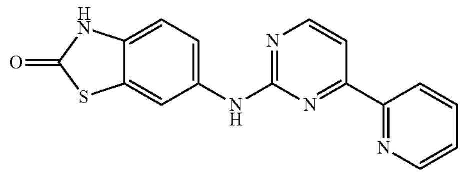 [SMILES: O=c1[nH]c2ccc(Nc3nccc(-c4ccccn4)n3)cc2s1] | 0.1826 | analogous to Example 287 | HPLC-MS: method J Rt = 1.61 min |
| 234 | 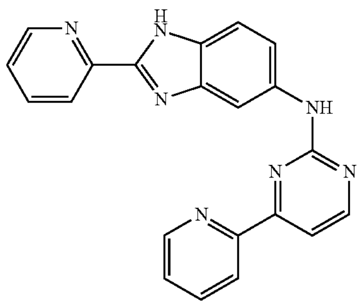 [SMILES: c1ccc(-c2ccnc(Nc3ccc4[nH]c(-c5ccccn5)nc4c3)n2)nc1] | 0.0630 | analogous to Example 287 | HPLC-MS: method J Rt = 1.45 min |
| 235 | 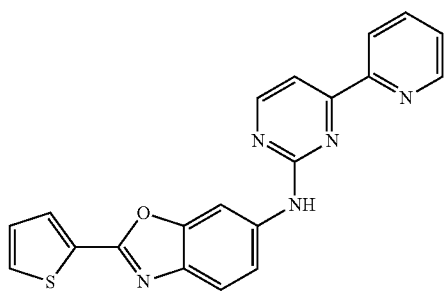 [SMILES: c1ccc(-c2ccnc(Nc3ccc4nc(-c5cccs5)oc4c3)n2)nc1] | 0.9219 | analogous to Example 287 | HPLC-MS: method J Rt = 2.10 min |
| 236 | 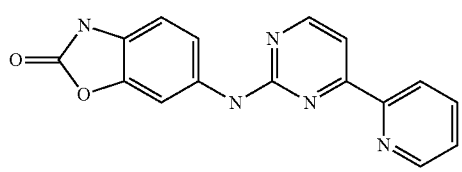 [SMILES: O=c1[nH]c2ccc(Nc3nccc(-c4ccccn4)n3)cc2o1] | 0.2902 | analogous to Example 287 | HPLC-MS: method J Rt = 1.51 min |
| 237 | 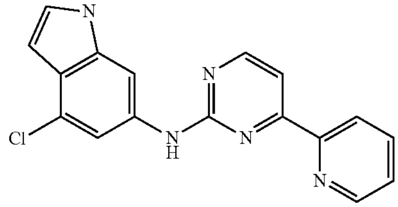 [SMILES: Clc1cc(Nc2nccc(-c3ccccn3)n2)cc2[nH]ccc12] | 0.0540 | analogous to Example 287 | HPLC-MS: method J Rt = 1.92 min |
| 238 | 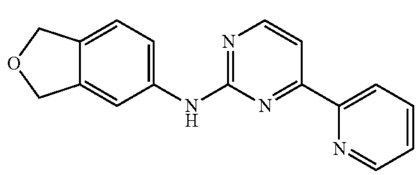 [SMILES: c1ccc(-c2ccnc(Nc3ccc4c(c3)COC4)n2)nc1] | 0.2582 | analogous to Example 287 | HPLC-MS: method J Rt = 1.67 min |

TABLE 1-continued

| Example No. | Structure | SYK Enzyme IC50 [µM] | Method of preparation | Analytical data |
|---|---|---|---|---|
| 239 | 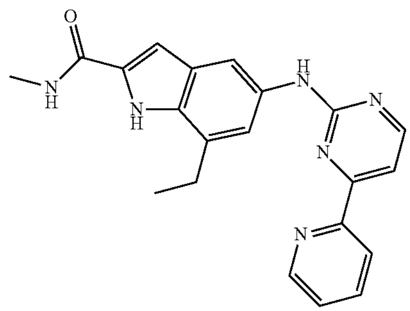 [SMILES: CCc1cc(Nc2nccc(-c3ccccn3)n2)cc2cc(C(=O)NC)[nH]c12] | 0.030 | see description 4.2.6 | HPLC-MS: method Rt = min |
| 240 | 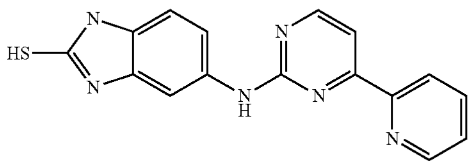 [SMILES: Sc1nc2cc(Nc3nccc(-c4ccccn4)n3)ccc2[nH]1] | 0.0449 | analogous to Example 287 | HPLC-MS: method J Rt = 1.54 min |
| 241 | 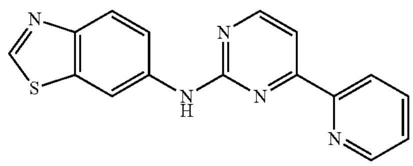 [SMILES: c1ccc(-c2ccnc(Nc3ccc4ncsc4c3)n2)nc1] | 0.1028 | analogous to Example 287 | HPLC-MS: method J Rt = 1.73 min |
| 242 | 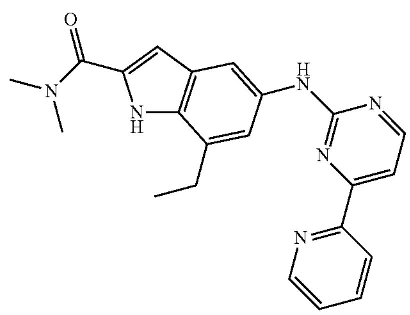 | 0.019 | analogous to Example 239 | HPLC-MS: method Rt = min |
| 243 | 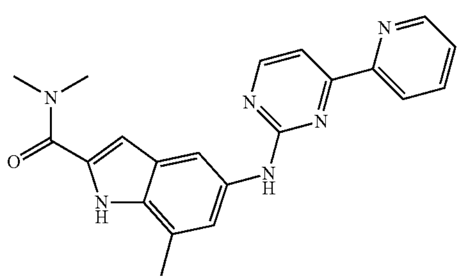 [SMILES: Cc1cc(Nc2nccc(-c3ccccn3)n2)cc2cc(C(=O)N(C)C)[nH]c12] | 0.0060 | analogous to Example 8 | HPLC-MS: method M Rt = 2.16 min |
| 244 | 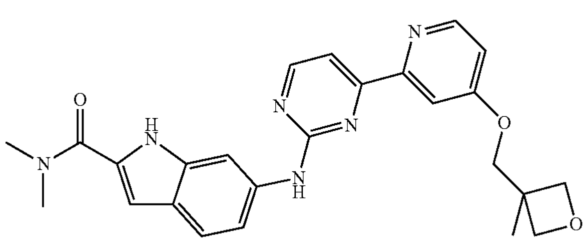 [SMILES: CN(C)C(=O)c1cc2ccc(Nc3nccc(-c4cc(OCC5(C)COC5)ccn4)n3)cc2[nH]1] | 0.0978 | analogous to Example 92 | HPLC-MS: method M Rt = 2.00 min |

TABLE 1-continued

| Example No. | Structure | SYK Enzyme IC50 [μM] | Method of preparation | Analytical data |
|---|---|---|---|---|
| 245 | 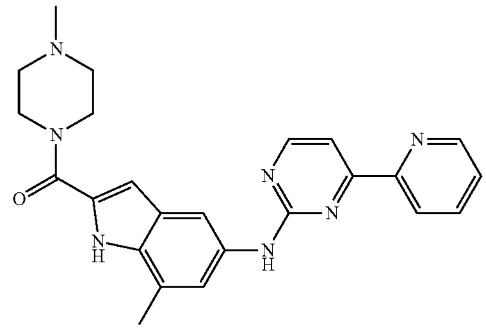 [SMILES: Cc1cc(Nc2nccc(-c3ccccn3)n2)cc2cc(C(=O)N3CCN(C)CC3)[nH]c12] | 0.0087 | analogous to Example 8 | HPLC-MS: method M Rt = 1.74 min |
| 246 | 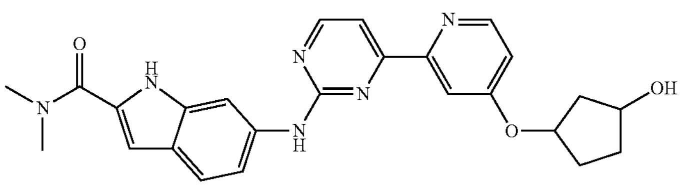 [SMILES: CN(C)C(=O)c1cc2ccc(Nc3nccc(-c4cc(OC5CCC(O)C5)ccn4)n3)cc2[nH]1] | 0.0106 | analogous to Example 92 | HPLC-MS: method C Rt = 1.73 min |
| 247 | 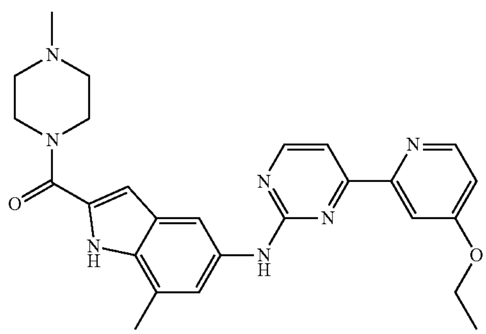 [SMILES: CCOc1ccnc(-c2ccnc(Nc3cc(C)c4[nH]c(C(=O)N5CCN(C)CC5)cc4c3)n2)c1] | 0.0061 | analogous to Example 8 | HPLC-MS: method M Rt = 1.83 min |
| 248 | 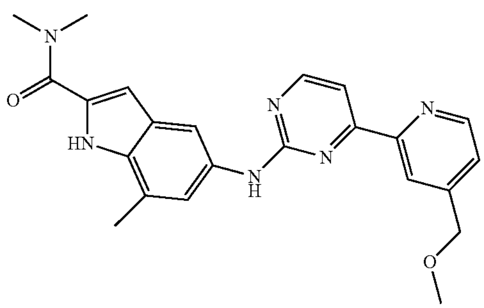 [SMILES: COCc1ccnc(-c2ccnc(Nc3cc(C)c4[nH]c(C(=O)N(C)C)cc4c3)n2)c1] | 0.0168 | analogous to Example 8 | HPLC-MS: method M Rt = 2.23 min |
| 249 | 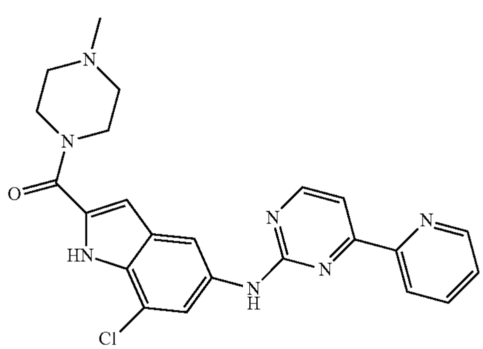 [SMILES: CN1CCN(C(=O)c2cc3cc(Nc4nccc(-c5ccccn5)n4)cc(Cl)c3[nH]2)CC1] | 0.0047 | analogous to Example 8 | HPLC-MS: method C Rt = 1.68 min |

TABLE 1-continued

| Example No. | Structure | SYK Enzyme IC50 [μM] | Method of preparation | Analytical data |
|---|---|---|---|---|
| 250 | 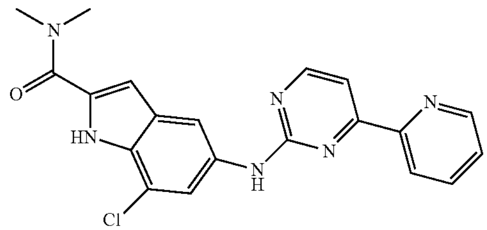 [SMILES: CN(C)C(=O)c1cc2cc(Nc3nccc(-c4ccccn4)n3)cc(Cl)c2[nH]1] | 0.0010 | analogous to Example 8 | HPLC-MS: method C Rt = 2.06 min |
| 251 | 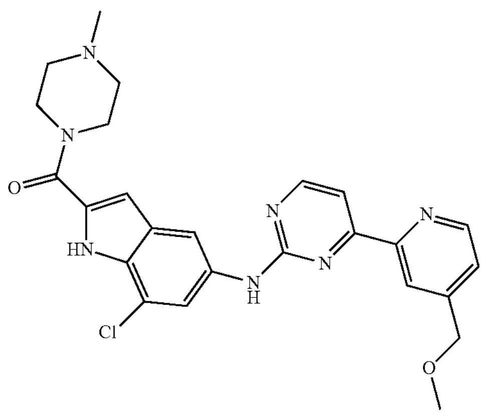 [SMILES: COCc1ccnc(-c2ccnc(Nc3cc(Cl)c4[nH]c(C(=O)N5CCN(C)CC5)cc4c3)n2)c1] | 0.0022 | analogous to Example 8 | HPLC-MS: method D Rt = 1.79 min |
| 252 | 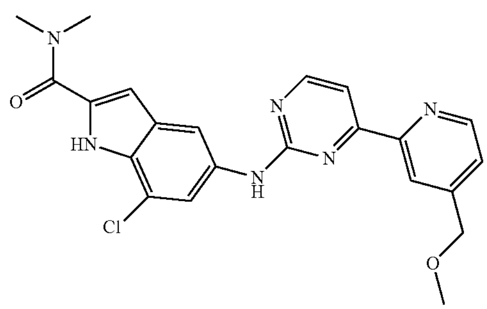 [SMILES: COCc1ccnc(-c2ccnc(Nc3cc(Cl)c4[nH]c(C(=O)N(C)C)cc4c3)n2)c1] | 0.0195 | analogous to Example 8 | HPLC-MS: method D Rt = 2.12 min |
| 253 | 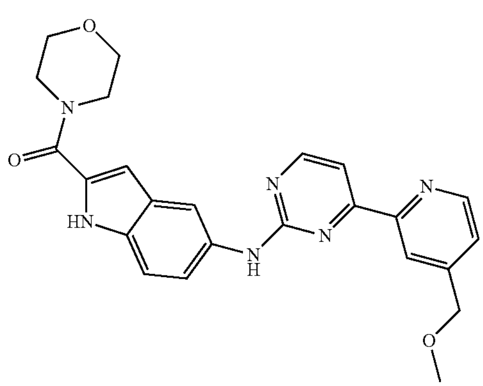 [SMILES: COCc1ccnc(-c2ccnc(Nc3ccc4[nH]c(C(=O)N5CCOCC5)cc4c3)n2)c1] | 0.0449 | analogous to Example 8 | HPLC-MS: method D Rt = 1.94 min |

TABLE 1-continued

| Example No. | Structure | SYK Enzyme IC50 [μM] | Method of preparation | Analytical data |
|---|---|---|---|---|
| 254 | 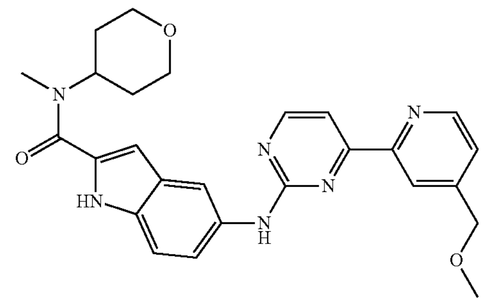 [SMILES: COCc1ccnc(-c2ccnc(Nc3ccc4[nH]c(C(=O)N(C)C5CCOCC5)cc4c3)n2)c1] | 0.0166 | analogous to Example 8 | HPLC-MS: method D Rt = 1.99 min |
| 255 | 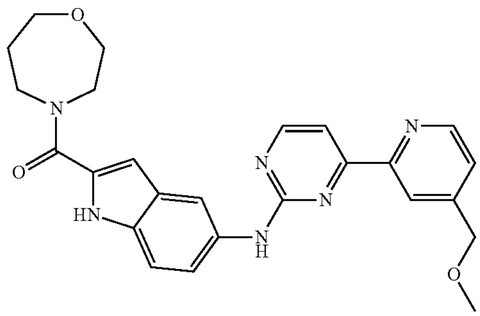 [SMILES: COCc1ccnc(-c2ccnc(Nc3ccc4[nH]c(C(=O)N5CCCOCC5)cc4c3)n2)c1] | 0.0116 | analogous to Example 8 | HPLC-MS: method D Rt = 1.94 min |
| 256 | 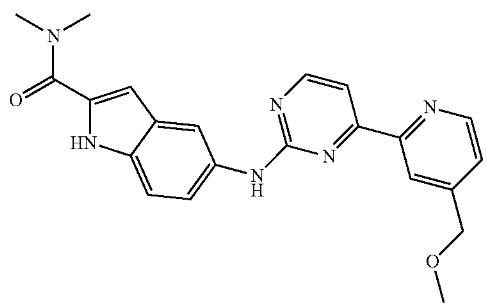 [SMILES: COCc1ccnc(-c2ccnc(Nc3ccc4[nH]c(C(=O)N(C)C)cc4c3)n2)c1] | 0.0323 | analogous to Example 8 | HPLC-MS: method D Rt = 1.93 min |
| 257 | 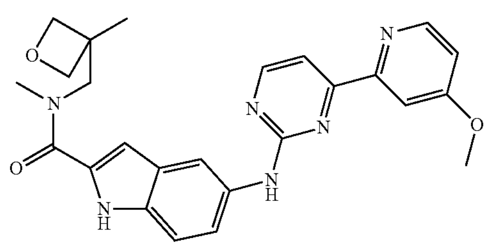 [SMILES: COc1ccnc(-c2ccnc(Nc3ccc4[nH]c(C(=O)N(C)CC5(C)COC5)cc4c3)n2)c1] | 0.0180 | analogous to Example 8 | HPLC-MS: method B Rt = 2.41 min |
| 258 | 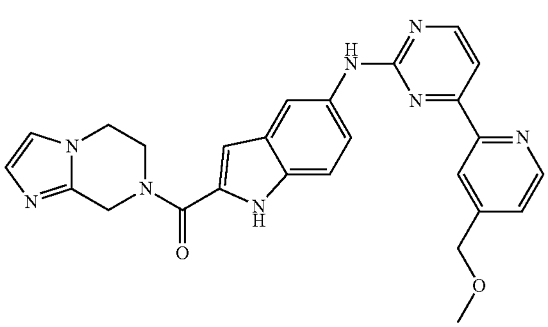 [SMILES: COCc1ccnc(-c2ccnc(Nc3ccc4[nH]c(C(=O)N5CCn6ccnc6C5)cc4c3)n2)c1] | 0.0290 | analogous to Example 8 | HPLC-MS: method D Rt = 1.61 min |

TABLE 1-continued

| Example No. | Structure | SYK Enzyme IC50 [µM] | Method of preparation | Analytical data |
|---|---|---|---|---|
| 259 | 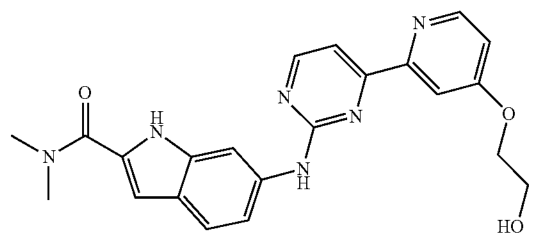 [SMILES: CN(C)C(=O)c1cc2ccc(Nc3nccc(-c4cc(OCCO)ccn4)n3)cc2[nH]1] | 0.0109 | analogous to Example 92 | HPLC-MS: method D Rt = 1.68 min |
| 260 | 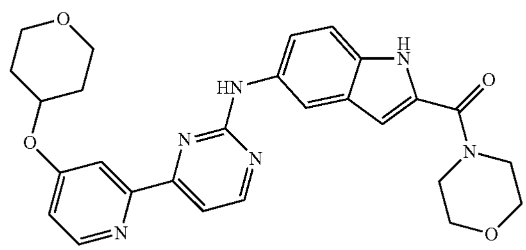 [SMILES: O=C(c1cc2cc(Nc3nccc(-c4cc(OC5CCOCC5)ccn4)n3)ccc2[nH]1)N1CCOCC1] | 0.0319 | analogous to Example 92 | HPLC-MS: method A Rt = 1.47 min |
| 261 | 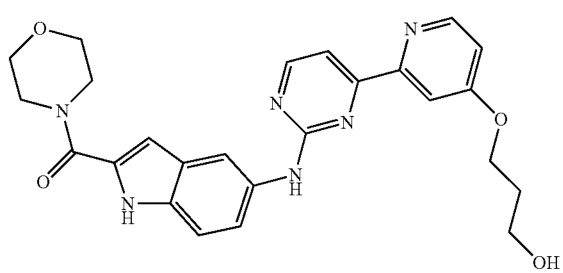 [SMILES: O=C(c1cc2cc(Nc3nccc(-c4cc(OCCCO)ccn4)n3)ccc2[nH]1)N1CCOCC1] | 0.0168 | analogous to Example 92 | HPLC-MS: method M Rt = 1.54 min |
| 262 | 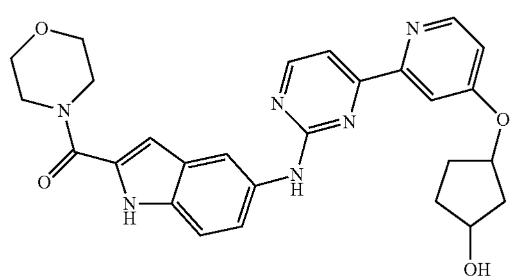 [SMILES: O=C(c1cc2cc(Nc3nccc(-c4cc(OC5CCC(O)C5)ccn4)n3)ccc2[nH]1)N1CCOCC1] | 0.0306 | analogous to Example 92 | HPLC-MS: method M Rt = 1.61 min |
| 263 | 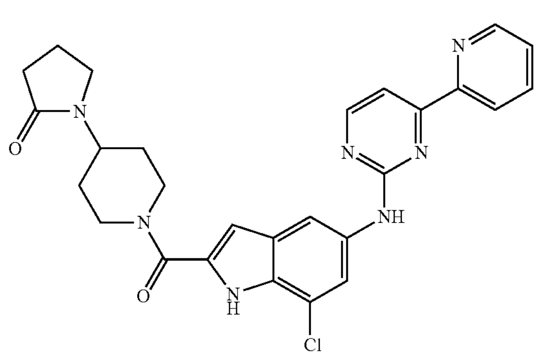 [SMILES: O=C(c1cc2cc(Nc3nccc(-c4ccccn4)n3)cc(Cl)c2[nH]1)N1CCC(N2CCCC2=O)CC1] | 0.0014 | analogous to Example 8 | HPLC-MS: method A Rt = 1.76 min |

TABLE 1-continued

| Example No. | Structure | SYK Enzyme IC50 [μM] | Method of preparation | Analytical data |
|---|---|---|---|---|
| 264 | 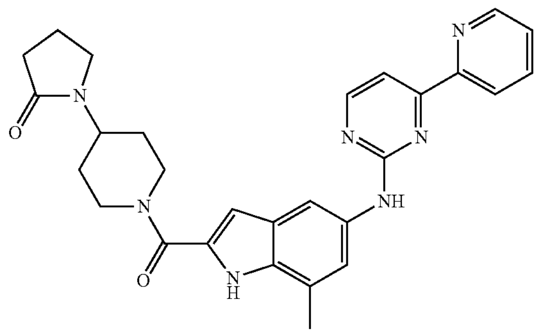 [SMILES: Cc1cc(Nc2nccc(-c3ccccn3)n2)cc2cc(C(=O)N3CCC(N4CCCC4=O)CC3)[nH]c12] | 0.0123 | analogous to Example 8 | HPLC-MS: method M Rt = 1.74 min |
| 265 | 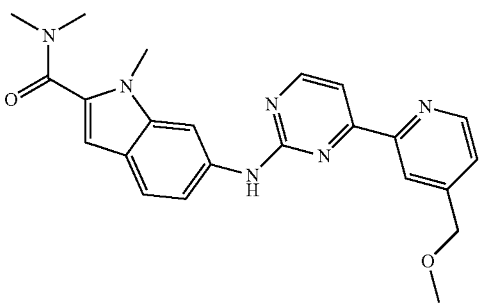 [SMILES: COCc1ccnc(-c2ccnc(Nc3ccc4cc(C(=O)N(C)C)n(C)c4c3)n2)c1] | 0.0351 | analogous to Example 8 | HPLC-MS: method M Rt = 2.10 min |
| 266 | 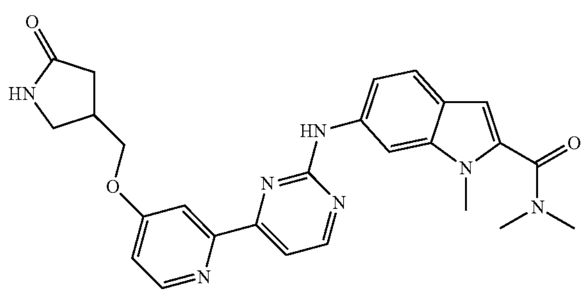 [SMILES: CN(C)C(=O)c1cc2ccc(Nc3nccc(-c4cc(OCC5CNC(=O)C5)ccn4)n3)cc2n1C] | 0.0155 | analogous to Example 92 | HPLC-MS: method M Rt = 1.69 min |
| 267 | 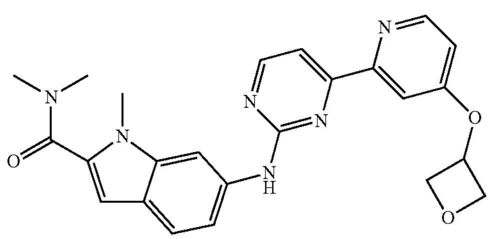 [SMILES: CN(C)C(=O)c1cc2ccc(Nc3nccc(-c4cc(OC5COC5)ccn4)n3)cc2n1C] | 0.0328 | analogous to Example 92 | HPLC-MS: method M Rt = 1.91 min |
| 268 | Chiral | 0.0021 | analogous to Example 92 | HPLC-MS: method M Rt = 1.71 min |

TABLE 1-continued

| Example No. | Structure | SYK Enzyme IC50 [μM] | Method of preparation | Analytical data |
|---|---|---|---|---|
| 269 | 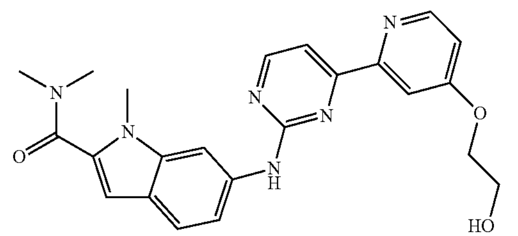 [SMILES: CN(C)C(=O)c1cc2ccc(Nc3nccc(-c4cc(OCCO)ccn4)n3)cc2n1C] | 0.0169 | analogous to Example 92 | HPLC-MS: method M Rt = 1.75 min |
| 270 | 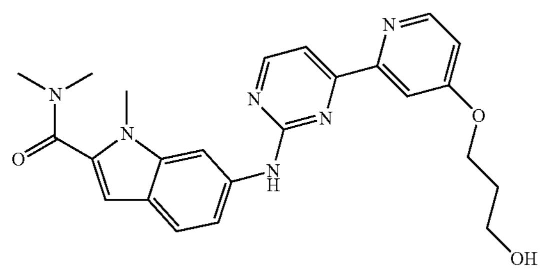 [SMILES: CN(C)C(=O)c1cc2ccc(Nc3nccc(-c4cc(OCCCO)ccn4)n3)cc2n1C] | 0.0109 | analogous to Example 92 | HPLC-MS: method M Rt = 1.71 min |
| 271 | 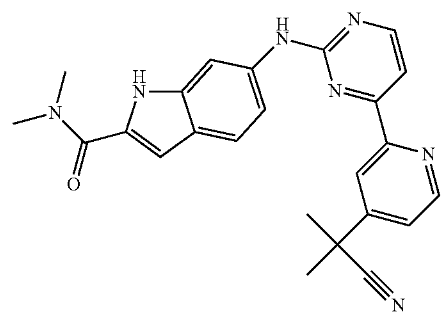 [SMILES: CN(C)C(=O)c1cc2ccc(Nc3nccc(-c4cc(C(C)(C)C#N)ccn4)n3)cc2[nH]1] | 0.0061 | see description 4.2.3 | HPLC-MS: method A Rt = 1.97 min |
| 272 | 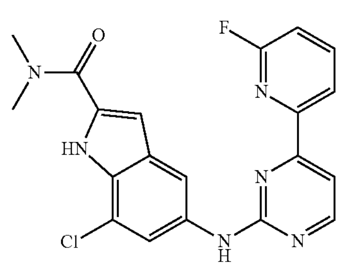 | 0.0174 | analogous to Example 8 | HPLC-MS: method A Rt = 2.21 min |
| 273 | 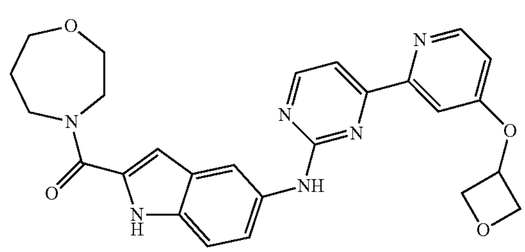 [SMILES: O=C(c1cc2cc(Nc3nccc(-c4cc(OC5COC5)ccn4)n3)ccc2[nH]1)N1CCCOCC1] | 0.0342 | analogous to Example 92 | HPLC-MS: method M Rt = 1.74 min |

TABLE 1-continued

| Example No. | Structure | SYK Enzyme IC50 [μM] | Method of preparation | Analytical data |
|---|---|---|---|---|
| 274 | 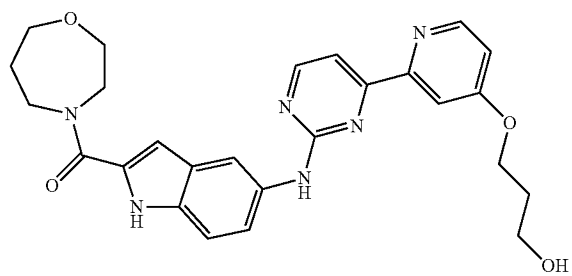 [SMILES: O=C(c1cc2cc(Nc3nccc(-c4cc(OCCCO)ccn4)n3)ccc2[nH]1)N1CCCOCC1] | 0.0127 | analogous to Example 92 | HPLC-MS: method M Rt = 1.68 min |
| 275 | 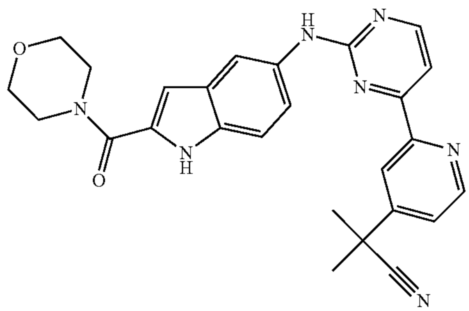 | 0.0045 | analogous to Example 271 | HPLC-MS: method A Rt = 2.01 min |
| 276 | 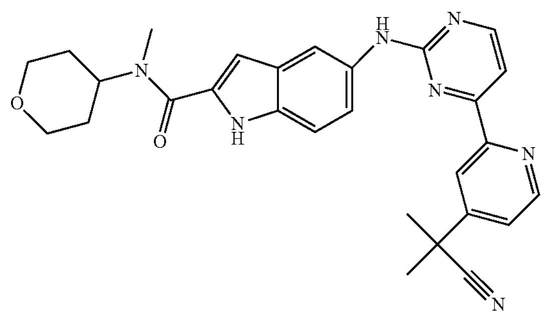 | 0.0057 | analogous to Example 271 | HPLC-MS: method B Rt = 2.48 min |
| 277 | 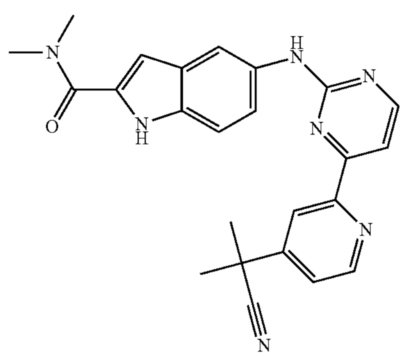 | 0.0059 | analogous to Example 271 | HPLC-MS: method A Rt = 2.02 min |
| 278 | 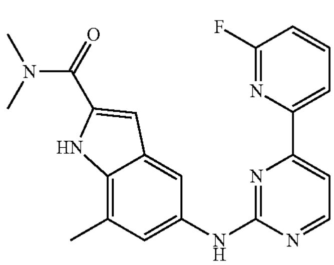 [SMILES: Cc1cc(Nc2nccc(-c3cccc(F)n3)n2)cc2cc(C(=O)N(C)C)[nH]c12] | 0.0186 | analogous to Example 8 | HPLC-MS: method A Rt = 2.10 min |

TABLE 1-continued

| Example No. | Structure | SYK Enzyme IC50 [μM] | Method of preparation | Analytical data |
|---|---|---|---|---|
| 279 | 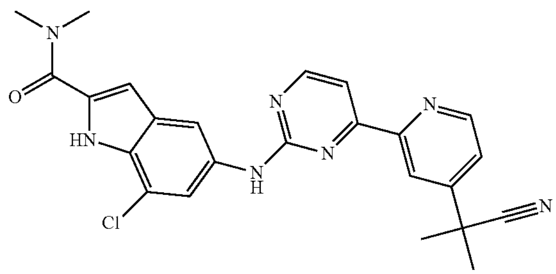 | 0.0224 | analogous to Example 271 | HPLC-MS: method A Rt = 2.19 min |
| 280 | 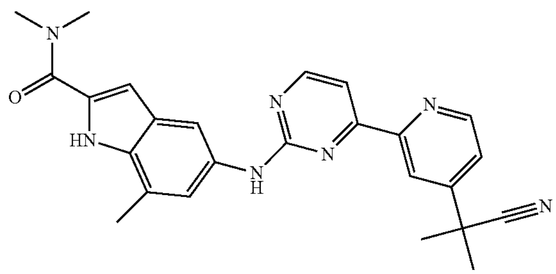 | 0.0189 | analogous to Example 271 | HPLC-MS: method A Rt = 1.88 min |
| 281 | 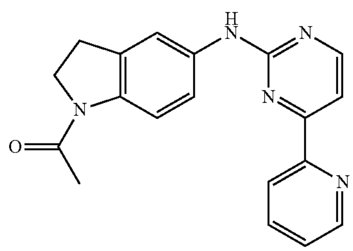 | 0.1584 | analogous to Example 287 | HPLC-MS: method A Rt = 1.60 min |
| 282 | 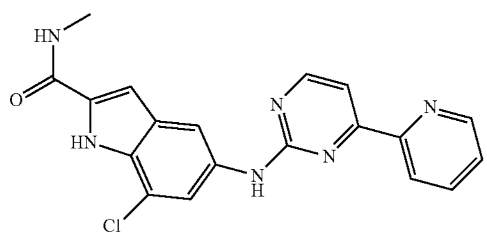 [SMILES: CNC(=O)c1cc2cc(Nc3nccc(-c4ccccn4)n3)cc(Cl)c2[nH]1] | 0.0018 | analogous to Example 8 | HPLC-MS: method A Rt = 1.95 min |
| 283 | 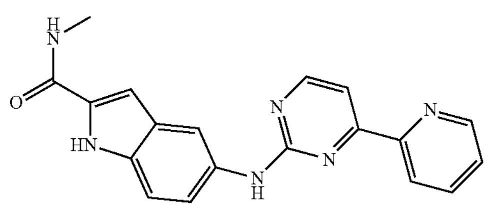 [SMILES: CNC(=O)c1cc2cc(Nc3nccc(-c4ccccn4)n3)ccc2[nH]1] | 0.0434 | analogous to Example 8 | HPLC-MS: method A Rt = 1.59 min |
| 284 | 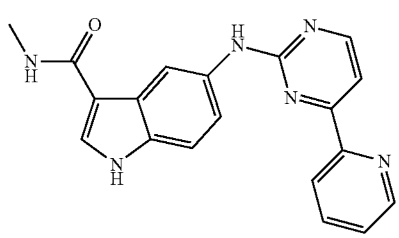 | 0.0177 | analogous to Example 287 | HPLC-MS: method A Rt = 1.22 min |

TABLE 1-continued

| Example No. | Structure | SYK Enzyme IC50 [µM] | Method of preparation | Analytical data |
|---|---|---|---|---|
| 285 | 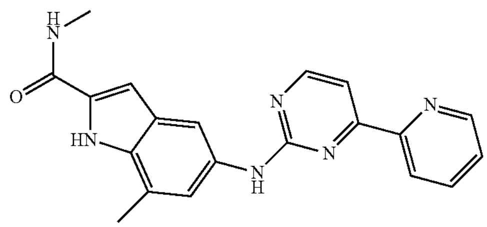 [SMILES: CNC(=O)c1cc2cc(Nc3nccc(-c4ccccn4)n3)cc(C)c2[nH]1] | 0.0027 | analogous to Example 8 | HPLC-MS: method A Rt = 1.53 min |
| 286 | 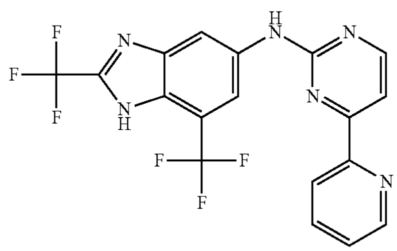 [SMILES: FC(F)(F)c1nc2cc(Nc3nccc(-c4ccccn4)n3)cc(C(F)(F)F)c2[nH]1] | 0.0103 | analogous to Example 287 | HPLC-MS: method A Rt = 2.27 min |
| 287 | 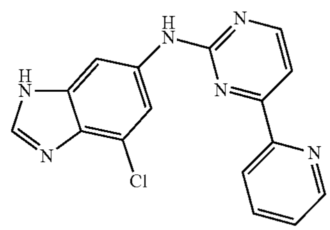 [SMILES: Clc1cc(Nc2nccc(-c3ccccn3)n2)cc2[nH]cnc12] | 0.0012 | see description 4.2.2 | HPLC-MS: method A Rt = 1.56 min |
| 288 | 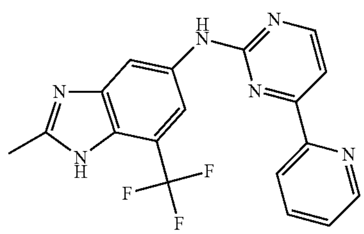 | 0.0024 | analogous to Example 287 | HPLC-MS: method A Rt = 1.64 min |
| 289 | 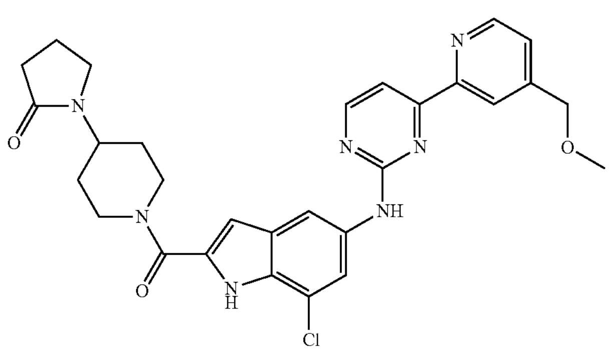 [SMILES: COCc1ccnc(-c2ccnc(Nc3cc(Cl)c4[nH]c(C(=O)N5CCC(N6CCCC6=O)CC5)cc4c3)n2)c1] | 0.0045 | analogous to Example 8 | HPLC-MS: method A Rt = 2.06 min |

TABLE 1-continued

| Example No. | Structure | SYK Enzyme IC50 [µM] | Method of preparation | Analytical data |
|---|---|---|---|---|
| 290 | 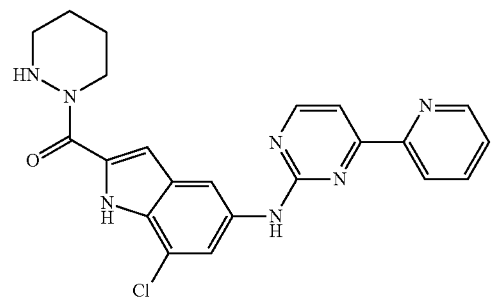 [SMILES: O=C(c1cc2cc(Nc3nccc(-c4ccccn4)n3)cc(Cl)c2[nH]1)N1CCCCN1] | 0.0323 | analogous to Example 8 | HPLC-MS: method A Rt = 2.12 min |
| 291 | 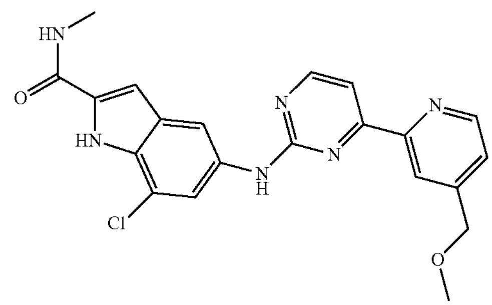 [SMILES: CNC(=O)c1cc2cc(Nc3nccc(-c4cc(COC)ccn4)n3)cc(Cl)c2[nH]1] | 0.0344 | analogous to Example 8 | HPLC-MS: method A Rt = 2.04 min |
| 292 | 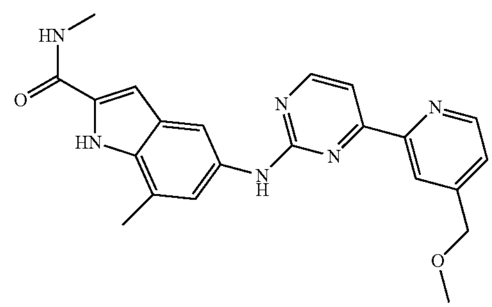 [SMILES: CNC(=O)c1cc2cc(Nc3nccc(-c4cc(COC)ccn4)n3)cc(C)c2[nH]1] | 0.0072 | analogous to Example 8 | HPLC-MS: method A Rt = 1.80 min |

6. INDICATIONS

As has been found, the compounds of formula 1 are characterised by their range of applications in the therapeutic field. Particular mention should be made of those applications for which the compounds of formula 1 according to the invention are preferably used on the basis of their pharmaceutical activity as SYK-inhibitors. Examples include respiratory complaints, allergic diseases, osteoporosis, gastrointestinal diseases or complaints, immune or autoimmune diseases, allergic diseases, inflammatory diseases, e.g. inflammatory diseases of the joints, skin and eyes and diseases of the peripheral or central nervous system.

Particular mention should be made of the prevention and treatment of respiratory tract and pulmonary diseases which are accompanied by increased mucus production, inflammation and/or obstructive diseases of the airways. Examples of these include asthma, paediatric asthma, ARDS (Adult Respiratory Distress Syndrome), acute, allergic or chronic bronchitis, autoimmune haemolytic anemia, chronic obstructive bronchitis (COPD) (including the treatment of Rhinovirus-induced exacerbations), coughs, allergic rhinitis or sinusitis, allergic rhinoconjunctivitis, chronic rhinitis or sinusitis, alveolitis, farmers' lung, hyperreactive airways, infectious bronchitis or pneumonitis, bronchiectasis, pulmonary fibrosis, bronchial oedema, pulmonary oedema, pneumonia or interstitial pneumonia triggered by various causes such as aspiration, inhalation of toxic gases or bronchitis, pneumonia or interstitial pneumonia triggered by cardiac insufficiency, radiation, chemotherapy, cystic fibrosis or mucoviscidosis, alpha1-antitrypsin deficiency.

The compounds according to the invention are preferably also suitable for the treatment of allergic diseases such as for example allergic rhinitis, allergic rhinoconjunctivitis, allergic conjunctivitis, and contact dermatitis, urticaria/angiooedema and allergic dermatitis.

Mention should also preferably be made of the treatment of inflammatory diseases of the gastrointestinal tract. Examples of these are Crohn's disease and ulcerative colitis.

The compounds according to the invention are preferably also suitable for the treatment of inflammatory diseases of the joints or inflammatory diseases of the skin and eyes. Examples of these are rheumatoid arthritis, antibody-based glomerulonephritis, psoriasis, Kawasaki syndrome, coeliac disease (sprue) and Wegener's granulomatosis.

The compounds according to the invention are preferably also suitable for the treatment of autoimmune diseases. Examples of these are hepatitis (autoimmune-based), lupus erythematodes, anti-phospholipid syndrome, Berger's disease, Evans's syndrome, immunohaemolytic anaemia, ITP (idiopathic thrombocytopenic purpura; adult, neonatal and paediatric), myasthenia gravis, Sjögren's syndrome and sclerodermy.

The compounds according to the invention are preferably also suitable for the treatment of B-cell lymphomas, like chronic lymphocytic leukaemia (CLL), diffuse large B-cell lymphoma (DLBCL) and non Hodgkin's lymphomas (NHL), T cell lymphomas and solid tumors including for example thyroid cancer, non-small cell lung carcinoma (NSCLC), hepatocellular carcinoma (HCC), renal cell carcinoma (RCC), head and neck sqamous cell carcinoma (H&N SCC).

Mention may preferably also be made of the prevention and treatment of diseases of the peripheral or central nervous system. Examples of these are acute and chronic multiple sclerosis or non-familial lateral sclerosis.

Mention may preferably also be made of the prevention and treatment of osteoporotic diseases such as for example disease-associated osteopenia, osteoporosis and osteolytic diseases.

The present invention relates particularly preferably to the use of compounds of formula 1 for preparing a pharmaceutical composition for the treatment of diseases selected from among asthma, COPD, allergic rhinitis, Adult Respiratory Distress Syndrome, bronchitis, allergic dermatitis, contact dermatitis, ITP, rheumatoid arthritis and allergic rhinoconjunctivitis.

Most preferably, the compounds of formula 1 may be used for the treatment of a disease selected from among asthma, allergic rhinitis, rheumatoid arthritis, allergic dermatitis and COPD.

7. COMBINATIONS

The compounds of formula 1 may be used on their own or in conjunction with other active substances of formula 1 according to the invention. The compounds of formula 1 may optionally also be used in conjunction with other pharmacologically active substances. Preferably the active substances used here may be selected for example from among the betamimetics, anticholinergics, corticosteroids, PDE4-inhibitors, LTD4-antagonists, EGFR-inhibitors, MRP4-inhibitors, dopamine agonists, H1-antihistamines, PAF-antagonists, iNos-inhibitors, H MG-CoA reductase inhibitors (statins), PI3-kinase-inhibitors, CCR3-antagonists, CCR2-antagonists, CCR1-antagonists, IKK2-inhibitors, A2a agonists, alpha-4-integrin-inhibitors, CRTH2-antagonists, histamine 1, combined H1/H3-antagonists, p38 kinase inhibitors, methylxanthines, ENaC-inhibitors, CXCR1-antagonists, CXCR2-antagonists, ICE-inhibitors, LTB4-antagonists, 5-LO antagonists, FLAP-antagonists. LTB4-antagonists; cromoglycine, dissociated glucocorticoid mimetics, anti-TNF-antibodies, anti-GM-CSF antibodies, anti-CD46-antibodies, anti-IL-1-antibodies, anti-IL-2-antibodies, anti-IL-4-antibodies, anti-IL-5-antibodies, anti-IL-13-antibodies, anti-IL-4/IL-13-antibodies, or double or triple combinations thereof, such as for example combinations of one, two or three compounds selected from among the SYK-inhibitors of formula 1, betamimetics, corticosteroids, EGFR-inhibitors and PDE4-antagonists,
SYK-inhibitors of formula 1, anticholinergics, betamimetics, corticosteroids, EGFR-inhibitors and PDE4-antagonists,
SYK-inhibitors of formula 1, PDE4-inhibitors, corticosteroids and EGFR-inhibitors,
SYK-inhibitors of formula 1, EGFR-inhibitors and PDE4-inhibitors,
SYK-inhibitors of formula 1 and EGFR-inhibitors,
SYK-inhibitors of formula 1, betamimetics and anticholinergics
SYK-inhibitors of formula 1, anticholinergics, betamimetics, corticosteroids and PDE4-inhibitors,
SYK-inhibitors of formula 1, anticholinergics, betamimetics, corticosteroids, iNOS inhibitors, H MG-CoA reductase inhibitors, CRTH2-antagonists.

Combinations of three active substances each taken from one of the above-mentioned categories of compounds are also an object of the invention.

Suitable betamimetics used are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramide, tolubuterol, zinterol, 6-Hydroxy-8-{1-hydroxy-2-[2-(4-methoxy-phenyl)-1,1-dimethyl-ethylamino]-ethyl}-4H-benzo[1,4]oxazine-3-one; 8-{2-[2-(2,4-Difluor-phenyl)-1,1-dimethyl-ethylamino]-1-hydroxy-ethyl}-6-hydroxy-4H-benzo[1,4]oxazine-3-one; 8-{2-[2-(3,5-Difluor-phenyl)-1,1-dimethyl-ethylamino]-1-hydroxy-ethyl}-6-hydroxy-4H-benzo[1,4]oxazine-3-one; 8-{2-[2-(4-Ethoxy-phenyl)-1,1-dimethyl-ethylamino]-1-hydroxy-ethyl}-6-hydroxy-4H-benzo[1,4]oxazine-3-one; 8-{2-[2-(4-Fluor-phenyl)-1,1-dimethyl-ethylamino]-1-hydroxy-ethyl}-6-hydroxy-4H-benzo[1,4]oxazine-3-one; N-(5-{2-[3-(4,4-Diethyl-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-fluoro-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-methoxy-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[1,1-Dimethyl-3-(2-oxo-4,4-dipropyl-4H-benzo[d][1,3]oxazine-1-yl)-propylamino]-1-hydroxy-ethyl}-2-hydroxy-phenyl)-methansulfonamide; 8-{2-[1,1-Dimethyl-3-(2-oxo-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(6-methyl-2-oxo-2,3-dihydro-benzoimidazole-1-yl)-propylamino]-1-hydroxy-ethyl}-6-hydroxy-4H-benzo[1,4]oxazine-3-one; 8-{2-[1,1-Dimethyl-3-(2-oxo-5-trifluormethyl-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(3-methyl-2-oxo-2,3-dihydro-benzoimidazol-1-yl)-propylamino]-1-hydroxy-ethyl}-6-hydroxy-4H-benzo[1,4]-oxazine-3-one; N-[2-Hydroxy-5-((1R)-1-hydroxy-2-{2-[4-(2-hydroxy-2-phenyl-ethyl-amino)-phenyl]-ethylamino}-ethyl)-phenyl]-formamide; 8-Hydroxy-5-((1R)-1-hydroxy-2-{2-[4-(6-methoxy-biphenyl-3-ylamino)-phenyl]-ethylamino}-ethyl)-1H-quinoline-2-one; 8-Hydroxy-5-[(1R)-1-hydroxy-2-(6-phenethylamino-hexylamino)-ethyl]-1H-quinoline-2-one; 5-[(1R)-2-(2-{4-[4-(2-Amino-2-methyl-propoxy)-phenylamino]-phenyl}-ethylamino)-1-hydroxy-ethyl]-8-hydroxy-1H-quinoline-2-one; [3-(4-{6-[(2R)-2-Hydroxy-2-(4-hydroxy-3-hydroxymethyl-phenyl)-ethylamino]-hexyloxy}-butyl)-5-methyl-phenyl]-urea; 4-((1R)-2-{6-[2-(2,6-Dichlor-benzyloxy)-ethoxy]-hexylamino}-1-hydroxy-ethyl)-2-hydroxymethyl-phenol; 3-(4-{6-[(2R)-2-Hydroxy- 2-(4-hydroxy-3-hydroxymethyl-phenyl)-ethylamino]-hexyloxy}-butyl)-benzenesulfonamide; 3-(3-{7-[(2R)-2-Hydroxy-2-(4-hydroxy-3-hydroxymethyl-phenyl)-ethylamino]-heptyloxy}-propyl)-benzenesulfonamide; 4-((1R)-2-{6-[4-(3-Cyclopentanesulfonyl-phenyl)-butoxy]-hexylamino}-1-hydroxy-ethyl)-2-hydroxymethyl-phenol, 4-(2-{6-[2-(2,6-dichloro-benzyloxy)-ethoxy]-hexyl-amino}-1-hydroxy-ethyl)-2-hydroxymethyl-phenol; Vilanterol; N-1-Adamantanyl-2-{3-[(2R)-2-({(2R)-2-hydroxy-2-[4-hydroxy-3-(hydroxymethyl)phenyl] ethyl}amino)propyl]phenyl}-acetamide; 2-(3-{2-[2-hydroxy-3-methanesulfonylamino-phenyl)-ethylamino]-propyl}-phenyl)-N-[4-(4-hydroxy-phenyl)-2-vinyl-penta-2,4-dienyl]-acetamide; (1R)-5-{2-[6-(2,2-Difluor-2-phenyl-ethoxy)-hexylamino]-1-hydroxy-ethyl}-8-hydroxy-1H-quinoline-2-one; (R,S)-4-(2-{[6-(2,2-Difluor-4-phenylbutoxy)hexyl]amino}-1-hydroxy-ethyl)-2-(hydroxymethyl)phenol; (R,S)-4-(2-{[6-(2,2-Difluor-2-phenylethoxy)hexyl]amino}-1-hydroxy-ethyl)-2-(hydroxymethyl)phenol; (R,S)-4-(2-{[4,4-Difluor-6-(4-phenylbutoxy)hexyl]amino}-1-hydroxy-ethyl)-2-(hydroxymethyl)-phenol; (R,S)-4-(2-{[6-(4,4-Difluor-4-phenylbutoxy)hexyl]amino}-1-hydroxy-ethyl)-2-(hydroxymethyl)phenol; (R,S)-5-(2-{[6-(2,2-Difluor-2-phenylethoxy)hexyl]amino}-1-hydroxy-ethyl)-8-hydroxyquinoline-2(1H)-one; (R,S)-[2-({6-[2,2-Difluor-2-(3-methylphenyl)ethoxy]hexyl}amino)-1-hydroxyethyl]-2-(hydroxymethyl)phenol; 4-(1R)-2-{[6-(2,2-Difluor-2-phenylethoxy)hexyl]-amino}-1-hydroxyethyl)-2-(hydroxymethyl)phenol; (R,S)-2-(Hydroxymethyl)-4-(1-hydroxy-2-{[4,4,5l5-tetrafluor-6-(3-phenylpropoxy)-hexyl] amino}ethyl)phenol; (R,S)-[5-(2-{[6-(2,2-Difluor-2-phenylethoxy)hexyl]amino}-1-hydroxy-ethyl)-2-hydroxyphenyl]formamide; (R,S)-4-[2-({6-[2-(3-Bromophenyl)-2,2-difluoroethoxy]hexyl}amino)-1-hydroxyethyl]-2-(hydroxymethyl)-phenol; (R,S)—N-[3-(1,1-Difluor-2-{[6-({2-hydroxy-2-[4-hydroxy-3-(hydroxymethyl)phenyl]-ethyl}amino)hexyl]oxy}ethyl) phenyl]-urea; 3-[3-(1,1-Difluor-2-{[6-({2-hydroxy-2-[4-hydroxy-3-(hydroxymethyl)phenyl]ethyl}amino)hexyl] oxy}ethyl)phenyl]imidazolidine-2,4-dione; (R,S)-4-[2-({6-[2,2-Difluor-2-(3-methoxyphenyl)ethoxy]hexyl}amino)-1-hydroxyethyl]-2-(hydroxy-methyl)phenol; 5-((1R)-2-{[6-(2,2-Difluor-2-phenylethoxy)hexyl]amino}-1-hydroxyethyl)-8-hydroxyquinoline-2(1H)-one; 4-((1R)-2-{[4,4-Difluor-6-(4-phenylbutoxy)hexyl]amino}-1-hydroxy-ethyl)-2-(hydroxymethyl)phenol; (R,S)-4-(2-{[6-(3,3-Difluor-3-phenylpropoxy)hexyl]-amino}-1-hydroxy-ethyl)-2-(hydroxymethyl)phenol; (R,S)-(2-{[6-(2,2-Difluor-2-phenylethoxy)-4,4-difluorohexyl]amino}-1-hydroxyethyl)-2-(hydroxymethyl)phenol; (R,S)-4-(2-{[6-(2,2-Difluor-3-phenylpropoxy)hexyl]amino}-1-hydroxy ethyl)-2-(hydroxymethyl)phenol; 3-[2-(3-Chlor-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide; N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-Chlor-phenyl)-ethylamino]-propylsulfanyl}-ethylamino)-1-hydroxy-ethyl]-4-hydroxy-3H-benzothiazol-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among tiotropium salts, particularly the bromide salt, oxitropium salts, particularly the bromide salt, flutropium salts, particularly the bromide salt, ipratropium salts, particularly the bromide salt, Aclidinium salts, particularly the bromide salt, glycopyrronium salts, particularly the bromide salt, trospium salts, particularly the chloride salt, tolterodin, (3R)-1-Phenethyl-3-(9H-xanthene-9-carbonyloxy)-1-azoniabicyclo[2.2.2]octan-salts; 2,2-Diphenyl propionic acid tropenole ester-methobromide; 2,2-Diphenyl propionic acid scopine ester-methobromide; 2-Fluor-2,2-Diphenyl acetic acid scopine ester-methobromide; 2-Fluor-2,2-Diphenyl acetic acid tropenole ester-methobromide; 3,3',4,4'-Tetrafluor benzilic acid tropenole ester-methobromide; 3,3',4,4'-Tetrafluor benzilic acid scopine ester-methobromide; 4,4'-Difluor benzilic acid tropenole ester-methobromide; 4,4'-Difluor benzilic acid scopine ester-methobromide; 3,3'-Difluor benzilic acid tropenole ester-methobromide; 3,3'-Difluor benzilic acid scopine ester-methobromide; 9-Hydroxy-fluorene-9-carboxylic acid tropenole ester-methobromide; 9-Fluor-fluorene-9-carboxylic acid tropenole ester-methobromide; 9-Hydroxy-fluorene-9-carboxylic acid scopine ester-methobromide; 9-Fluor-fluorene-9-carboxylic acid scopine ester-methobromide; 9-Methyl-fluorene-9-carboxylic acid tropenole ester-methobromide; 9-Methyl-fluorene-9-carboxylic acid scopine ester-methobromide; Benzilic acid cyclopropyl tropine ester-methobromide; 2,2-Diphenyl propionic acid cyclopropyltropine ester-methobromide; 9-Hydroxy-xanthene-9-carboxylic acid cyclopropyltropine ester-methobromide; 9-Methyl-fluorene-9-carboxylic acid cyclopropyltropine ester-methobromide; 9-Methyl-xanthene-9-carboxylic acid cyclopropyltropine ester-methobromide; 9-Hydroxy-fluorene-9-carboxilic acid cyclopropyltropine ester-methobromide; 4,4'-Difluor benzilic acid methyl ester cyclopropyltropine ester-methobromide; 9-Hydroxy-xanthene-9-carboxylic acid tropenole ester-methobromide; 9-Hydroxy-xanthene-9-carboxylic acid scopine ester-methobromide; 9-Methyl-xanthene-9-carboxylic acid tropenole ester-methobromide; 9-Methyl-xanthene-9-carboxylic acid scopine ester-methobromide; 9-Ethyl-xanthene-9-carboxylic acid tropenole ester-methobromide; 9-Difluormethyl-xanthene-9-carboxylic acid tropenole ester-methobromide; 9-Hydroxymethyl-xanthene-9-carboxylic acid scopine ester-methobromide;

3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide;

N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide;

7-[2-(2-{3-[2-(2-Chloro-phenyl)-ethylamino]-propylsulfanyl}-ethylamino)-1-hydroxy-ethyl]-4-hydroxy-3H-benzothiazol-2-one and Darotropium;

optionally in the form of the solvates or hydrates thereof.

In the above-mentioned salts the cations, as for example tiotropium, oxitropium, flutropium, ipratropium, glycopyrronium, aclidinium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among beclomethasone, betamethasone, budesonide, butixocorte, ciclesonide, deflazacorte, dexamethasone, etiprednole, flunisolide, fluticasone, loteprednole, mometasone, prednisolone, prednisone, rofleponide, triamcinolone, tipredane;
{20R-16α,17α-[butylidenebis(oxy)]-6α,9α-difluoro-11β-hydroxy-17β-(methylthio)androsta-4-en-3-one};
9-fluoro-11beta,17,21-trihydroxy-16alpha-methylpregna-1,4-diene-3,20-dione 21-cyclohexanecarboxylate 17-cyclopropanecarboxylate;
16,17-butylidene dioxy-6,9-difluoro-11-hydroxy-17-(methylthio)androst-4-en-3-one;
Flunisolide-21-[4'-(nitrooxymethyl)benzoate];
6,9-Difluoro-17-[(2-furanylcarbonyl)oxy]-11-hydroxy-16-methyl-3-oxo-androsta-1,4-dien-17-carbothion acid (S)-fluoromethylester,
6,9-Difluoro-11-hydroxy-16-methyl-3-oxo-17-propionyloxy-androsta-1,4-dien-17-carbothion acid (S)-(2-oxo-tetrahydro-furan-3S-yl)ester, and
6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester and
Pregna-1,4-diene-3,20-dione, 6-fluoro-11-hydroxy-16,17-[(1-methylethylidene)bis(oxy)]-21-[[4-[nitrooxy)methyl]-benzoyl]oxy]-, (6-alpha,11-beta,16-alpha)-(9Cl); 16,17-butylidenedioxy-6,9-difluoro-11-hydroxy-17-(methylthio)androst-4-en-3-one; (S)-fluoromethyl 6,9-difluoro-17-[(2-furanylcarbonyl)oxy]-11-hydroxy-16-methyl-3-oxo-androsta-1,4-diene-17-carbothionate; each optionally in the form of the racemates, enantiomers or diastereomers thereof and optionally in the form of the salts and derivatives, solvates and/or hydrates thereof.

Particularly preferably the steroid is selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, apremilast, arofyllin, atizoram, oglemilast, tetomilast; 5-[(N-(2,5-dichloro-3-pyridinyl)-carboxamide]-8-methoxy-Quinoline (D-4418); 5-[N-(3,5-dichloro-1-oxido-4-pyridinyl)-carboxamide]-8-methoxy-2-(trifluoromethyl)-Quinoline (D-4396 (Sch-351591)); N-(3,5-dichloropyrid-4-yl)-[1-(4-fluorobenzyl)-5-hydroxy-indol-3-yl]glyoxylic acid amide (AWD-12-281 (GW-842470)); 9-[(2-fluorophenyl)methyl]-N-methyl-2-(trifluoromethyl)-9H-Purin-6-amine (NCS-613); 4-[(2R)-2-[3-(cyclopentyloxy)-4-methoxyphenyl]-2-phenylethyl]-Pyridine (CDP-840); N-[(3R)-3,4,6,7-tetrahydro-9-methyl-4-oxo-1-phenylpyrrolo[3,2,1-jk][1,4]benzodiazepin-3-yl]-4-Pyridinecarboxamide (PD-168787); 4-[6,7-diethoxy-2,3-bis(hydroxymethyl)-1-naphthalenyl]-1-(2-methoxyethyl)-2(1H)-Pyridinone (T-440); 2-[4-[6,7-diethoxy-2,3-bis(hydroxymethyl)-1-naphthalenyl]-2-pyridinyl]-4-(3-pyridinyl)-1(2H)-Phthalazinone (T-2585); (3-(3-cyclopenyloxy-4-methoxybenzyl)-6-ethylamino-8-isopropyl-3H-purine (V-11294A); beta-[3-(cyclopentyloxy)-4-methoxyphenyl]-1,3-dihydro-1,3-dioxo-2H-Isoindole-2-propanamide (CDC-801); Imidazo[1,5-a]pyrido[3,2-e]pyrazine-6(5H)-one, 9-ethyl-2-methoxy-7-methyl-5-propyl-(D-22888); 5-[3-(cyclopentyloxy)-4-methoxyphenyl]-3-[(3-methylphenyl)methyl]-, (3S,5S)-2-Piperidinon (HT-0712); 4-[1-[3,4-bis(difluoromethoxy)phenyl]-2-(3-methyl-1-oxido-4-pyridinyl)ethyl]-alpha,alpha-bis(trifluoromethyl)-Benzenemethanol (L-826141); N-(3,5-Dichloro-1-oxo-pyridin-4-yl)-4-difluormethoxy-3-cyclopropylmethoxybenzamide; (−)p-[(4aR*,10bS*)-9-Ethoxy-1,2,3,4,4a,10b-hexahydro-8-methoxy-2-methylbenzo[s][1,6]-naphthyridin-6-yl]-N,N-diisopropylbenzamide; (R)-(+)-1-(4-Brombenzyl)-4-[(3-cyclopentyloxy)-4-methoxyphenyl]-2-pyrrolidon; 3-(Cyclopentyloxy-4-methoxyphenyl)-1-(4-N'-[N-2-cyano-S-methyl-isothioureido]benzyl)-2-pyrrolidon; cis[4-Cyano-4-(3-cyclopentyloxy-4-methoxy-phenyl)cyclohexan-1-carboxylic acid]; 2-carbomethoxy-4-cyano-4-(3-cyclopropylmethoxy-4-difluoromethoxyphenyl)cyclohexan-1-one; cis[4-Cyano-4-(3-cyclopropylmethoxy-4-difluor-methoxyphenyl)cyclohexan-1-ol]; (R)-(+)-Ethyl [4-(3-cyclopentyloxy-4-methoxyphenyl)-pyrrolidin-2-yliden]acetat; (S)-(−)-Ethyl[4-(3-cyclopentyloxy-4-methoxyphenyl)pyrrolidin-2-yliden]acetat; 9-Cyclopentyl-5,6-dihydro-7-ethyl-3-(2-thienyl)-9H-pyrazolo[3,4-c]-1,2,4-triazolo[4,3-a]pyridin; 9-Cyclopentyl-5,6-dihydro-7-ethyl-3-(tert-butyl)-9H-pyrazolo[3,4-c]-1,2,4-triazolo[4,3-a]pyridin,
optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

CRTH2-antagonists which may be used are preferably compounds selected from the group consisting of Ramatroban, Laropiprant, 5-Fluoro-2-methyl-3-quinolin-2-yl-methyl-indol-1-yl)-acetic acid (=OC000459; Oxagen), Vidupiprant (=AMG 853 or [5-chloro-4-(2-{[(2-chloro-4-cyclopropylphenyl)sulfonyl]amino}-4-[(1,1-dimethylethyl)

carbamoyl]phenoxy)-2-fluorophenyl]-acetic acid or 2-{4-[4-(tert-butylcarbamoyl)-2-(2-chloro-4-cyclopropyl-benzenesulfonamino)-phenoxy]-5-chloro-2-fluoro-phenyl}-acetic acid) and [4-Acetylamino-3-(4-chloro-phenylsulfanyl)-2-methyl-indol-1-yl]-acetic acid (=AZD1981, Astra Zeneca), optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned CRTH2-antagonists might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast; (E)-8-[2-[4-[4-(4-Fluorophenyl)butoxy]phenyl]ethenyl]-2-(1H-tetrazol-5-yl)-4H-1-benzopyran-4-one (MEN-91507); 4-[6-Acetyl-3-[3-(4-acetyl-3-hydroxy-2-propylphenylthio)propoxy]-2-propylphenoxy]-butyric acid (MN-001); 1-(((R)-(3-(2-(6,7-Difluor-2-quinolinyl)ethenyl)phenyl)-3-(2-(2-hydroxy-2-propyl)phenyl)thio)methyl-cyclopropane-acetic acid; 1-(((1(R)-3(3-(2-(2,3-Dichlorthieno[3,2-b]pyridin-5-yl)-(E)-ethenyl)-phenyl)-3-(2-(1-hydroxy-1-methylethyl)phenyl)propyl)thio)methyl)cyclopropane acetic acid; [2-[[2-(4-tert-Butyl-2-thiazolyl)-5-benzofuranyl]oxymethyl]phenyl]acetic acid,
optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from the group consisting of hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholine-4-yl)-1-oxo-2-butene-1-yl]amino}-7-cyclopropylmethoxy-quinazoline, 4-[(3-chloro-4-fluorophenyl)amino]-6-{[4-(N,N-diethyl-amino)-1-oxo-2-butene-1-yl]amino}-7-cyclopropylmethoxy-quinazoline, 4-[(3-chloro-4-fluoro-phenyl)amino]-6-{[4-(N,N-dimethylamino)-1-oxo-2-butene-1-yl]amino}-7-cyclopropylmethoxy-quinazoline, 4-[(R)-(1-phenyl-ethyl)amino]-6-{[4-(morpholine-4-yl)-1-oxo-2-butene-1-yl]amino}-7-cyclopentyloxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-cyclopropylmethoxy-quinazoline, 4-[(3-chloro-4-fluorophenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholine-4-yl)-1-oxo-2-butene-1-yl]amino}-7-cyclopropyl-methoxy-quinazoline, 4-[(3-chloro-4-fluoro-phenyl)amino]-6-[2-((S)-6-methyl-2-oxo-morpho-line-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopentyloxy-quinazoline, 4-[(R)-(1-phenyl-ethyl)amino]-6-({4-[N,N-bis-(2-methoxy-ethyl)-amino)-1-oxo-2-butene-1-yl]amino}-7-cyclopropyl-methoxy-quinazoline, 4-[(R)-(1-phenyl-ethyl)amino]-6-({4-[N-(2-methoxy-ethyl)-N-ethyl-amino]-1-oxo-2-butene-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-((R)-tetrahydrofuran-3-yloxy)-quinazoline, 4-[(3-chloro-4-fluorophenyl)amino]-6-{[4-(N,N-dimethyl-amino)-1-oxo-2-butene-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopentyloxy-quinazoline, 4-[(3-chloro-4-fluorophenyl)amino]-6-{[4-(N-cyclo-propyl-N-methyl-amino)-1-oxo-2-butene-1-yl]amino}-7-cyclopentyloxy-quinazoline, 4-[(3-chloro-4-fluorophenyl)amino]-6-{[4-(N,N-dimethylamino)-1-oxo-2-butene-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-butene-1-yl]amino}-7-[(S)-(tetrahydrofuran-2-yl)methoxy]-quinazoline, 4-[(3-ethynyl-phenyl)amino]-6.7-bis-(2-methoxy-ethoxy)-quinazoline, 4-[(3-chloro-4-fluorophenyl)amino]-7-[3-(morpholine-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-butene-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl) quinazoline, 4-[(R)-(1-phenyl-ethyl)amino]-6-{[4-((R)-6-methyl-2-oxo-morpholine-4-yl)-1-oxo-2-butene-1-yl]amino}-7-methoxy-quinazoline, 4-[(3-chloro-4-fluorophenyl)amino]-6-{[4-(morpholine-4-yl)-1-oxo-2-butene-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline, 4-[(3-ethynyl-phenyl)amino]-6-{[4-(5.5-dimethyl-2-oxo-morpholine-4-yl)-1-oxo-2-butene-1-yl]amino}-quinazoline, 4-[(3-chloro-4-fluoro-phenyl)amino]-6-[2-(2.2-dimethyl-6-oxo-morpholine-4-yl)-ethoxy]-7-methoxy-quinazoline, 4-[(3-chloro-4-fluoro-phenyl)amino]-6-[2-(2.2-dimethyl-6-oxo-morpholine-4-yl)-ethoxy]-7-[(R)-(tetrahydrofuran-2-yl)methoxy]-quinazoline, 4-[(3-chloro-4-fluoro-phenyl)

amino]-7-[2-(2.2-dimethyl-6-oxo-morpholine-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholine-4-yl)-pipendine-1-yl]-ethoxy}-7-methoxy-quinazoline, 4-[(3-chloro-4-fluoro-phenyl)amino]-6-[1-(tert.-butyloxycarbonyl)-pipendine-4-yloxy]-7-methoxy-quinazoline, 4-[(3-chloro-4-fluoro-phenyl)amino]-6-(trans-4-amino-cyclo-hexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-pipendine-4-yloxy)-7-methoxy-quinazoline, 4-[(3-chloro-4-fluoro-phenyl)amino]-6-{1-[(morpholine-4-yl)carbonyl]-pipendine-4-yl-oxy}-7-methoxy-quinazoline, 4-[(3-chloro-4-fluoro-phenyl)amino]-6-{1-[(methoxymethyl)carbonyl]-pipendine-4-yloxy}-7-methoxy-quinazoline, 4-[(3-chloro-4-fluoro-phenyl)amino]-6-(pipendine-3-yloxy)-7-methoxy-quinazoline, 4-[(3-chloro-4-fluoro-phenyl)amino]-6-[1-(2-acetylamino-ethyl)-pipendine-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholine-4-yl)carbonylamino]-cyclohexan-1-yloxy}-7-methoxy-quinazoline, 4-[(3-chloro-4-fluoro-phenyl)amino]-6-{trans-4-[(morpholine-4-yl)-sulphonylamino]-cyclohexan-1-yloxy}-7-methoxy-quinazoline, 4-[(3-chloro-4-fluoro-phenyl)-amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidine-1-yl)carbonyl]-piperidine-4-yloxy}-7-methoxy-quinazoline, 4-[(3-chloro-4-fluoro-phenyl)amino]-6-(1-aminocarbonyl-methyl-piperidine-4-yloxy)-7-methoxy-quinazoline, 4-[(3-chloro-4-fluoro-phenyl)amino]-6-cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholine-4-yl)carbonyl]-N-methyl-amino}-cyclohexan-1-yloxy)-7-methoxy-quinazolin; 4-{2-[4-(3-chloro-4-fluoro-phenyl-amino)-7-methoxy-quinazolin-6-yloxy]-ethyl}-6-methyl-morpholine-2-one, 4-{4-[4-(3-chloro-2-fluoro-phenylamino)-7-methoxy-quinazolin-6-yloxy]-cyclohexyl}-1-methyl-piperazine-2-one, 4-[(3-chloro-4-fluoro-phenyl)amino]-6-(cis-4-{N-[(morpholine-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidine-4-yloxy)-7-ethoxy-quinazoline, 4-[(3-chloro-4-fluoro-phenyl)amino]-6-(1-methanesulphonyl-piperidine-4-yloxy)-7-(2-methoxy-ethoxy)-quinazoline, 4-[(3-chloro-4-fluoro-phenyl)amino]-6-[1-(2-methoxy-acetyl)-piperidine-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxy-carbonyl)-piperidine-4-yloxy]-7-methoxy-quinazoline, 4-[(3-ethynyl-phenyl)amino]-6-(tetra-hydropyran-4-yloxy)-7-methoxy-quinazoline, 4-[(3-chloro-4-fluoro-phenyl)amino]-6-(cis-4-{N-[(piperidine-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazine-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholine-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidine-4-yloxy}-7-methoxy-quinazoline, 4-[(3-chloro-4-fluoro-phenyl)amino]-6-{1-[(morpholine-4-yl)carbonyl]-piperidine-4-yloxy}-7-(2-methoxy-ethoxy)-quinazoline, 4-[(3-ethynyl-phenyl)amino]-6-(1-acetyl-piperidine-4-yloxy)-7-methoxy-quinazoline, 4-[(3-ethynyl-phenyl)amino]-6-(1-methyl-pipendine-4-yloxy)-7-methoxy-quinazoline, 4-[(3-ethynyl-phenyl)amino]-6-(1-methane-sulphonyl-pipendine-4-yloxy)-7-methoxy-quinazoline, 4-[(3-chloro-4-fluoro-phenyl)amino]-6-(1-methyl-piperidine-4-yloxy)-7(2-methoxy-ethoxy)-quinazoline, 4-[(3-chloro-4-fluoro-phenyl)-amino]-6-(1-isopropyloxycarbonyl-pipendine-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(pipendine-4-yloxy)-7-methoxy-quinazoline, 4-[(3-ethynyl-phenyl)amino]-6-[1-(2-methoxy-acetyl)-pipendine-4-yloxy]-7-methoxy-quinazoline, 4-[(3-ethynyl-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(cis-2,6-dimethyl-morpholine-4-yl)carbonyl]-pipendine-4-yloxy}-7-methoxy-quinazoline, 4-[(3-chloro-4-fluoro-phenyl)amino]-6-{1-[(2-methyl-morpholine-4-yl)carbonyl]-pipendine-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidine-4-yloxy}-7-methoxy-quinazoline, 4-[(3-chloro-4-fluoro-phenyl)amino]-6-{1-[(N-methyl-N-2-methoxyethyl-amino)carbonyl]-pipendine-4-yloxy}-7-methoxy-quinazoline, 4-[(3-chloro-4-fluoro-phenyl)amino]-6-(1-ethyl-piperidine-4-yloxy)-7-methoxy-quinazoline, 4-[(3-chloro-4-fluoro-phenyl)amino]-6-{1-[(2-methoxy-ethyl)carbonyl]-pipendine-4-yloxy}-7-methoxy-quinazoline, 4-[(3-chloro-4-fluoro-phenyl)amino]-6-{1-[(3-methoxypropyl-amino)-carbonyl]-pipendine-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)-amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpho-line-4-yl)carbonyl]-N-methyl-amino}-cyclohexan-1-yloxy)-7-methoxy-quinazoline, 4-[(3-chloro-4-fluoro-phenyl)amino]-6-[2-(2.2-dimethyl-6-oxo-morpholine-4-yl)-ethoxy]-7-[(S)-(tetra-hydrofuran-2-yl)methoxy]-quinazoline, 4-[(3-chloro-4-fluoro-phenyl)amino]-6-(1-methane-sulphonyl-pipendine-4-yloxy)-7-methoxy-quinazoline, 4-[(3-chloro-4-fluoro-phenyl)-amino]-6-(1-cyano-pipendine-4-yloxy)-7-methoxy-quinazoline, 3-Cyano-4-[(3-chlor-4-fluorphenyl)-amino]-6-{[4-(N,N-dimethylamino)-1-oxo-2-butene-1-yl]amino}-7- ethoxy-quinoline, [4-[(3-chloro-4-fluoro-phenyl)amino]-6-{[4-(homomorpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinyl-carbonyl)amino]-quinazoline, 4-[(3-chloro-4-fluoro-phenyl)amino]-7-[2-((S)-6-methyl-2-oxo-morpholine-4-O-ethoxy]-6-[(vinylcarbonyl)amino]-quinazoline, 4-[(3-chloro-4-fluoro-phenyl)-amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, cetuximab, trastuzumab, panitumumab (=ABX-EGF), Mab ICR-62, gefitinib, pelitinib, canertinib and erlotinib, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, olopatadine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among lexipafant, 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpho-linyl)carbonyl]-4H,7H-cyclo-penta-[4,5]thieno-[3,2-f][1,2,4]triazolo[4,3-a][1,4]diazepines. Any reference to the above-mentioned PAF-antagonists includes within the scope of the present invention a reference to any pharmacologically acceptable acid addition salts thereof which may exist.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the SYK-inhibitors of formula 1 and MRP4-inhibitors according to the invention, the MRP4-inhibitors preferably being selected from among dehydroepiandrosterone 3-sulphate, estradiol 3,17-disulphate, flurbiprofen, indomethacin, indoprofen, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the SYK-inhibitors of formula 1, MRP4-inhibitors and another active substance according to the invention, such as, for example, an anticholinergic, a PDE4 inhibitor, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-aminomethylpyridine, 5,6-dihydro-6-methyl-4H-1,3-Thiazine-2-amine (=AMT), L-canavanine, 2-iminopiperidine, S-isopropylisothiourea, S-methylisothiourea, S-ethylisothiourea, S-methyltiocitrullin, S-ethylthiocitrulline, L-NA ($N^\omega$-nitro-L-arginine), L-NAME ($N^\omega$-nitro-L-argininemethylester), L-NMMA ($N^G$-monomethyl-L-arginine), L-NIO ($N^\omega$-iminoethyl-L-ornithine), L-NIL ($N^\omega$-iminoethyl-lysine), (S)-6-acetimidoylamino-2-amino-hexanoic acid (1H-tetrazol-5-yl)-amide (SC-51) (*J. Med.*

*Chem.* 2002, 45, 1686-1689), N-[[3-(aminomethyl)phenyl]methyl]-Ethanimidamide (=1400W), (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S.4R)-2-amino-4-(2-chloro-5-trifluoromethyl-phenylsulphanyl)-4-thiazol-5-yl-butan-1-o1 (WO 2004/041794), 2-((1R.3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. (1S.5S.6R)-7-chloro-5-methyl-2-aza-bicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chlorophenyl)-N-(1-{2-oxo-2-[4-(6-trifluoromethyl-pyrimidin-4-yloxy)-piperidine-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-yl-methyl-phenoxy)-ethoxy]-2-phenyl-pyridine (PPA250) (*J. Pharmacol. Exp. Ther.* 2002, 303, 52-57), 3-{[(benzo[1,3]dioxol-5-ylmethyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Suitable HMG-CoA reductase inhibitors (also called statins) which may be preferably used in double or triple combinations with the compounds of formula 1 are selected from among Atorvastatin, Cerivastatin, Flurvastatin, Lovastatin, Pitavastatin, Pravastatin, Rosuvastatin, Simvastatin, optionally in form of their pharmaceutically available acid addition salts, prodrugs, solvates or hydrates thereof.

8. FORMULATIONS

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with a naphthyridine according to formula 1 and one or more combination partners selected from those described above.

The invention claimed is:
1. A compound of formula 1

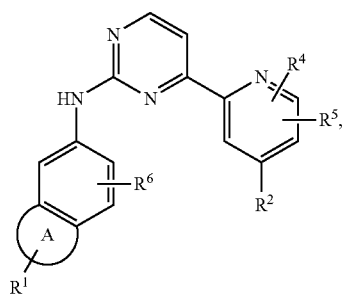

wherein
ring A is a five-membered saturated or unsaturated carbocyclic ring which optionally comprises one, two or three heteroatoms each independently from each other selected from the group N, S and O, wherein ring A may optionally be further substituted by one or two residues which are both independently from each other selected from the group consisting of H, halogen, $C_{1-3}$-alkyl, -oxo, —$NH_2$, —CO—($C_{1-3}$-alkyl), —CO—NH($C_{1-3}$-alkyl), —CO—N($C_{1-3}$-alkyl)$_2$, —SO$_2$-phenyl and —SO$_2$—($C_{1-3}$-alkyl), and wherein $R^1$ is selected from the group consisting of H, -halogen, SH, -oxo, —$NH_2$, —CO—Y, —CO—N(CH$_3$)—Y, —CO—N(CH$_3$)—($C_{1-3}$-alkylene)-Y, —CS—Y, —CS—N(CH$_3$)—Y, —CS—N(CH$_3$)—($C_{1-3}$-alkylene)-Y, —$C_{1-6}$-alkyl, —$C_{1-3}$-haloalkyl, —CO—NH—Y, —CO—NH—$C_{1-4}$-alkylene-Y, —CO—NH—$C_{1-4}$-alkylene-(Y)$_2$, —CO—N(CH$_3$)—($C_{2-3}$-alkylene)-O—($C_{1-3}$-alkyl), —$NH_2$, —$C_{1-6}$-alkylene-L, —SO$_2$-phenyl, —SO$_2$—($C_{1-3}$-alkyl), —CO—N($C_{1-4}$-alkyl)$_2$, —CO—N($C_{2-4}$-alkylene-O—$C_{1-3}$-alkyl)$_2$, a five- or six-membered heteroaromatic group comprising 1, 2 or 3 heteroatoms each independently selected from the group N, S and O, with Y being a group selected from the group consisting of —$NH_2$, —NH(CH$_3$), —N(CH$_3$)$_2$, —$C_{1-6}$-alkylene-N(CH$_3$)$_2$, —O—$C_{1-3}$-alkyl, —OH and —N(ethyl)$_2$, or with Y being a group selected from the group consisting of a four-, five-, six- or seven-membered monocyclic fully saturated or partially unsaturated heterocycle comprising 1, 2 or 3 heteroatoms each independently selected from the group N, S and O, with the proviso that this heterocycle comprises at least one N-atom and that this heterocycle is directly attached to the molecule via this N-atom, a five- or six-membered monocyclic heteroaromatic group comprising 1, 2 or 3 heteroatoms each independently selected from the group of N, S and O, and a $C_{3-6}$-cycloalkyl, or with Y being a 9- to 11-membered bicyclic annellated fully saturated or partially unsaturated heterocycle comprising 1, 2, 3 or 4 heteroatoms each independently from each other selected from the group N, S and O, or with Y being an 8- to 11-membered bicyclic fully saturated spiro-heterocycle comprising 1, 2 or 3 heteroatoms each independently selected from the group N, S and O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional $C_{1-3}$-alkylene-unit, whereby each Y may optionally be substituted by one or more groups Z each independently from each other selected from the group consisting of halogen, -oxo, OH, $C_{1-5}$-alkyl, —$C_{1-5}$-alkanol, —O—$C_{1-3}$-alkyl, a five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO-L, —$C_{1-3}$-alkylene-CO-L, —$C_{1-3}$-alkylene-O—$C_{1-3}$-alkyl, —N(CH$_3$)$_2$ and —N(ethyl)$_2$, whereby each group Z may optionally be further substituted by one, two or three groups T each independently selected from the group consisting of -oxo, OH, halogen, —$C_{1-3}$-alkyl, —O—$C_{1-3}$-alkyl, —N(methyl)$_2$, —N(ethyl)$_2$, 5- to 6-membered fully saturated, partially unsaturated or aromatic heterocycle comprising 1 or 2 heteroatoms each independently selected from the group N, O and S, a $C_{3-6}$-cycloalkyl and —CN, wherein each group T may also optionally be substituted by a group selected from the group consisting of $C_{1-3}$-alkyl, halogen, OH, oxo and —O—$C_{1-3}$-alkyl, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, halogen, OH and -oxo, wherein $R^2$ denotes a group selected from the group consisting of hydrogen, —OH, halogen, —CO—NH—$NH_2$ and —CO—$NH_2$, or $R^2$ denotes a group selected from the group consisting of linear or branched $C_{1-6}$-alkyl, —$C_{1-6}$-haloalkyl, —$R^3$, —O—$R^3$, —O—$C_{1-3}$-alkylene-$R^3$, —$C_{1-3}$-alkylene-O—$C_{1-3}$-alkyl, linear or branched —O—$C_{2-8}$-alkanol, linear or branched —O—$C_{1-3}$-haloalkyl, —$C_{3-6}$-cycloalkyl, —O—$C_{2-4}$-alkylene-O—$C_{1-3}$-alkyl, —CO—$R^3$, —$C_{1-4}$-alkylene-$R^3$, —O—$C_{2-6}$-alkenyl, —O—$C_{2-4}$-alkylene-N(CH$_3$)—$C_{1-3}$-alkyl, —CO—N($C_{1-3}$-alkyl)$_2$ and —CO—NH($C_{1-3}$-alkyl), which may optionally be substituted by one, two or three substituents each independently selected from the group consisting of —CN, —$NH_2$, —$C_{1-2}$-alkylene-CN, —OH, —$C_{1-2}$-alkylene-OH, halogen, -oxo, —$C_{1-3}$-alkyl, —O—$R^3$, —$C_{1-3}$-alkylene-O—$R^3$, —CO—$C_{1-6}$-alkyl, —CO—$NH_2$, —CO—N(CH$_3$)$_2$, —$C_{1-3}$-alkylene-$NH_2$, phenyl, —$C_{1-2}$-alkylene-OH and —CO—$C_{1-2}$-alkyl, wherein each $R^3$ denotes independently from each other a group selected from a linear or branched $C_{1-10}$-alkyl, linear or branched $C_{1-4}$-haloalkyl, fully saturated or partially unsaturated $C_{3-8}$-cycloalkyl, —$C_{1-3}$-alkylene-$C_{3-6}$-cycloalkyl, a four-, five- or six-membered monocyclic either fully saturated or partially unsaturated heterocycle comprising 1, 2 or 3 heteroatoms each independently selected from N, S or O, a five- to six-membered heteroaromatic group comprising 1, 2 or 3 heteroatoms each independently selected from the group N, S and O, linear or branched —$C_{2-5}$-alkenyl, phenyl and a nine- or ten-membered fully saturated, aromatic or partially unsaturated, bicyclic heterocycle comprising 1, 2 or 3 heteroatoms each independently selected from the group N, S and O wherein $R^4$ denotes a group selected from H, F, Cl, Br, OH, —O—$C_{1-3}$-alkyl, —$C_{1-4}$-alkyl, —$C_{1-3}$-alkylene-OH and —CN, wherein $R^5$ denotes a group selected from H, F, Cl, Br, OH, —O—$C_{1-3}$-alkyl, —$C_{1-4}$-alkyl, —$C_{1-3}$-alkylene-OH and —CN, wherein $R^6$ denotes a group selected from H, halogen, $C_{1-3}$-alkyl, —$NH_2$, —$C_{1-3}$-haloalkyl and —$C_{1-4}$-alkoxy or a pharmaceutically acceptable salt thereof.

2. The compound of formula 1 according to claim 1, wherein ring A is selected from the group consisting of

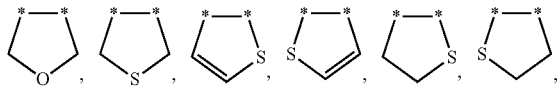

-continued

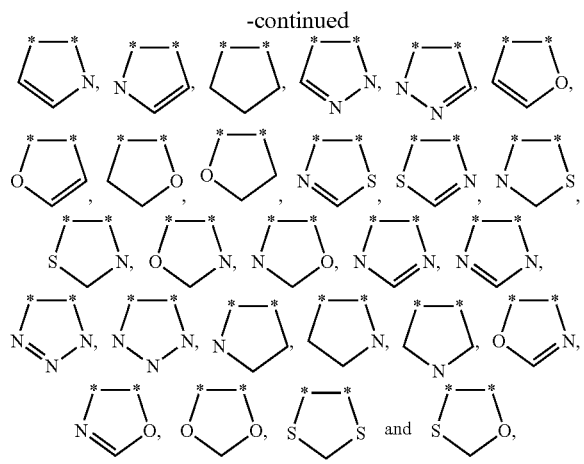

or a pharmaceutically acceptable salt thereof.

3. The compound of formula 1 according to claim 2, wherein ring A is selected from the group consisting of

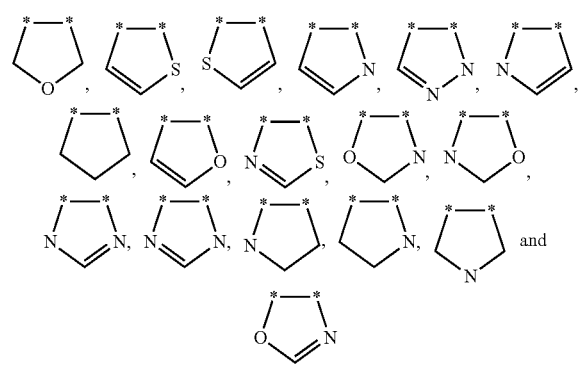

or a pharmaceutically acceptable salt thereof.

4. The compound of formula 1 according to claim 3, wherein
$R^2$ denotes a group selected from the group consisting of hydrogen, —OH, F, Cl, —CO—NH—$NH_2$ and —CO—$NH_2$,
or wherein
$R^2$ denotes a group selected from the group consisting of linear or branched $C_{1-6}$-alkyl, —$C_{1-6}$-fluoroalkyl, —$C_{1-6}$-chloroalkyl, —$R^3$, —O—$R^3$, —O—$C_{1-3}$-alkylene-$R^3$, —$C_{1-3}$-alkylene-O—$C_{1-3}$-alkyl, linear or branched —O—$C_{2-8}$-alkanol, linear or branched —O—$C_{1-3}$-haloalkyl, cyclopropyl, cyclobutyl, cyclopentyl, cyclohexyl, —O—$C_{2-4}$-alkylene-O—$C_{1-3}$-alkyl, —CO—$R^3$, —$C_{1-4}$-alkylene-$R^3$, —O—$C_{2-6}$-alkenyl, —O—$C_{2-3}$-alkylene-N($CH_3$)—$C_{1-3}$-alkyl, —CO—N($CH_3$)$_2$ and —CO—NH—$C_{1-3}$-alkyl, which may optionally be substituted by one, two or three substituents each independently selected from the group consisting of —CN, —$NH_2$, —$C_{1-2}$-alkylene-CN, —OH, —$C_{1-2}$-alkylene-OH, F, Cl, -oxo, —$C_{1-3}$-alkyl, —O—$R^3$, —$C_{1-3}$-alkylene-O—$R^3$, —CO—$C_{1-6}$-alkyl, —CO—$NH_2$, —CO—N($CH_3$)$_2$, —$C_{1-3}$-alkylene-$NH_2$, phenyl, —$C_{1-2}$-alkylene-OH and —CO—$C_{1-2}$-alkyl,
wherein each $R^3$ denotes independently from each other a group selected from a linear or branched $C_{1-6}$-alkyl, linear or branched $C_{1-4}$-fluoroalkyl, linear or branched $C_{1-4}$-chloroalkyl, linear or branched $C_{2-5}$-alkenyl, fully saturated or partially unsaturated $C_{3-8}$-cycloalkyl, —$C_{1-3}$-alkylene-$C_{3-6}$-cycloalkyl, a four-, five- or six-membered monocyclic, either fully saturated or partially unsaturated heterocycle comprising 1, 2 or 3 heteroatoms each independently selected from the group N, S and O, a five- to six-membered heteroaromatic group comprising 1, 2 or 3 heteroatoms each independently selected from the group N, S and O, phenyl and a nine- or ten-membered fully saturated, aromatic or partially unsaturated, bicyclic heterocycle comprising 1, 2 or 3 heteroatoms each independently selected from the group N, S and O,
or a pharmaceutically acceptable salt thereof.

5. The compound of formula 1 according to claim 4, wherein
$R^1$ is selected from the group consisting of H, F, Cl, SH, -oxo, —$NH_2$, —CO—Y, —CO—N($CH_3$)—Y, —CO—N($CH_3$)—($C_{1-3}$-alkylene)-Y, —CS—Y, —CS—N($CH_3$)—Y, —CS—N($CH_3$)—($C_{1-3}$-alkylene)-Y, methyl, ethyl, propyl, isopropyl, butyl, tert-butyl, —$C_{1-3}$-fluoroalkyl, —$C_{1-3}$-chloroalkyl, —CO—NH—Y, —CO—NH—$C_{1-4}$-alkylene-Y, —CO—NH—$C_{1-4}$-alkylene-(Y)$_2$, —CO—N($CH_3$)—($C_{2-3}$-alkylene)-O—($C_{1-3}$-alkyl), —$NH_2$, —$C_{1-6}$-alkylene-L, —$SO_2$-phenyl, —$SO_2$—($C_{1-3}$-alkyl), —CO—N($C_{1-4}$-alkyl)$_2$, —CO—N($C_{2-4}$-alkylene-O—$C_{1-3}$-alkyl)$_2$, a five- or six-membered heteroaromatic group comprising 1, 2 or 3 heteroatoms each independently selected from the group N, S and O,
with Y being a group selected from the group consisting of —$NH_2$, —NH($CH_3$), —N($CH_3$)$_2$, —$C_{1-6}$-alkylene-N($CH_3$)$_2$; —O—$C_{1-3}$-alkyl, OH and —N(ethyl)$_2$,
or with Y being a group selected from the group consisting of a four-, five-, six- or seven-membered monocyclic fully saturated or partially unsaturated heterocycle comprising 1, 2 or 3 heteroatoms each independently selected from the group N, S and O with the proviso hat this heterocycle comprises at least one N-atom and that this heterocycle is directly attached to the molecule via this N-atom, a five- or six-membered monocyclic heteroaromatic group comprising 1, 2 or 3 heteroatoms each independently selected from the group of N, S and O, and a $C_{3-6}$-cycloalkyl,
or with Y being a 9- to 11-membered bicyclic annellated fully saturated or partially unsaturated heterocycle comprising 1, 2, 3 or 4 heteroatoms each independently from each other selected from the group N, S and O,
or with Y being an 8- to 11-membered bicyclic fully saturated spiro-heterocycle comprising 1, 2 or 3 heteroatoms each independently selected from the group N, S and O with the proviso that this spiro-heterocycle comprises at least one N-atom and that this heterocycle is directly attached to the molecule via this N-atom,
or with Y being a six- or seven-membered fully saturated heterocycle comprising 1, 2 or 3 heteroatoms each independently selected from the group N, S and O, which is bridged by an additional —$C_{1-3}$-alkylene-unit,
whereby each Y may optionally be substituted by one or more groups Z each independently from each other selected from the group consisting of F, Cl, -oxo, OH, $C_{1-5}$-alkyl, —$C_{1-5}$-alkanol, —O—$C_{1-3}$-alkyl, a five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO-L, —C$_{1-3}$-alkylene-CO-L, —C$_{1-3}$-alkylene-O—C$_{1-3}$-alkyl, —N(CH$_3$)$_2$ and —N(ethyl)$_2$, whereby each group Z may optionally be further substituted by one, two or three groups T each independently selected from the group consisting of -oxo, OH, F, Cl, methyl, ethyl, propyl, —O-methyl, —O-ethyl, —O-propyl, —O-isopropyl, —N(methyl)$_2$, —N(ethyl)$_2$, 5- to 6-membered fully saturated, partially unsaturated or aromatic heterocycle comprising 1 or 2 heteroatoms each independently selected from the group N, O and S; a cyclopropyl, cyclobutyl, cyclopentyl, cyclohexyl and —CN, wherein each group T may also optionally be substituted by a group selected from the group consisting of methyl, ethyl, propyl, isopropyl, F, Cl, OH, oxo, —O-methyl, —O-ethyl, —O-propyl and —O-isopropyl, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, F, Cl, OH and -oxo, or a pharmaceutically acceptable salt thereof.

6. The compound of formula 1 according to claim 5, wherein
R$^6$ denotes a group selected from H, Br, Cl, F, methyl,
or a pharmaceutically acceptable salt thereof.

7. The compound of formula 1 according to claim 6, wherein R$^4$ denotes a group selected from H, F, Cl, OH, —OCH$_3$, —CH$_2$—OH, —CN
wherein R$^5$ denotes a group selected from H, F, Cl, OH, —OCH$_3$, —C$_{1-4}$-alkyl, —CH$_2$—OH and —CN,
or a pharmaceutically acceptable salt thereof.

8. The compound of formula 1 according to claim 7, wherein R$^1$ is not hydrogen and wherein R$^1$ is attached to a C-atom of ring A,
or a pharmaceutically acceptable salt thereof.

9. The compound of formula 1 according to claim 7, wherein ring A is selected from the group consisting of

or a pharmaceutically acceptable salt thereof.

10. The compound of formula 1 according to claim 7, wherein
R$^1$ is selected from the group consisting of
—CO—Y, —CO—N(CH$_3$)—Y, —CO—N(CH$_3$)—(C$_{1-3}$-alkylene)-Y, —CO—NH—Y,
with Y being a group selected from the group consisting of —NH$_2$, —NH(CH$_3$), —N(CH$_3$)$_2$, —C$_{1-4}$-alkylene-N(CH$_3$)$_2$, —O-methyl, —O-ethyl, —OH and —N(ethyl)$_2$,
or with Y being selected from the group consisting of a five- or six-membered monocyclic fully saturated or partially unsaturated heterocycle comprising 1, 2 or 3 heteroatoms each independently selected from the group N, S and O with the proviso hat this heterocycle comprises at least one N-atom and that this heterocycle is directly attached to the molecule via this N-atom, a five- or six-membered monocyclic heteroaromatic group comprising 1, 2 or 3 heteroatoms each independently selected from the group of N, S and O; —C$_{3-6}$-cycloalkyl and a 9- to 10-membered bicyclic fully saturated spiro-heterocycle comprising 1, 2 or 3 heteroatoms each independently selected from the group N, S and O, with the proviso that this heterocycle is directly attached to the molecule via this N-atom, whereby each Y may optionally be substituted by one or more groups Z, whereby each group Z may optionally be further substituted by one, two or three groups T, wherein each group T may also optionally be substituted by a group selected from the group consisting of methyl, ethyl, propyl, isopropyl, F, Cl, OH, oxo, —O-methyl, —O-ethyl, —O-propyl and —O-isopropyl, or a pharmaceutically acceptable salt thereof.

11. The compound of formula 1 according to claim 10, wherein
Y is selected from the group consisting of —NH$_2$, —NH(CH$_3$), —N(CH$_3$)$_2$, —C$_{1-4}$-alkylene-N(CH$_3$)$_2$, —O-methyl, —O-ethyl and —N(ethyl)$_2$,
or wherein
Y is selected from the group consisting of
piperazine-1-yl, piperidine-1-yl, morpholine-4-yl, pyrrolidine-1-yl, azetidine-1-yl, [1,4]oxazepane-4-yl, [1,4]diazepane-1-yl), pyridine-1-yl, 4-Oxa-1,9-diaza-spiro[5.5]undecan-9-yl and cyclohexyl, whereby each Y may optionally be substituted by one or more groups Z, whereby each group Z may optionally be further substituted by one, two or three groups T, wherein each group T may also optionally be substituted by a group selected from the group consisting of methyl, ethyl, propyl, isopropyl, F, Cl, OH, oxo, —O-methyl, —O-ethyl, —O-propyl and —O-isopropyl, or a pharmaceutically acceptable salt thereof.

12. The compound of formula 1 according to claim 11, wherein R$^1$ is CO—Y,
wherein
Y is selected from the group consisting of —NH(CH$_3$), —N(CH$_3$)$_2$,

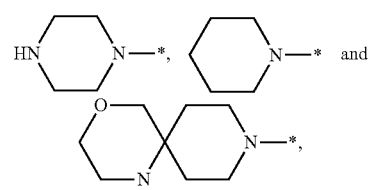

whereby each Y may optionally be substituted by one or more groups Z, each Z independently from one another selected from the group consisting of methyl, oxo, CO-L, pyrrolidinyl, tetrahydrofuranyl, tetrahydrothiophenyl, piperidinyl, piperazinyl, pyranyl and morpholinyl, whereby each group Z may optionally be further substituted by one, two or three groups T, each T independently from one another selected from the group consisting of methyl, oxo, F and Cl, whereby each L is selected from the group consisting of pyrrolidinyl, tetrahydrofuranyl, tetrahydrothiophenyl, piperidinyl, piperazinyl, pyranyl and morpholinyl, or a pharmaceutically acceptable salt thereof.

13. The compound of formula 1 according to claim 12, wherein
R$^2$ is selected from the group consisting of H, —R$^3$, —O—R$^3$, —O—C$_{1-3}$-alkylene-R$^3$ and —C$_{1-3}$-alkylene-O—C$_{1-3}$-alkyl, which may optionally be substituted by one, two or three substituents as defined in one of claims 1 to 5, wherein $R^3$ is selected from the group consisting of linear or branched $C_{1-6}$-alkyl, linear or branched $C_{1-4}$-haloalkyl, or a pharmaceutically acceptable salt thereof.

14. The compound of formula 1 according to claim 13, wherein $R^2$ is H or wherein $R^2$ is selected from the group consisting of —$R^3$, —O—$R^3$, —O—$C_{1-3}$-alkylene-$R^3$ and —$C_{1-3}$-alkylene-O—$C_{1-3}$-alkyl, which may optionally be substituted by one or more substituents selected from the group consisting of OH, oxo, methyl, —CN, F, Cl, —O—$CH_3$, wherein $R^3$ is selected from the group consisting of linear or branched $C_{1-6}$-alkyl and a linear or branched $C_{1-4}$-haloalkyl, or a pharmaceutically acceptable salt thereof.

15. The compound of formula 1 according to claim 14, wherein $R^6$ is selected from the group consisting of H, Cl and methyl or a pharmaceutically acceptable salt thereof.

16. A compound selected from the group consisting of

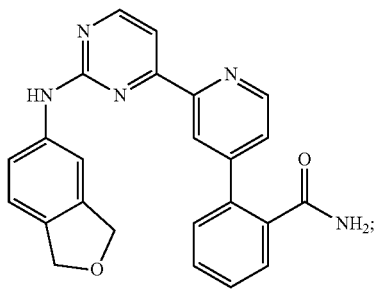

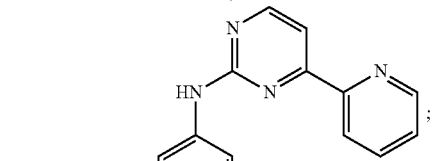

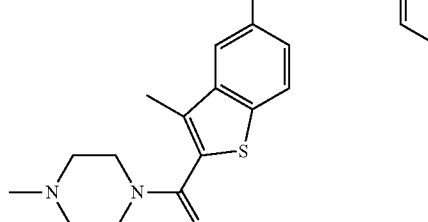

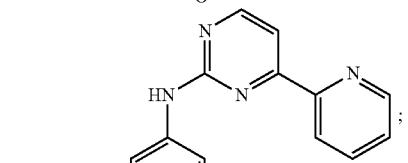

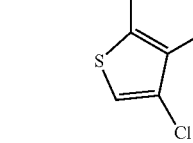

-continued

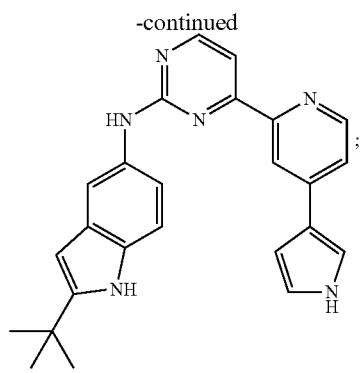

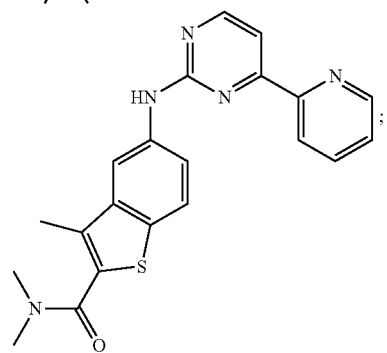

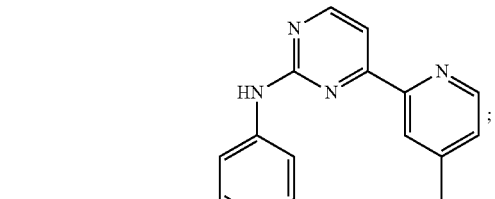

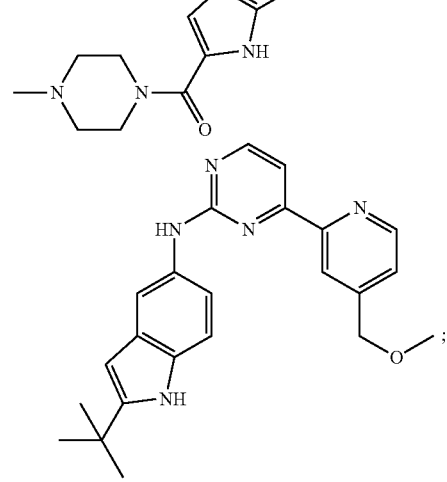

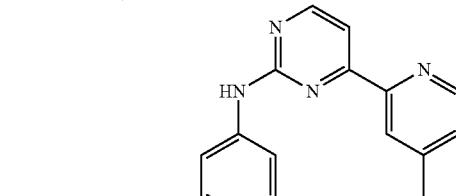

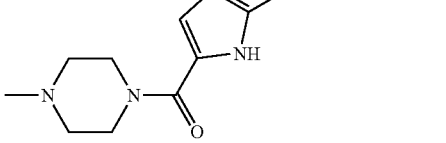

321
-continued
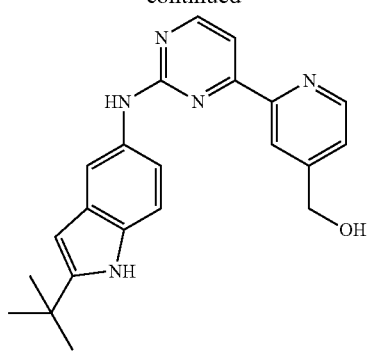
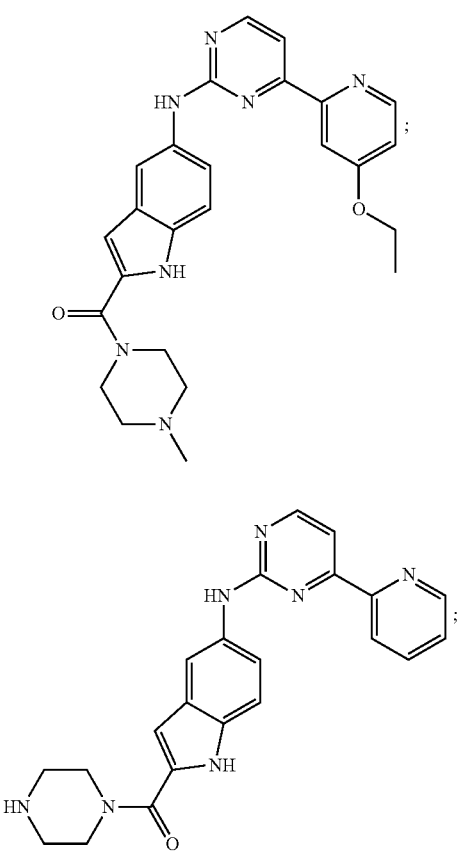
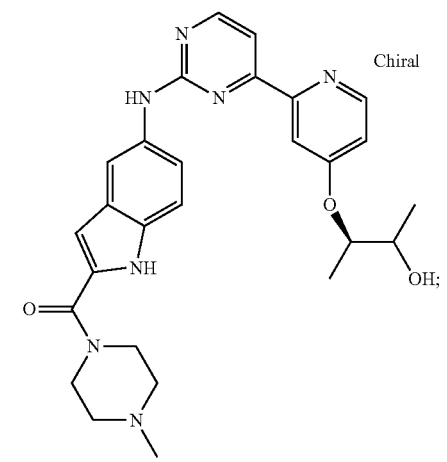
322
-continued
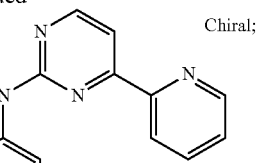
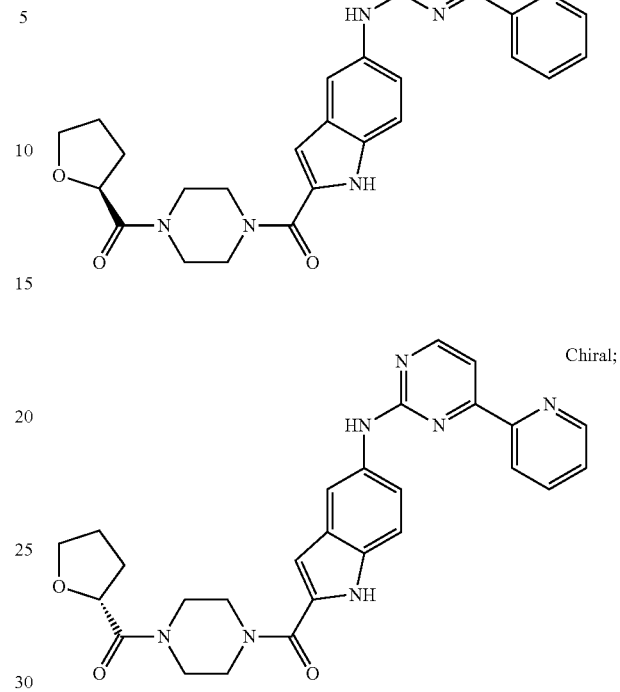
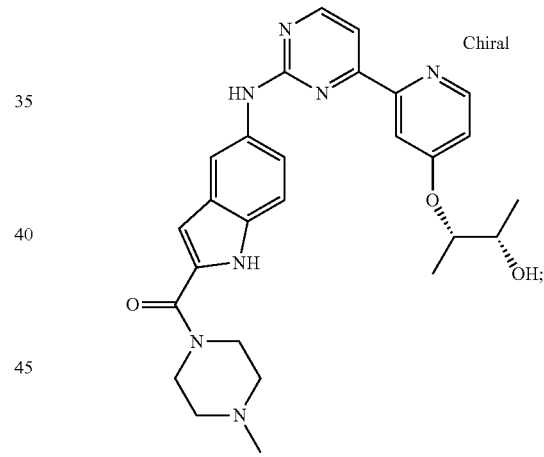
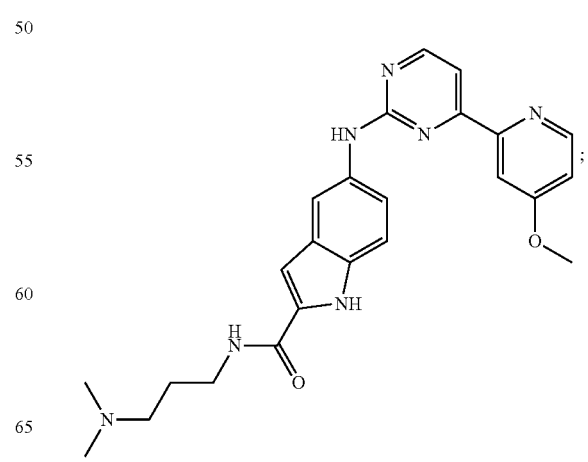

323
-continued
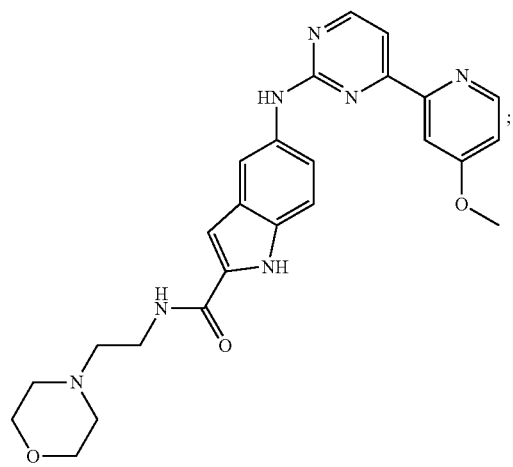
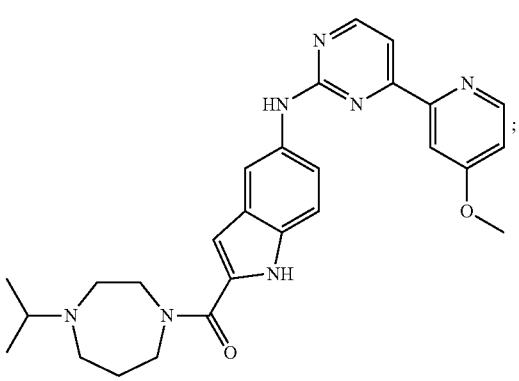
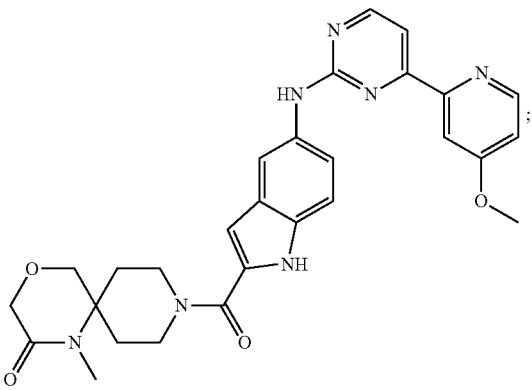
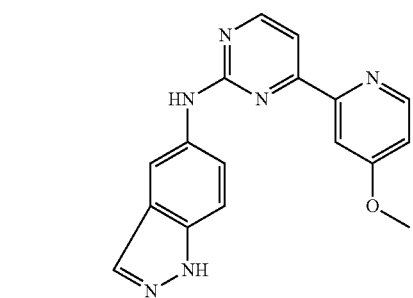
324
-continued
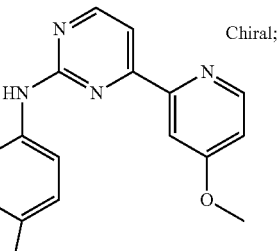
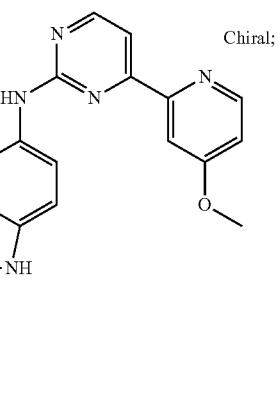
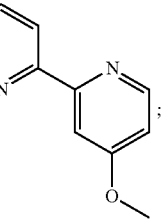
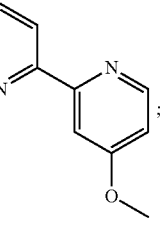
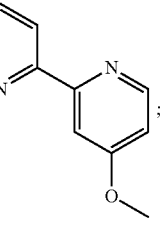

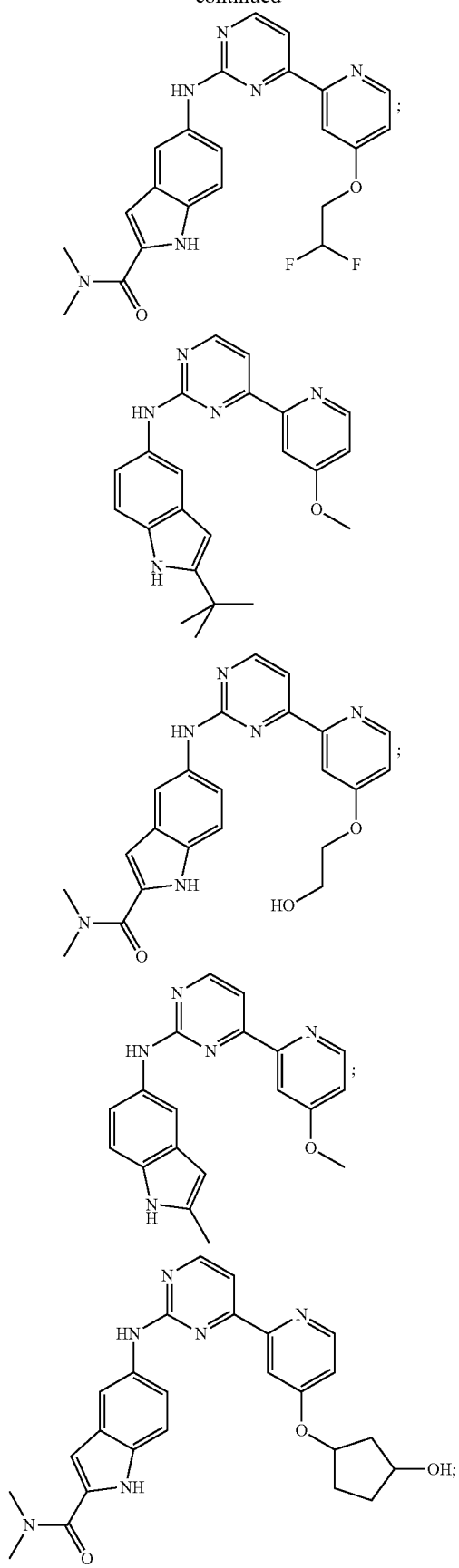
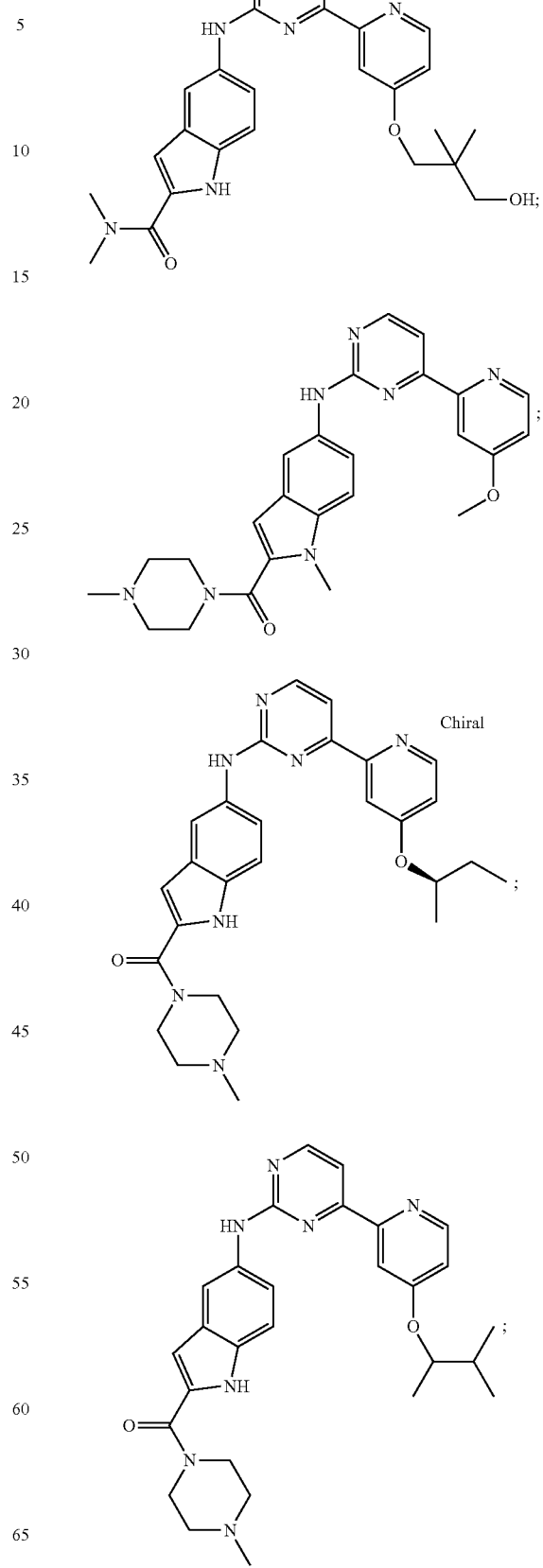

327
-continued
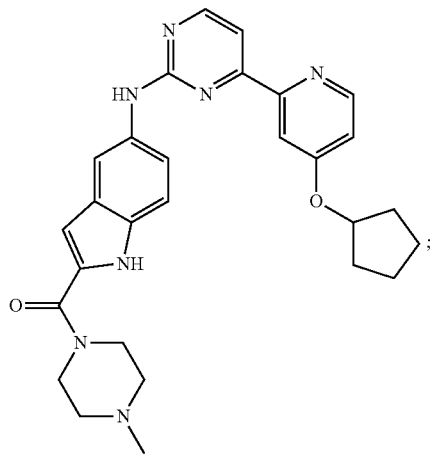
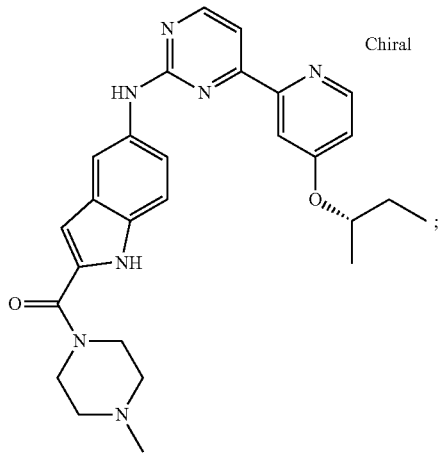
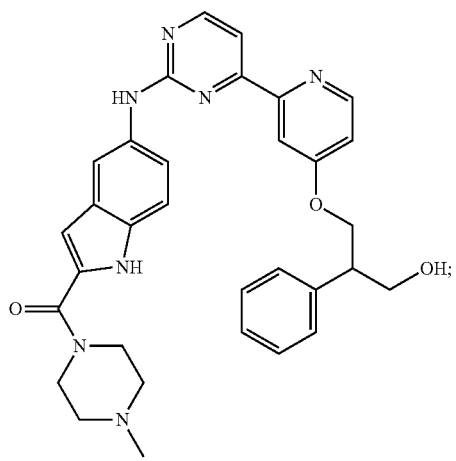
328
-continued
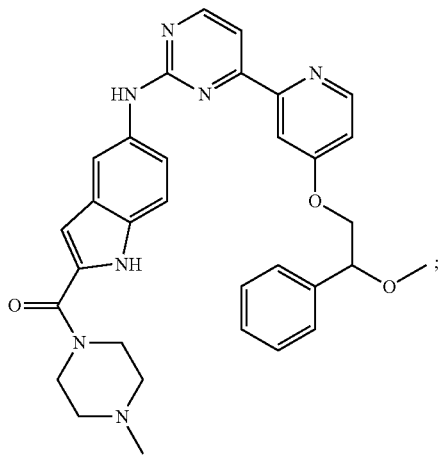
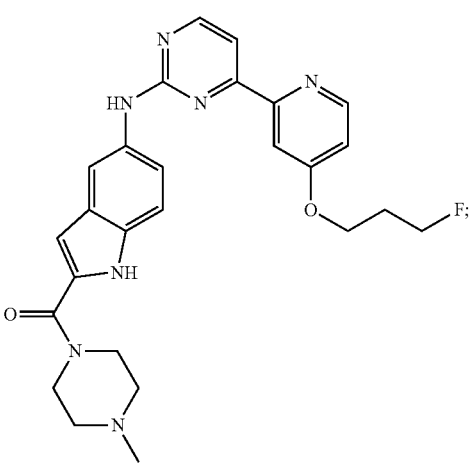

329
-continued
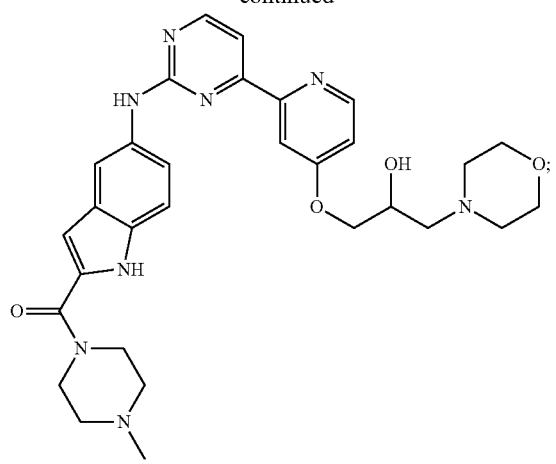
330
-continued
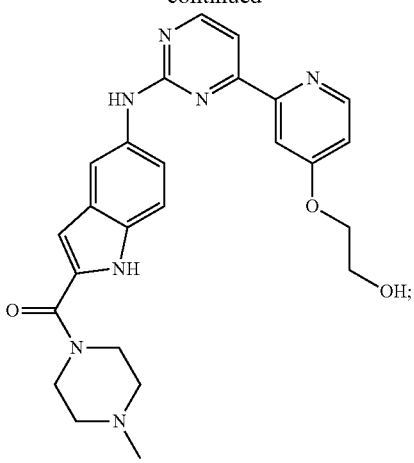
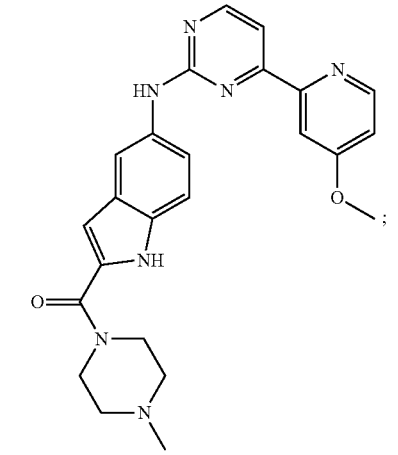
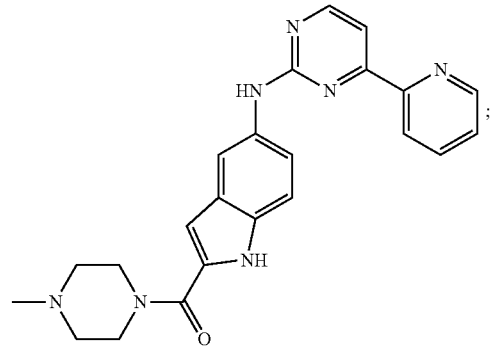
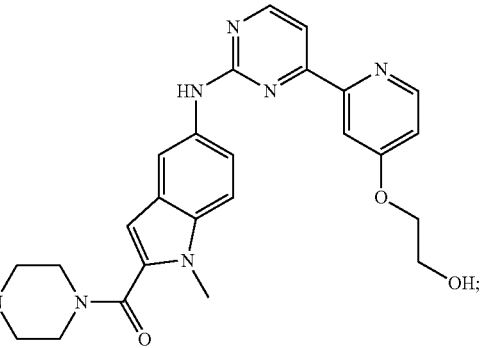
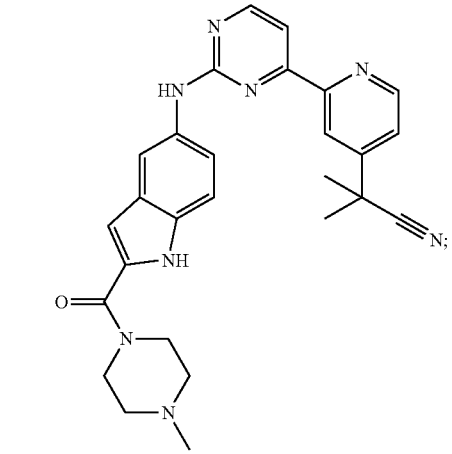
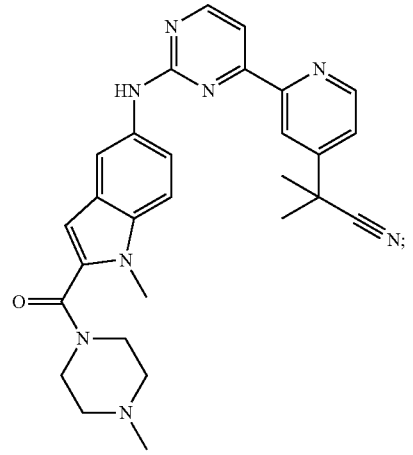

331
-continued
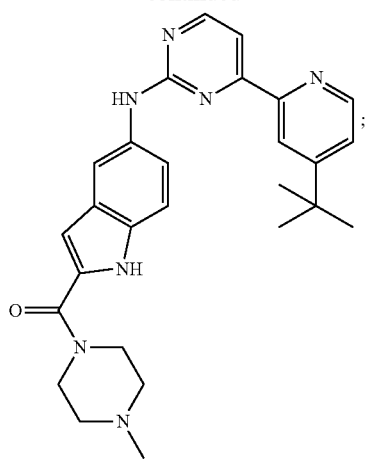
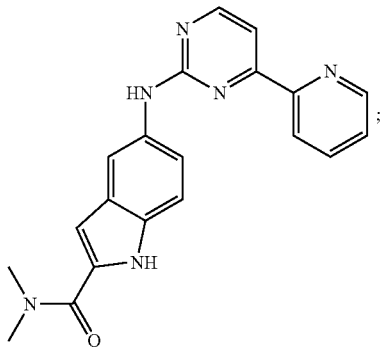
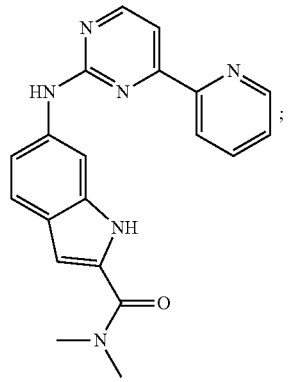
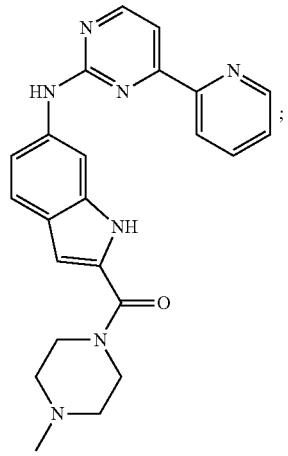
332
-continued
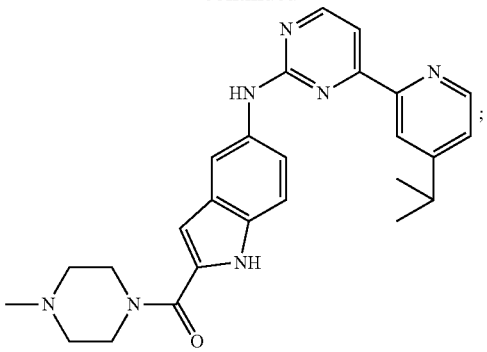
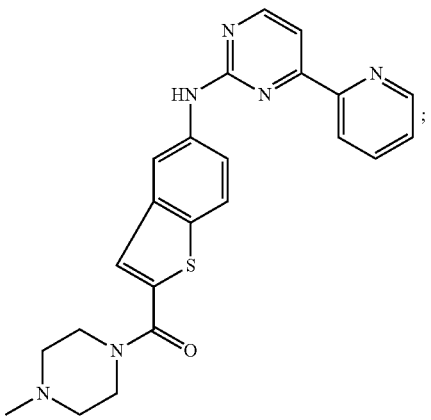
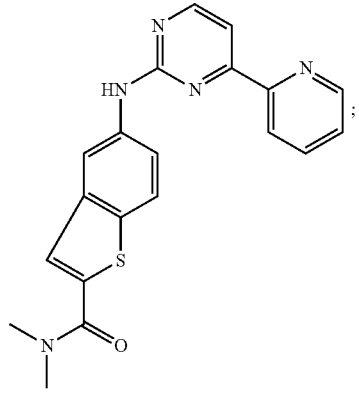
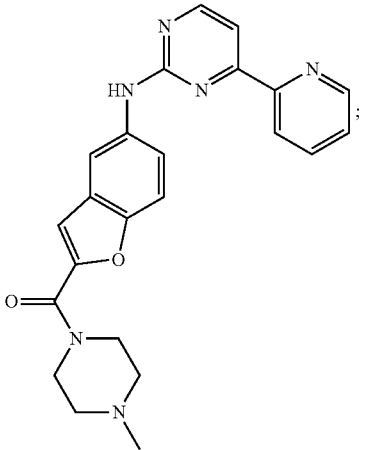

-continued
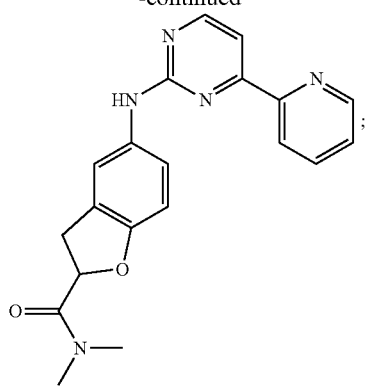
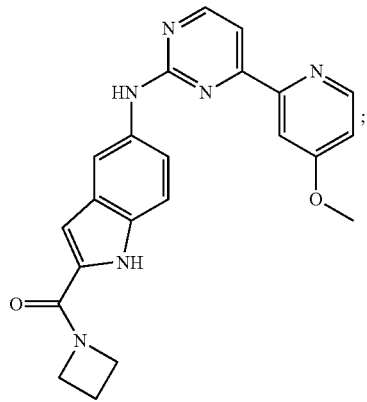
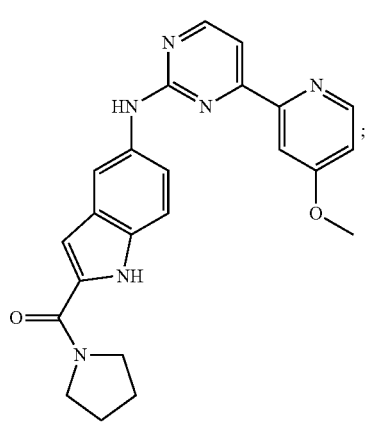
-continued
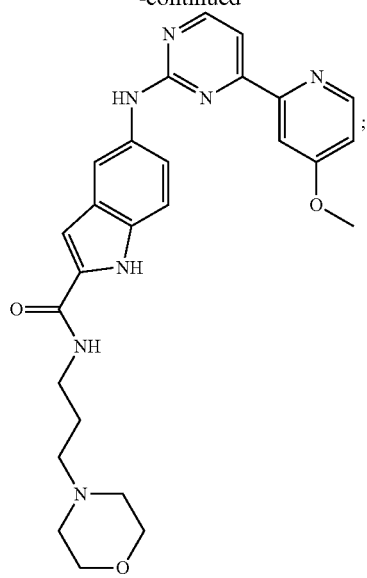
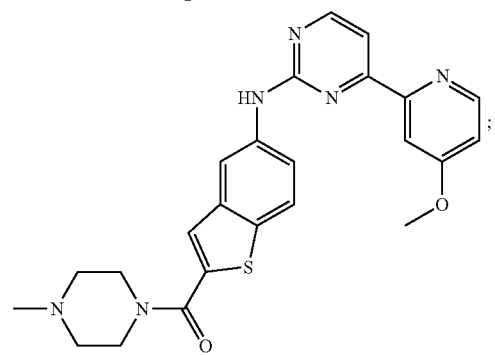
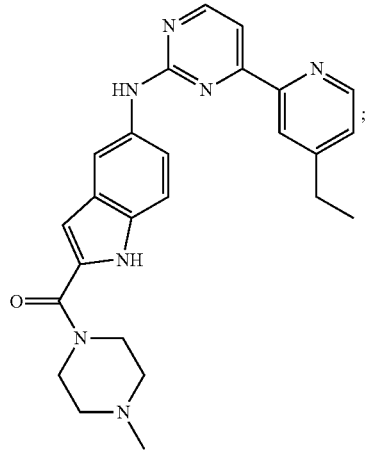
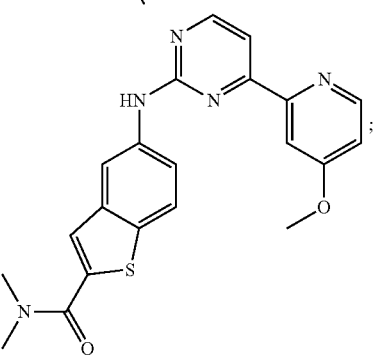

335
-continued
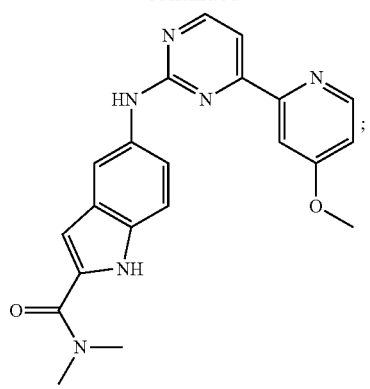
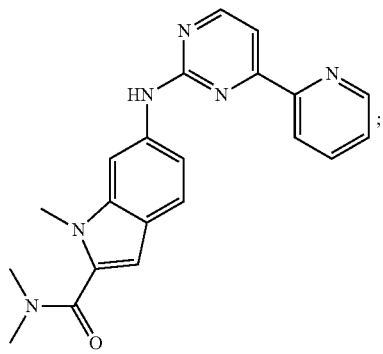
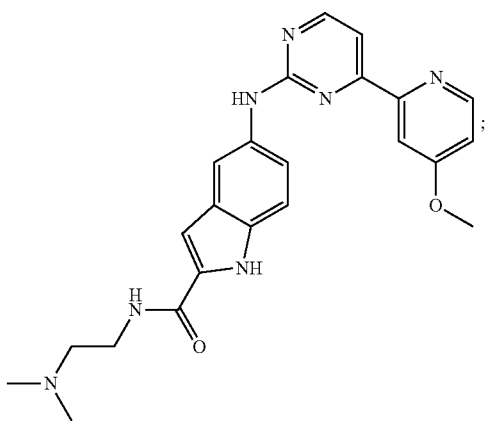
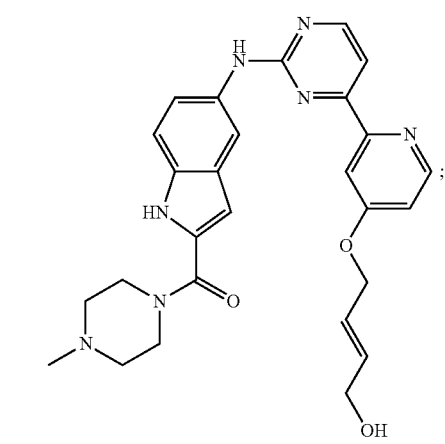
336
-continued
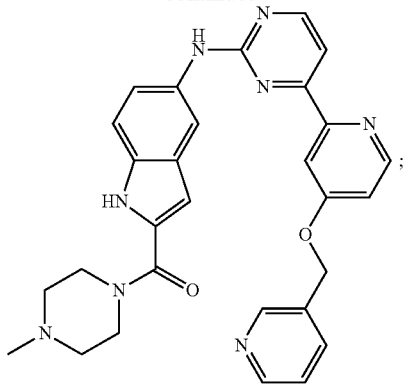
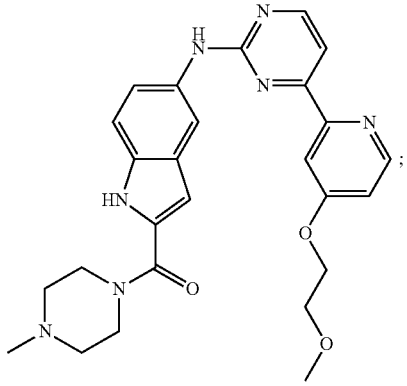
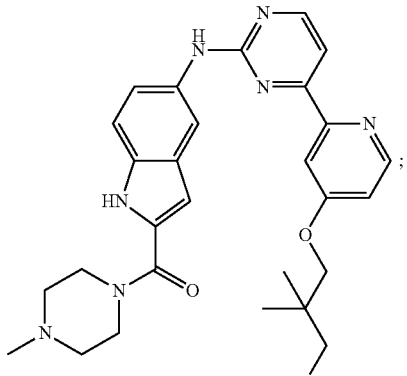
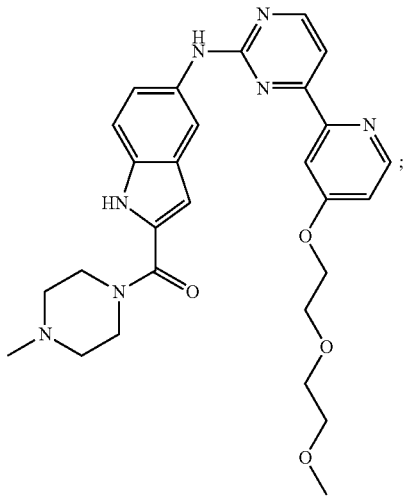

337
-continued
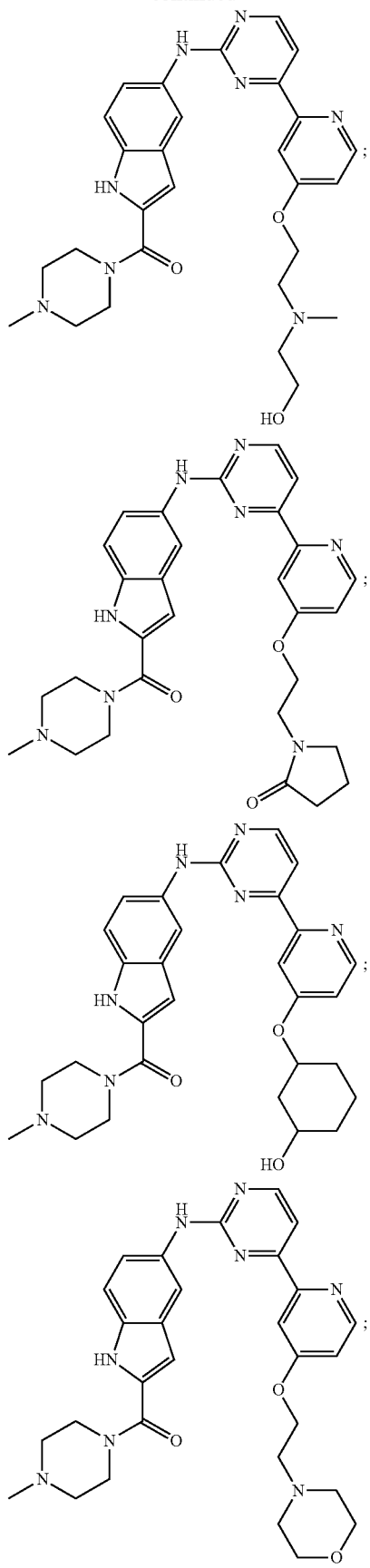
338
-continued
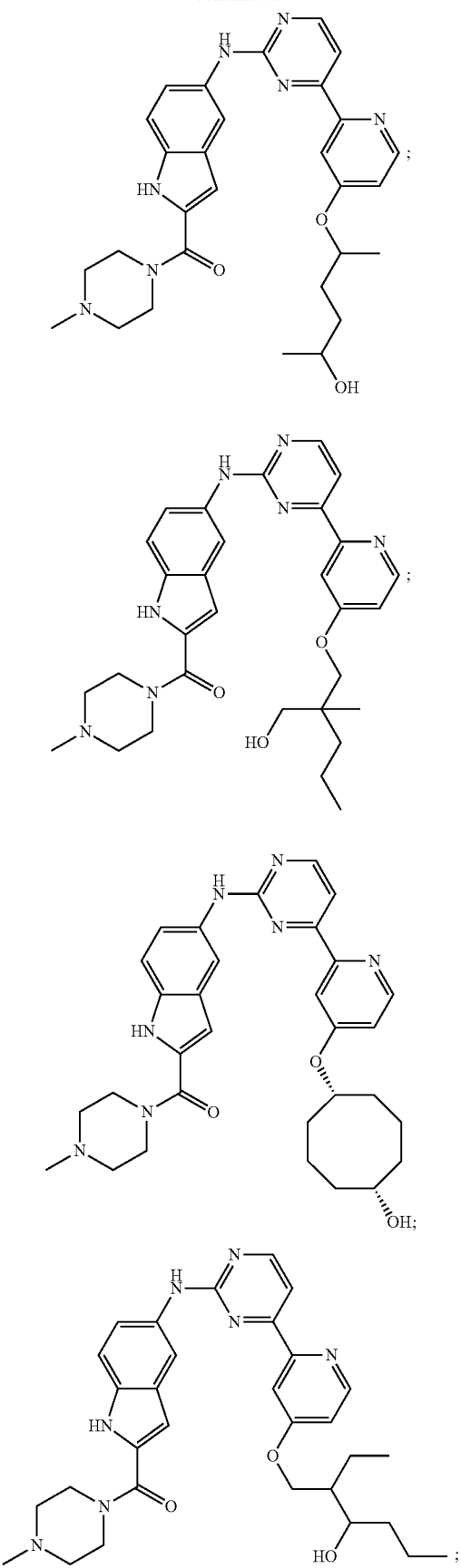

-continued
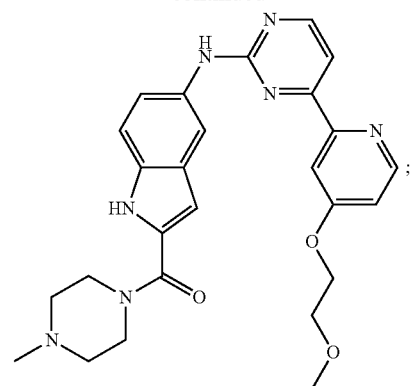
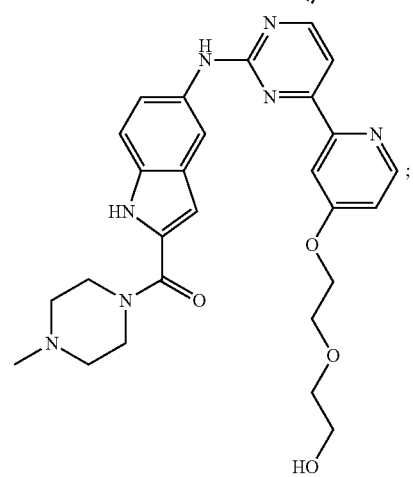
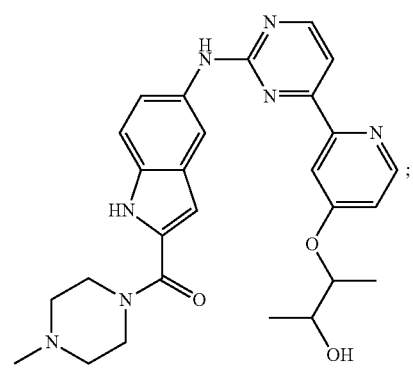
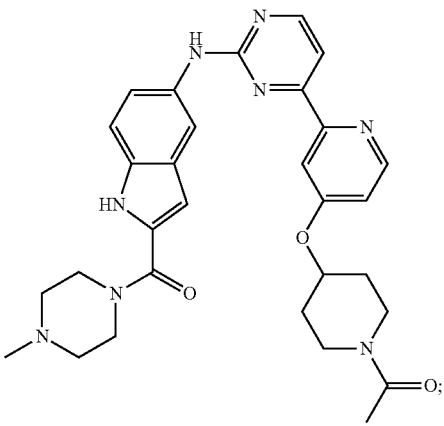
-continued
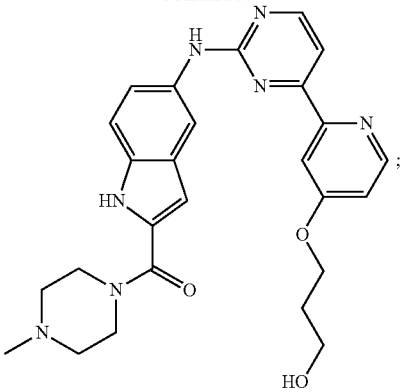
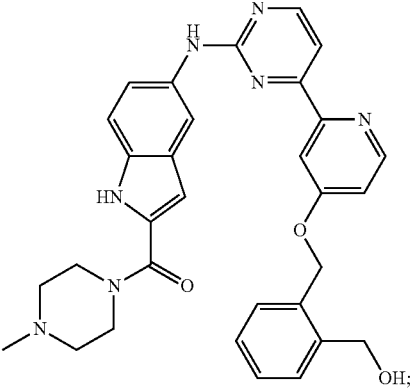
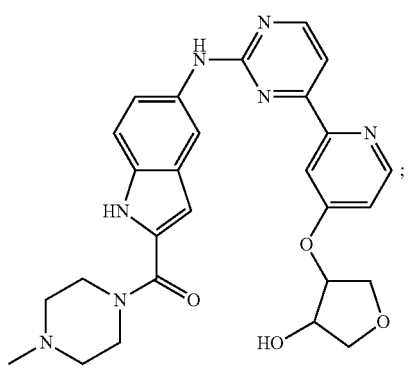
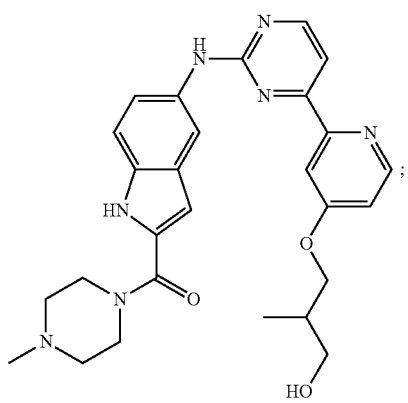

341
-continued
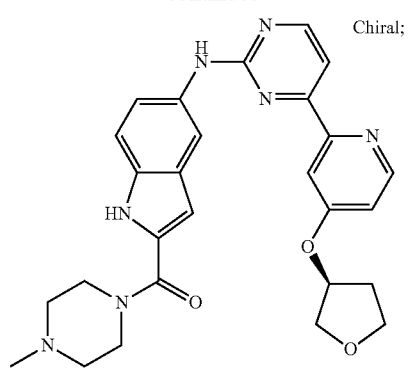
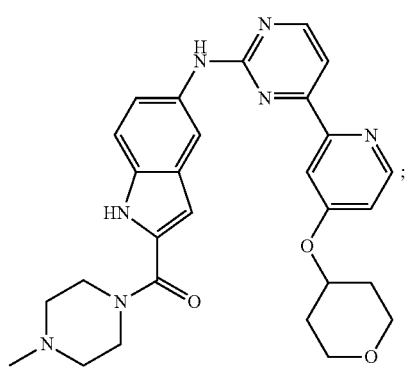
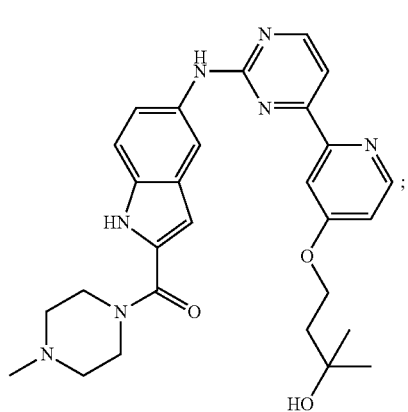
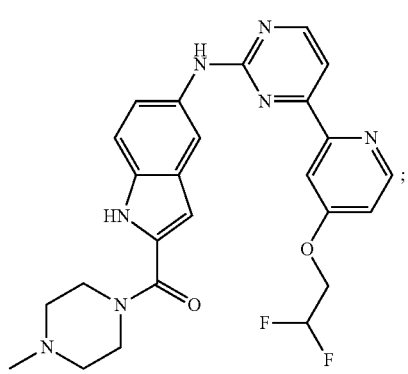
342
-continued
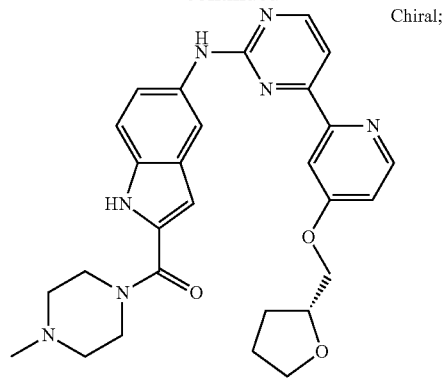
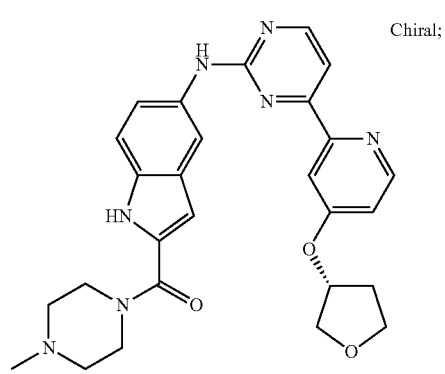
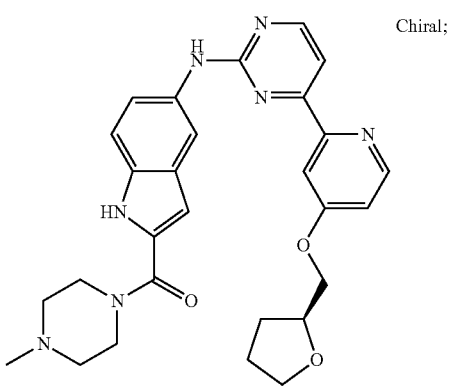
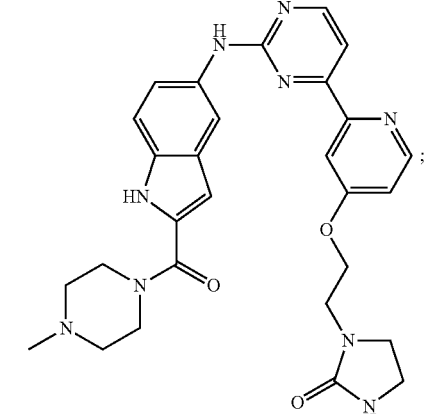

343
-continued
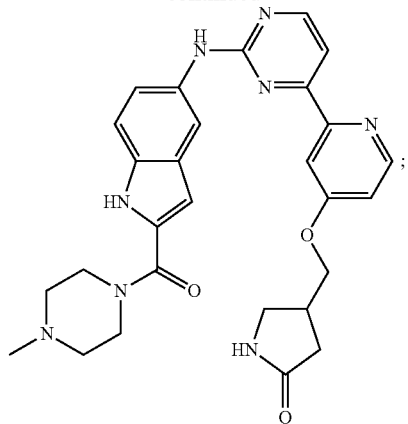
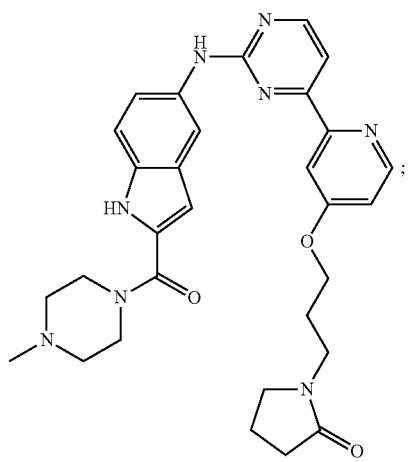
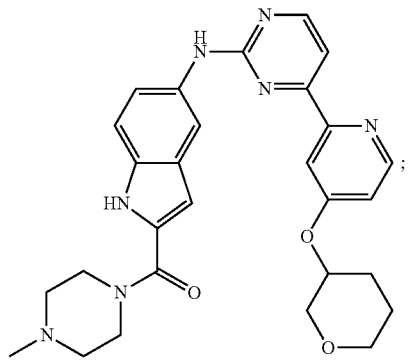
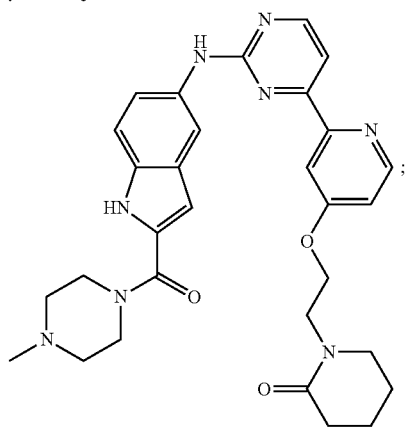
344
-continued
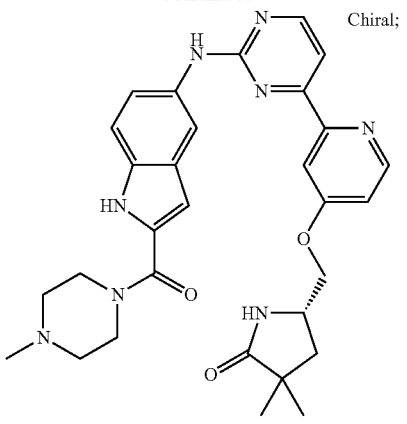
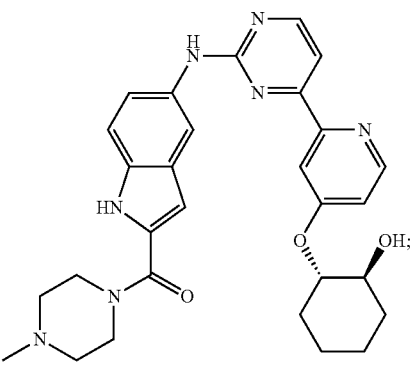
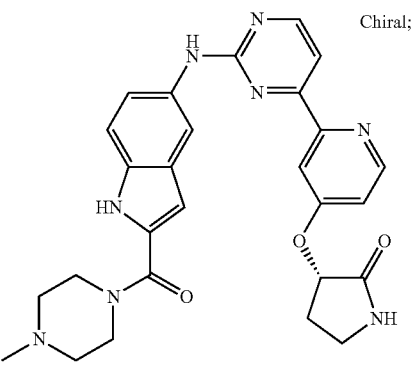
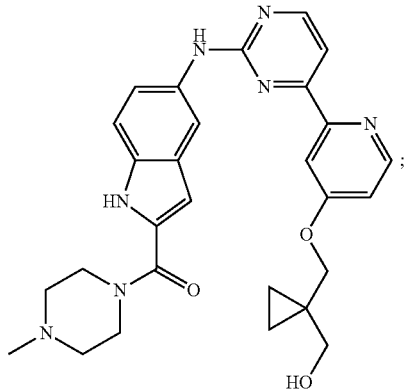

345
-continued
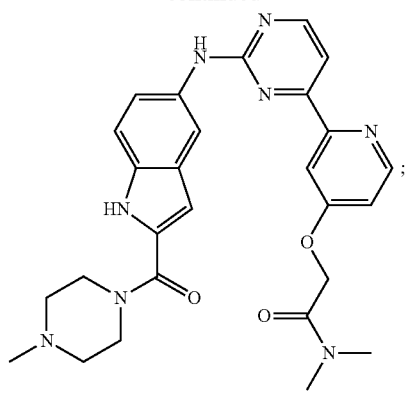
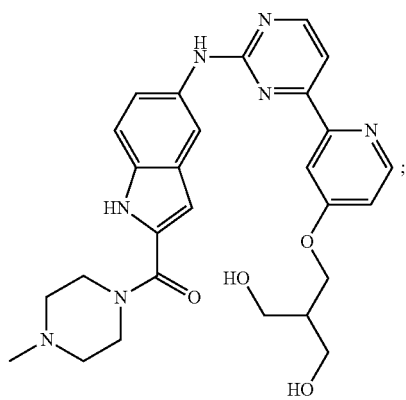
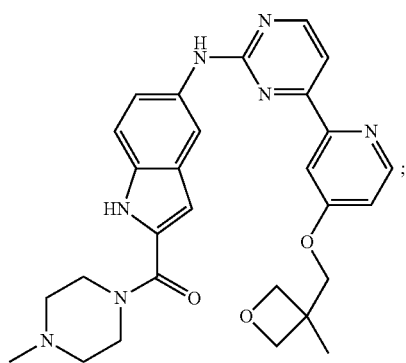
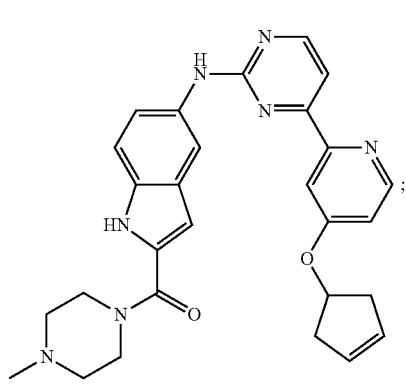
346
-continued
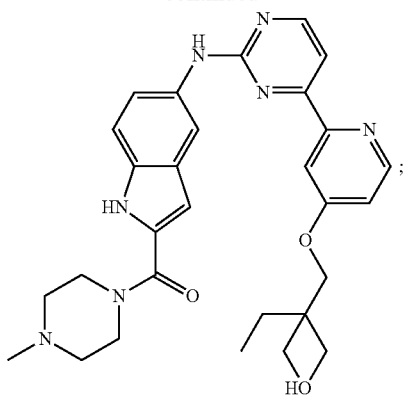
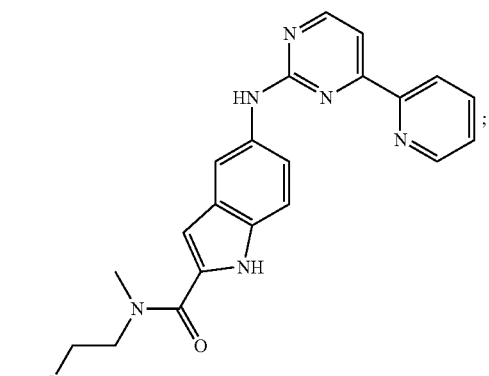
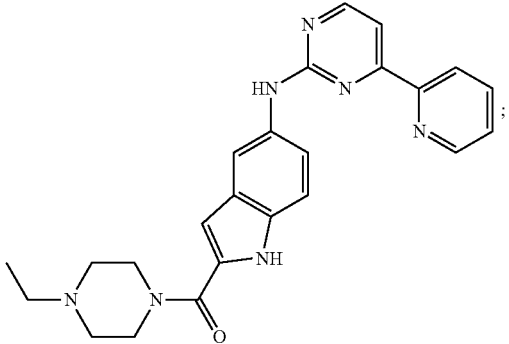
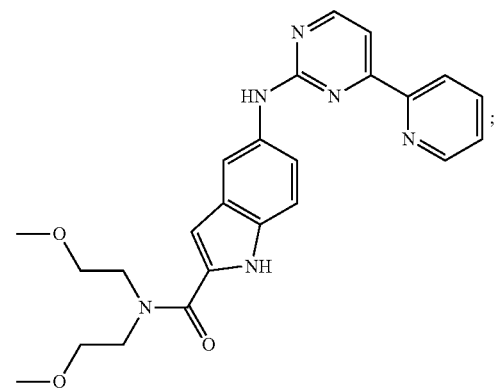

347
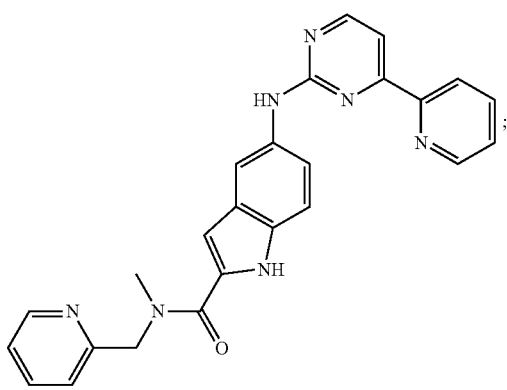
348
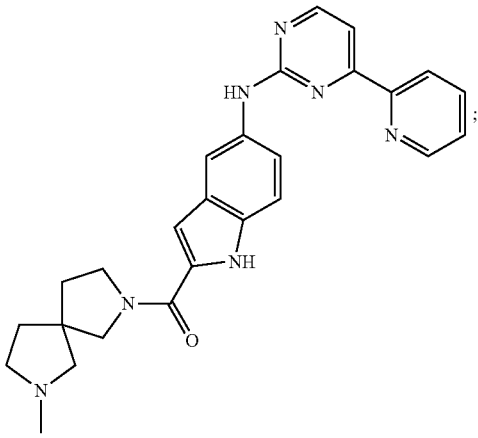
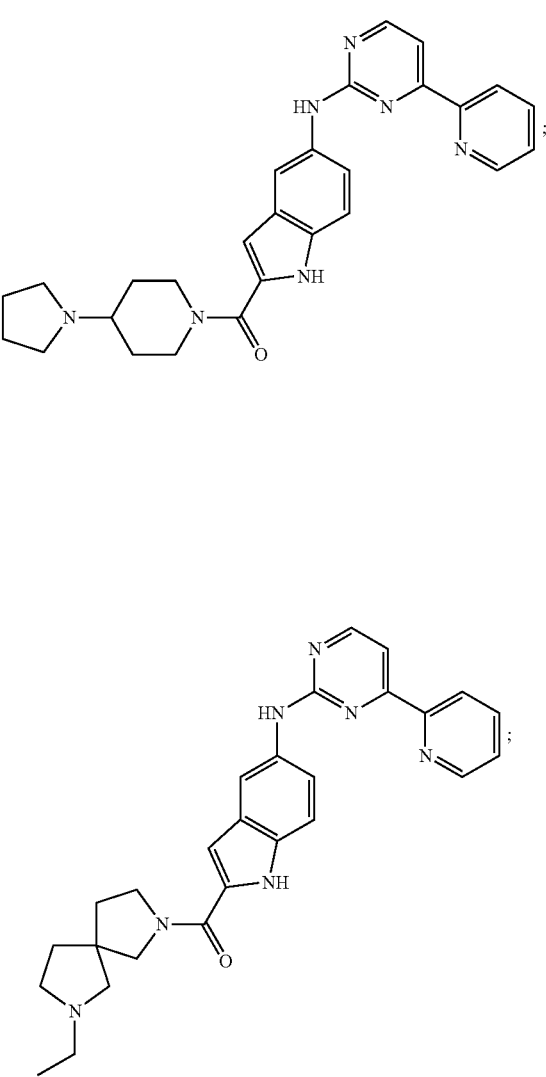

349
-continued
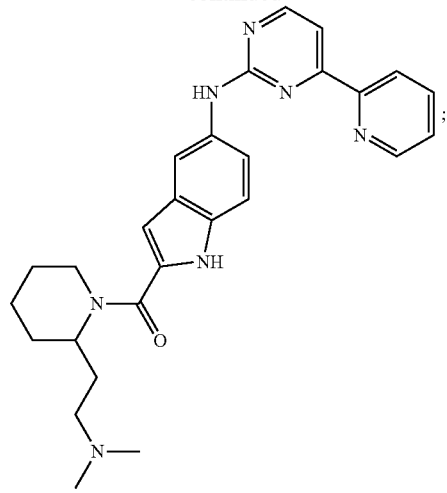
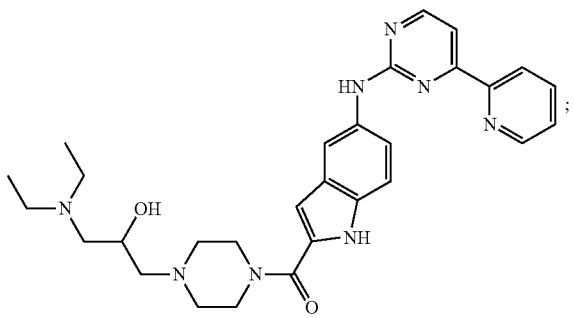
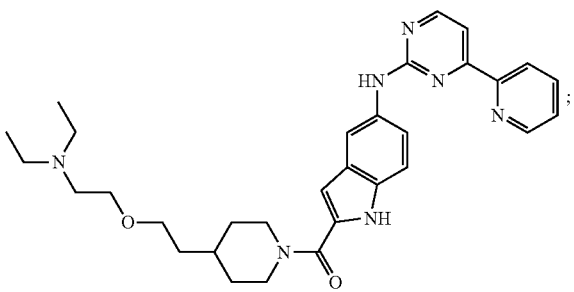
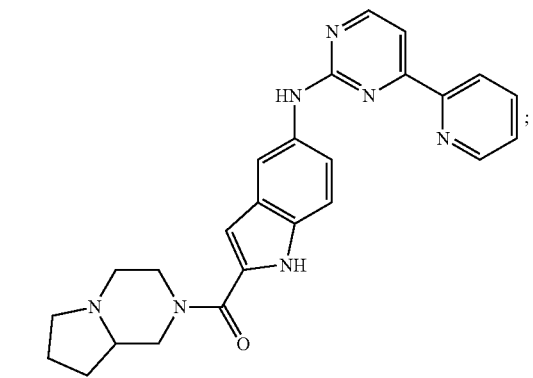
350
-continued
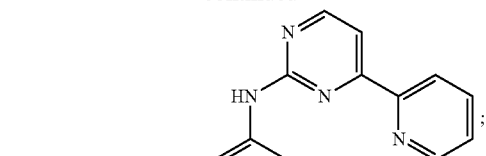
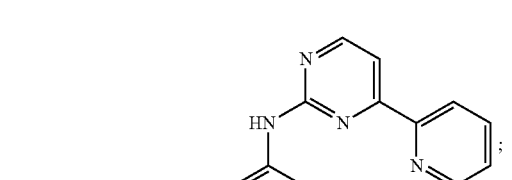
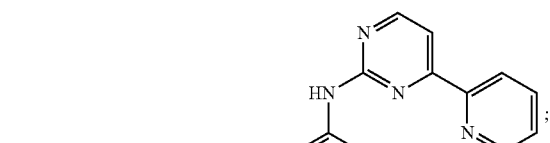
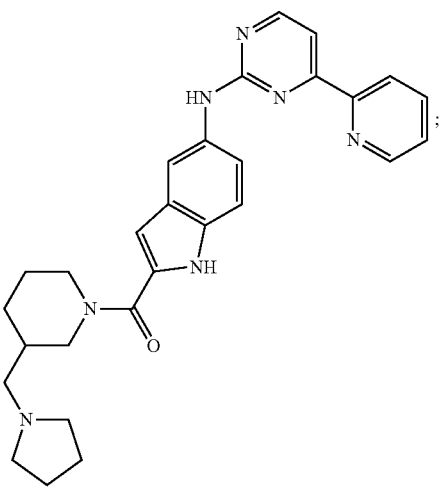

351
-continued
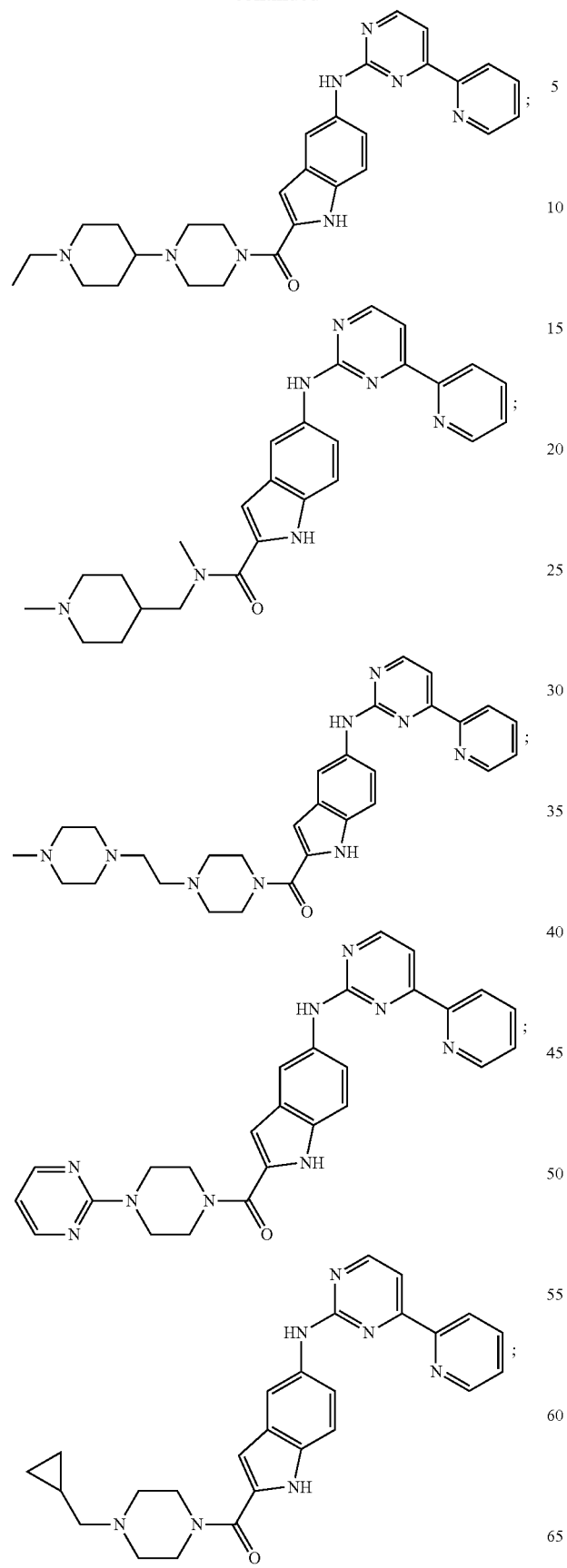
352
-continued
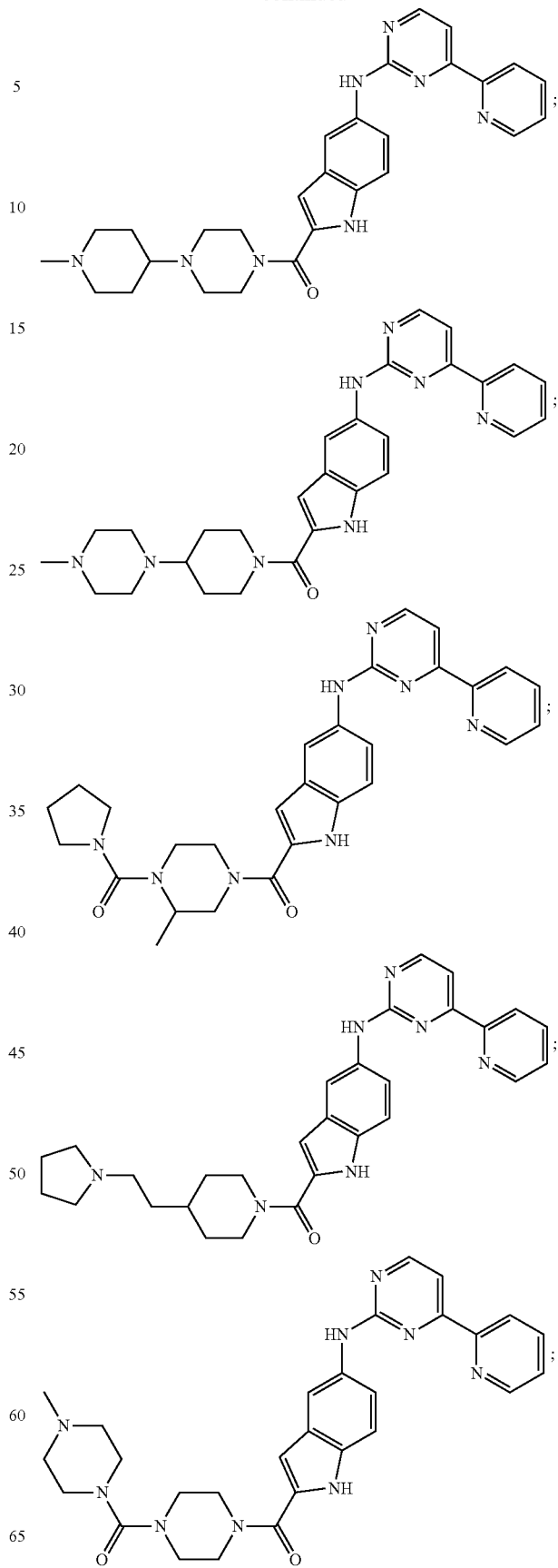

353
-continued
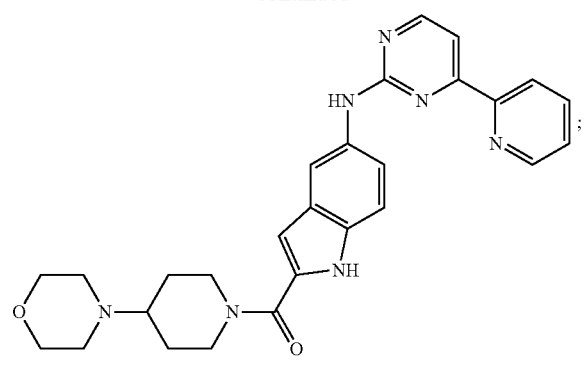
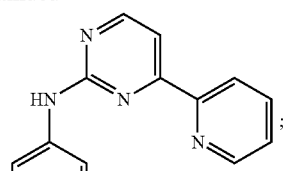
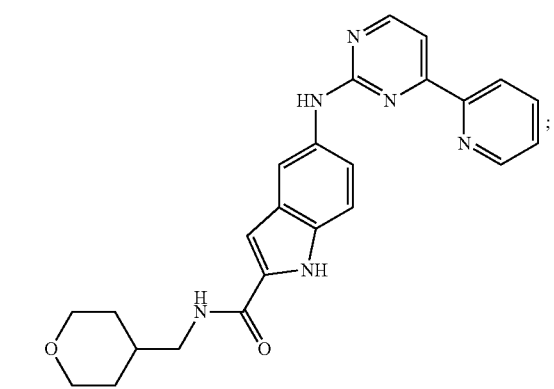
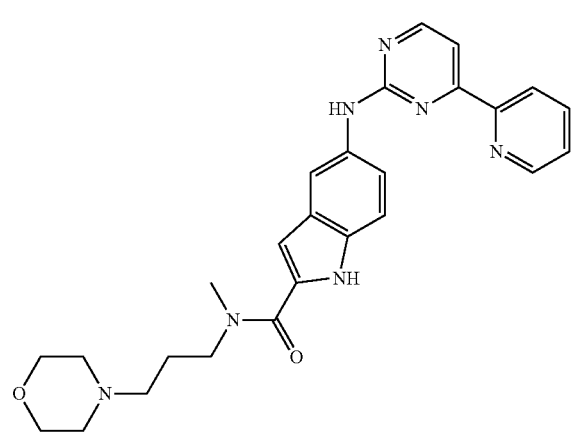
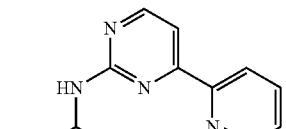
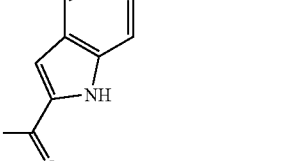
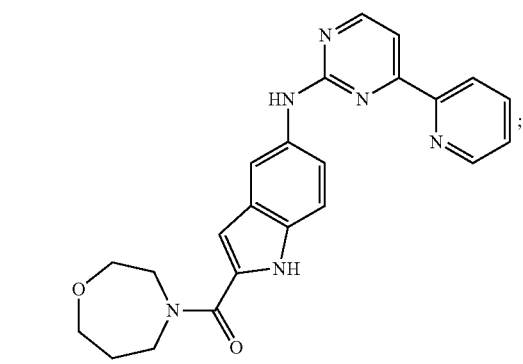
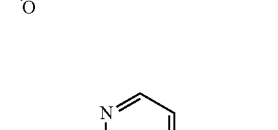
354
-continued
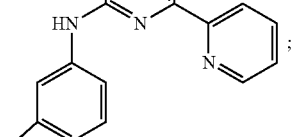
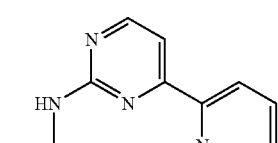
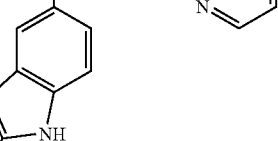

355
-continued
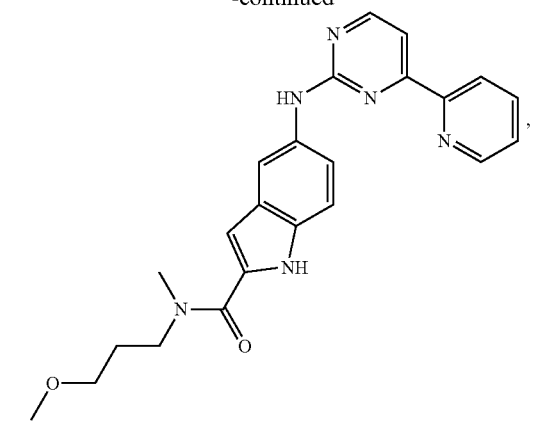
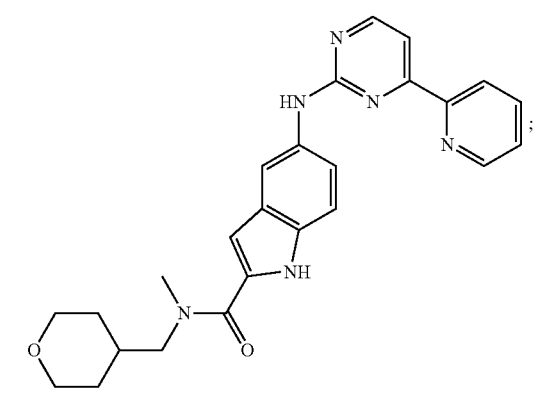
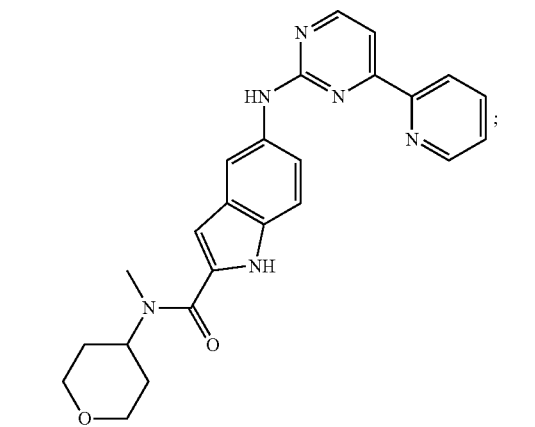
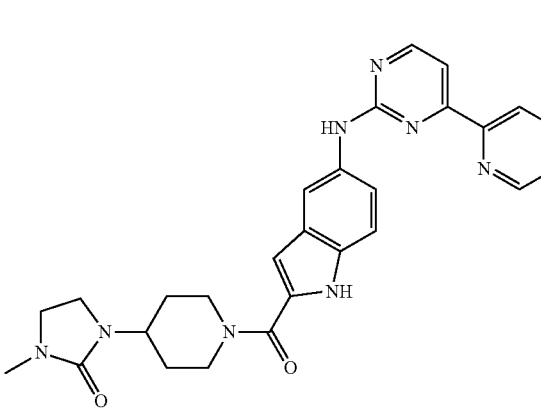
356
-continued
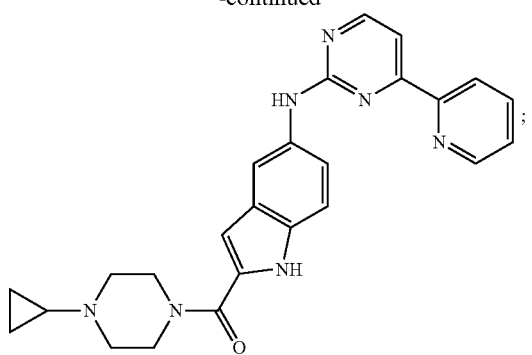
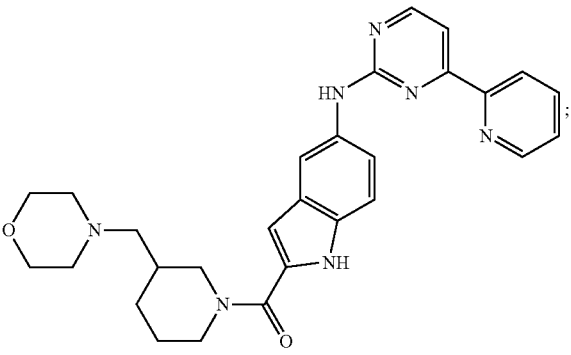
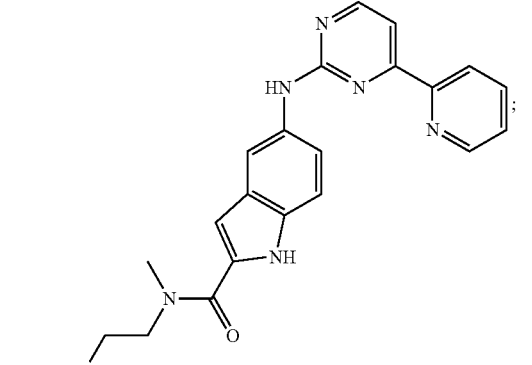
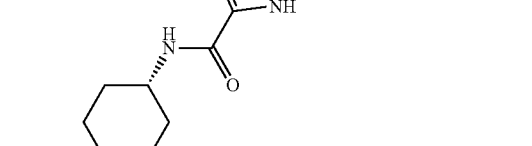

357
-continued
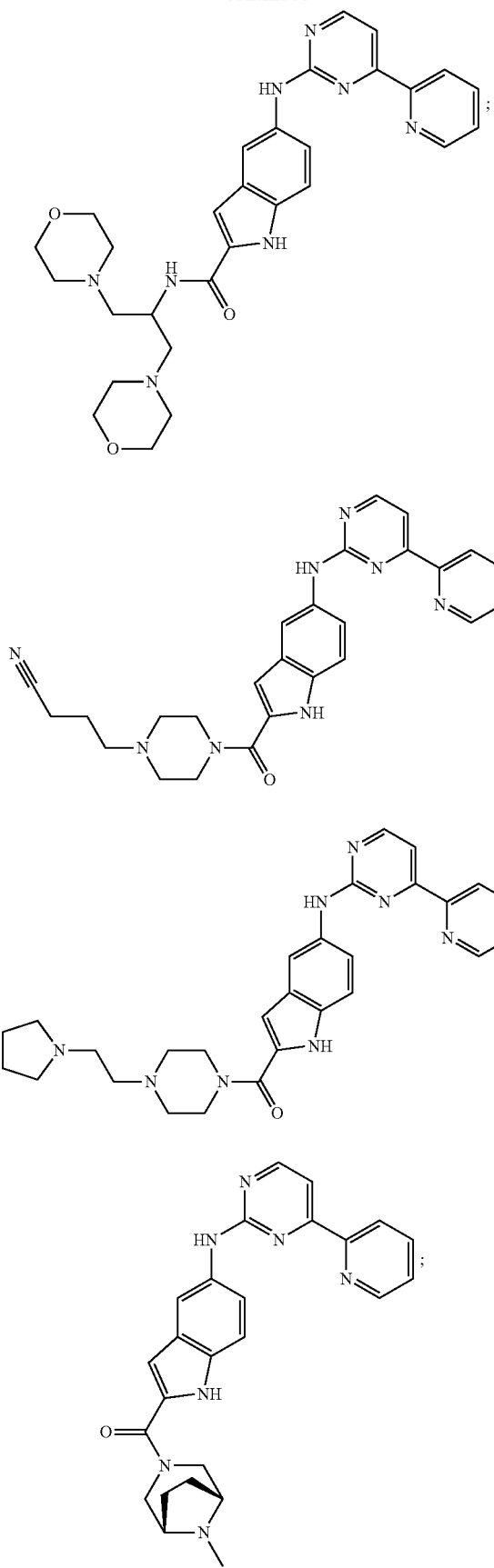
358
-continued
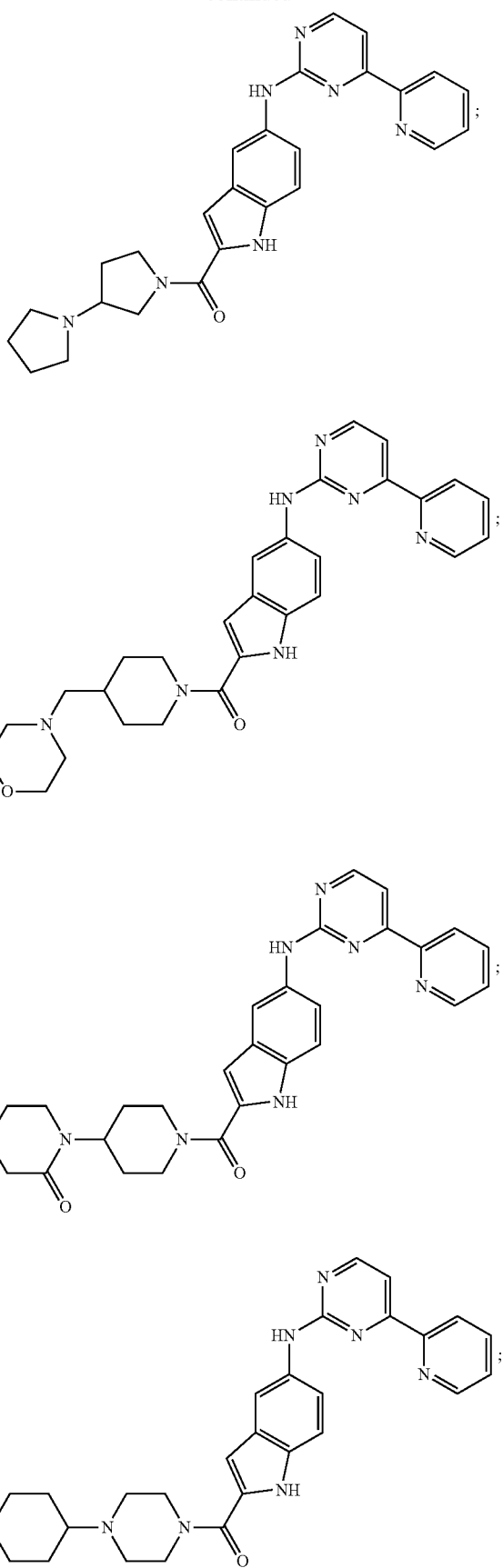

359
-continued
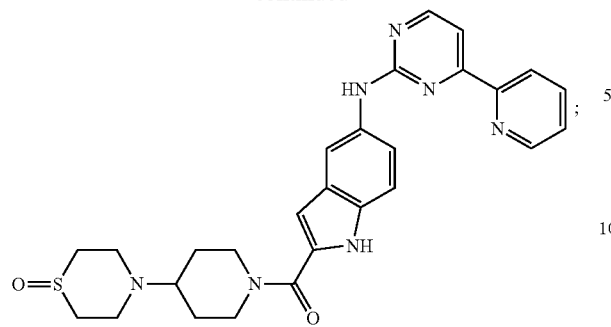
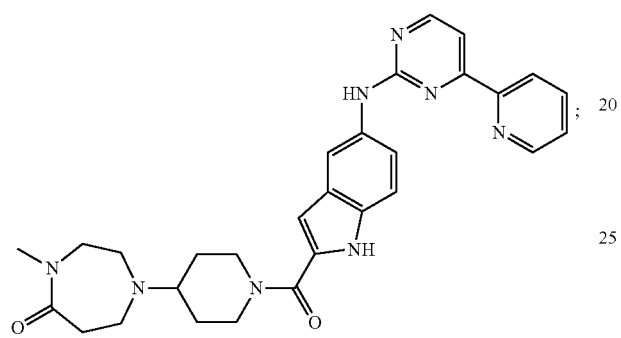
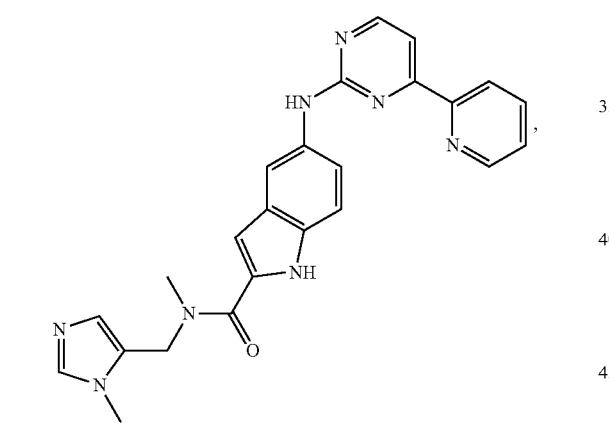
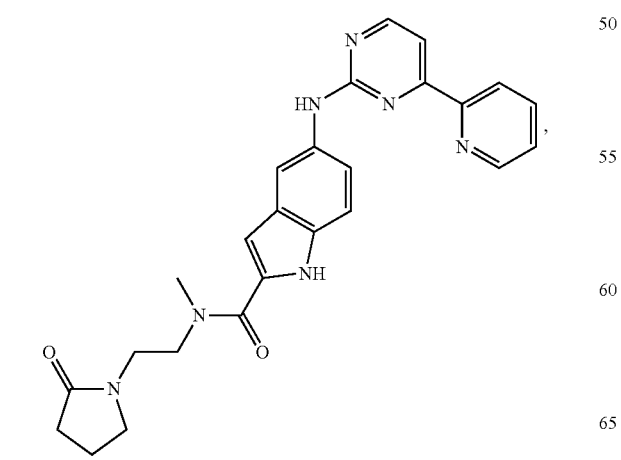
360
-continued
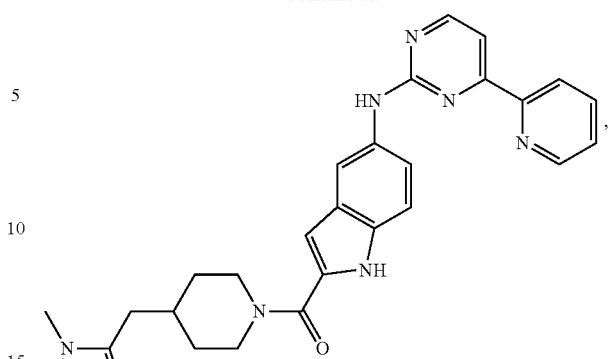
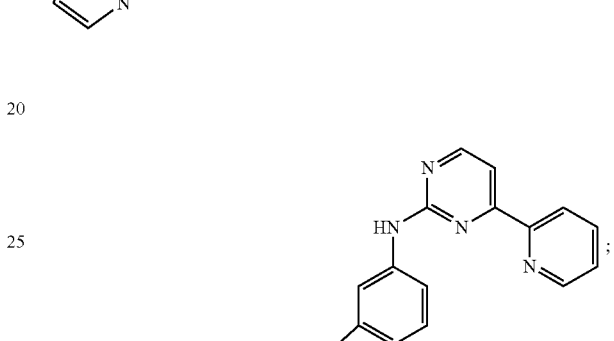
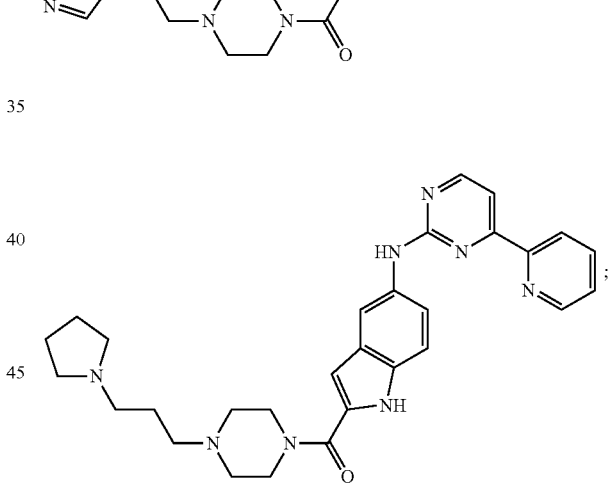
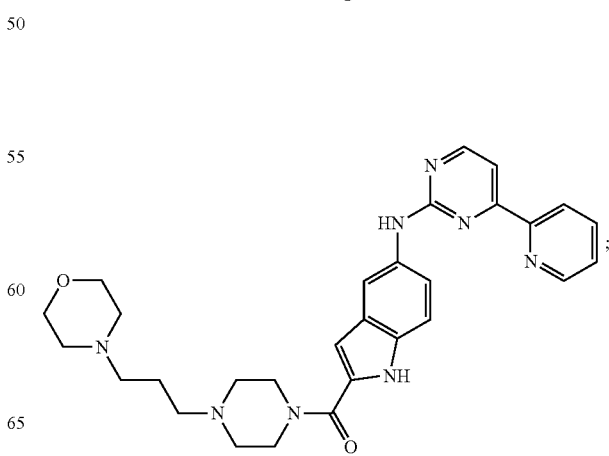

361
-continued
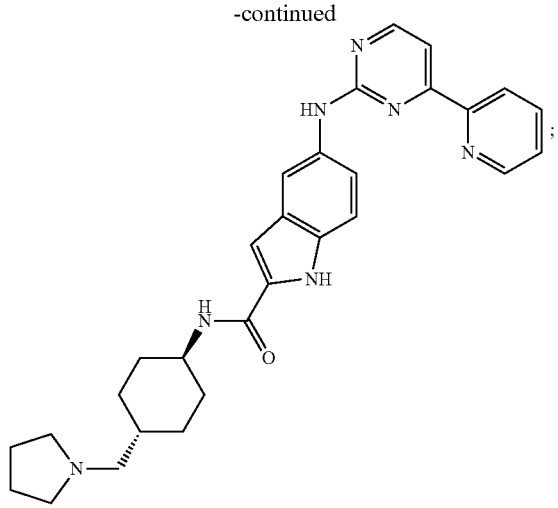
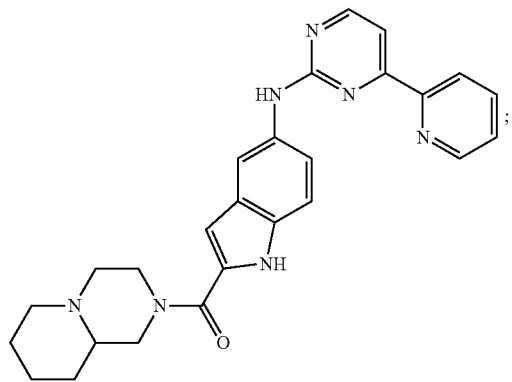
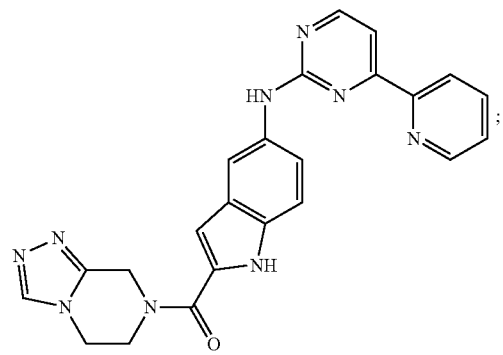
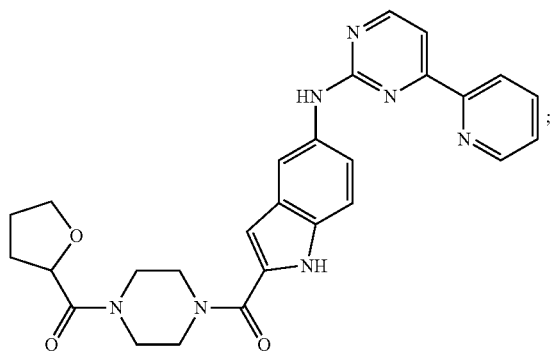
362
-continued
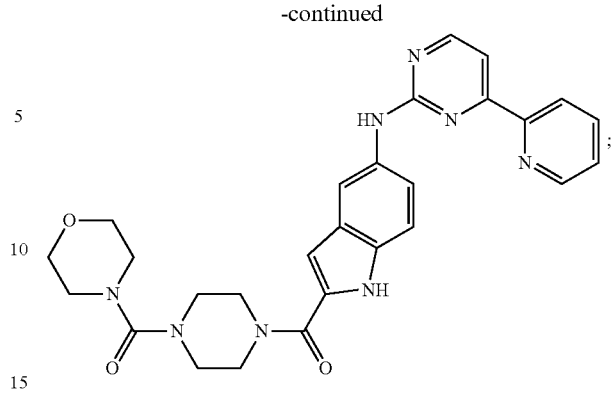
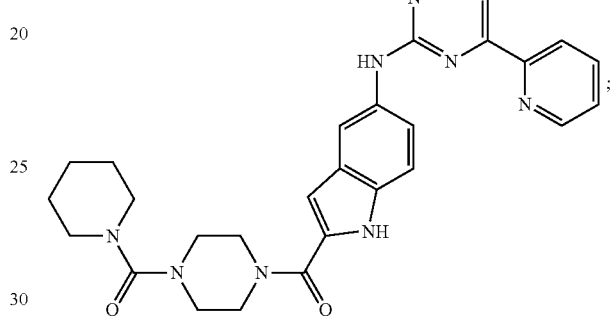
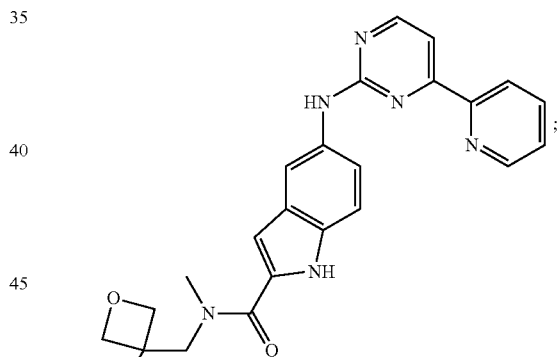
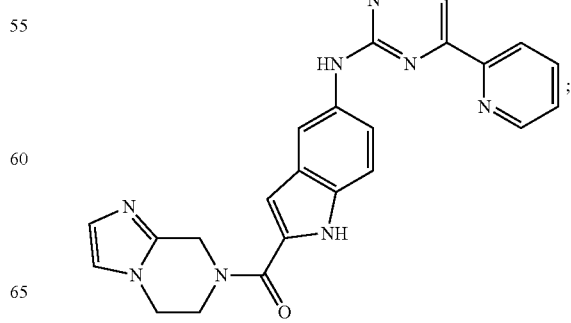

363
-continued
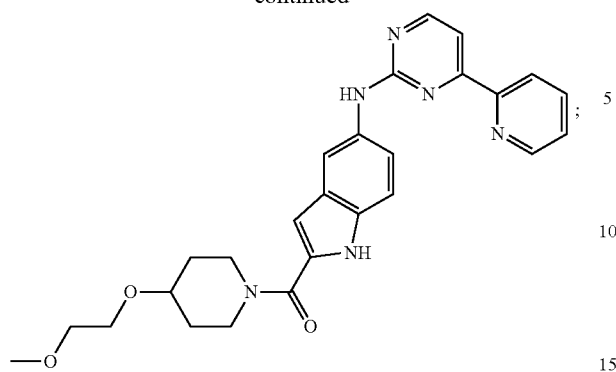
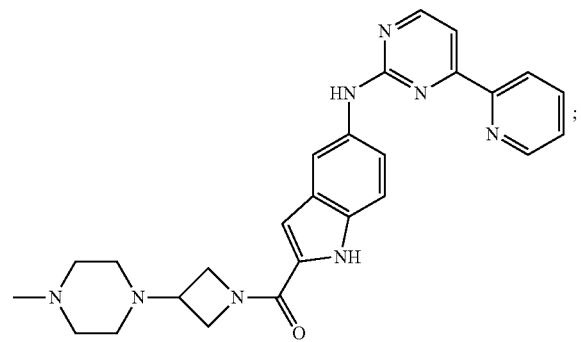
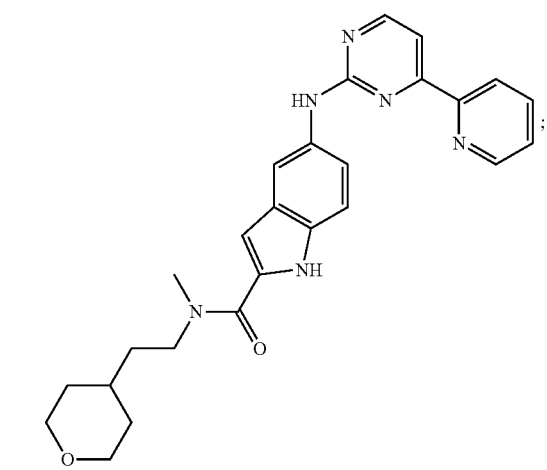
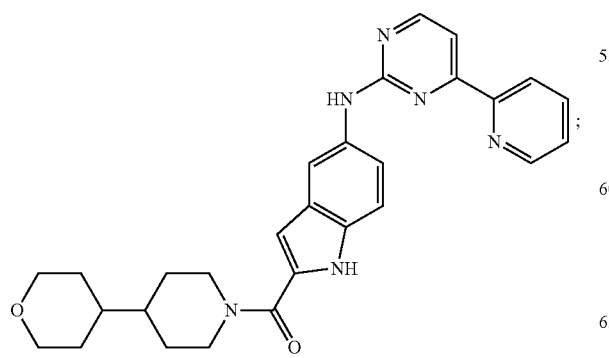
364
-continued
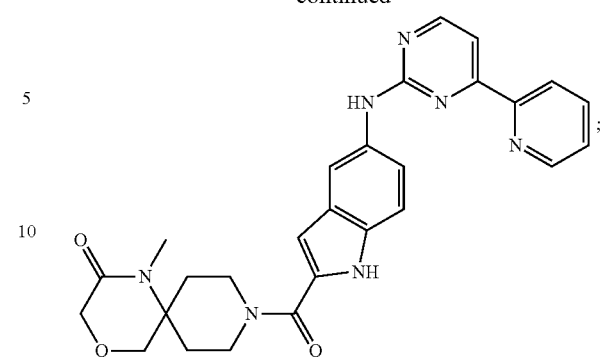
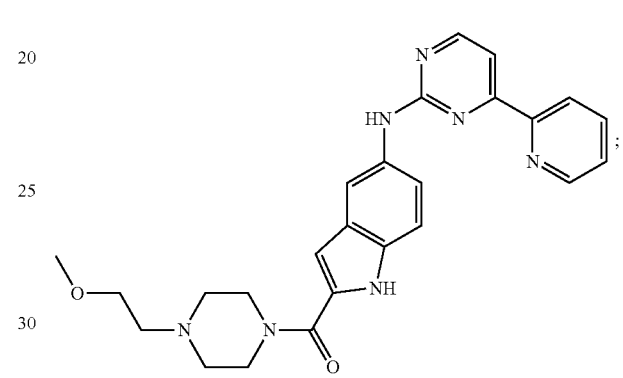
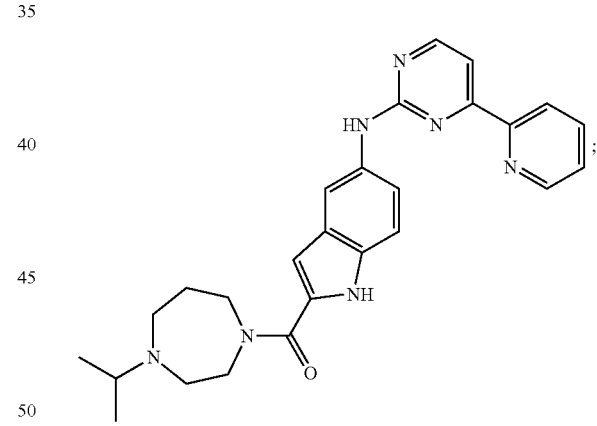
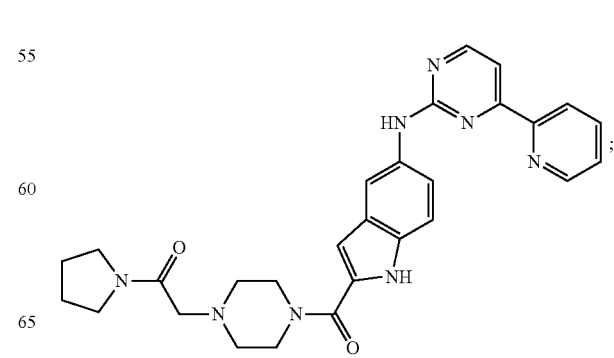

-continued

367
-continued
368
-continued
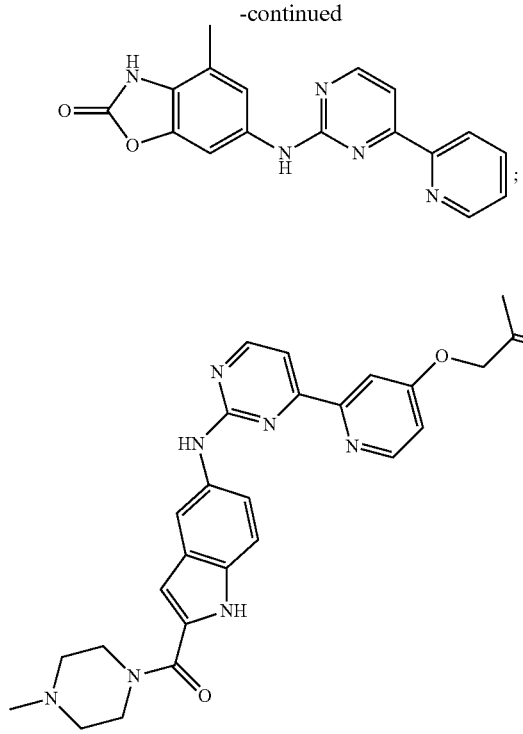
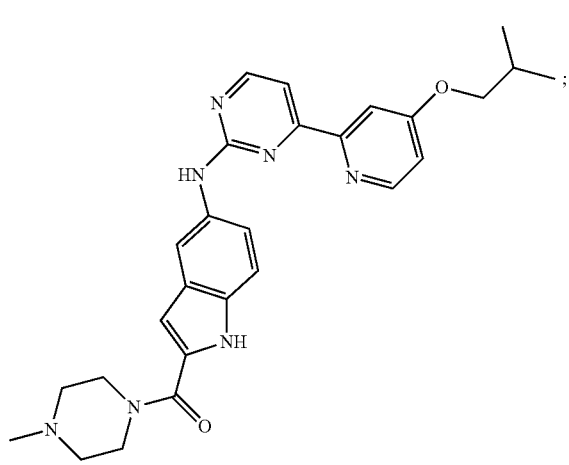
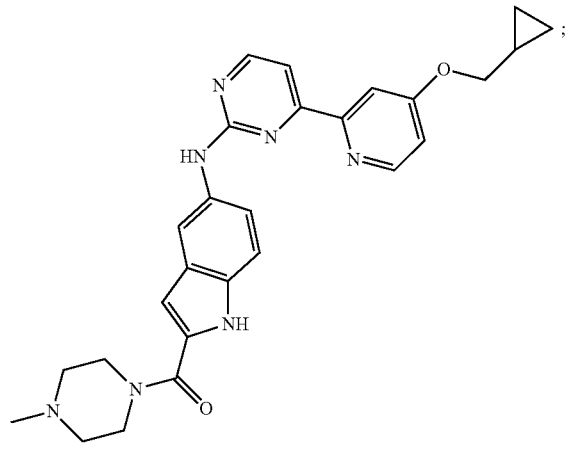
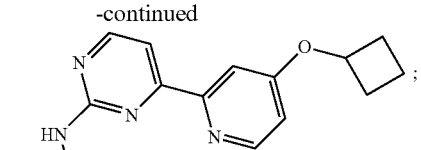
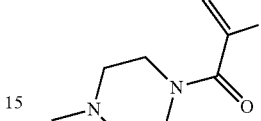
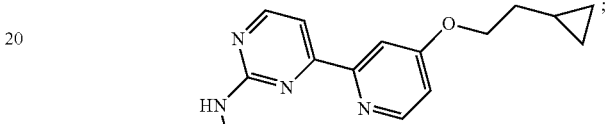
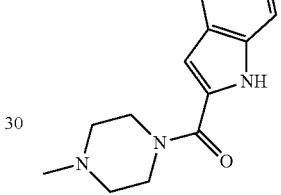
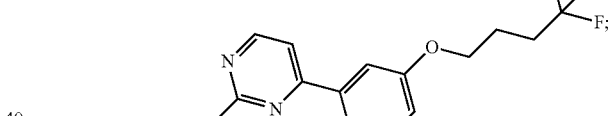
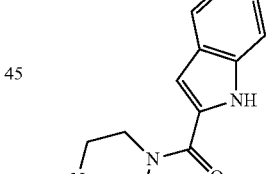
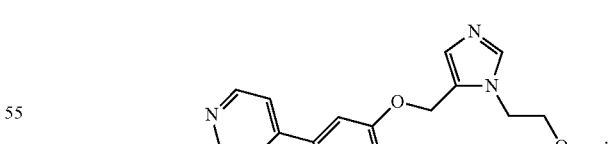
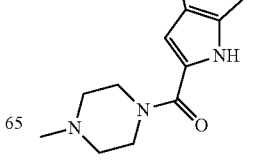
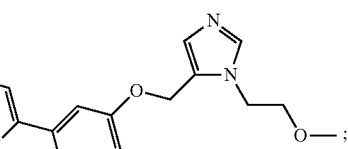

369
-continued
370
-continued
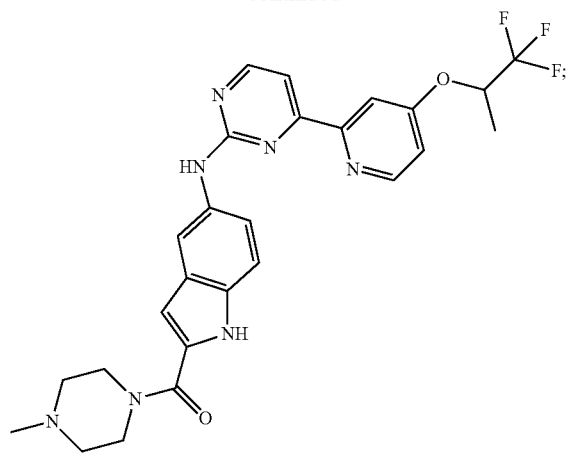
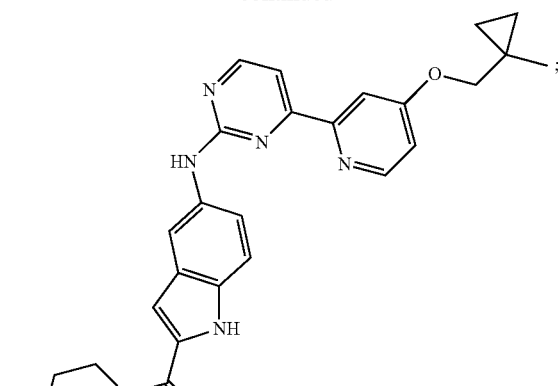

371
-continued
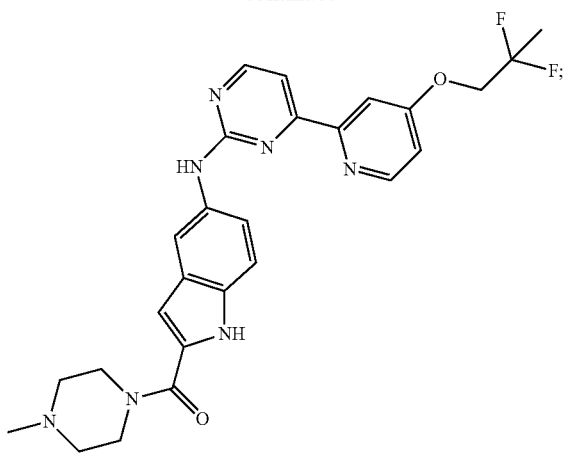
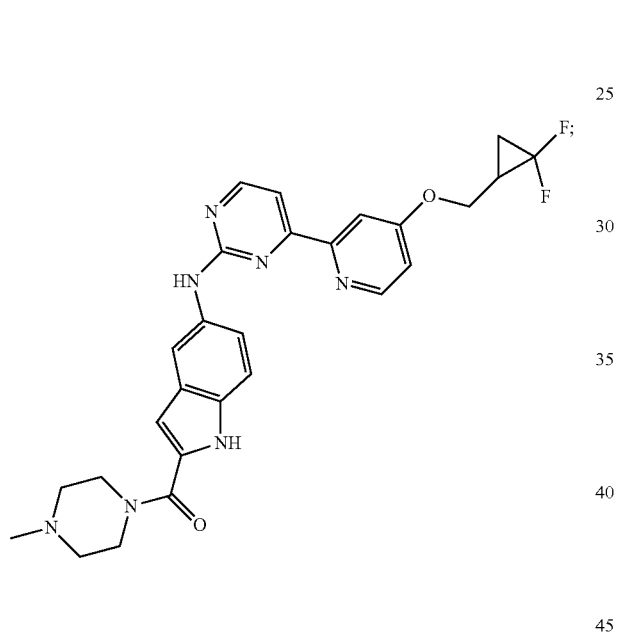
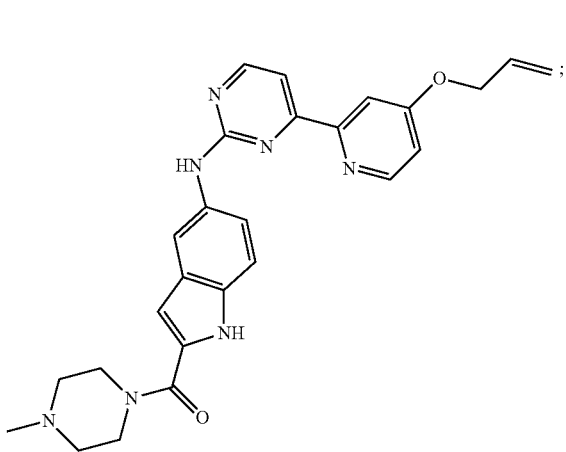
372
-continued
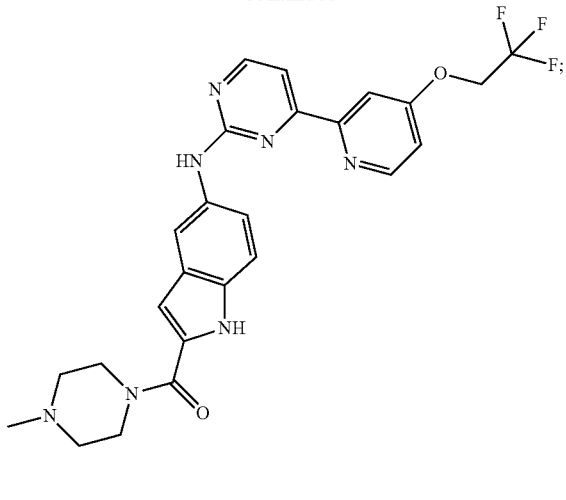
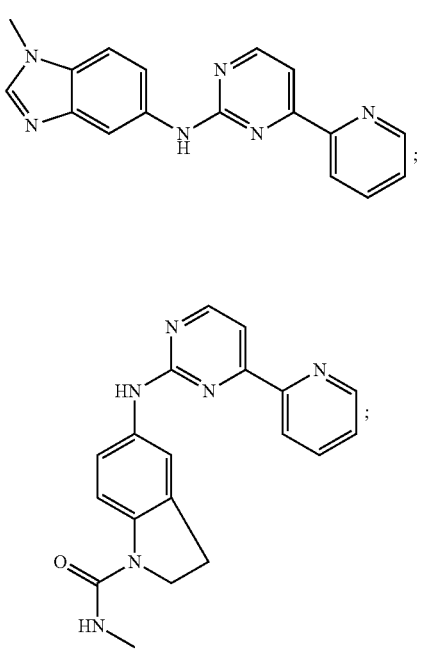
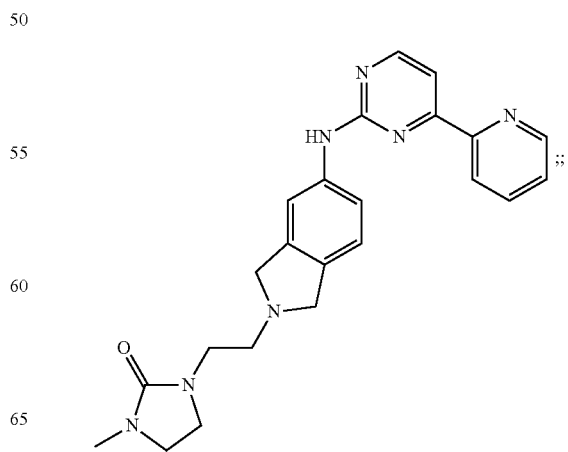

373
-continued
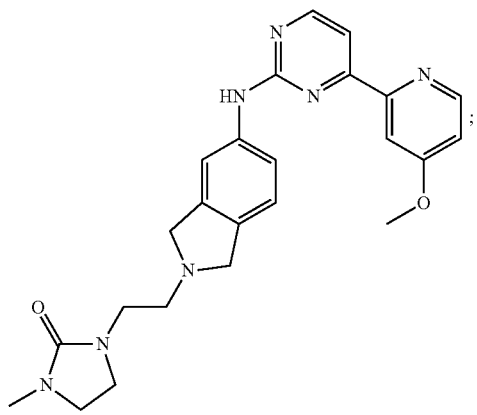
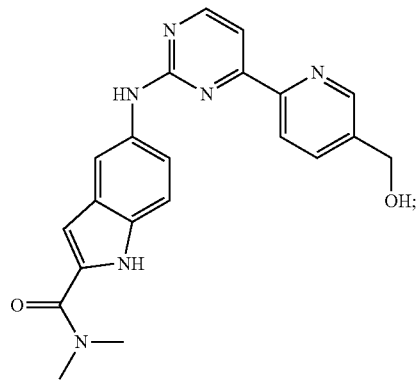
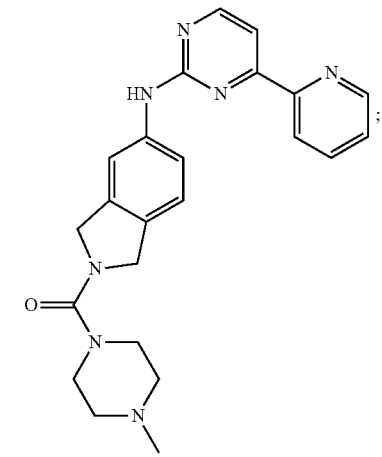
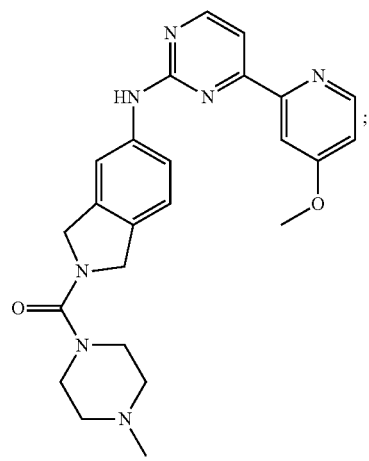
374
-continued
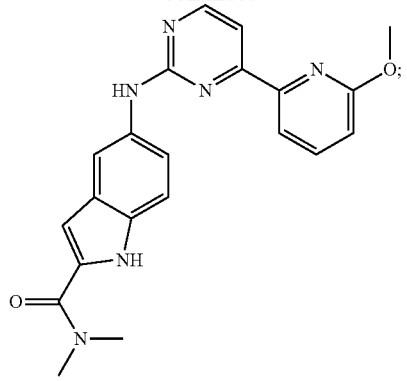
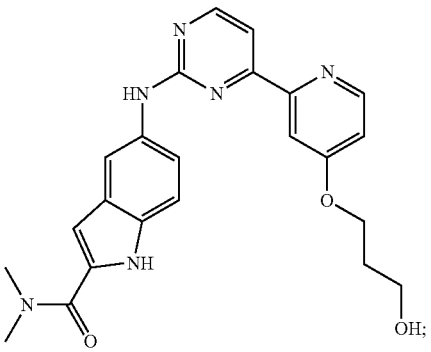
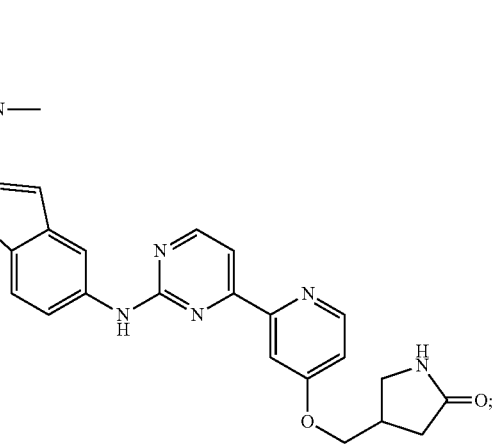
Chiral
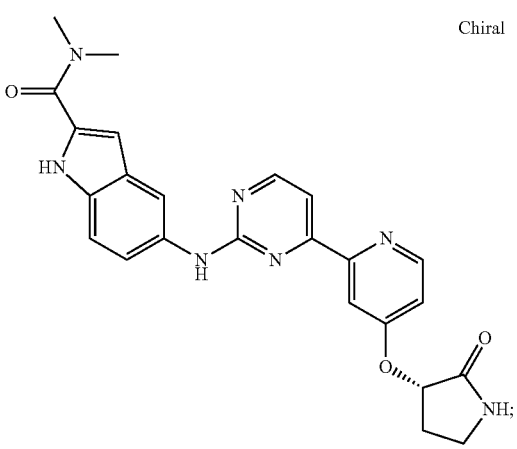

375
-continued
Chiral
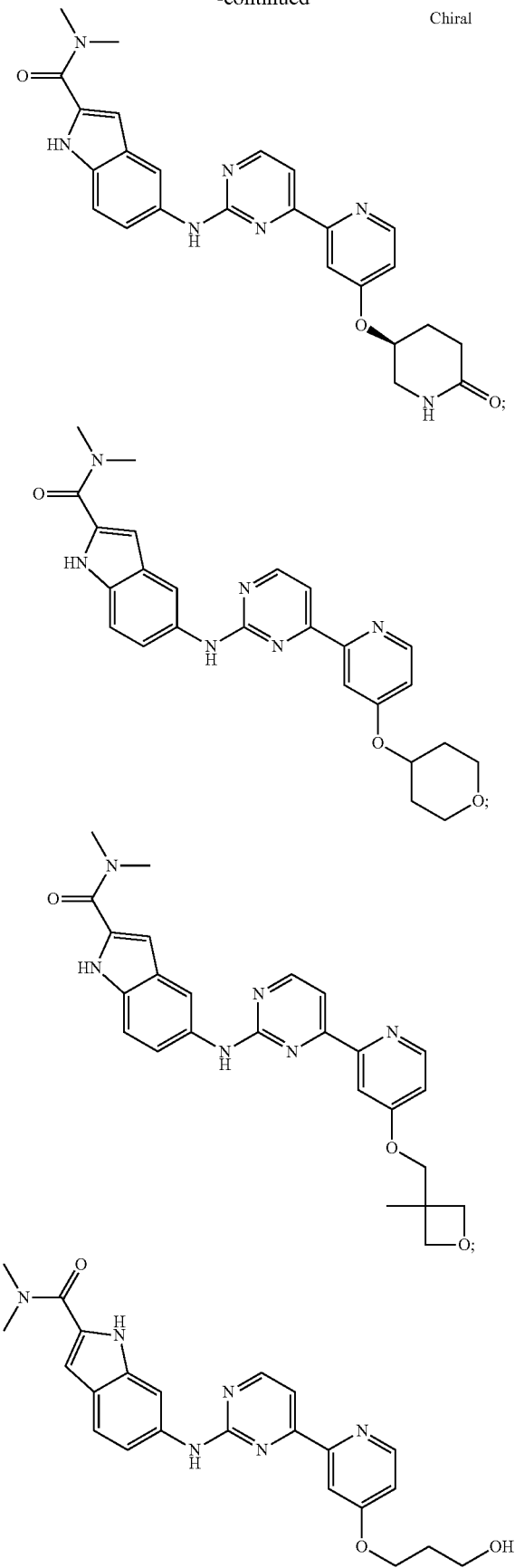
376
-continued
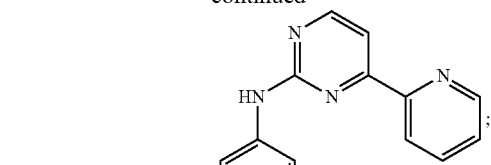
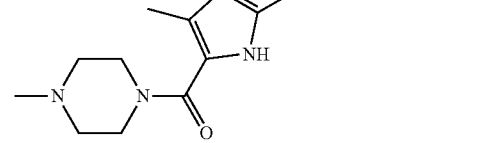
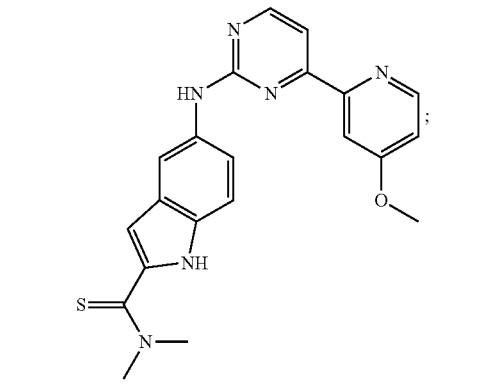
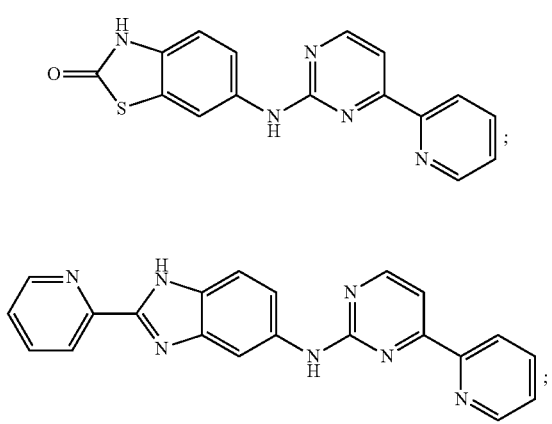

377
-continued
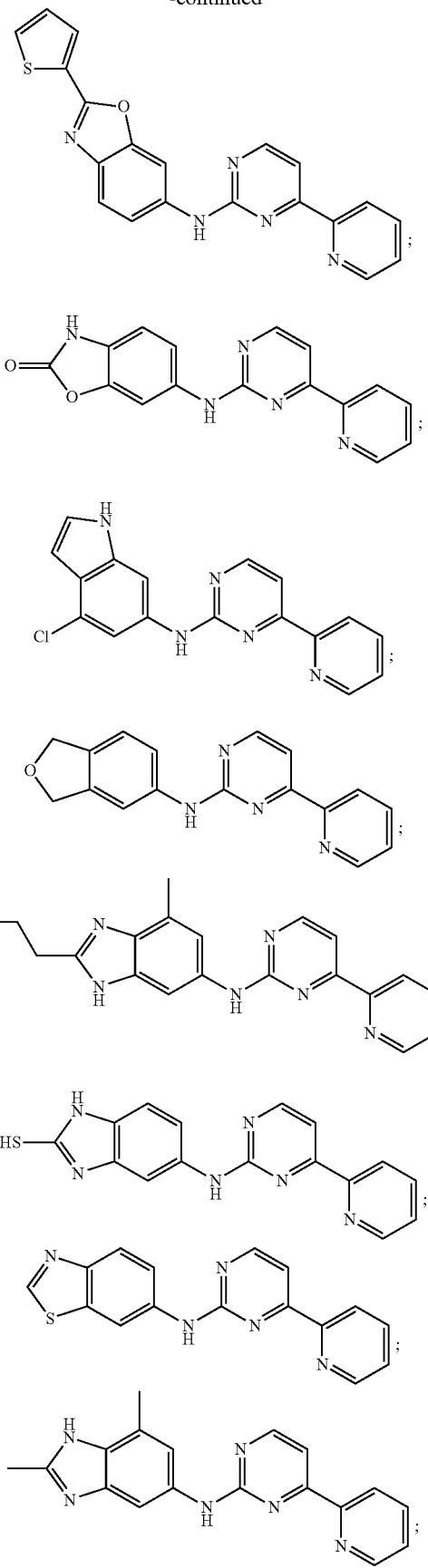
378
-continued
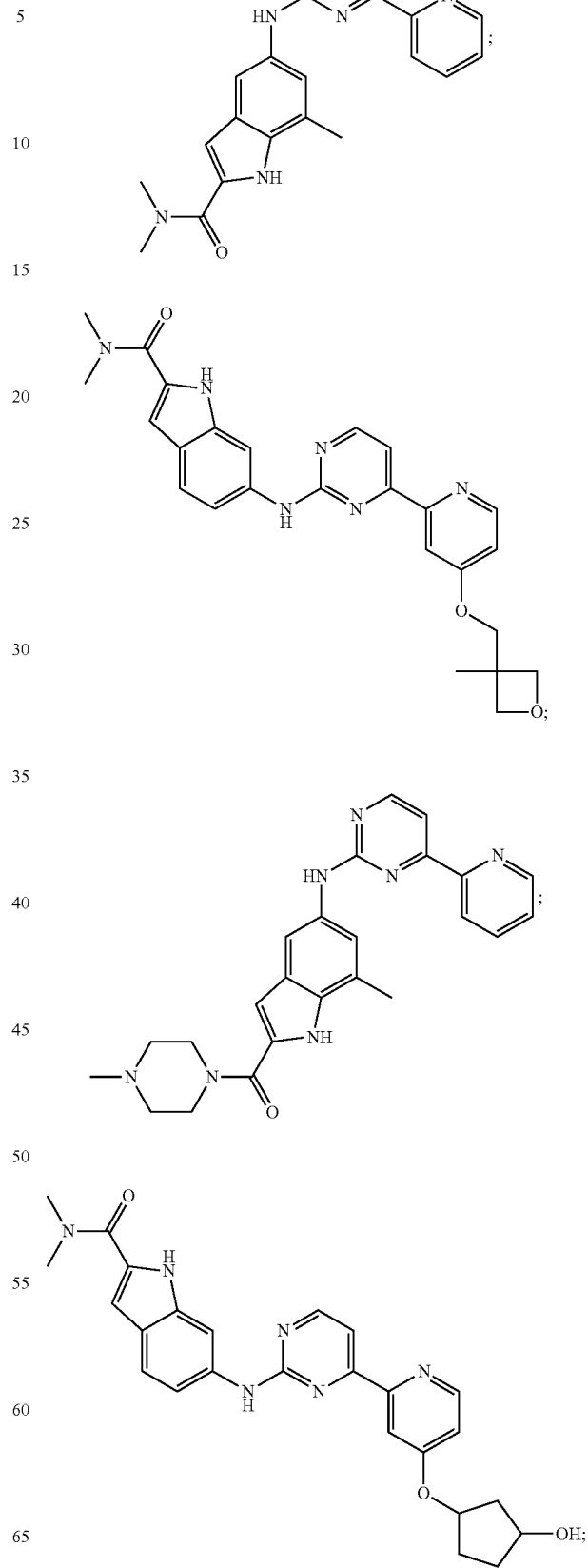

379
-continued
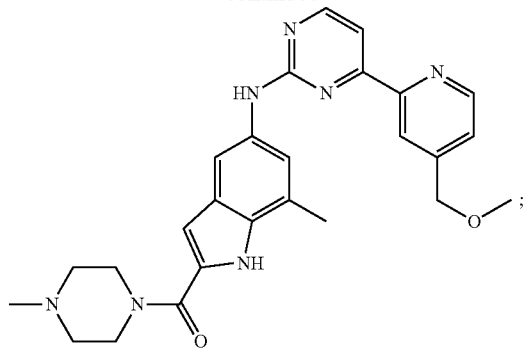
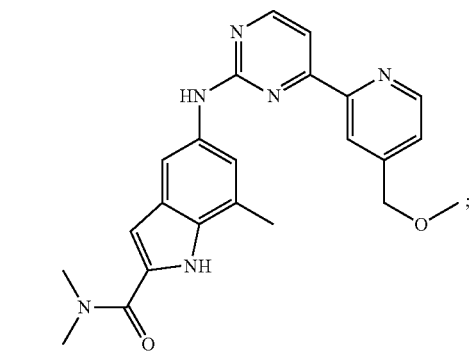
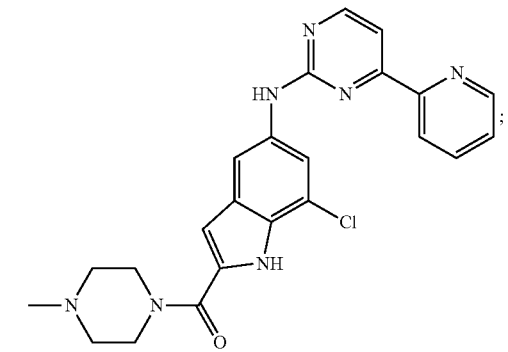
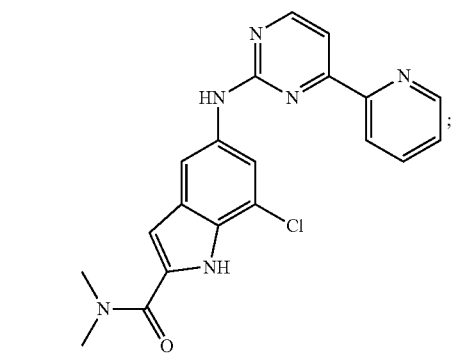
380
-continued
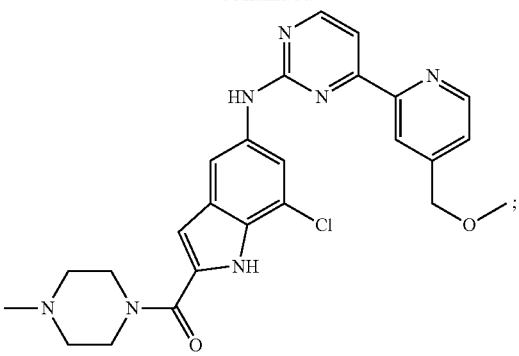
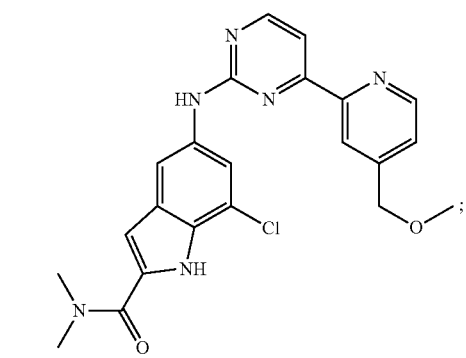
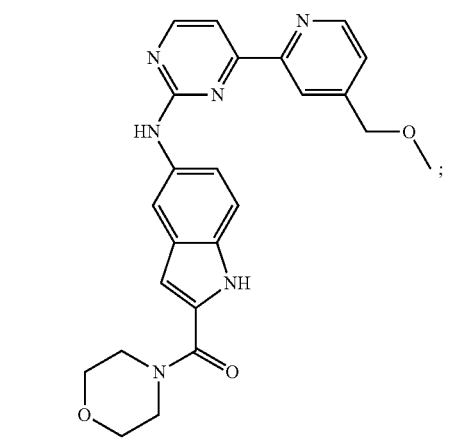
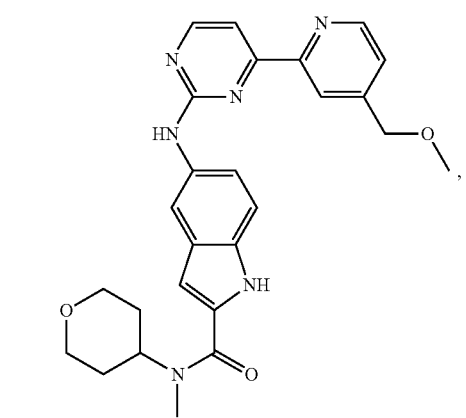

381
-continued
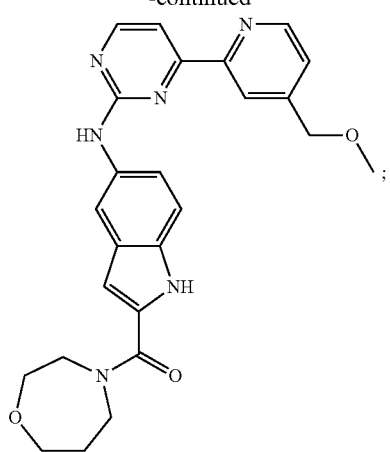
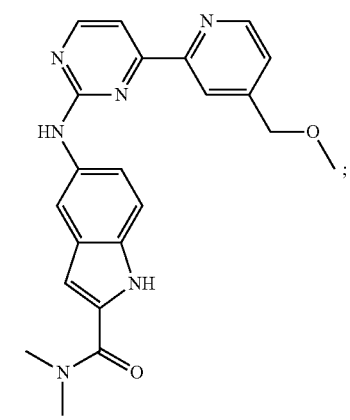
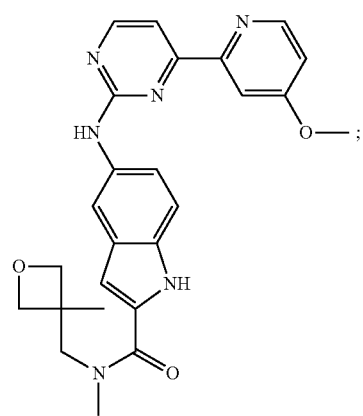
382
-continued
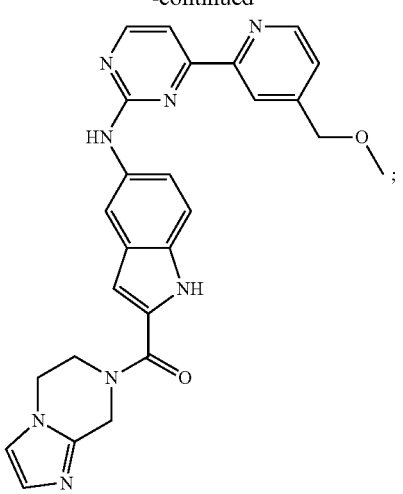
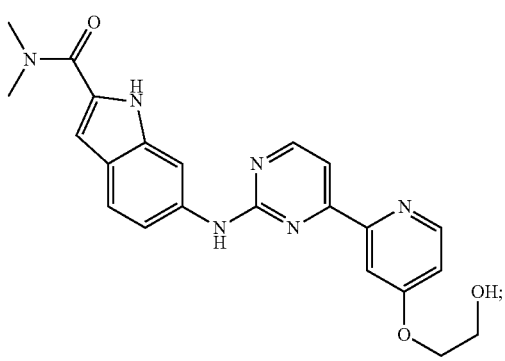
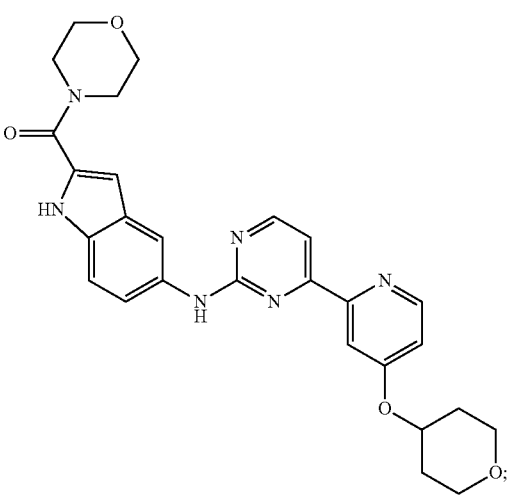

383
-continued
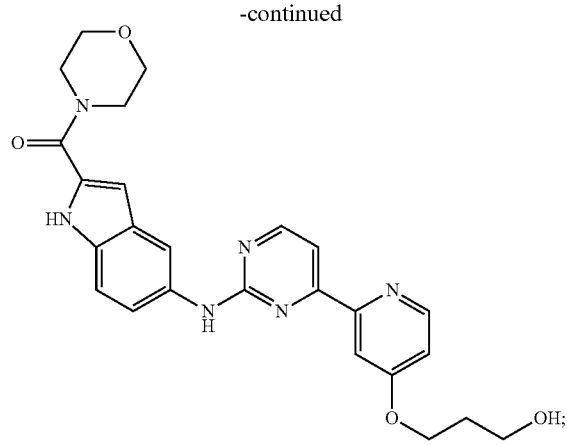
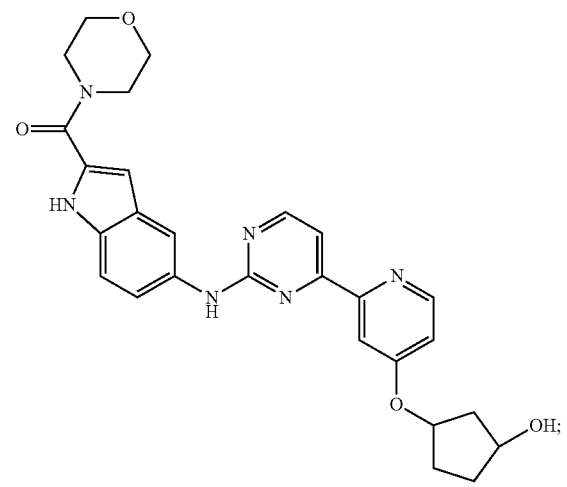
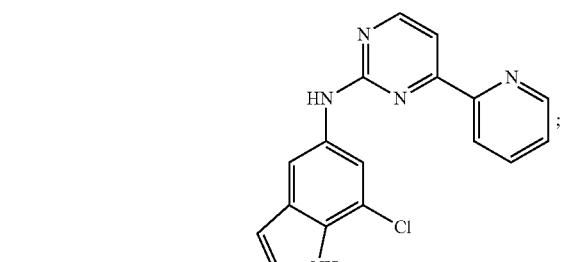
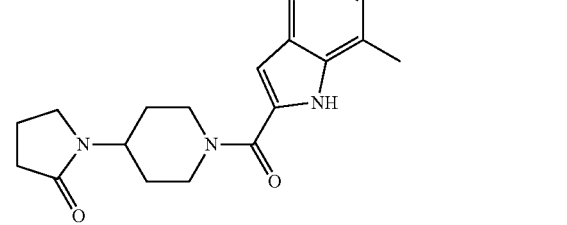
384
-continued
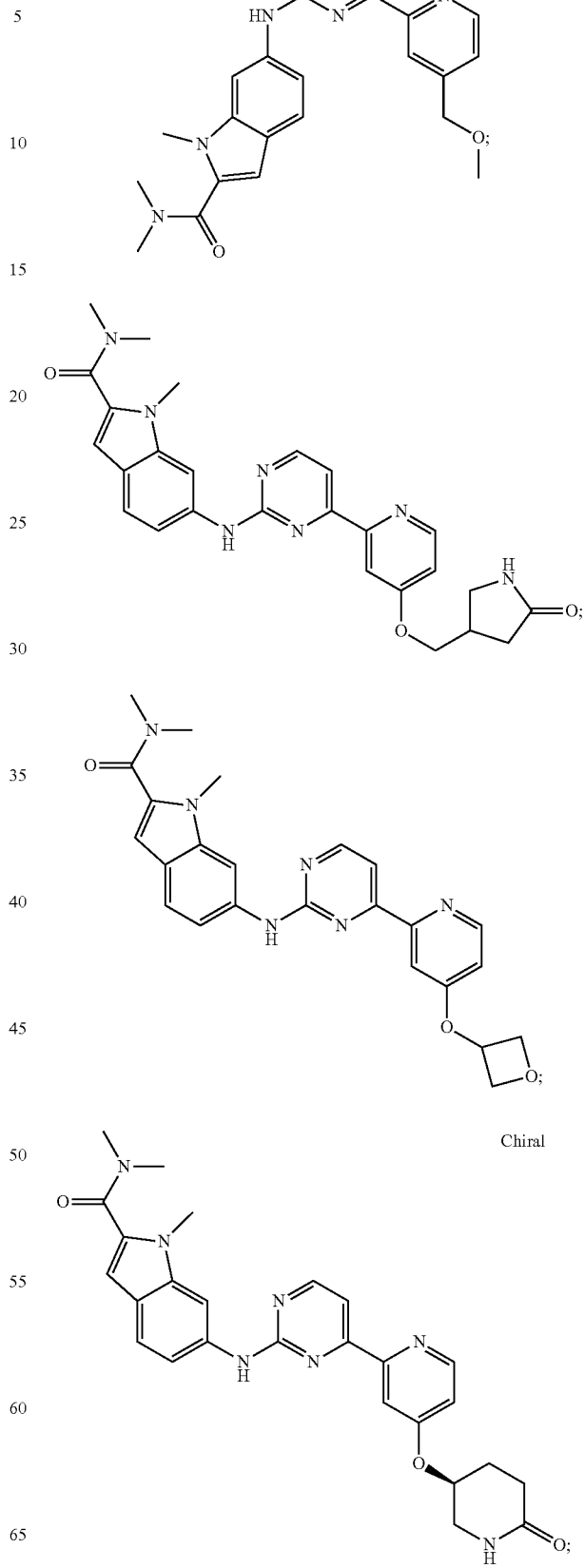

385
-continued
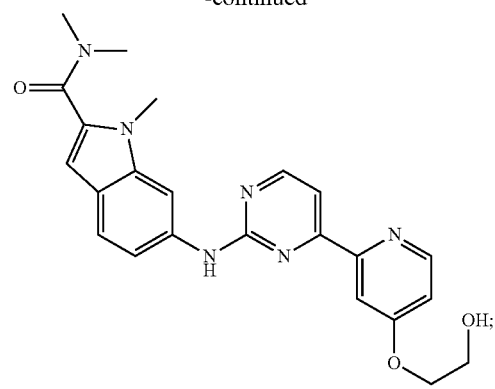
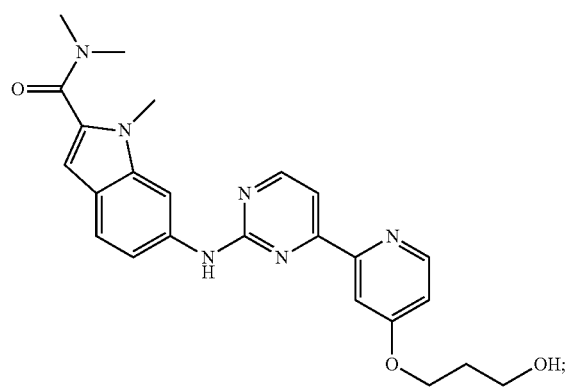
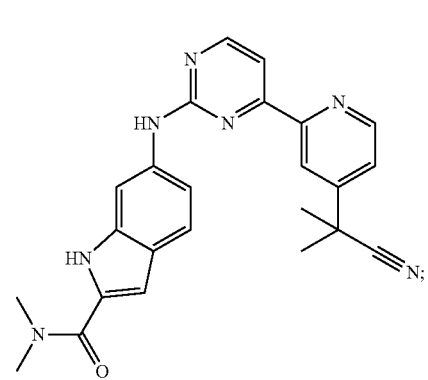
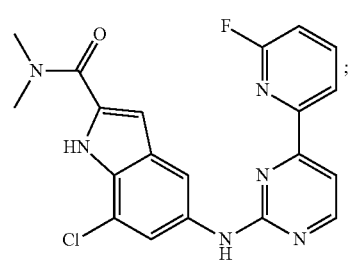
386
-continued
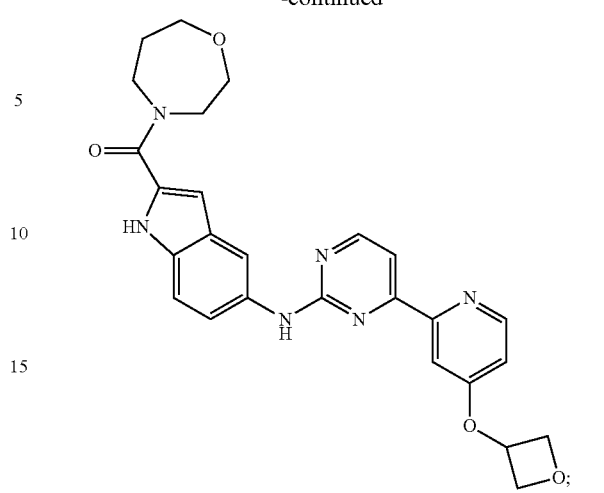
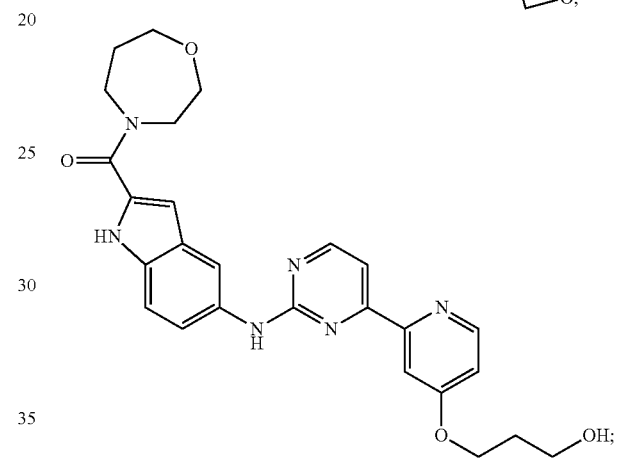
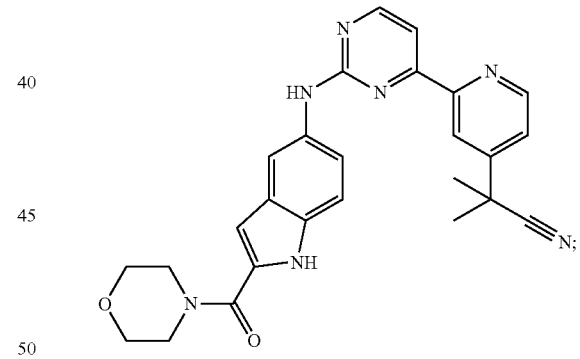
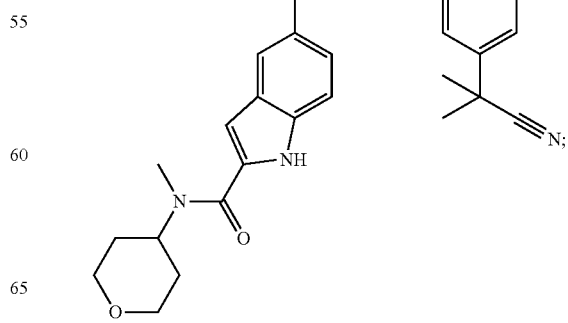

387
-continued
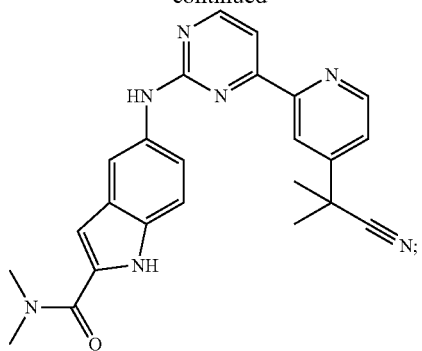
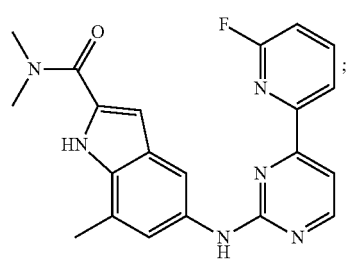
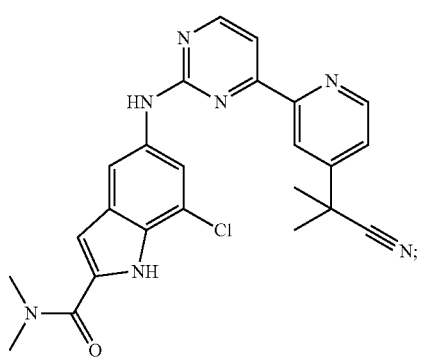
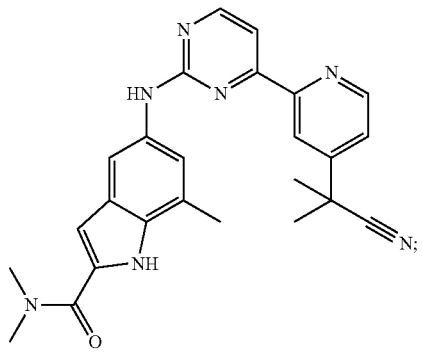
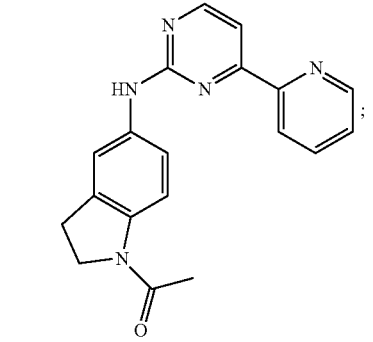
388
-continued
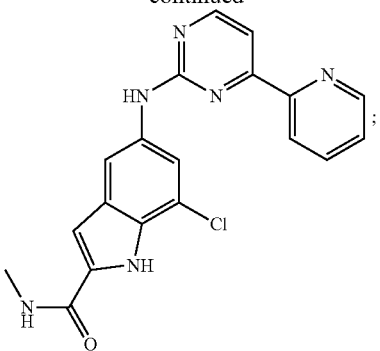
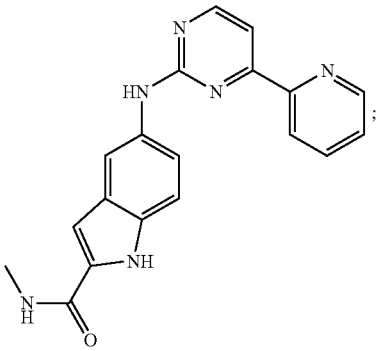
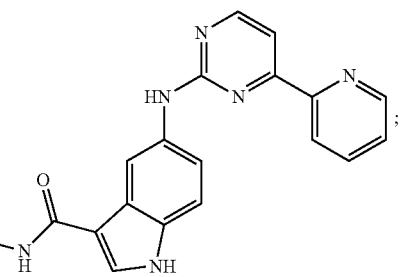
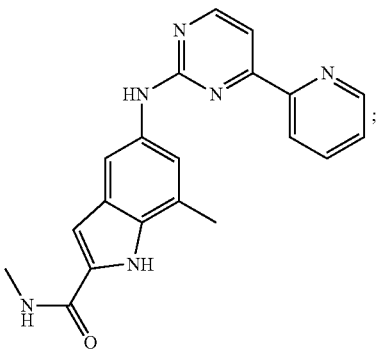
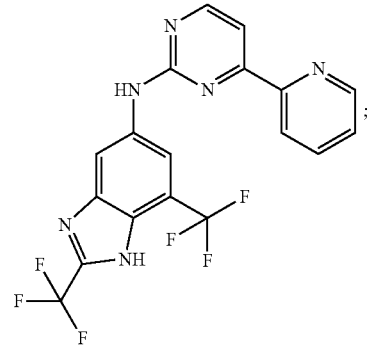

389
-continued

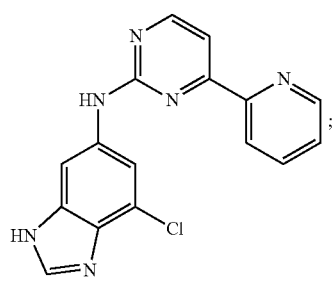

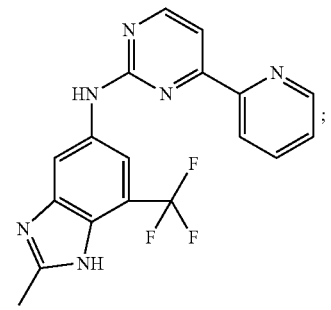

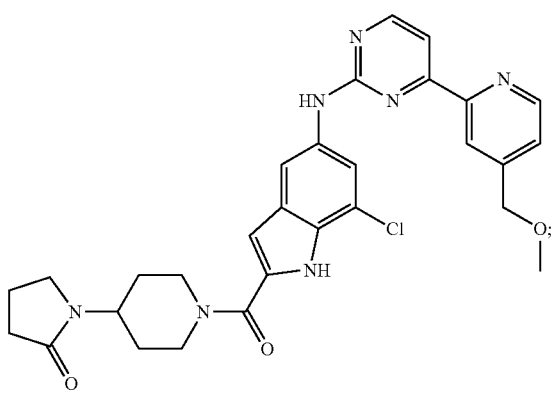

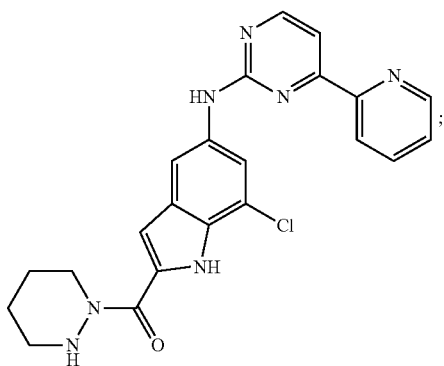

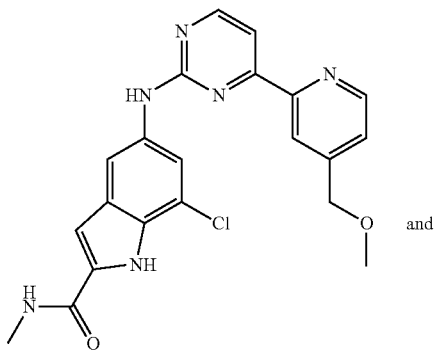
and

390
-continued

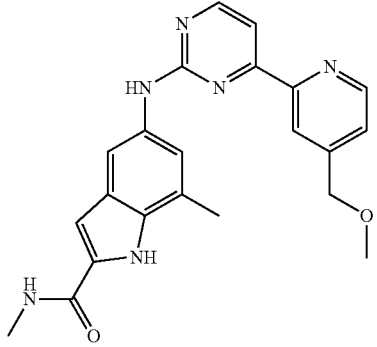

or a pharmaceutically acceptable salt thereof.

17. A method of treating diseases selected from among allergic rhinitis, asthma, COPD, adult respiratory distress syndrome, bronchitis, B-cell lymphoma, dermatitis, allergic dermatitis, rheumatoid arthritis, idiopathic thrombocytopenic purpura, lupus erythematodes, Lymphoma, Crohn's disease, multiple sclerosis, psoriasis, T cell lymphoma, comprising administering to a patient a therapeutically effective amount of a compound according to claim 1.

18. The method according to claim 17 wherein the diseases are selected from among asthma, COPD, allergic rhinitis, adult respiratory distress syndrome, bronchitis, allergic dermatitis, idiopathic thrombocytopenic purpura, and rheumatoid arthritis.

19. The method according to claim 17 wherein the diseases are selected from among asthma, COPD, allergic rhinitis, allergic dermatitis and rheumatoid arthritis.

20. A pharmaceutical composition comprising therapeutically effective amount of a compound according to claim 1 and one or more pharmaceutically acceptable carriers and/or adjuvants.

21. The pharmaceutical composition according to claim 20 further in combination with an active substance selected from among anticholinergics, betamimetics, corticosteroids, PDE4-inhibitors, EGFR-inhibitors, LTD4-antagonists, CCR3-inhibitors, iNOS-inhibitors, CRTH2-antagonists and HMG-CoA reductase inhibitors.

22. A compounds selected from the group consisting of formula 10

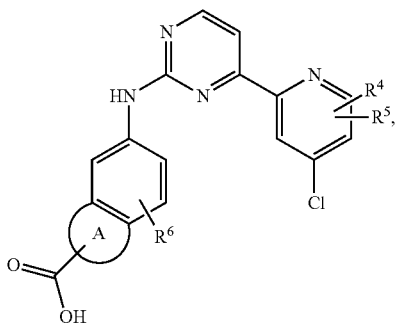

formula 12
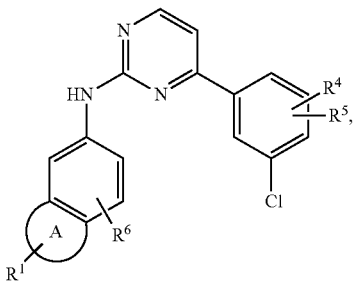
formula 15
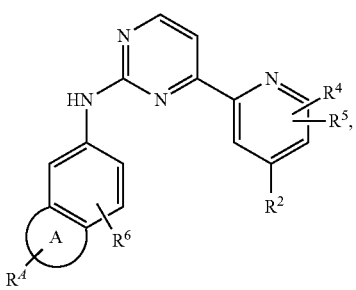
formula 15'
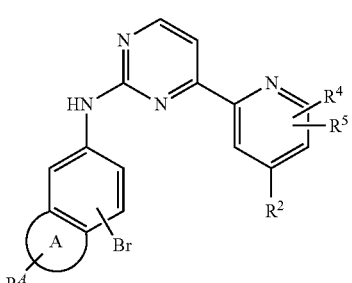
formula 16
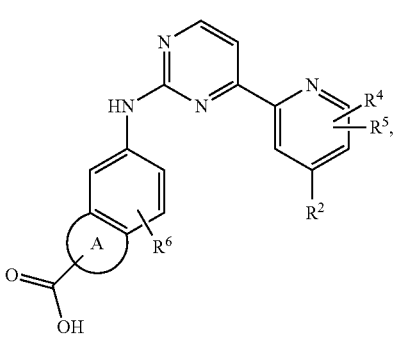
formula 16'
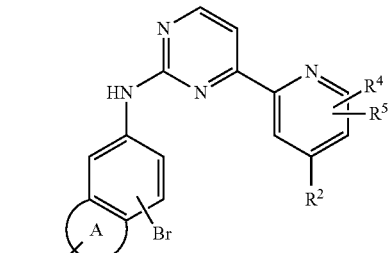
formula 17
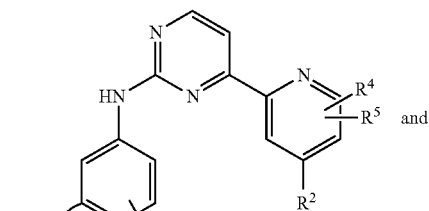
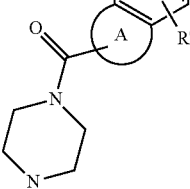
formula 19
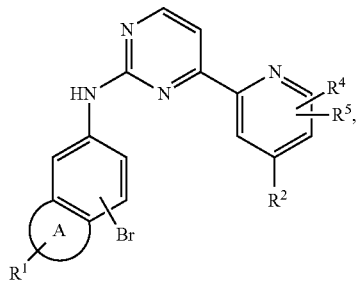
wherein $R^1$, $R^2$, $R^4$, $R^5$, $R^6$ and A are defined as in claim 1 and wherein $R^4$ is —CO—O—CH$_3$ or —CO—O—CH$_2$—CH$_3$,
or a pharmaceutically acceptable salt thereof.
* * * * *